US012280207B2

(12) United States Patent
Sing et al.

(10) Patent No.: US 12,280,207 B2
(45) Date of Patent: Apr. 22, 2025

(54) MULTI-MODE RESPIRATORY THERAPY APPARATUS, SYSTEM, AND METHOD

(71) Applicant: HILL-ROM SERVICES PTE. LTD., Singapore (SG)

(72) Inventors: Jack Barney Sing, Batesville, IN (US); Yong Guan Tay, Singapore (SG); Song Chiun Yong, Johor (MY); Wee Chin Tay, Singapore (SG); Pratheep Kumar Mahalingam, Singapore (SG); Sangadi Nookarajesh Varma, Singapore (SG); Ravivarman Ganesan, Struer (DK); Shu Hwa Liau, Johor (MY); Leonardo B. Artiaga, Jr., Singapore (SG); Jiang Cong, Singapore (SG); Leah Noaeill, New Brighton, MN (US); Susan Malaret, Chanhassen, MN (US); Baoyi Wu, Singapore (SG); Travis A. Pelo, Columbus, IN (US); Justin Liew, Singapore (SG)

(73) Assignee: HILL-ROM SERVICE PTE. LTD., Singapore (SG)

(*) Notice: Subject to any disclaimer, the term of this patent is extended or adjusted under 35 U.S.C. 154(b) by 134 days.

(21) Appl. No.: 18/183,329

(22) Filed: Mar. 14, 2023

(65) Prior Publication Data
US 2023/0218842 A1 Jul. 13, 2023

Related U.S. Application Data

(63) Continuation of application No. 16/952,166, filed on Nov. 19, 2020, now Pat. No. 11,633,559.
(Continued)

(51) Int. Cl.
*A61M 16/00* (2006.01)
*A61M 11/02* (2006.01)
(Continued)

(52) U.S. Cl.
CPC ........ *A61M 16/0057* (2013.01); *A61M 11/02* (2013.01); *A61M 16/0066* (2013.01);
(Continued)

(58) Field of Classification Search
CPC .............. A61M 16/00; A61M 16/0057; A61M 16/0066; A61M 16/024; A61M 16/0816;
(Continued)

(56) References Cited

U.S. PATENT DOCUMENTS 4,620,536 A   11/1986  Hartley, Sr.
4,852,563 A    8/1989  Gross
(Continued)

FOREIGN PATENT DOCUMENTS

EP    3431065 A1    1/2019
WO  2006102345 A2   9/2006
(Continued)

OTHER PUBLICATIONS

3M, "RFID 401: Tag Quality and Reliability"; retrieved from https://multimedia.3m.com/mws/media/5138270/rfid-401-southafrica.pdf (Year: 2008).*
(Continued)

*Primary Examiner* — Joseph D. Boecker
(74) *Attorney, Agent, or Firm* — Barnes & Thornburg LLP

(57) ABSTRACT

A respiratory therapy apparatus is operable to deliver multiple types of therapy to a patient. The apparatus includes a main housing and a nebulizer tray that selectively attaches to a bottom of the main housing. The apparatus also includes a filter housing unit having an antenna surrounding a pneumatic passage and a transponder chip coupled to the antenna. The main housing has also has an antenna that surrounds a respective pneumatic passage of a main outlet port of the apparatus. The main housing includes a reader that controls
(Continued)

communication between the antennae. The main housing of the apparatus also has a pivotable hose support plate, a firmware upgrade port underneath part of the top wall of the housing, and a graphical user interface (GUI) that displays various user inputs for control of the apparatus and that displays various alert conditions that are detected.

26 Claims, 156 Drawing Sheets

Related U.S. Application Data

(60) Provisional application No. 62/951,079, filed on Dec. 20, 2019.

(51) Int. Cl.
*A61M 16/04* (2006.01)
*A61M 16/06* (2006.01)
*A61M 16/08* (2006.01)
*A61M 16/10* (2006.01)
*A61M 16/20* (2006.01)

(52) U.S. Cl.
CPC .......... *A61M 16/024* (2017.08); *A61M 16/06* (2013.01); *A61M 16/0833* (2014.02); *A61M 16/0875* (2013.01); *A61M 16/105* (2013.01); *A61M 16/106* (2014.02); *A61M 16/107* (2014.02); *A61M 16/20* (2013.01); *A61M 16/0488* (2013.01); *A61M 16/0816* (2013.01); *A61M 2205/14* (2013.01); *A61M 2205/3368* (2013.01); *A61M 2205/3561* (2013.01); *A61M 2205/3592* (2013.01); *A61M 2205/502* (2013.01); *A61M 2205/505* (2013.01); *A61M 2205/52* (2013.01); *A61M 2205/584* (2013.01); *A61M 2205/6054* (2013.01); *A61M 2205/6072* (2013.01); *A61M 2205/8206* (2013.01); *A61M 2230/00* (2013.01)

(58) Field of Classification Search
CPC .............. A61M 16/105; A61M 16/106; A61M 16/107; A61M 2205/125; A61M 2205/14; A61M 2205/3523; A61M 2205/3561; A61M 2205/3569; A61M 2205/3592; A61M 2205/502; A61M 2205/52; A61M 2205/60; A61M 2205/6072; A62B 23/02
See application file for complete search history.

(56) References Cited

U.S. PATENT DOCUMENTS

| | | | |
|---|---|---|---|
| 4,867,151 A | | 9/1989 | Bird |
| D376,199 S | | 12/1996 | Rozek et al. |
| 6,550,476 B1 | | 4/2003 | Ryder |
| 6,632,194 B1 * | | 10/2003 | Mehner ............... A61M 13/003 604/23 |
| 6,708,688 B1 | | 3/2004 | Rubin et al. |
| 6,718,969 B1 | | 4/2004 | Rubin et al. |
| 6,792,946 B1 | | 9/2004 | Waldo et al. |
| 7,018,348 B2 | | 3/2006 | Van Brunt et al. |
| 7,191,780 B2 | | 3/2007 | Faram |
| 7,909,033 B2 | | 3/2011 | Faram |
| 8,051,854 B2 | | 11/2011 | Faram |
| 8,052,626 B2 | | 11/2011 | Huster et al. |
| 8,365,727 B2 | | 2/2013 | Dunsmore et al. |
| 8,460,223 B2 | | 6/2013 | Huster et al. |
| 8,485,179 B1 | | 7/2013 | Meyer et al. |
| 8,539,952 B2 | | 9/2013 | Carbone et al. |
| 8,573,203 B2 | | 11/2013 | Addington et al. |
| 8,663,138 B2 | | 3/2014 | Huster et al. |
| 8,845,562 B2 | | 9/2014 | Receveur et al. |
| 8,931,478 B2 | | 1/2015 | Dunsmore et al. |
| 8,940,085 B2 | | 1/2015 | Markham et al. |
| 9,050,434 B2 | | 6/2015 | Faram |
| 9,180,271 B2 | | 11/2015 | Guo et al. |
| 9,272,115 B2 | | 3/2016 | Bobey et al. |
| 9,675,775 B2 | | 6/2017 | Bobey et al. |
| 9,757,528 B2 | | 9/2017 | Rubin |
| 9,795,752 B2 | | 10/2017 | Birnkrant et al. |
| 9,968,511 B2 | | 5/2018 | Huster et al. |
| 11,633,559 B2 | | 4/2023 | Sing et al. |
| 2005/0211761 A1 * | | 9/2005 | Anttila ................. A61M 16/22 235/376 |
| 2005/0217666 A1 | | 10/2005 | Fink et al. |
| 2006/0278222 A1 * | | 12/2006 | Schermeier ........... A61M 16/08 128/204.23 |
| 2011/0146670 A1 | | 6/2011 | Gallem et al. |
| 2012/0229272 A1 * | | 9/2012 | Jacob .................... A61M 16/06 340/539.12 |
| 2014/0150791 A1 | | 6/2014 | Birnkrant et al. |
| 2014/0158128 A1 | | 6/2014 | Heimel |
| 2014/0171843 A1 | | 6/2014 | Huster et al. |
| 2015/0165142 A1 * | | 6/2015 | Tham ................ A61M 16/0051 128/202.22 |
| 2015/0297306 A1 * | | 10/2015 | Lazar .................... A61B 90/98 600/543 |
| 2016/0106947 A1 | | 4/2016 | Flynn |
| 2016/0279378 A1 | | 9/2016 | Cipollone et al. |
| 2017/0007797 A1 | | 1/2017 | Islava |
| 2017/0095631 A1 | | 4/2017 | Fukunaga |
| 2018/0085541 A1 | | 3/2018 | Ye et al. |
| 2018/0177962 A1 * | | 6/2018 | Bonano ............... A61M 16/024 |
| 2018/0243518 A1 * | | 8/2018 | Sing .................. A61M 16/0683 |
| 2019/0021925 A1 | | 1/2019 | Jiang et al. |
| 2019/0107302 A1 * | | 4/2019 | Liu .......................... F24F 8/10 |
| 2019/0232001 A1 | | 8/2019 | Ye et al. |
| 2021/0187223 A1 | | 6/2021 | Sing et al. |
| 2022/0347420 A1 | | 11/2022 | Liew et al. |
| 2022/0379048 A1 * | | 12/2022 | Sing .................. A61M 16/1055 |

FOREIGN PATENT DOCUMENTS

| | | |
|---|---|---|
| WO | 2009042187 A1 | 4/2009 |
| WO | 2014120024 A1 | 8/2014 |
| WO | 2016159889 A1 | 10/2016 |

OTHER PUBLICATIONS

Extended European Search Report for European Patent Application No. 22175907.9 dated Sep. 14, 2022 (8 pages).

* cited by examiner

MULTI-MODE RESPIRATORY THERAPY APPARATUS, SYSTEM, AND METHOD

The present application is a continuation of U.S. application Ser. No. 16/952,166, filed Nov. 19, 2020, now U.S. Pat. No. 11,633,559, which claims the benefit, under 35 U.S.C. § 119 (e), to U.S. Provisional Patent Application No. 62/951,079, filed Dec. 20, 2019, each of which is hereby incorporated by reference herein in its entirety.

BACKGROUND

The present disclosure relates to respiratory therapy apparatuses, systems and methods, and particularly to a multi-mode respiratory therapy apparatus operable to deliver multiple types of respiratory therapies to a patient. More particularly, the present disclosure relates to a multi-mode respiratory therapy apparatus, system and method having various components that selectively attach to a base module and having a multitude of user interface screens for selecting and controlling the available respiratory therapies.

Respiratory therapy apparatuses for applying various respiratory therapies to patients are known. For example, Hill-Rom Company, Inc. markets THE VITALCOUGH® SYSTEM which is operable to provide mechanical insufflation/exsufflation (MIE) therapy to patients. Hill-Rom Company, Inc. also markets THE METANEB® SYSTEM which is operable to provide therapy for the mobilization of secretions, for lung expansion therapy, and for the treatment and prevention of pulmonary atelectasis. THE METANEB® SYSTEM is operable in a continuous high frequency oscillation (CHFO) mode and a continuous positive expiratory pressure (CPEP) mode. THE METANEB® SYSTEM also has a nebulizer that is operable to introduce aerosolized medication into the airway of a patient. THE METANEB® SYSTEM is powered pneumatically by pressurized gas, such as 50 pounds per square inch (psi) oxygen, available from gas outlets in various rooms of a healthcare facility.

Caregivers such as respiratory therapists would appreciate a single respiratory therapy apparatus that is operable to provide to patients multiple respiratory therapies such as MIE, CHFO, and CPEP therapies. Such a combined respiratory therapy apparatus having a nebulizer would also be desirable. However, it is also desirable that such a combined respiratory therapy apparatus should be lightweight, compact, and have a user interface that is intuitive and easy to use. Wireless communication with various external devices and various types of networks using multiple types of wireless communication technologies would also represent an improvement over existing respiratory therapy devices.

SUMMARY

An apparatus, system, or method may comprise one or more of the features recited in the appended claims and/or the following features which, alone or in any combination, may comprise patentable subject matter:

According to a first aspect of the present disclosure, a respiratory therapy apparatus may include a housing that may have a bottom wall and a pneumatic system that may be carried by the housing. The pneumatic system may include a first pressure source, at least one valve, and control circuitry. The respiratory therapy apparatus may also have a pneumatic patient circuit and an outlet port that may be carried by the housing. The pneumatic system may be configured to deliver respiratory therapy to a patient via the outlet port and the pneumatic patient circuit. A nebulizer may be coupled to the pneumatic patient circuit. A nebulizer tray may be selectively couplable to a bottom of the housing so as to underlie at least a majority of the bottom wall. A second pressure source may be carried by the nebulizer tray and may be operable to provide pressurized air to the nebulizer.

In some embodiments of the first aspect, the first pressure source may include a blower and the second pressure source may include a pump. Optionally, the bottom wall of the housing may have an opening through which an electrical cable may be routed from the control circuitry to the second pressure source. The control circuitry, therefore, may be configured to turn the second pressure source on and off in response to user inputs.

The respiratory therapy apparatus of the first aspect may further include a graphical user interface (GUI) that may be carried by the housing and that may be coupled to the control circuitry. The GUI may be operable to display at least one icon that may be selectable by a user to turn the second pressure source on and off. For example, the at least one icon may include a nebulizer icon that may be pressed successively to turn the second pressure source on and off. If desired, the nebulizer icon may be color coded to indicate whether the second pressure source is on or off.

Optionally, a temperature signal from a temperature sensor that may be located inside an interior region of the housing above the bottom wall may be used by the control circuitry to turn the second pressure source off in response to the temperature signal indicating that a threshold temperature may have been reached or exceeded. Further optionally, the temperature signal from the temperature sensor may also be used by the control circuitry to turn the first pressure source off in response to the temperature signal indicating that the threshold temperature may have been reached or exceeded.

In some embodiments of the first aspect, the second pressure source may be operable regardless of whether the pneumatic system is being operated to deliver respiratory therapy to the patient. In the absence of respiratory therapy being delivered to the patient by the pneumatic system, the first pressure source may be operated to deliver a minimum threshold positive pressure to the outlet port when the second pressure source is operated to provide pressurized air to the nebulizer. For example, the minimum threshold of positive pressure may be about 5 centimeters of water (cmH2O).

If desired, the pneumatic patient circuit may include a hose and a patient interface. The hose may be coupled to the outlet port and the nebulizer may be coupled to the patient interface. The respiratory therapy apparatus of the first aspect may further include a nebulizer port that may be coupled to the tray and a tube may extend from the nebulizer port to the nebulizer. Optionally, the hose may have a first outer diameter, the tube may have a second outer diameter, and the first outer diameter may be larger than the second outer diameter. Further optionally, the hose may include a corrugated hose having corrugations and the tube may be devoid of corrugations.

In some embodiments, the pneumatic patient circuit further may include a filter housing that may have a first end that may be configured to couple to the outlet port and a second end that may be configured to attach to a first terminal end of the hose. A pneumatic passage may extend between the first end and the second end of the filter housing.

Optionally, the filter housing further may include a first antenna that may surround the pneumatic passage and a transponder chip that may be electrically coupled to the antenna. If desired, the pneumatic circuit further may include a filter that may be carried by the filter housing. The first antenna and the transponder chip may be situated between the filter and the second end of the filter housing such that filter may be situated between the first end and the antenna and transponder chip. Optionally, the outlet port may have an outlet passage therethrough and the respiratory therapy apparatus of the first aspect further may include a second antenna that may surround the outlet passage.

The second antenna may be operable to emit energy to the first antenna to power the transponder chip. The control circuitry may read data from the transponder chip that may be transmitted from the first antenna to the second antenna. The data may include a total number of prior uses of the filter housing during prior sessions of respiratory therapy, for example. If desired, the control circuitry may be configured to write new data to the transponder chip. Thus, the new data may be transmitted from the second antenna to the first antenna. The new data may include a new total number of uses of the filter housing which may include incrementing by one the total number of prior uses of the filter housing.

According to a second aspect of the present disclosure, a respiratory therapy apparatus may include a housing that may have a bottom wall and a pneumatic system that may be carried by the housing. The pneumatic system may include a first pressure source, at least one valve, and control circuitry. The respiratory therapy apparatus of the second aspect may also include a pneumatic patient circuit and an outlet port that may be carried by the housing. The pneumatic system may be configured to deliver respiratory therapy to a patient via the outlet port and the pneumatic patient circuit. The respiratory therapy apparatus of the second aspect may further include a nebulizer that may be coupled to the pneumatic patient circuit and a nebulizer tray that may be selectively couplable to a bottom of the housing. A second pressure source may be carried by the nebulizer tray and may be operable to provide pressurized air to the nebulizer. A temperature sensor may be located inside an interior region of the housing above the bottom wall. The temperature sensor may provide a temperature signal to the control circuitry. The control circuitry may be configured to turn the second pressure source off in response to the temperature signal indicating that a threshold temperature may have been reached or exceeded.

In some embodiments of the second aspect, the temperature signal from the temperature sensor may also be used by the control circuitry to turn the first pressure source off in response to the temperature signal indicating that the threshold temperature may have been reached or exceeded. Optionally, the first pressure source may include a blower and the second pressure source may include a pump. Further optionally, the bottom wall of the housing may have an opening through which an electrical cable may be routed from the control circuitry to the second pressure source. The control circuitry may be configured to turn the second pressure source on and off in response to user inputs.

If desired, the respiratory therapy apparatus of the second aspect may further include a graphical user interface (GUI) that may be carried by the housing and that may be coupled to the control circuitry. The GUI may be operable to display at least one icon that may be selectable by a user to turn the second pressure source on and off. The at least one icon may include a nebulizer icon that may be pressed successively to turn the second pressure source on and off. Optionally, the nebulizer icon may be color coded to indicate whether the second pressure source is on or off.

It is contemplated by the present disclosure that the temperature sensor may include a thermistor. It is also contemplated by the present disclosure that the second pressure source may be operable regardless of whether the pneumatic system is being operated to deliver respiratory therapy to the patient. In the absence of respiratory therapy being delivered to the patient by the pneumatic system, the first pressure source may be operated to deliver a minimum threshold positive pressure to the outlet port when the second pressure source is operated to provide pressurized air to the nebulizer. For example, the minimum threshold of positive pressure may be about 5 centimeters of water (cmH2O).

In some embodiments of the respiratory therapy apparatus of the second aspect, the pneumatic patient circuit may include a hose and a patient interface. The hose may be coupled to the outlet port and the nebulizer may be coupled to the patient interface. A nebulizer port may be coupled to the tray and a tube may extend from the nebulizer port to the nebulizer. Optionally, the hose may have a first outer diameter, the tube may have a second outer diameter, and the first outer diameter may be larger than the second outer diameter. Further optionally, the hose may include a corrugated hose that may have corrugations and the tube may be devoid of corrugations.

If desired, the pneumatic patient circuit further may include a filter housing that may have a first end that may be configured to couple to the outlet port and a second end that may be configured to attach to a first terminal end of the hose. A pneumatic passage may extend between the first end and the second end of the filter housing. Optionally, the filter housing further may include a first antenna that may surround the pneumatic passage and a transponder chip that may be electrically coupled to the antenna. Further optionally, the pneumatic circuit further may include a filter that may be carried by the filter housing. The first antenna and transponder chip may be situated between the filter and the second end of the filter housing.

It is contemplated by the present disclosure that the outlet port may have an outlet passage therethrough. The respiratory therapy apparatus of the second aspect further may include a second antenna surrounding the outlet passage. The second antenna may be operable to emit energy to the first antenna to power the transponder chip. If desired, the control circuitry may read data from the transponder chip that may be transmitted from the first antenna to the second antenna. For example, the data may include a total number of prior uses of the filter housing during prior sessions of respiratory therapy. Optionally, the control circuitry may be configured to write new data to the transponder chip. Thus, the new data may be transmitted from the second antenna to the first antenna. The new data may include a new total number of uses of the filter housing which may include incrementing by one the total number of prior uses of the filter housing, for example.

According to third aspect of the present disclosure, a method of converting a respiratory therapy apparatus from a first configuration to a second configuration may include providing a respiratory therapy apparatus of a first configuration. The respiratory therapy apparatus of the first configuration may have a housing and a pneumatic system that may be carried by the housing. The pneumatic system may include a first pressure source, at least one valve, and control circuitry. The respiratory therapy apparatus of the first configuration may include a pneumatic patient circuit and an outlet port that may be carried by the housing. The pneumatic system may be configured to deliver respiratory therapy to a patient via the outlet port and the patient circuit. For example, the respiratory therapy apparatus of the first configuration may be operable to provide a plurality of respiratory therapies to the patient. The method of the third aspect also may include providing a nebulizer, coupling the nebulizer to the patient circuit, providing a nebulizer tray that may carry a second pressure source, and coupling the nebulizer tray to a bottom of the housing so as to underlie at least a majority of a bottom wall of the housing. The method of the third aspect further may include pneumatically coupling the second pressure source that may be carried by the nebulizer tray to the nebulizer so that operation of the second pressure may provide pressurized air to the nebulizer. The respiratory therapy apparatus of the second configuration may be formed by the coupling of the nebulizer tray that may carry the second pressure source to the housing. The respiratory therapy apparatus of the second configuration may be operable to provide nebulization to the patient along with at least one respiratory therapy of the plurality of respiratory therapies.

In some embodiments of the third aspect, the first pressure source may include a blower and the second pressure source may include a pump. Optionally, the method of the third aspect further may include routing an electrical cable between the control circuitry and the second pressure source by passing the electrical cable through an opening in the bottom wall. The method of the third aspect also include removing a cover from blocking the opening prior to passing the electrical cable through the opening.

If desired, the pneumatic system of the third aspect further may include a graphical user interface (GUI) that may be carried by the housing and that may be coupled to the control circuitry. The GUI may be operable to display at least one icon that may be selectable by a user to turn the second pressure source on and off. Optionally, the method of the third aspect further may include displaying the at least one icon on the GUI in response to the electrical cable electrically interconnecting the control circuitry and the second pressure source. Further optionally, the at least one icon may include a nebulizer icon that is pressed successively to turn the second pressure source on and off. Still further optionally, the nebulizer icon may be color coded to indicate whether the second pressure source is on or off.

In some embodiments, the method of the third aspect further may include providing a temperature sensor that may be located inside an interior region of the housing above the bottom wall and may also include using the control circuitry to turn the second pressure source off in response to a temperature signal from the temperature sensor indicating that a threshold temperature may have been reached or exceeded. The method further may include using the control circuitry to turn the first pressure source off in response to the temperature signal indicating that the threshold temperature may have been reached or exceeded.

Optionally, the method of the third aspect further may include operating the second pressure source regardless of whether the pneumatic system is being operated to deliver respiratory therapy to the patient. In the absence of respiratory therapy being delivered to the patient by the pneumatic system, the method may also include operating the first pressure source to deliver a minimum threshold positive pressure to the outlet port when the second pressure source is operated to provide pressurized air to the nebulizer. For example, the minimum threshold of positive pressure may be about 5 centimeters of water (cmH2O).

It is contemplated by the present disclosure that the pneumatic patient circuit of the third aspect may include a hose and a patient interface. The hose may be coupled to the outlet port and the nebulizer may be coupled to the patient interface. The method of the third aspect further may include coupling a tube to a nebulizer port of the tray and to the nebulizer. If desired, the pneumatic patient circuit further may include a filter housing having a first end that may be configured to couple to the outlet port and a second end that may be configured to attach to a first terminal end of the hose. A pneumatic passage may extend between the first end and the second end of the filter housing.

Optionally, the filter housing further may include a first antenna that may surround the pneumatic passage and a transponder chip that may be electrically coupled to the antenna. Further optionally, the pneumatic patient circuit may include a filter that may be carried by the filter housing. The first antenna and transponder chip may be situated between the filter and the second end of the filter housing. In some embodiments of the third aspect, the outlet port may have an outlet passage therethrough and a second antenna may surround the outlet passage. The method of the third aspect further may include using the second antenna to emit energy to the first antenna to power the transponder chip.

If desired, the method of the third aspect further may include using the control circuitry to read data from the transponder chip that is transmitted from the first antenna to the second antenna. For example, the data may include a total number of prior uses of the filter housing during prior sessions of respiratory therapy. The method the third aspect further may include using the control circuitry to write new data to the transponder chip. The new data may be transmitted from the second antenna to the first antenna. The new data may include a new total number of uses of the filter housing which may include incrementing by one the total number of prior uses of the filter housing.

According to a fourth aspect of the present disclosure, a filter apparatus for use in a respiratory therapy device may include a filter housing that may have a first end, a second end that may be spaced from the first end, and a pneumatic passage that may extend between the first end and the second end. An antenna may surround the pneumatic passage. A transponder chip electrically may be coupled to the antenna.

In some embodiments, the filter apparatus further may include a filter that may be carried by the filter housing. The antenna and the transponder chip may be situated between the filter and the second end of the filter housing. Optionally, the filter may have a first substantially circular outer periphery of a first diameter and the antenna may have a second substantially circular periphery of a second diameter. The first diameter may be larger than the second diameter. In such embodiments, the antenna may be configured as a substantially flat annular ring and may be substantially parallel with the filter.

Optionally, the antenna of the filter apparatus of the fourth aspect may be configured as a substantially flat annular ring. Further optionally, the antenna may be sandwiched between a face material and a substrate. If desired, at least one of the face material and the substrate may include a polyethylene terephthalate (PET) material. For example, both of the face material and the substrate may include PET material. Alternatively or additionally, the face material and the substrate both may be configured as substantially flat annular rings.

The filter apparatus of the fourth aspect further may include an adhesive layer on the substrate and backing paper that may be attached to the adhesive layer such that the adhesive layer may be situated between the backing paper and the substrate. Optionally, the backing paper may include a silicon liner. Further optionally, the backing paper may include siliconized paper. If desired, the antenna may be made of copper.

In some embodiments of the fourth aspect, the filter housing may include a substantially cylindrical first tubular portion that may include the first end, a substantially cylindrical second tubular portion that may include a second end, a first substantially frustoconical portion that may extend from the first tubular portion, and a second substantially frustoconical portion that may extend from the second tubular portion. The first and second substantially frustoconical portions may meet at a joint that may define an annular apex of the filter housing. Optionally, a shoulder wall portion may be formed on the second substantially frustoconical portion and the antenna may be mounted to the shoulder wall portion.

If desired, the first and second tubular portions may be aligned along an axis of the pneumatic passage. The shoulder wall portion may include a shoulder surface that may surround the axis and that may be substantially perpendicular to the axis of the pneumatic passage. The antenna may be mounted to the shoulder surface. Optionally, the antenna may be formed as a substantially flat annular ring that may mount to the shoulder surface.

The filter apparatus of the fourth aspect further may include a filter that may be carried by the filter housing. For example, the filter may be formed as a substantially circular disk that may be substantially parallel with the antenna and the shoulder surface. Optionally, the filter being may be formed as a substantially circular disk that may have an outer periphery that may be adjacent the annular apex of the joint. Further optionally, the transponder chip and the antenna may cooperate to send and receive wireless communications within a frequency range between about 12 Mega Hertz (MHz) and about 14 MHz. For example, the transponder chip and antenna may cooperate to send and receive wireless communications at about 13.56 MHz.

According to a fifth aspect of the present disclosure, a respiratory therapy apparatus may include a housing that may have a hose port that may extend from a front wall of the housing and that may define a pneumatic passage through the front wall. A tag reader may be located in the housing and may have a first antenna that may be situated adjacent an inner surface of the front wall and that may surround the hose port. A filter housing may be sized to couple to the hose port. The filter housing may have a filter receiving space that may be positioned between a filter inlet and a filter outlet. A filter passage may extend though the filter housing between the filter inlet and the filter outlet. A filter may be located in the filter receiving space. A second antenna may be coupled to the filter housing and may surround the filter passage. An identification (ID) chip may be carried by the filter housing and may be coupled to the second antenna. The tag reader may be configured to read the ID chip via wireless signals between the first antenna and the second antenna to confirm the filter housing may be an authorized filter housing for use with the respiratory therapy apparatus.

In some embodiments of the fifth aspect, the ID chip may be a radio frequency (RF) ID chip and the wireless signals may include RF signals that may be communicated between the first antenna and the second antenna. If desired, the respiratory therapy apparatus of the fifth aspect further may include control circuitry that may be located in the housing and that may be electronically coupled to the tag reader. The control circuitry may be configured to command operation of a pressure source that may be located in the housing. The RF signals may include data regarding a prior number of uses of the filter. The control circuitry may disable operation of the pressure source if the prior number of uses of the filter exceeds a threshold number of uses.

Optionally, the control circuitry may be configured to command the tag reader to write new data to the RF ID tag. The new data may be transmitted from the second antenna to the first antenna, for example. The new data may include a new total number of uses of the filter which may comprise incrementing by one the number of prior uses of the filter. Further optionally, the respiratory therapy apparatus of the fifth aspect further may include a display and the prior number of uses of the filter may be shown on the display in response to the filter housing being coupled to the hose port. If the prior number of uses of the filter exceeds the threshold number of uses a notification may be provided on the display. If desired, the notification may indicate that the filter needs to be replaced. Alternatively or additionally, the notification may include an icon that may be shown on the display. The respiratory therapy apparatus of the fifth aspect further may include an alarm and the alarm may be triggered if the prior number of uses of the filter exceeds the threshold number of uses.

In some embodiments of the fifth aspect, the tag reader may be configured to use the first antenna to emit energy to the second antenna to power the ID tag. Optionally, the filter may have a first substantially circular outer periphery of a first diameter, the second antenna may have a second substantially circular periphery of a second diameter, and the first diameter may be larger than the second diameter. Further optionally, the antenna may be configured as a substantially flat annular ring and may be substantially parallel with the filter.

If desired, the antenna which may be configured as a substantially flat annular ring, may be sandwiched between a face material and a substrate. Optionally, either or both of the face material and the substrate may include a polyethylene terephthalate (PET) material. Further optionally, the face material and the substrate may both be configured as substantially flat annular rings. The respiratory therapy apparatus of the fifth aspect further may include an adhesive layer that may be on the substrate and may also include backing paper that may be attached to the adhesive layer such that the adhesive layer may be situated between the backing paper and the substrate. The backing paper may include a silicon liner or a siliconized paper, for example. Optionally, the second antenna may be made of copper.

In some embodiments of the fifth aspect, the filter housing may include a substantially cylindrical first tubular portion that may include the filter inlet, a substantially cylindrical second tubular portion that may include the filter outlet, a first substantially frustoconical portion that may extend from the first tubular portion, and a second substantially frustoconical portion that may extend from the second tubular portion. The first and second substantially frustoconical portions may meet at a joint that may define an annular apex of the filter housing. A shoulder wall portion may be formed on the second substantially frustoconical portion and the second antenna may be mounted to the shoulder wall portion.

Optionally, the first and second tubular portions may be aligned along an axis of the filter passage. The shoulder wall portion may include a shoulder surface that may surround the axis and that may be substantially perpendicular to the axis of the filter passage. In such embodiments of the fifth aspect, the second antenna may be mounted to the shoulder surface. For example, the second antenna may be formed as a substantially flat annular ring that may mount to the shoulder surface. If desired, the filter may include a substantially circular disk that may be substantially parallel with the second antenna and the shoulder surface. The filter may include a substantially circular disk that may have an outer periphery that may be adjacent the annular apex of the joint. In some embodiments of the fifth aspect, the ID chip and the second antenna may cooperate to send and receive wireless communications within a frequency range between about 12 Mega Hertz (MHz) and about 14 MHz.

According to a sixth aspect of the present disclosure, a method for determining when a filter unit of a respiratory therapy apparatus may need to be replaced may be provided. The method may include coupling a filter unit to a hose port of a housing of a respiratory therapy apparatus. The filter unit may have a transponder chip and a first antenna that may be coupled to the transponder chip and that may surround a flow path through the filter unit. The method also may include reading data from the transponder chip with a tag reader that may be coupled to a second antenna that may be positioned in proximity to the hose port. The second antenna may surround a flow passage through the hose port. The data may include a prior number of uses of the filter. The method further may include comparing the prior number of uses of the filter with a threshold number using control circuitry of the respiratory therapy apparatus that may be coupled to the tag reader. The method further may include disabling a pressure source of the respiratory therapy apparatus if the prior number of uses equals or exceeds the threshold number.

In some embodiments of the sixth aspect, reading data from the transponder chip may include communicating radio frequency (RF) signals between the first antenna and the second antenna. Optionally, the method of the sixth aspect may include enabling the pressure source for operation if the prior number of uses is less than the threshold number. Further optionally, the method of the sixth aspect further may include using the tag reader to write new data to the transponder chip. The new data may be transmitted from the second antenna to the first antenna. The new data may include a new total number of uses of the filter unit which may comprise incrementing by one the number of uses of the filter unit.

If desired, the method of the sixth aspect further may include showing on a display of the respiratory therapy apparatus the prior number of uses of the filter unit in response to the filter unit being coupled to the hose port. Optionally, the method of the sixth aspect may include showing a notification on the display if the prior number of uses of the filter unit exceeds the threshold number of uses. For example, the notification may indicate that the filter unit needs to be replaced. Alternatively or additionally, the notification may include an icon shown on the display. Further optionally, the method of the sixth aspect further may include triggering an alarm if the prior number of uses equals or exceeds the threshold number. Still further optionally, reading the transponder chip may include emitting energy from the second antenna to the first antenna to power the transponder chip.

According to a seventh aspect of the present disclosure, a respiratory therapy apparatus may include a housing that may have a back wall and a pneumatic system that may be carried by the housing. The pneumatic system may include a first pressure source, at least one valve, and control circuitry. An outlet port may be carried by the housing. A pneumatic patient circuit may include a hose and a patient interface that may be coupled to hose. The patient interface may be configured to communicate pneumatically with an airway of a patient. The pneumatic system may be configured to deliver respiratory therapy to the patient via the outlet port and the pneumatic patient circuit. The respiratory therapy apparatus may also have a plate for supporting the hose. The plate may be movable between a deployed position in which a portion of the plate may extend above a top wall of the housing so that a hose receiving notch of the plate may be situated above a top wall of the housing and a storage position in which the plate may be situated behind the back wall of the housing. The hose may be receivable in the hose receiving notch when the plate is in the deployed position.

In some embodiments of the seventh aspect, a front surface of the plate may confront a portion of a battery cover or a battery that may be received in a battery receiving compartment of the housing when the plate is in the storage position. Optionally, a first stop may extend from a back wall of the housing and the plate may be configured to contact the first stop when the plate is in the deployed position. Further optionally, a second stop may extend from the back wall of the housing and the plate may be configured to contact the second stop when the plate is in the storage position. If desired, at least one of the first and second stops may be molded integrally with the back wall of the housing.

It is contemplated by the present disclosure that the plate may rotate about an axis when moving between the deployed position and the storage position. For example, the axis may be substantially perpendicular to the back wall of the housing. Optionally, the outlet port may be substantially cylindrical about a port axis and the axis of the plate may be substantially parallel with the port axis. Further optionally, the housing may have spaced apart first and second sidewalls and the axis may be situated closer to the first sidewall than to the second sidewall.

If desired, the respiratory therapy apparatus of the seventh aspect further may include a first filter. The back wall may have an air inlet filter receiving space that may be configured to receive the first filter therein. Optionally, the air inlet filter receiving space may be situated below the plate when the plate is in the storage position. Further optionally, the respiratory therapy apparatus of the seventh aspect further may include a nebulizer tray that may be selectively attachable to a bottom of the housing and that may be configured to support the housing thereabove. A second pressure source may be carried by the nebulizer tray. The respiratory therapy apparatus of the seventh aspect also may have a second filter. The nebulizer tray may have a nebulizer filter receiving space that may be configured to receive the second filter therein. The nebulizer filter receiving space may be situated below the plate when the plate is in the storage position.

In some embodiments of the seventh aspect, the first filter may be shaped as a first rectangular prism that may have a first long dimension that may be oriented generally vertically when the first filter is received in the air inlet filter receiving space. If desired, the second filter may be shaped as a second rectangular prism that may have a second long dimension that may be oriented substantially horizontally when the second filter is received in the nebulizer filter receiving space. Optionally, the first filter may occupy a larger volume than the second filter. Further optionally, the first and second filters each may include a foam material. If desired, the hose receiving notch may include a substantially V-shaped notch that may have a rounded surface at a lower end of the hose receiving notch when the plate is in the deployed position.

According to an eighth aspect of the present disclosure, a respiratory therapy apparatus may include a housing that may have a top wall that may include a first top wall portion that may be formed to include a recess and a second top wall portion that may be selectively receivable in the recess. A pneumatic system may be carried by the housing. The pneumatic system may include a first pressure source, at least one valve, and control circuitry. The control circuitry may include a controller that may include a processor and a memory. An outlet port may be carried by the housing. A pneumatic patient circuit may be configured to communicate pneumatically with an airway of a patient. The pneumatic system may be configured to deliver respiratory therapy to the patient via the outlet port and the pneumatic patient circuit. The control circuitry may include a firmware upgrade port that may be accessible in the recess of the first top wall portion when the second top wall portion is removed from the recess.

In some embodiments of the eighth aspect, a handle receiving space may be formed between an outer edge of the second top wall portion and a recess that may define an edge of the first top wall portion that may defines the recess. The respiratory therapy apparatus of the eighth aspect further may include a handle that may be received in the handle receiving space when the handle is situated in a storage position. The handle may be movable to a position in which the handle may extend upwardly from the handle receiving recess when the handle is situated in a use position. If desired, the handle may be coupled to the top wall for pivoting movement between the storage position and the use position. Optionally, the handle may be U-shaped.

It is contemplated by the present disclosure that the second top wall portion may have a finger receiving depression that may be sized to receive one or more of a user's fingers to facilitate movement of the handle from the storage position to the use position. Alternatively or additionally, the first top wall portion may have a finger receiving depression that may be sized to receive one or more of a user's fingers to facilitate movement of the handle from the storage position to the use position.

The respiratory therapy apparatus of the eighth aspect further may include at least one fastener that may be configured to removably couple the second top wall portion to the first top wall portion. For example, the at least one fastener may include a plurality of screws. If desired, the top wall of the housing may be inclined at an angle from a front of the housing to a back of the housing when the housing is resting on a horizontal surface.

In some embodiments of the eighth aspect, the control circuitry may include a graphical user interface (GUI) that may have user inputs that may be configured for controlling firmware updates to the control circuitry via the firmware upgrade port. Optionally, the firmware upgrade port may include a universal serial bus (USB) port and the firmware updates may be provided on a USB drive that may couple to the USB port. Further optionally, the control circuitry may include a foot pedal port that may be accessible on an exterior of the housing for coupling of a foot pedal that may be configured to turn the first pressure source on and off. If desired, the control circuitry may be configurable for wireless communication with a bar code scanner. Alternatively or additionally, the control circuitry may be configurable for wireless communication with a pulse oximeter.

According to a ninth aspect of the present disclosure, a respiratory therapy apparatus may include a housing and a pneumatic system that may be carried by the housing. The pneumatic system may include a first pressure source, at least one valve, and control circuitry. The control circuitry may include a controller that may include a processor and a memory. An outlet port may be carried by the housing. A pneumatic patient circuit may be configured to communicate pneumatically with an airway of a patient. The pneumatic system may be configured to deliver respiratory therapy to the patient via the outlet port and the pneumatic patient circuit. At least one sensor may be coupled to the control circuitry and may be configured to sense at least one of inhalation and exhalation of the patient. The control circuitry may include a graphical user interface (GUI). The controller may command the GUI to display a first caution message in response to the patient's inhalation or exhalation being sensed to have exceeded a predetermined time threshold.

In some embodiments of the ninth aspect, the predetermined time period may be about ten seconds. Optionally, the respiratory therapy apparatus of the ninth aspect further may include a ventilation fan that may be carried by the housing and that may be coupled to the control circuitry. In such embodiments of the ninth aspect, the controller may be configured to command the GUI to display a second caution message in response to a ventilation fan fault condition being detected.

If desired, the respiratory therapy apparatus of the ninth aspect further may include a rechargeable battery that may be carried by the housing and that may be coupled to the control circuitry. In such embodiments of the ninth aspect, the controller may be configured to command the GUI to display a second caution message in response to an electrical charge of the rechargeable battery being below 10% of a full charge or being below 20% of a full charge. Optionally, a foot switch may be coupled to a port on the housing and may be coupled to the control circuitry. The foot switch may be usable to turn the first pressure source on and off. In such embodiments, the controller may be configured to command the GUI to display a second caution message in response to a foot switch fault condition being detected.

It is contemplated by the present disclosure that the respiratory therapy apparatus of the ninth aspect further may include a stepper motor that may be carried by the housing and that may be coupled to the control circuitry. The stepper motor may be operated to control a position of the at least one valve. In such embodiments, the controller may be configured to command the GUI to display a second caution message in response to a stepper motor fault condition being detected. Optionally, the at least one sensor may include a pressure sensor and the controller may be configured to command the GUI to display a second caution message in response to the pressure sensor sensing that an excessive pressure or an inadequate pressure condition has been detected.

In some embodiments of the ninth aspect, the respiratory therapy apparatus may further include a temperature sensor that may be carried by the housing and that may be coupled to the control circuitry. In such embodiments, the controller may be configured to command the GUI to display a second caution message in response to an over-heating condition being detected by the temperature sensor. For example, the over-heating condition may pertain to one or more of the following: air outlet temperature adjacent the outlet port, temperature of the first pressure source, temperature of a stepper motor that may be operable to move the at least one valve, or temperature of a battery that may be carried by the housing.

Optionally, the respiratory therapy apparatus of the ninth aspect further includes a rechargeable battery that may be carried by the housing and that may be coupled to the control circuitry. In such embodiments, the controller may be configured to command the GUI to display a second caution message in response to a battery recharging fault condition being detected. Further optionally, the control circuitry may be configured for wireless communication and the controller may be configured to command the GUI to display a second caution message in response to a wireless communication fault condition being detected.

If desired, the patient circuit of the ninth aspect may include a filter unit that may be configured to couple to the outlet port. Optionally, the filter unit may include a transponder chip and the controller may be configured to command the GUI to display a second caution message in response to a reader of the control circuitry being unable to detect the transponder chip of the filter unit. Further optionally, the control circuitry may include a reader that may be configured to read wireless signals from a transponder chip of the patient circuit and of other patient circuits. In such embodiments, the controller may be configured to command the GUI to display a second caution message in response to the reader detecting multiple transponder chips.

It is contemplated by the present disclosure that the control circuitry of the ninth aspect may include a reader and the patient circuit may include a filter unit that may be configured to couple to the outlet port. Optionally, the filter unit may include a transponder chip and the controller may be configured to command the GUI to display a second caution message in response to the reader reading data from the transponder chip of the filter unit that indicates a total number of uses of the filter unit has equaled or exceed a threshold number of uses. If desired, the at least one sensor may be operable to detect air leakage that may be occurring from the patient circuit. In such embodiments, the controller may be configured to command the GUI to display a second caution message in response to excessive air leakage being detected.

Optionally, the respiratory therapy apparatus of the ninth aspect further may include a temperature sensor that may be carried by the housing and that may be coupled to the control circuitry. In such embodiments, the controller may be configured to command the GUI to display a second caution message in response to a below operational temperature condition being detected by the temperature sensor. If desired, the below operation temperature condition may pertain to one or more of the following: air outlet temperature adjacent the outlet port, temperature of the first pressure source, temperature of a stepper motor that may be operable to move the at least one valve, or temperature of a battery that may be carried by the housing.

In some embodiments of the respiratory therapy apparatus of the ninth aspect, the control circuitry may include a real-time clock (RTC) battery and the controller may be configured to command the GUI to display a second caution message in response to a charge of the RTC battery being depleted or below a threshold charge amount. If desired, the control circuitry may include first and second portions that may form a controller area network (CAN) and the controller may be configured to command the GUI to display a second caution message in response to a loss of a CAN heartbeat message between the first and second portions of the control circuitry.

It is contemplated by the present disclosure that the first pressure source of the ninth aspect may include a speed sensor and the controller may be configured to command the GUI to display a second caution message in response to a first pressure source fault condition being detected by the speed sensor. Optionally, the controller may be configured to command the GUI to display a second caution message in response to a sensor fault condition of the at least one sensor being detected. The at least one sensor of the ninth aspect may include a pressure sensor or a flow sensor or both. Further optionally, the controller may be configured to command the GUI to display a second caution message in response to a memory fault condition of the memory being detected.

In some embodiments, the respiratory therapy apparatus of the ninth aspect further may include a nebulizer that may be configured to couple to the patient circuit and a second pressure source that may be removably coupleable to the housing. The second pressure source may be operable to provide pressurized air to the nebulizer. In such embodiments, the controller may be configured to command the GUI to display a second caution message in response to a nebulizer fault condition being detected in connection with the second pressure source.

Optionally, the control circuitry of the ninth aspect may include a tone generator and the controller may be configured to command the tone generator to beep one time if an activity is successful. Further optionally, the controller may be configured to command the tone generator to beep three times in connection with the first caution message or another caution message being displayed on the GUI. Still further optionally, the controller may be configured to command the tone generator to beep three times every minute in connection with attention being needed for the respiratory therapy apparatus along with on-screen instructions being shown on the GUI.

It is contemplated by the present disclosure that the controller of the ninth aspect may be configured to command the tone generator to beep three times, followed by beeping two times after a pause, repeating in connection with a critical fault occurring that prevents operation of the respiratory therapy apparatus. Optionally, the control circuitry may be configured for wireless communication with a wireless network and the controller may be configured to command the tone generator to beep five times in connection with the wireless communication with the wireless network being lost. Alternatively or additionally, the controller may be configured to command the tone generator to sound a continuous tone in response to the patient circuit becoming disconnected from the outlet port or in response to an unexpected pressure loss.

According to a tenth aspect of the present disclosure, a respiratory therapy apparatus may include a housing and a pneumatic system that may be carried by the housing. The pneumatic system may include a first pressure source, at least one valve, and control circuitry. The control circuitry may include a controller including a processor and a memory. An outlet port may be carried by the housing. A pneumatic patient circuit may be configured to communicate pneumatically with an airway of a patient. The pneumatic system may be configured to deliver a plurality of respiratory therapies to the patient via the outlet port and the pneumatic patient circuit. The control circuitry may include a graphical user interface (GUI). The controller may command the GUI to display a plurality of navigable screens that may be usable to control features and functions of the respiratory therapy apparatus. A first group of screens of the plurality of navigable screens may be usable to establish wireless communication between the control circuitry and a scanner, such as a bar code scanner, which may be operable to scan identification (ID) codes, such as identification (ID) bar codes of a patient and a respiratory therapist for storage in the memory of the control circuitry. A second group of screens of the plurality of navigable screens may be usable to select a first set of operating parameters for a first respiratory therapy. A third group of screens of the plurality of navigable screens may be usable to select a second set of operating parameters for a second respiratory therapy. A fourth group of screens of the plurality of navigable screens may be usable to establish wireless communication between the control circuitry and a patient monitor that may be operable to sense a physiological parameter of the patient.

In some embodiments, the first group of screens may include a bar code scanner connecting screen that may appear on the GUI in response to selection on the GUI of any of a selected respiratory therapy from among the plurality of respiratory therapies. The bar code scanner connecting screen may indicate that the control circuitry may be attempting to connect wirelessly with the bar code scanner. If desired, the first group of screens may include a device connect error screen that may appear on the GUI if no connection with the bar code scanner occurs within a threshold period of time. The threshold period of time may be about fifteen seconds, for example.

Optionally, the first group of screens may include a scan patient screen that may appear on the GUI in response to the control circuitry establishing wireless communications with the bar code scanner. The scan patient screen may include a message instructing a user to scan the ID bar code of the patient. Further optionally, the first group of screens may include a scan therapist screen that may appear on the GUI in response to the bar code identifying the patient being scanned. The scan therapist screen may include a message instructing the user to scan the ID bar code of the respiratory therapist. If desired, the scan therapist screen may include a first text box that may show a first alphanumeric code corresponding to the ID bar code of the patient and a second text box which may be blank until the ID bar code of the respiratory therapist is scanned with the bar code reader.

It is contemplated by the present disclosure that the first group of screens may include a review and confirm screen that may appears on the GUI after the ID bar code of the respiratory therapist is scanned such that a second alphanumeric code corresponding to the ID bar code of the respiratory therapy may be shown in the second text box. Furthermore, the first group of screens may include a scanning error screen that may appear on the GUI in response to the first alphanumeric code matching the second alphanumeric code due to inadvertent duplicate bar code scanning of the ID bar code of the patient or the ID bar code of the respiratory therapist. After the ID bar code of the patient and the ID bar code of the respiratory therapist have been successfully scanned, a confirm button may be activated on the review and confirm screen and selection of the confirm button may result in the GUI displaying a main therapy screen of the selected respiratory therapy.

In some embodiments of the respiratory therapy apparatus of the tenth aspect, the first respiratory may include an automatic mode of mechanical insufflation/exsufflation (MIE) therapy and the second group of screens may includes at least one parameter input screen that may have inputs for setting the following: a first positive pressure value of a first positive pressure to be applied to the patient during insufflation, a first duration of time during which the first positive pressure is to be applied to the patient, a first negative pressure value of a first negative pressure to be applied to the patient during exsufflation, a second duration of time during which the first negative pressure is to be applied to the patient, a second positive pressure value of a second positive pressure to be applied to the patient during a positive airway pressure (PAP) portion of the automatic mode of MIE therapy, and a third duration of time during which the second positive pressure is to be applied to the patient.

Optionally, the at least one parameter input screen of the second group of screens may include oscillation inputs for setting an amplitude and frequency of pressure oscillations to be superimposed on one or more of the first positive pressure, the first negative pressure, and the second positive pressure during occurrence of the automatic mode of MIE therapy. Further optionally, the at least one parameter input screen of the second group of screens may include a breathing synchrony screen that may include at least one input used to enable and disable a breathing synchrony function of the respiratory therapy apparatus. If desired, the breathing synchrony screen may include at least one sensitivity input to select whether breathing synchrony function operates according to low, medium, or high sensitivity.

It is contemplated by the present disclosure that the breathing synchrony function may include sensing an inspiration of the patient and, in response, starting the insufflation of the automatic mode of MIE therapy. Optionally, the breathing synchrony screen may include sigh control inputs that may include a first sigh control input for enabling and disabling a sigh function at the end of the automatic mode of MIE therapy, a second sigh control input for setting a third positive pressure to apply to the patient during the sigh function at the end of the automatic mode of MIE therapy, and a third sigh control input for setting a fourth duration of time during which the third positive pressure is applied to the patient.

In some embodiments, the second group of screens of the tenth aspect may include a main automatic MIE therapy screen that may be shown on the GUI in response to selection of a settings complete icon on the at least one parameter input screen of the second group of screens. If desired, the main automatic MIE therapy screen may include a graph that may show the selected first positive pressure value, the first duration of time, the first negative pressure value, the second duration of time, the second positive pressure value, and the third duration of time. Prior to the start of the automatic mode of MIE therapy, the main automatic MIE therapy screen may include a flow input that may be selectable to set an air flow rate of the pneumatic system at high, medium, or low levels.

Optionally, the main automatic MIE therapy screen may include a therapy progress indicator that may move along the graph during the automatic mode of MIE therapy, a digital manometer that may have icons that may indicate an insufflation peak positive pressure set point, an exsufflation peak negative pressure set point, and a PAP peak positive pressure set point. Further optionally, the main automatic MIE therapy screen may show heart rate and pulse oximetry data of the patient if a pulse oximeter is communicating with the control circuitry during occurrence of the automatic mode of MIE therapy. Alternatively or additionally, the main automatic MIE therapy screen may show peak cough flow ($P_{CF}$) data and tidal volume ($V_t$) data for the patient if available from the control circuitry during occurrence of the automatic mode of MIE therapy.

It is contemplated by the present disclosure that the main automatic MIE therapy screen may show a graphical start button that may be selected to start the automatic mode of MIE therapy and a graphical stop button that may be selected to stop the automatic mode of MIE therapy. Optionally, the graphical stop button may be inactive until after the graphical start button is selected to start the automatic mode of MIE therapy. Further optionally, the graphical start button may be converted to a graphical pause button after the graphical start button has been selected and the automatic mode of MIE therapy is occurring.

In some embodiments of the tenth aspect, in response to selection of the graphical start button, the control circuitry may wirelessly query a transponder chip of a filter unit of the patient circuit to determine whether a number of prior uses of the filter unit may be less than a threshold number of uses. In such embodiments, the automatic mode of MIE therapy may be prevented from occurring by the control circuitry if the number of prior uses exceeds or is equal to the threshold number of uses and a notification message is provided on the GUI. Optionally, in response to selection of the graphical start button, the control circuitry may check a battery charge status if the respiratory therapy apparatus is operating under battery power. If the battery charge status is less than or equal to a threshold amount, the automatic mode of MIE therapy may be prevented from occurring by the control circuitry. For example, the threshold amount may be 10% or 20% of a full charge of the battery.

If desired, the graph of the main automatic MIE therapy screen may show one cycle of insufflation, exsufflation, and the PAP portion of the automatic mode of MIE therapy and the main automatic MIE therapy screen may show a total number of cycles to be completed during the automatic mode of MIE therapy. The graph also optionally may show how many cycles have been completed at any given time during the occurrence of the automatic mode of MIE therapy.

In some embodiments of the tenth aspect, after completion of the automatic mode of MIE therapy, an automatic MIE therapy session complete screen may appear on the GUI. The automatic MIE therapy session complete screen may include a first set of data that may include a first pressure value that may indicate average positive pressure applied to the patient during insufflation, a second pressure value that may indicate average negative pressure applied to the patient during exsufflation, a third pressure value that may indicate average pressure applied to the patient during the PAP portion of the automatic mode of MIE therapy, a total number of uses of a filter unit of the patient circuit, whether a sigh mode at the end of the automatic mode of MIE therapy was on or off, the date that the automatic mode of MIE therapy occurred, a start time and a finish time of the automatic mode of MIE therapy, a total time of the automatic mode of MIE therapy, a total number of cycles of the automatic mode of MIE therapy, a peak cough flow ($P_{CF}$) that occurred during the automatic mode of MIE therapy, and average tidal volume detected during the automatic mode of MIE therapy. Optionally, the control circuitry of the tenth aspect may wirelessly send the first set of data for storage in a remote computer if a wireless communication function of the control circuitry is enabled and the control circuitry is successfully communicating wirelessly with a wireless access point.

It is contemplated by the present disclosure that the second respiratory therapy may include a manual mode of mechanical insufflation/exsufflation (MIE) therapy and the third group of screens may include a main manual MIE therapy screen that may include inputs for adjusting one or more of the following: a third positive pressure value of a third positive pressure to be applied to the patient during insufflation, a second negative pressure value of a second negative pressure to be applied to the patient during exsufflation, and a fourth positive pressure value of a fourth positive pressure to be applied to the patient during a positive airway pressure (PAP) portion of the manual mode of MIE therapy. Optionally, the main manual MIE therapy screen may include a flutter button and the third group of screens may include an oscillation input screen that may appear on the GUI in response to selection of the flutter button. The oscillation input screen may include oscillation inputs for setting an amplitude and frequency of pressure oscillations to be superimposed on one or more of the third positive pressure, the second negative pressure, and the fourth positive pressure during occurrence of the manual mode of MIE therapy.

Optionally, the main manual MIE screen may include an inhale icon that may be touched and held to implement insufflation of the patient during the manual mode of MIE therapy and an exhale icon that may be touched and held to implement exsufflation of the patient during the manual mode of MIE therapy. Further optionally, the PAP portion of the manual mode of MIE therapy may be implemented during the manual mode of MIE therapy if neither of the inhale icon or exhale icon is being pressed and held. If desired, the inputs for adjusting may include up and down arrow icons that may be adjacent to each of the third positive pressure value, second negative pressure value, and fourth positive pressure value.

In some embodiments of the tenth aspect, prior to the start of the manual mode of MIE therapy, the main manual MIE therapy screen may include a flow input that may be selectable to set an air flow rate of the pneumatic system at high, medium, or low levels. Optionally, the main manual MIE therapy screen may show heart rate and pulse oximetry data of the patient if a pulse oximeter is communicating with the control circuitry during occurrence of the manual mode of MIE therapy. Alternatively or additionally, the main manual MIE therapy screen may show peak cough flow ($P_{CF}$) data and tidal volume ($V_t$) data for the patient if available from the control circuitry during occurrence of the manual mode of MIE therapy.

If desired, the main manual MIE therapy screen may show a graphical start button that may be selected to start the manual mode of MIE therapy and, after selection of the graphical start button, the graphical start button may be converted to a graphical stop button that may be selected to stop the manual mode of MIE therapy. Optionally, in response to selection of the graphical start button, the control circuitry may wirelessly query a transponder chip of a filter unit of the patient circuit to determine whether a number of prior uses of the filter unit is less than a threshold number of uses. Further optionally, the manual mode of MIE therapy may be prevented from occurring by the control circuitry if the number of prior uses exceeds or is equal to the threshold number of uses and a notification message is provided on the GUI.

In some embodiments of the tenth aspect, in response to selection of the graphical start button, the control circuitry may check a battery charge status if the respiratory therapy apparatus is operating under battery power. If the battery charge status is less than or equal to a threshold amount, the manual mode of MIE therapy may be prevented from occurring by the control circuitry. The threshold amount may be 10% or 20% of a full charge of the battery, for example. If desired, the main manual MIE therapy screen may show a first number of counts of insufflation that have occurred during the manual mode of MIE therapy, a first total time that insufflation has occurred during the manual mode of MIE therapy, a second number of counts of exsufflation that have occurred during the manual mode of MIE therapy, a second total time that exsufflation has occurred during the manual mode of MIE therapy, and an overall total time that the manual mode of MIE therapy has occurred.

Optionally, after completion of the manual mode of MIE therapy, a manual MIE therapy session complete screen may appear on the GUI. The manual MIE therapy session complete screen may include a first set of data including a first pressure value indicating average positive pressure applied to the patient during insufflation, a second pressure value indicating average negative pressure applied to the patient during exsufflation, a third pressure value indicating average pressure applied to the patient during the PAP portion of the manual mode of MIE therapy, a total number of uses of a filter unit of the patient circuit, the date that the automatic mode of MIE therapy occurred, a start time and a finish time of the manual mode of MIE therapy, a total time of the manual mode of MIE therapy, a total number of cycles of the manual mode of MIE therapy, a peak cough flow ($P_{CF}$) that occurred during the manual mode of MIE therapy, and average tidal volume detected during the manual mode of MIE therapy. If desired, the control circuitry may wirelessly send the first set of data for storage in a remote computer if a wireless communication function of the control circuitry is enabled and the control circuitry is successfully communicating wirelessly with a wireless access point.

In some embodiments of the respiratory therapy apparatus of the tenth aspect, the first respiratory therapy may include an automatic mode of oscillatory lung expansion (OLE) therapy and the second group of screens may include at least one parameter input screen having inputs for setting the following: a first positive pressure value of a first positive pressure to be applied to the patient during a continuous positive expiratory pressure (CPEP) therapy portion of the automatic mode of OLE therapy, whether a nebulizer coupled to the patient circuitry is to be on or off during the CPEP therapy portion, a first duration of time during which the first positive pressure is to be applied to the patient, a second positive pressure value of a second positive pressure to be applied to the patient during a continuous high frequency oscillation (CHFO) therapy portion of the automatic mode of OLE therapy, whether the nebulizer is to be on or off during the CHFO therapy portion, a second duration of time during which the second positive pressure is to be applied to the patient, and whether a frequency of oscillations to be superimposed on the second positive pressure during the CHFO therapy portion is to be at high, medium, or low levels, and a third duration of time during which the nebulizer is to be turned on without the CPEP therapy portion and without the CHFO therapy portion occurring.

Optionally, the at least one parameter input screen of the second group of screens may include a cough pause screen that may include at least one input that may be used to enable and disable a cough pause function of the respiratory therapy apparatus. If desired, the cough pause screen may include a first input to select a cough pause interval between which the cough pause function is to occur during the automatic mode of OLE therapy and a second input to select a cough pause duration during which the cough pause function occurs when the cough pause function is activated.

It is contemplated by the present disclosure that the second group of screens may include a main automatic OLE therapy screen that may be shown on the GUI in response to selection of a settings complete icon on the at least one parameter input screen of the second group of screens. Optionally, the main automatic OLE therapy screen may include a graph that may show the selected first positive pressure value, the first duration of time, the second positive pressure value, the second duration of time, and the third duration of time. Further optionally, the main automatic OLE therapy screen may include a therapy progress indicator that may move along the graph during the automatic mode of OLE therapy, a digital manometer that may have a first icon that may indicate a peak positive pressure set point, and a second icon that may indicate a current positive pressure being applied to the patient during the automatic mode of OLE therapy.

If desired, the main automatic OLE therapy screen may show heart rate and pulse oximetry data of the patient if a pulse oximeter is communicating with the control circuitry during occurrence of the automatic mode of OLE therapy. Alternatively or additionally, the main automatic OLE therapy screen may show peak cough flow ($P_{CF}$) data and tidal volume ($V_t$) data for the patient if available from the control circuitry during occurrence of the automatic mode of OLE therapy. Further alternatively or additionally, the main automatic OLE therapy screen may show a graphical start button that may be selected to start the automatic mode of OLE therapy and a graphical stop button that may be selected to stop the automatic mode of OLE therapy.

In some embodiments of the tenth aspect, the graphical stop button may be inactive until after the graphical start button is selected to start the automatic mode of OLE therapy. If desired, the graphical start button may be converted to a graphical pause button after the graphical start button has been selected and the automatic mode of OLE therapy may be occurring. Optionally, in response to selection of the graphical start button the control circuitry may wirelessly query a transponder chip of a filter unit of the patient circuit to determine whether a number of prior uses of the filter unit is less than a threshold number of uses. Further optionally, the automatic mode of OLE therapy may be prevented from occurring by the control circuitry if the number of prior uses exceeds or is equal to the threshold number of uses and a notification message is provided on the GUI.

In response to selection of the graphical start button in some embodiments of the respiratory therapy apparatus of the tenth aspect, the control circuitry may check a battery charge status if the respiratory therapy apparatus is operating under battery power. In such embodiments, if the battery charge status is less than or equal to a threshold amount, the automatic mode of OLE therapy may be prevented from occurring by the control circuitry. For example, the threshold amount may be 10% or 20% of a full charge of the battery.

If desired, the graph of the main automatic OLE therapy screen may show a total number of stages that are to occur during the automatic mode of OLE therapy. For example, each stage may correspond to one of the CPEP portions, one of the CHFO portions, or one of the portions in which the nebulizer is turned on without either of the CPEP or CHFO portions occurring. Alternatively or additionally, the graph of the main automatic OLE therapy screen may show how many stages have been completed at any given time during the occurrence of the automatic mode of OLE therapy.

In some embodiments of the respiratory therapy apparatus of the tenth aspect, after completion of the automatic mode of OLE therapy, an automatic OLE therapy session complete screen may appear on the GUI. The automatic OLE therapy session complete screen may include a first set of data that may include a first pressure value that may indicate average positive peak pressure that may be applied to the patient during the CHFO portion of the automatic mode of OLE therapy, a second pressure value that may indicate average positive peak pressure that may be applied to the patient during the CPEP portion of the automatic mode of OLE therapy, a total nebulizer time during which the nebulizer was turned on, a total number of uses of a filter unit of the patient circuit, a cough pause interval and duration, the date that the automatic mode of OLE therapy occurred, a start time and a finish time of the automatic mode of OLE therapy, a total time of the automatic mode of OLE therapy, and a total number of stages of the automatic mode of OLE therapy. If desired, the control circuitry may wirelessly send the first set of data for storage in a remote computer if a wireless communication function of the control circuitry is enabled and the control circuitry is successfully communicating wirelessly with a wireless access point.

The present disclosure contemplates that the second respiratory therapy of the tenth aspect may include a manual mode of oscillatory lung expansion (OLE) therapy and the third group of screens may include a main manual OLE therapy screen that may include inputs for adjusting one or more of the following: a third positive pressure value of a third positive pressure to be applied to the patient during the CPEP therapy portion of the manual mode of OLE therapy, a fourth positive pressure value of a fourth positive pressure to be applied to the patient during the CHFO therapy portion of the manual mode of OLE therapy, whether a nebulizer coupled to the patient circuit is to be on or off during the CPEP therapy portion or the CHFO therapy portion, and whether a frequency of oscillations to be superimposed on the fourth positive pressure during the CHFO therapy portion of the manual mode of OLE therapy is to be at high, medium, or low levels.

Optionally, the main manual OLE therapy screen may include a first flutter button that may correspond to one of the high, medium, or low levels of oscillations. Further optionally, pressing and holding the first flutter button for a first threshold period of time may result in second and third flutter buttons corresponding to the other two of the high, medium, or low levels of oscillations appearing on the main manual OLE therapy screen. Still further optionally, pressing and holding a selected one of the first, second or third flutter buttons for a second threshold period of time may result in selection of the corresponding high, medium, or low levels of oscillations for the CHFO therapy portion of the manual mode of OLE therapy.

In some embodiments of the respiratory therapy apparatus of the tenth aspect, the main manual OLE screen may include a CPEP icon that may be touched and held to implement the CPEP therapy portion of the manual mode of OLE therapy and a CHFO icon that may be touched and held to implement the CHFO therapy portion of the manual mode of OLE therapy. It is contemplated by the present disclosure that medication may be provided to the patient from the nebulizer of the tenth aspect if the nebulizer is turned on regardless of whether the CPEP icon is touched and held, the CHFO icon is touched and held, or neither of the CPEP icon and CHFO icon is touched and held. Optionally, the inputs for adjusting include up and down arrow icons adjacent to each of the third positive pressure value and fourth positive pressure value. If desired, the main manual OLE therapy screen may show heart rate and pulse oximetry data of the patient if a pulse oximeter is communicating with the control circuitry during occurrence of the manual mode of OLE therapy.

Optionally, the main manual OLE therapy screen may show a graphical start button that may be selected to start the manual mode of OLE therapy and wherein, after selection of the graphical start button, the graphical start button may be converted to a graphical stop button that may be selected to stop the manual mode of OLE therapy. Alternatively or additionally, in response to selection of the graphical start button, the control circuitry may wirelessly query a transponder chip of a filter unit of the patient circuit to determine whether a number of prior uses of the filter unit is less than a threshold number of uses. Further alternatively or additionally, the manual mode of OLE therapy may be prevented from occurring by the control circuitry if the number of prior uses exceeds or is equal to the threshold number of uses and a notification message is provided on the GUI.

In some embodiments of the respiratory therapy apparatus of the tenth aspect, in response to selection of the graphical start button, the control circuitry may check a battery charge status if the respiratory therapy apparatus is operating under battery power. In such embodiments, if the battery charge status is less than or equal to a threshold amount, the manual mode of OLE therapy may be prevented from occurring by the control circuitry. For example, the threshold amount may be 10% or 20% of a full charge of the battery.

The present disclosure contemplates that the main manual OLE therapy screen of the tenth aspect may show a first number of counts of stages of the CPEP therapy portion that may have occurred during the manual mode of OLE therapy, a first total time that the CPEP therapy portion may have occurred during the manual mode of OLE therapy, a second number of counts of stages of the CHFO therapy portion that may have occurred during the manual mode of OLE therapy, a second total time that the CHFO therapy portion may have occurred during the manual mode of OLE therapy, and an overall total time that the manual mode of OLE therapy may have occurred.

If desired, after completion of the manual mode of OLE therapy, a manual OLE therapy session complete screen may appear on the GUI. The manual OLE therapy session complete screen may include a first set of data that may include a first pressure value that may indicate average positive peak pressure that may be applied to the patient during the CHFO portion of the manual mode of OLE therapy, a second pressure value that may indicate average positive peak pressure that may be applied to the patient during the CPEP portion of the manual mode of OLE therapy, a total nebulizer time during which the nebulizer was turned on, a total number of uses of a filter unit of the patient circuit, a cough pause interval and duration, the date that the manual mode of OLE therapy occurred, a start time and a finish time of the manual mode of OLE therapy, a total time of the manual mode of OLE therapy, and a total number of stages of the manual mode of OLE therapy. Optionally, the control circuitry may wirelessly send the first set of data for storage in a remote computer if a wireless communication function of the control circuitry is enabled and the control circuitry is successfully communicating wirelessly with a wireless access point.

In some embodiments of the respiratory therapy apparatus of the tenth aspect, wherein the first respiratory therapy may include a mechanical insufflation/exsufflation (MIE) therapy and the second respiratory therapy may include an oscillatory lung expansion (OLE) therapy. Each of the MIE therapy and the OLE therapy may have a manual mode of operation and an automatic mode of operation. Optionally, the patient monitor may include a pulse oximeter. Further optionally, data from the pulse oximeter may be received by the control circuitry and wherein, based on the data, an SpO2 value and a heart rate of the patient may be shown on the GUI during therapy.

It is contemplated by the present disclosure that the pneumatic patient circuit of the tenth aspect may include a filter unit that may be configured to couple to the outlet port. The filter unit may include a transponder chip and antenna that may be configured to communicate wirelessly with the control circuitry. If desired, the control circuitry may command the GUI to display a caution message in response to data from the transponder chip of the filter unit indicating that a total number of uses of the filter unit may have equaled or exceed a threshold number of uses. Optionally, the filter unit of the tenth aspect may include a filter unit housing having a pneumatic flow passage therethrough and the antenna may be attached to the filter unit housing and may surround the pneumatic flow passage.

Optionally, the respiratory therapy apparatus of the tenth aspect further may include a nebulizer that may be coupled to the pneumatic patient circuit. The nebulizer tray selectively may be couplable to a bottom of the housing so as to underlie a bottom wall of the housing, for example. A second pressure source may be carried by the nebulizer tray and may be operable to provide pressurized air to the nebulizer. If desired, the controller may command the GUI to display at least one input to turn the second pressure source on or off after the second pressure source is electrically coupled to the control circuitry of the pneumatic system.

In some embodiments, the respiratory therapy apparatus of the tenth aspect further may include a foot switch that may be electrically coupleable to the control circuitry and that may be operable to control the first respiratory therapy or the second respiratory therapy or both. If desired, the controller may command the GUI to display a foot switch icon in response to the foot switch being electrically coupled to the control circuitry. The foot switch icon may indicate a status of use of the foot switch, for example.

Optionally, a settings screen of the plurality of navigable screens may appear on the GUI in response to a settings button of a main menu being selected. The settings screen may include information that may pertain to one or more of the following: model number of the respiratory therapy apparatus, serial number of the respiratory therapy apparatus, software version of the control circuitry, bootloader version of the control circuitry, Federal Communications Commission (FCC) identification (ID) number, radio frequency (RF) identification (ID) firmware version, Bluetooth firmware version, total therapy run time, total nebulization time, WiFi MAC address, WiFi firmware version, or LTE firmware version.

In some embodiments of the respiratory therapy apparatus of the tenth aspect, a date-time screen of the plurality of navigable screens may appear on the GUI in response to selection of a date-time tab that may appear on the GUI in response to a device button being selected on the settings screen. If desired, the date-time screen may include inputs that may permit a user to set the following: a date and time, a time format, whether daylight savings time is on or off, and a time zone. Alternatively or additionally, a language screen of the plurality of navigable screens may appear on the GUI in response to selection of a language tab that may appear on the GUI in response to selection of a device button on the settings screen. Further alternatively or additionally, the language screen may include a menu of language inputs that may permit a user to set the language that appears on the plurality of navigable screens.

If desired, a controls screen of the plurality of navigable screens may appear on the GUI in response to selection of a controls tab that may appear on the GUI in response to a device button being selected on the settings screen. The controls screen may include inputs permitting a user to set the following: screen brightness, whether wireless communication with the bar code scanner is on or off, and whether wireless communication with the patient monitor is on or off. Optionally, a data screen of the plurality of navigable screens may appear on the GUI in response to a data button being selected on the settings screen. The data screen may include inputs permitting a user to review and export a therapy log, review and export an error log, import and export device settings, upgrade firmware, and import health level seven (HL7) information.

The present disclosure contemplates that an insufficient memory message may be displayed on the GUI in response to an attempt to export the therapy log or error log to a recipient device that has insufficient memory as determined by the control circuitry in response to communicating with the recipient device to verify available memory. Alternatively or additionally, an insufficient memory message may be displayed on the GUI in response to an attempt to import the therapy log or the error log to the control circuitry from an originating device if a portion of the memory of the control circuitry allocated for the therapy log or the error log, respectively, does not have sufficient memory space.

Optionally, the GUI of the tenth aspect may display a dynamic progress icon to indicate progress toward exporting the therapy log or the error log to a recipient device. For example, the progress icon may include a numerical percentage representing an amount toward export completion and a circle having a portion of its periphery filled in by an amount that may match the numerical percentage. Further optionally, the GUI of the tenth aspect may display a dynamic progress icon to indicate progress toward importing the therapy log or the error log to the control circuitry from an originating device. For example, the progress icon may include a numerical percentage representing an amount toward import completion and a circle having a portion of its periphery filled in by an amount that may match the numerical percentage.

In some embodiments of the respiratory therapy apparatus of the tenth aspect, the GUI may display a dynamic progress icon to indicate progress toward exporting the device settings to a recipient device. If desired, the progress icon may include a numerical percentage representing an amount toward export completion and a circle having a portion of its periphery filled in by an amount that may match the numerical percentage. Alternatively or additionally, the GUI may display a dynamic progress icon to indicate progress toward importing the device settings from an originating device. For example, the progress icon may include a numerical percentage representing an amount toward import completion and a circle having a portion of its periphery filled in by an amount that may match the numerical percentage.

If desired, the GUI may display a dynamic progress icon to indicate progress toward downloading upgraded firmware to the control circuitry from an originating device. Like the scenarios mentioned above, the progress icon may include a numerical percentage representing an amount toward download completion of the upgraded firmware and a circle having a portion of its periphery filled in by an amount that may match the numerical percentage. Alternatively or additionally, the GUI of the tenth aspect may display a dynamic progress icon to indicate progress toward importing the HL7 information from an originating device. Again, the progress icon may include a numerical percentage representing an amount toward import completion and a circle having a portion of its periphery filled in by an amount that may match the numerical percentage.

It is contemplated by the present disclosure that, for the respiratory therapy apparatus of the tenth aspect, the recipient device may include a USB memory stick that may be coupled to a USB port of the control circuitry. Alternatively or additionally, the originating device may include a USB memory stick coupled to a USB port of the control circuitry. Further alternatively or additionally, a wireless connection screen of the plurality of navigable screens of the ninth aspect may appear on the GUI in response to a connect button being selected on the settings screen. The connect screen may include inputs that may permit a user to control whether Bluetooth or WiFi wireless communications or both, are enabled or disabled for the control circuitry.

Optionally, the wireless connection screen may include a Bluetooth tab and a WiFi tab. Selection of the Bluetooth tab may result in a first slider button appearing on the GUI for turning Bluetooth wireless communication functionality of the control circuitry on and off. Similarly, selection of the WiFi tab may result in a second slider button appearing on the GUI for turning WiFi wireless communication functionality of the control circuitry on and off. Thus, in response to the first slider button being moved to an on position, the control circuitry may initiate Bluetooth communication with external devices that may have Bluetooth communication functionality. In such situations, the GUI may list device information for any of the external devices with which successful Bluetooth communication is established. For example, the external devices may include the bar code scanner or the patient monitor or both. If desired, selection of an external device from the list of device information on the GUI may result in additional information about the external device appearing on the GUI.

In some embodiments of the ninth aspect, in response to the first slider button being moved to an on position, a scan button may appear on the GUI. In response to the scan button being selected, the control circuitry may scan for external devices that may have Bluetooth communication functionality. In such situations, the GUI may list device ID's of the external devices with which Bluetooth communication is possible. If desired, selection of a particular one of the device ID's from the list of device ID's may result in a pair new device screen appearing on the GUI. The pair new device screen may include a proceed button that may be selectable to initiate a Bluetooth pairing operation between the control circuitry and the external device corresponding to the particular one of the device ID's.

Optionally, in response to the first slider button being moved to an on position, a manual setup button may appears on the GUI and in response to the manual setup button being selected, the GUI may display a field in which a device ID of an external device with which the control circuitry is to establish Bluetooth communication may be enterable. Further optionally, the device ID may include a MAC address of the external device with which the control circuitry is to establish Bluetooth communication. Alternatively of additionally, in response to the second slider button being moved to an on position, a scan available screen may appear on the GUI. The scan available screen may have a scan button and in response to the scan button being selected, the control circuitry may scan for wireless access points (WAP's) having WiFi communication functionality and the GUI may list WAP ID's of the WAP's with which WiFi communication is possible.

If desired, selection of a particular one of the WAP ID's from the list of WAP ID's may result in an enterprise setup screen appearing on the GUI. The enterprise setup screen may include setup fields in which an Extensible Authentication Protocol (EAP) method may be enterable, in which a Microsoft Challenge Handshake Authentication Protocol (MSCHAP) method may be enterable, in which a user ID may be enterable, and in which a password may be enterable. After the setup fields are populated, the enterprise setup screen may include a proceed button that may be selectable to authenticate WiFi communication between the WAP corresponding to the particular one of the WAP ID's and the control circuitry.

In some embodiments of the respiratory therapy apparatus of the tenth aspect, an indicia of authentication success may be shown on the GUI adjacent to the particular one of the WAP ID's if authentication is successful between the WAP corresponding to the particular one of the WAP ID's and the control circuitry. Furthermore, an unable to connect screen may be shown on the GUI if authentication between the WAP corresponding to the particular one of the WAP ID's and the control circuitry is unsuccessful. If desired, the unable to connect screen may include a message pertaining to the unsuccessful authentication. Also if desired, a status tab may appear on the GUI if authentication is successful between the WAP corresponding to the particular one of the WAP ID's and the control circuitry. The status tab may be selectable to display information pertaining to one or more of the following: service set ID (SSID) name, security type, MAC address, IP address, subnet mask, and gateway.

Optionally, in response to the second slider button being moved to an on position, a settings tab may appear on the GUI and, in response to the settings tab being selected, a network window and a server window may appear on the GUI. The network window may have a third slider button that may be usable to select between having a static IP address assigned to the control circuitry and having an IP address assigned to the control circuitry based on a Dynamic Host Configuration Protocol (DHCP). Further optionally, the server window may have a fourth slider button that may be usable to select between a first server and a second server for receipt of messages from the control circuitry.

The present disclosure contemplates that, if the third slider button of the tenth aspect is in a static slider position to select having the static IP address assigned, then fields may appear in the network window for entry of one or more of the following: the IP address of the control circuitry, a gateway IP address of a gateway, a subnet IP address of a subnet, and a digital multiplexed system (DMS) IP address of a DMS. The present disclosure also contemplates that, for each position of the fourth slider button of the tenth aspect, fields may appear in the server window for entry of one or more of the following for the first server or the second server depending upon the position of the fourth slider button: a server IP address of a server, a port ID of a server port, and a network time protocol (NTP) IP address.

In some embodiments of the respiratory therapy apparatus of the tenth aspect, the server window may include a test connection button that may be selectable to test whether the control circuitry may be successfully connected with each of the network, the first server, and the second server. If desired, after the test connection button is selected, the GUI may display a message that may indicate whether connections between the control circuitry and each of the network, the first server, and the second server is successful or unsuccessful, respectively.

Optionally, a wireless connection screen of the plurality of navigable screens of the tenth aspect may appear on the GUI in response to a connect button being selected on the settings screen. The wireless connection screen may include an input permitting a user to control whether Long Term Evolution (LTE) communication is enabled or disabled for the control circuitry. If desired, in response to the input being configured in an on position, the control circuitry may operate to search for an LTE carrier, and if an LTE carrier is found, the GUI may display carrier information. For example, the carrier information may include one or more of the following: carrier name, international mobile equipment identity (IMEI), and subscriber identity module (SIM) card ID. The present disclosure contemplates that, if the LTE carrier is found, the GUI may display a test connection button that may be selectable to test whether the control circuitry is successfully connected with an LTE network of the LTE carrier. After the test connection button is selected, the GUI may display a message indicating whether a connection between the LTE network and the control circuitry is successful or unsuccessful.

In some embodiments of the respiratory therapy apparatus of the tenth aspect, selection of a help icon on the GUI in connection with any of the screens of the second group of screens or the third group of screens may result in a select category for help screen appearing on the GUI. The select category for help screen may include a menu of category buttons that may correspond to categories for which help may be available. Optionally, the menu of category buttons may include one or more of the following: an automatic therapy button, a manual therapy button, a therapy overview button, a therapy options button, and a modify therapy button. Further optionally, selection of one of the menu of category buttons may result in an annotated screen with textual explanations of screen features of a corresponding screen being displayed on the GUI.

If desired, the plurality of navigable screens may include a pressure ceiling screen that may be usable to set a pressure ceiling which may be a maximum therapy pressure boundary above which the pneumatic system may be prevented from operating. In some embodiments, the pneumatic system may be operable to produce a baseline pressure and pressure oscillations that may be above and below the baseline pressure. Peaks of the pressure oscillations may be compared to the pressure ceiling to prevent the pneumatic system from operating such that the peaks exceed the pressure ceiling. Alternatively or additionally, the plurality of navigable screens may include an auto lock screen that may be usable to choose between having an advanced settings function locked or unlocked after each power cycle of the respiratory therapy apparatus.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which:

FIG. 18 is a screen shot of a main therapy selection screen having a selectable mechanical insufflation/exsufflation (MIE) button or icon and a selectable oscillatory lung expansion (OLE) button or icon;

FIG. 37 is a screen shot of a first example of an automatic MIE therapy complete screen that appears on the GUI at the end of the automatic MIE therapy session, the first example of the MIE therapy complete screen showing a variety of statistical data and other information pertaining to the automatic MIE therapy that has just been completed including indicating that the sigh function at the end of the automatic MIE therapy was turned on;

Figure 18:
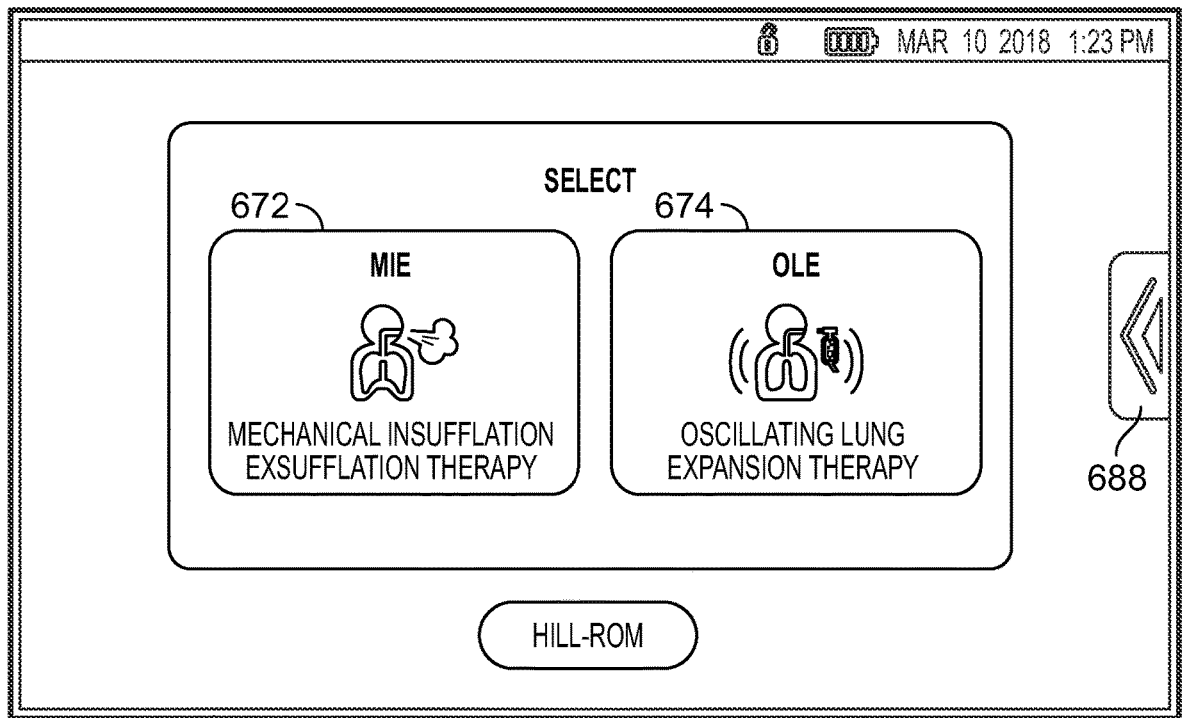
FIGS. 18-274 are examples of screen shots of a plurality of navigable control screens that appear on the GUI of the respiratory therapy apparatus and that are usable to control features and functions of the respiratory therapy apparatus of the present disclosure.
Figure 19:
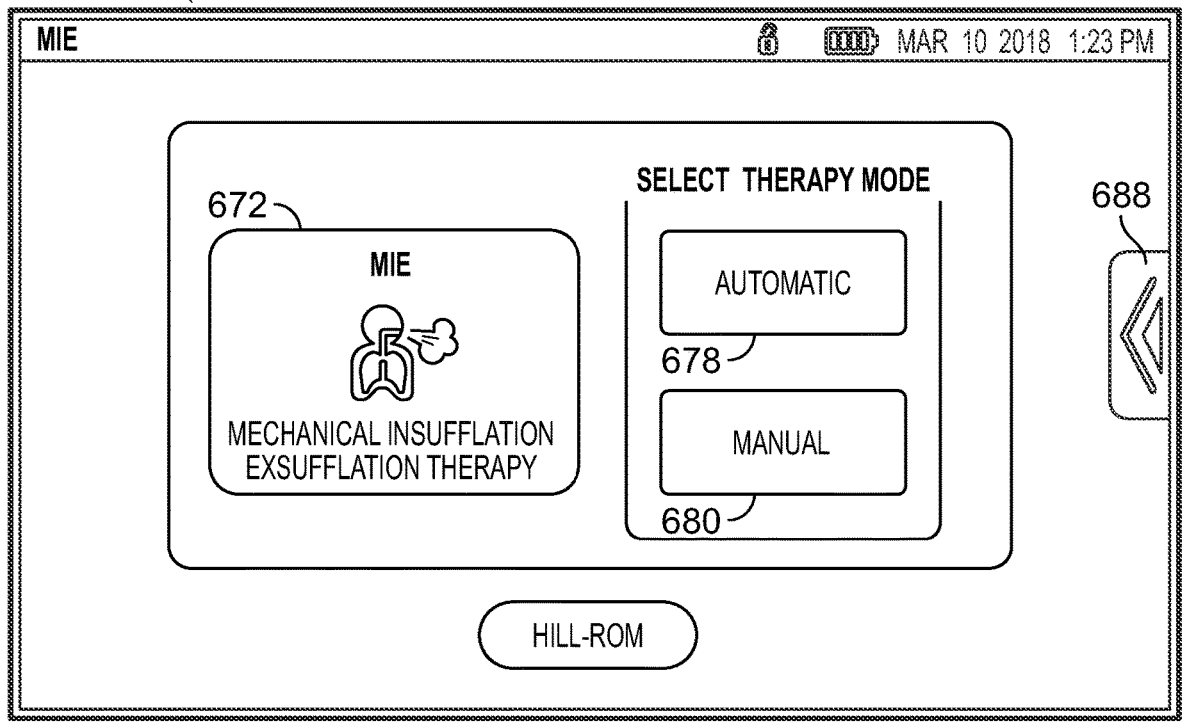
FIG. 19 is a screen shot of a main MIE therapy selection screen that appears on the GUI in response to the MIE icon being selected on the main therapy selection screen of FIG. 18, the main MIE therapy selection screen having a selectable automatic button and a selectable manual button for selecting automatic and manual modes of MIE therapy, respectively.
Figure 20:
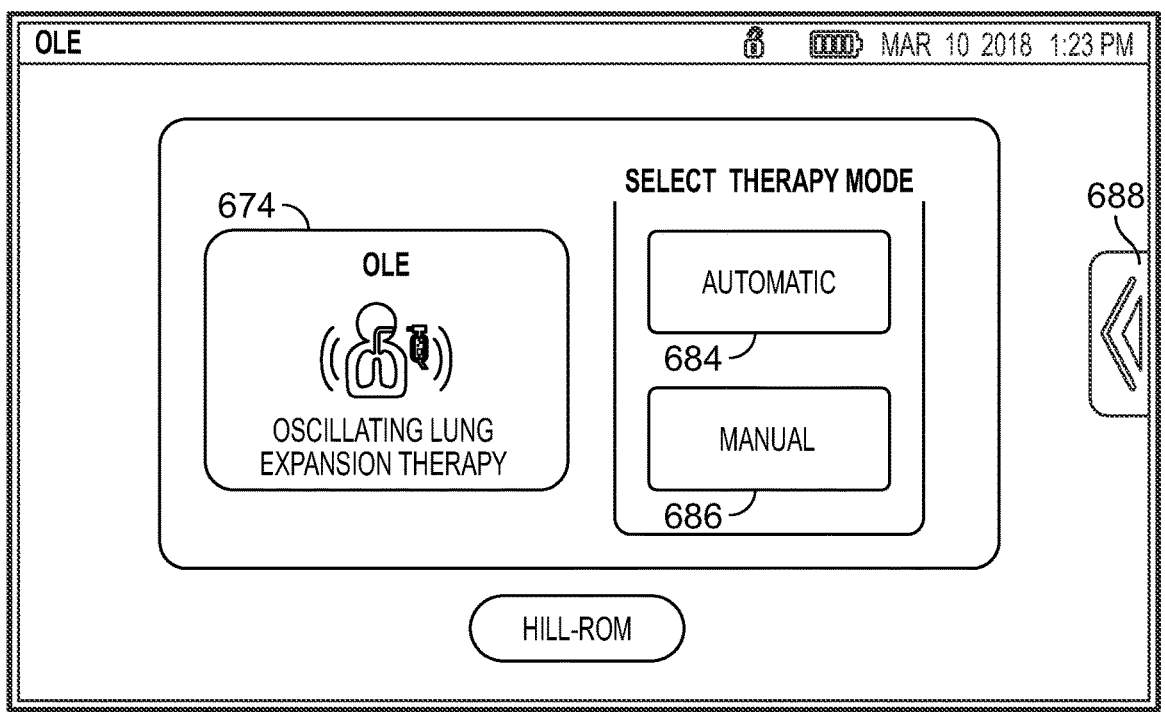
FIG. 20 is a screen shot of a main OLE therapy selection screen that appears on the GUI in response to the OLE icon being selected on the main therapy selection screen of FIG. 18, the main OLE therapy selection screen having a selectable automatic button and a selectable manual button for selecting automatic and manual modes of OLE therapy, respectively.
Figure 21:
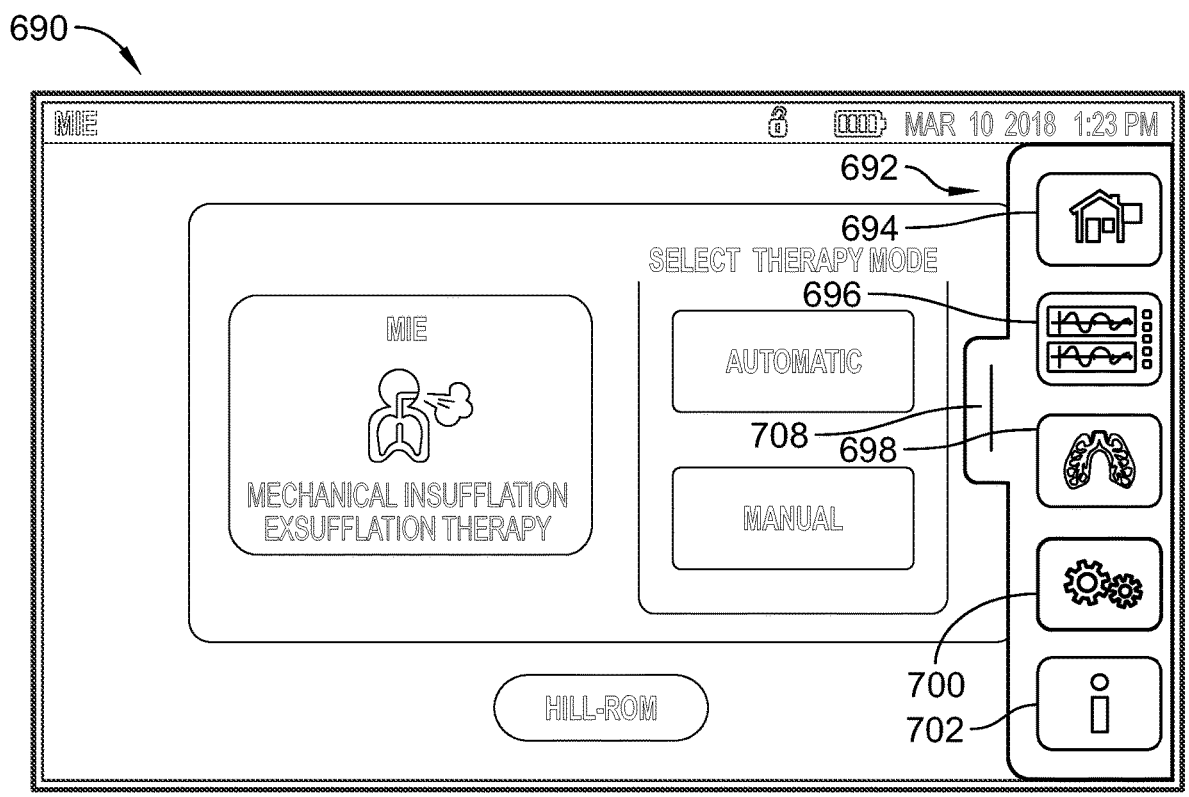
FIG. 21 is a screen shot of a menu screen that appears on the GUI in response to selection of a menu arrow icon on the right hand side of the main MIE therapy selection screen of FIG. 19 and on the right hand side of the main OLE therapy selection screen of FIG. 20, the menu screen including a vertical menu of icons including, from top to bottom, a home icon, a graph icon, a lung icon, a settings icon, and an information or help icon.
Figure 22:
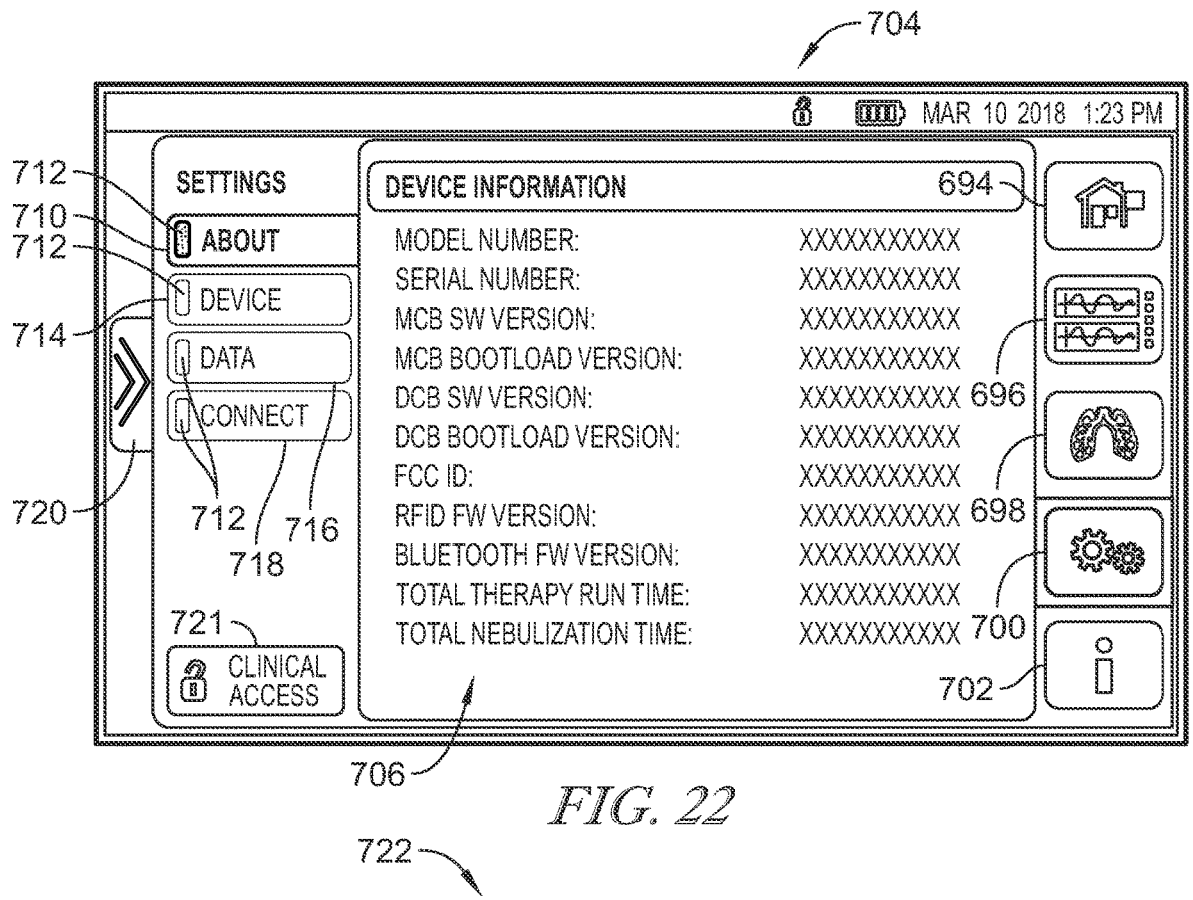
FIG. 22 is a screen shot of a settings screen that appears on the GUI in response to the settings icon being selected from the menu of FIG. 21, the settings screen including a window of device information pertaining to the respiratory therapy apparatus.
Figure 29:
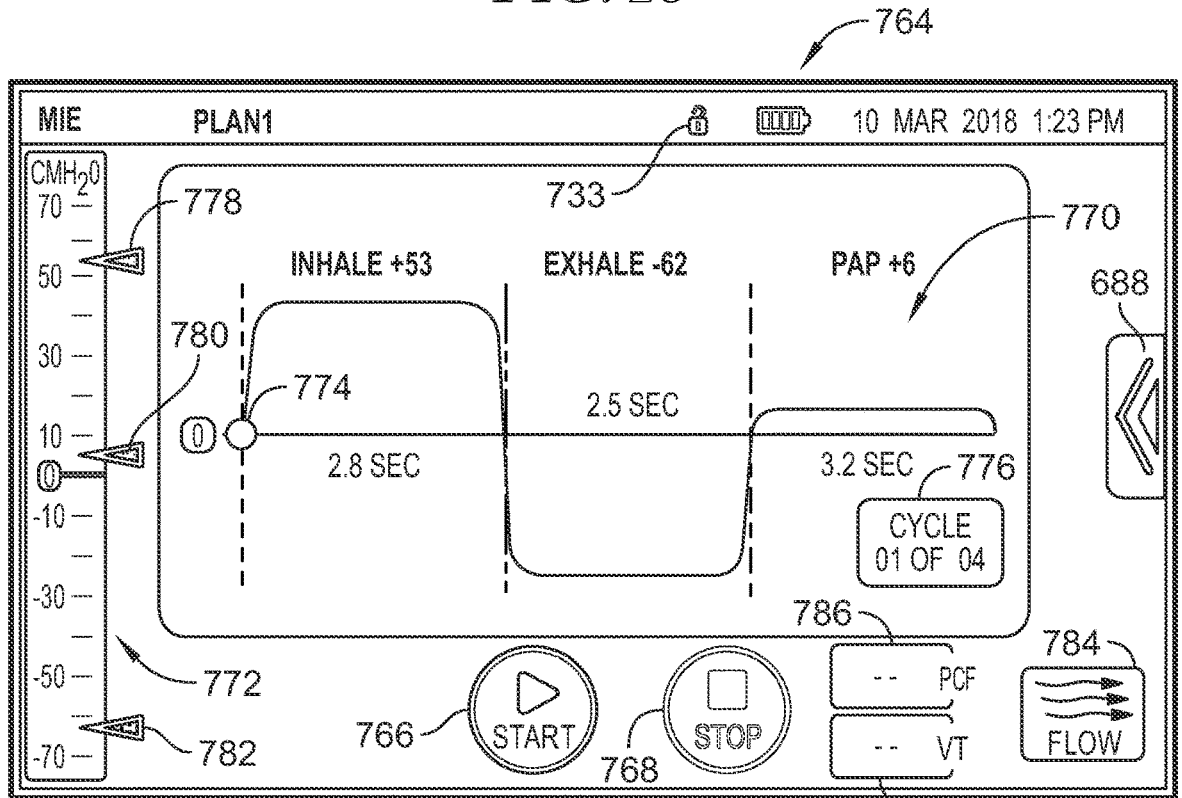
FIG. 29 is a screen shot of a main automatic MIE therapy screen that appears on the GUI in response to the automatic button of the main MIE therapy selection screen of FIG. 19 being selected.
Figure 31:
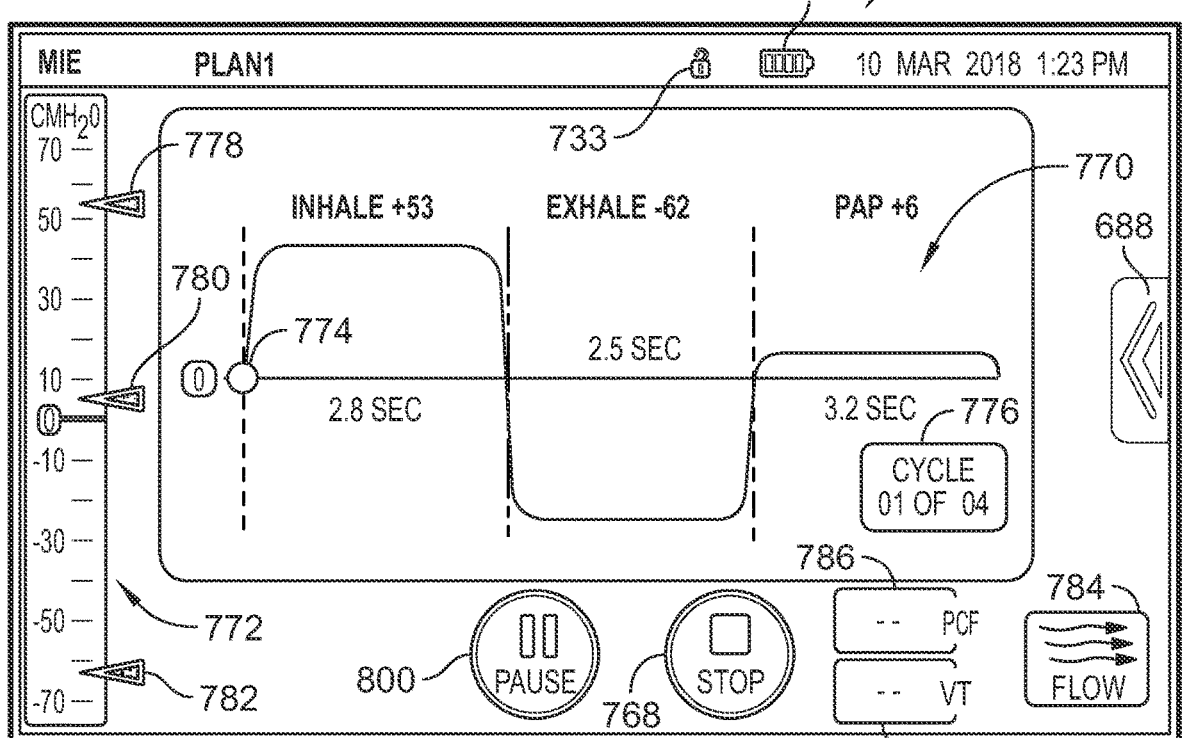
FIG. 31 is a screen shot of an automatic MIE therapy start screen that appears on the GUI if a start button of the main automatic MIE therapy screen of FIG. 29 is selected while the respiratory therapy apparatus is operating under battery power and the battery charge is greater than 20% of a full battery charge, and in response to the automatic MIE therapy beginning the start button being converted graphically to a pause button that can be selected to pause the therapy.
Figure 39:
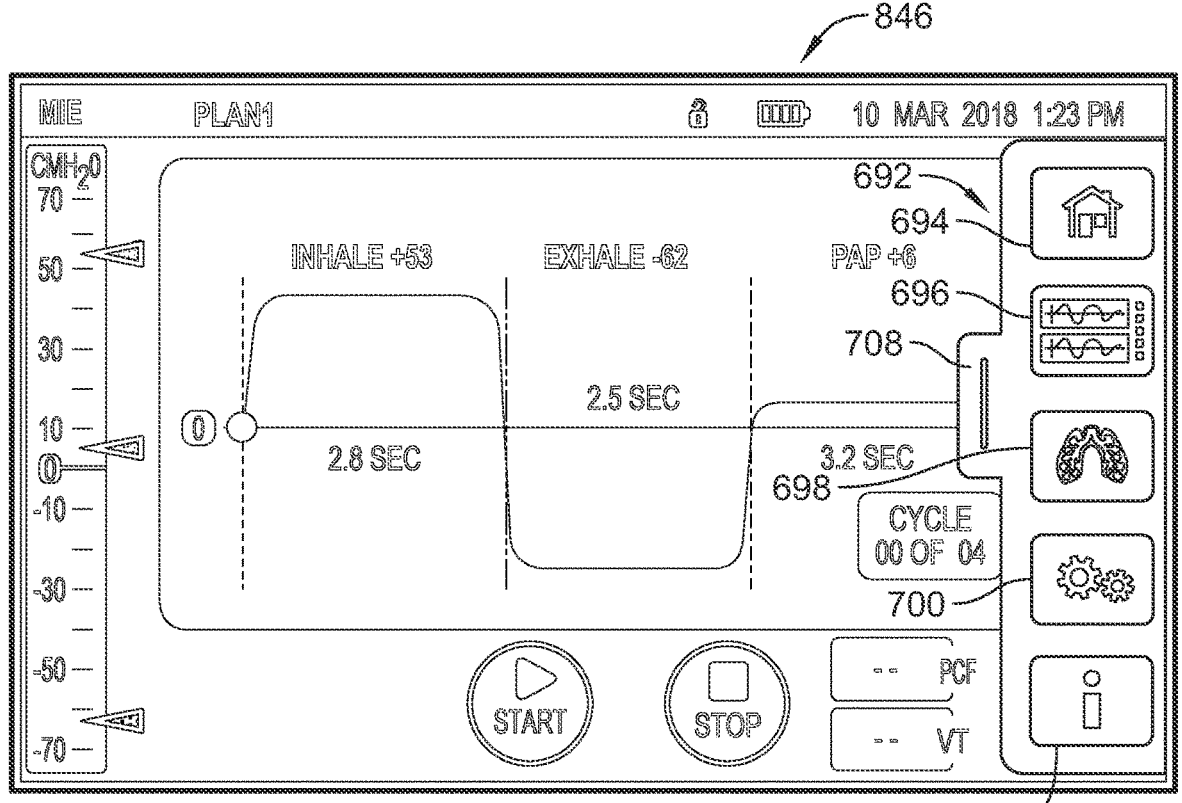
FIG. 39 is a screen shot of the menu screen, similar to FIG. 21, that appears on the GUI in response to selection of the menu arrow icon on the right hand side of the main automatic MIE therapy selection screen of FIG. 29, the menu screen including the vertical menu of icons.
Figure 66:
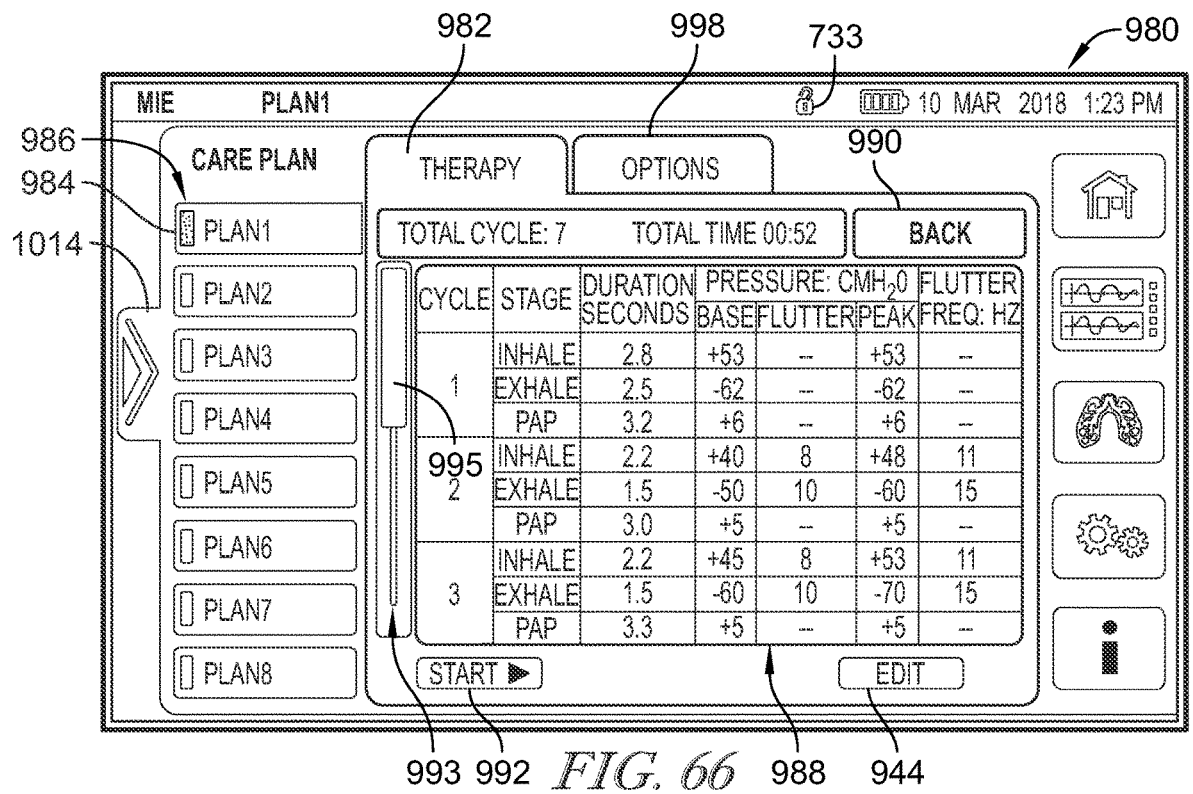
FIG. 66 is a screen shot of a first care plan screen for automatic MIE therapy that appears on the GUI after the lung icon of the vertical menu of icons of FIG. 39 is selected, the first care plan screen for automatic MIE therapy having a therapy tab selected for a first care plan, and a table of the parameters for inhale, exhale, and PAP portions of the first care plan being shown in the table.
Figure 101:
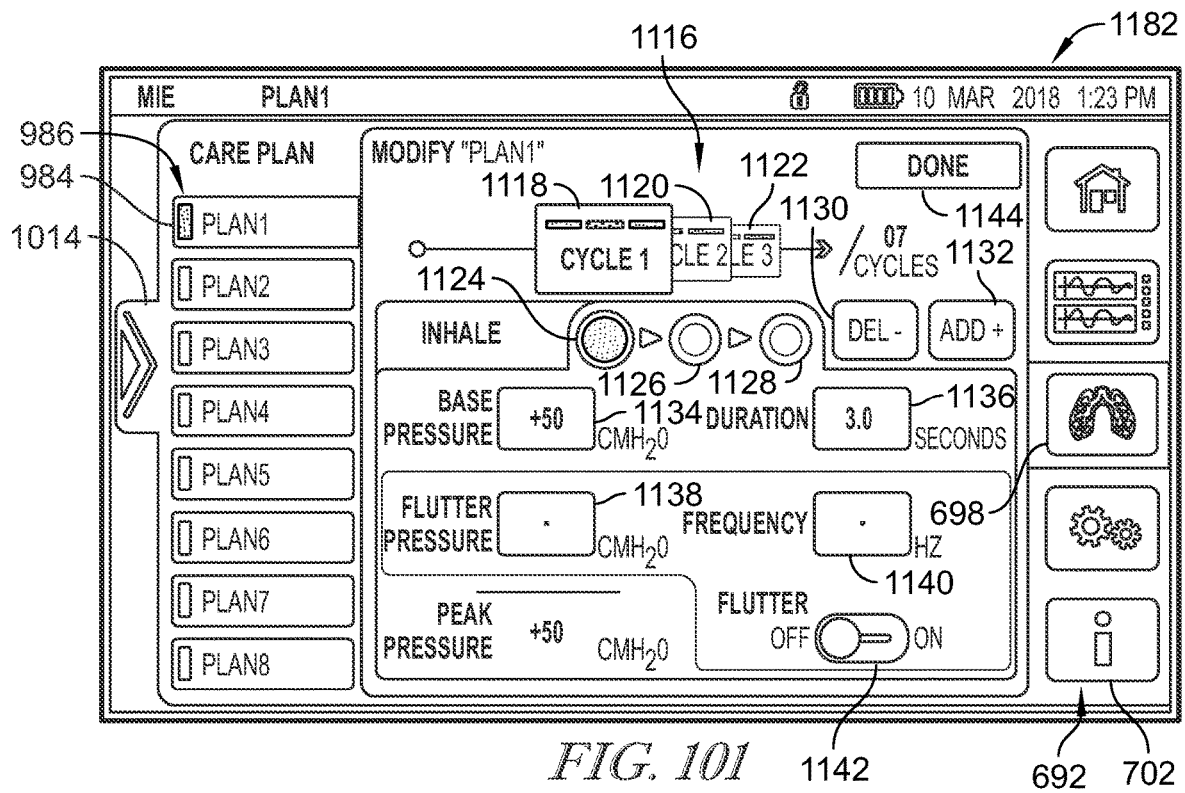
FIG. 101 is a screen shot of a tenth modify therapy screen showing the new inhale base pressure in the respective field after the save icon of the ninth modify therapy screen of FIG. 100 has been selected.
Figure 115:
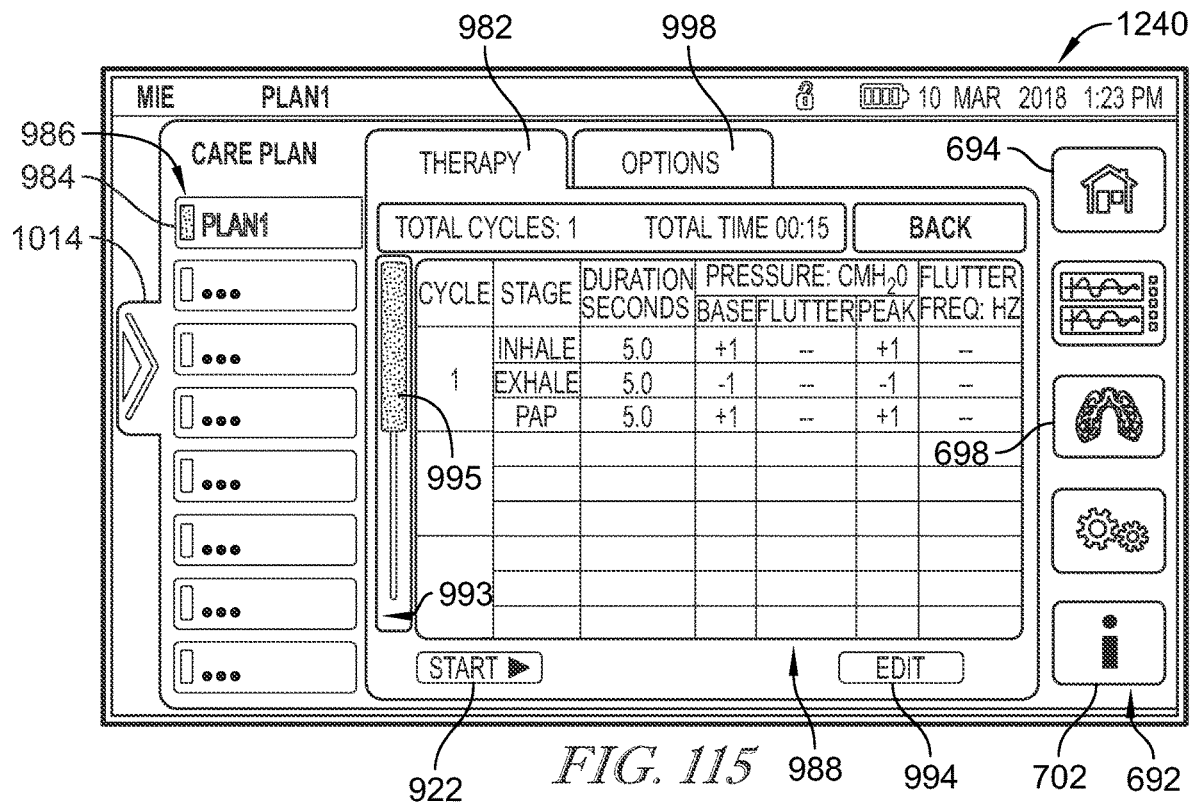
FIG. 115 is a screen shot of a second create new therapy screen that appears on the GUI in response to selection of a done button on the first create new therapy screen of FIG. 114, the second create new therapy screen having a therapy tab selected for the new care plan and a table of the default parameters for inhale, exhale, and PAP portions of the new care plan being shown in the table.
Figure 116:
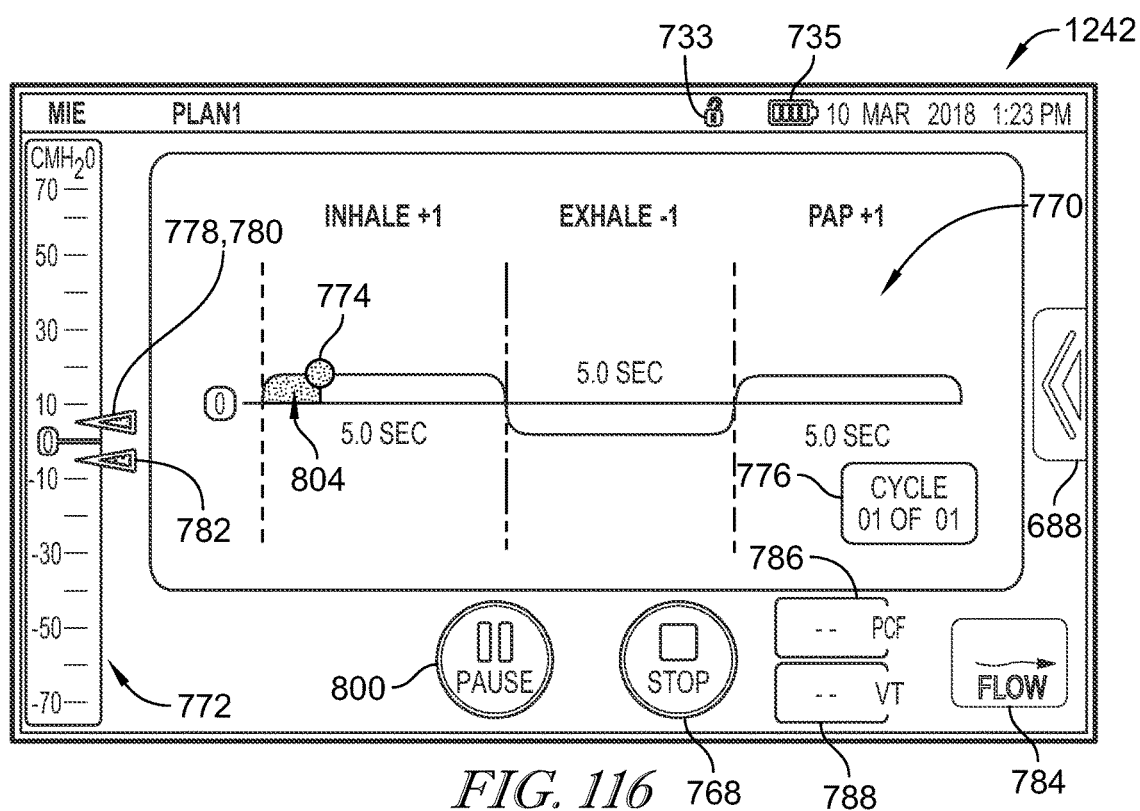
Figure 117:
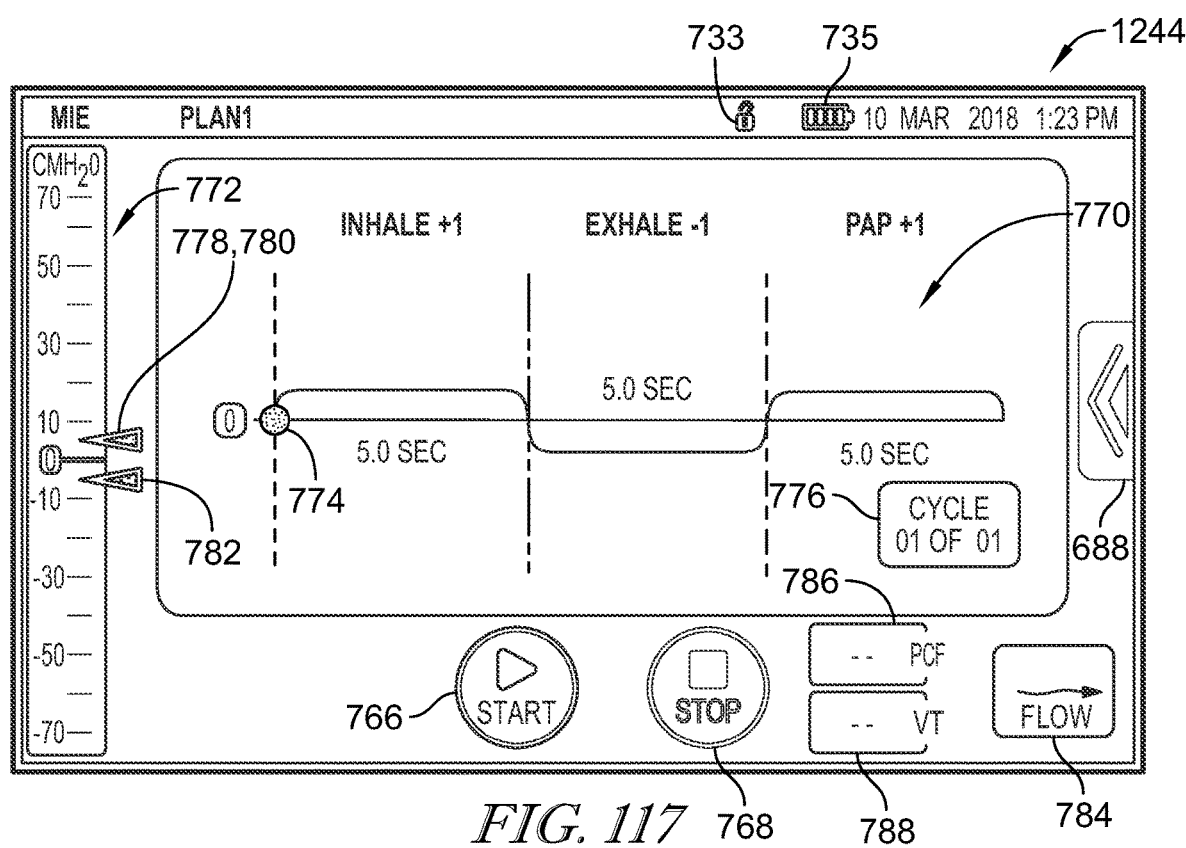
Figure 118:
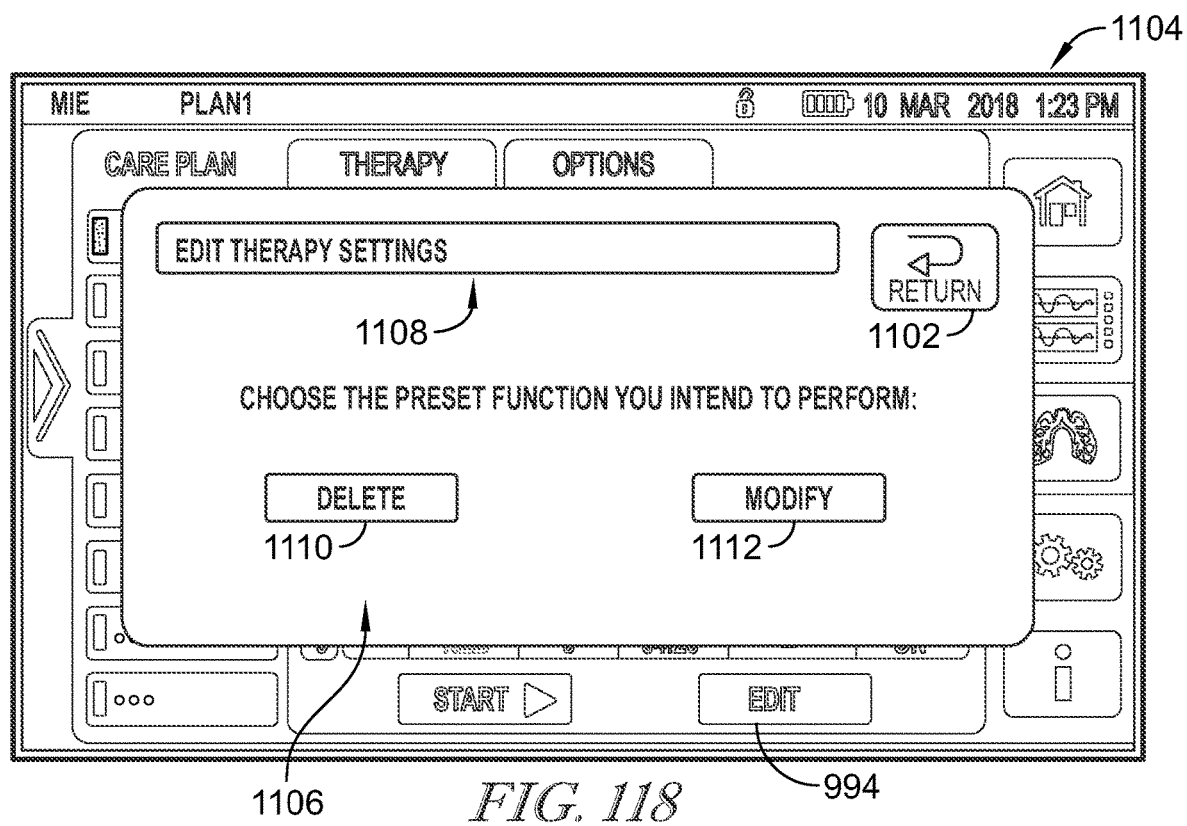
Figure 119:
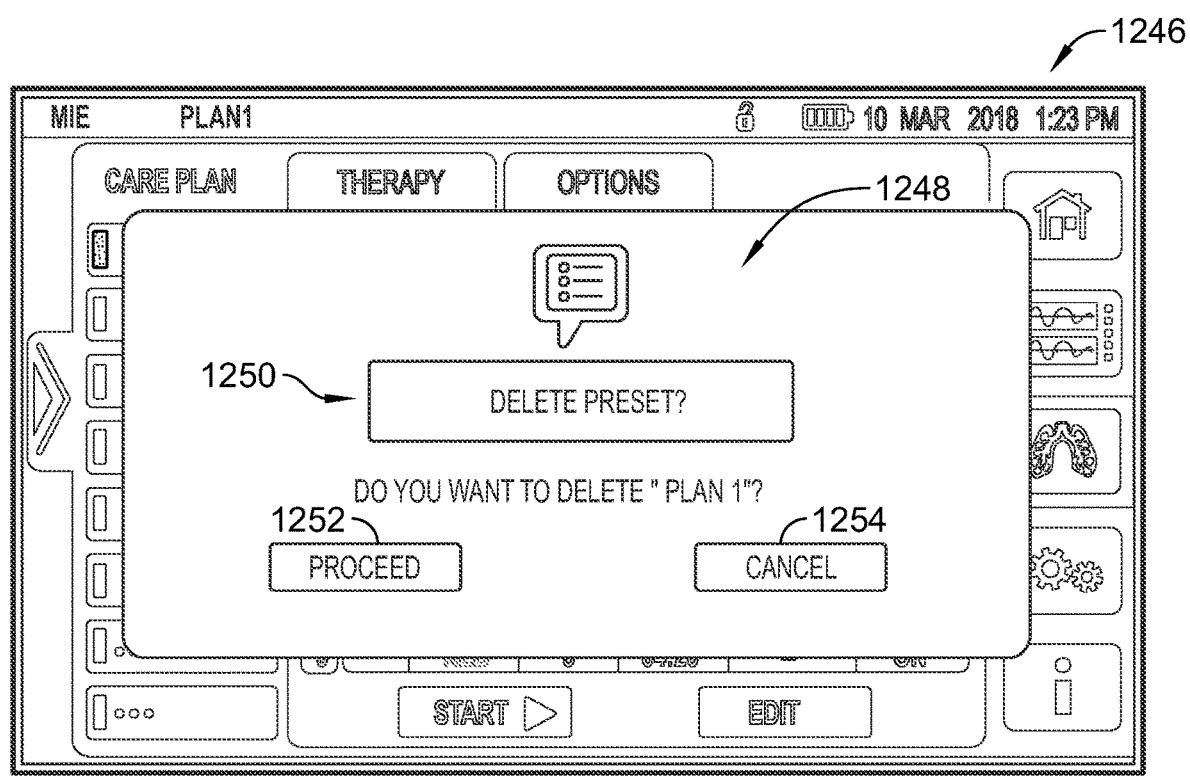
Figure 120:
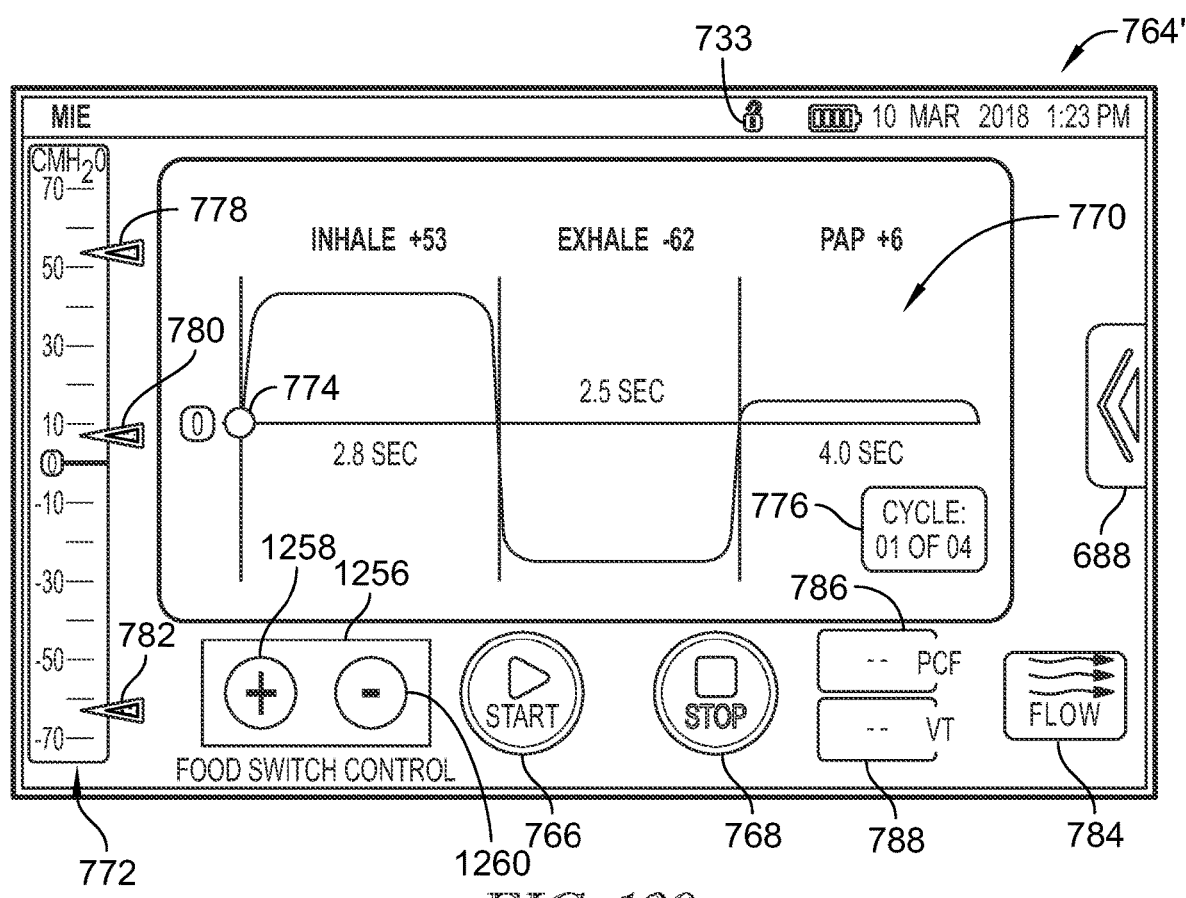
Figure 121:
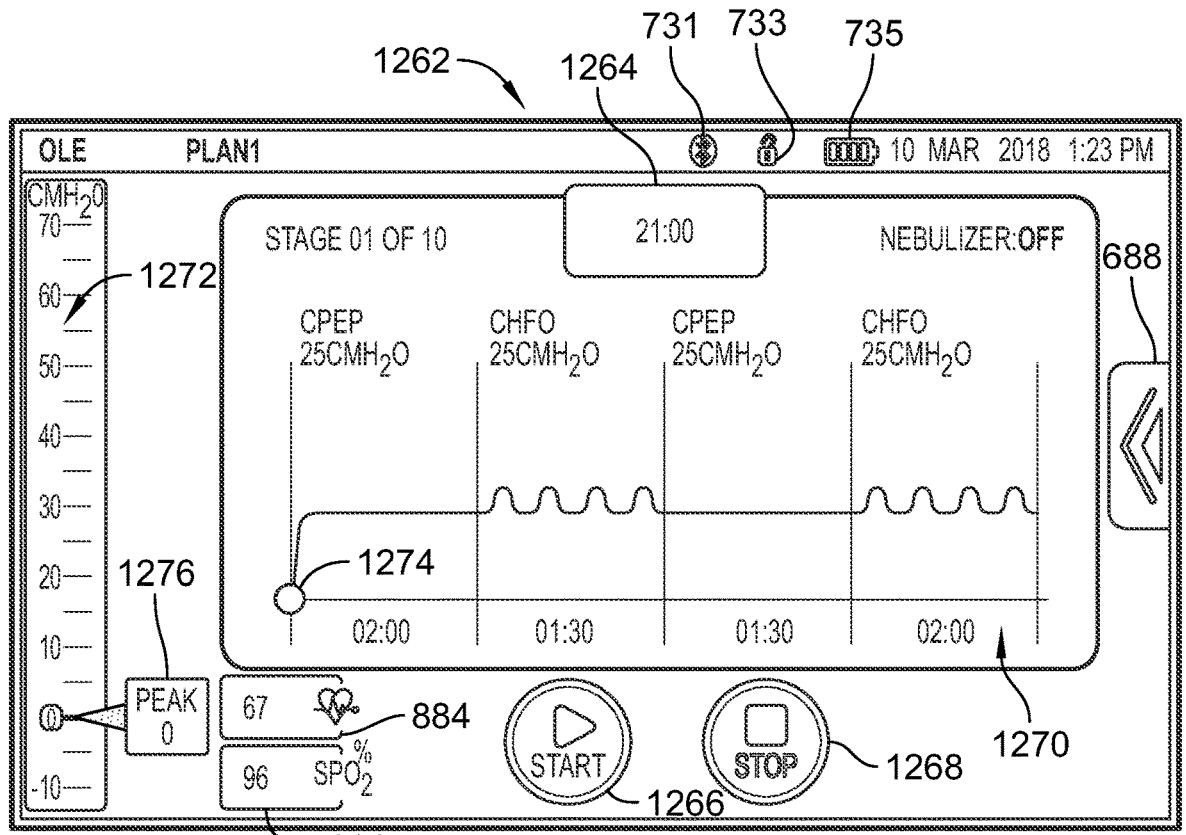
Figure 122:
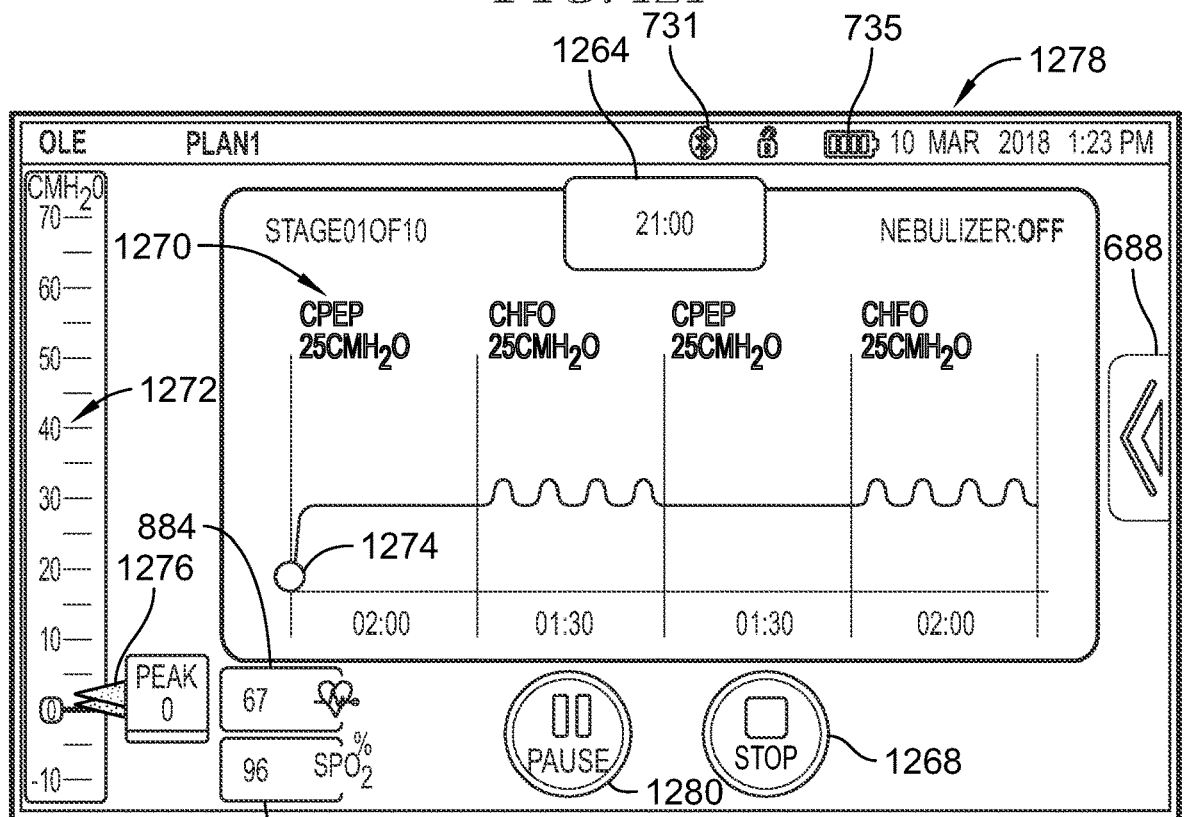
Figure 123:
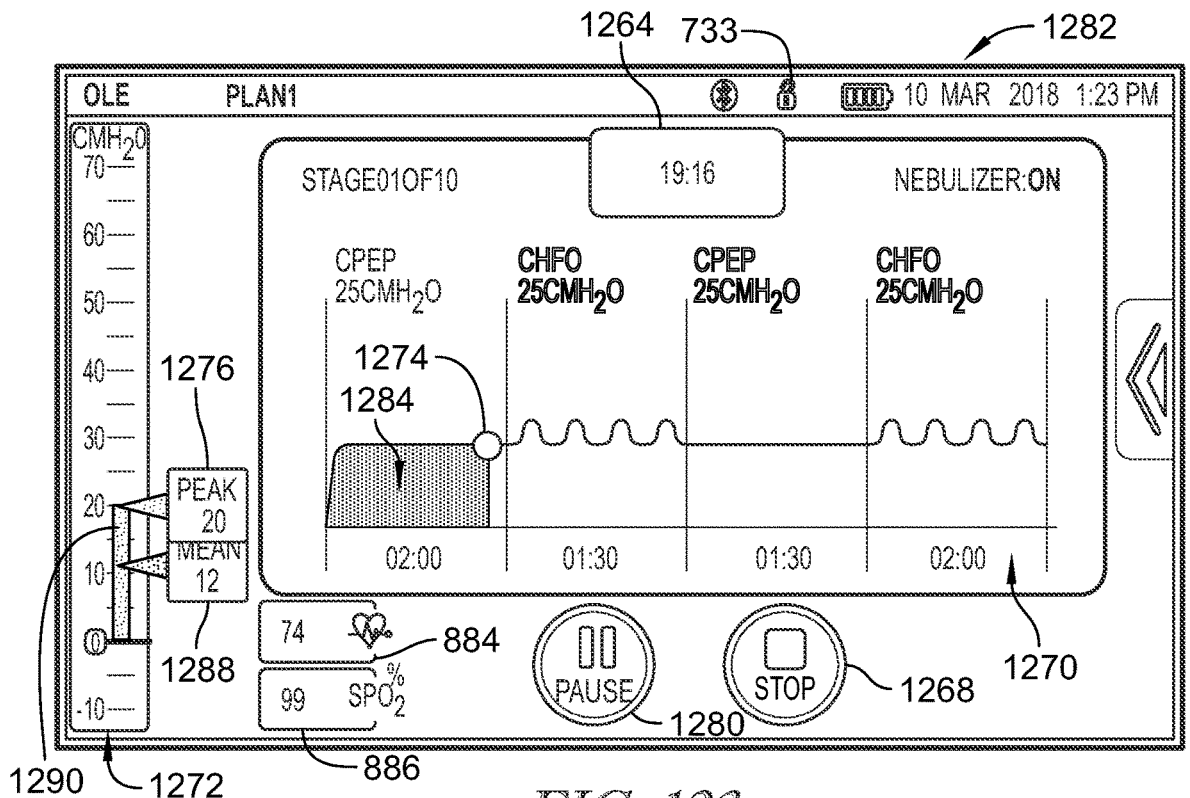
Figure 124:
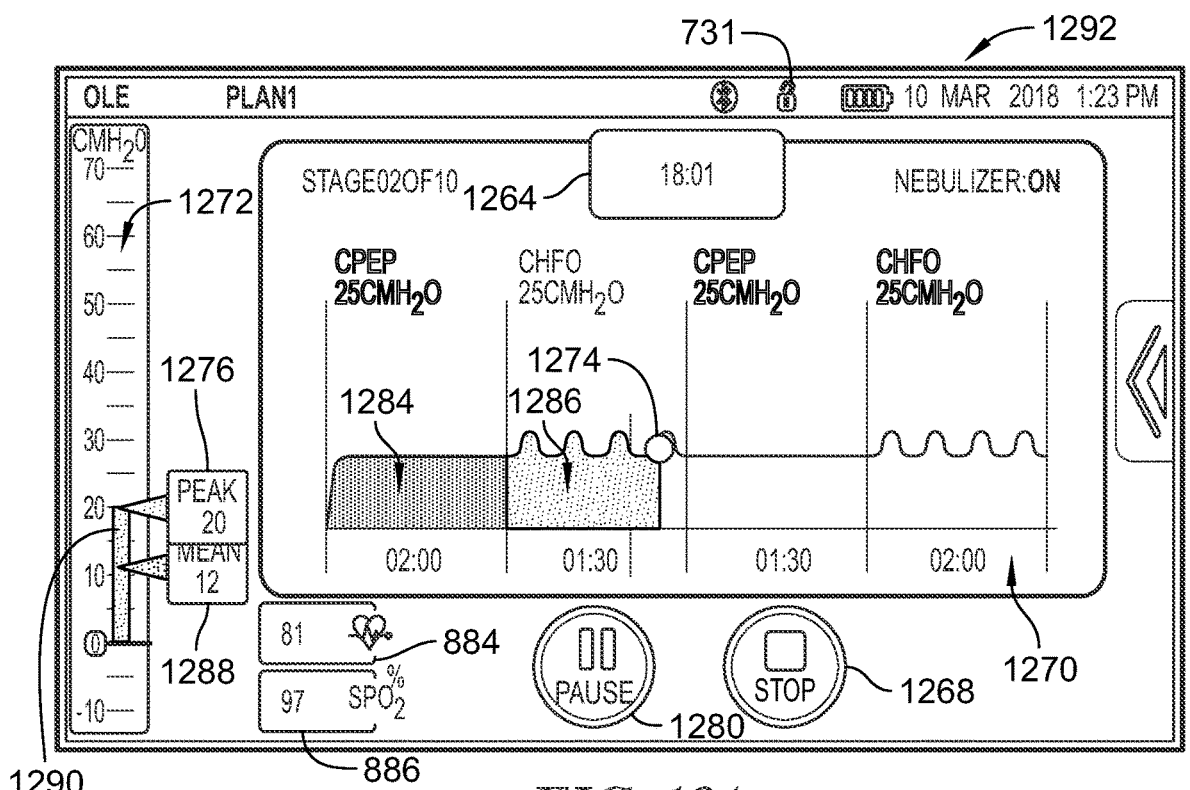
Figure 125:
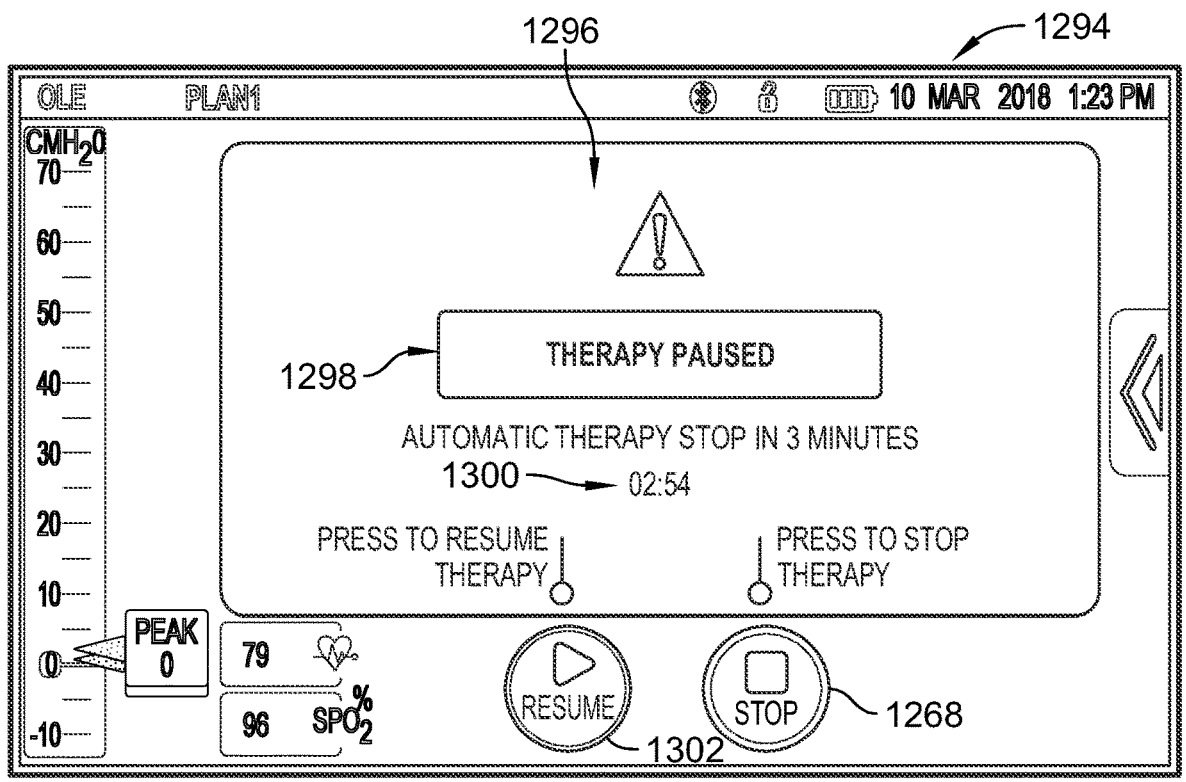
Figure 126:
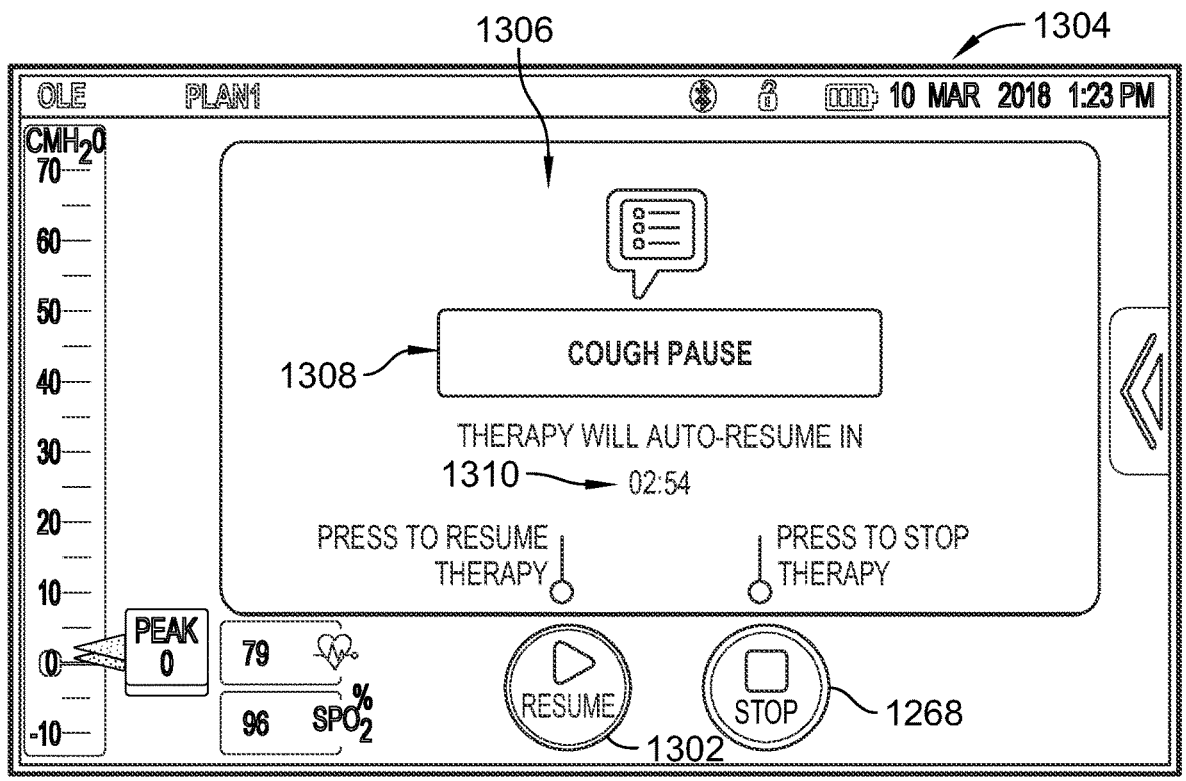
Figure 127:
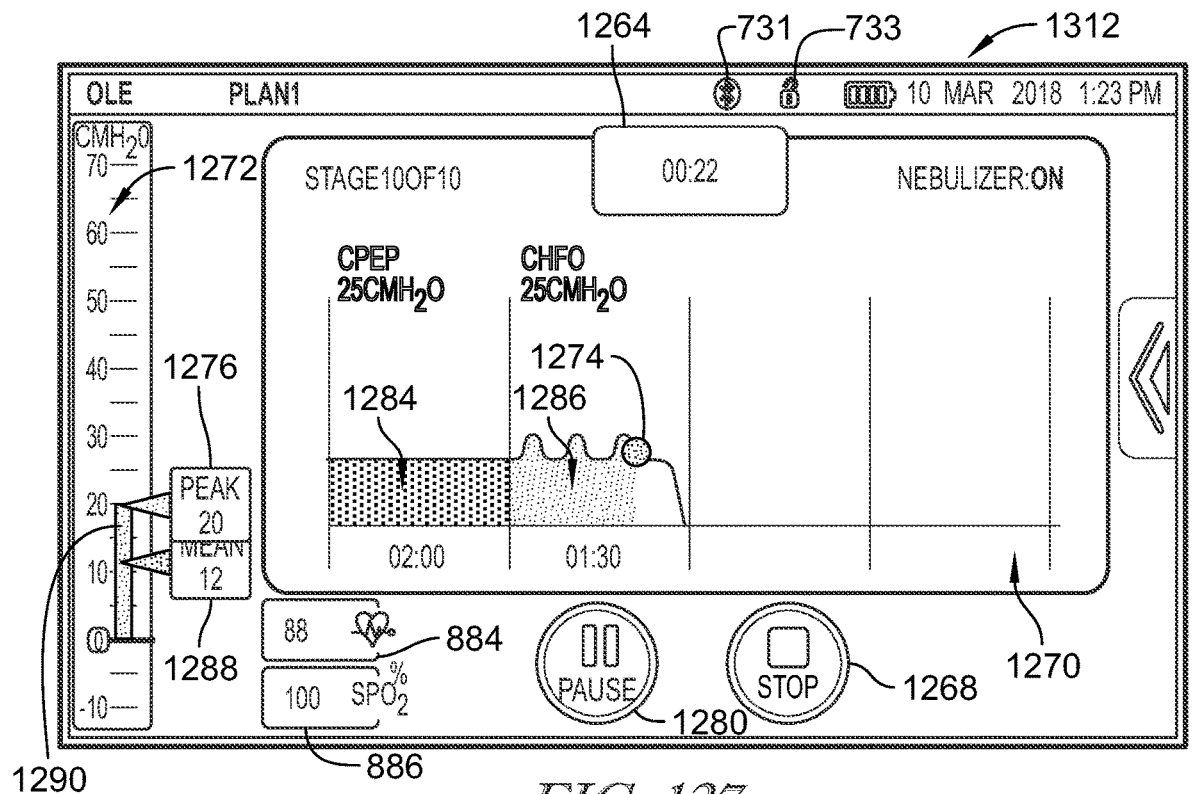
Figure 128:
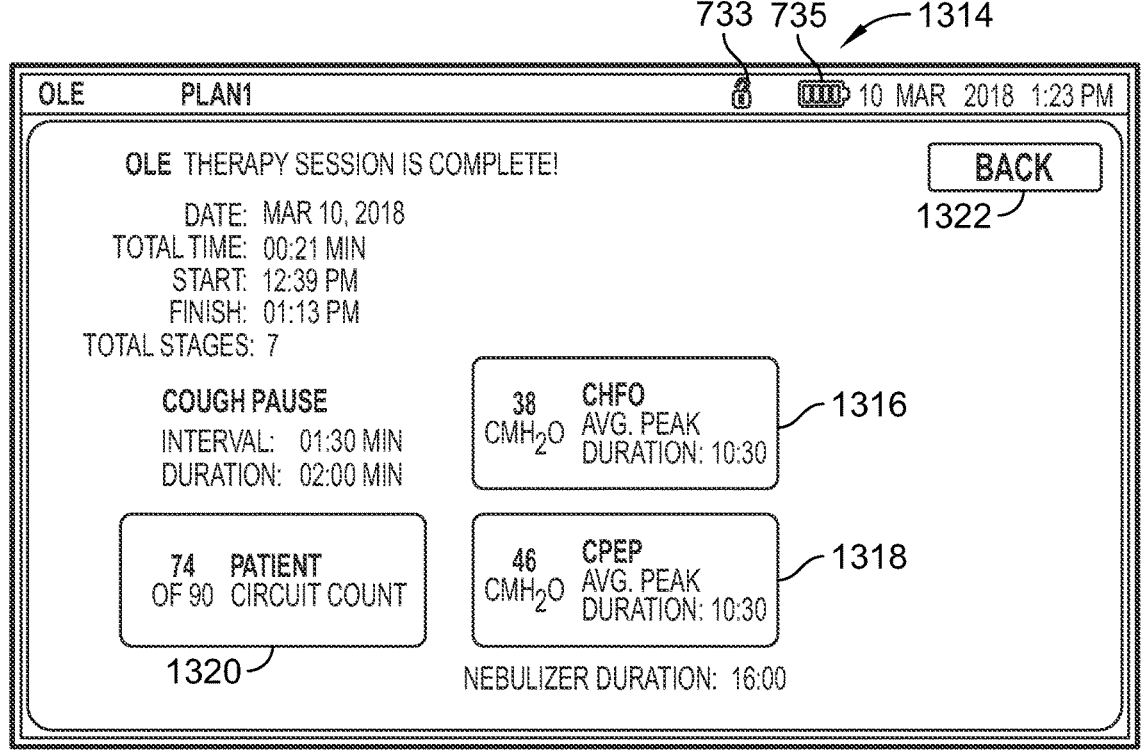
Figure 129:
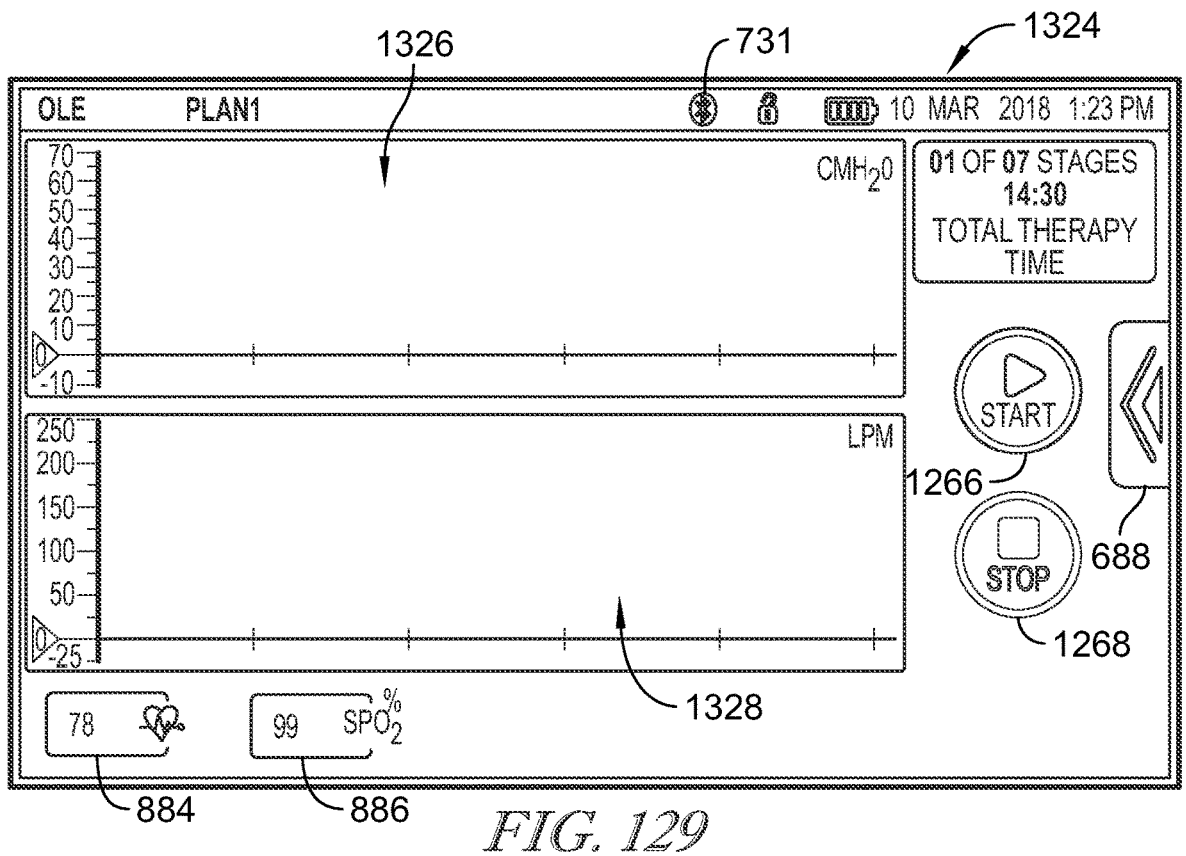
Figure 130:
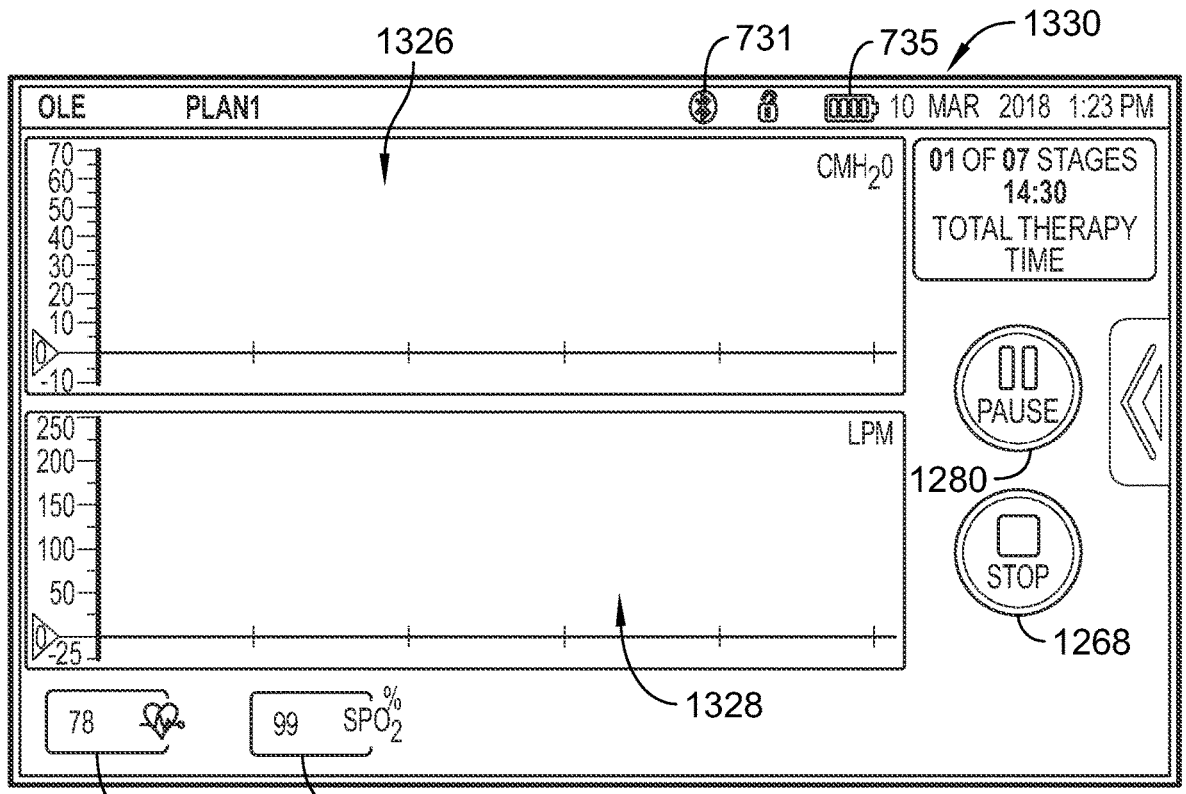
Figure 131:
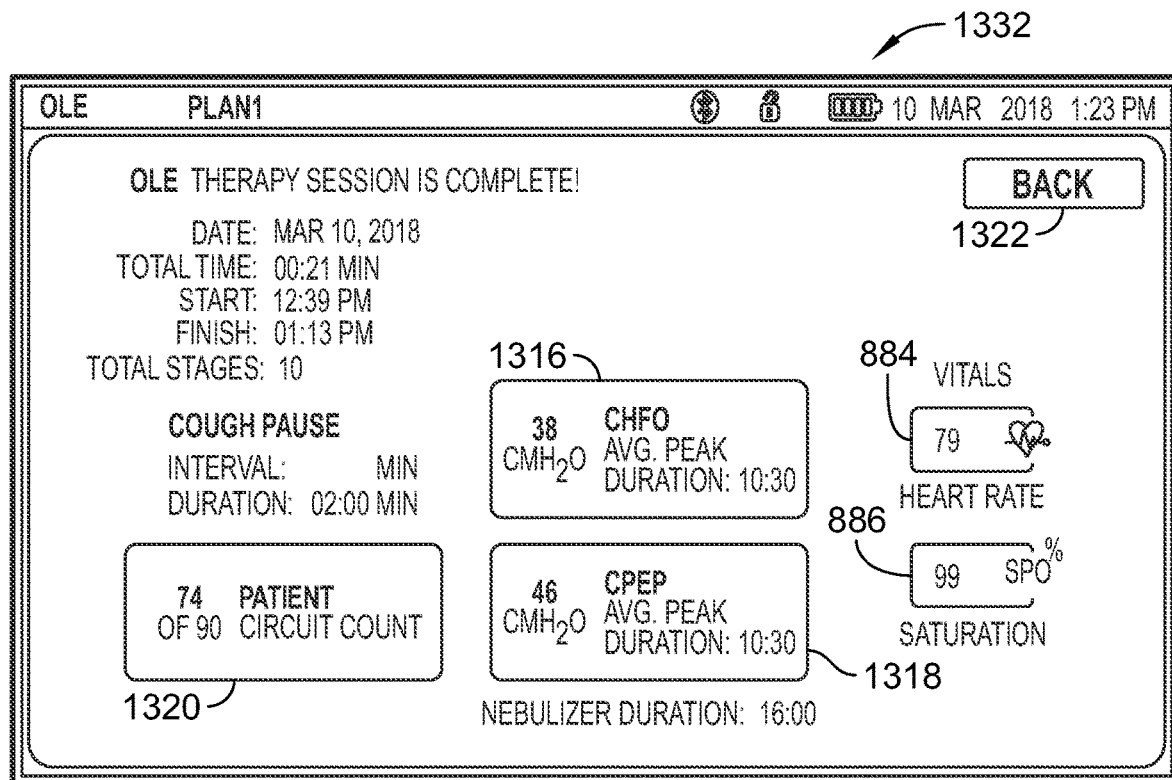
Figure 132:
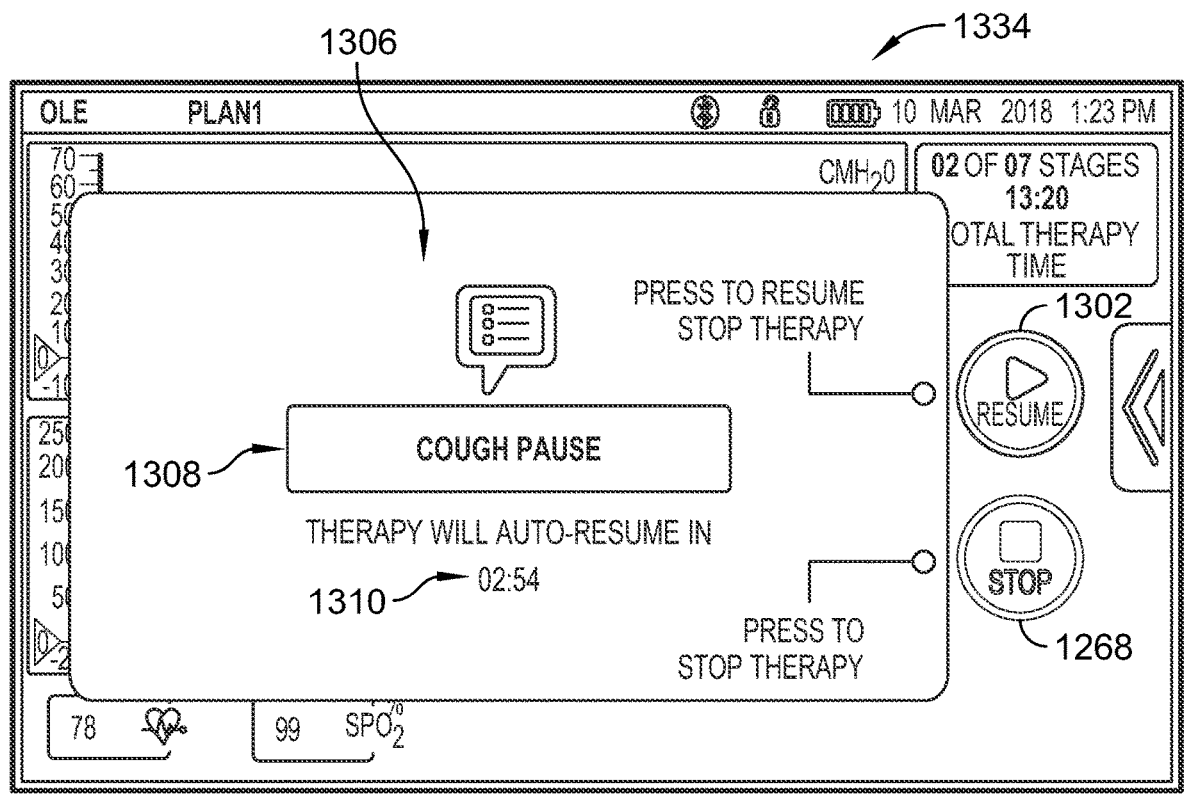
Figure 133:
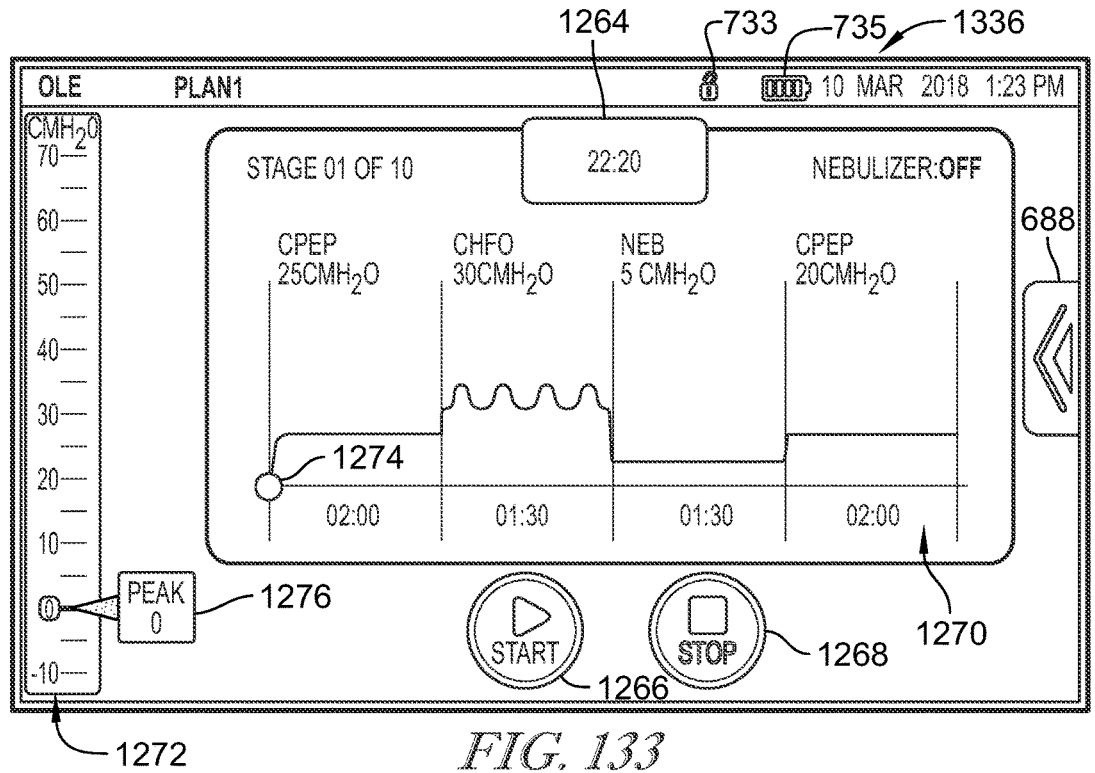
Figure 134:
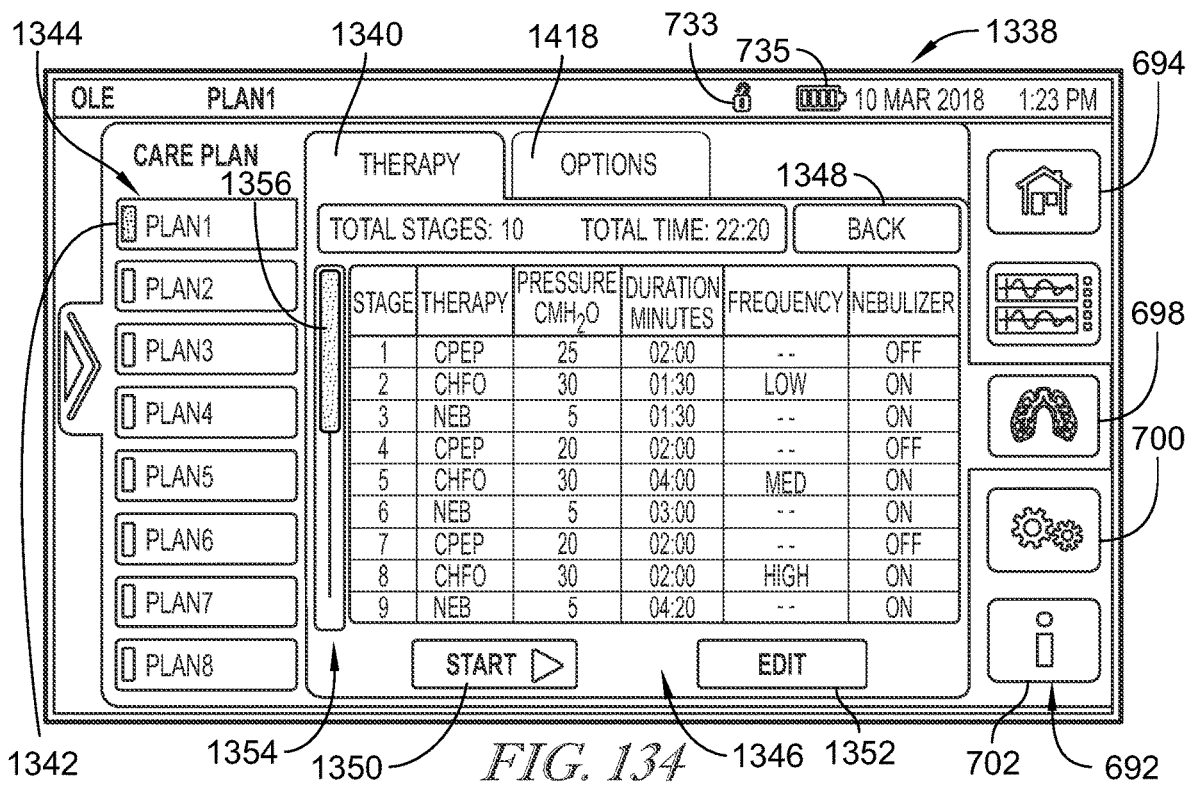
Figure 135:
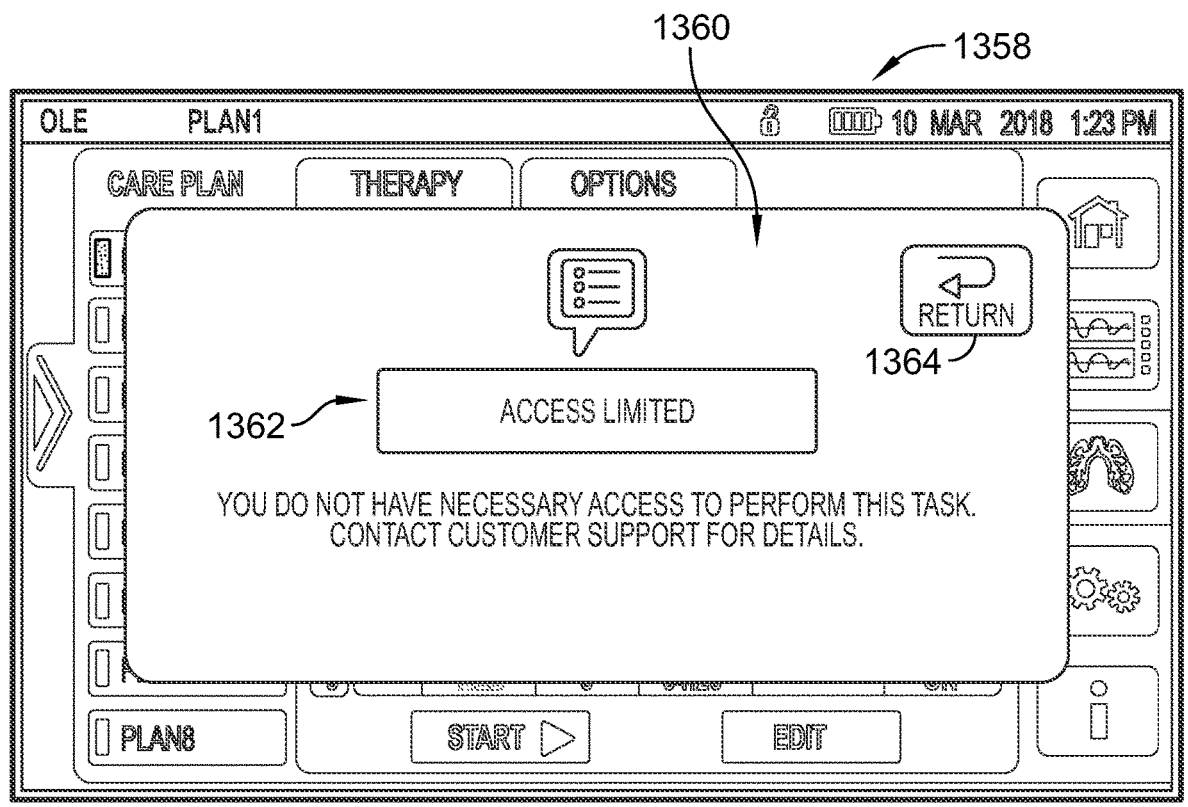
Figure 136:
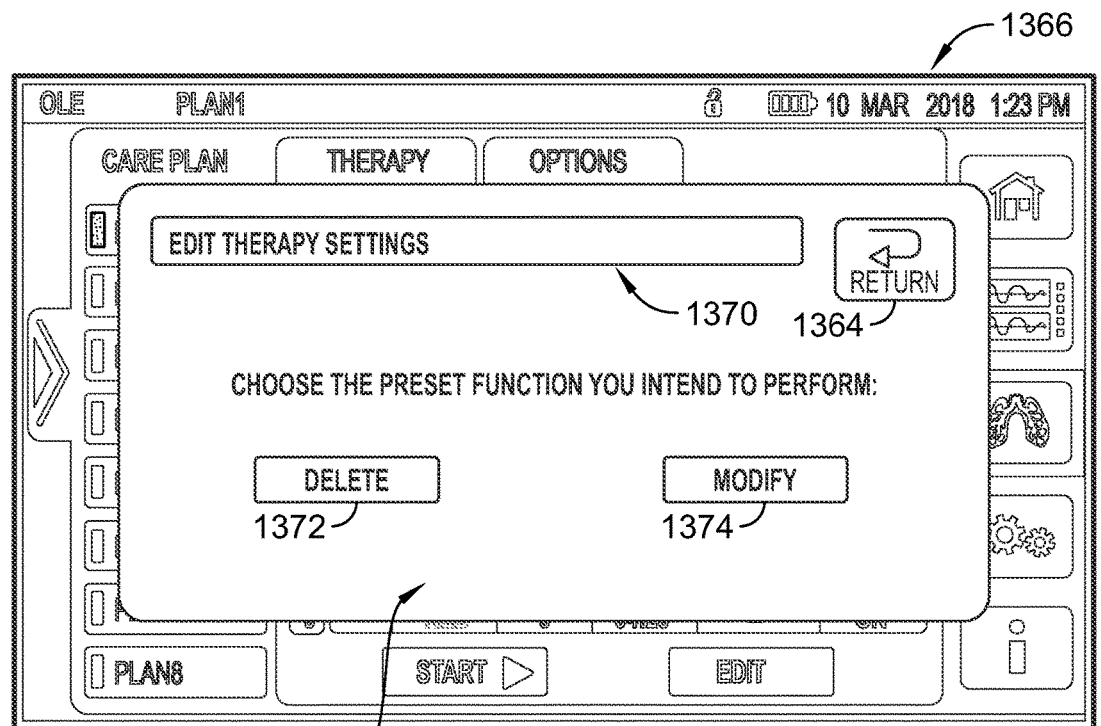
Figure 137:
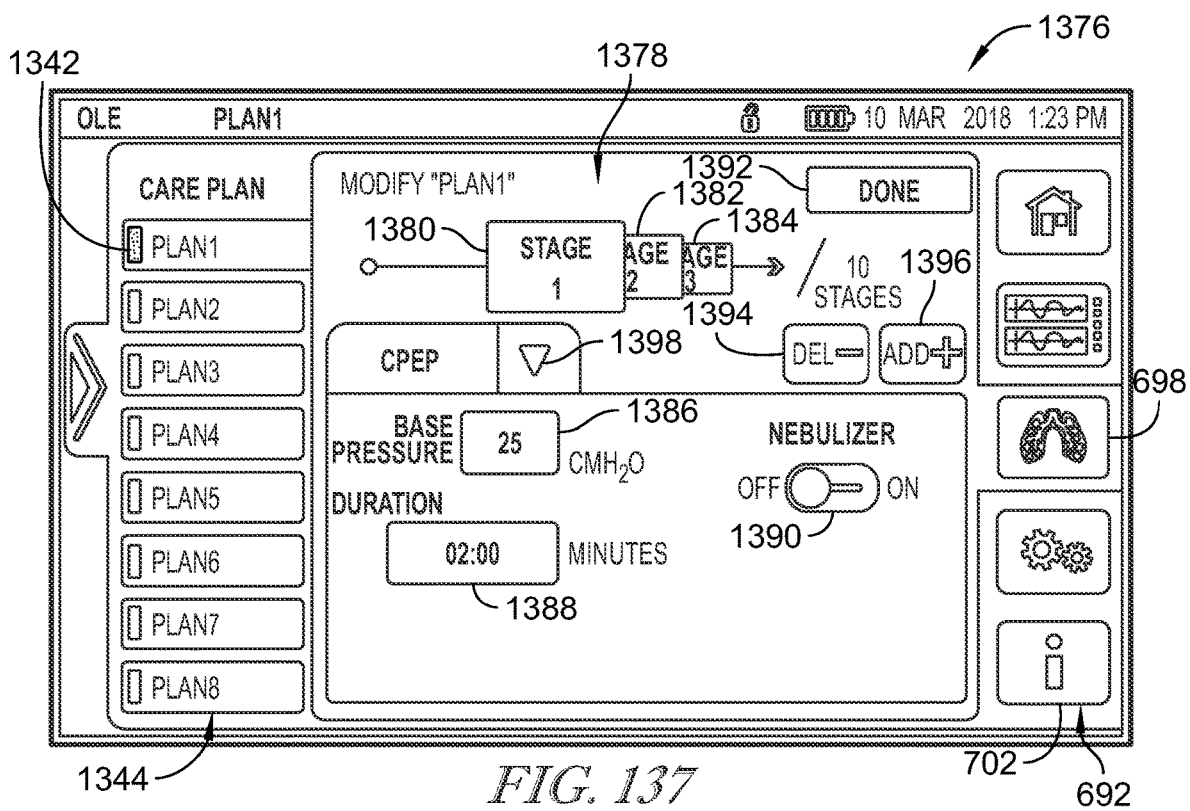
Figure 138:
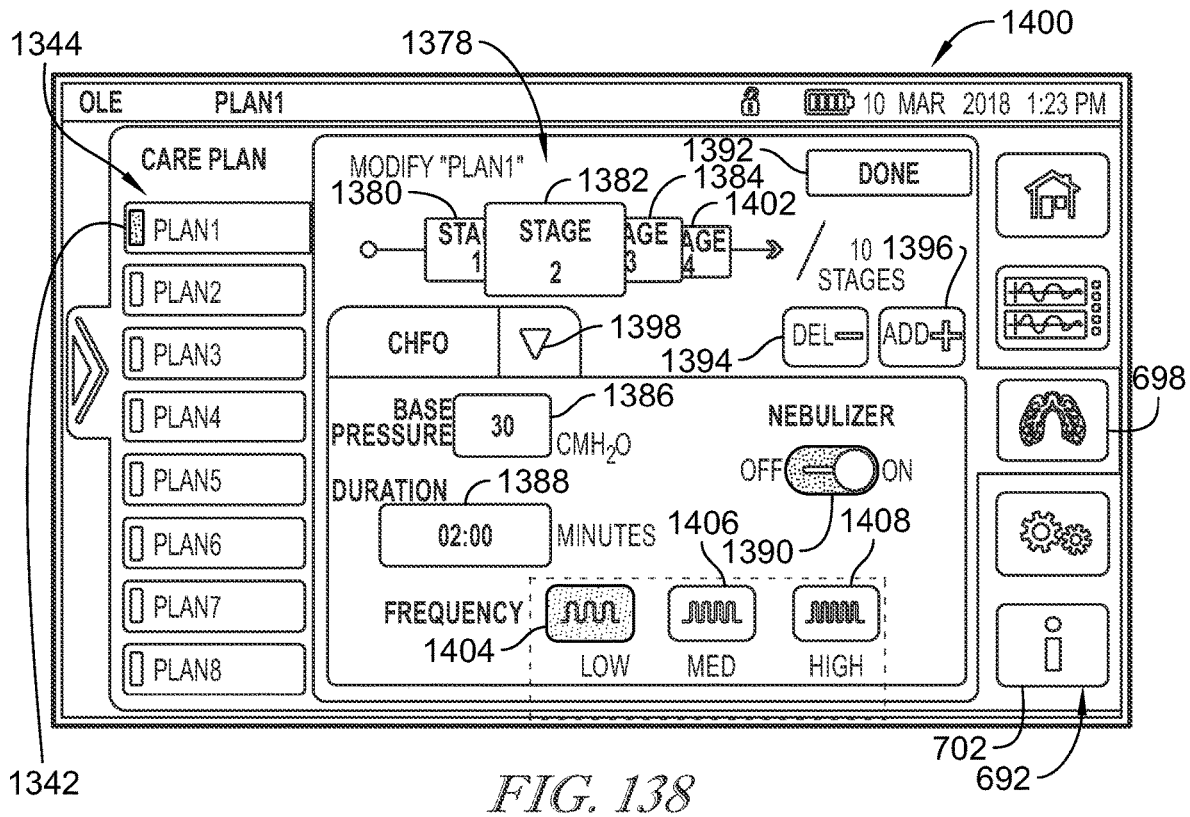
Figure 139:
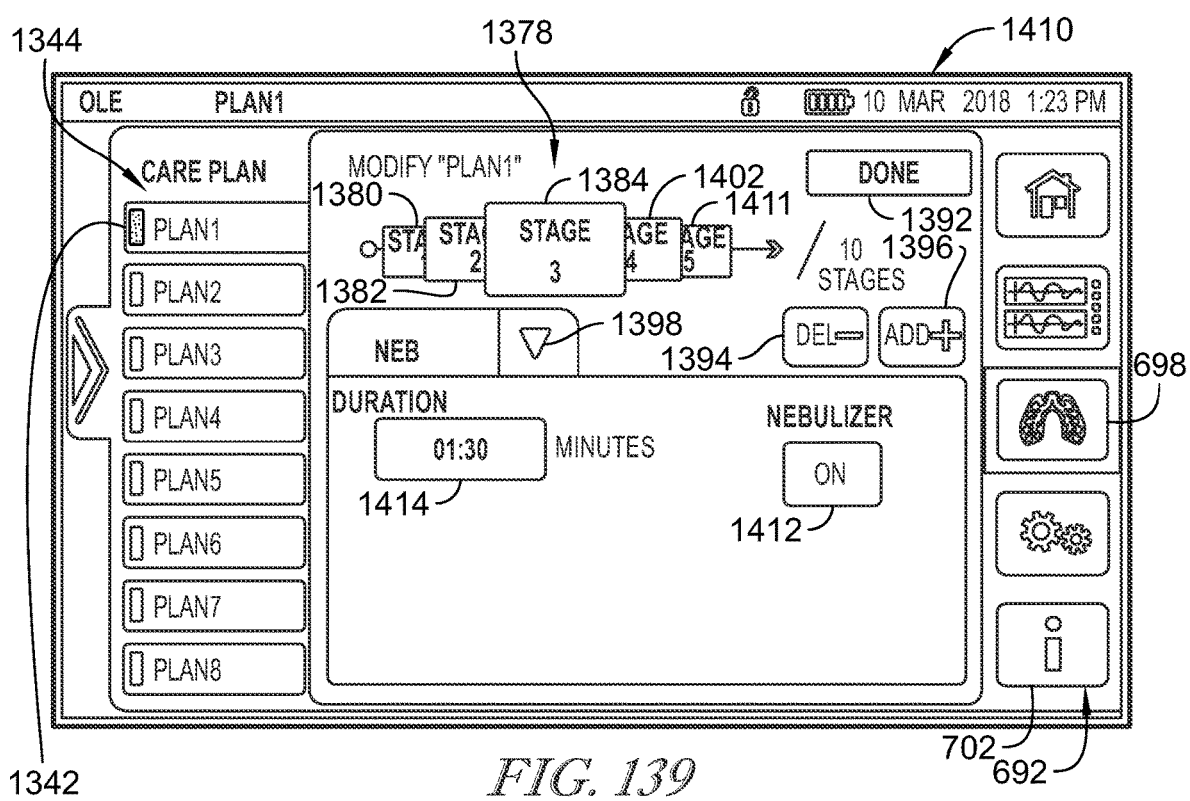
Figure 140:
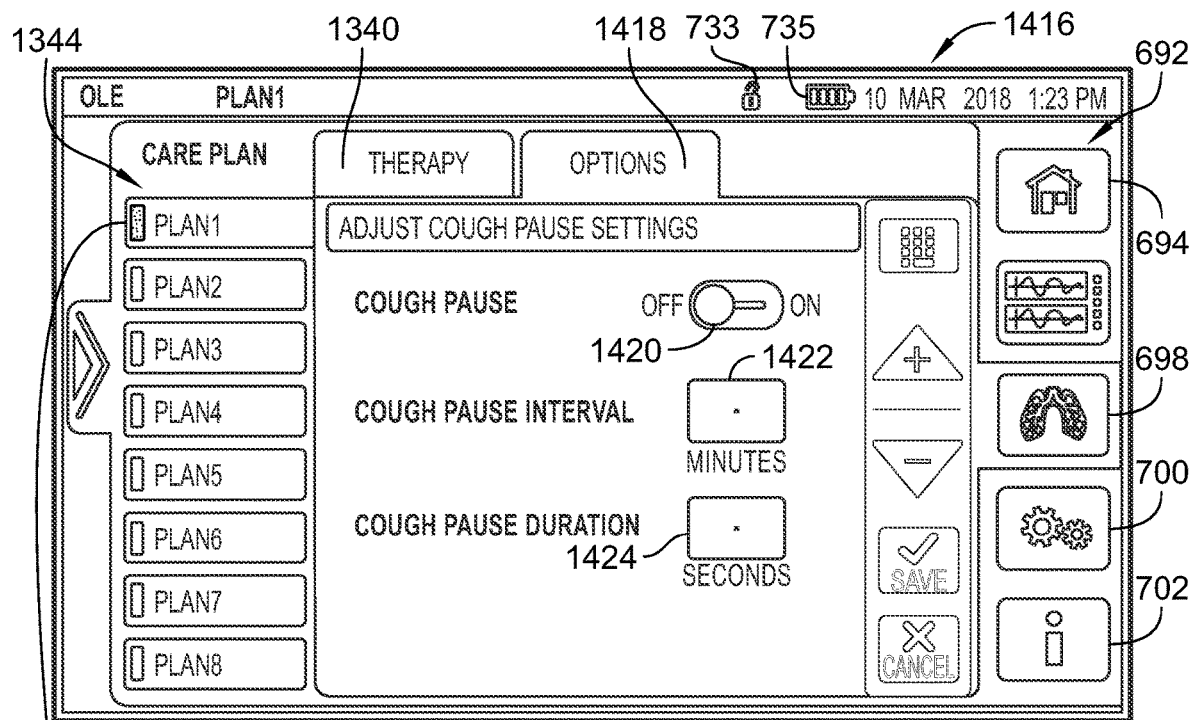
Figure 141:
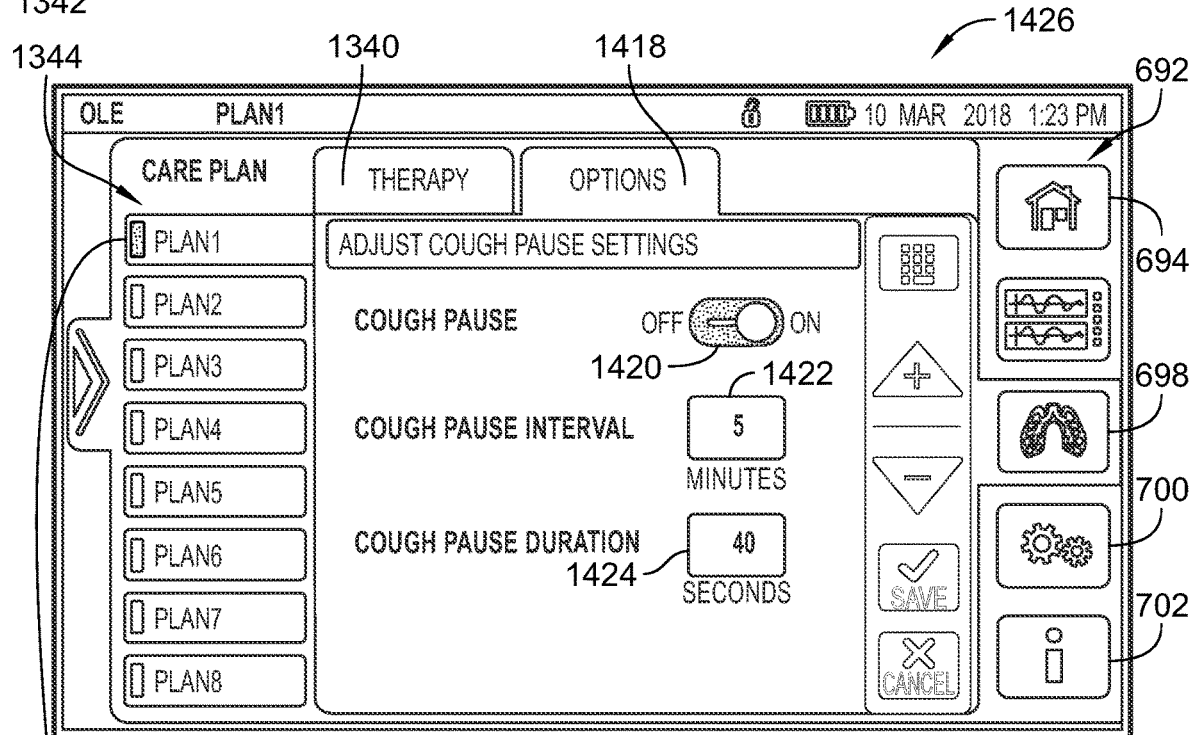
Figure 142:
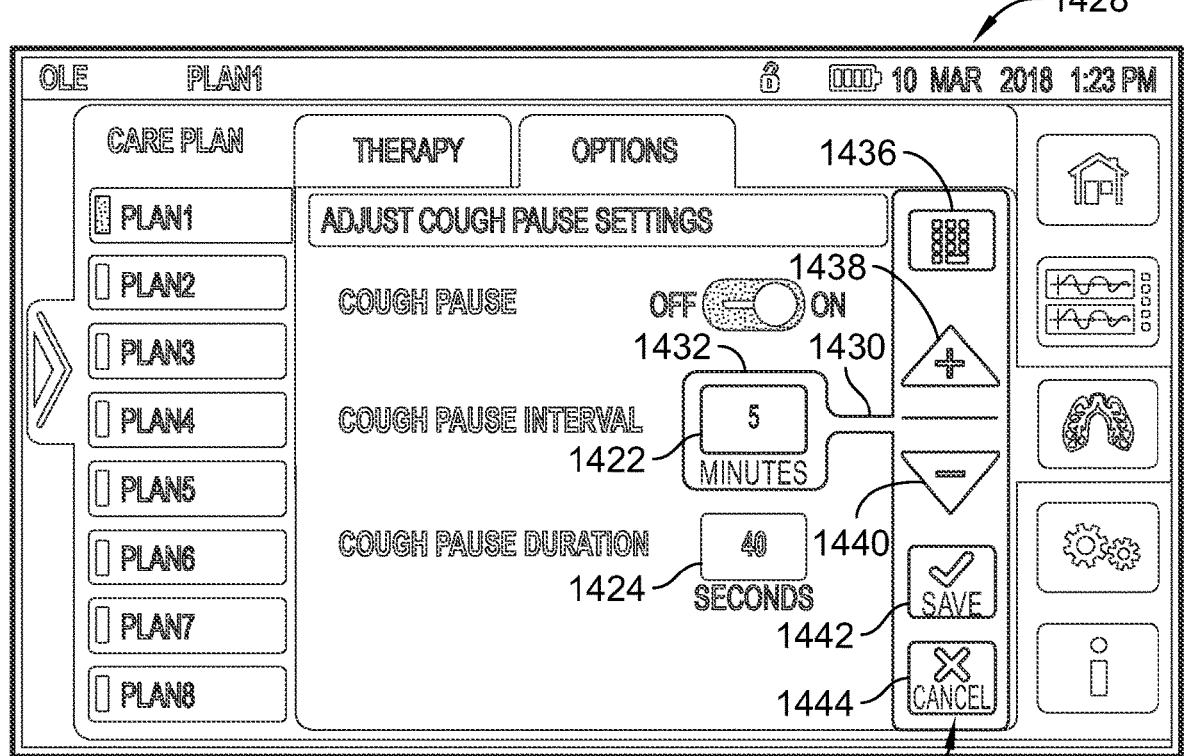
Figure 143:
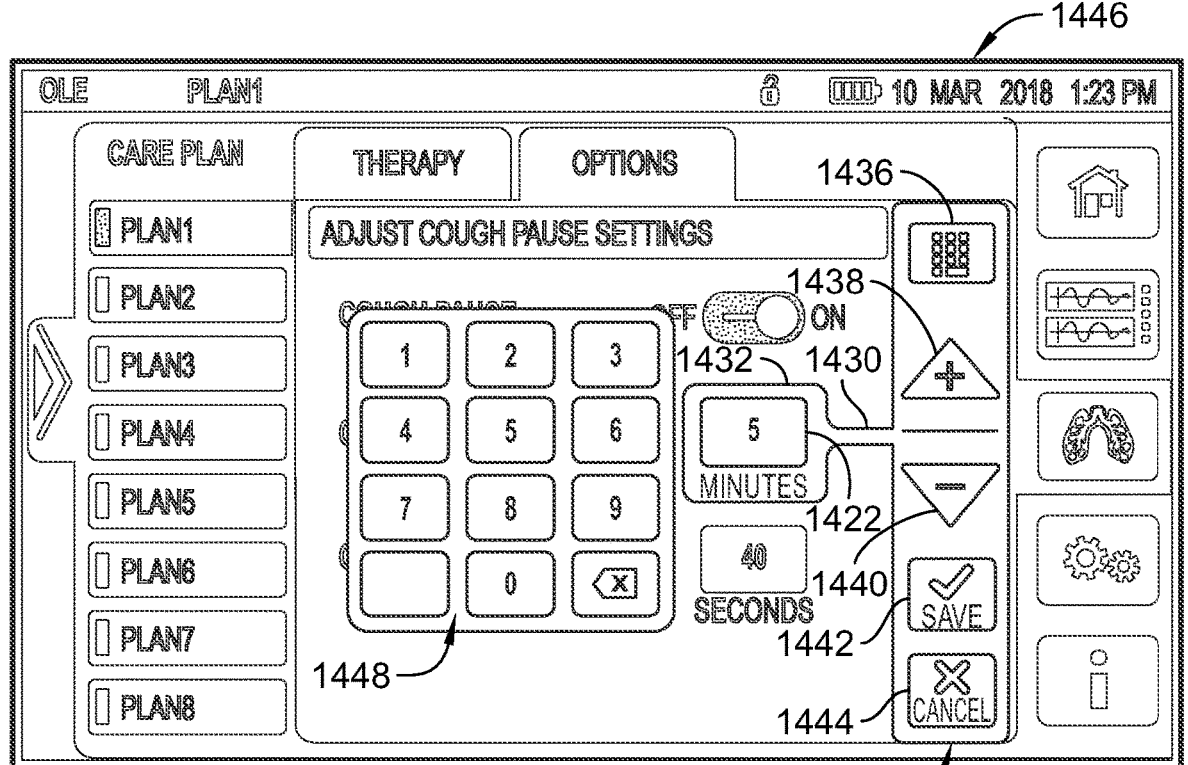
Figure 144:
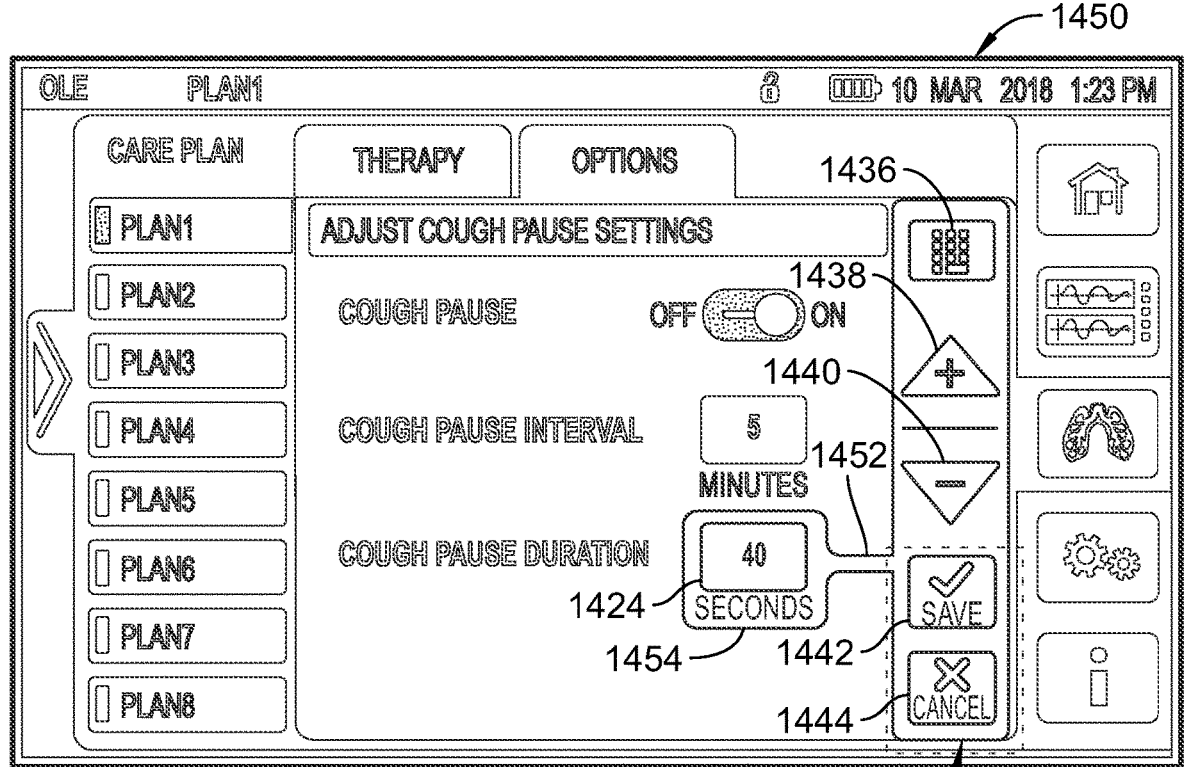
Figure 145:
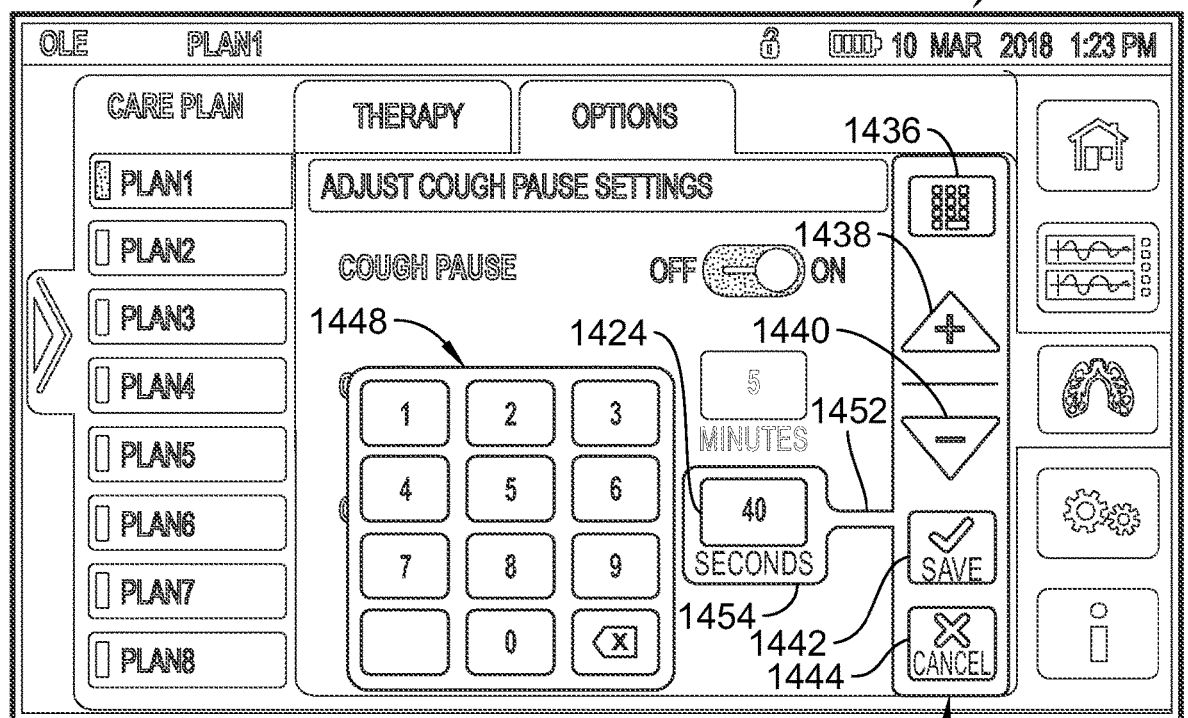
Figure 146:
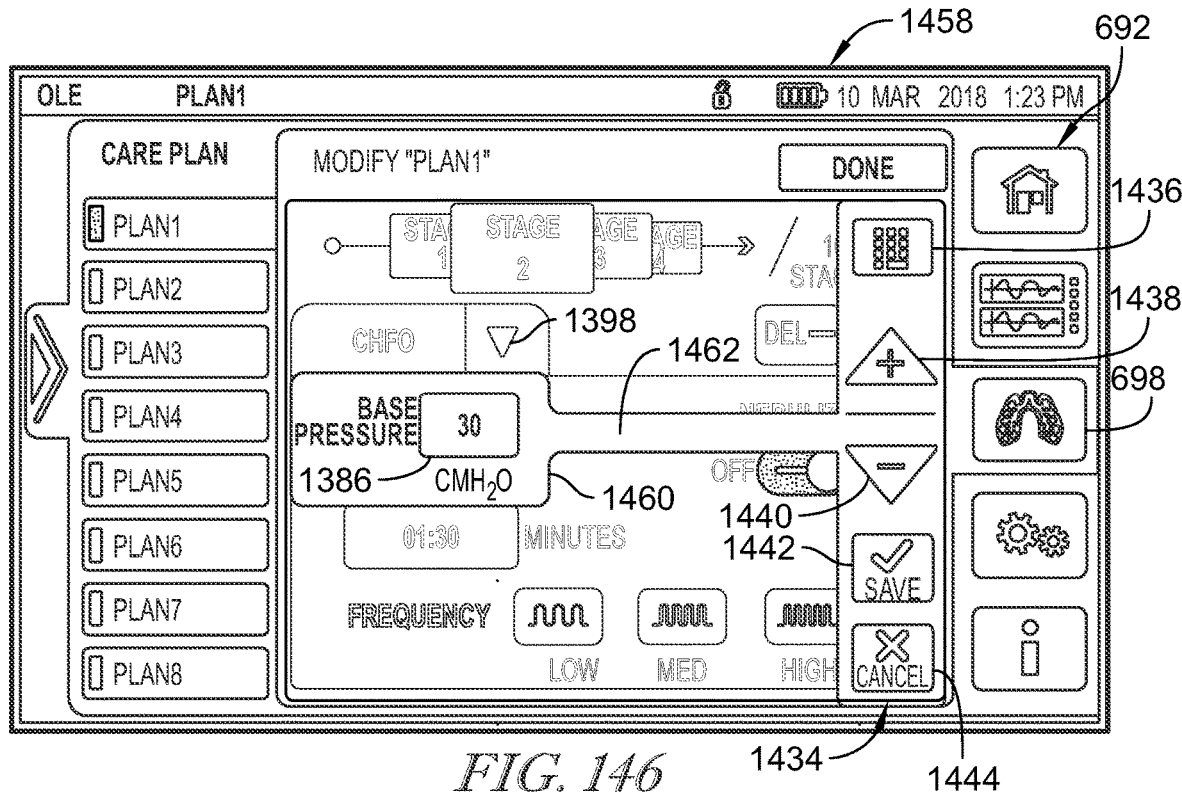
Figure 147:
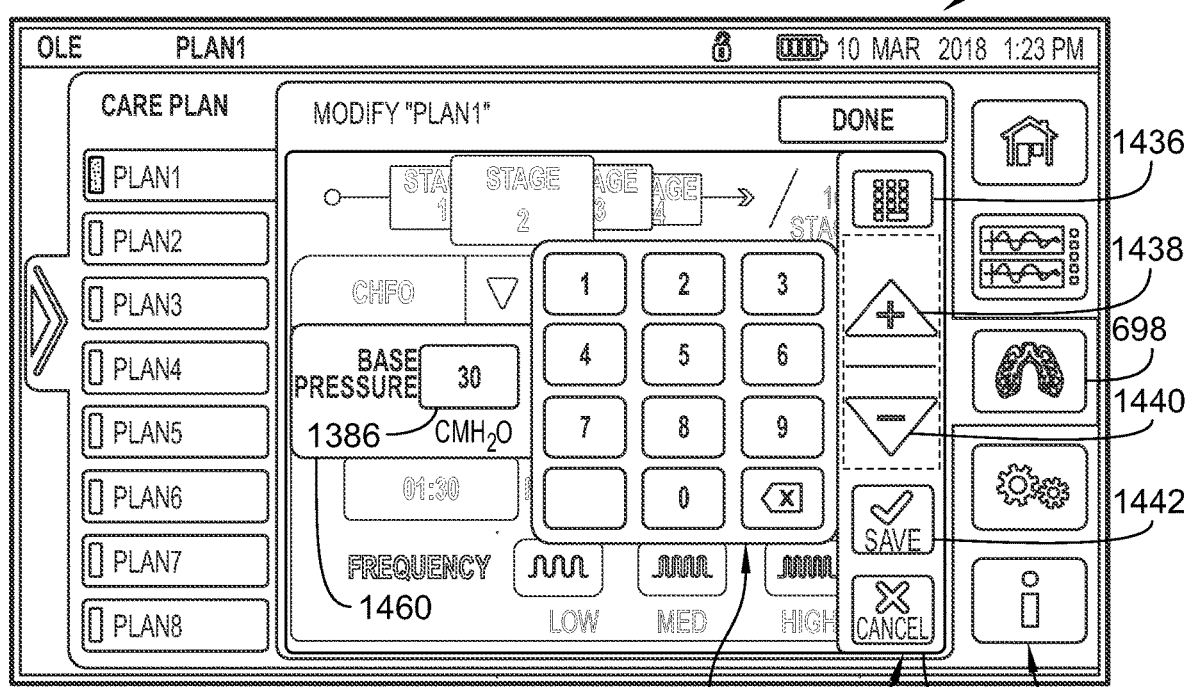
Figure 148:
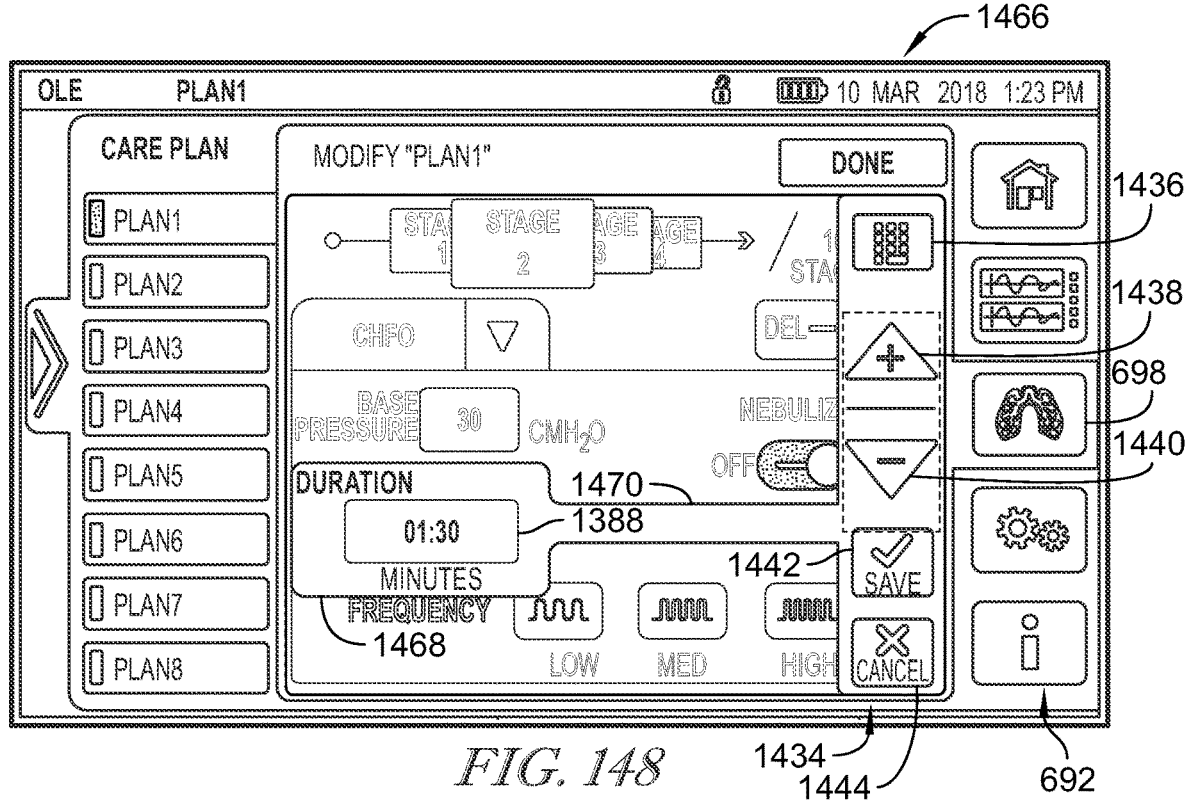
Figure 149:
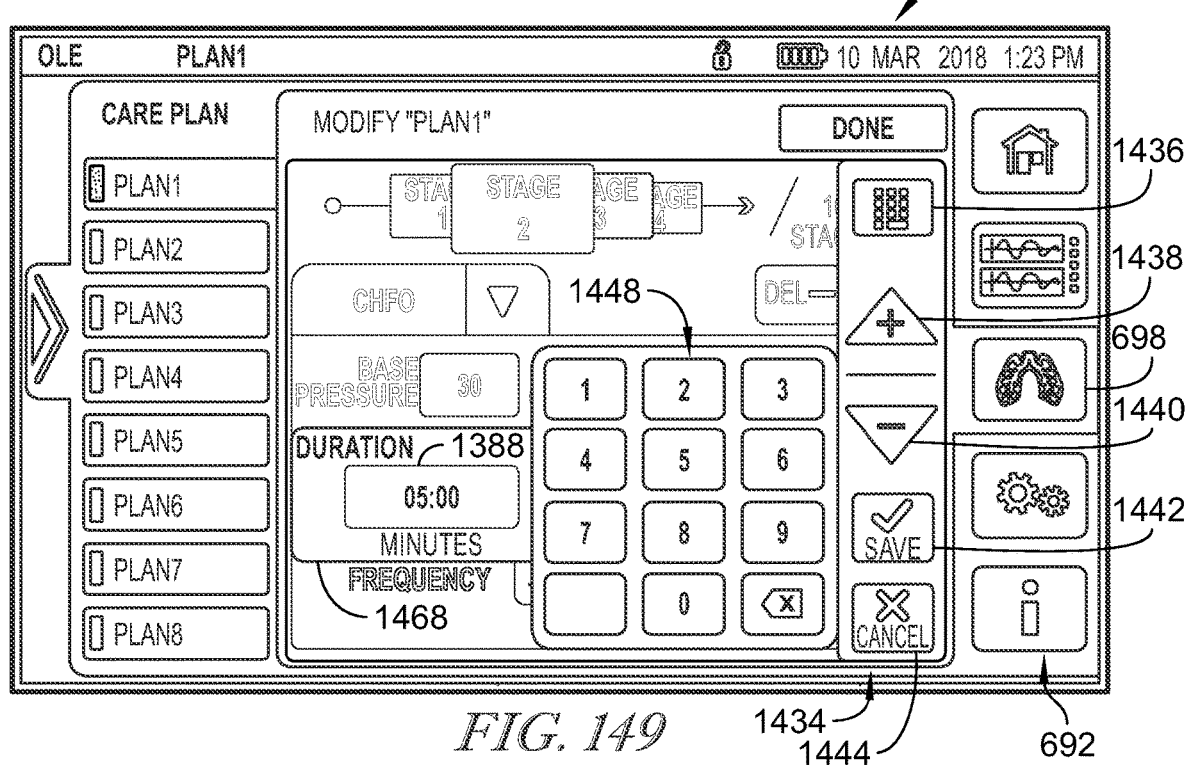
Figure 150:
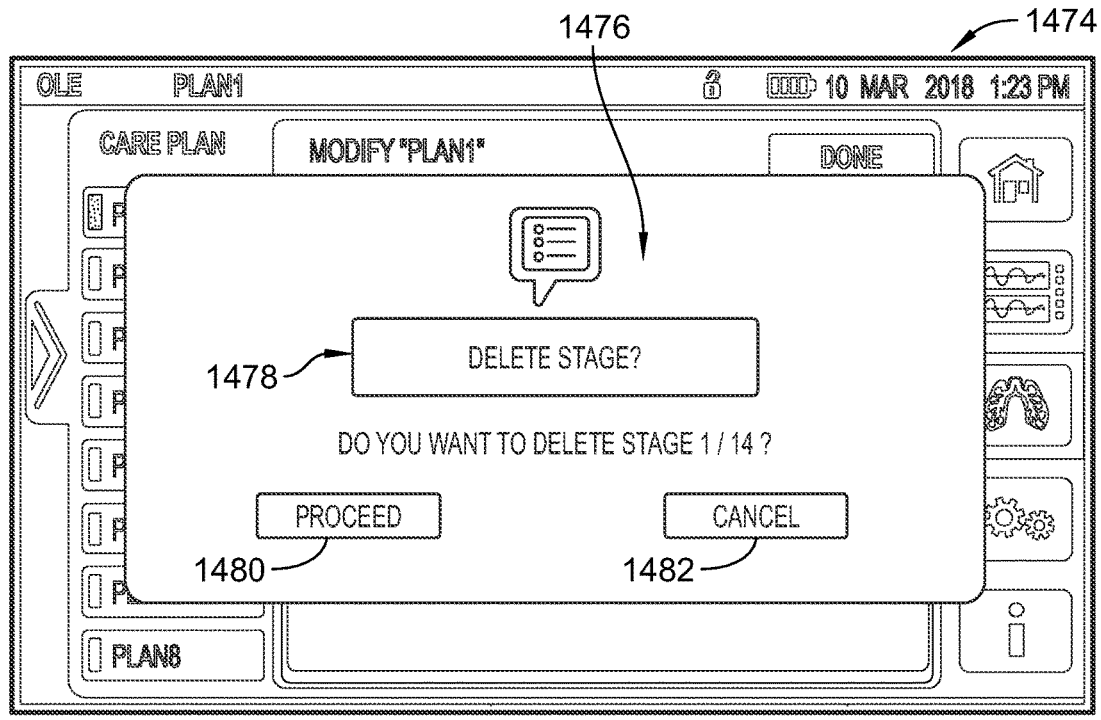
Figure 151:
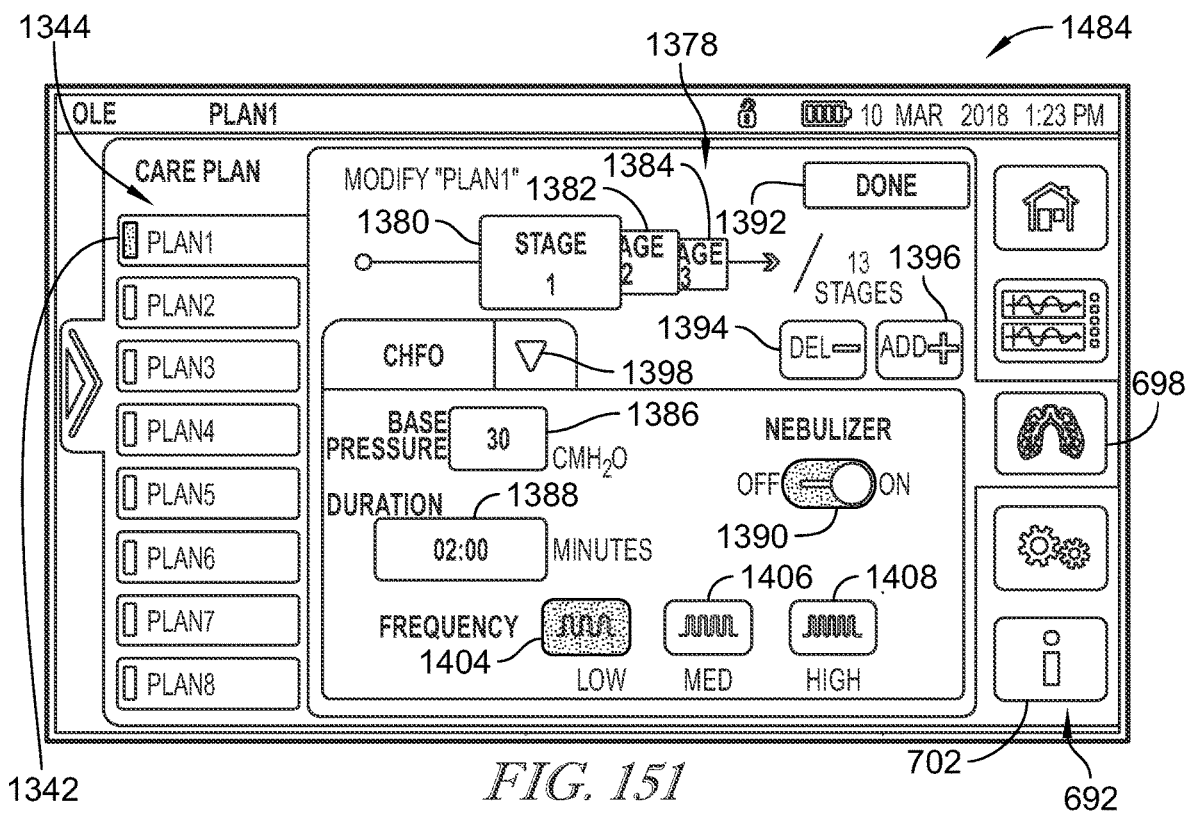
Figure 152:
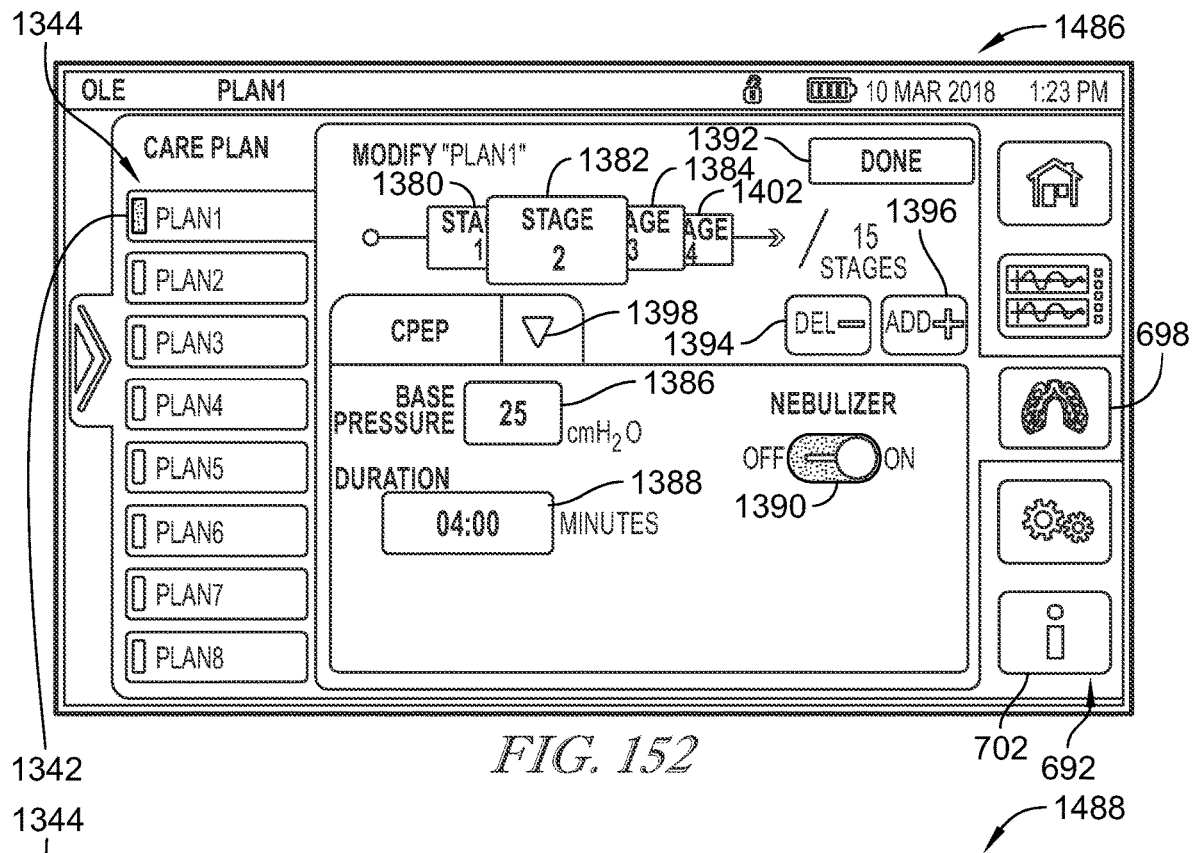
Figure 153:
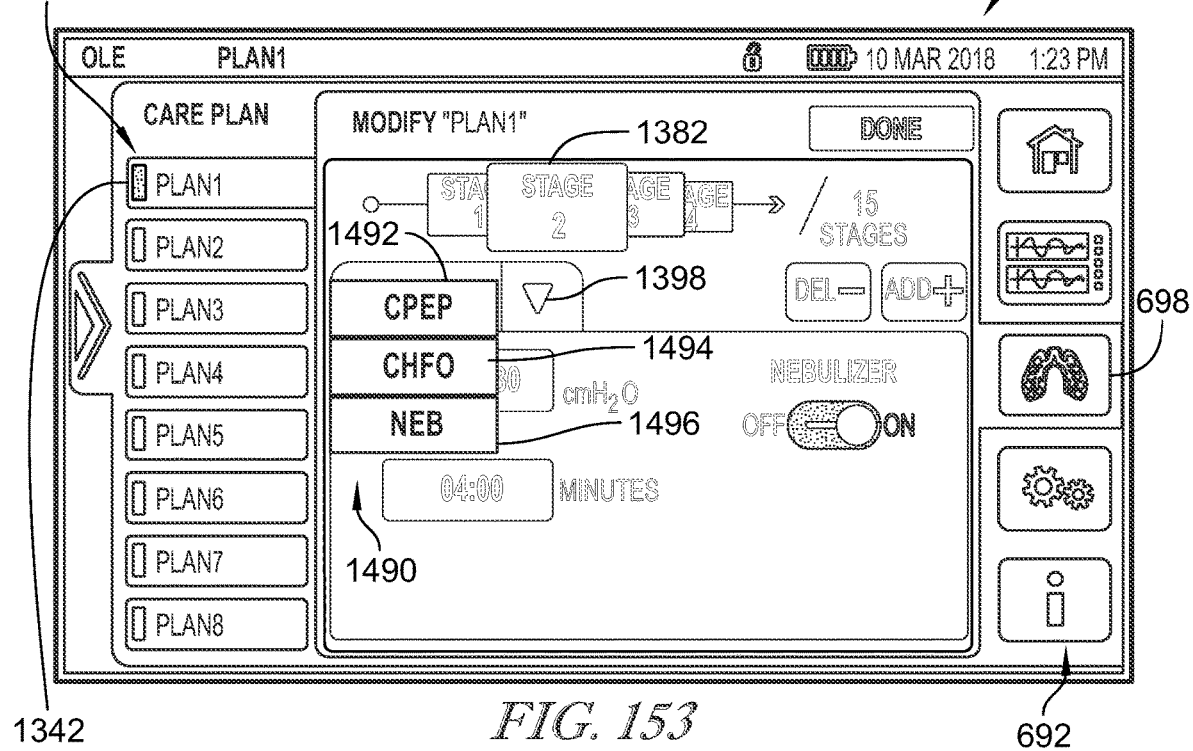
Figure 154:
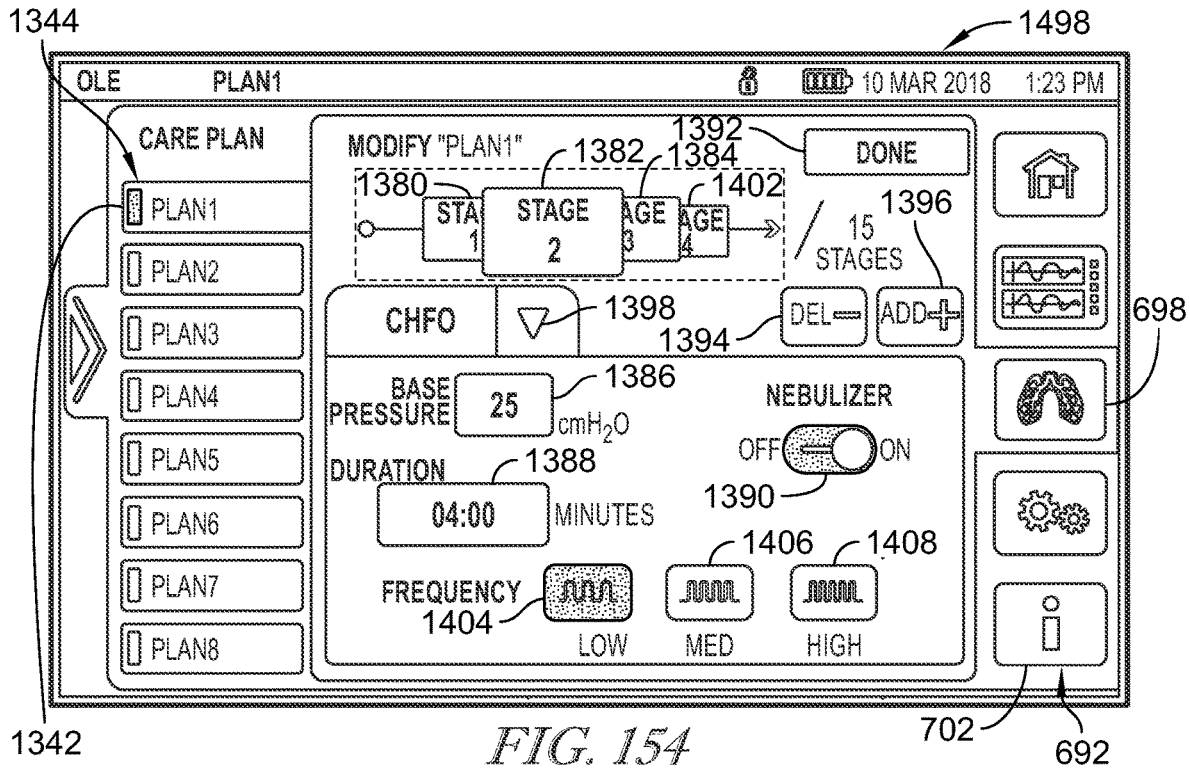
Figure 155:
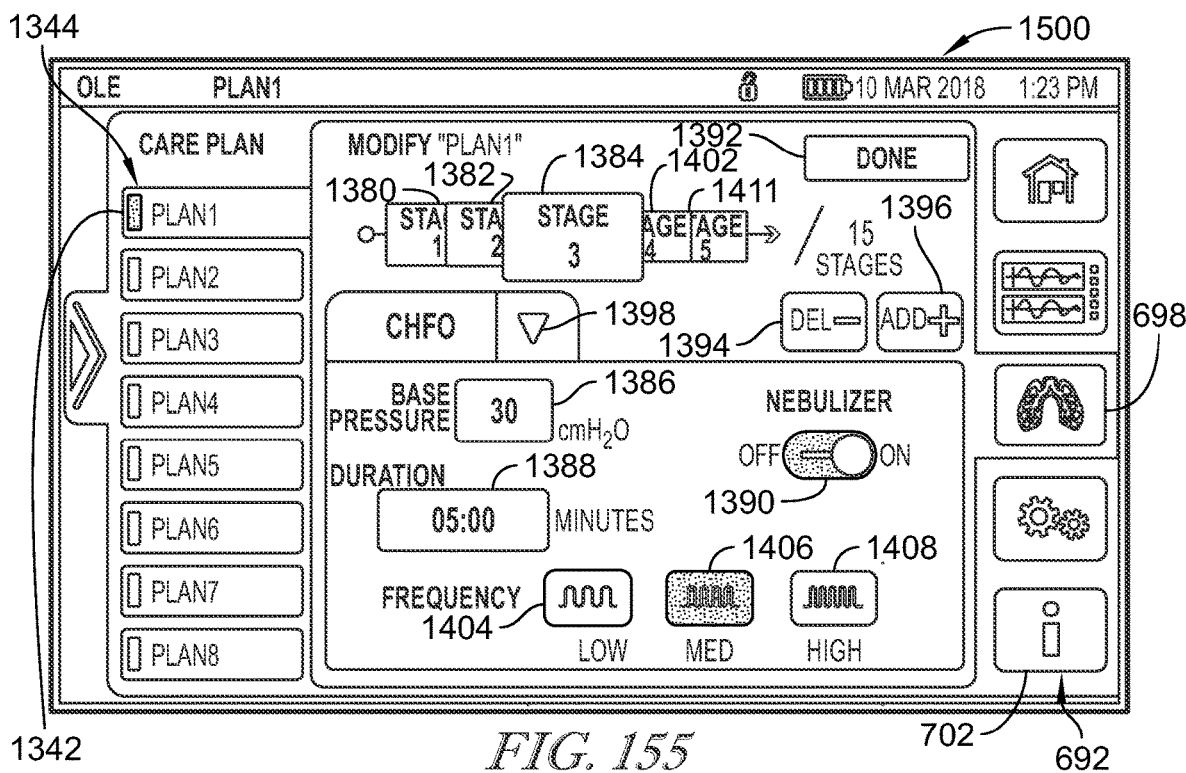
Figure 156:
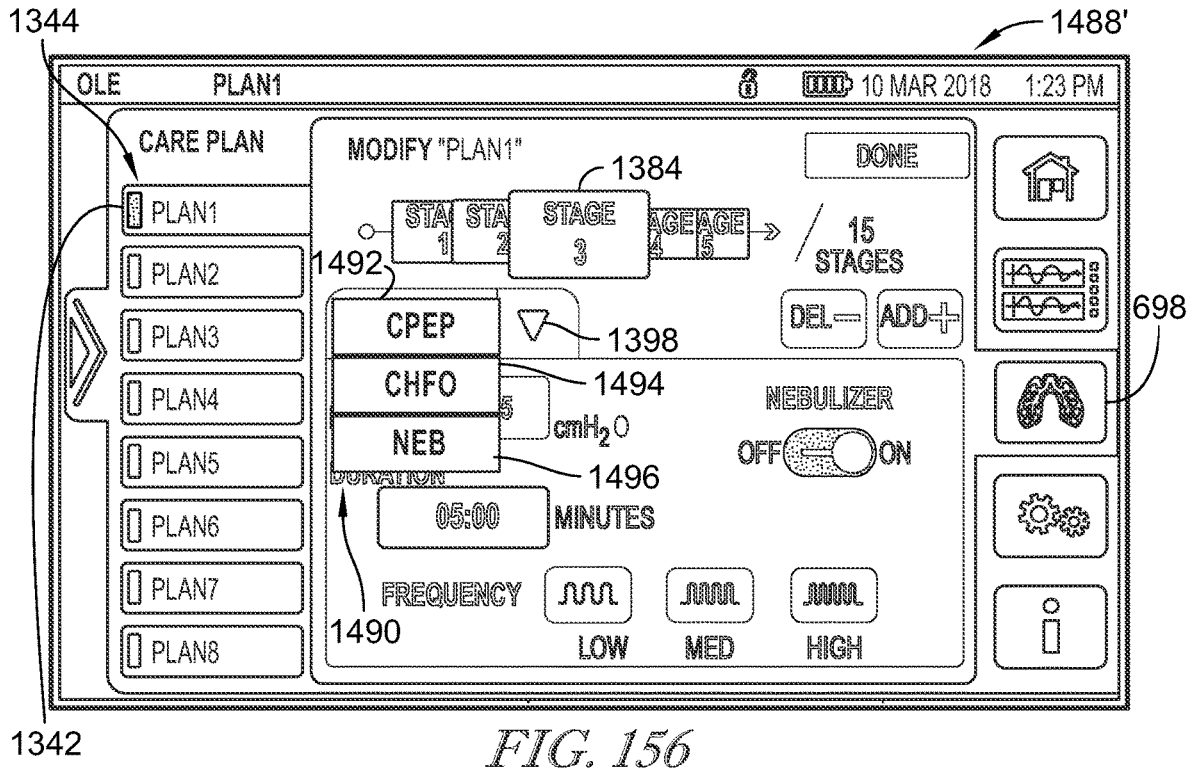
Figure 157:
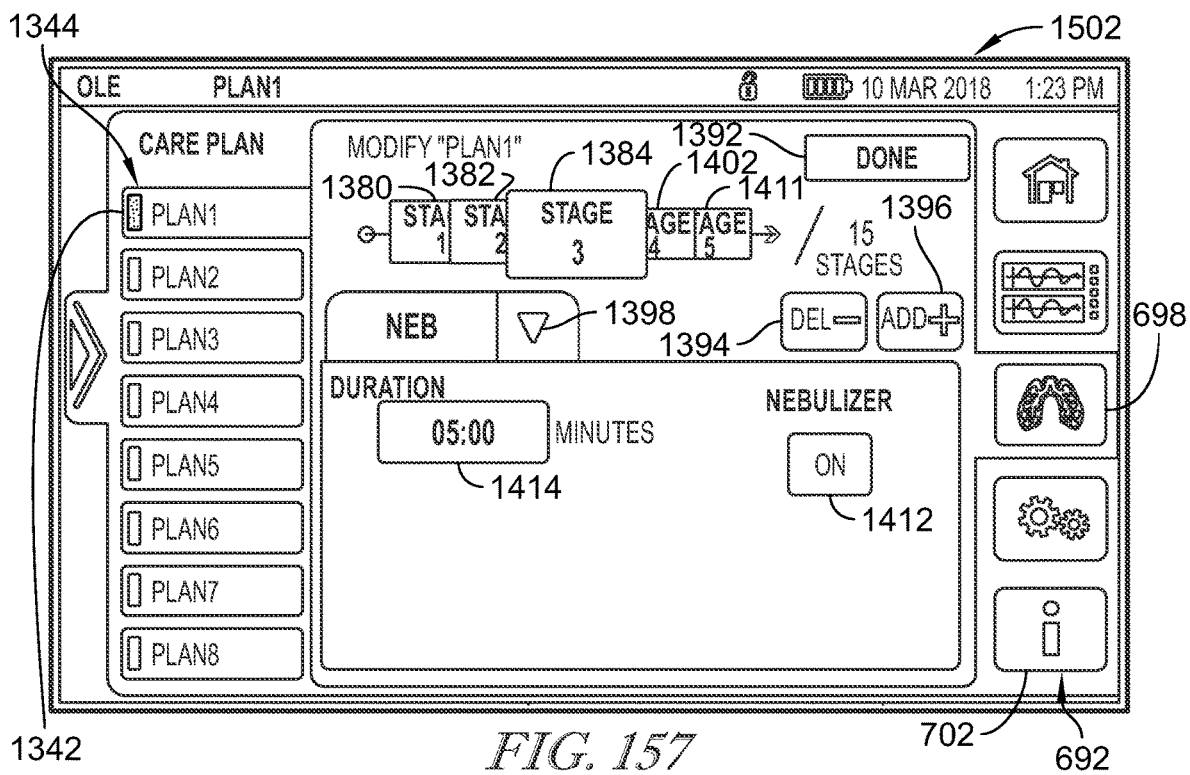
Figure 158:
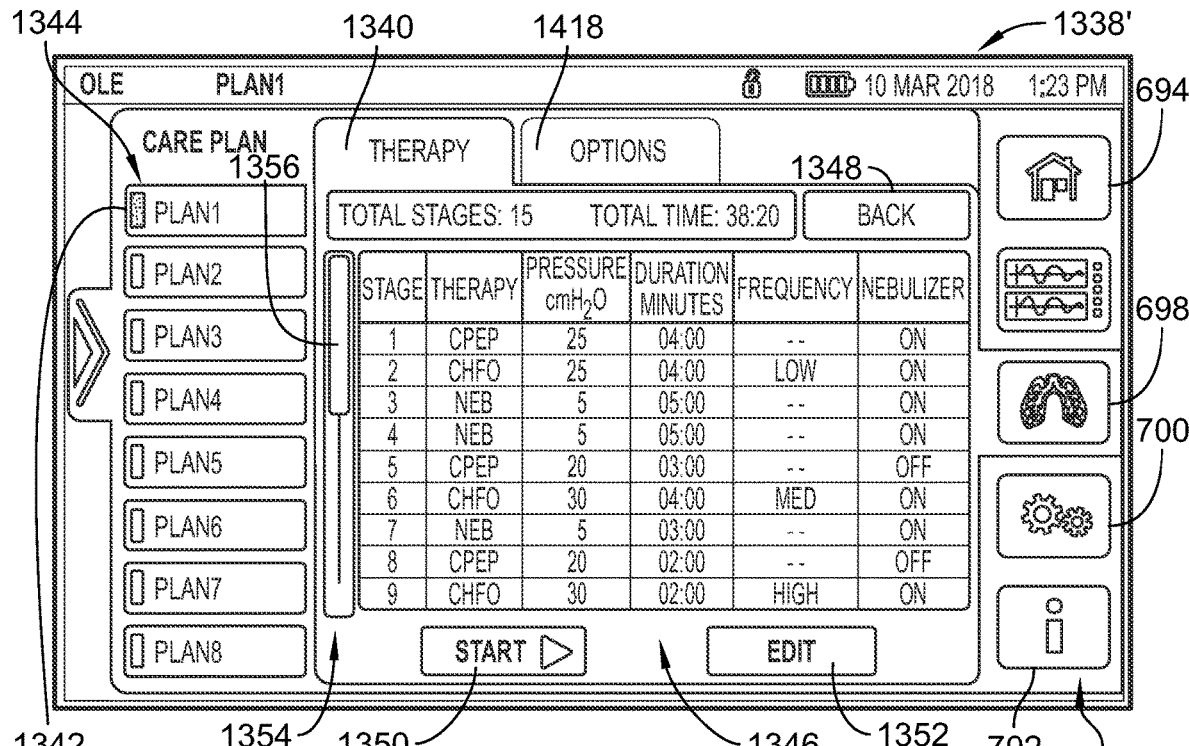
Figure 159:
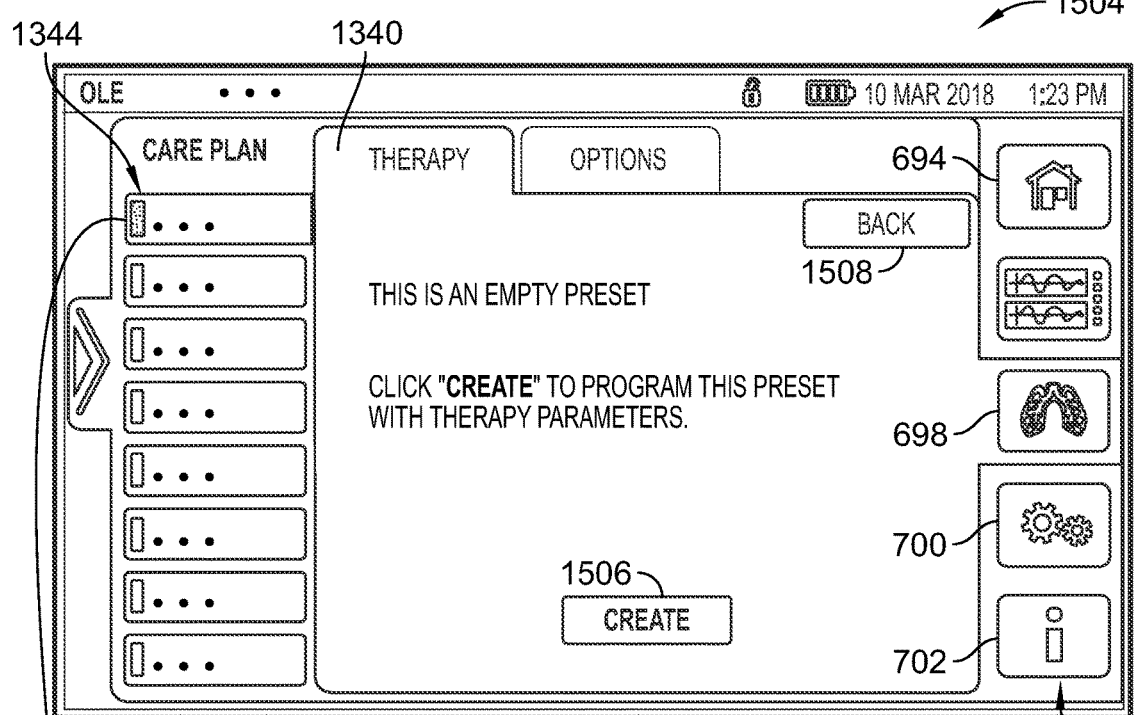
Figure 160:
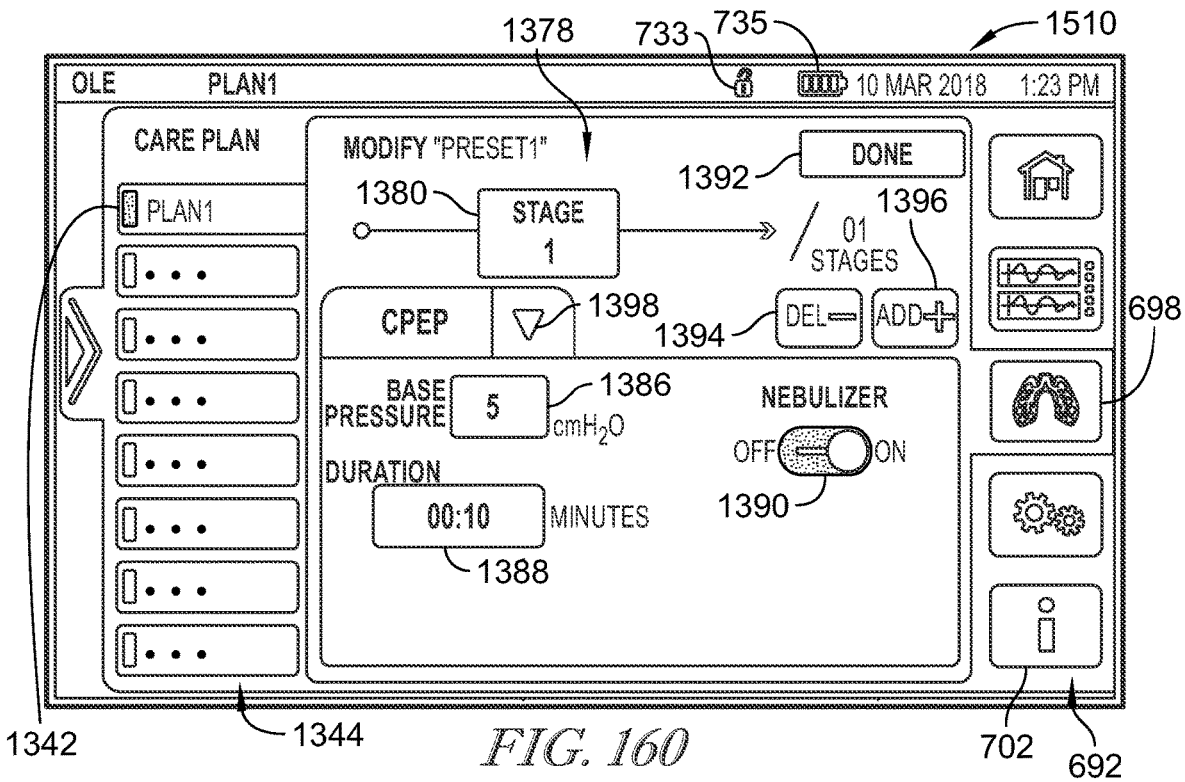
Figure 161:
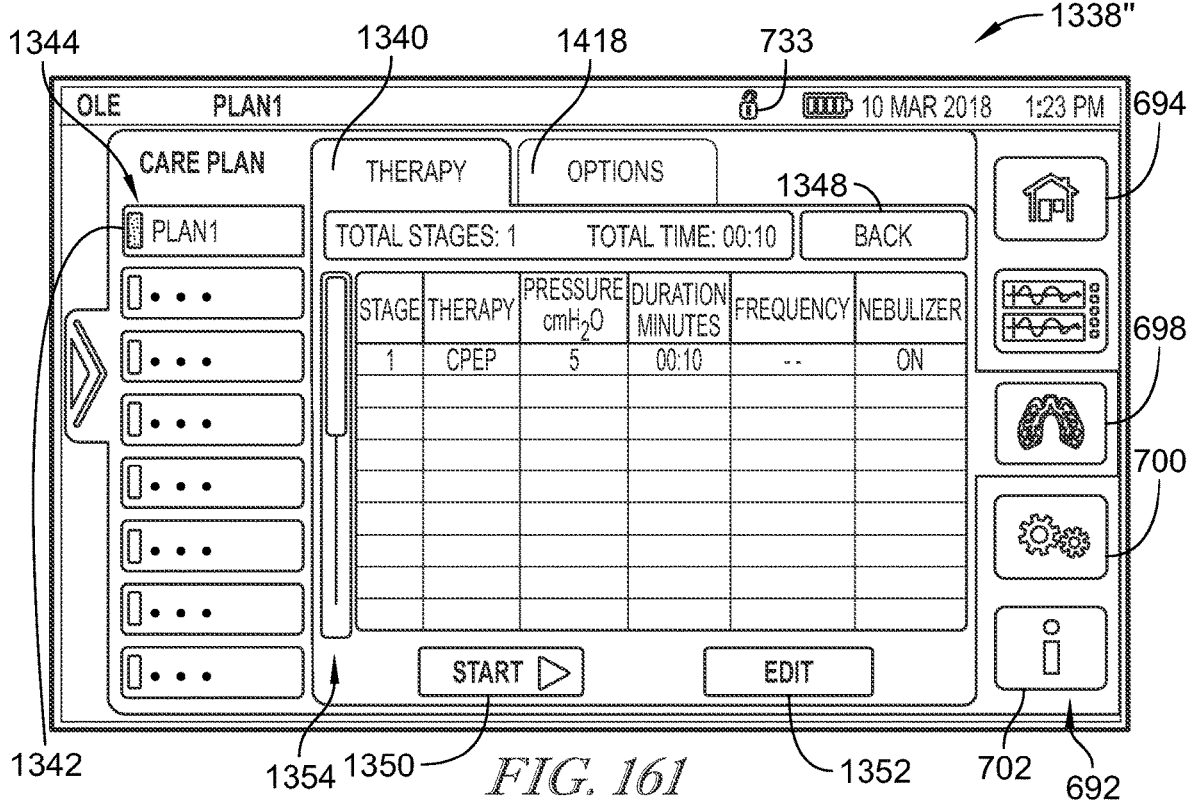
Figure 162:
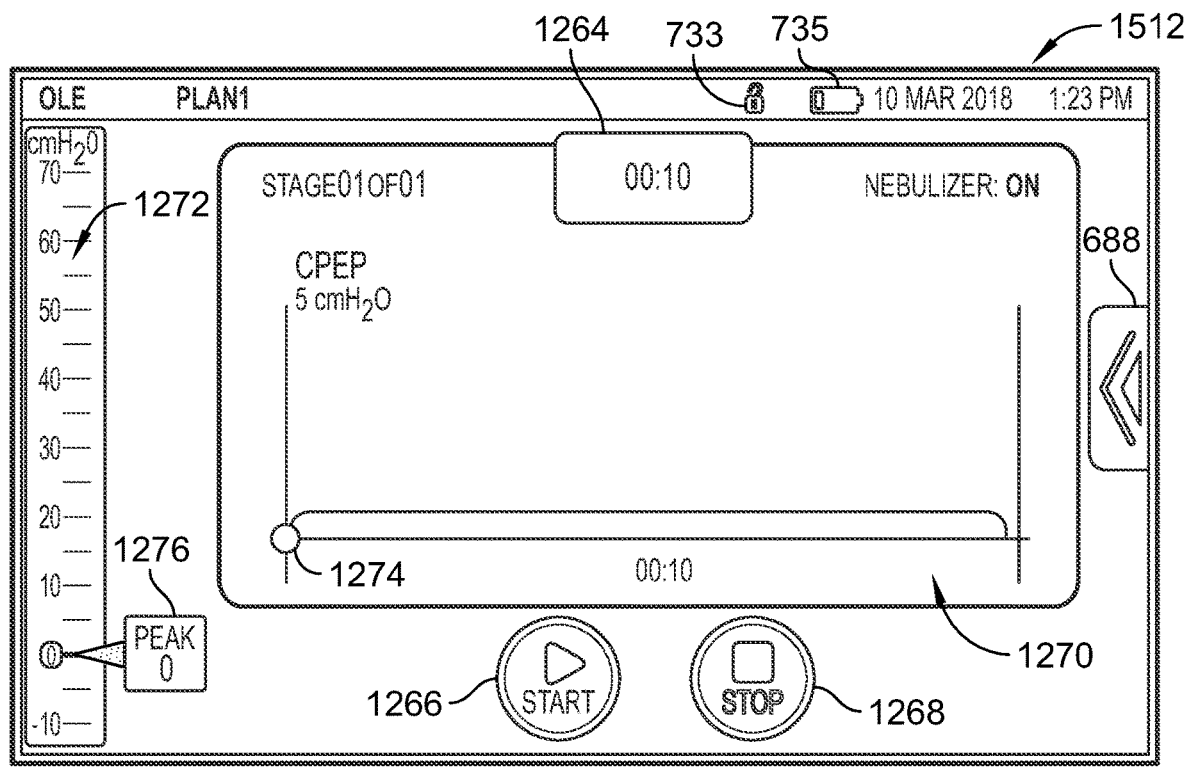
Figure 163:
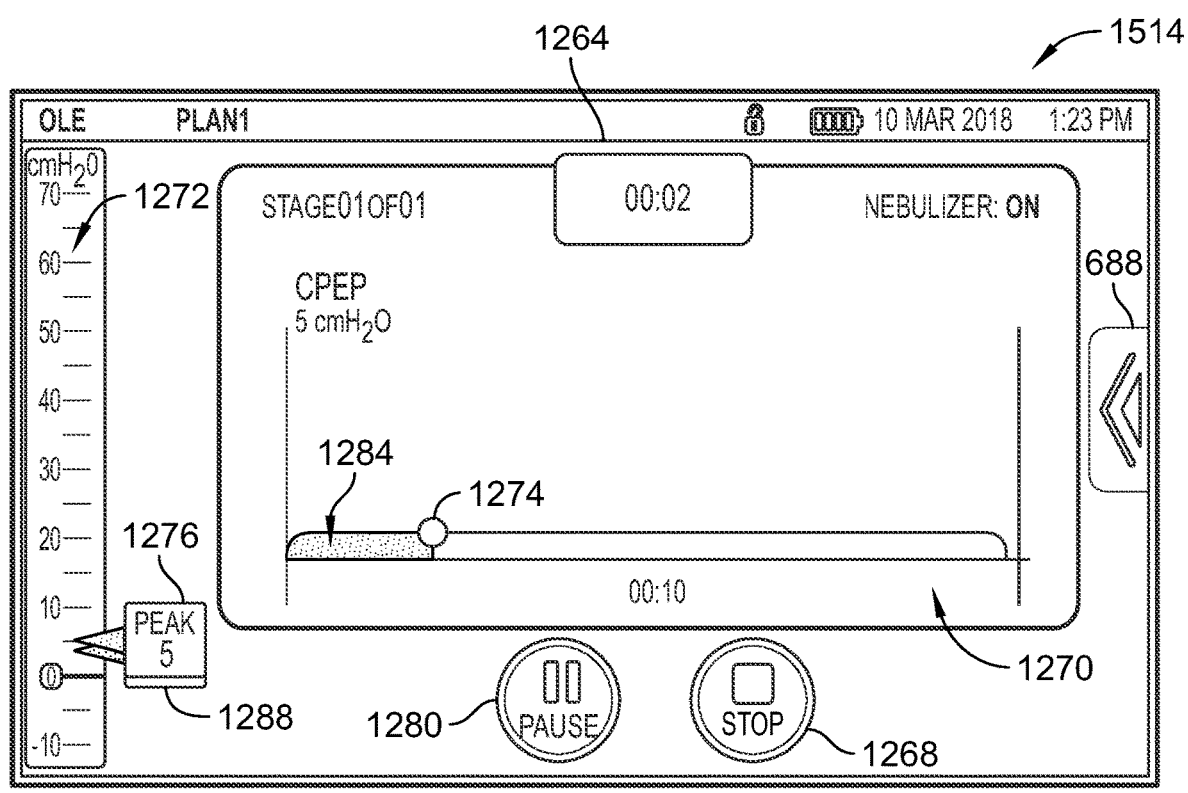
Figure 164:
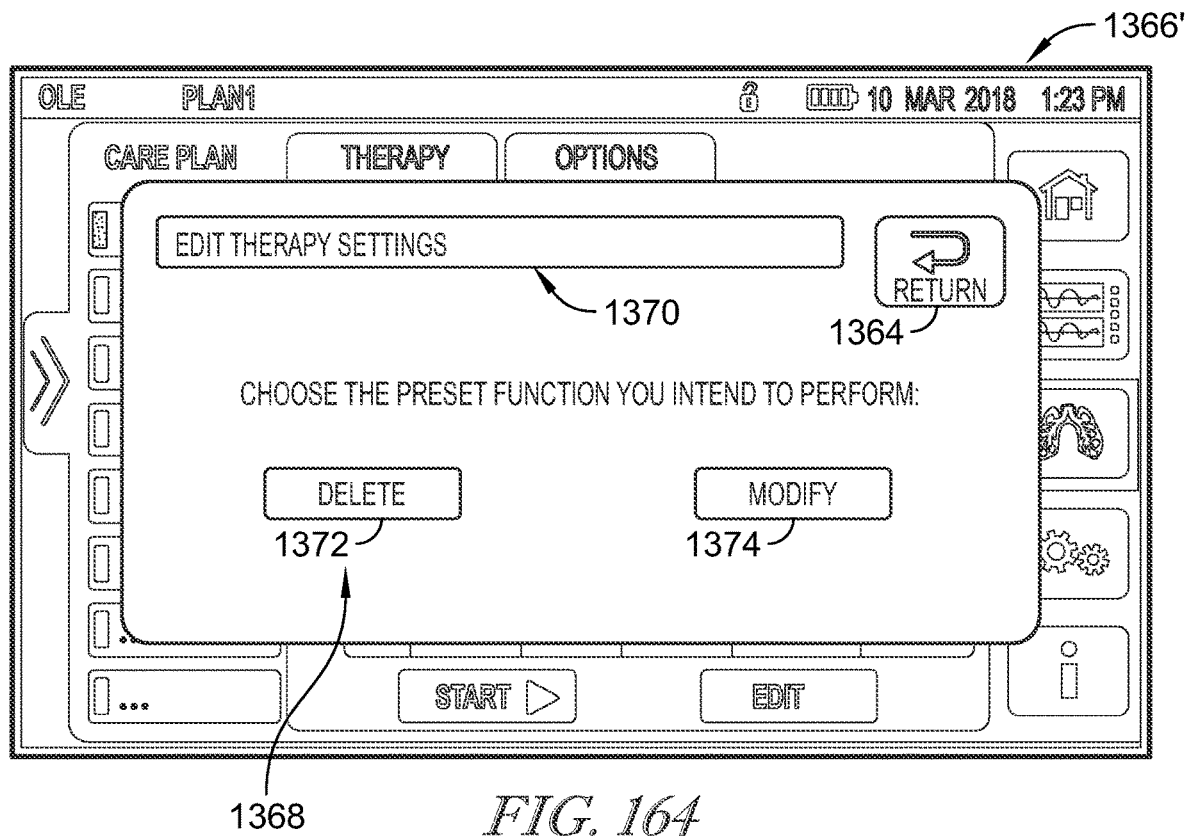
Figure 165:
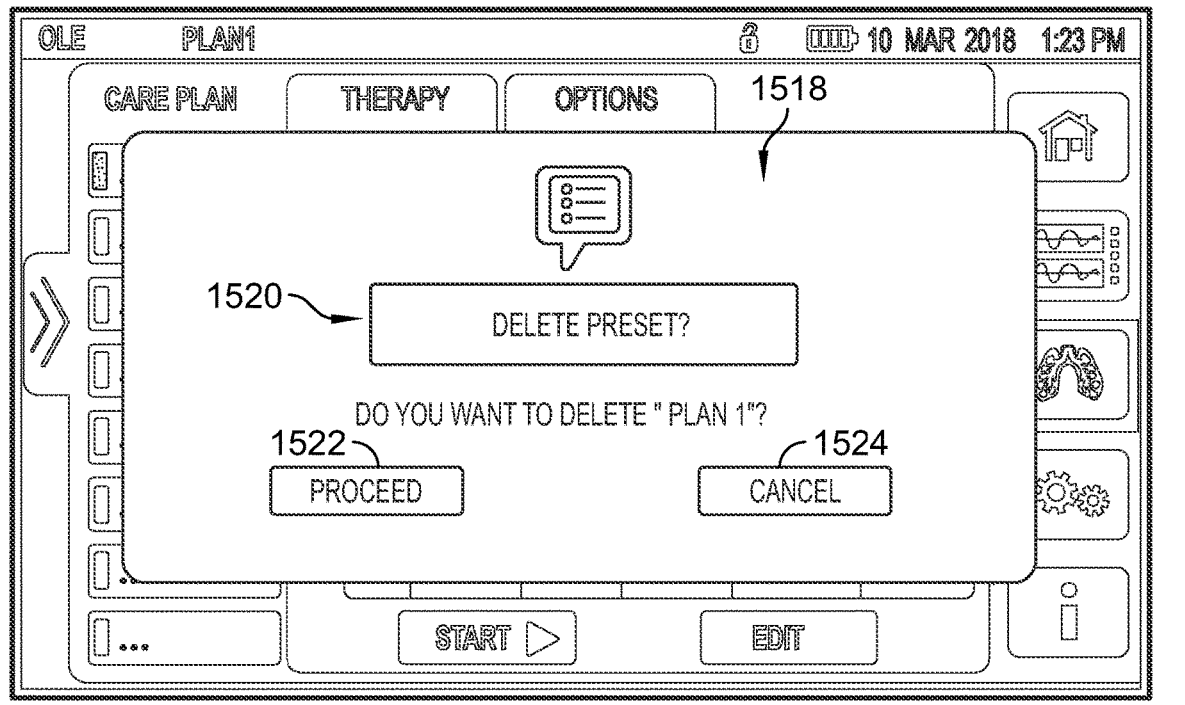
Figure 166:
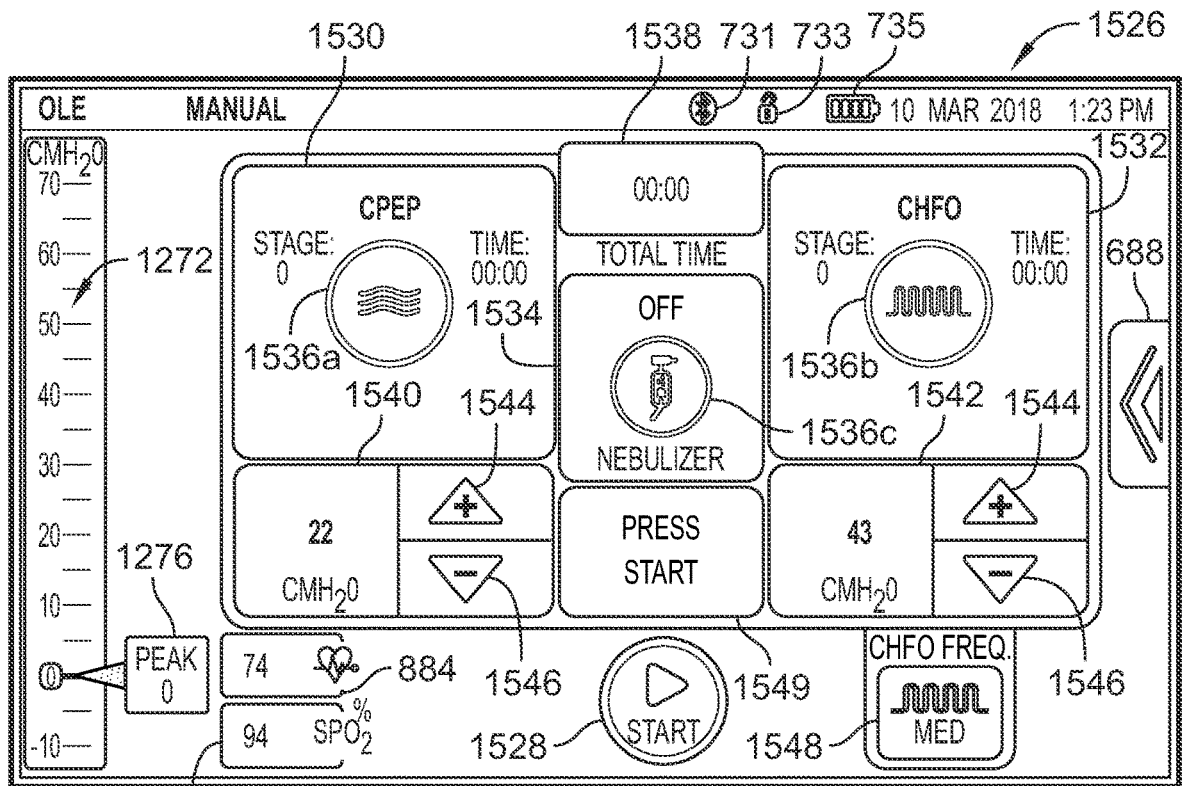
Figure 167:
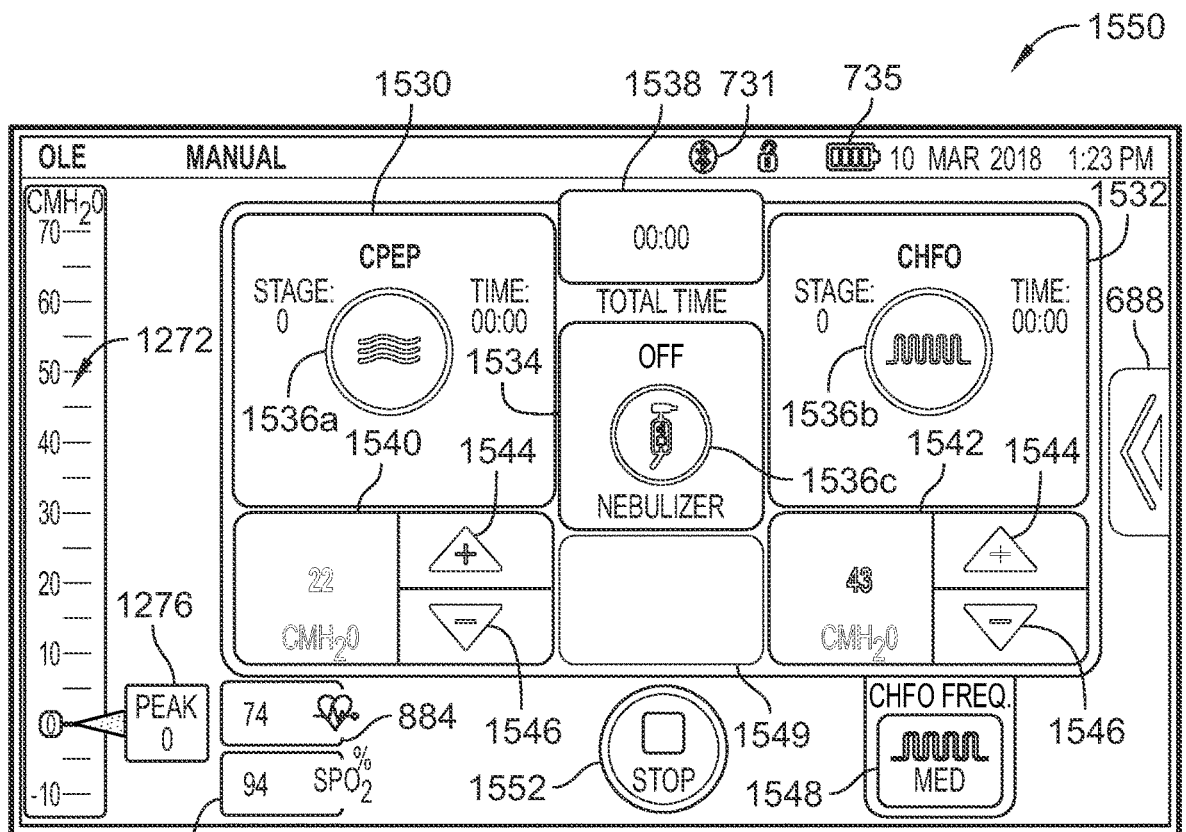
Figure 168:
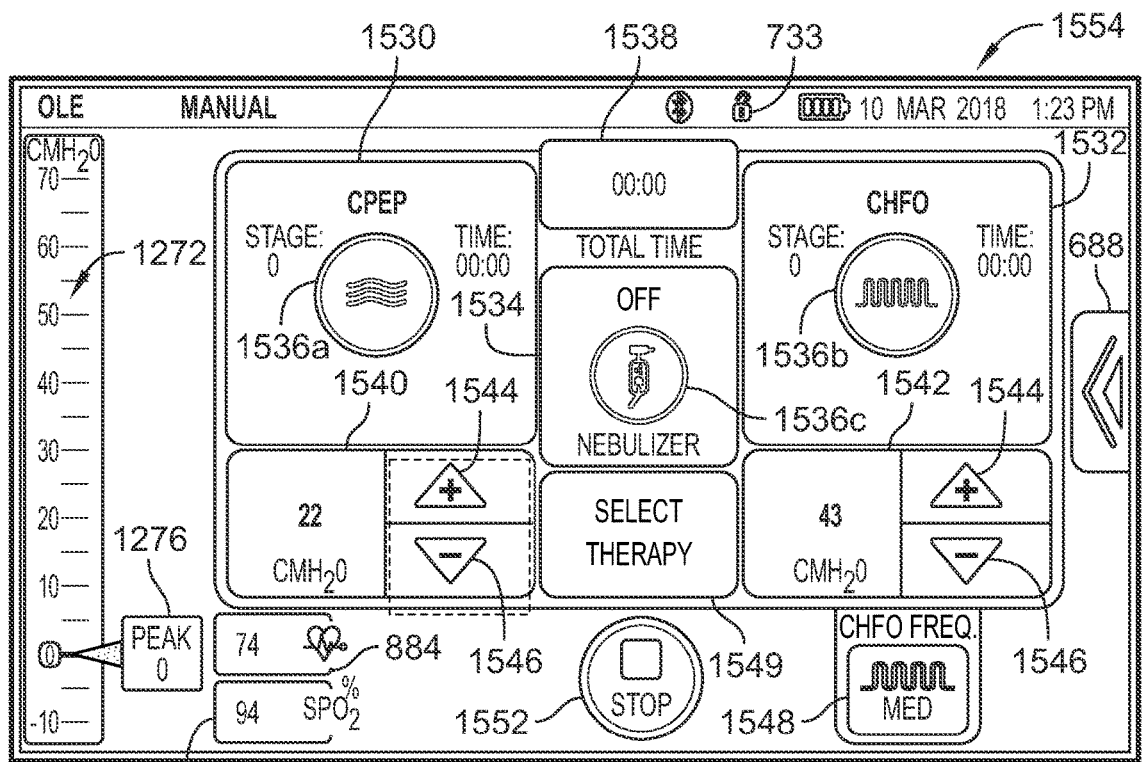
Figure 169:
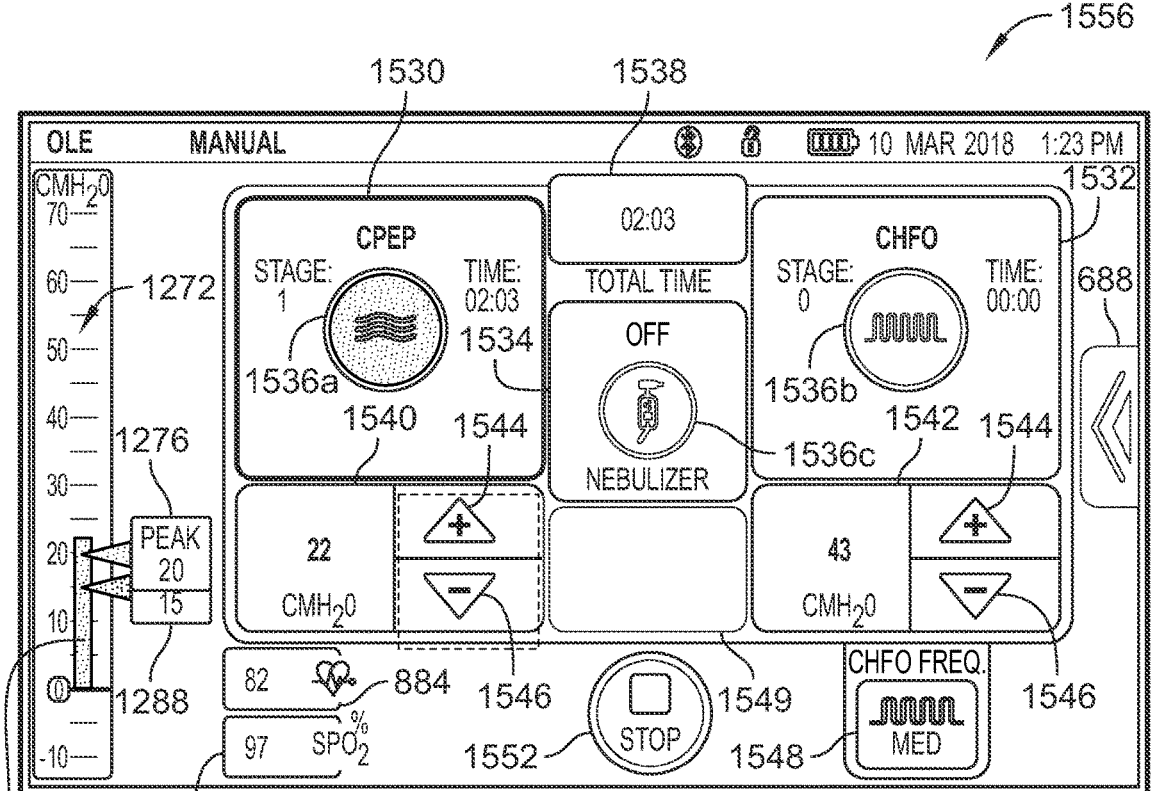
Figure 170:
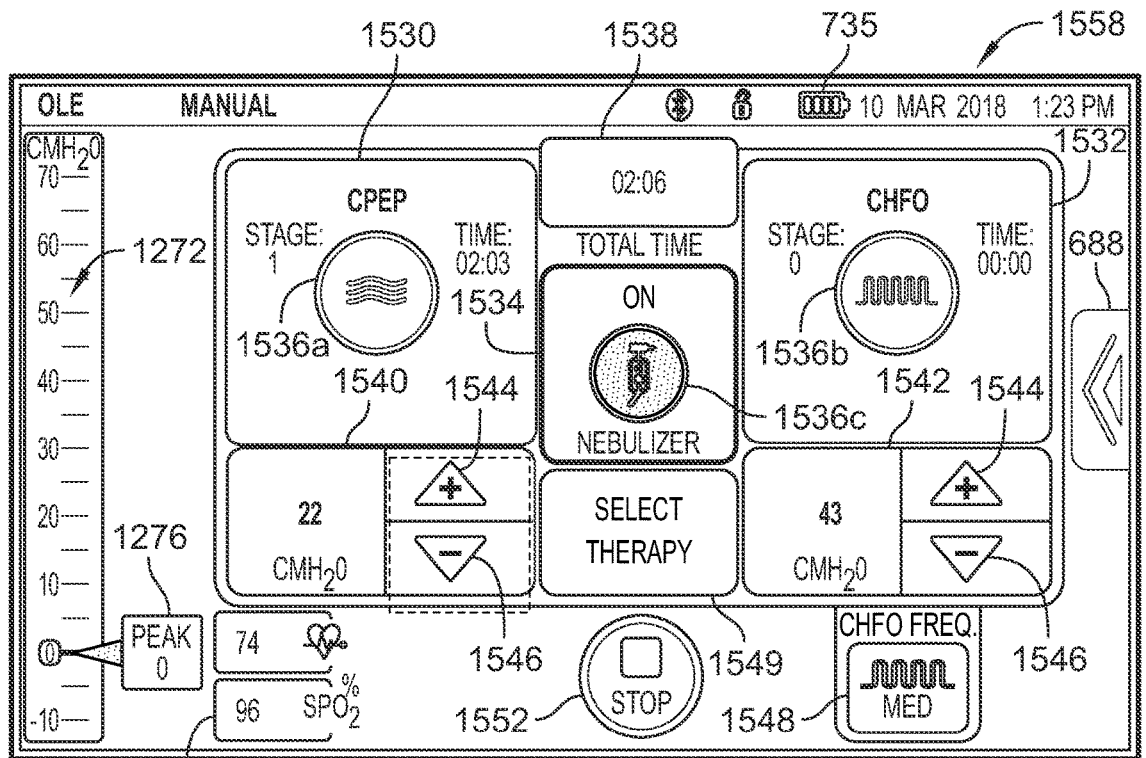
Figure 171:
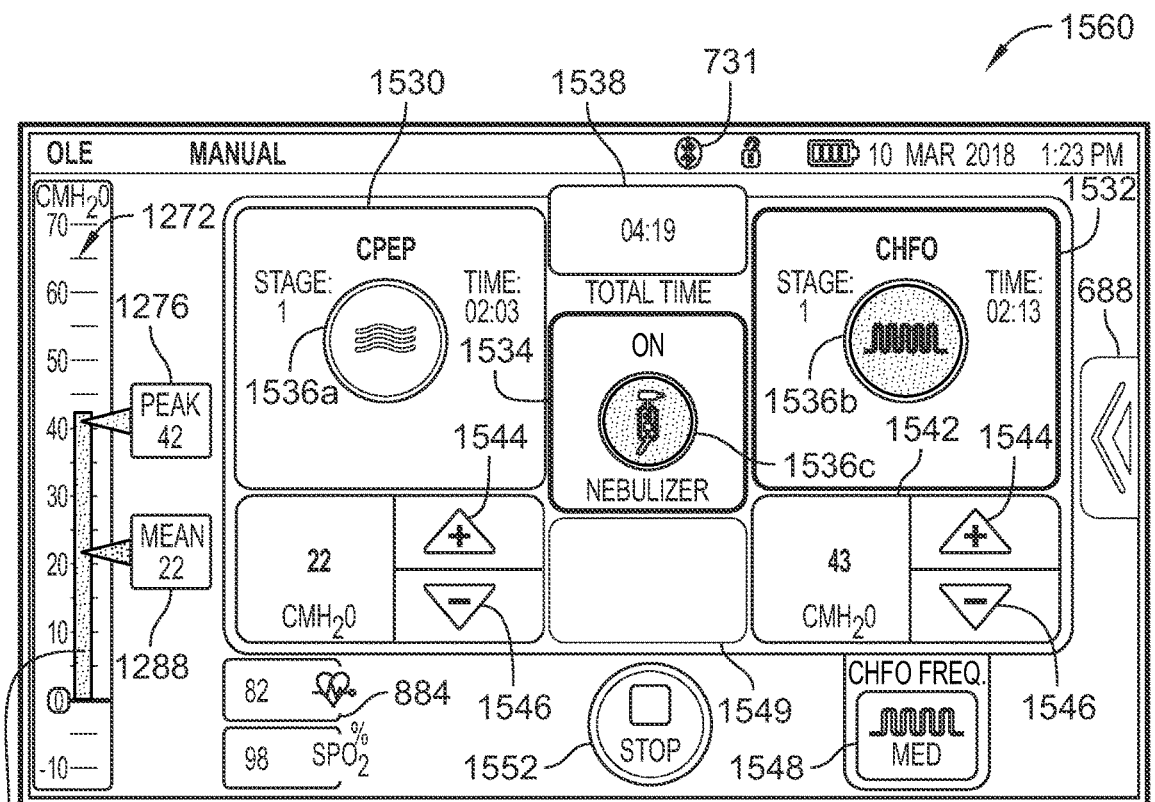
Figure 172:
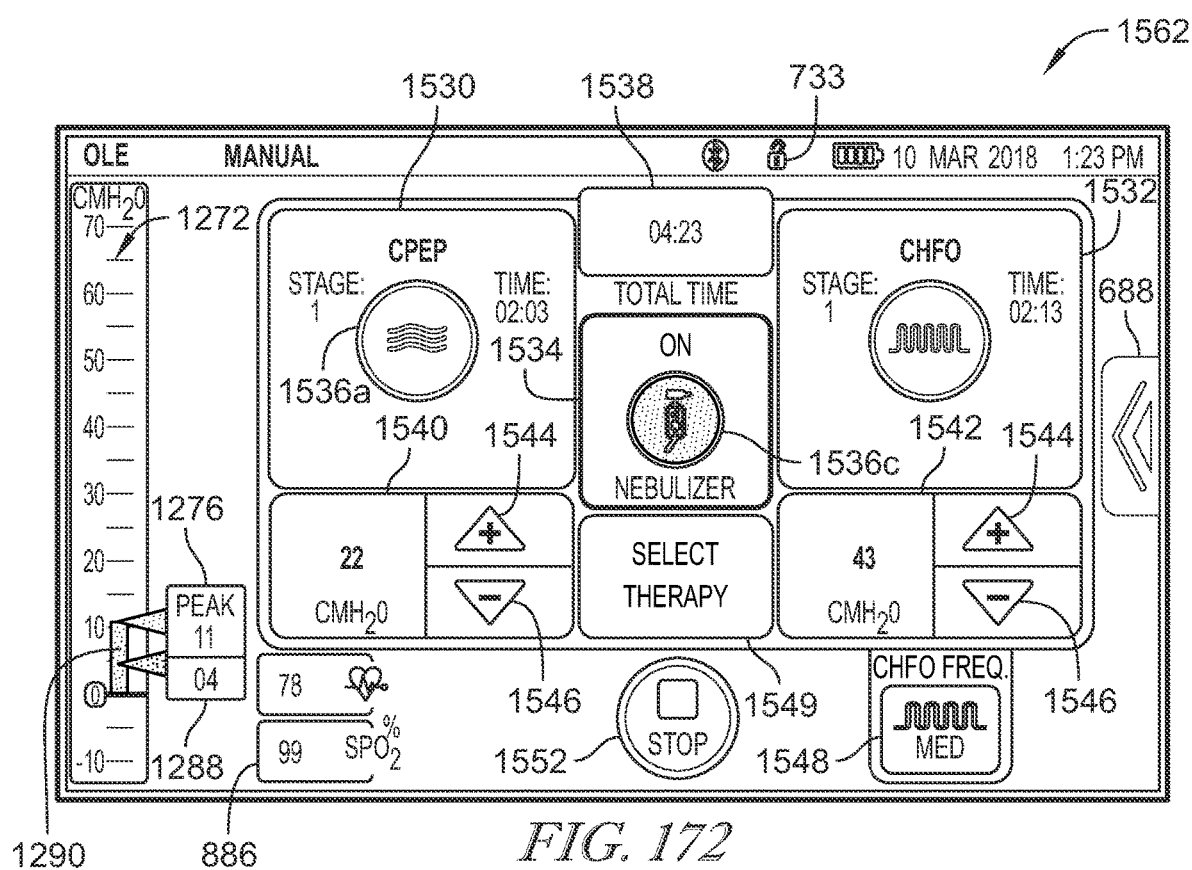
Figure 173:
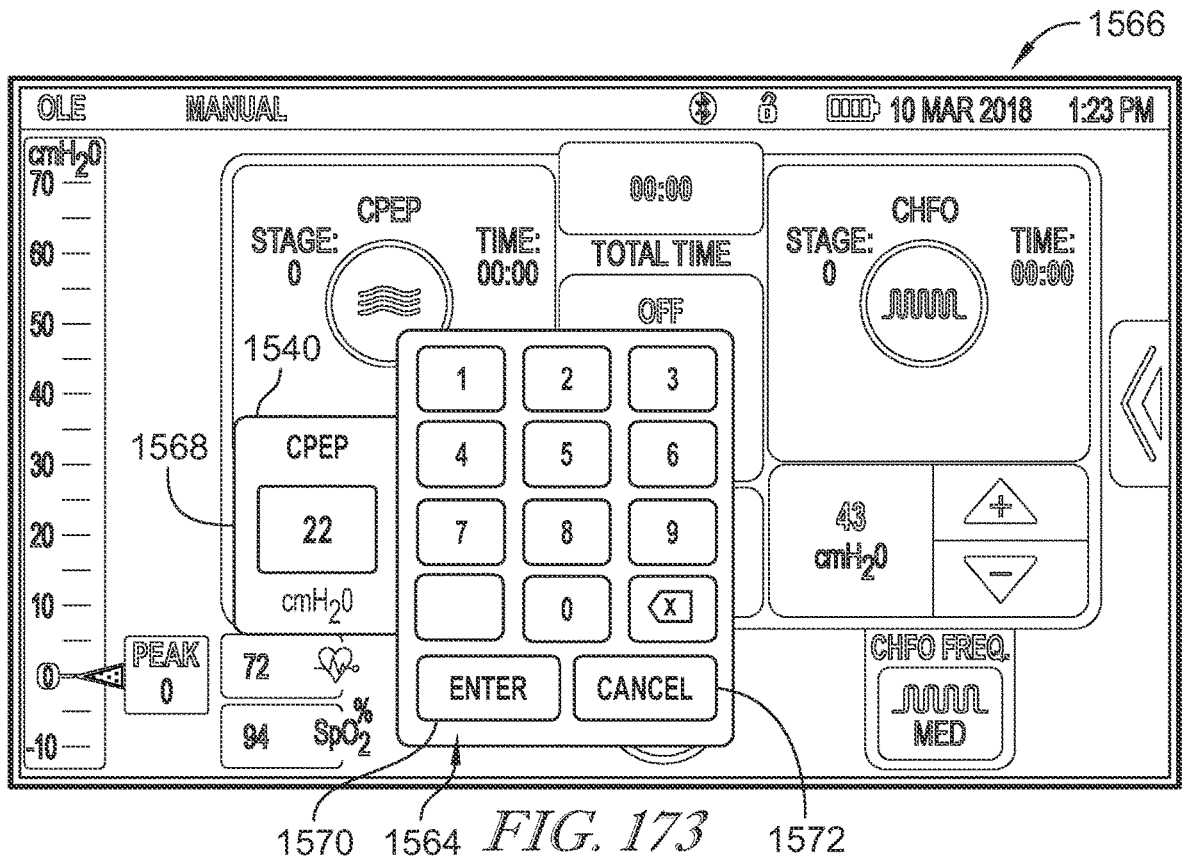
Figure 174:
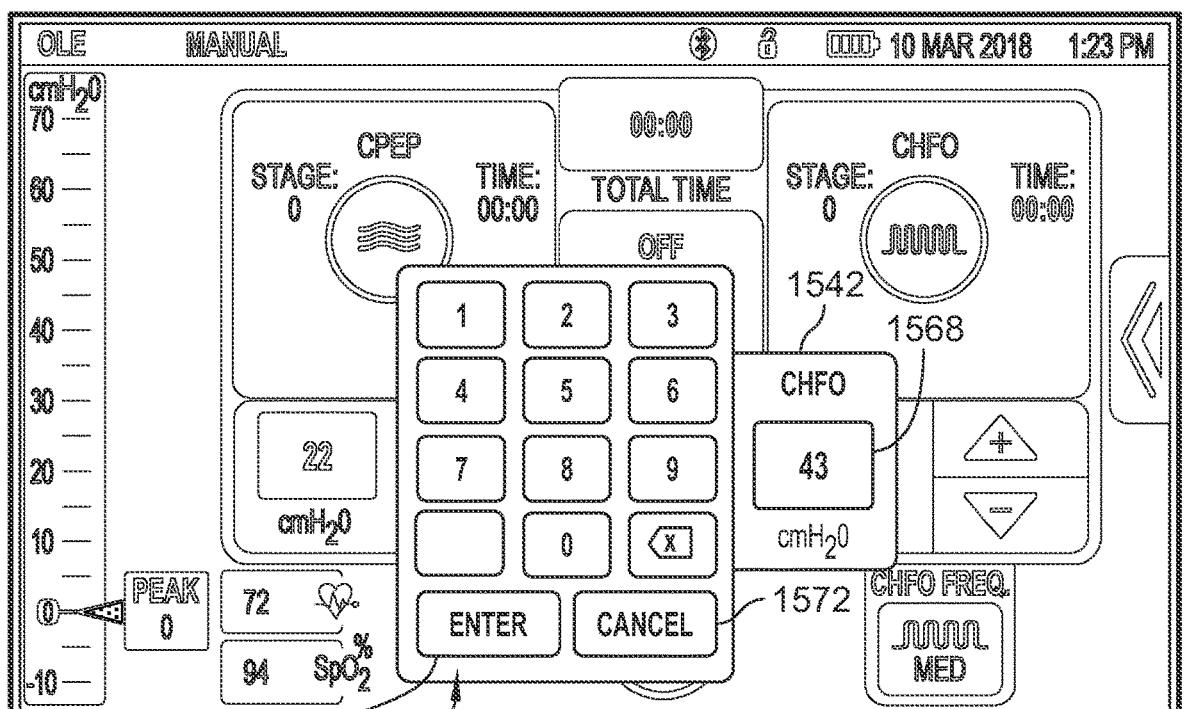
Figure 175:
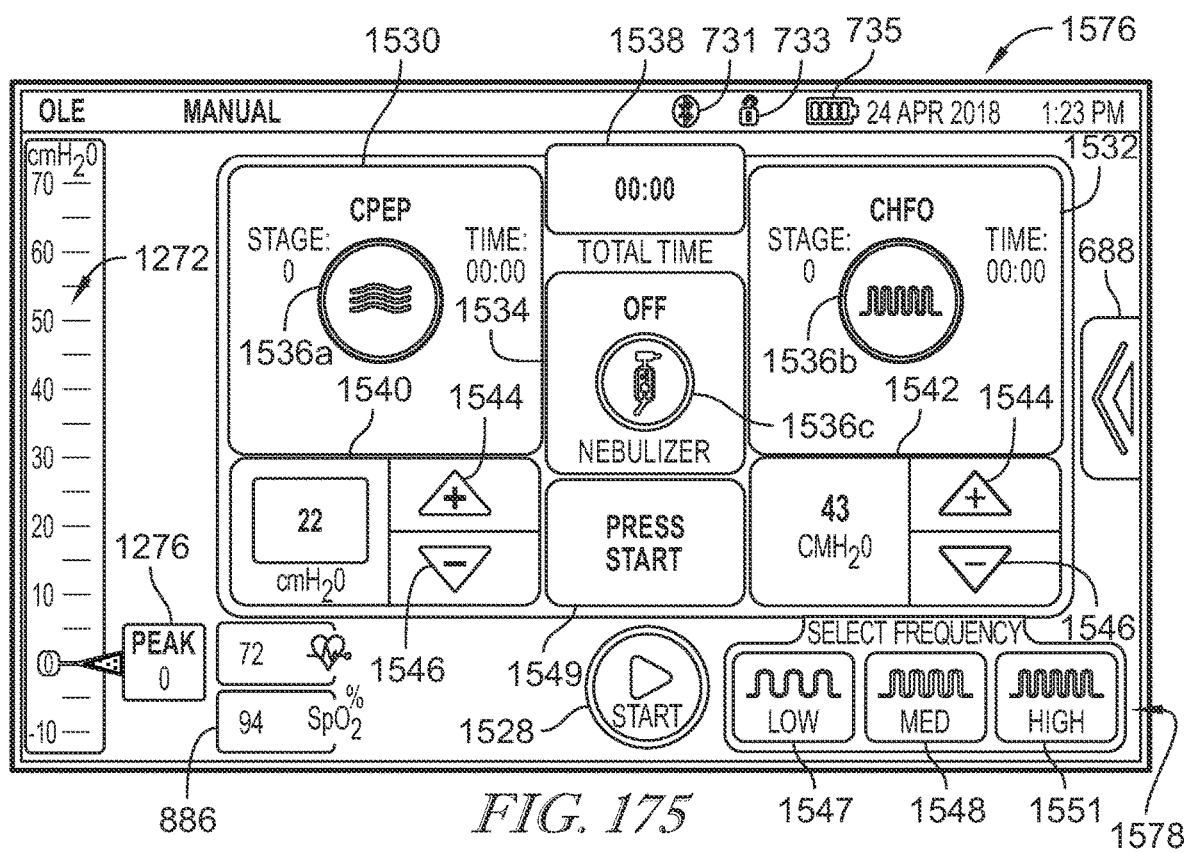
Figure 176:
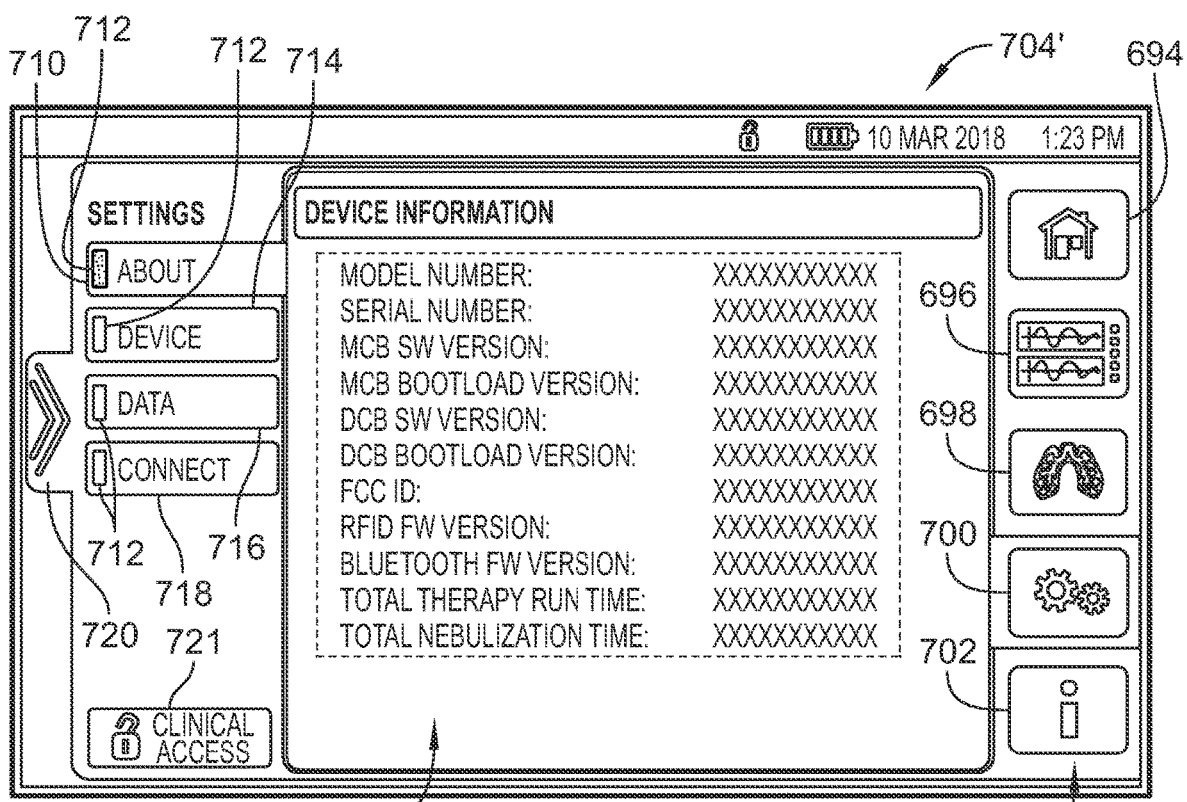
Figure 177:
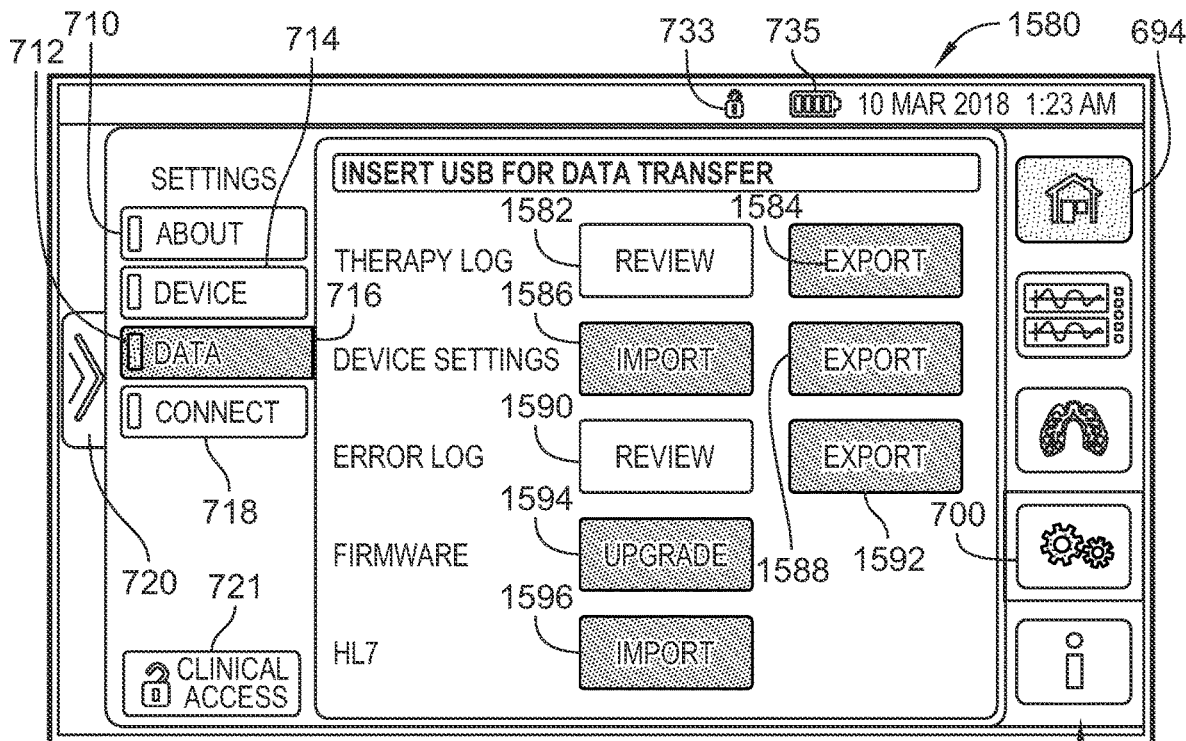
Figure 178:
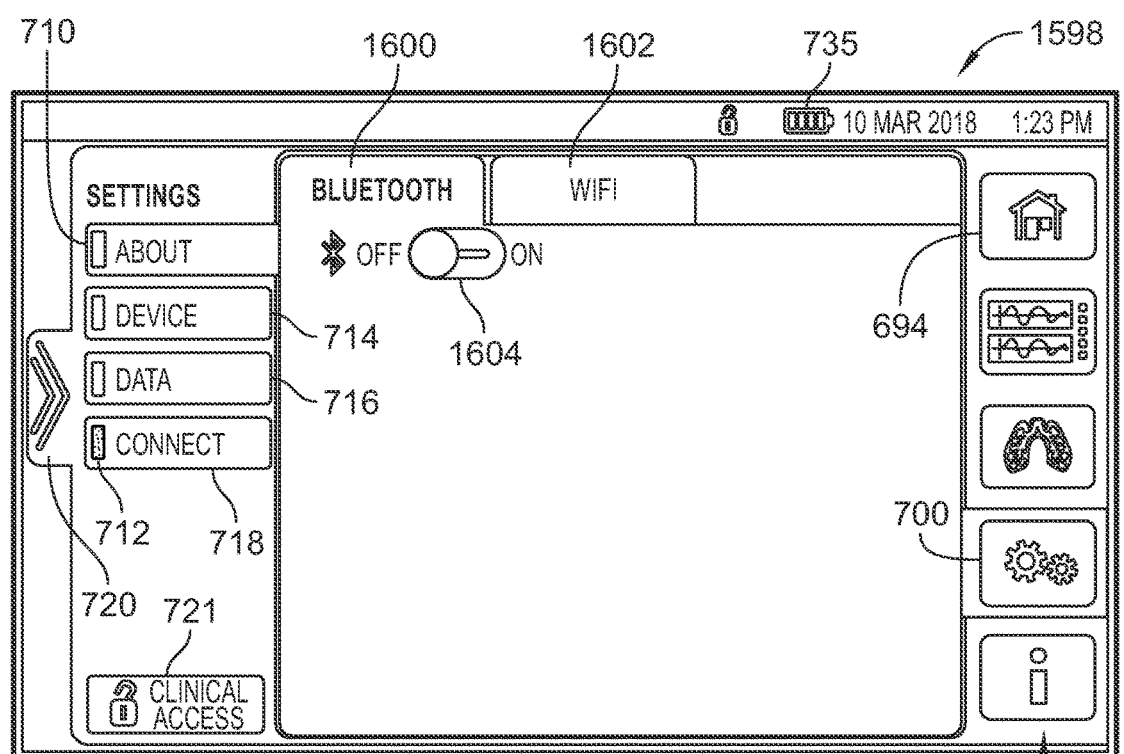
Figure 179:
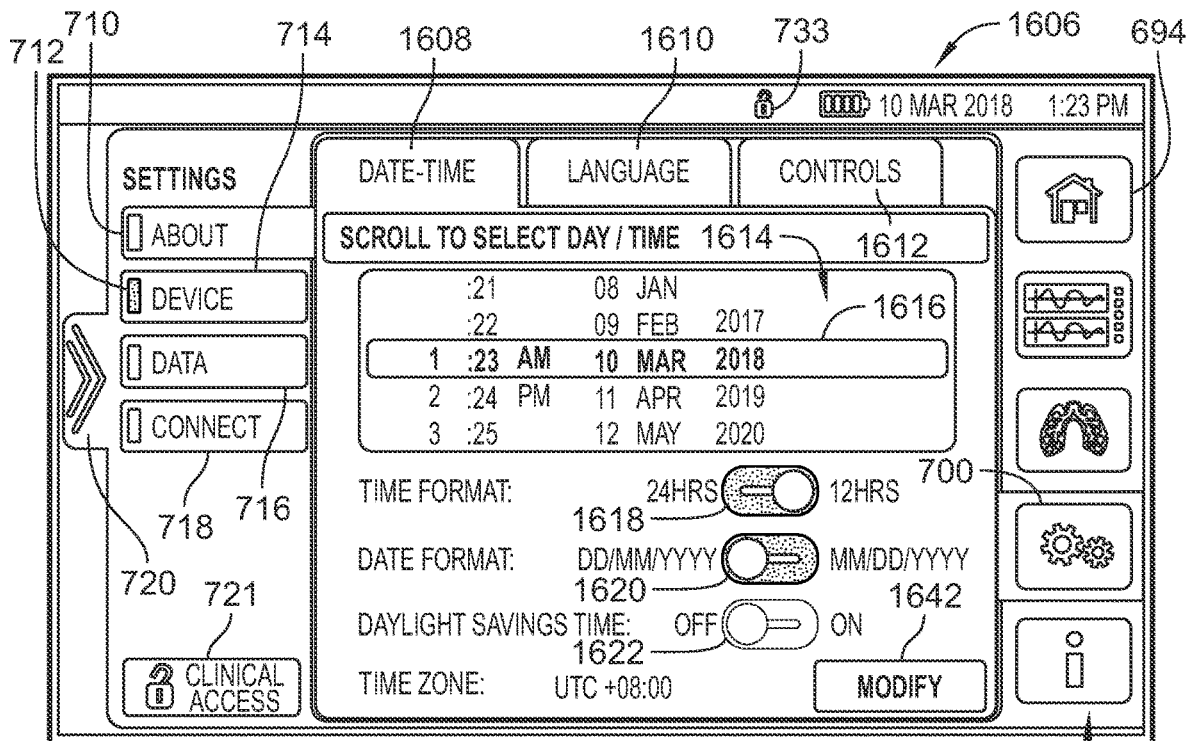
Figure 180:
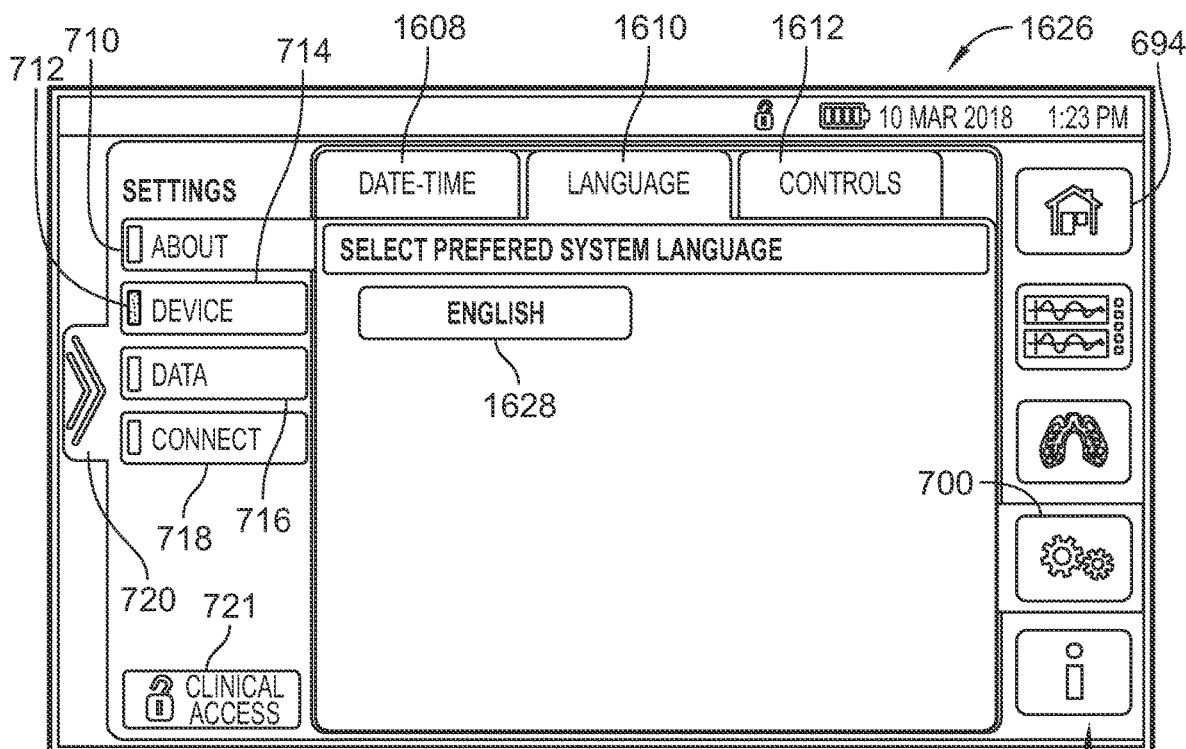
Figure 181:
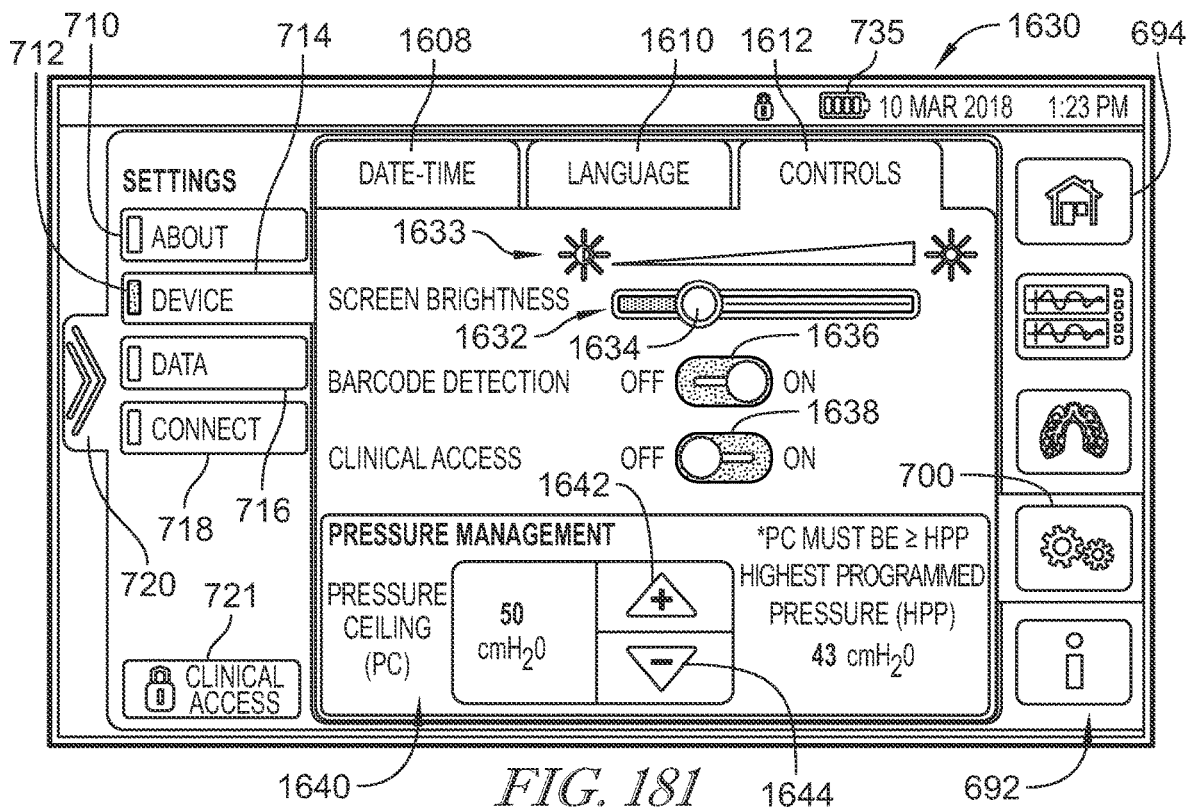
Figure 182:
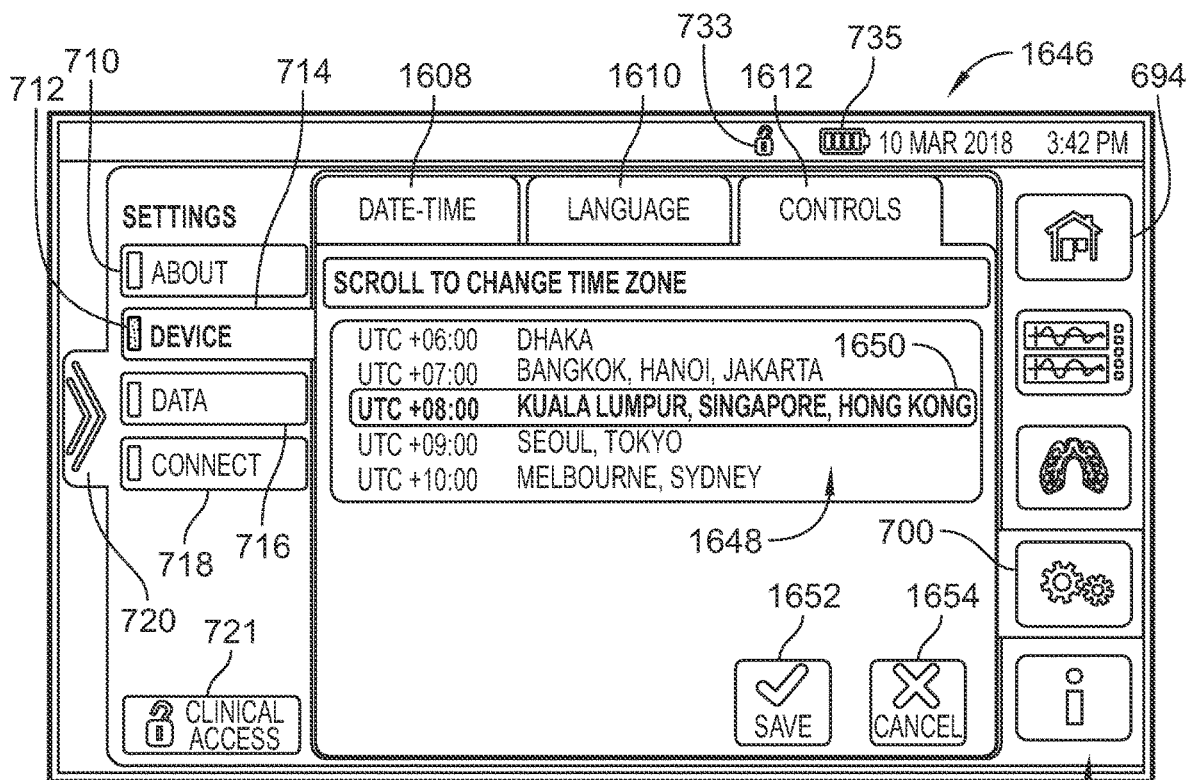
Figure 183:
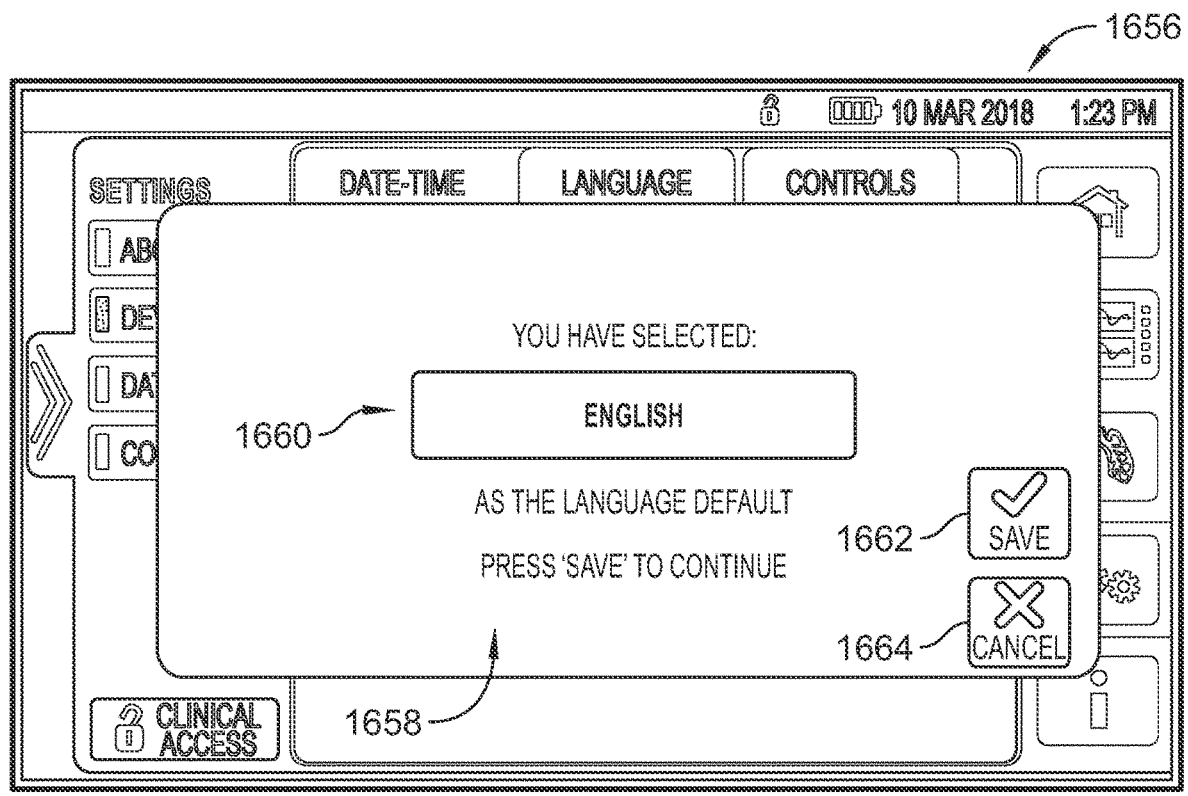
Figure 184:
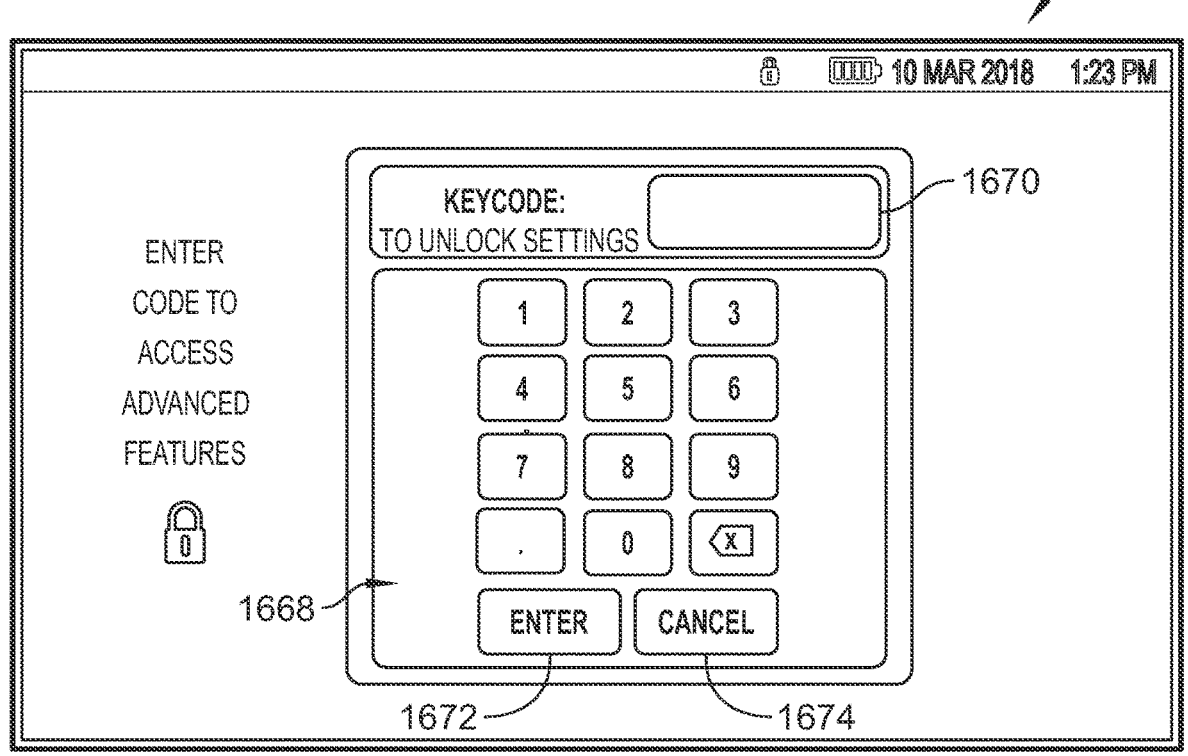
Figure 185:
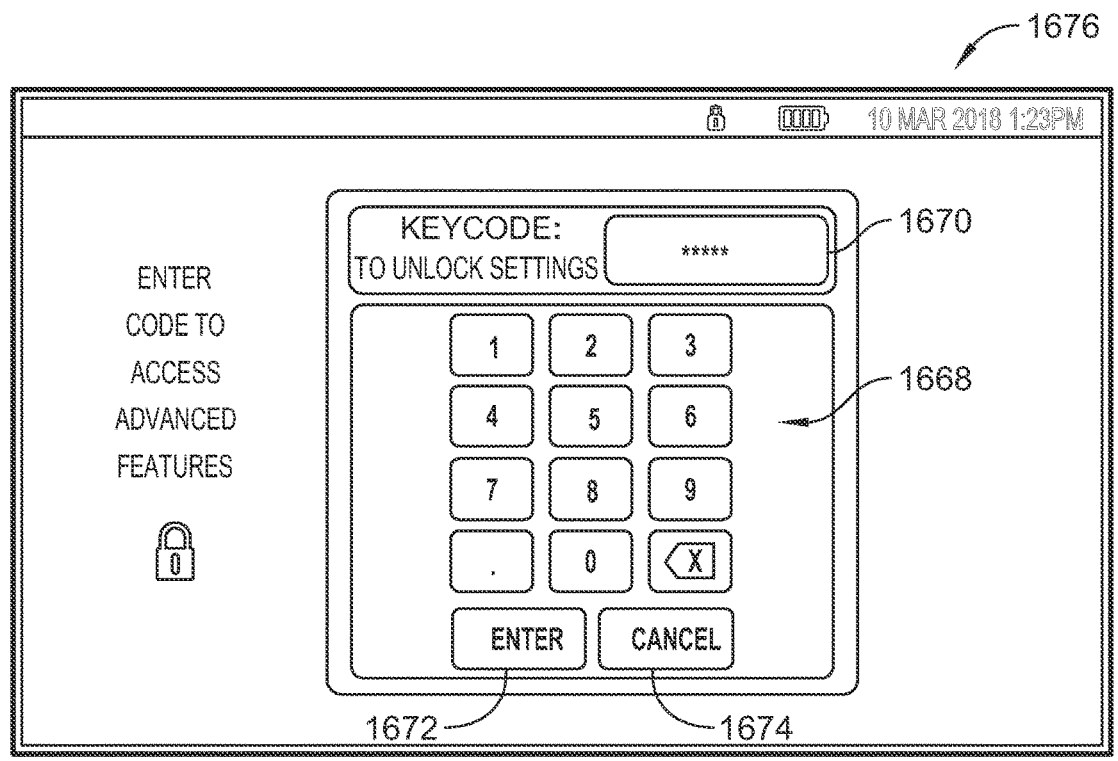
Figure 186:
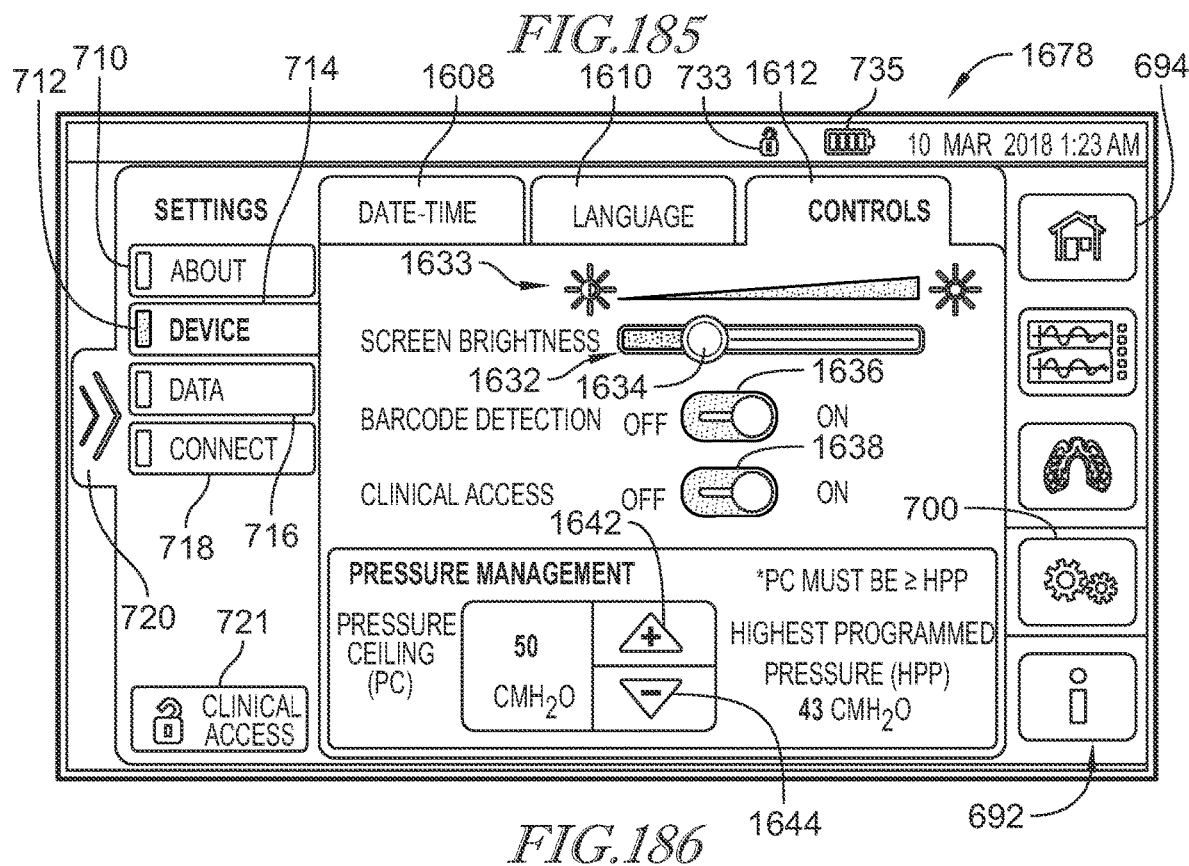
Figure 187:
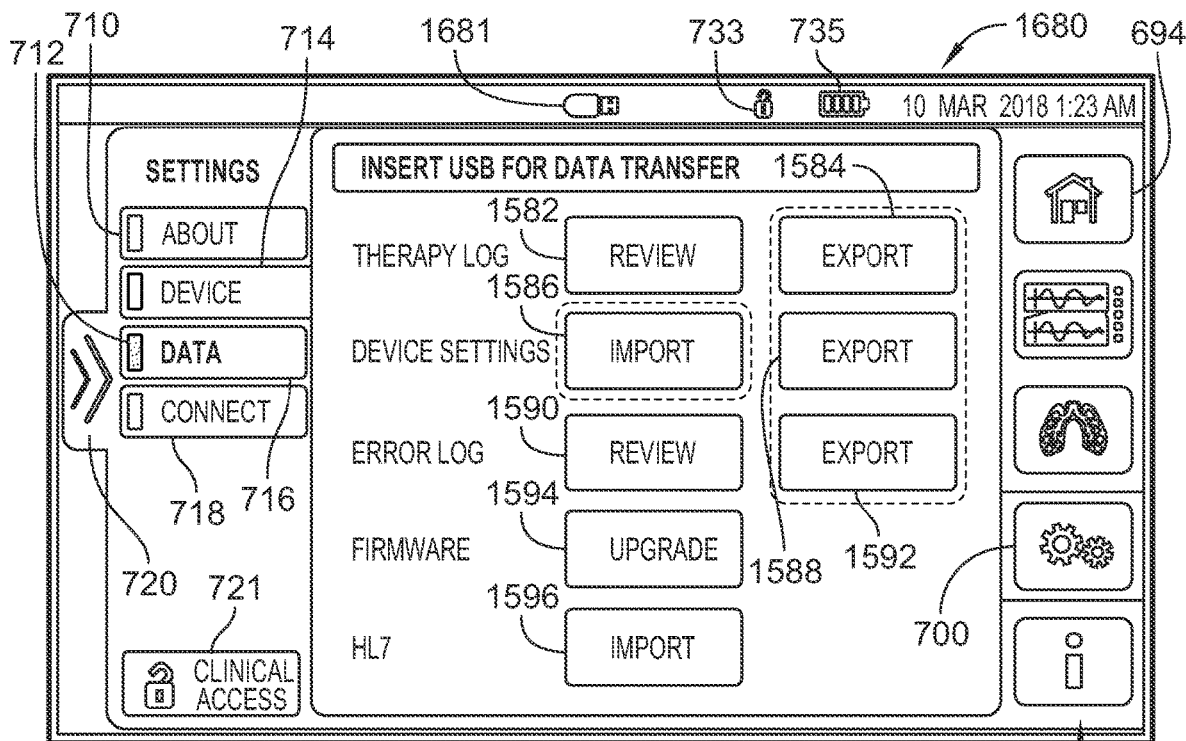
Figure 188:
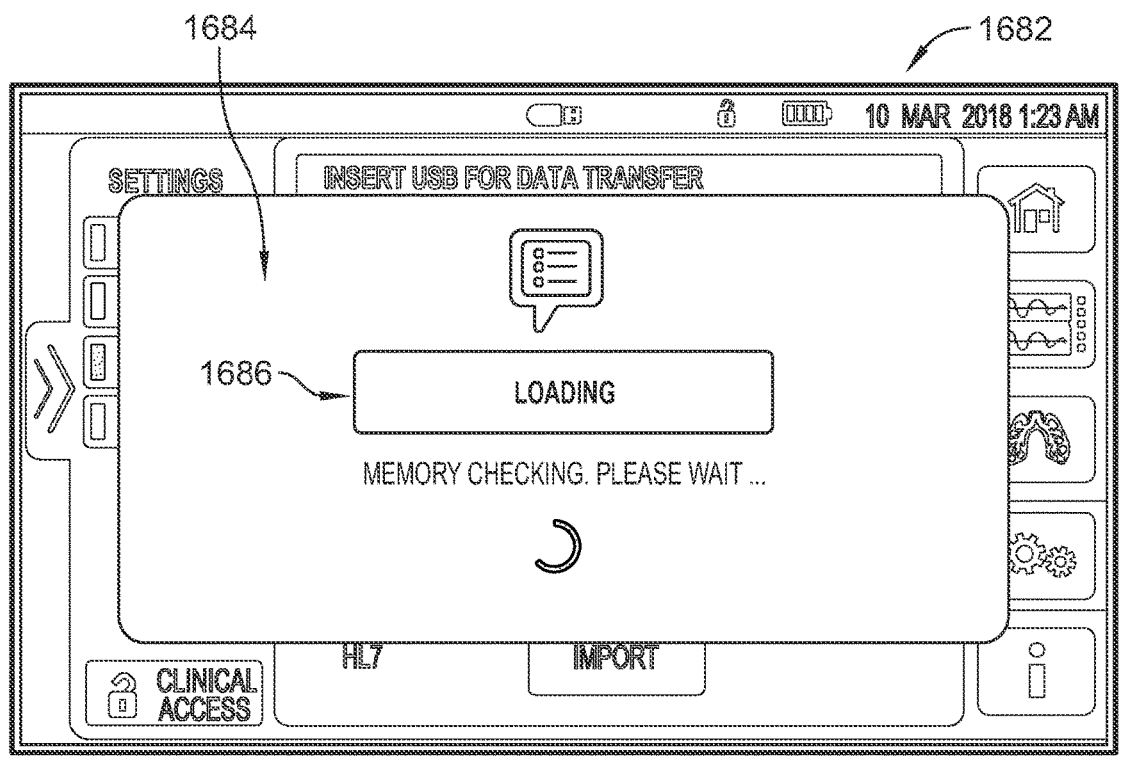
Figure 189:
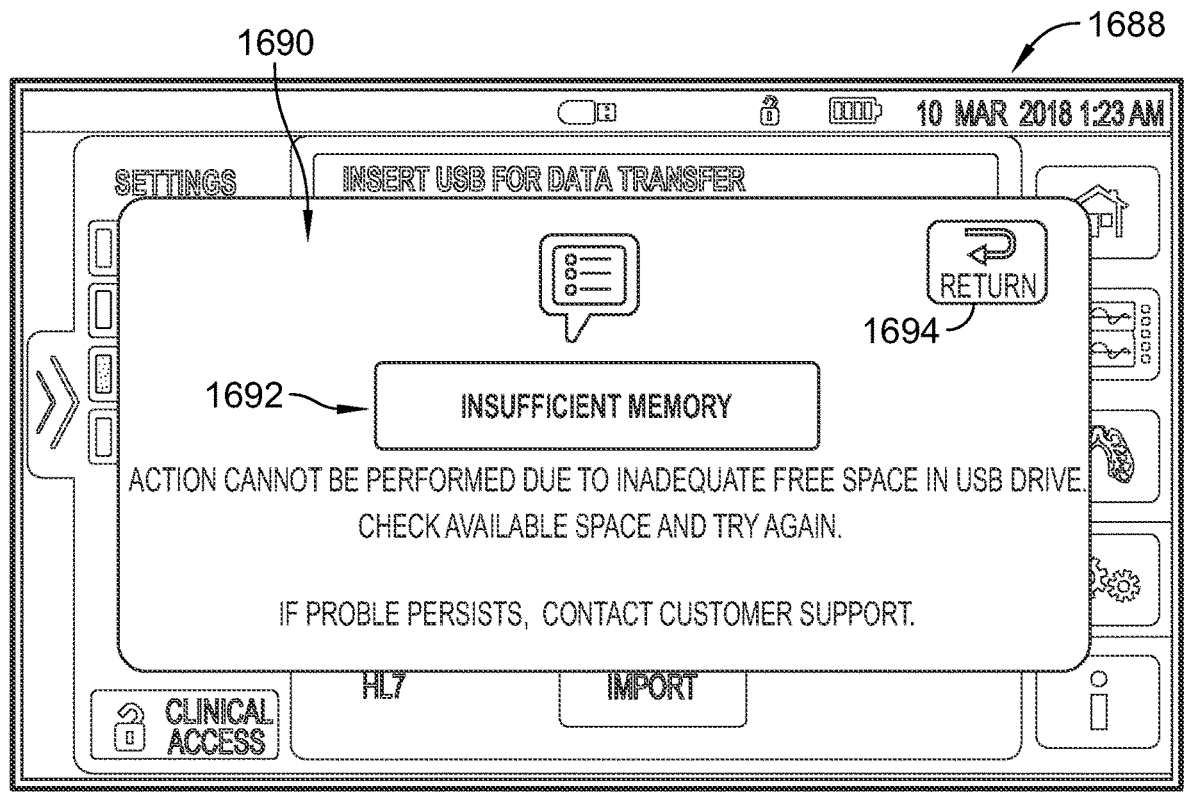
Figure 190:
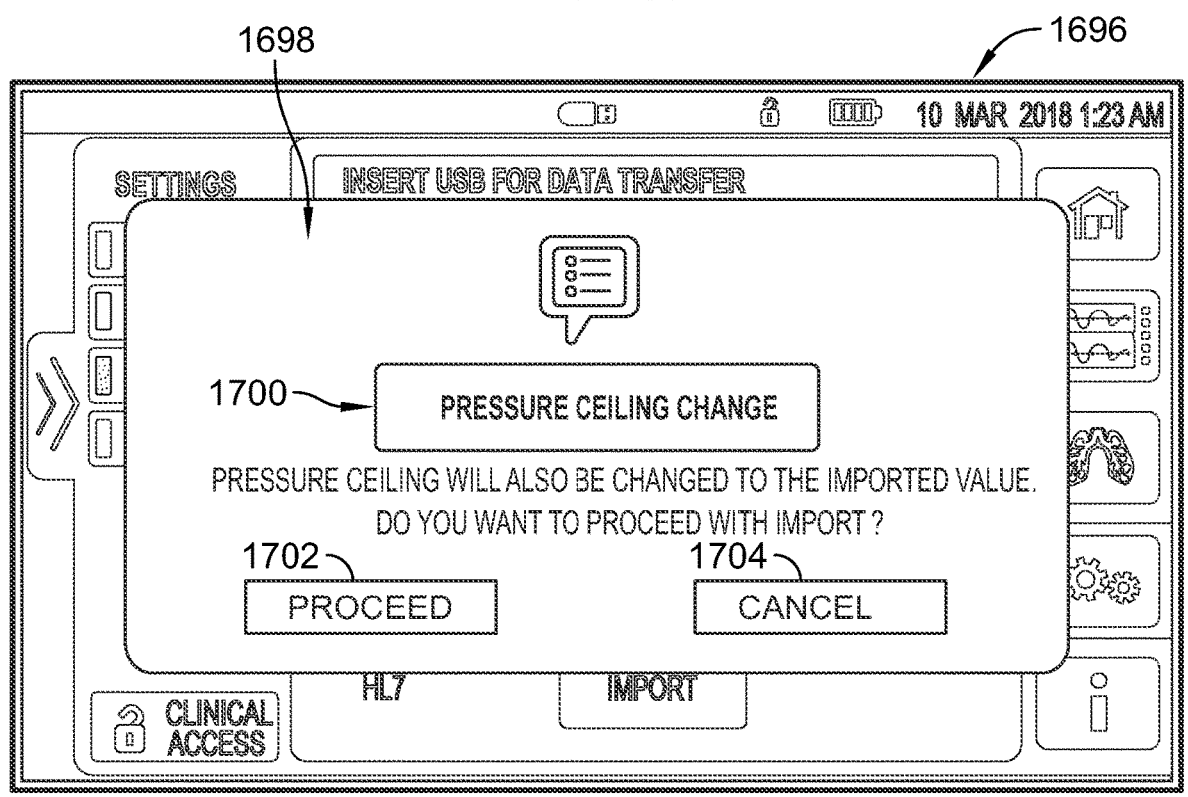
Figure 191:
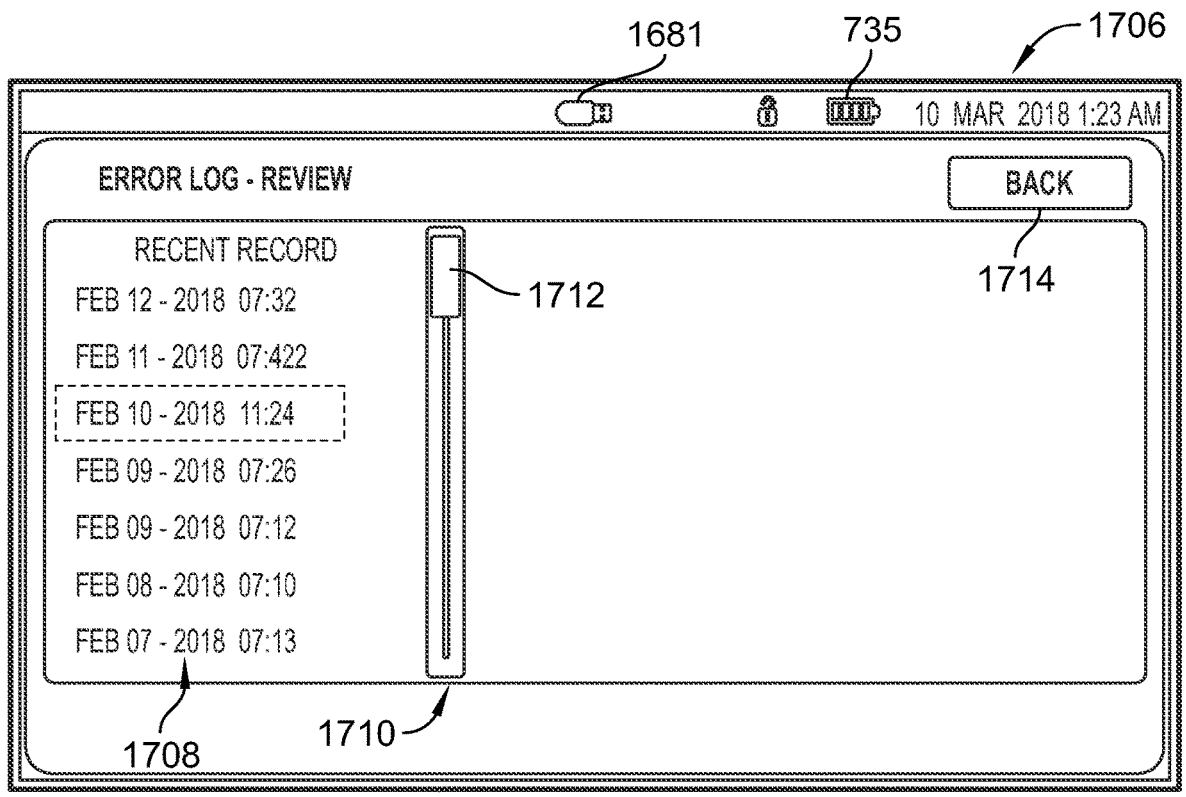
Figure 192:
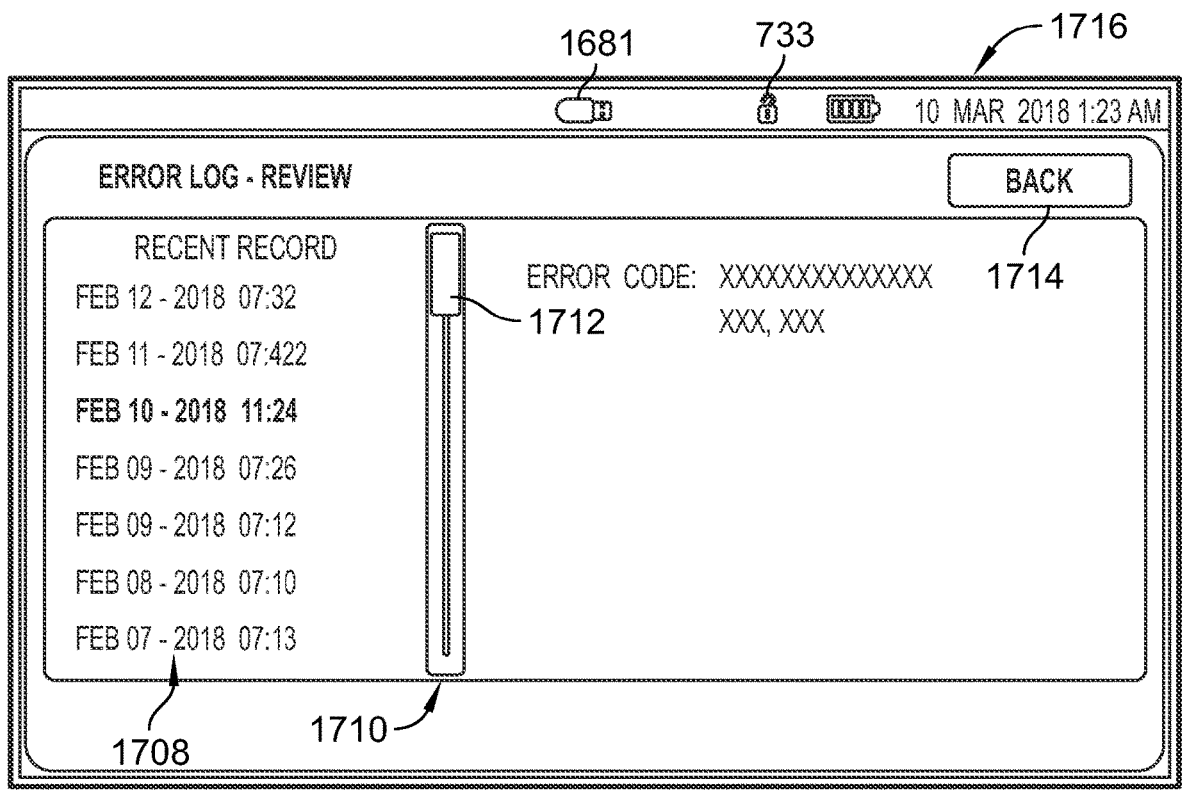
Figure 193:
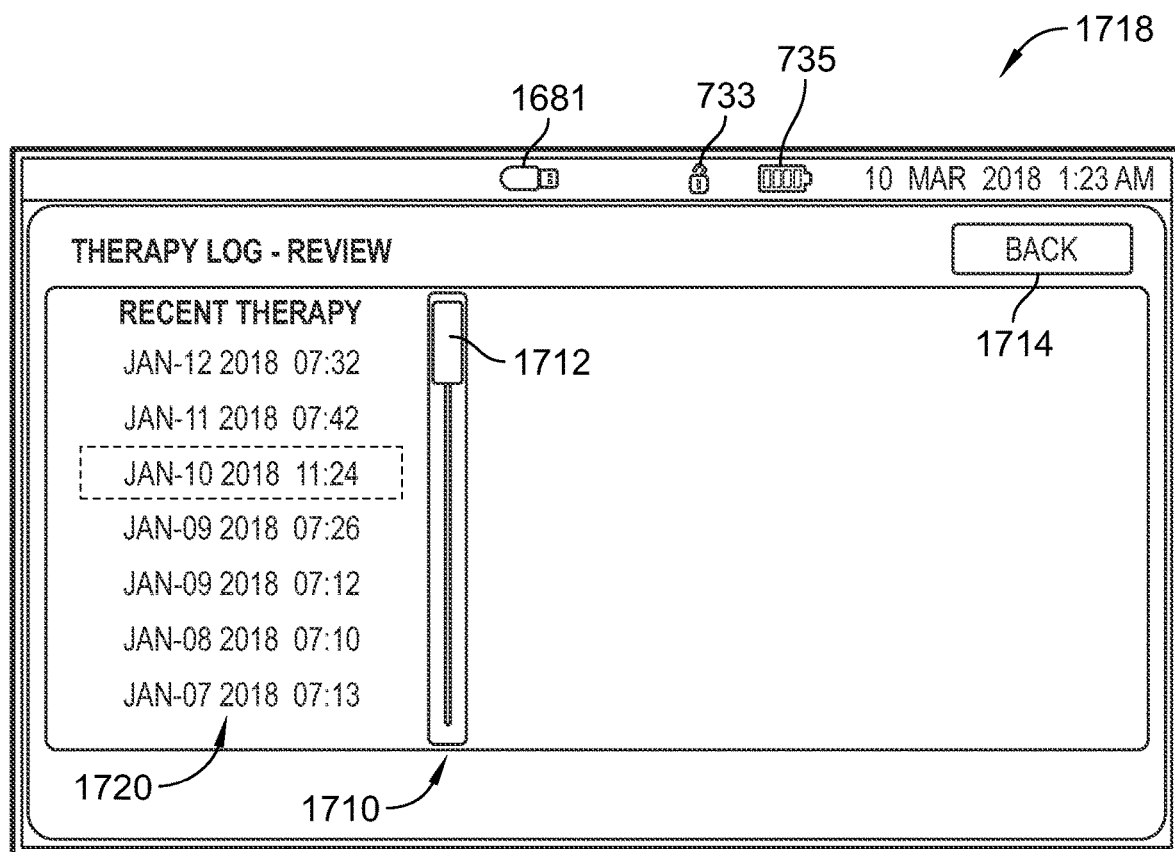
Figure 194:
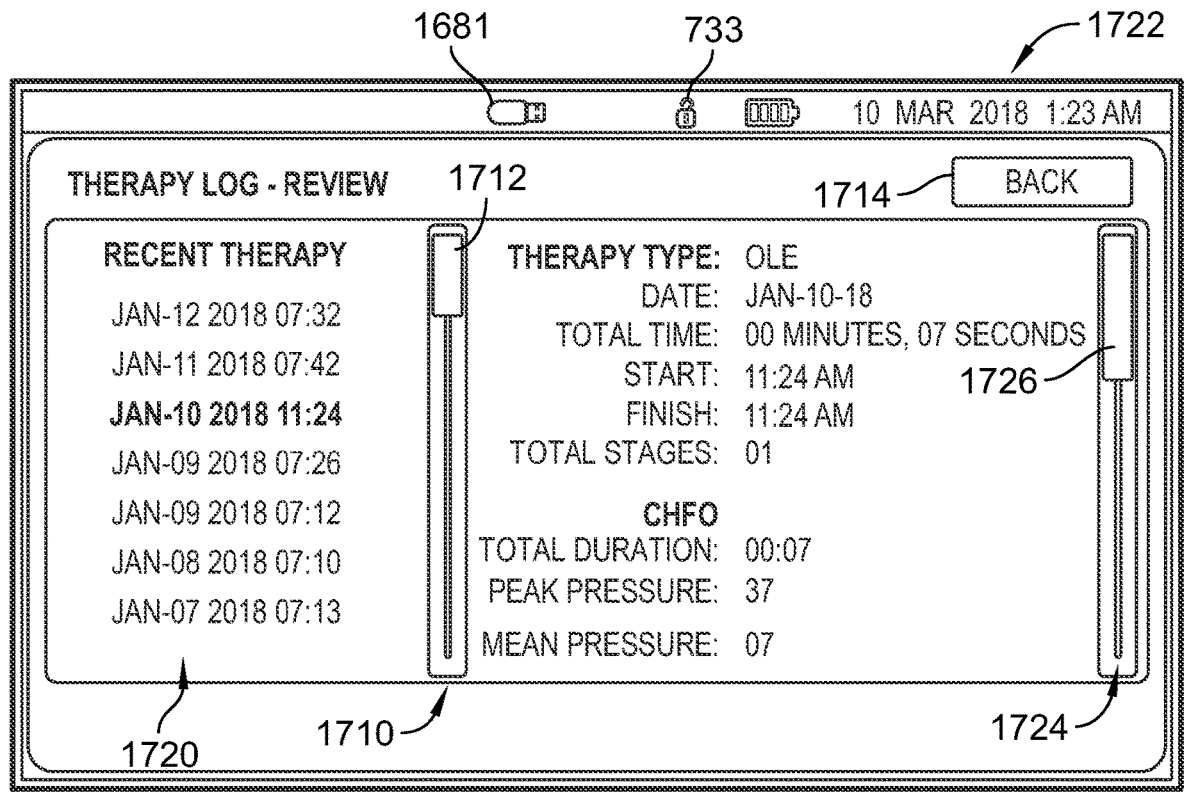
Figure 195:
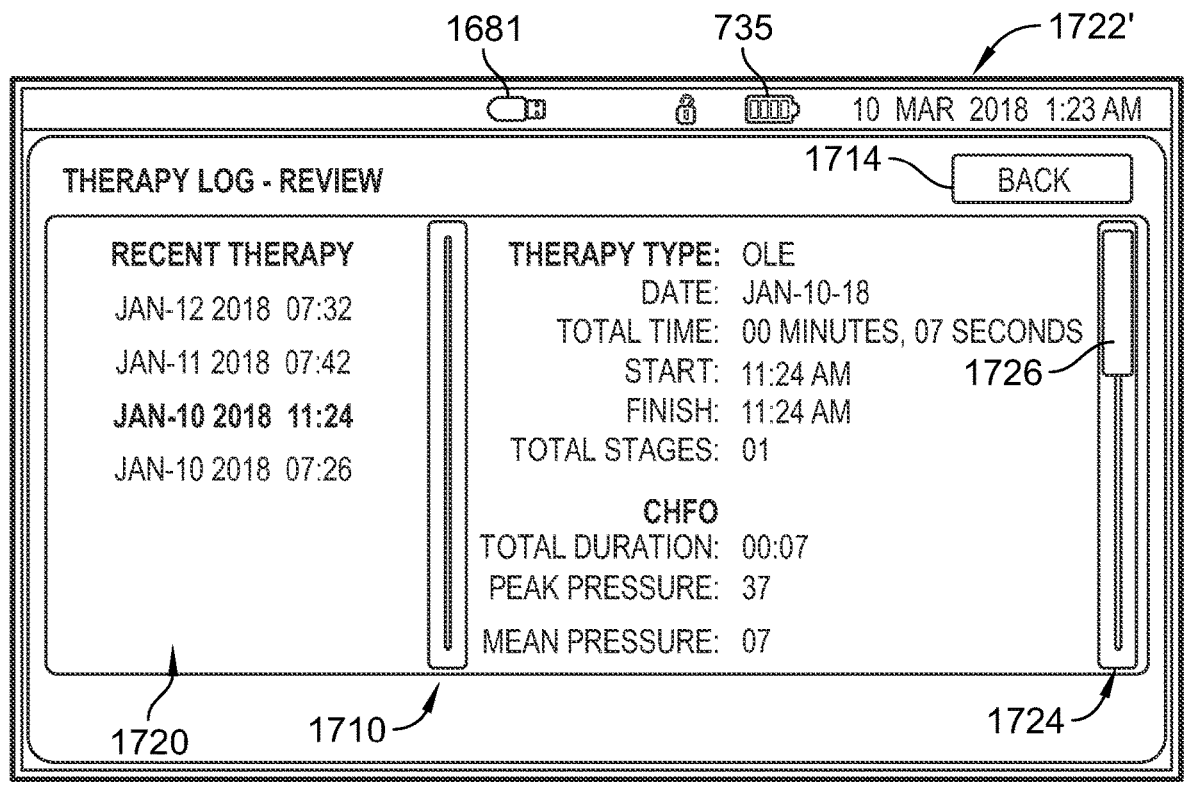
Figure 196:
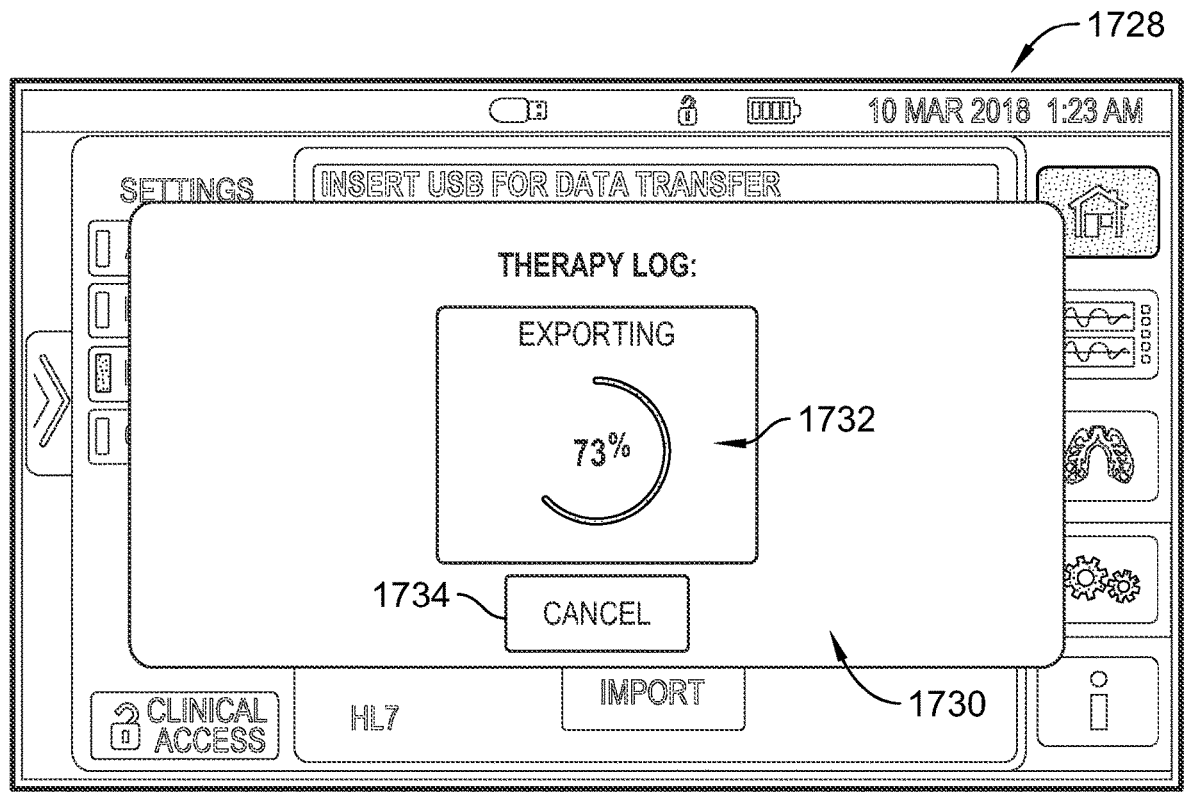
Figure 197:
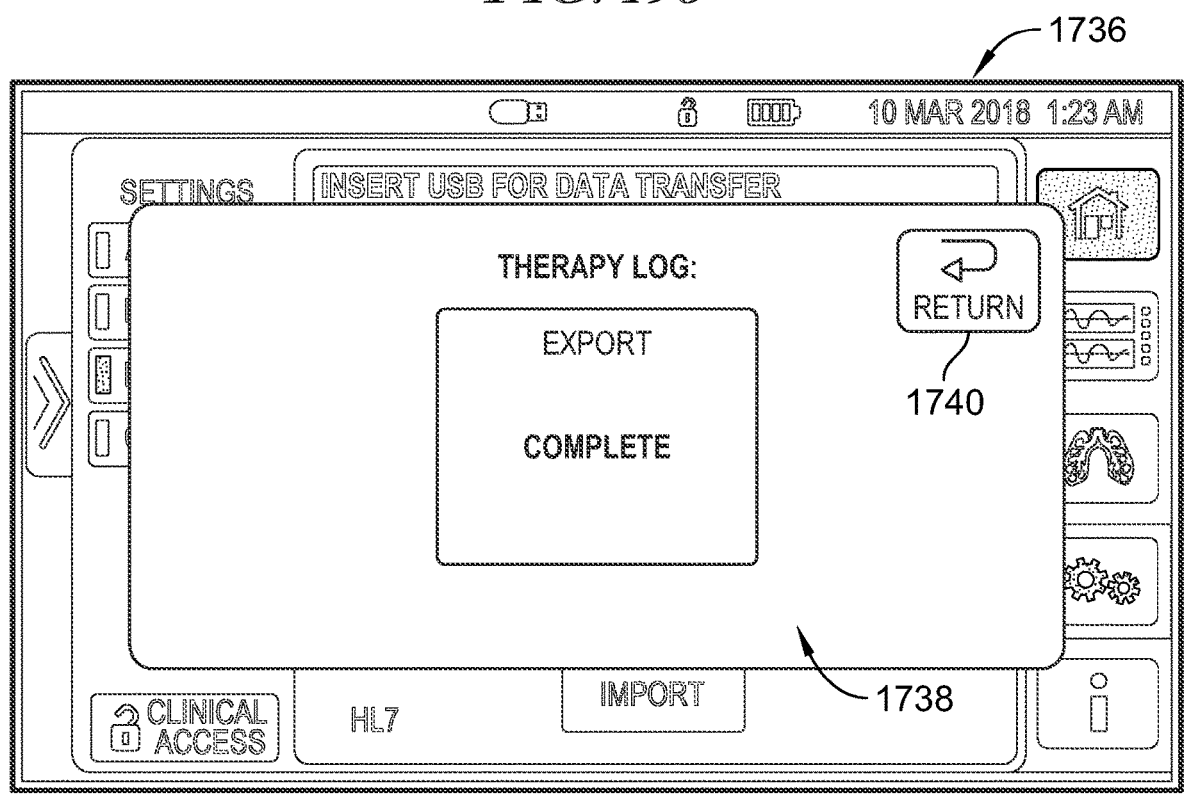
Figure 198:
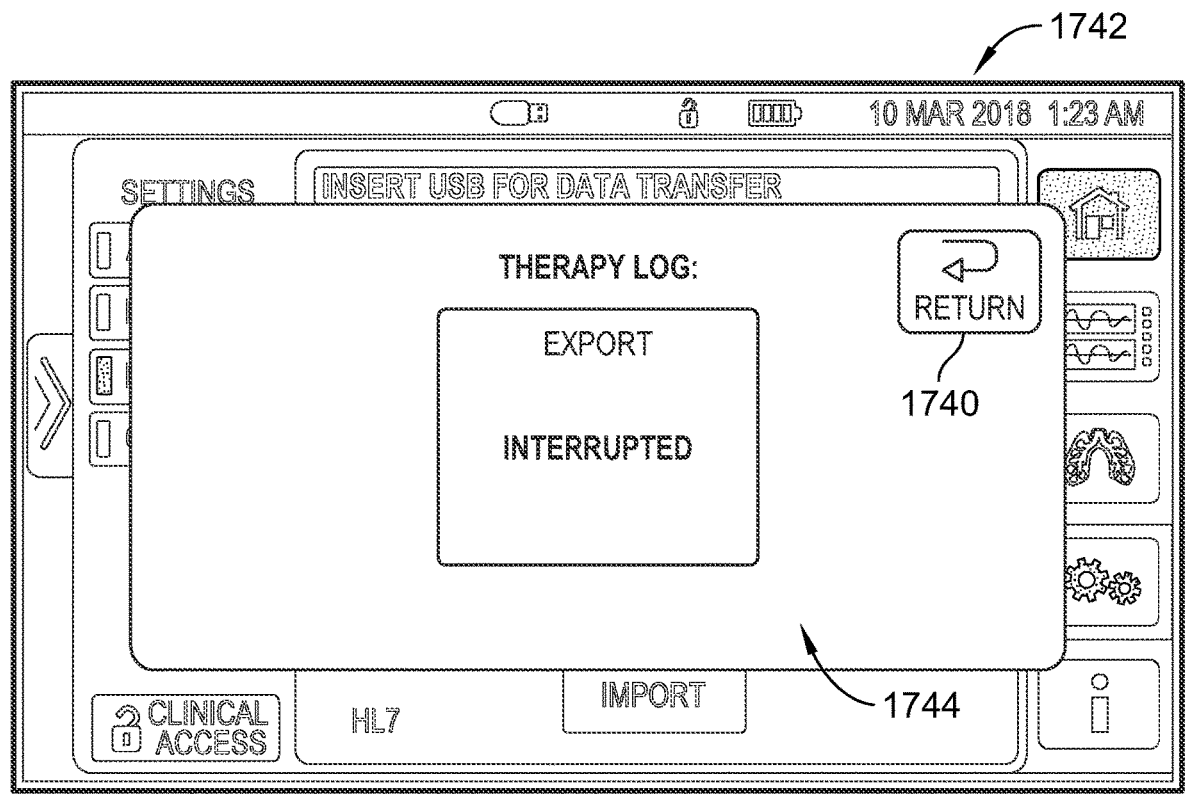
Figure 199:
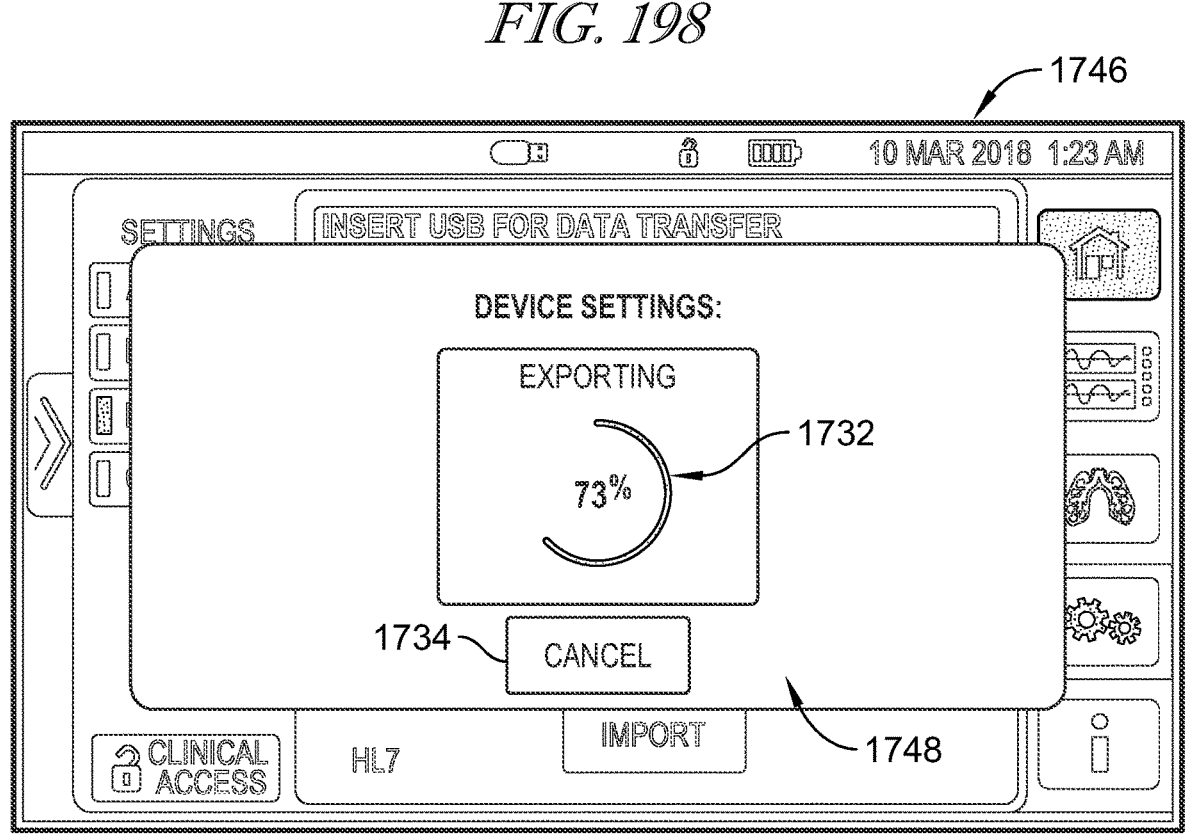
Figure 200:
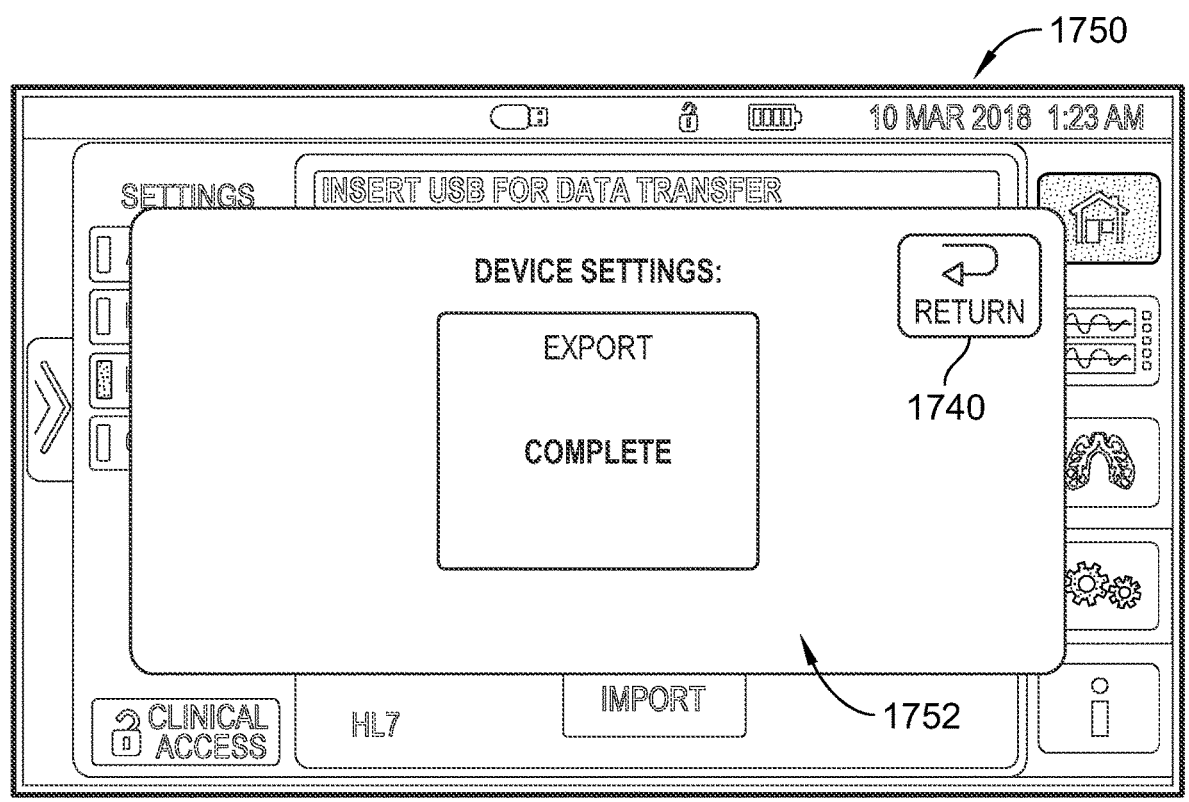
Figure 201:
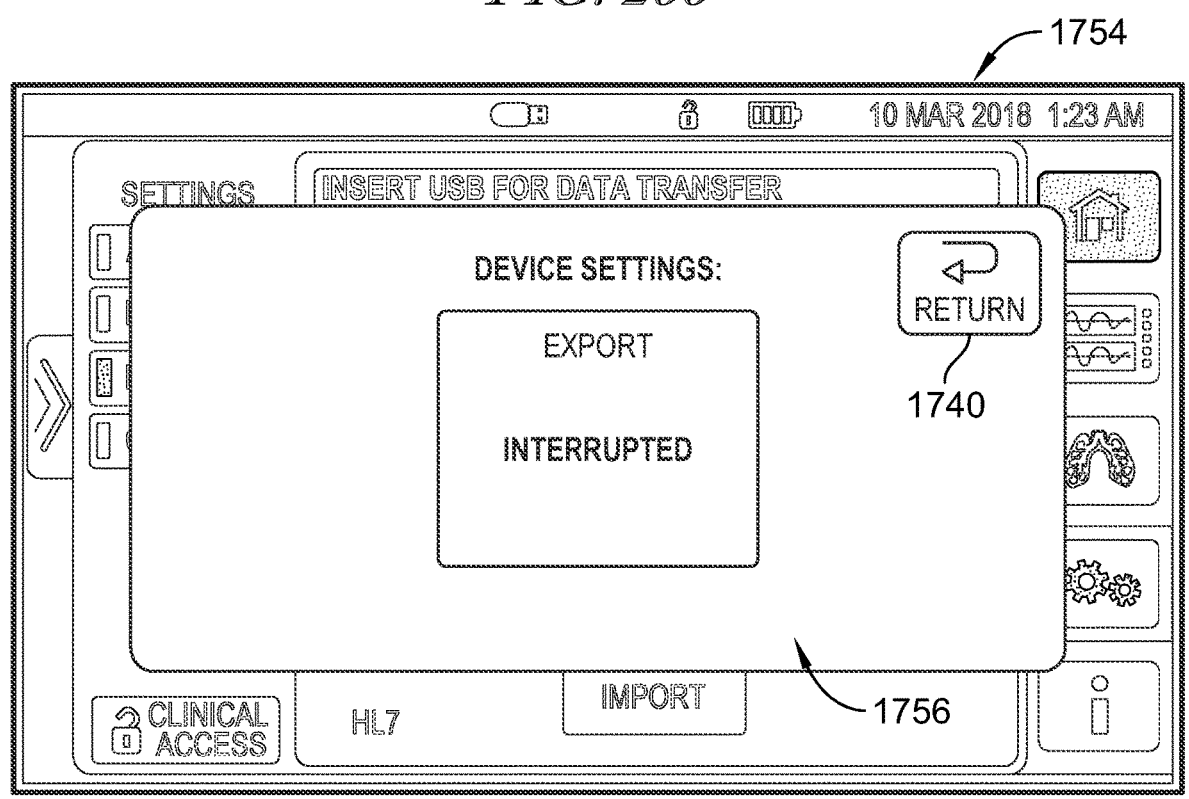
Figure 202:
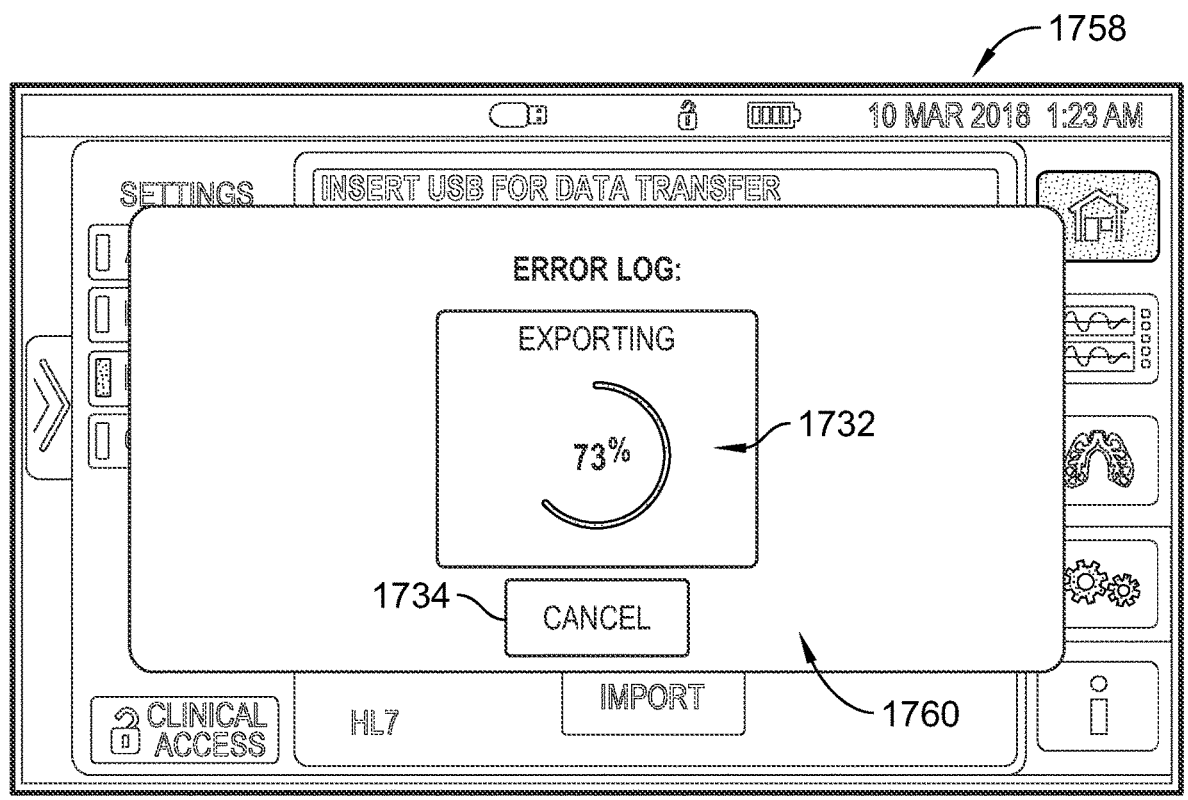
Figure 203:
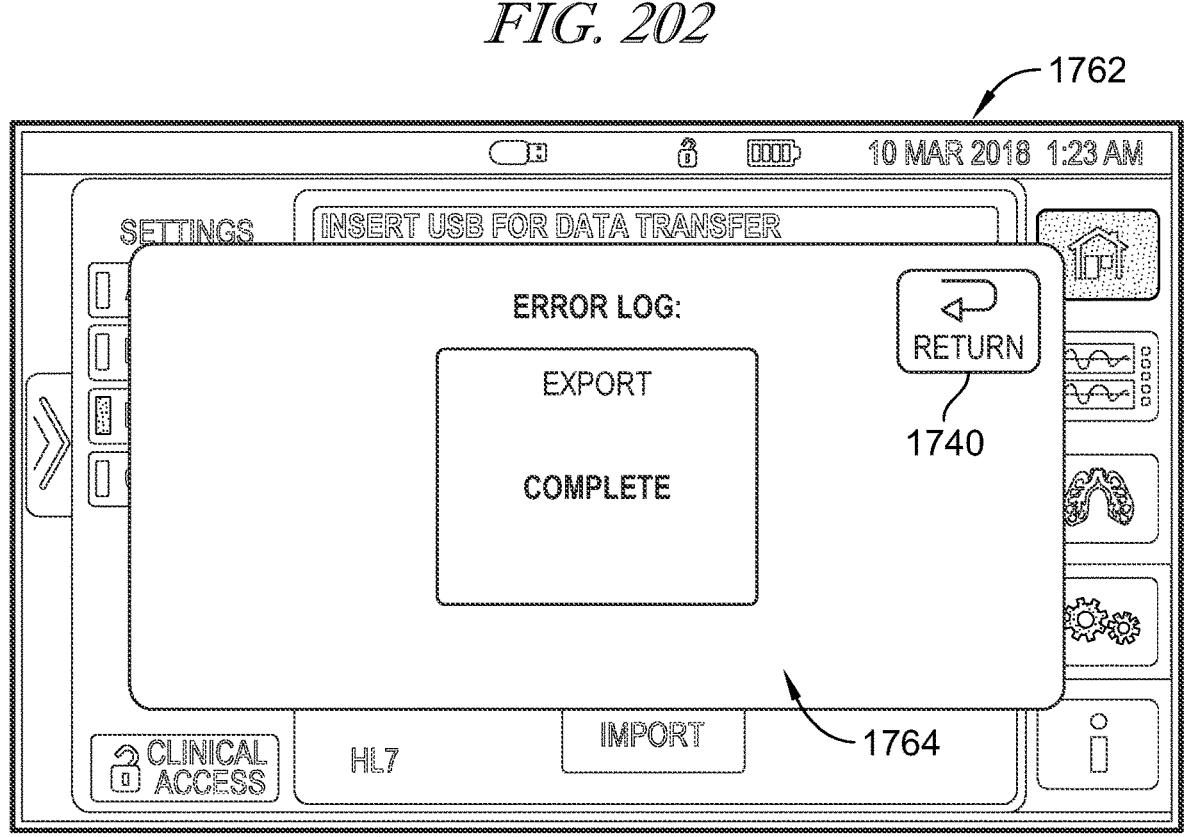
Figure 204:
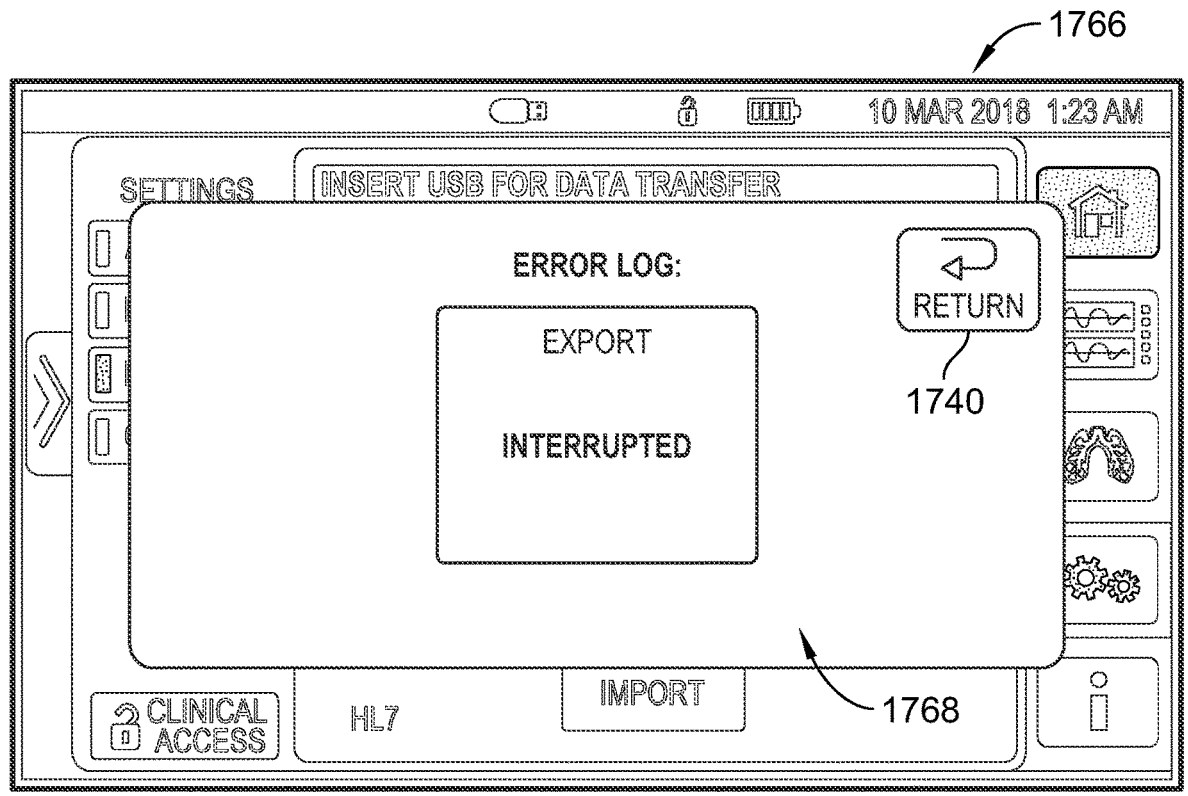
Figure 205:
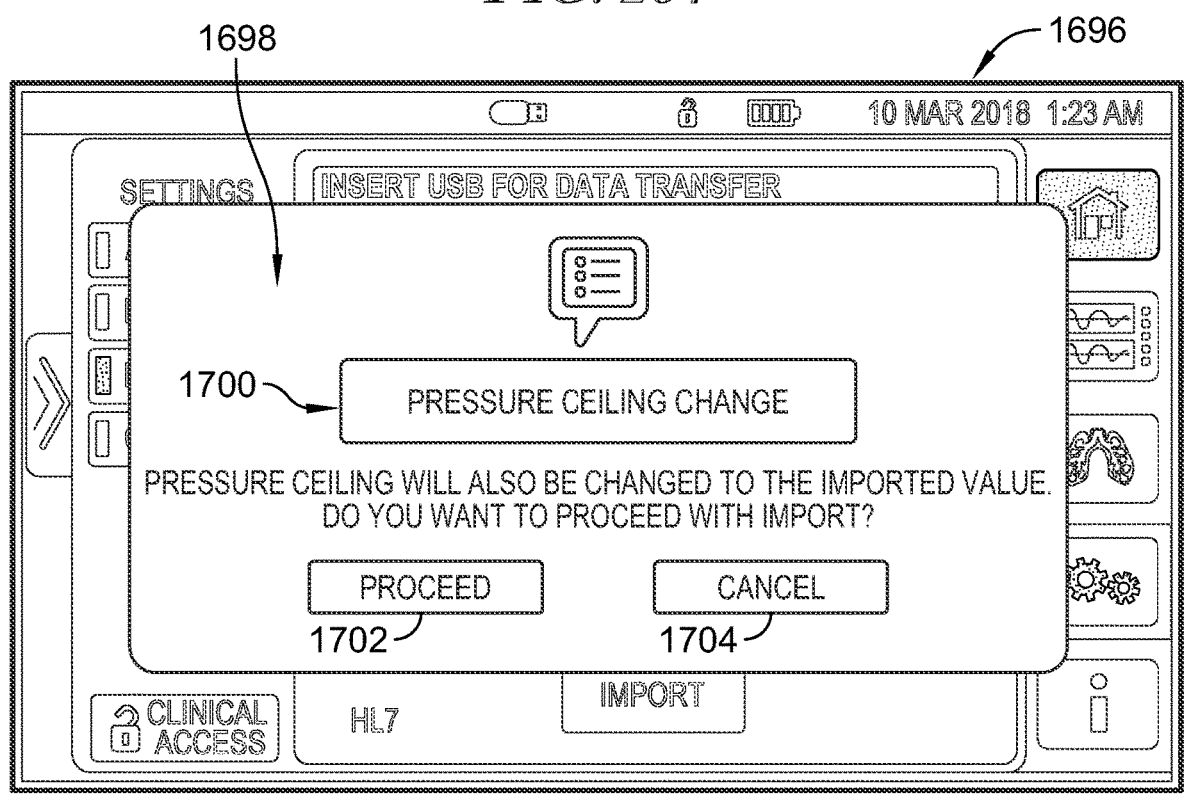
Figure 206:
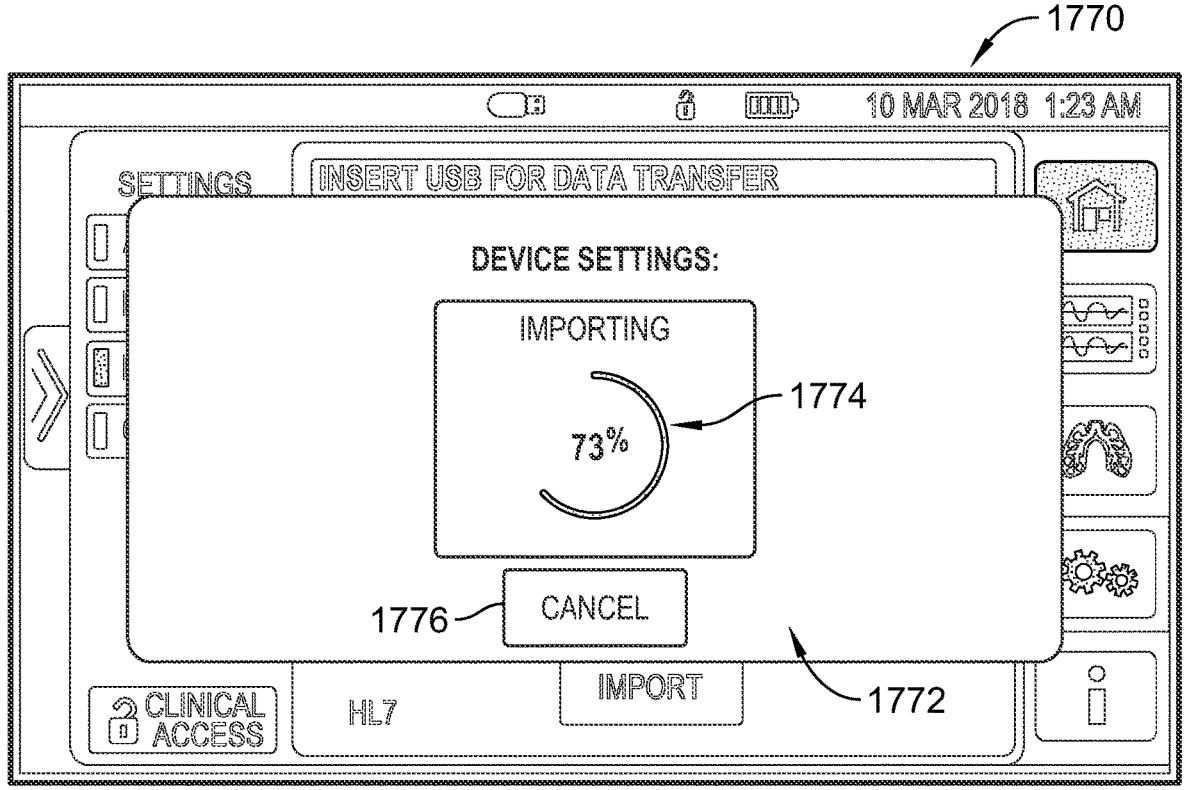
Figure 207:
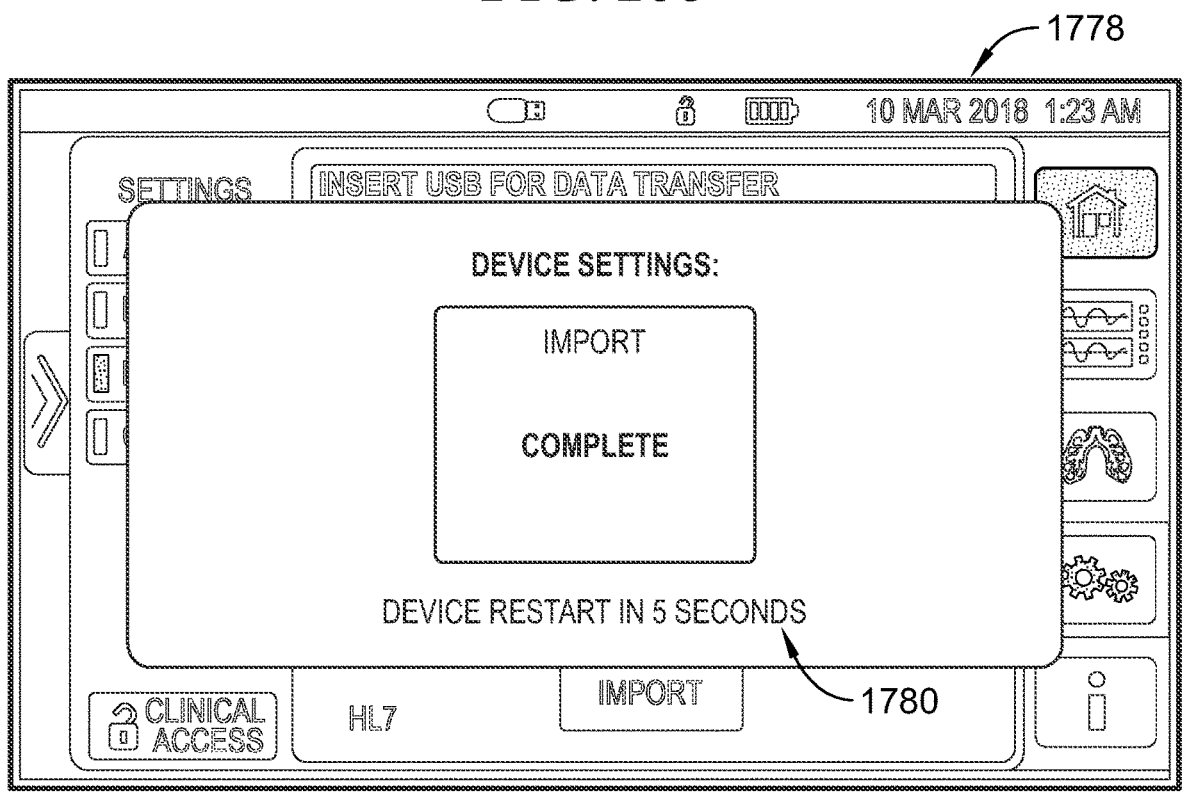
Figure 208:
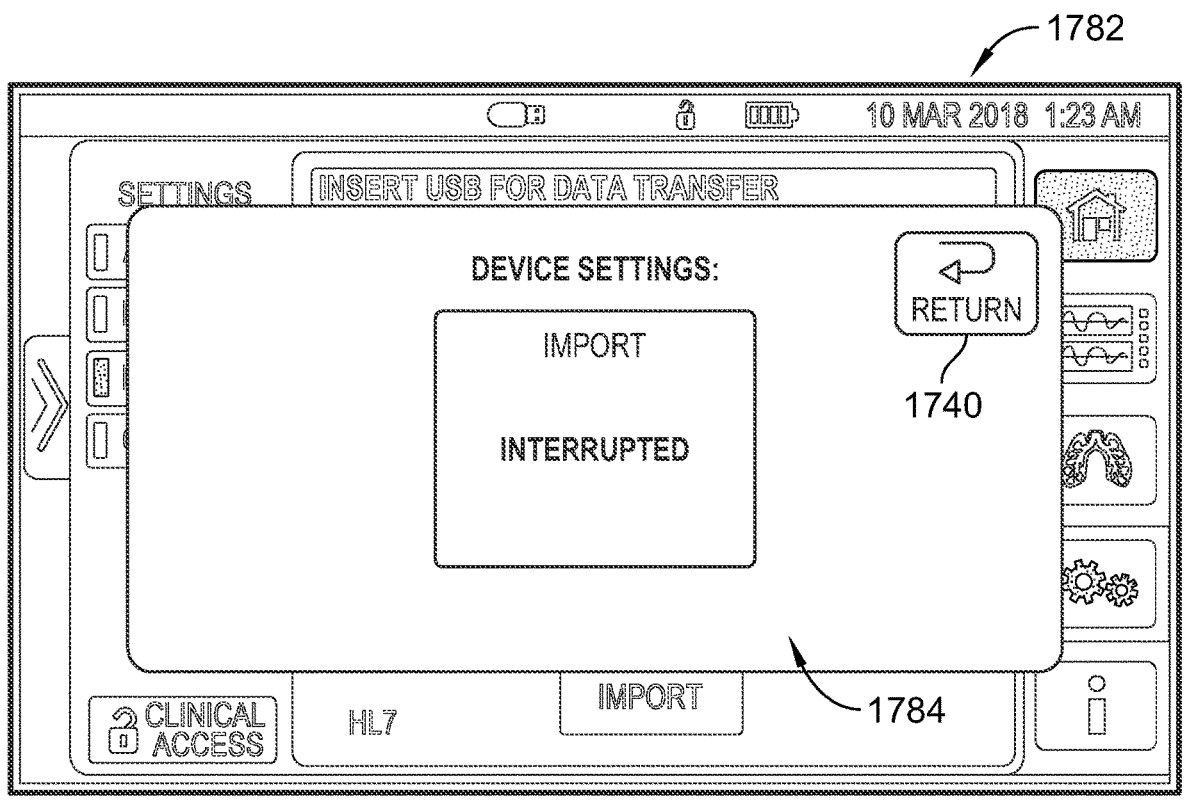
Figure 209:
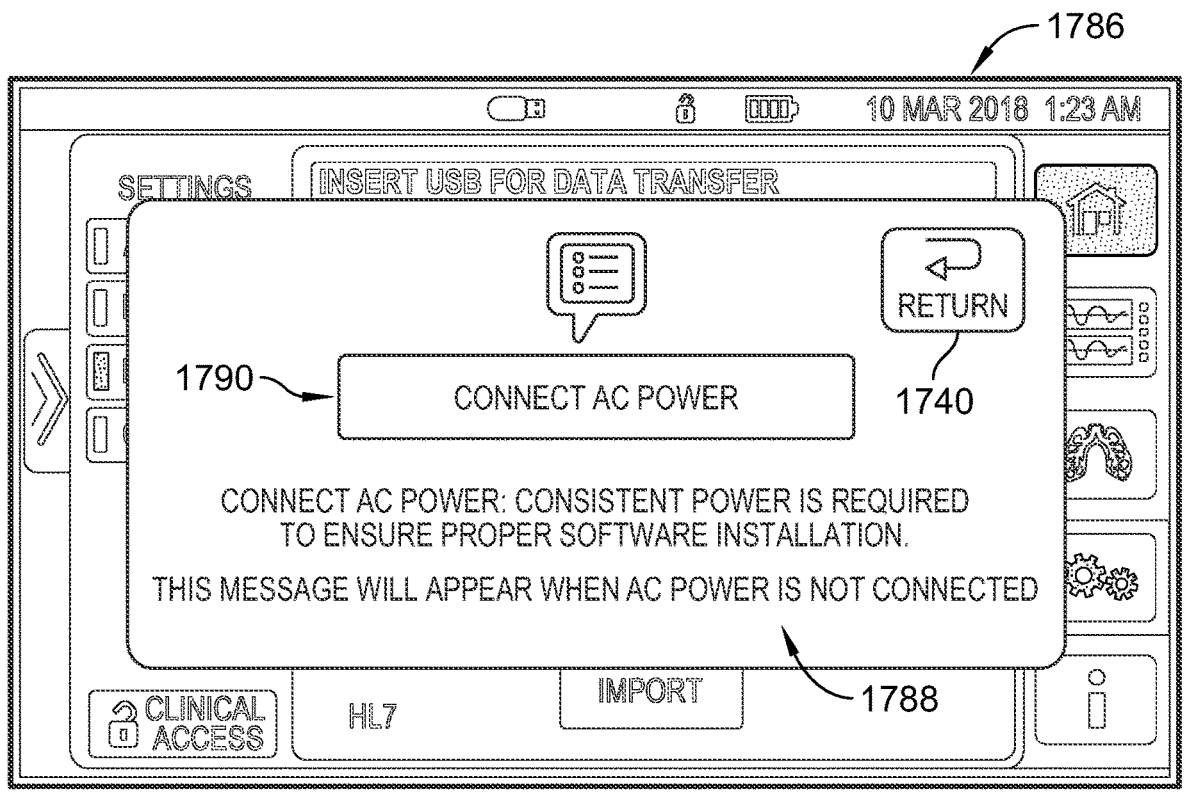
Figure 210:
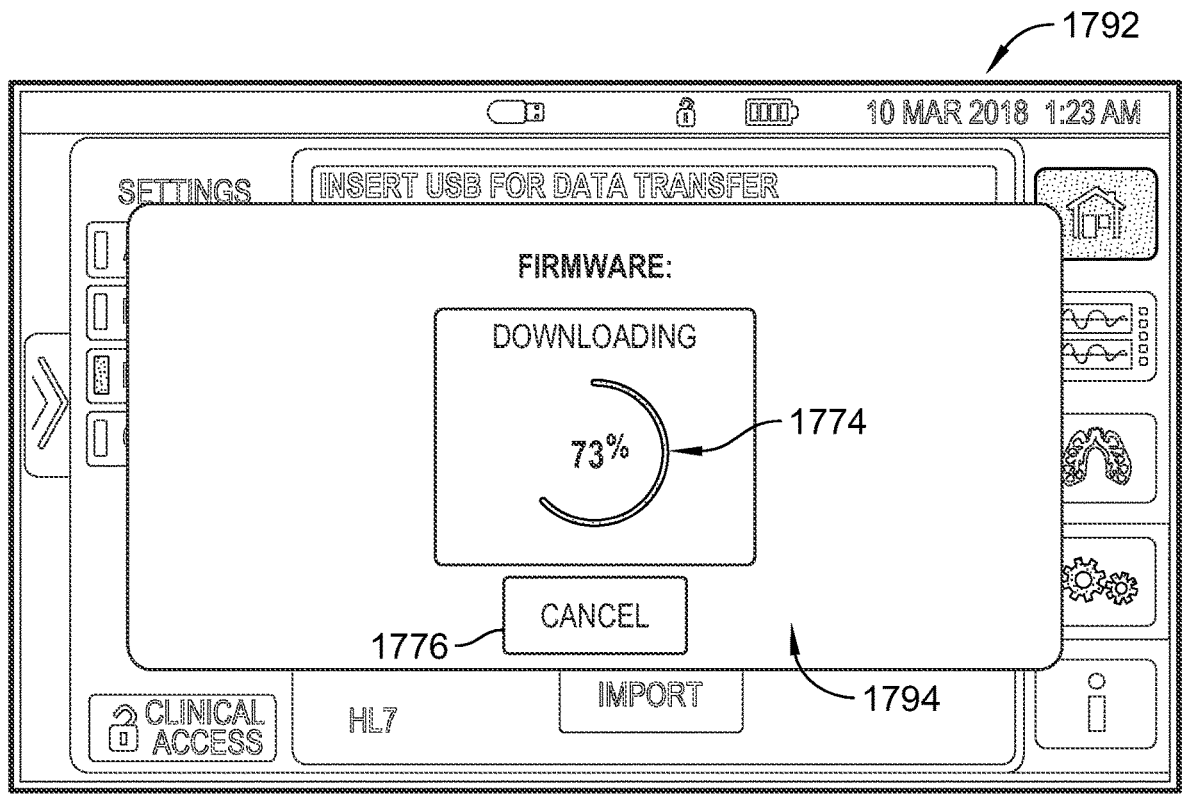
Figure 211:
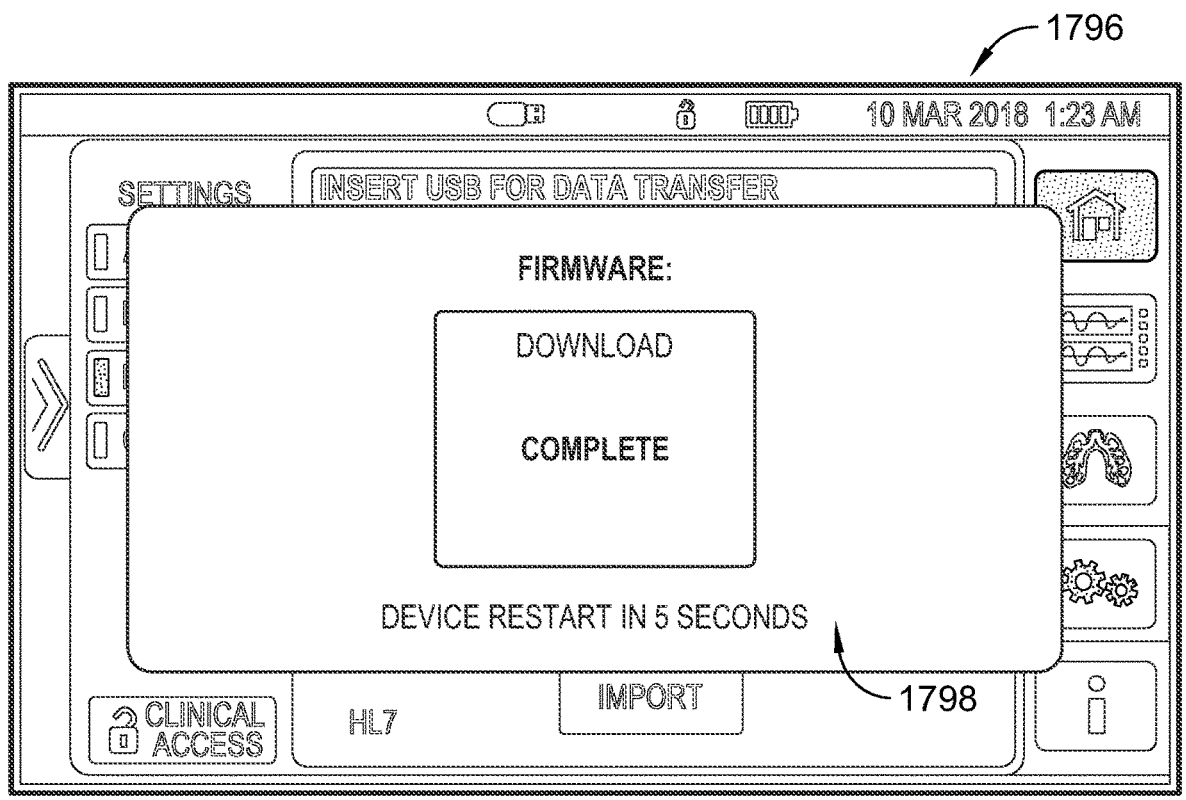
Figure 212:
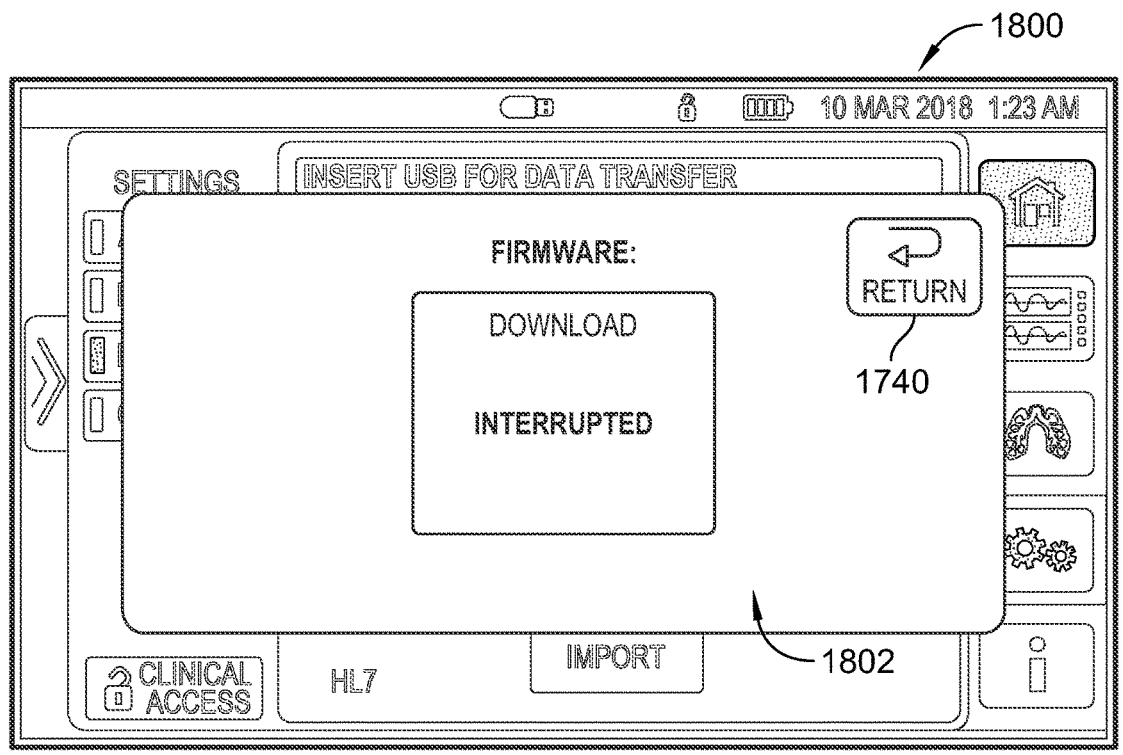
Figure 213:
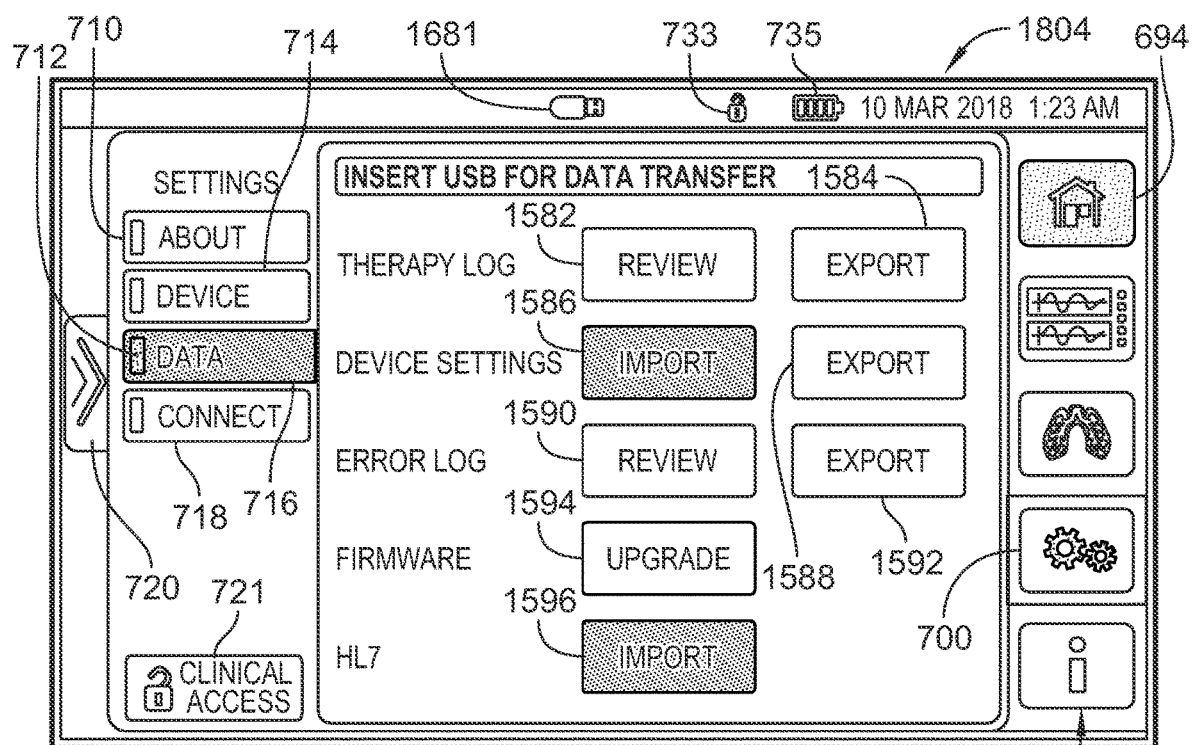
Figure 214:
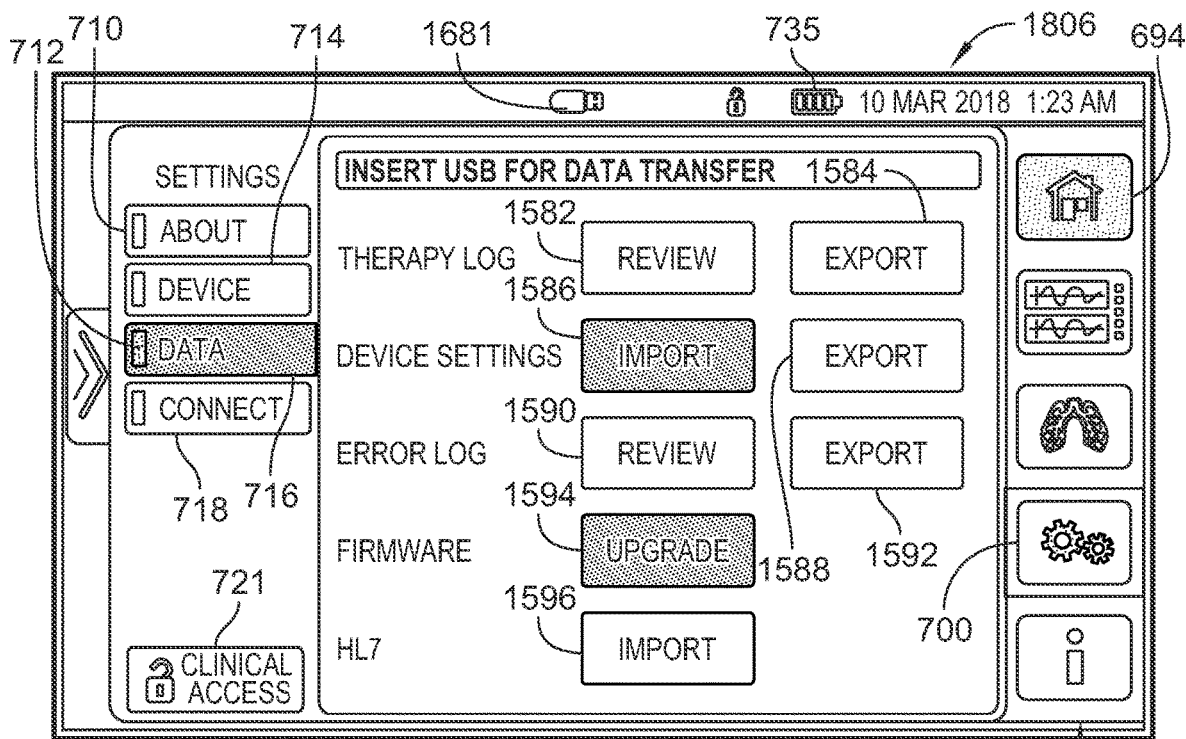
Figure 215:
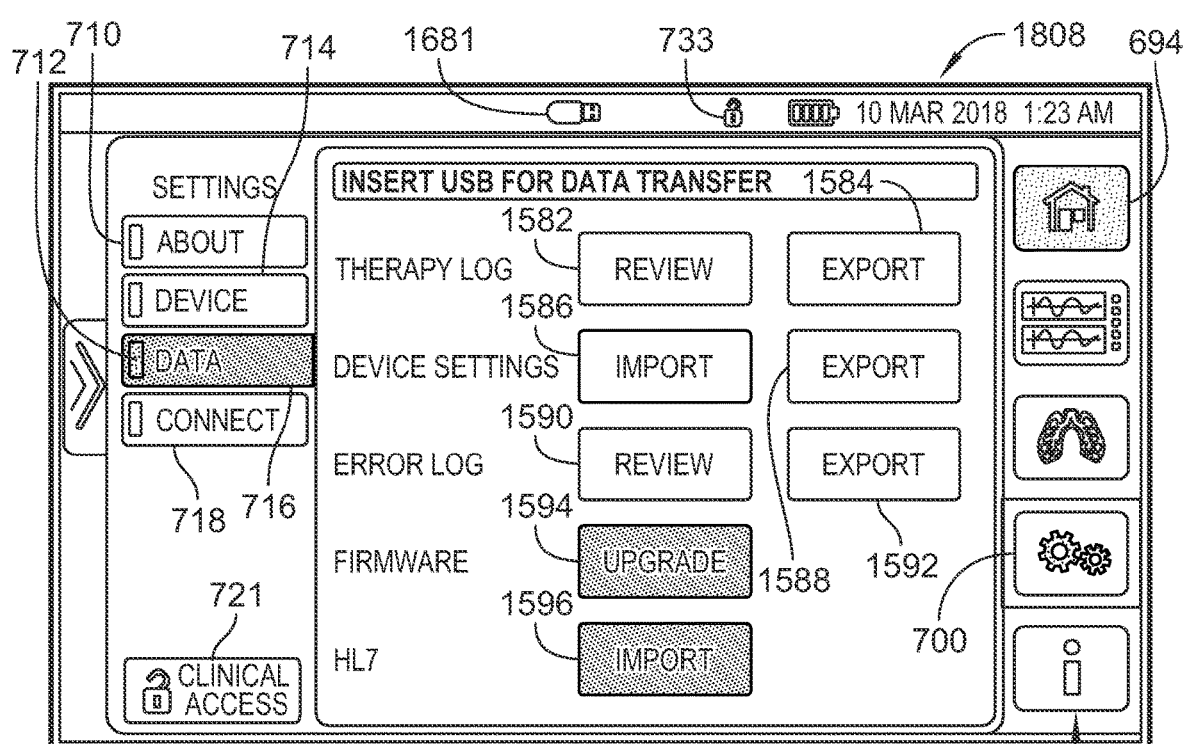
Figure 216:
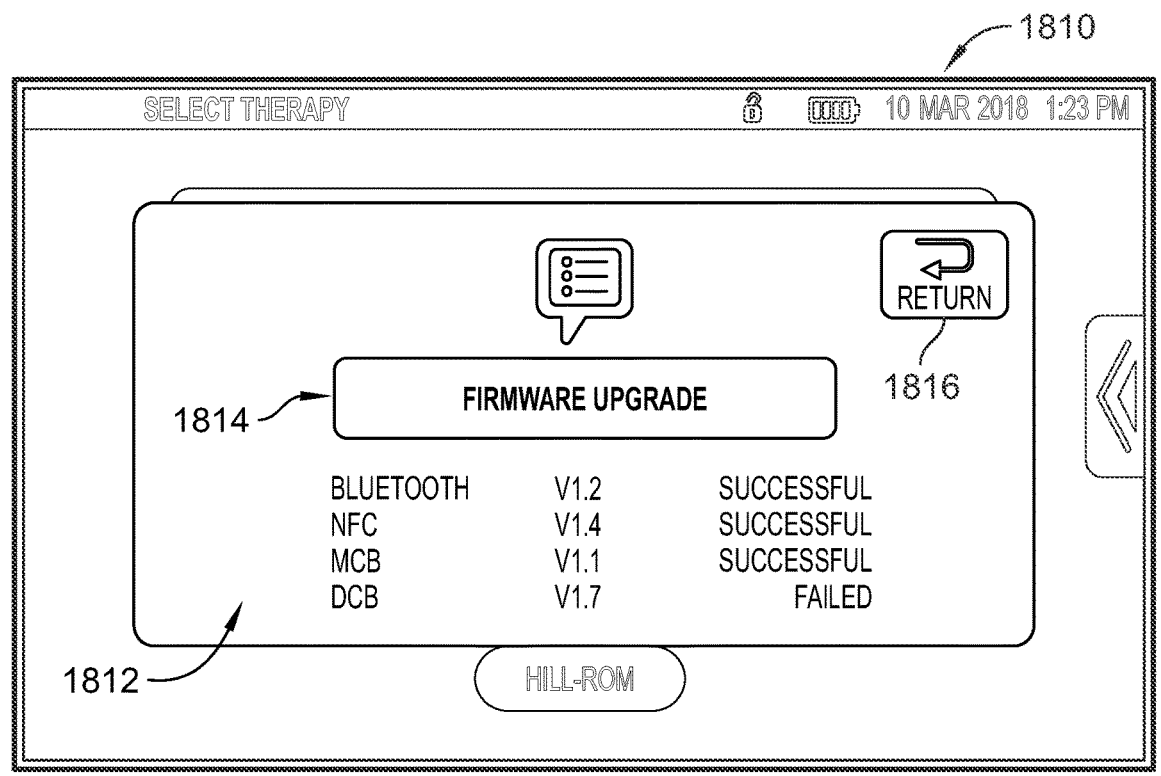
Figure 217:
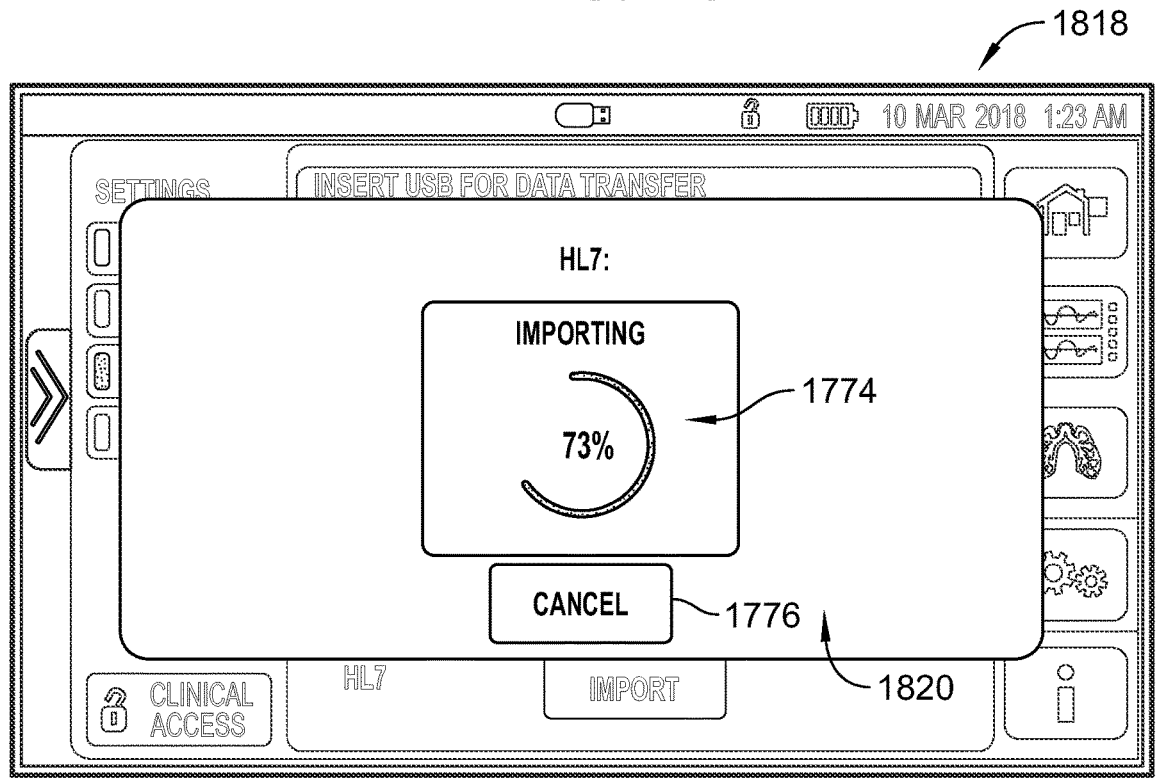
Figure 218:
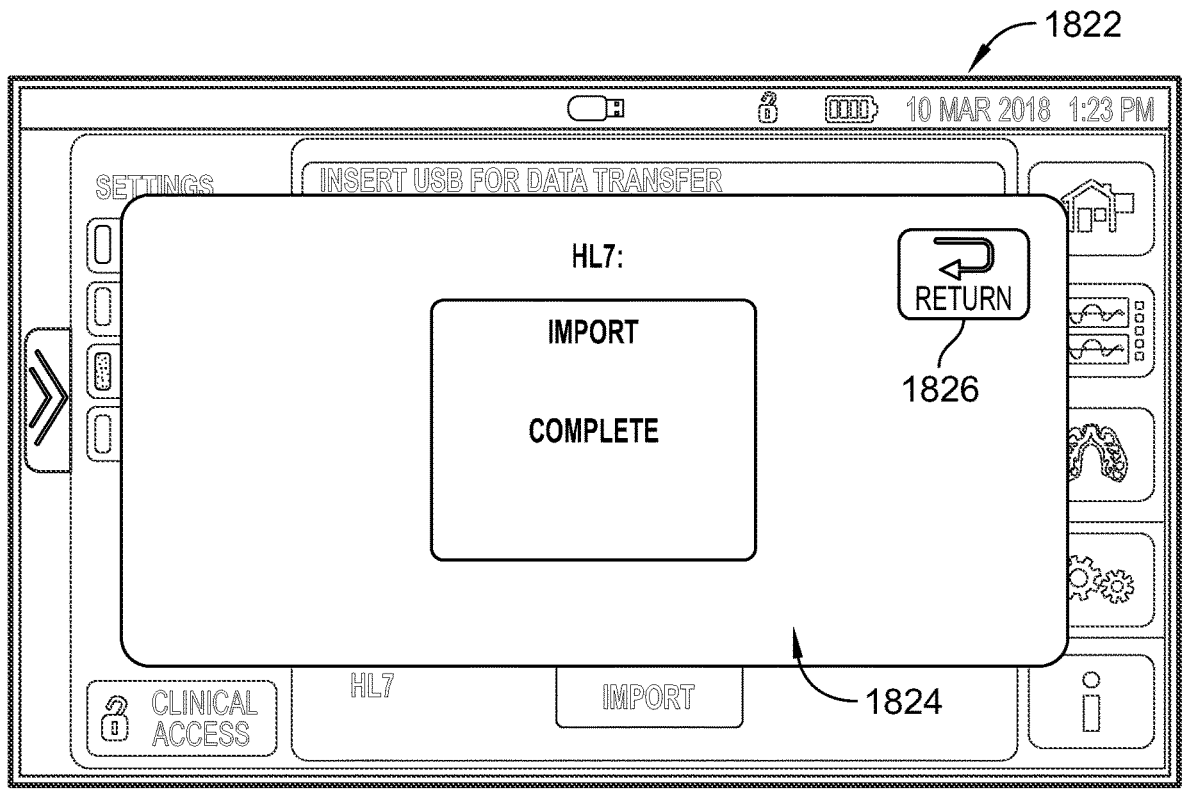
Figure 219:
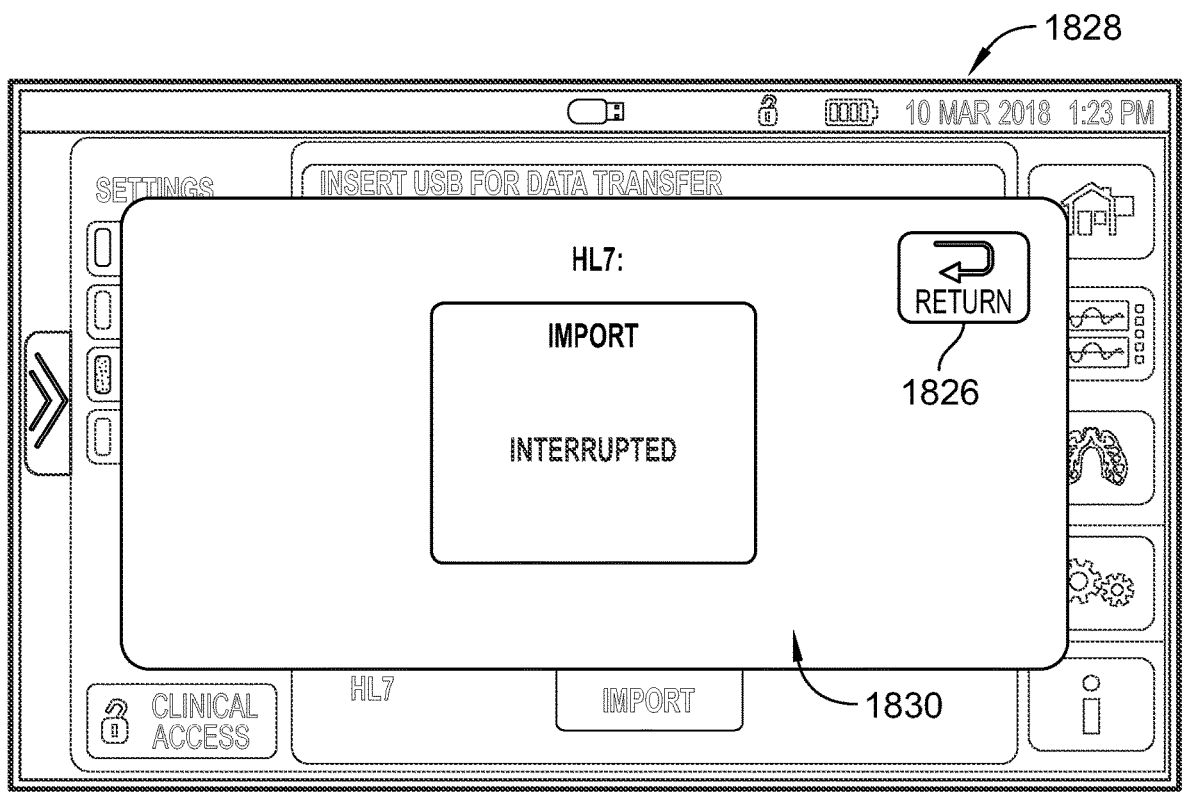
Figure 220:
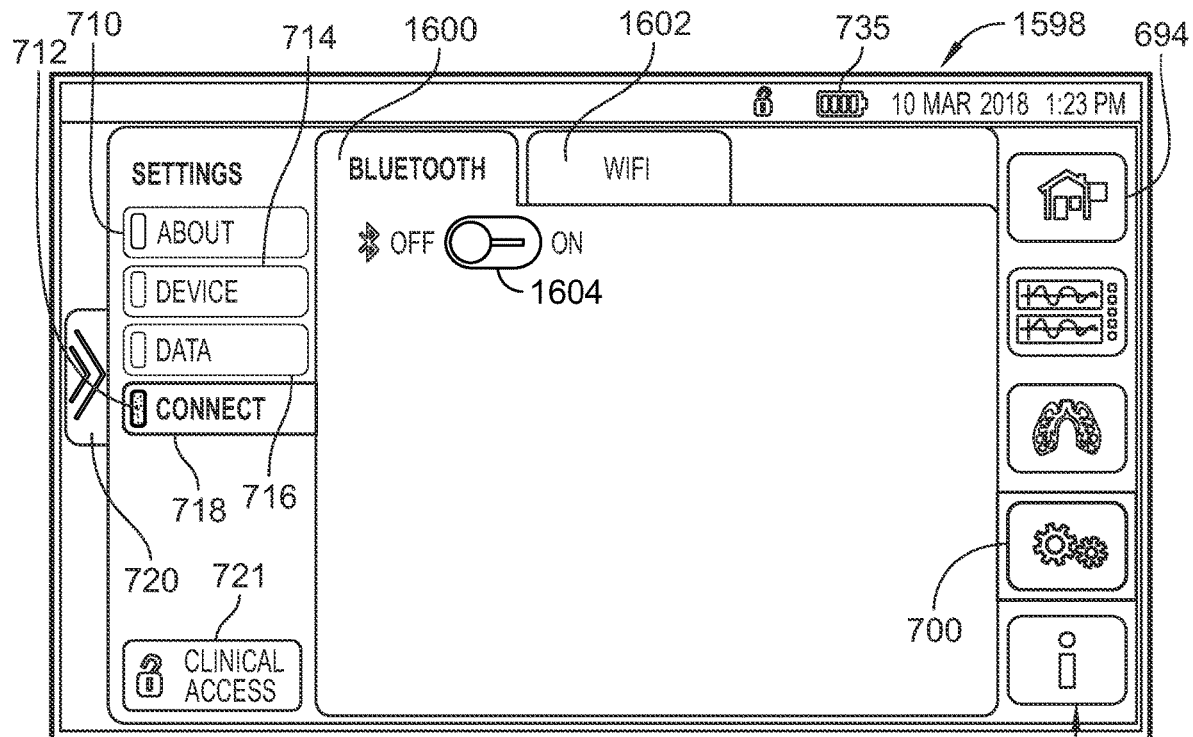
Figure 221:
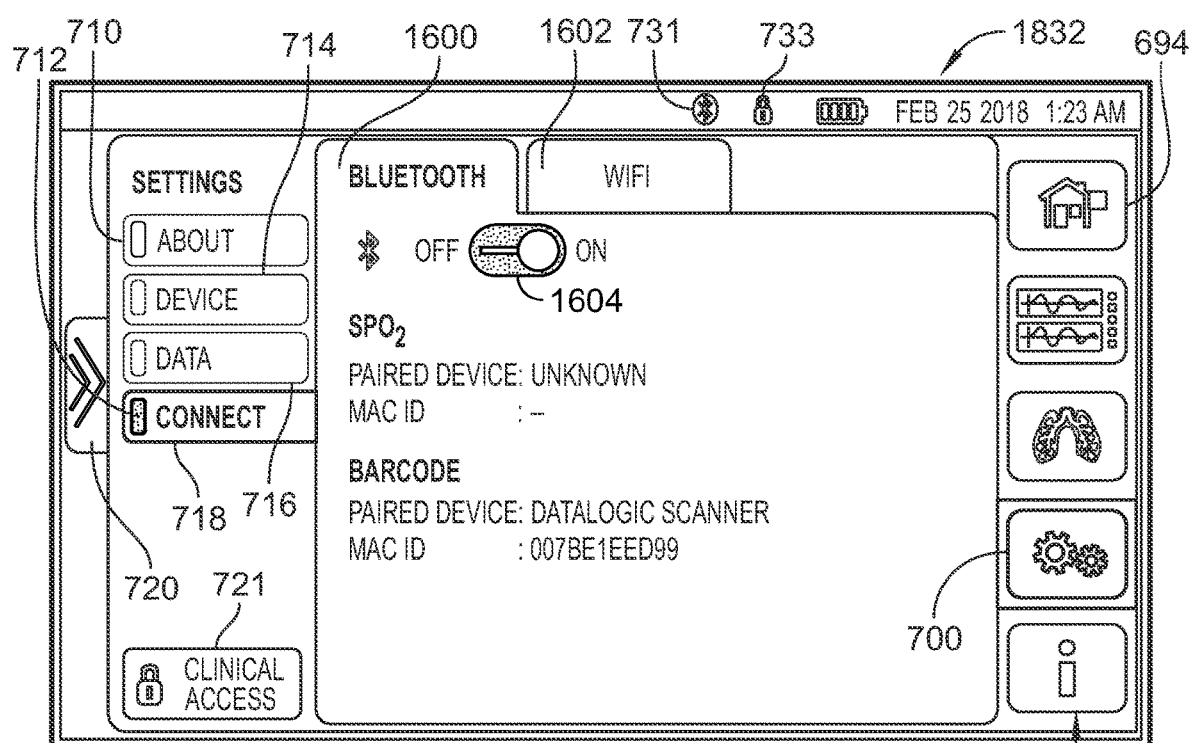
Figure 222:
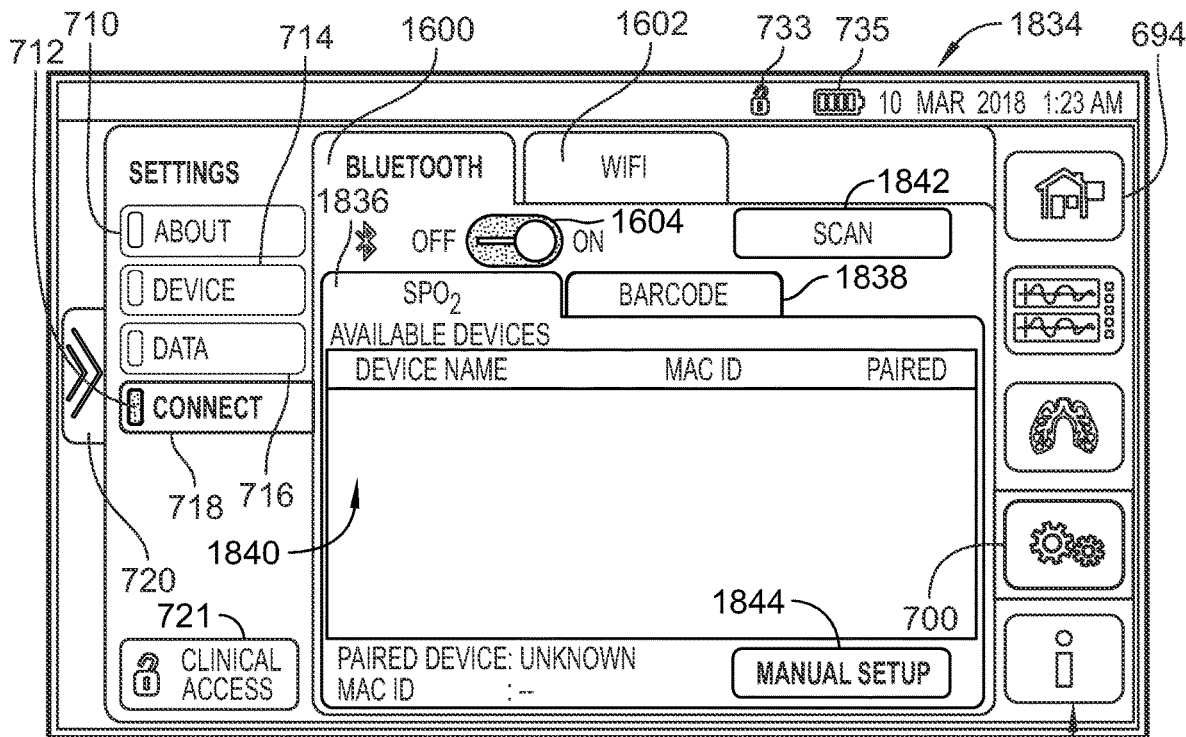
Figure 223:
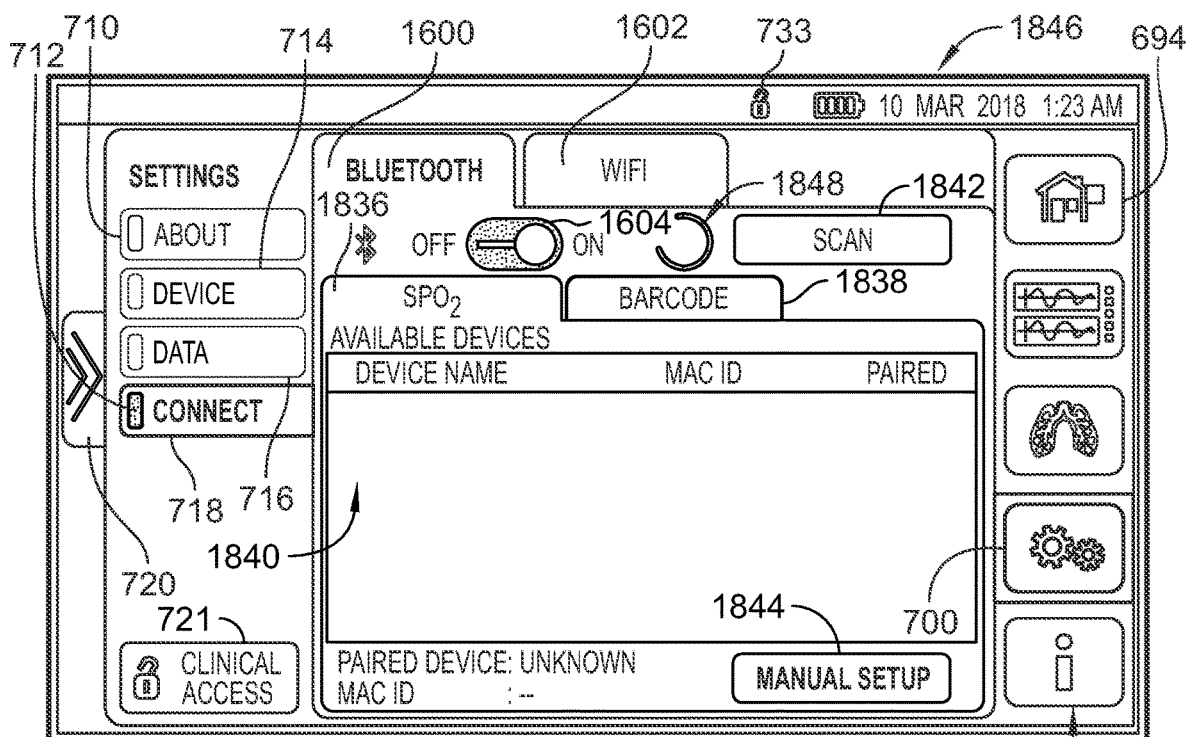
Figure 224:
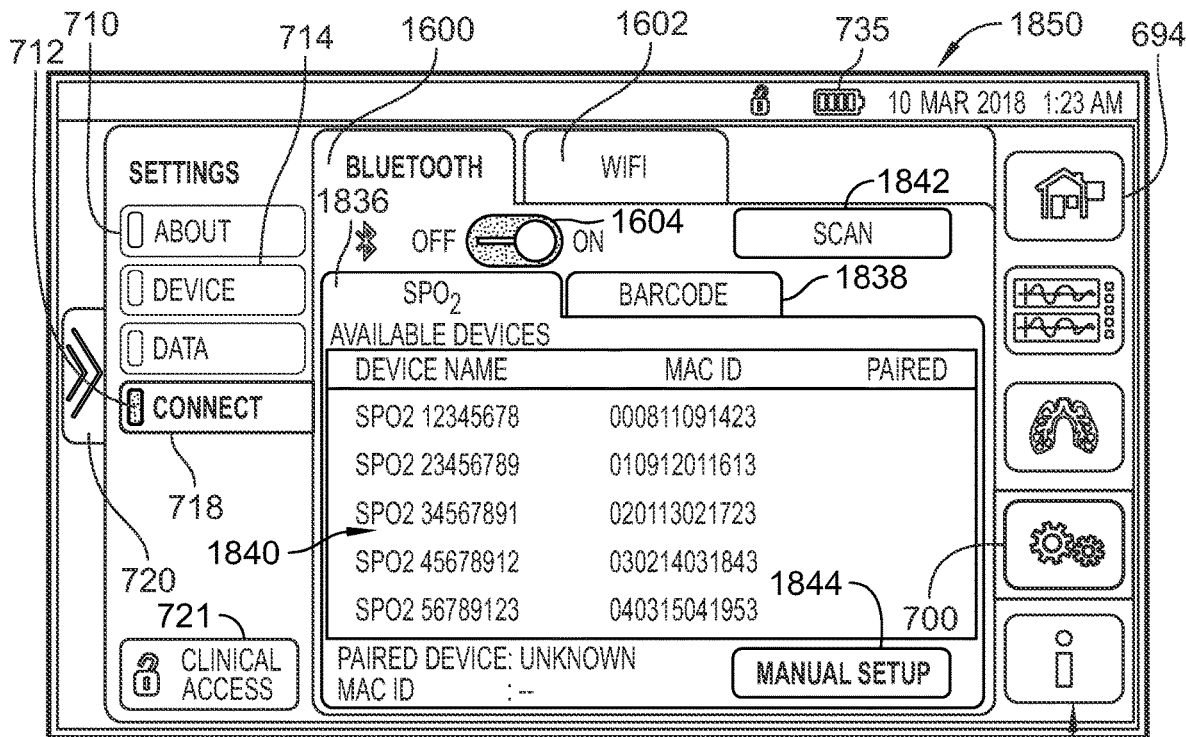
Figure 225:
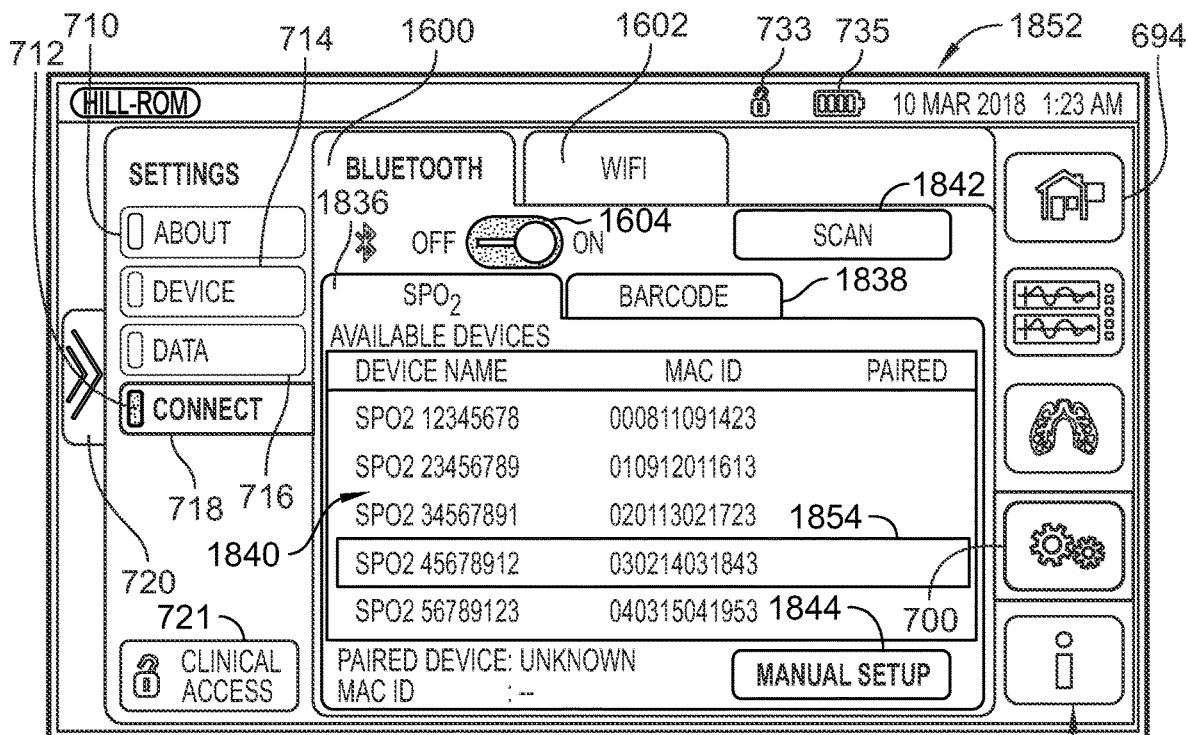
Figure 226:
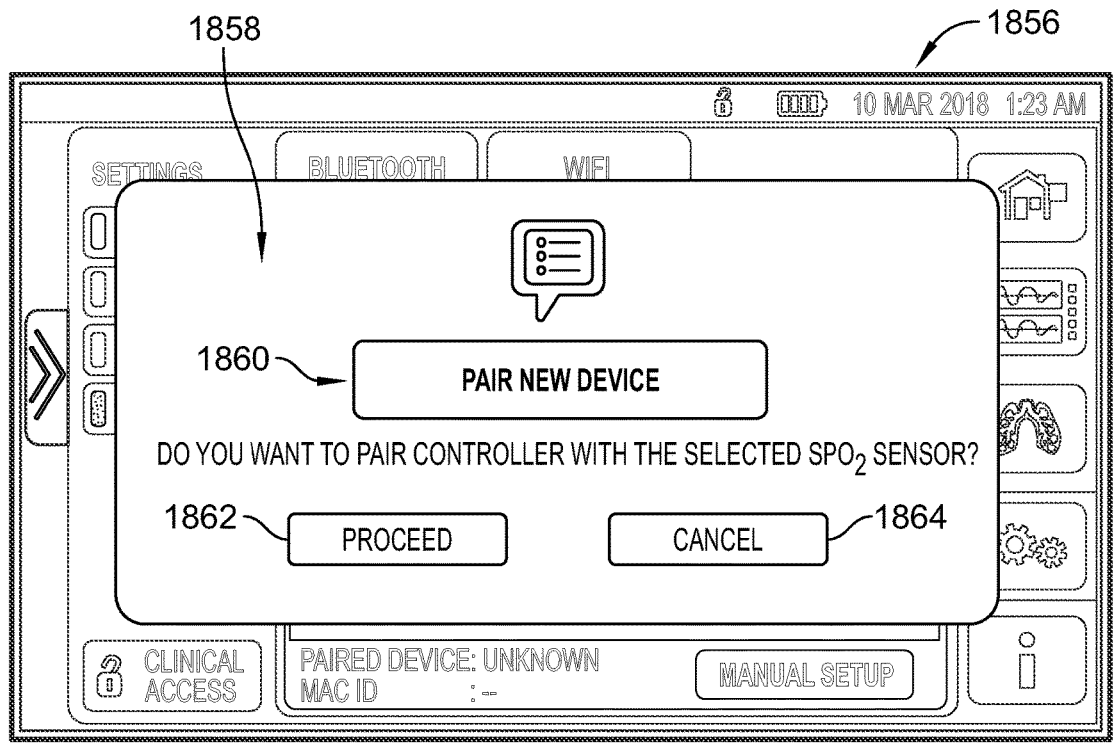
Figure 227:
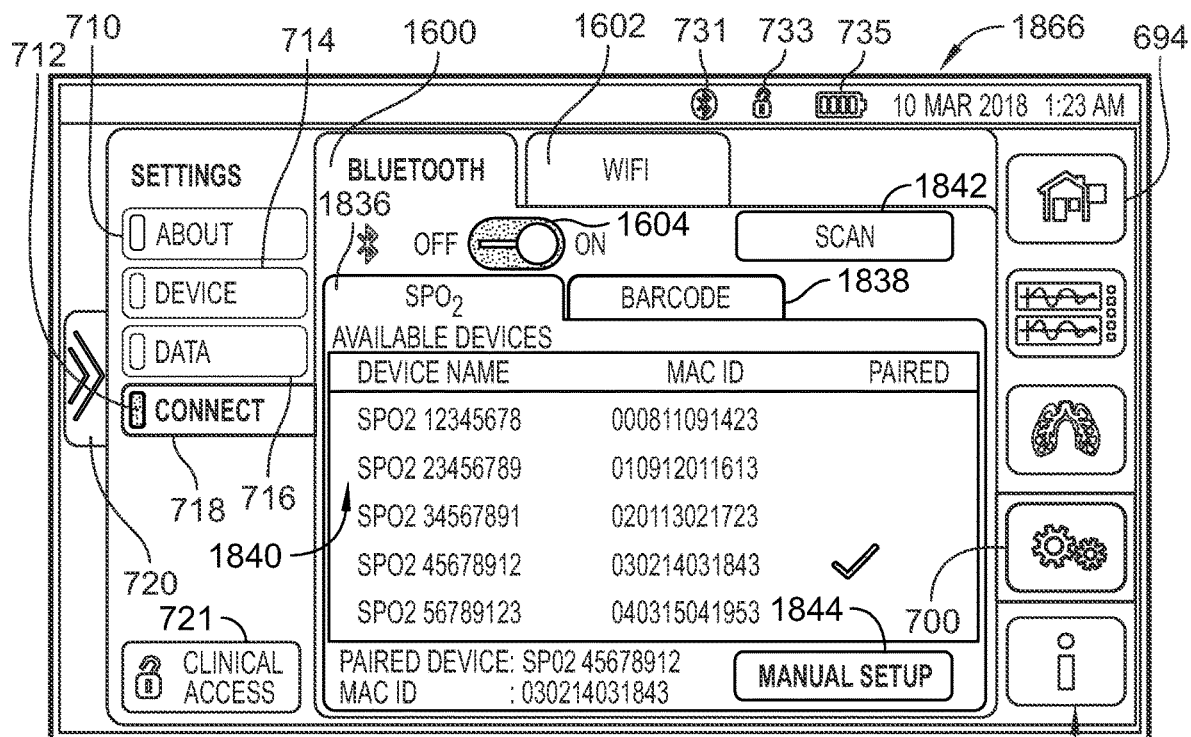
Figure 228:
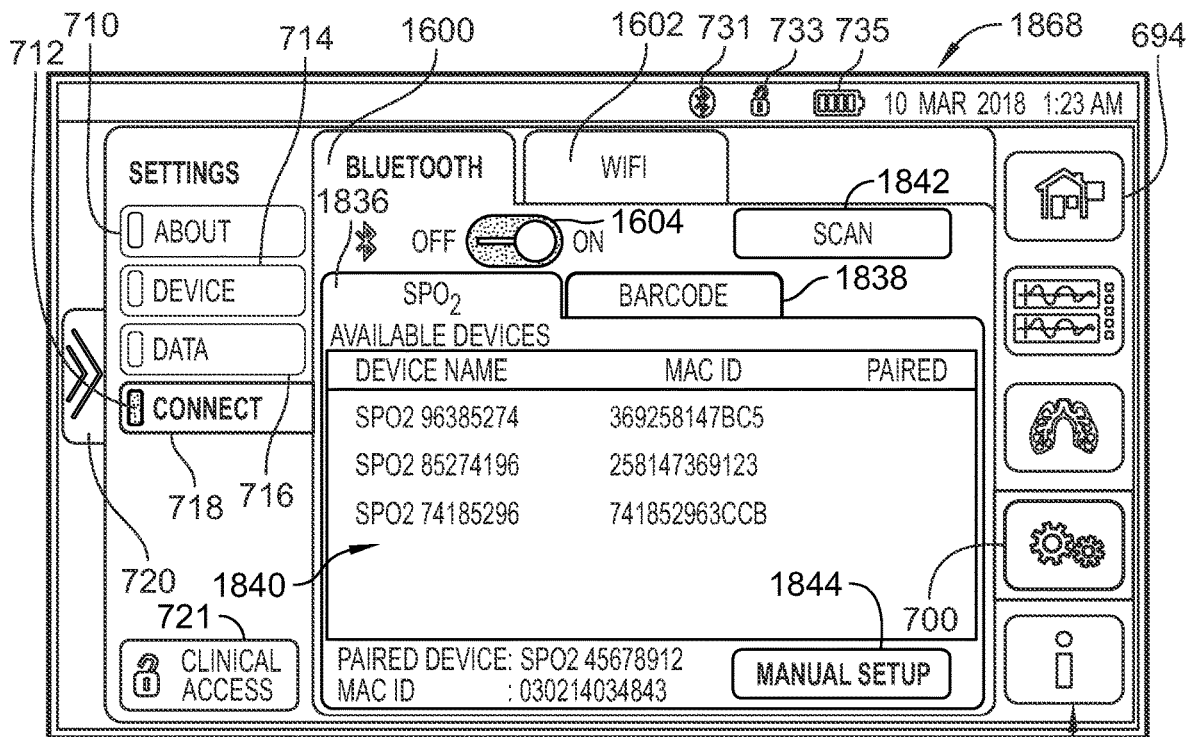
Figure 229:
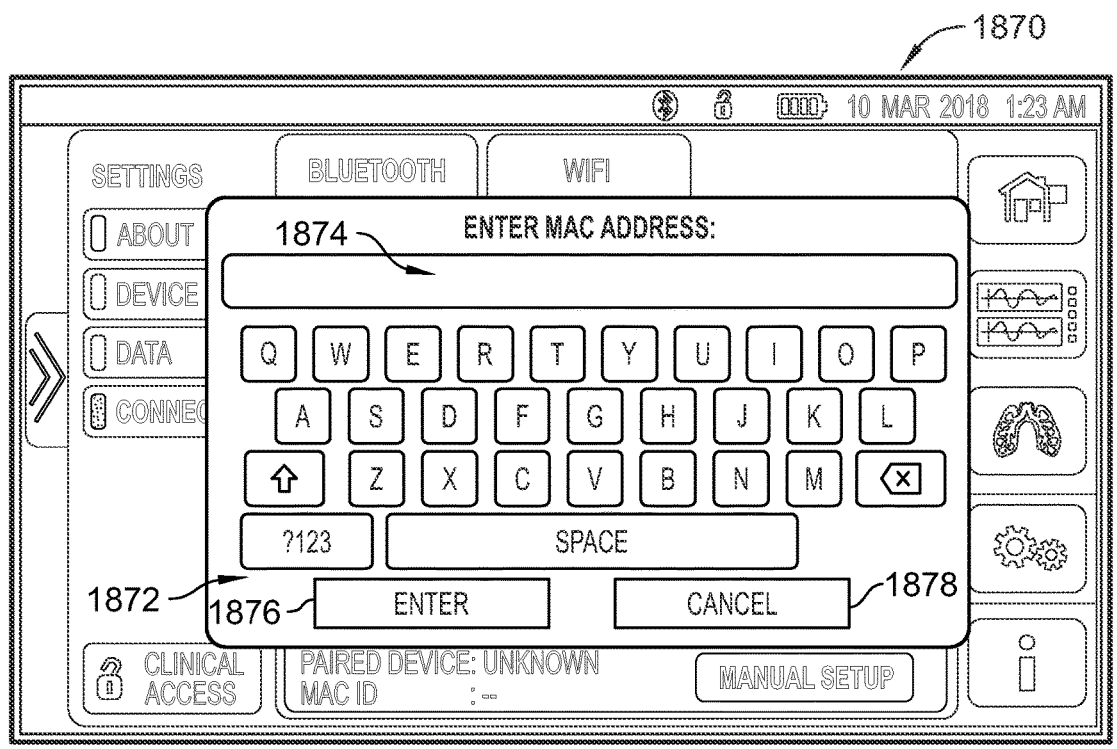
Figure 230:
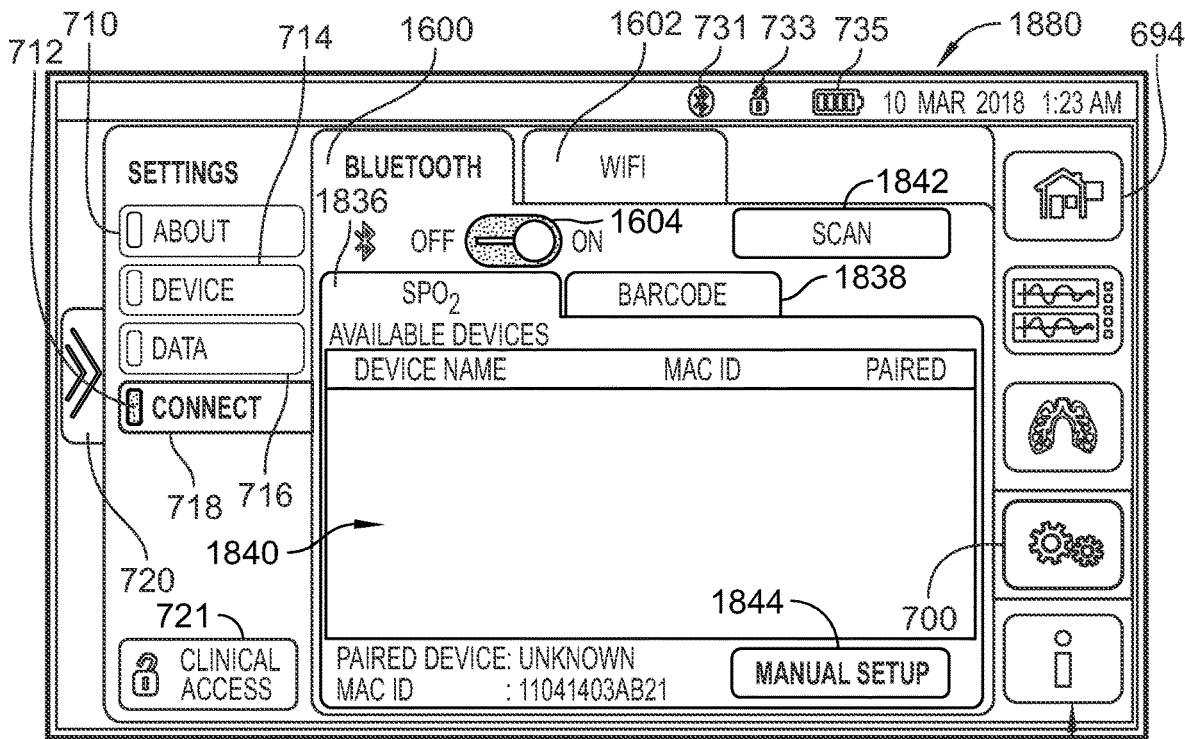
Figure 231:
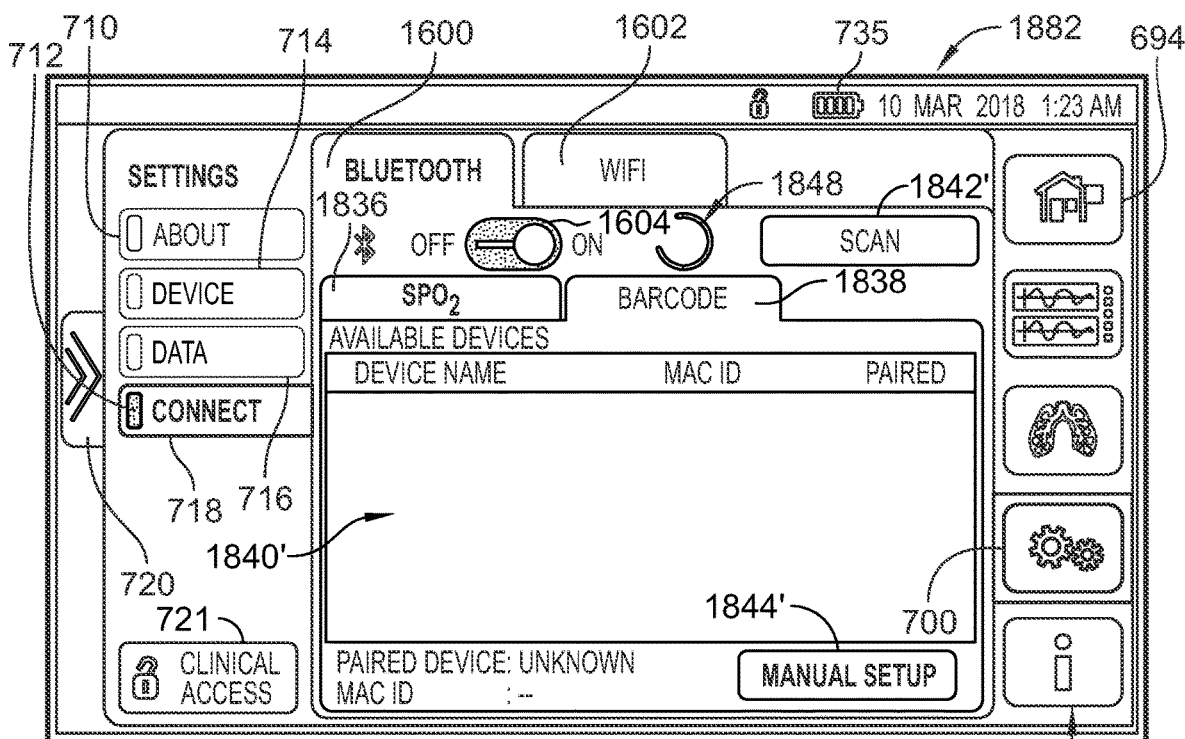
Figure 232:
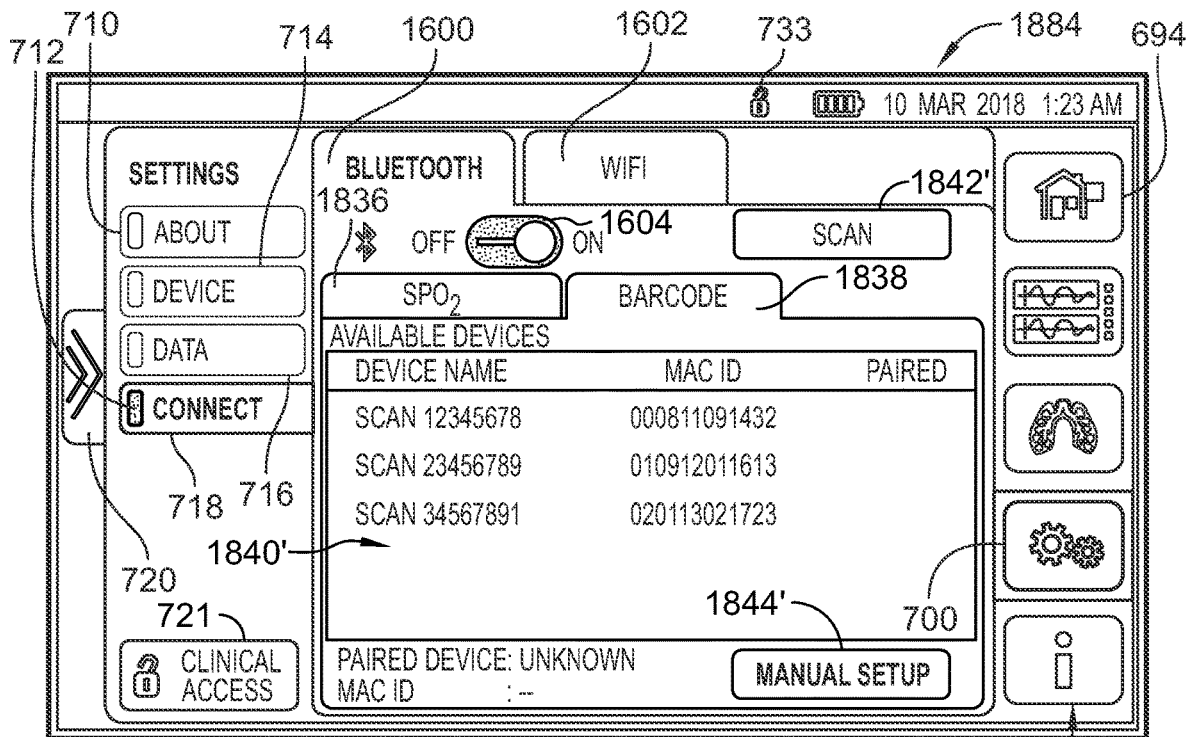
Figure 233:
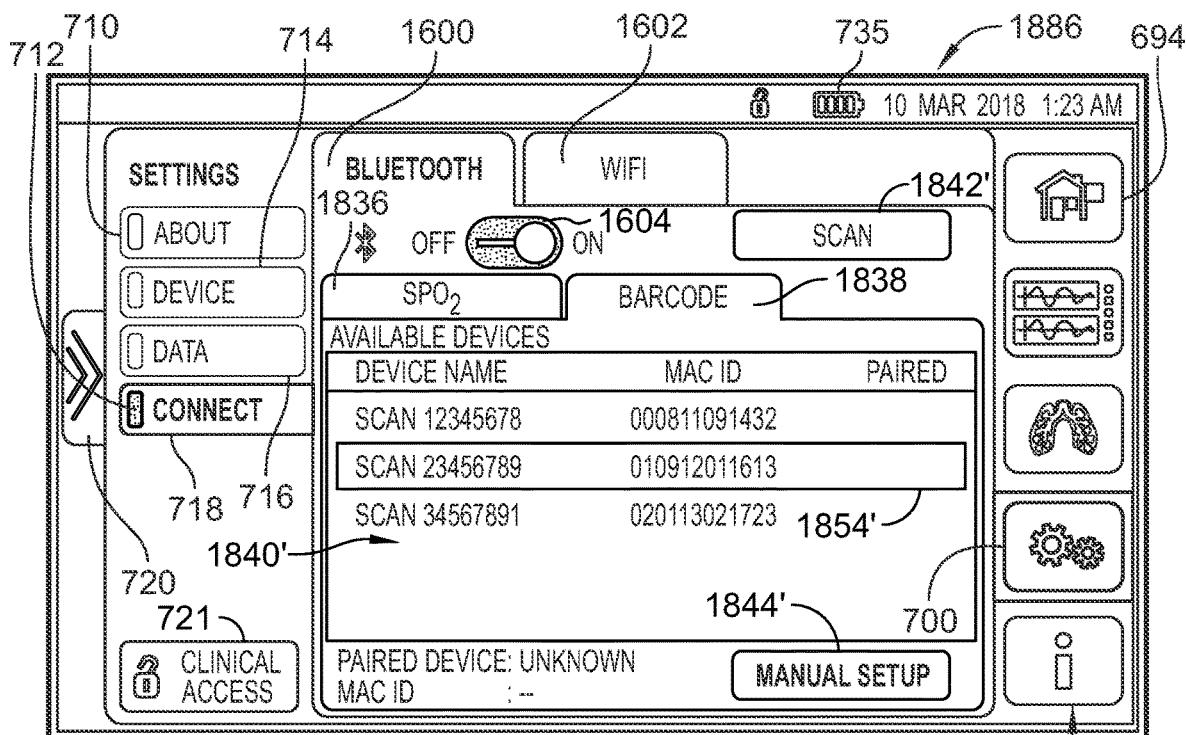
Figure 234:
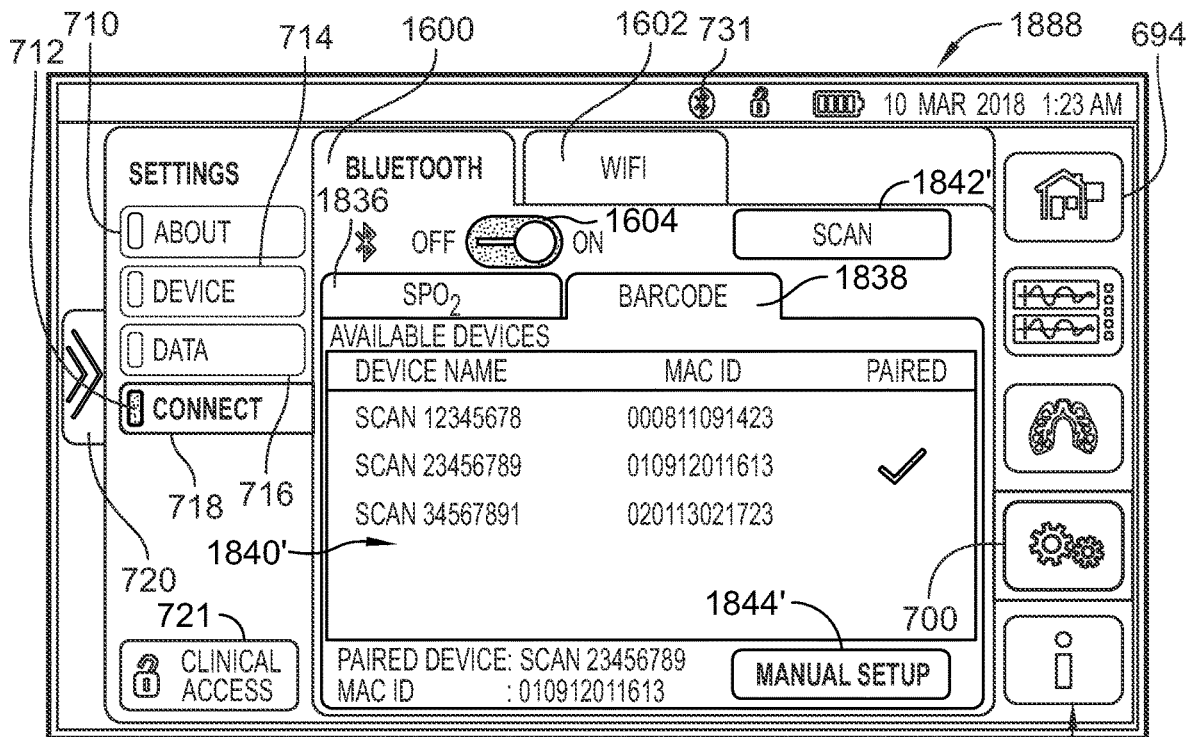
Figure 235:
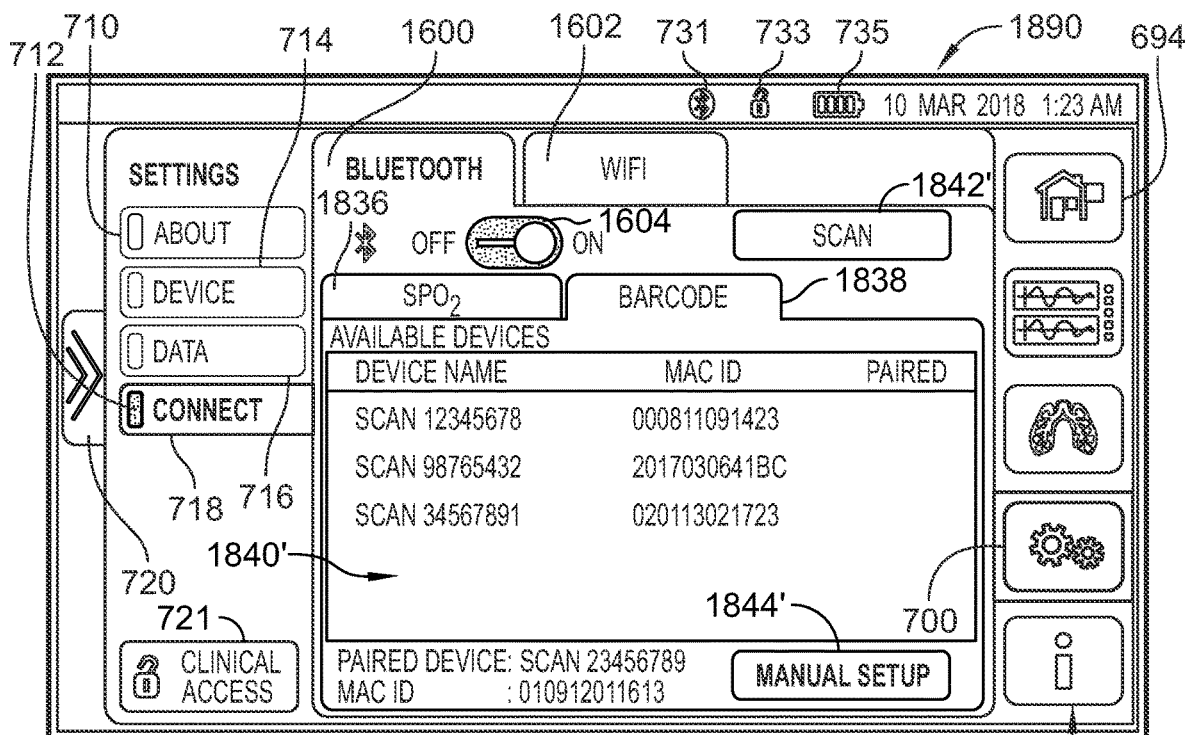
Figure 236:
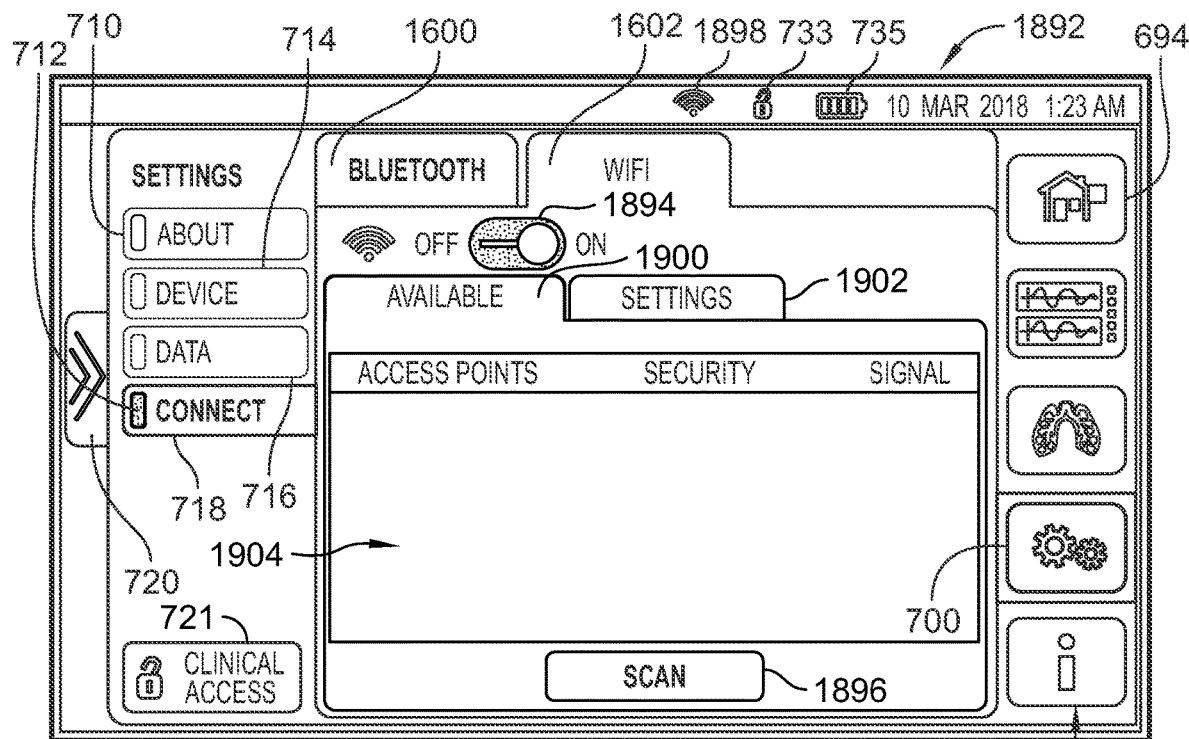
Figure 237:
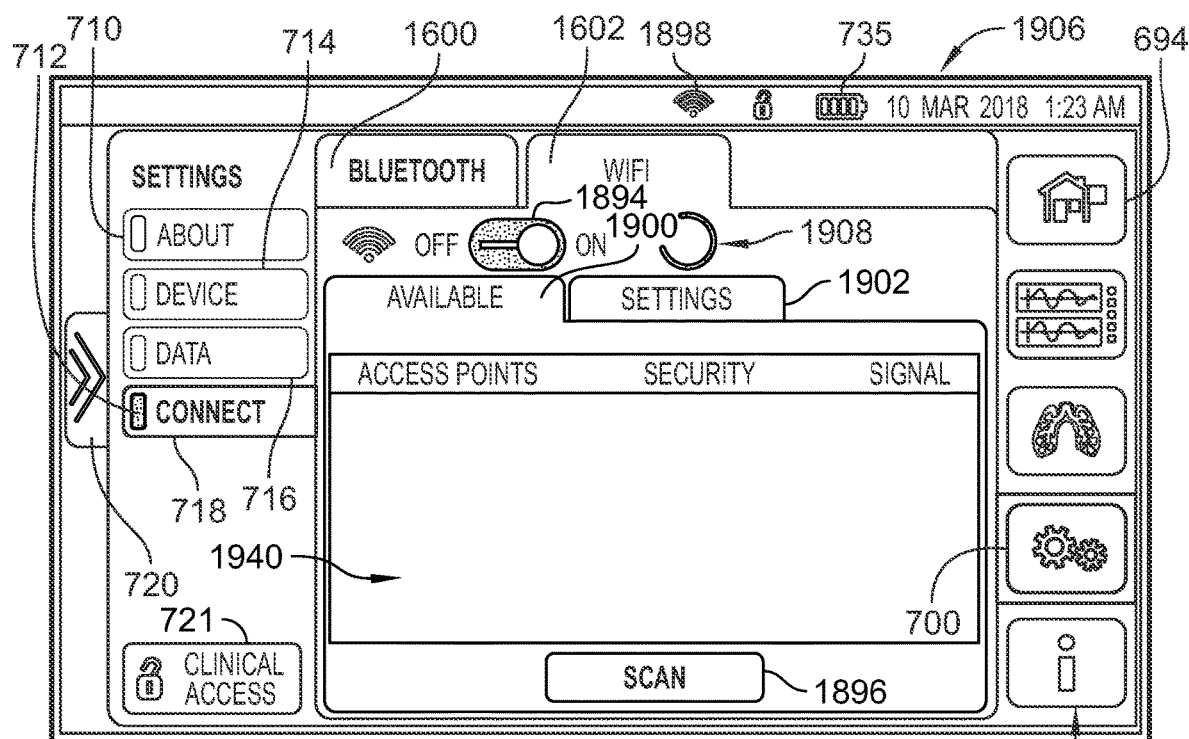
Figure 238:
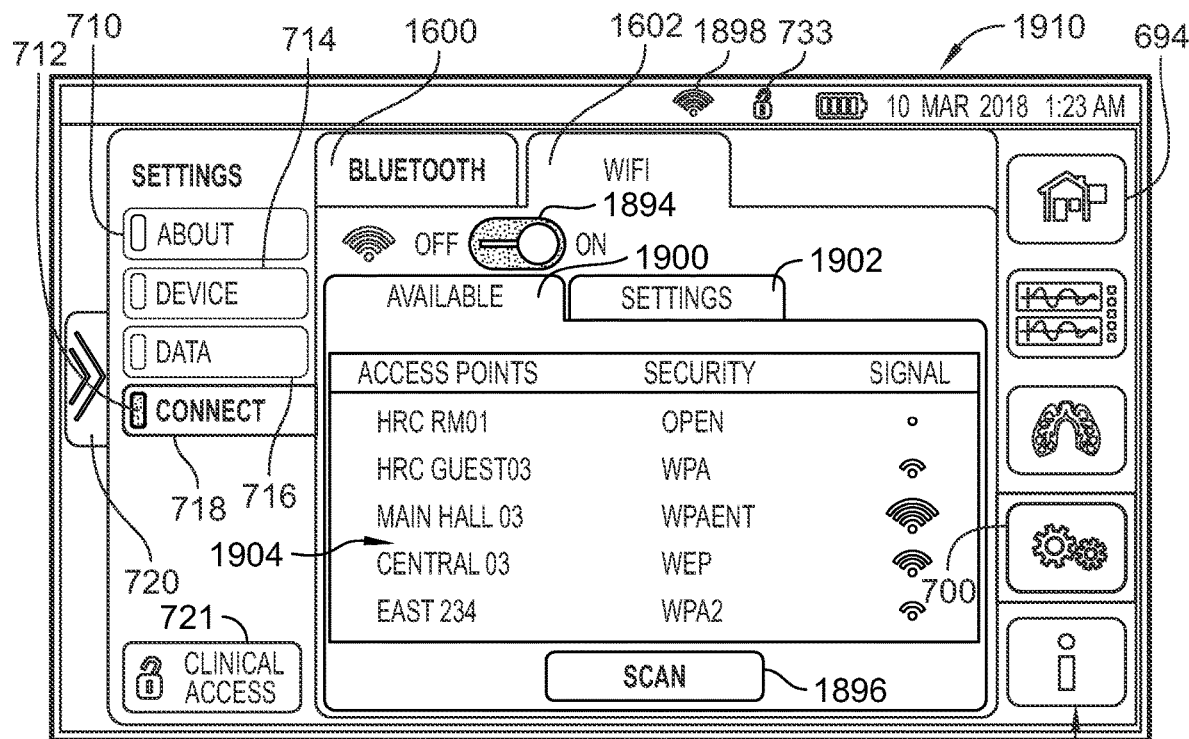
Figure 239:
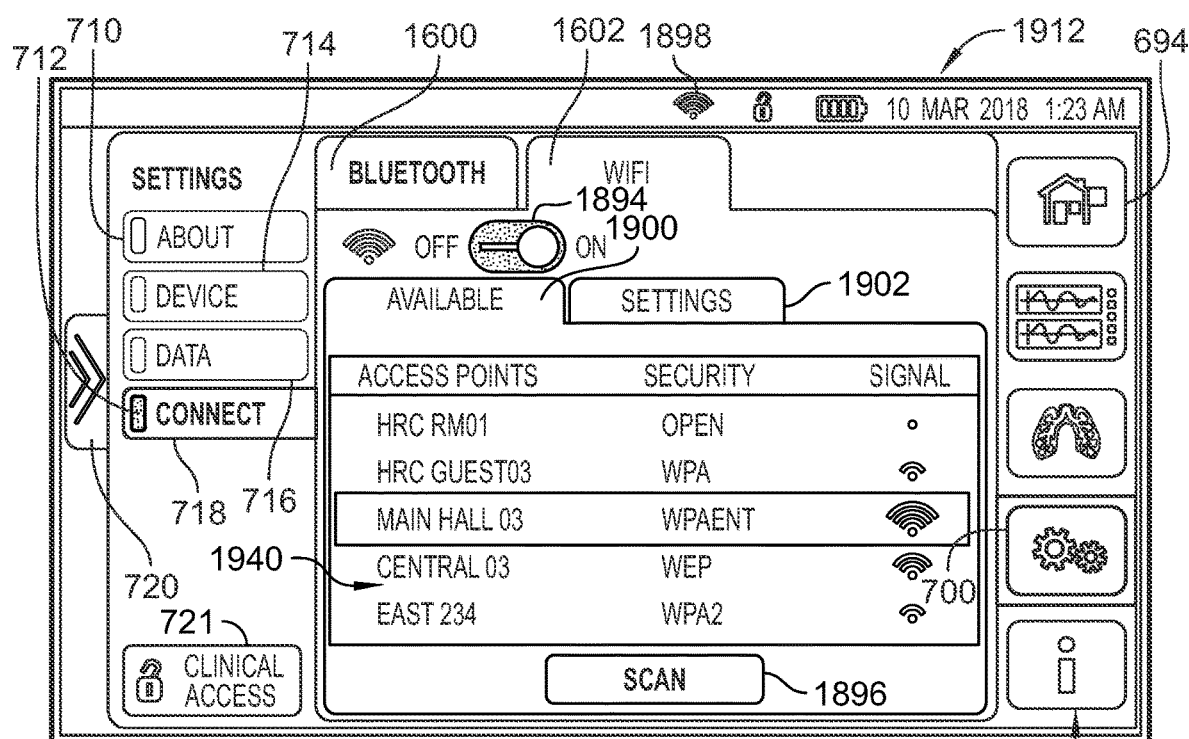
Figure 240:
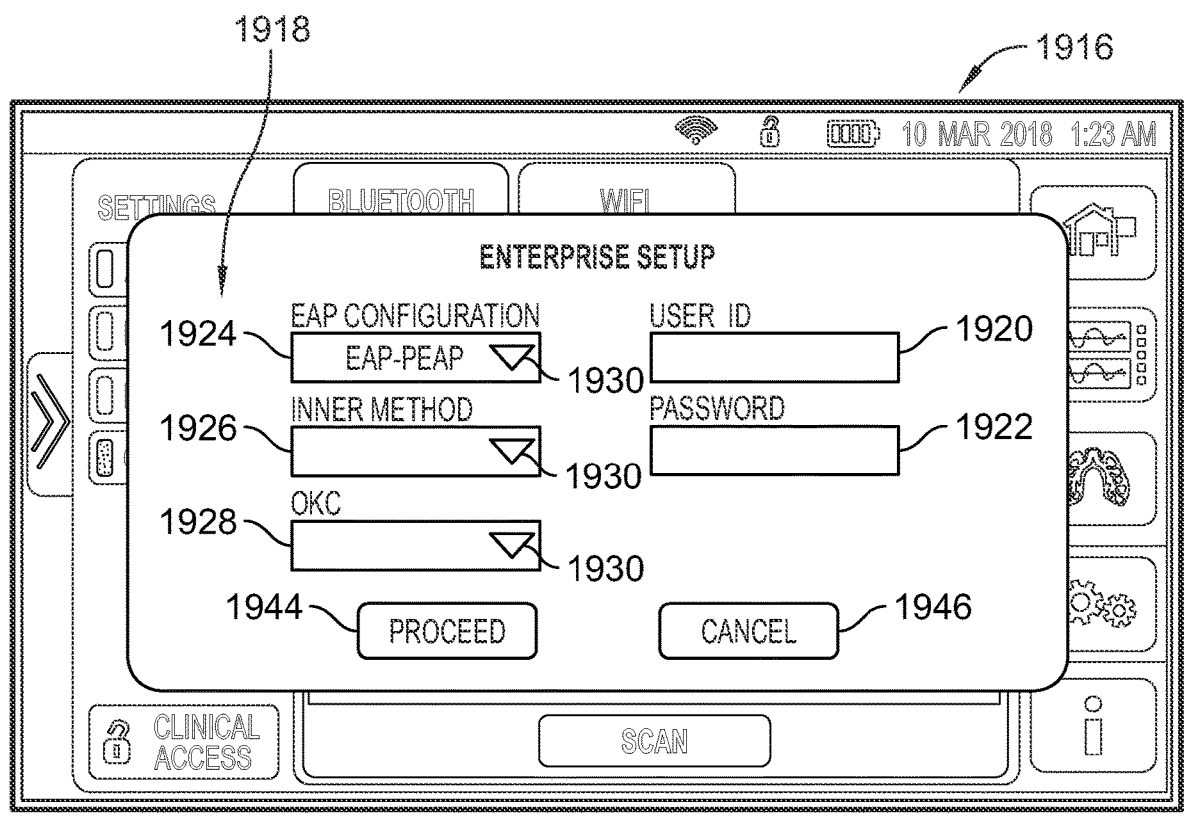
Figure 241:
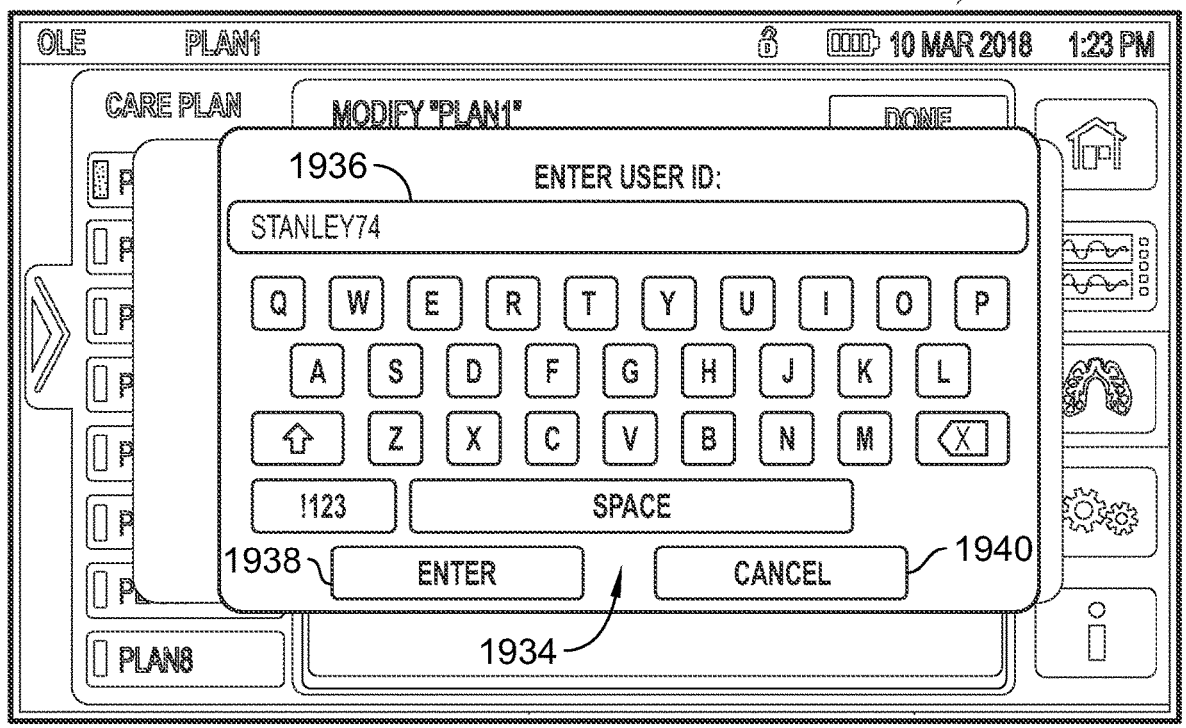
Figure 242:
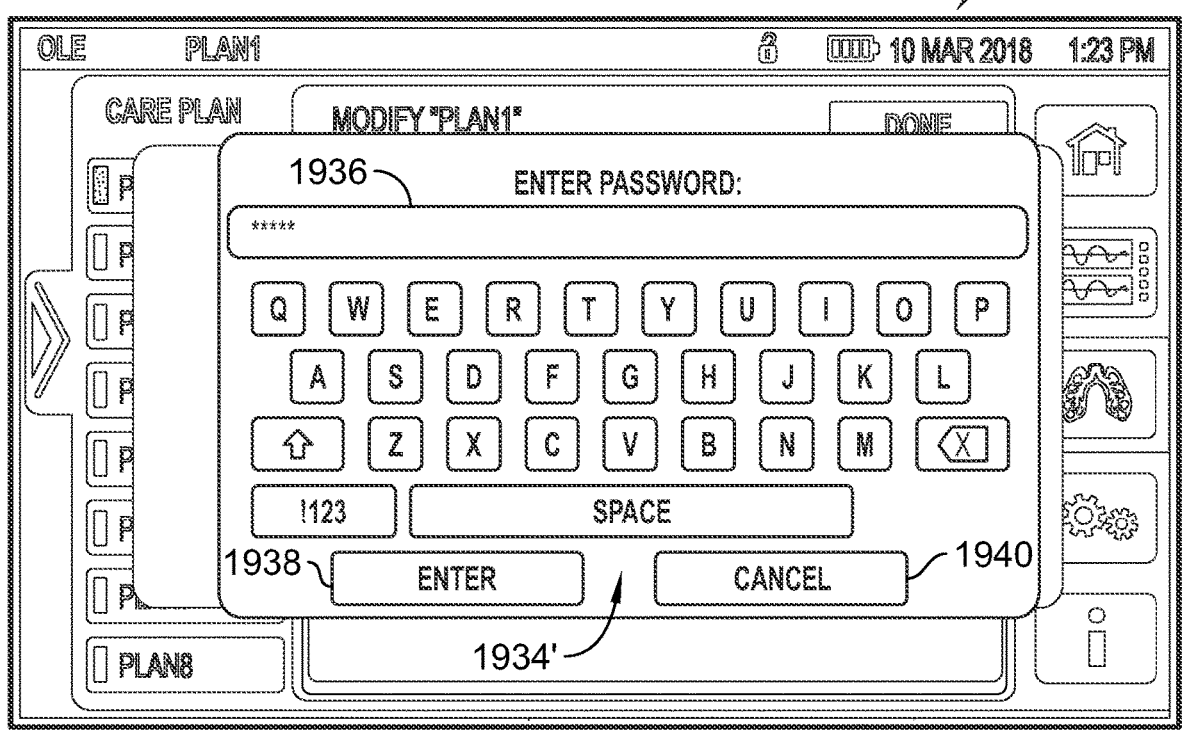
Figure 243:
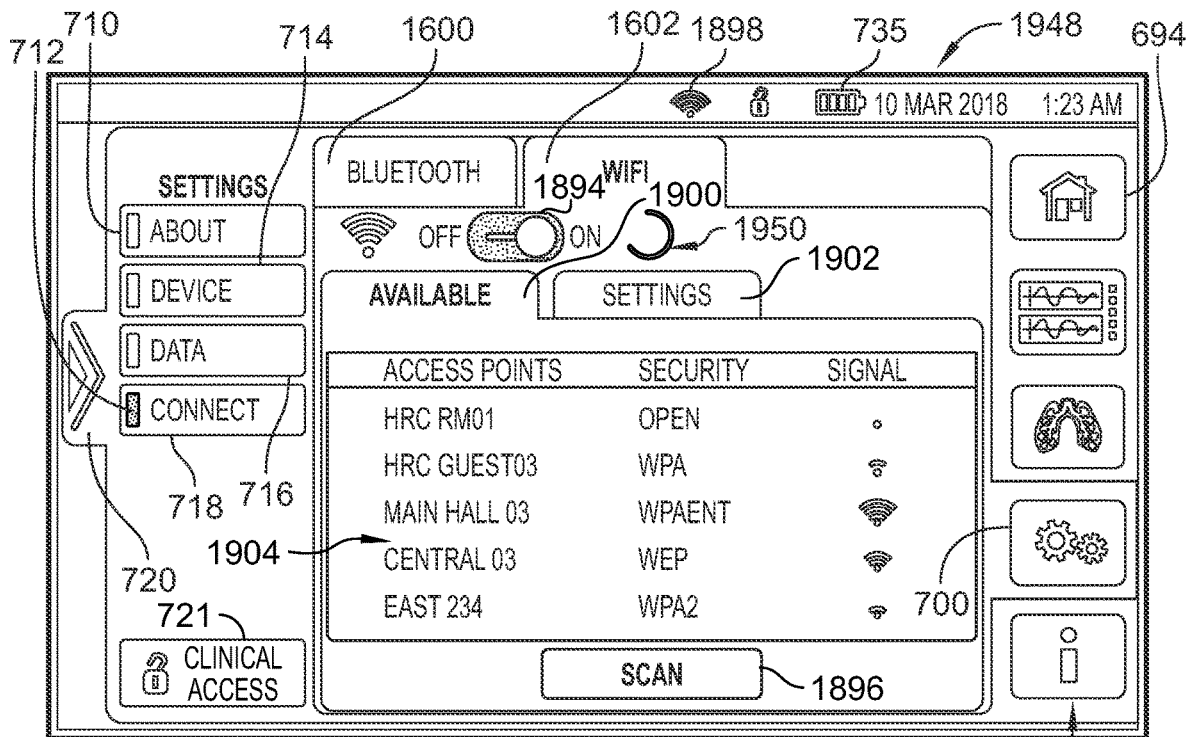
Figure 244:
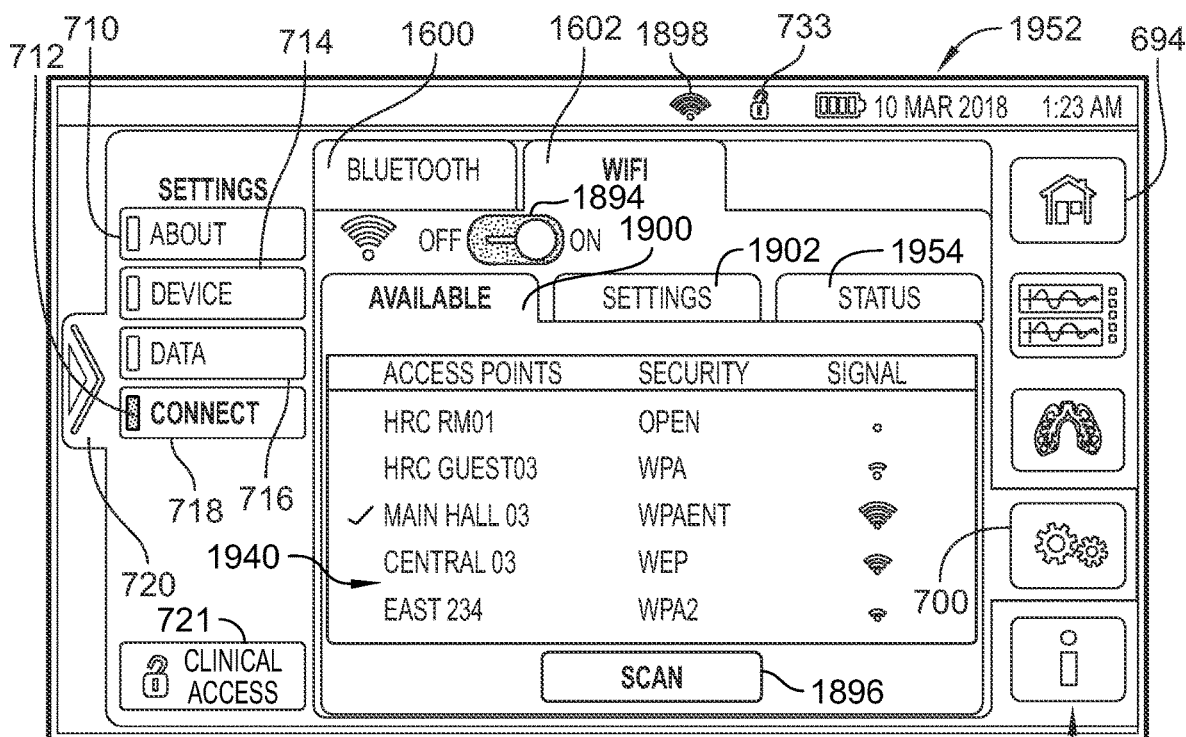
Figure 245:
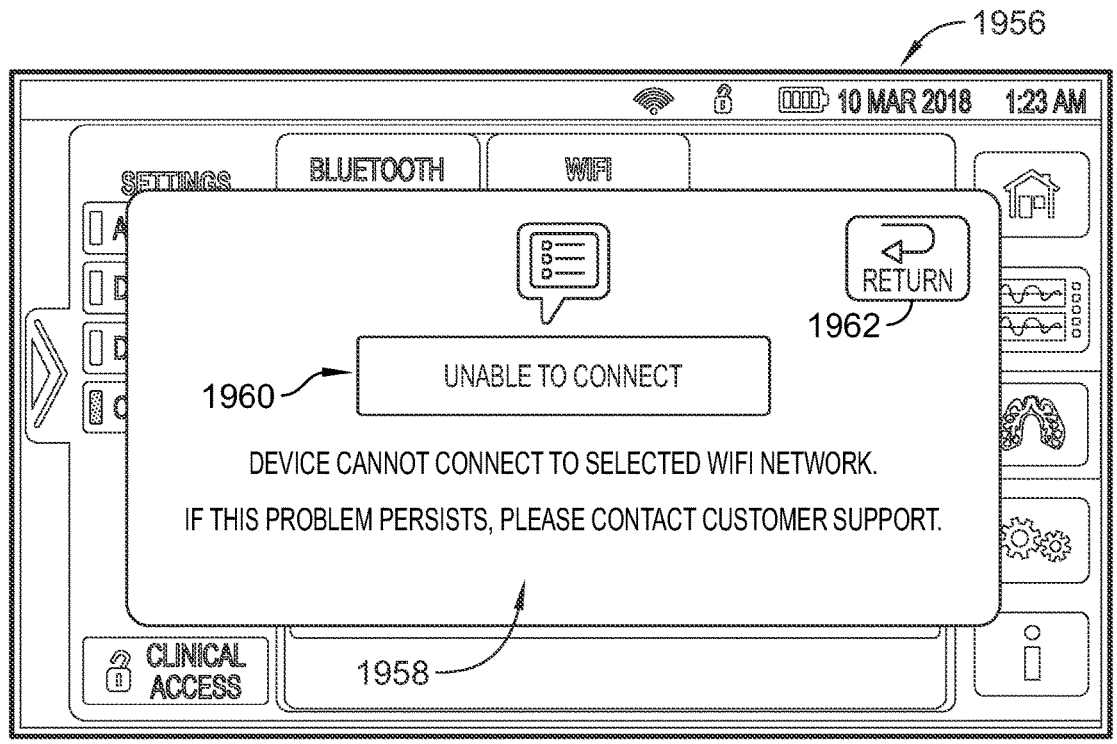
Figure 246:
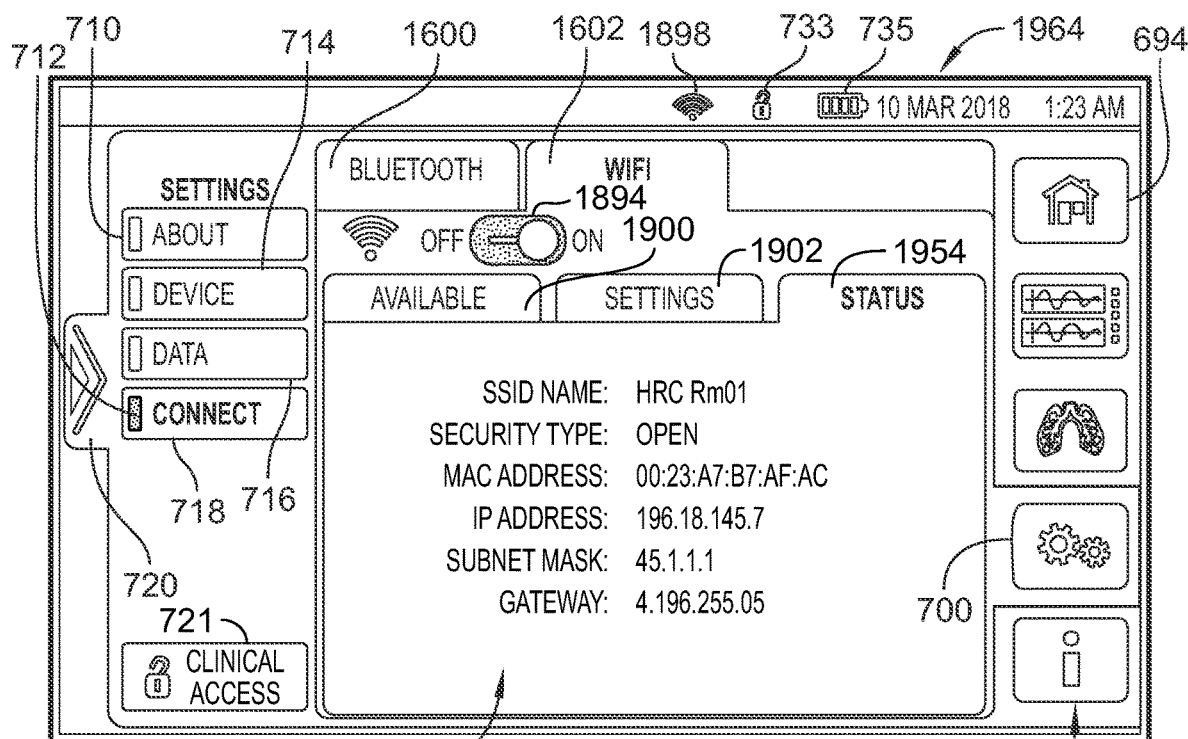
Figure 247:
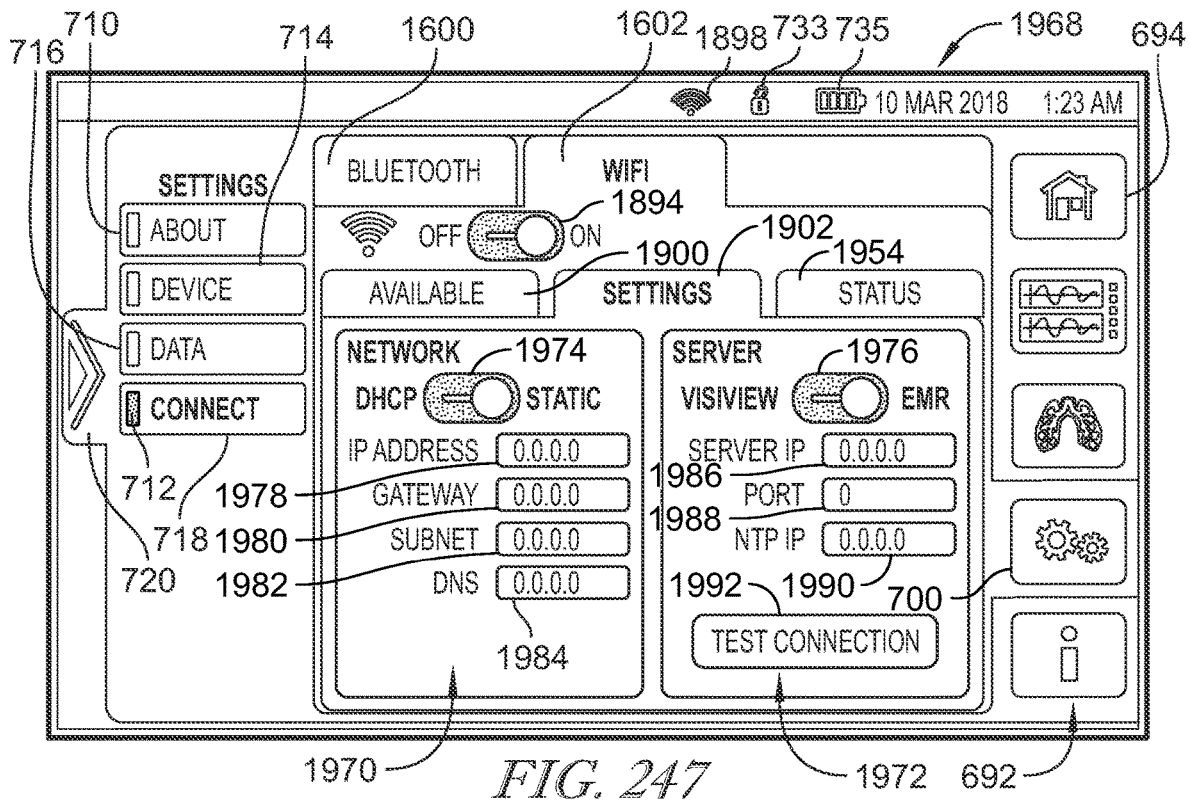
Figure 248:
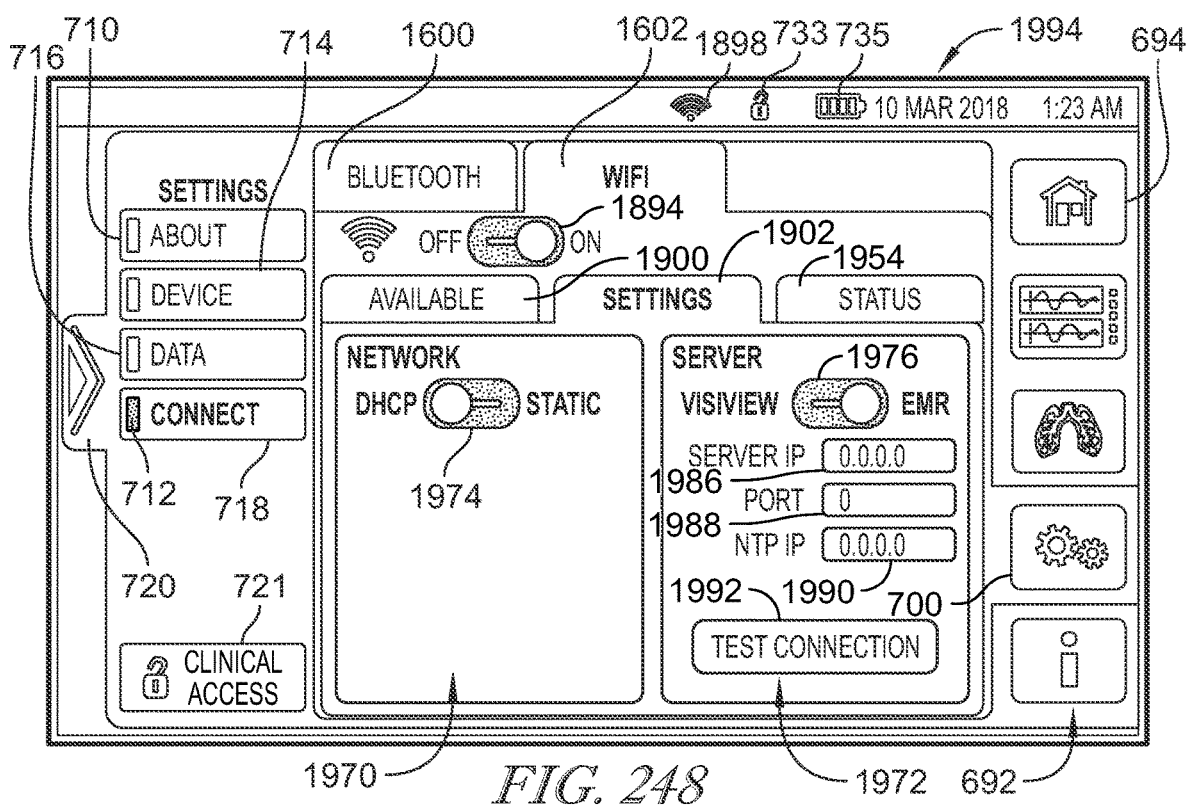
Figure 249:
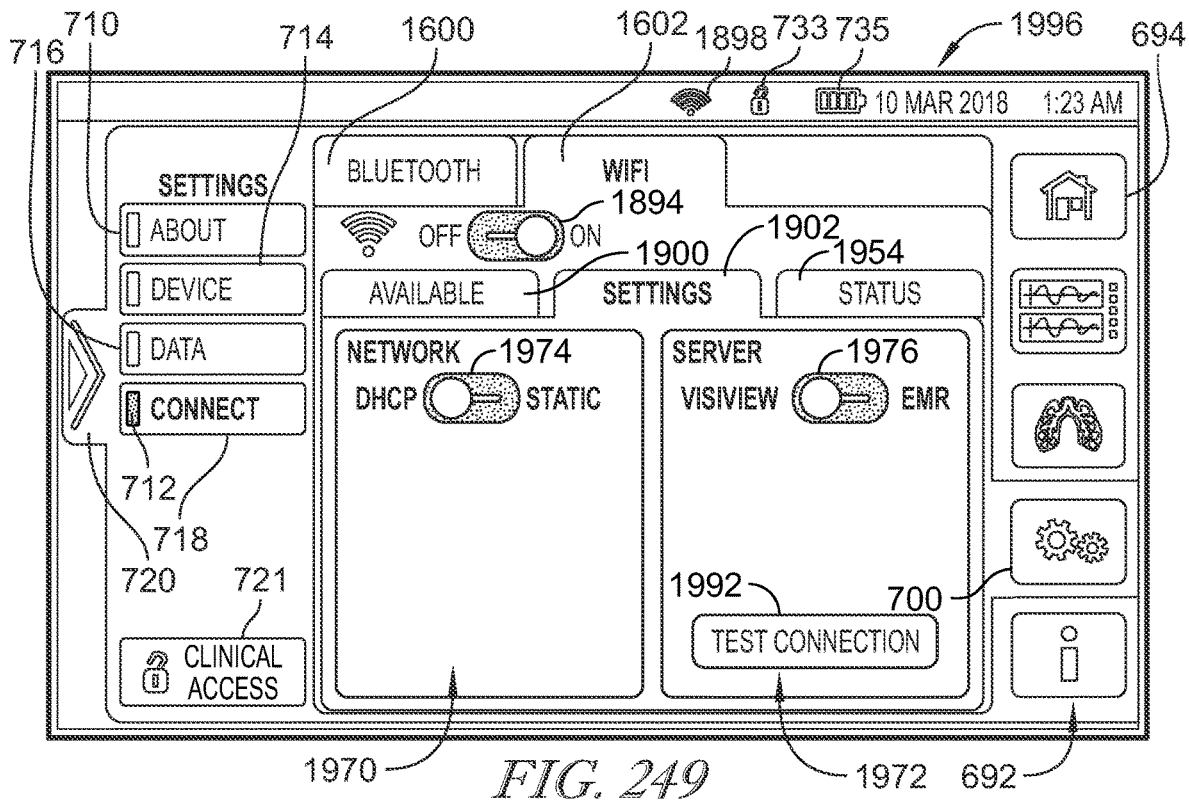
Figure 250:
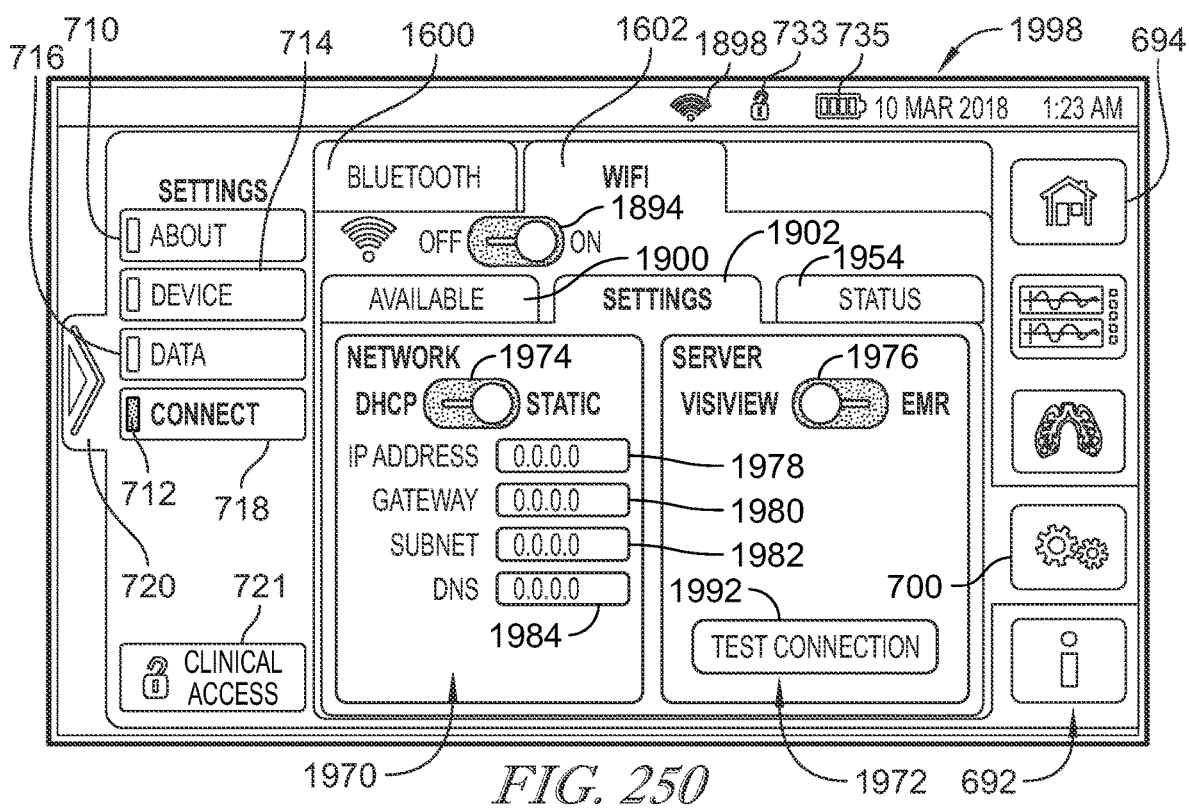
Figure 251:
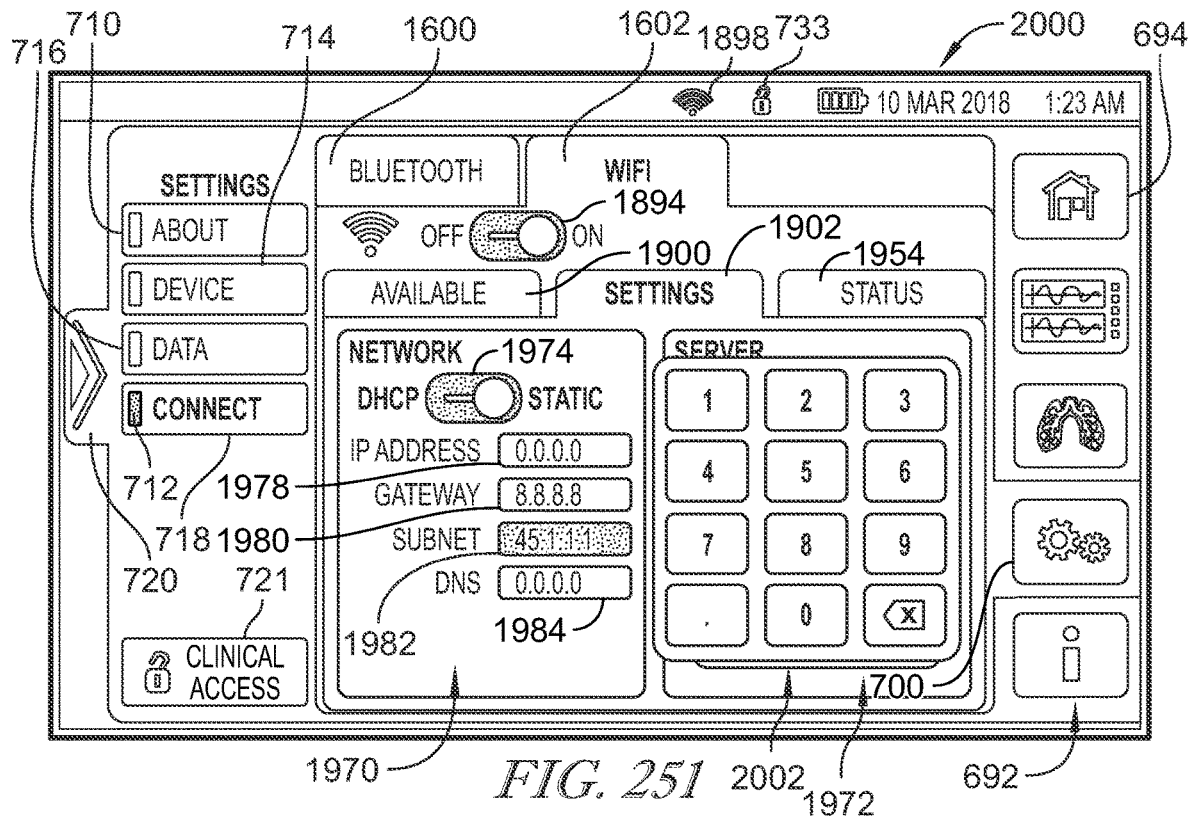
Figure 252:
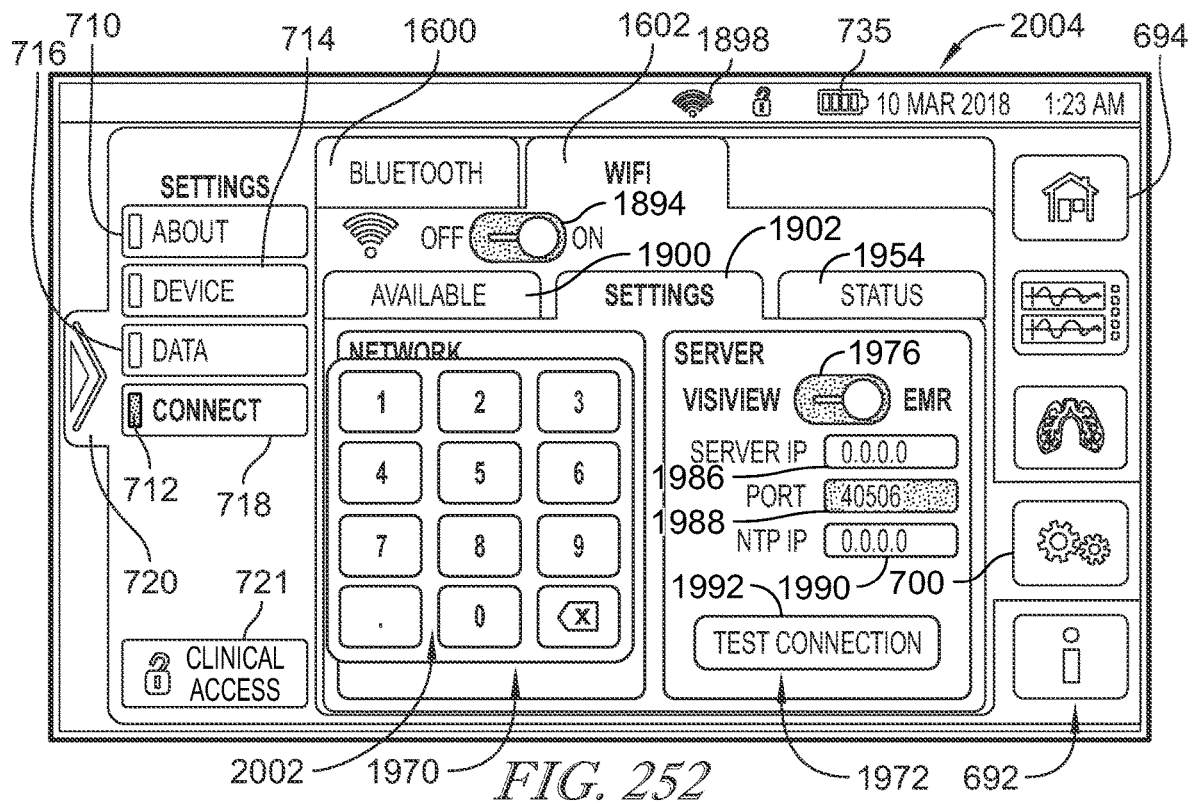
Figure 253:
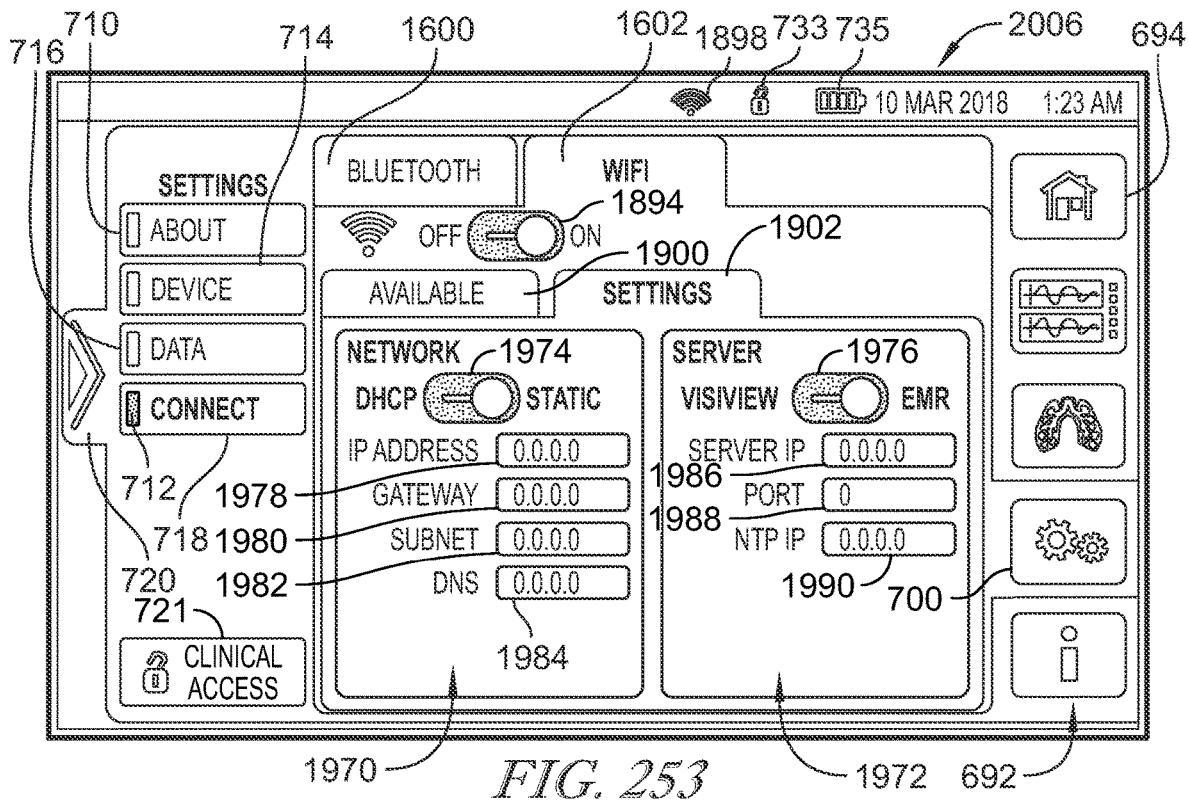
Figure 254:
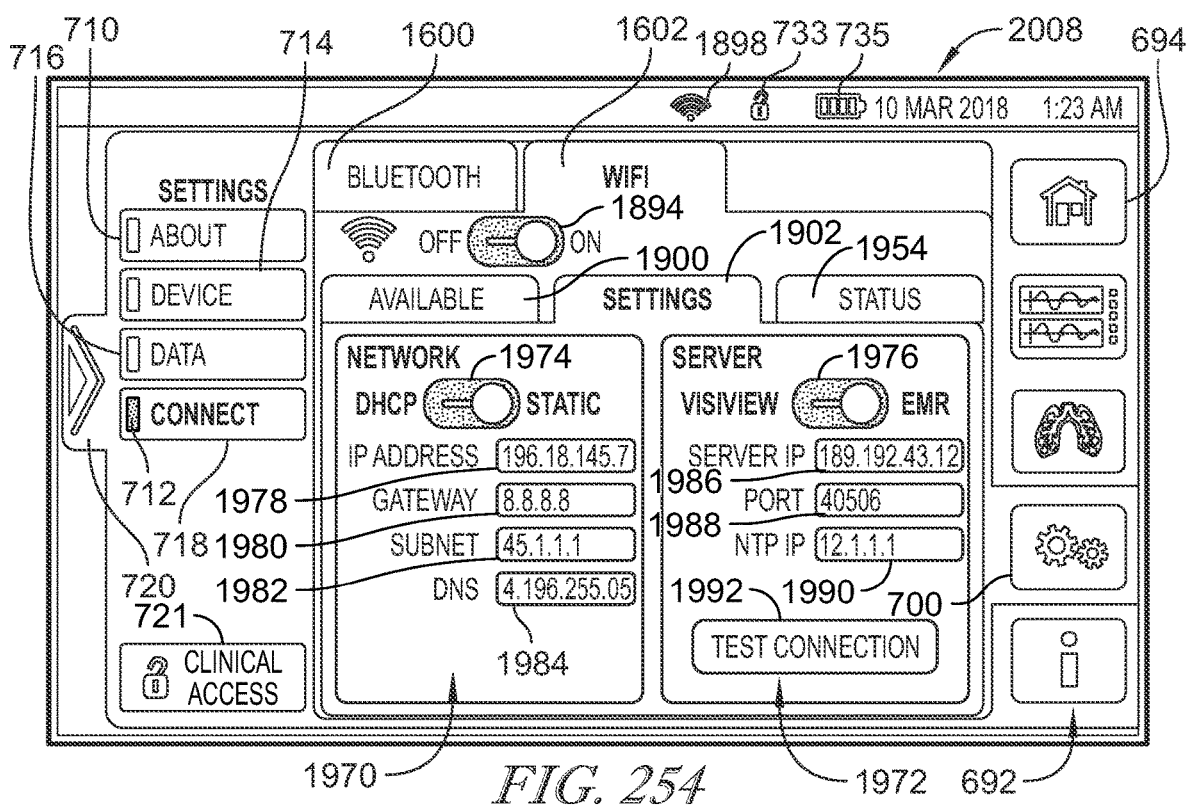
Figure 255:
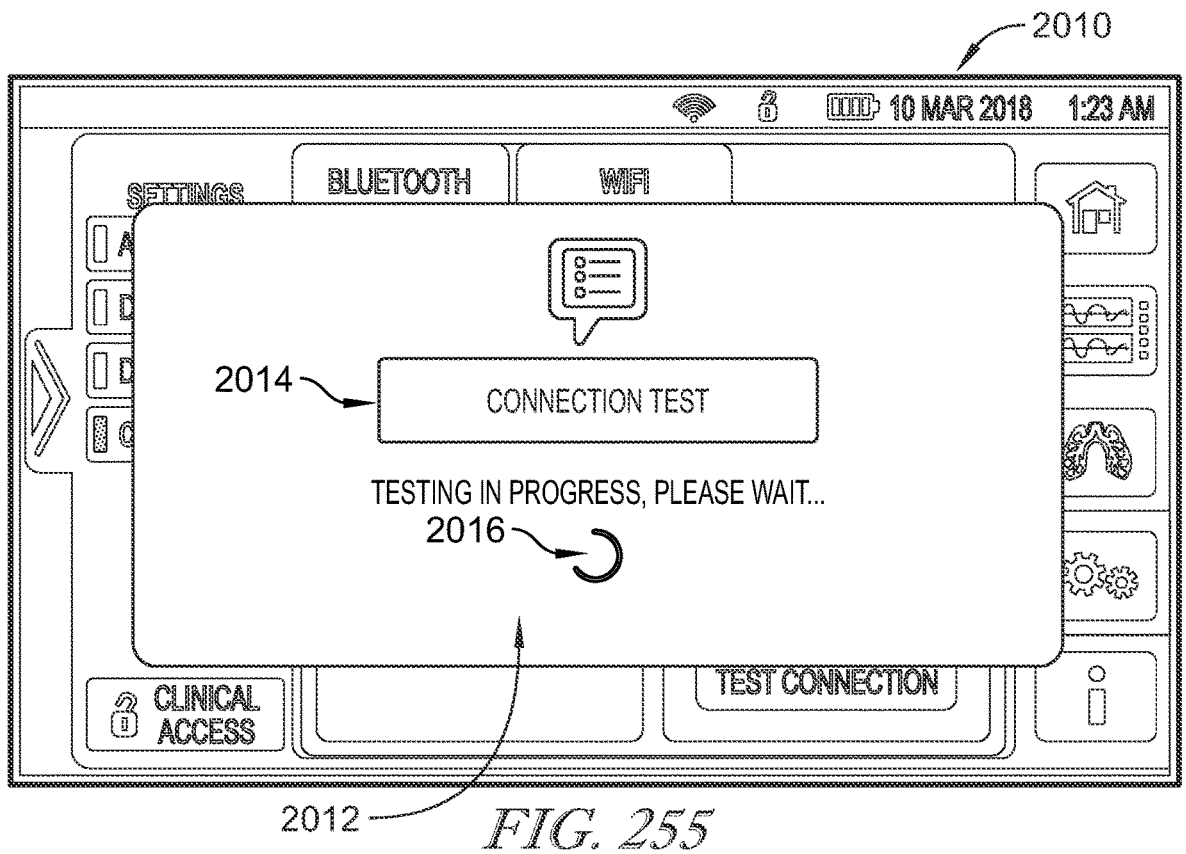
Figure 256:
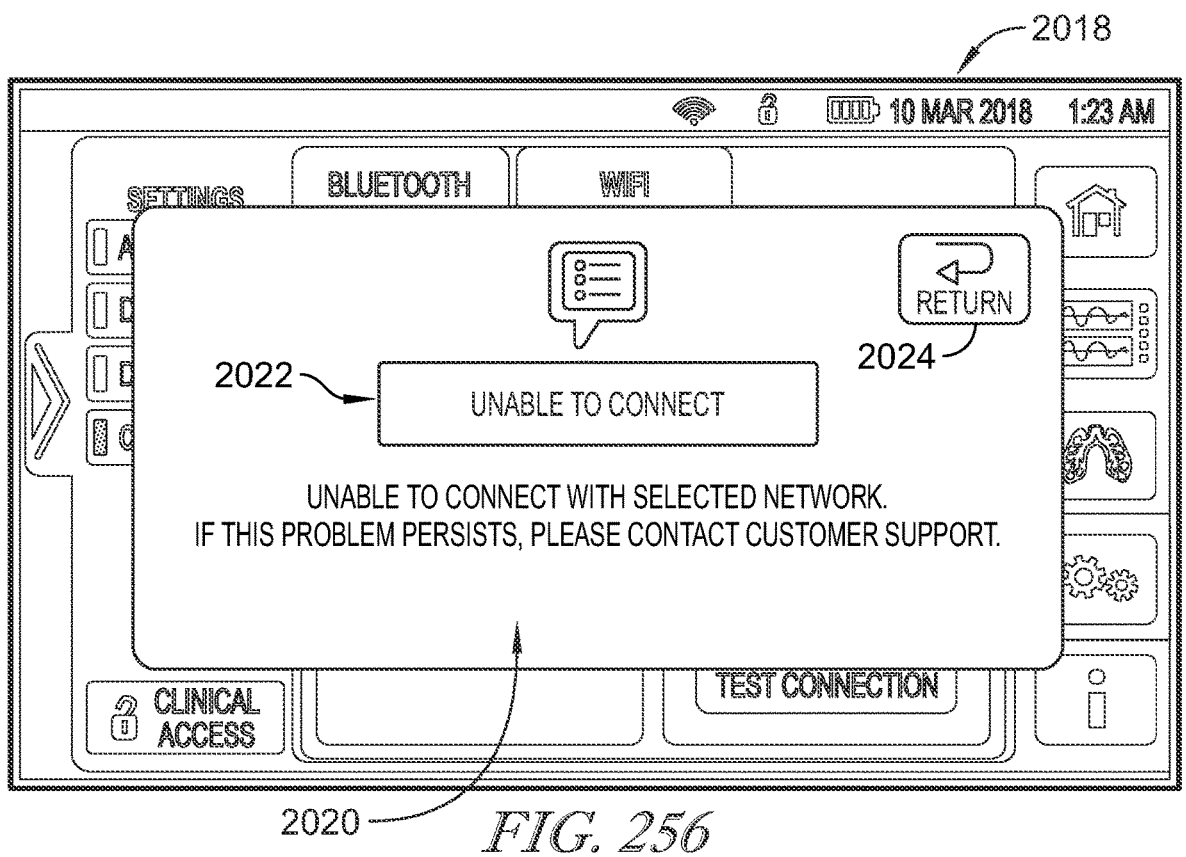
Figure 257:
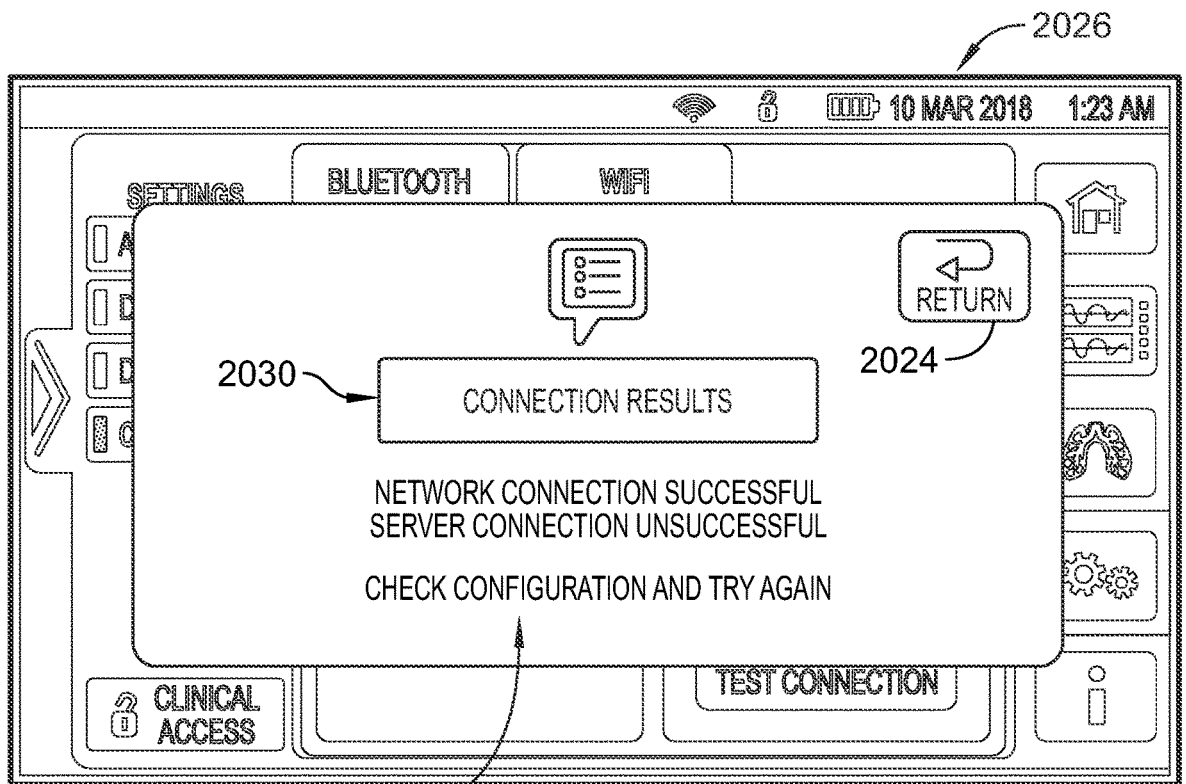
Figure 258:
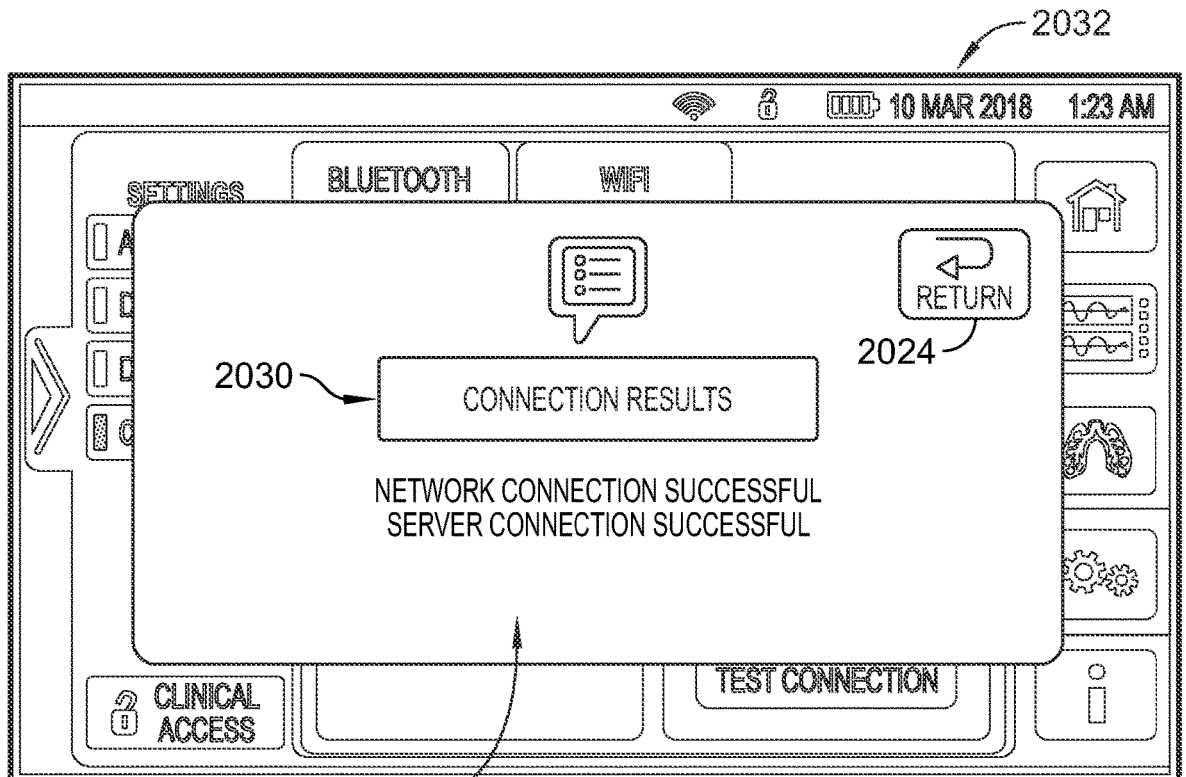
Figure 259:
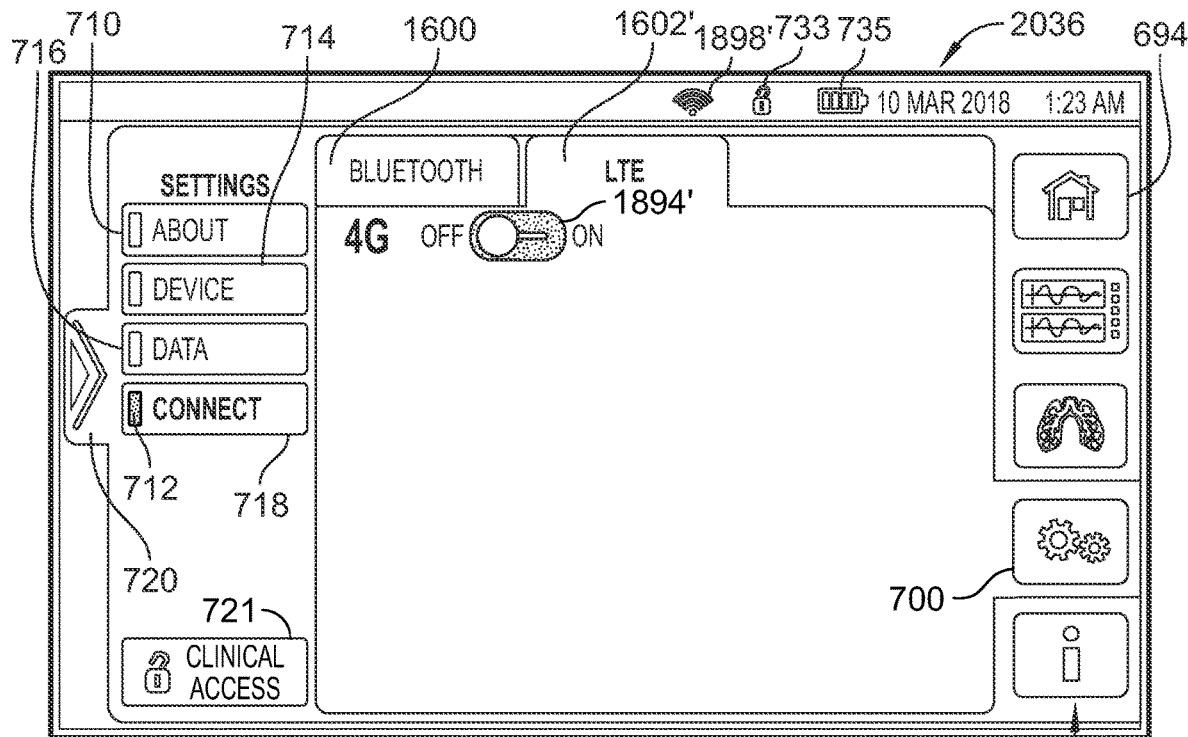
Figure 260:
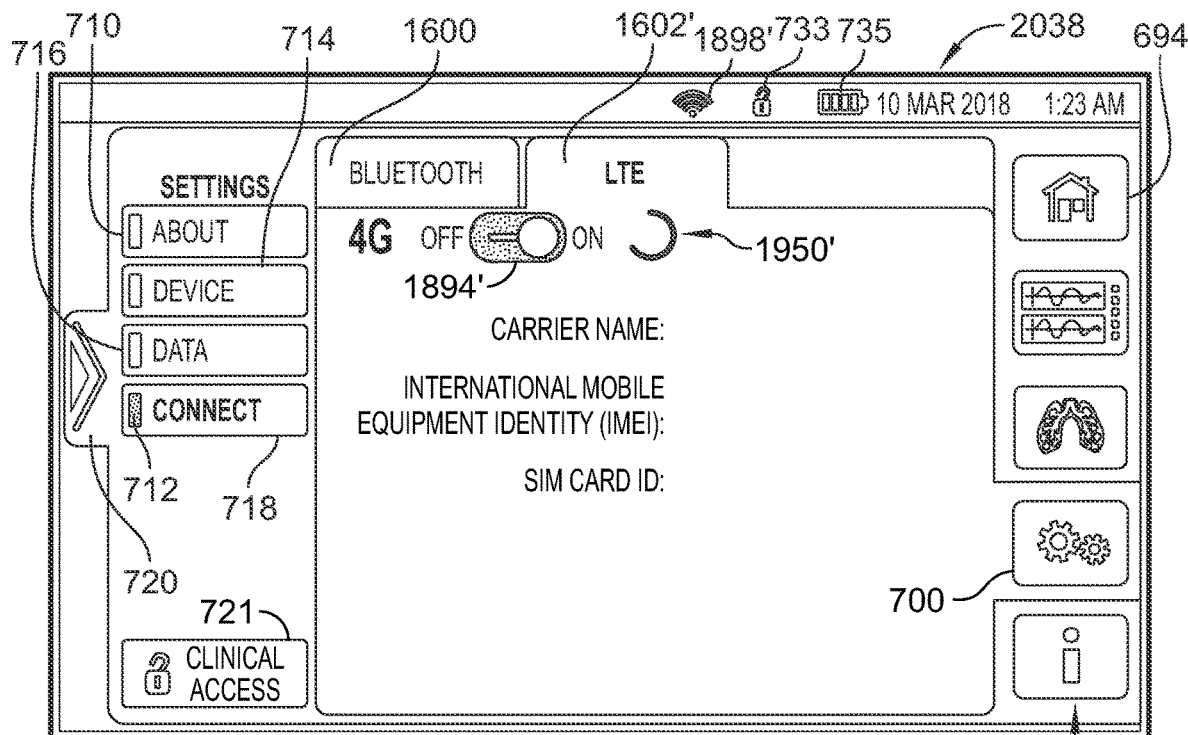
Figure 261:
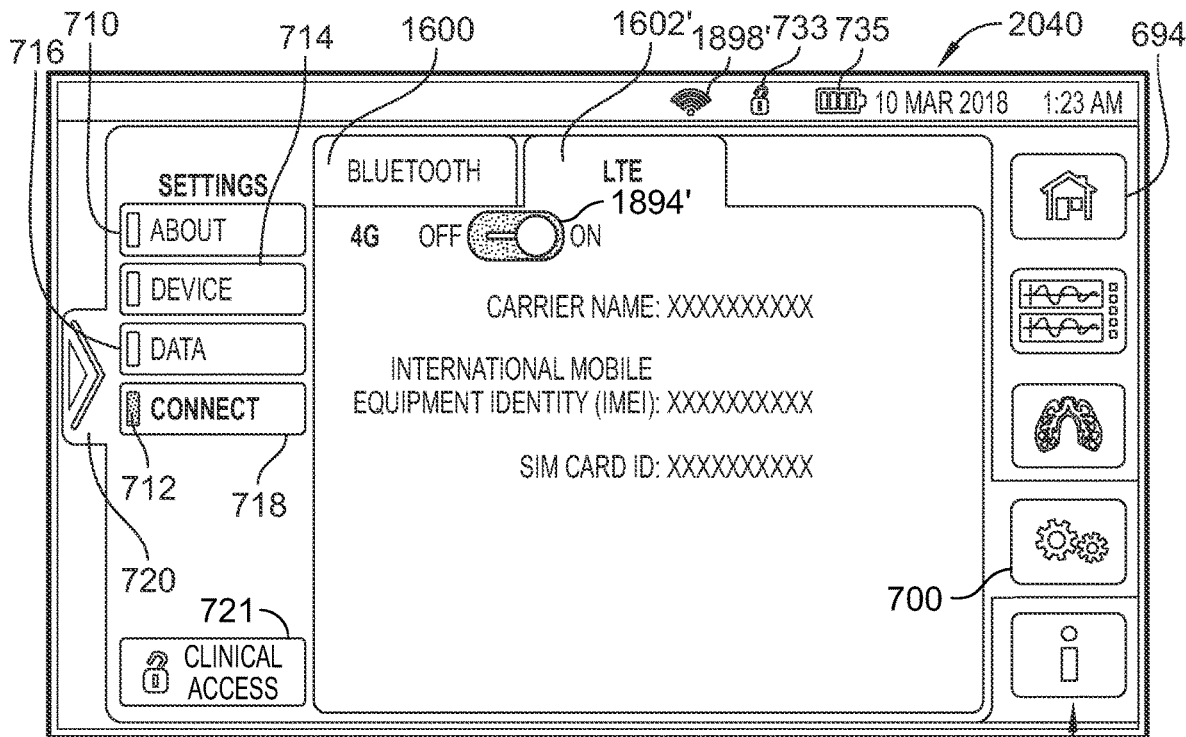
Figure 262:
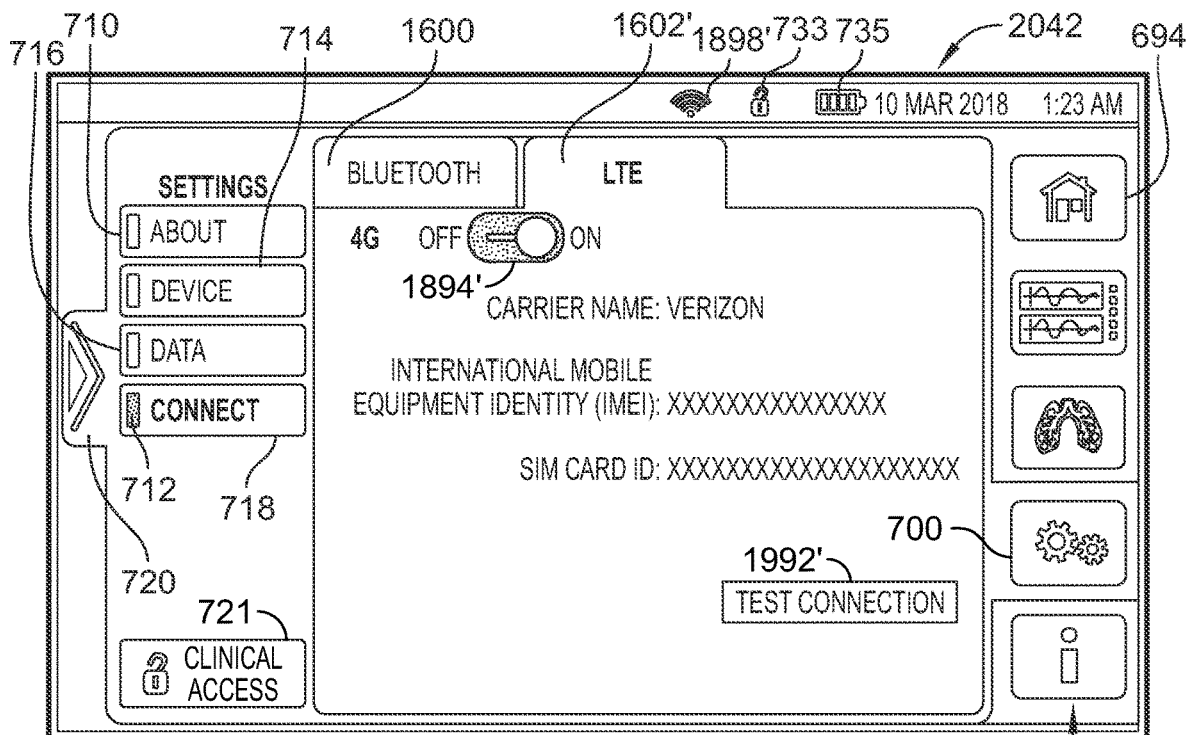
Figure 263:
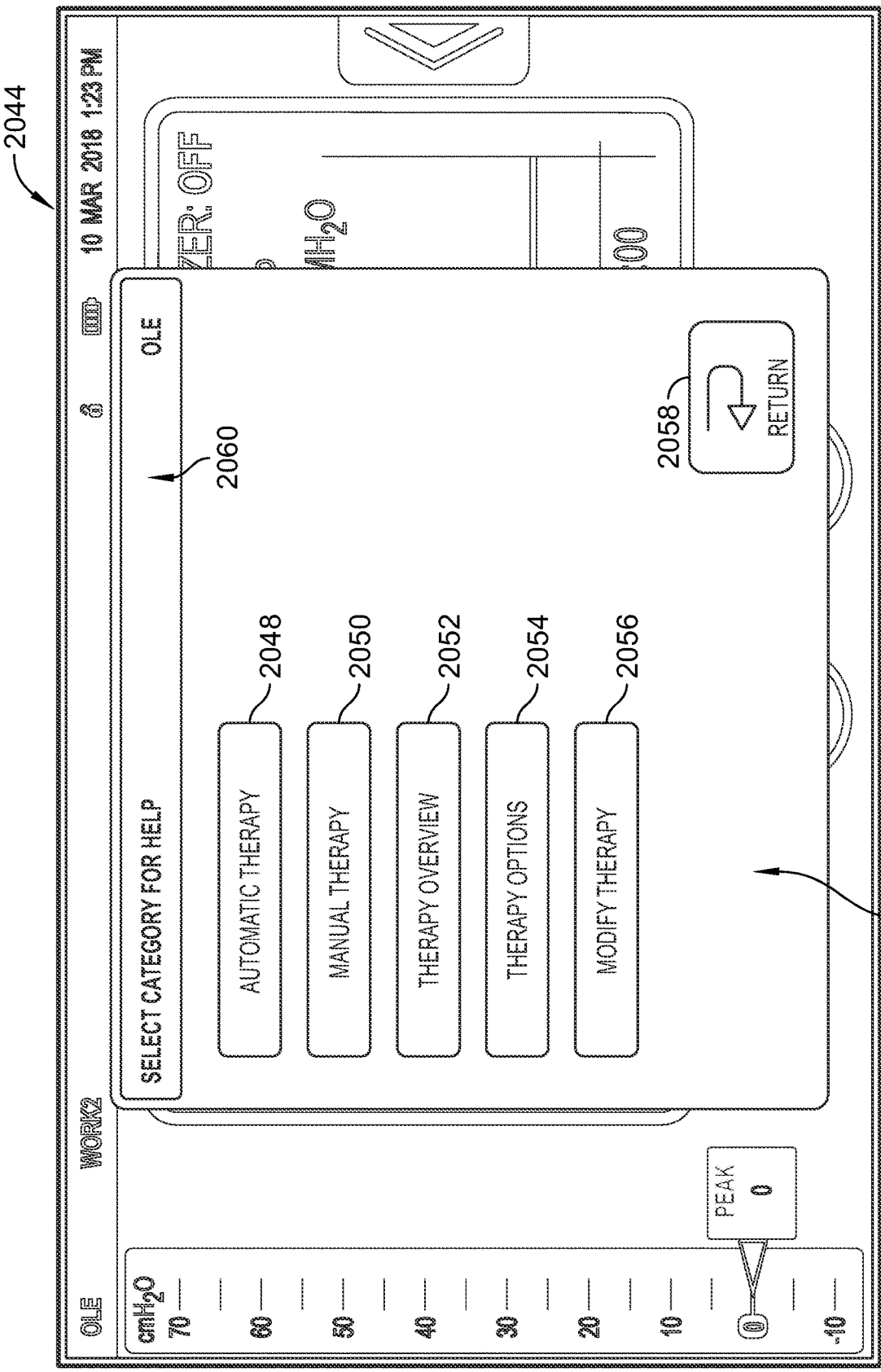
Figure 264:
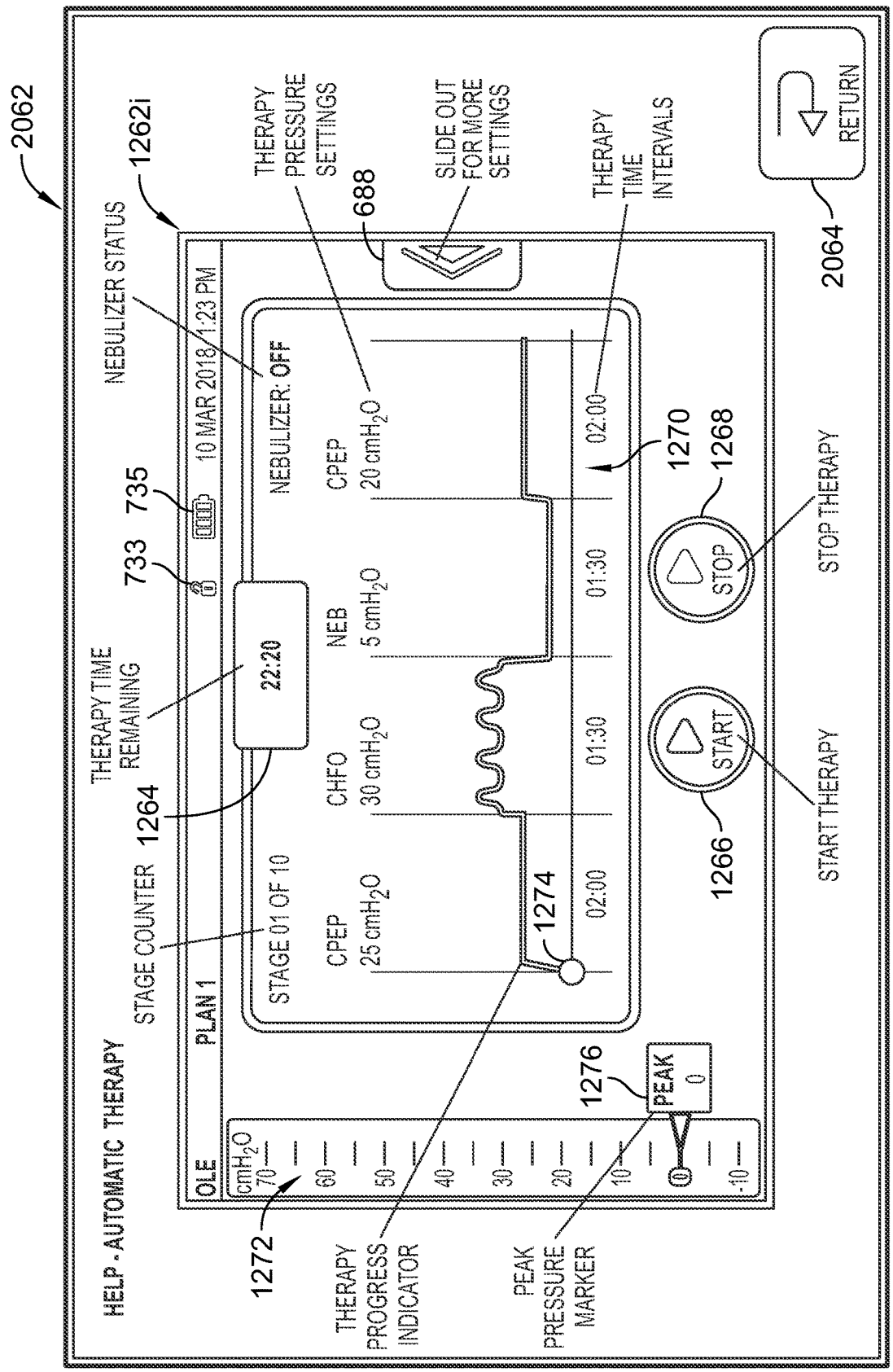
Figure 265:
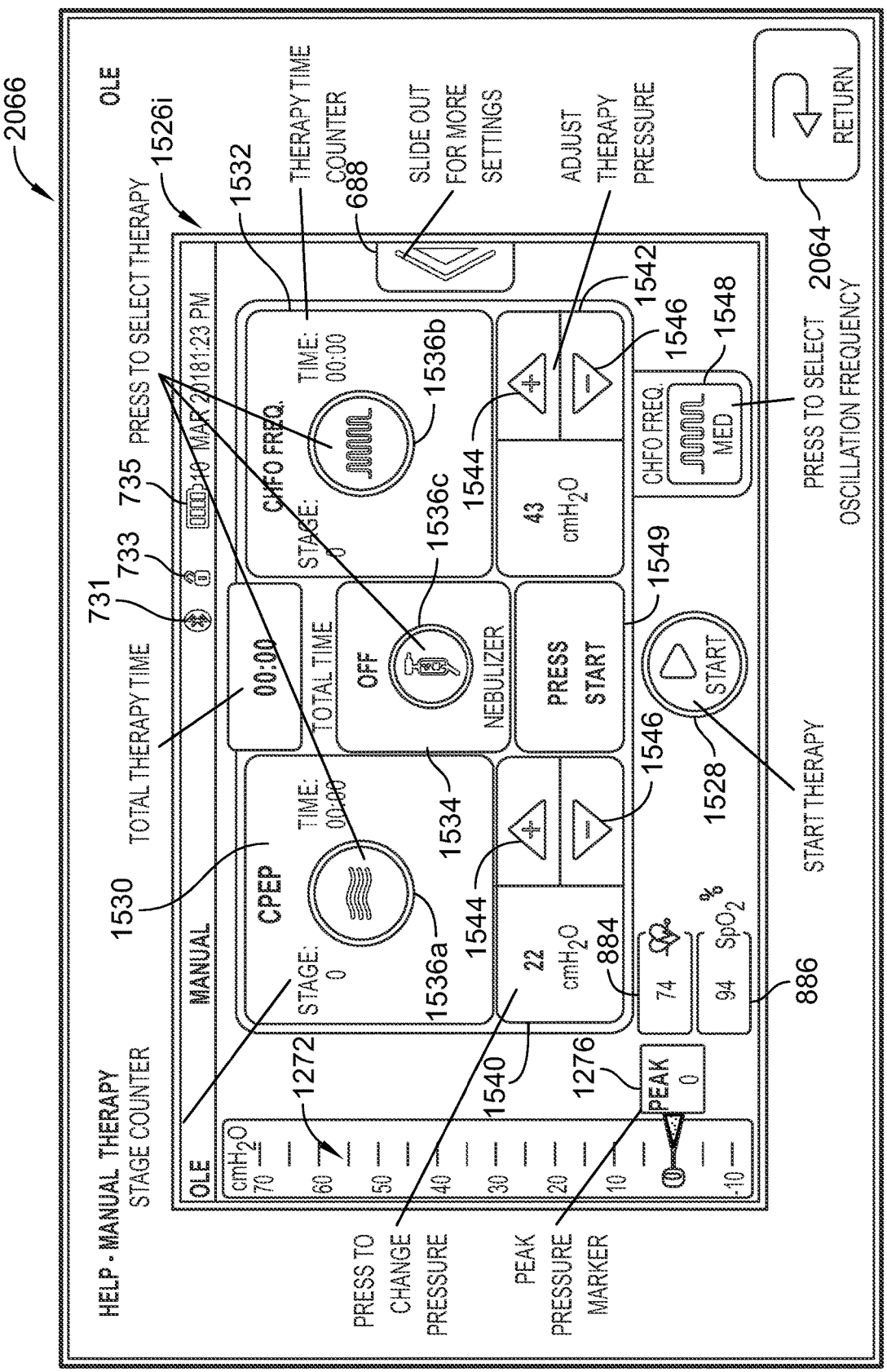
Figure 266:
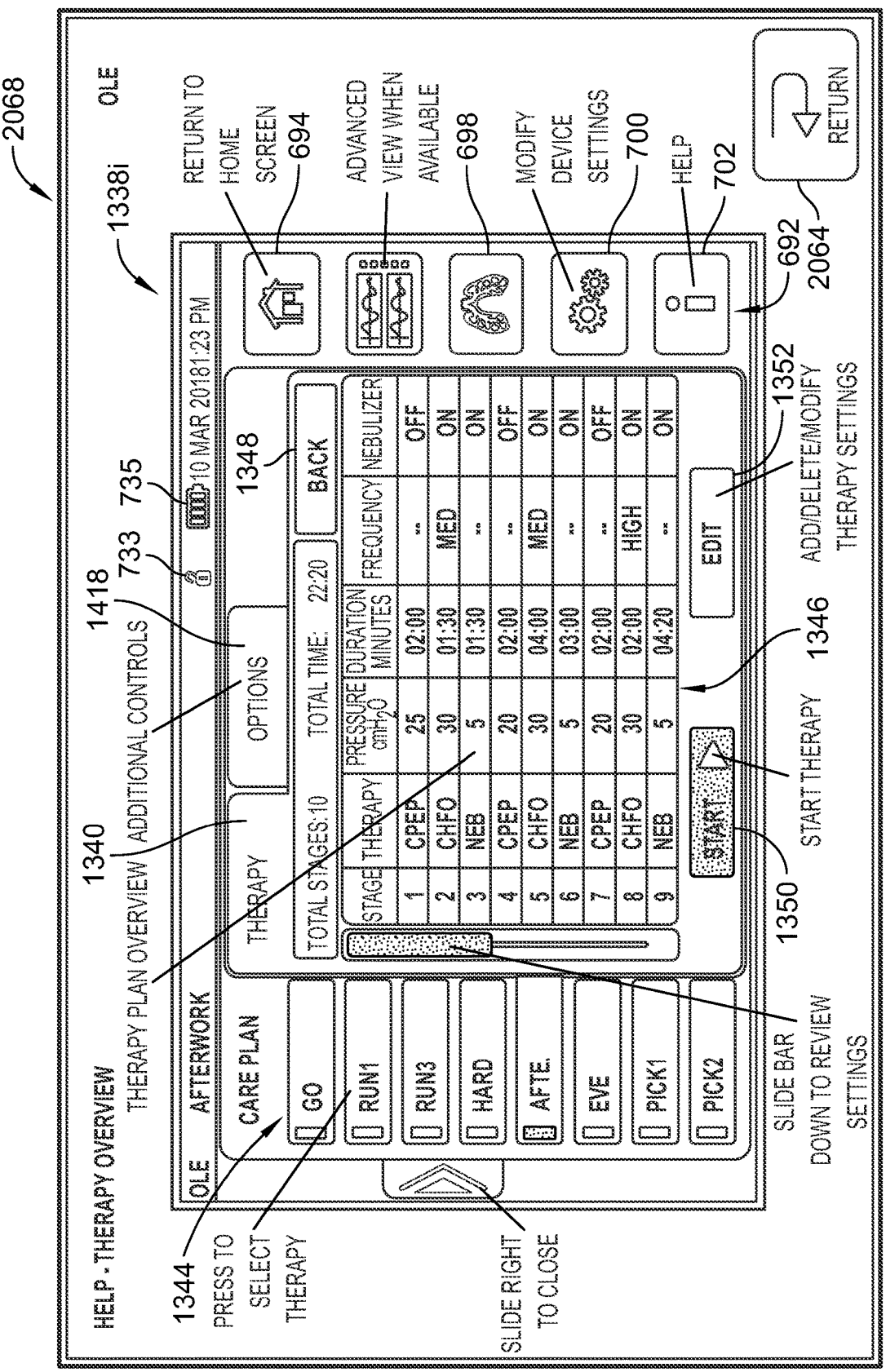
Figure 267:
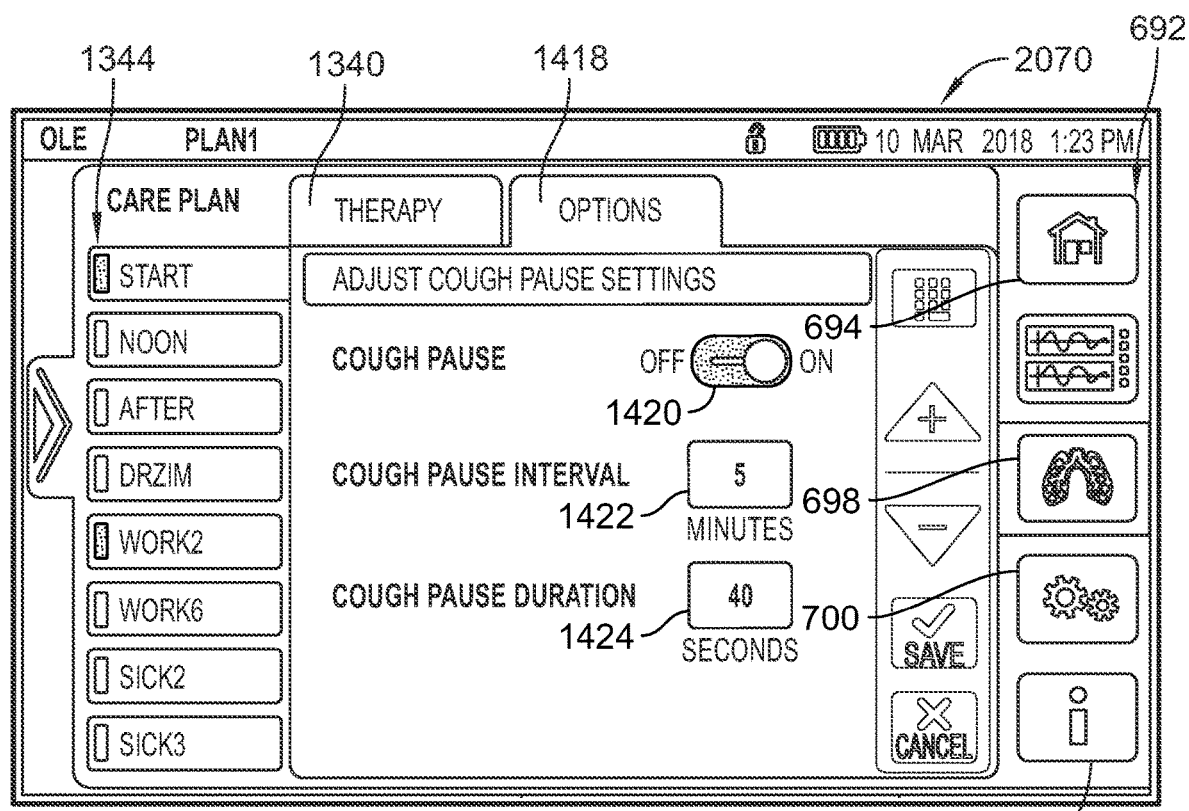
Figure 268:
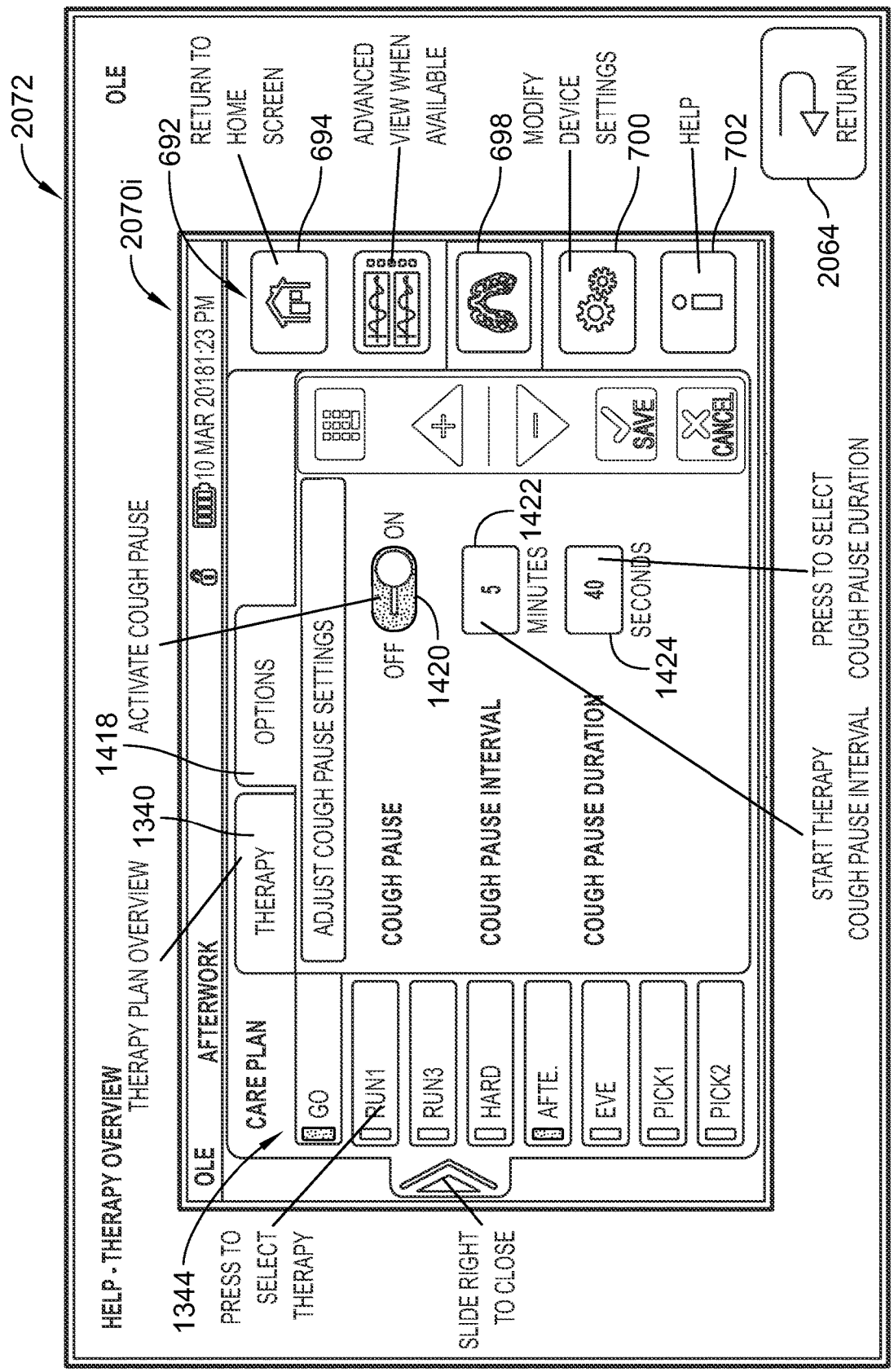
Figure 269:
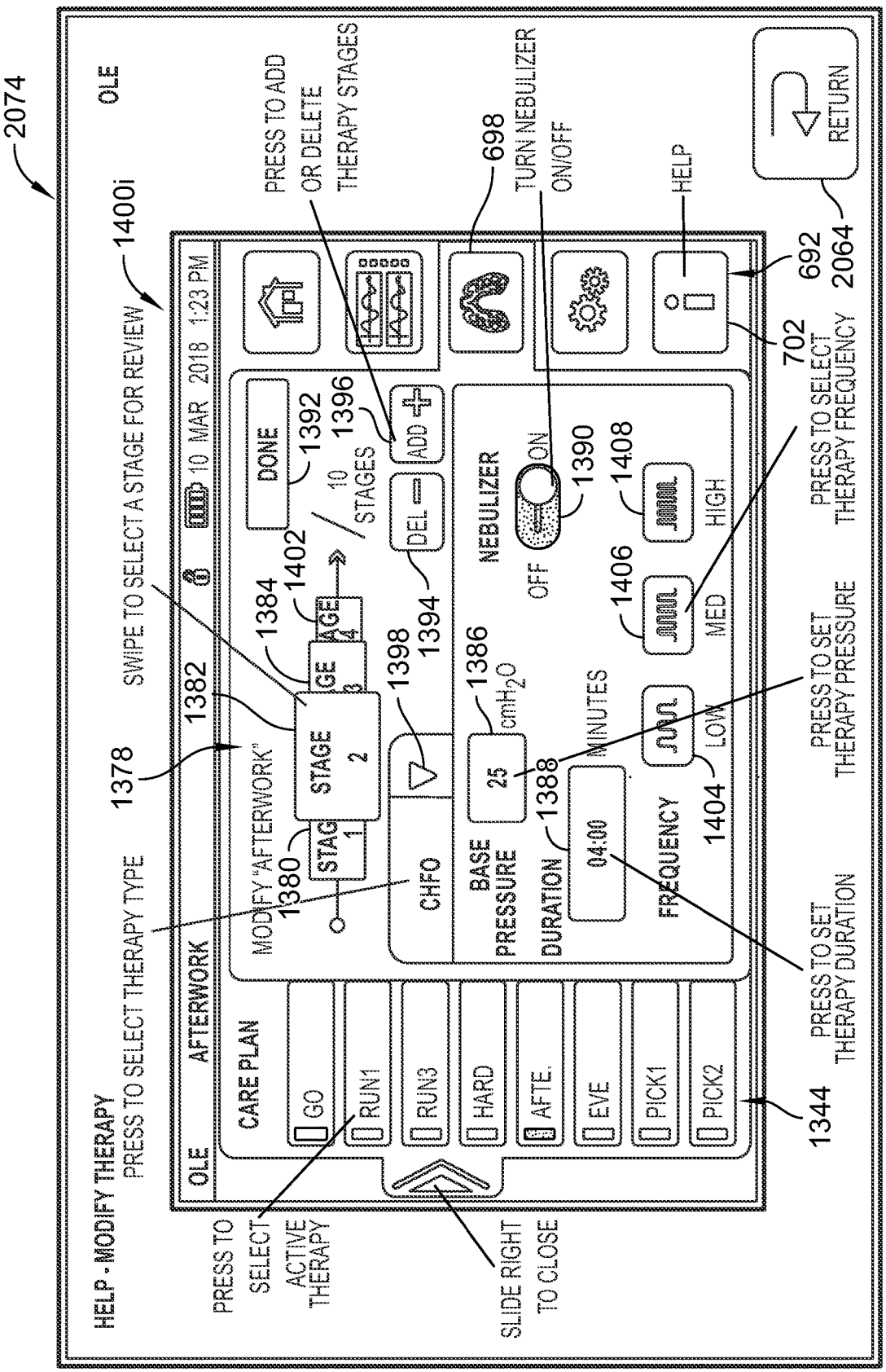
Figure 270:
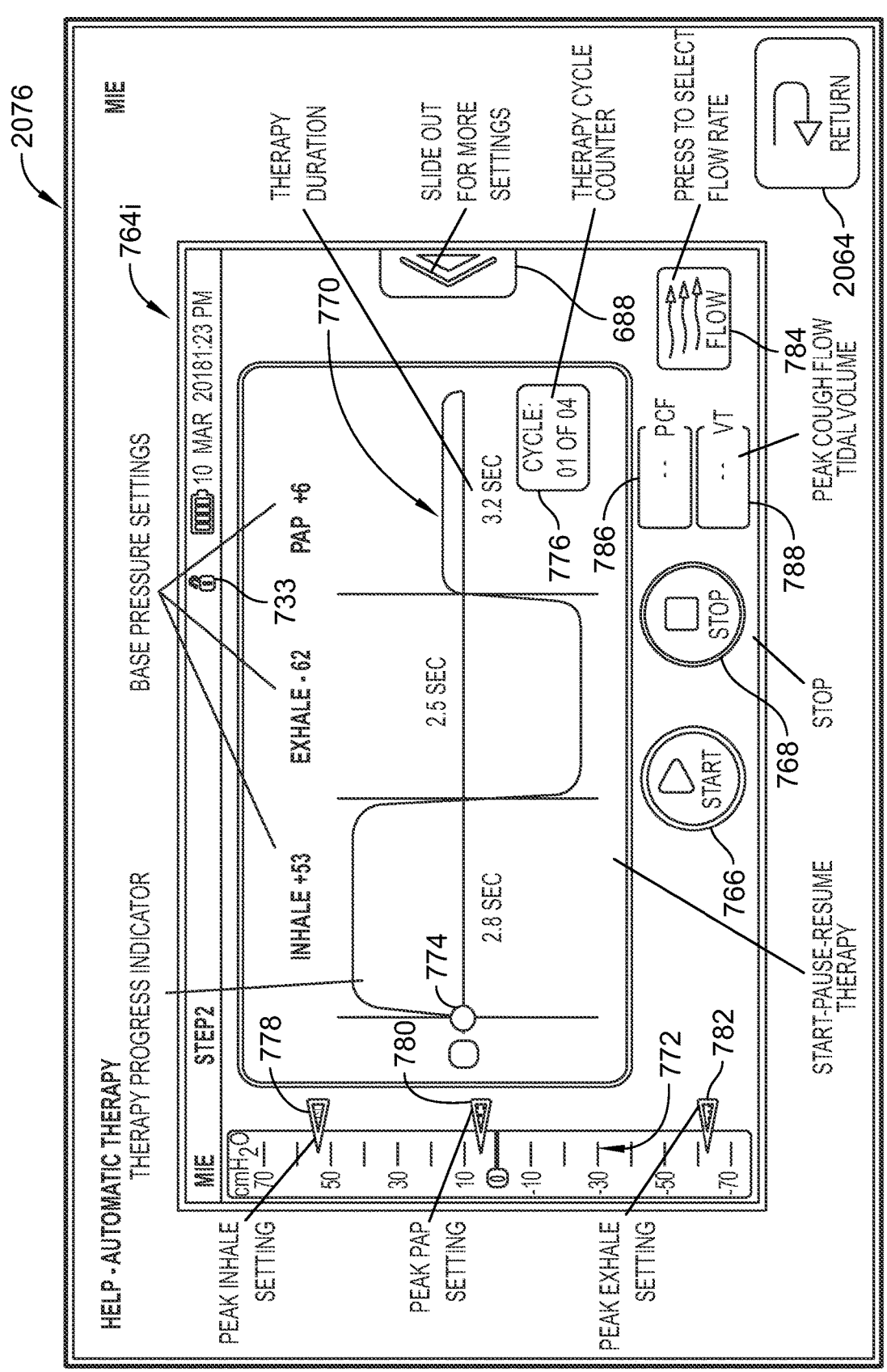
Figure 271:
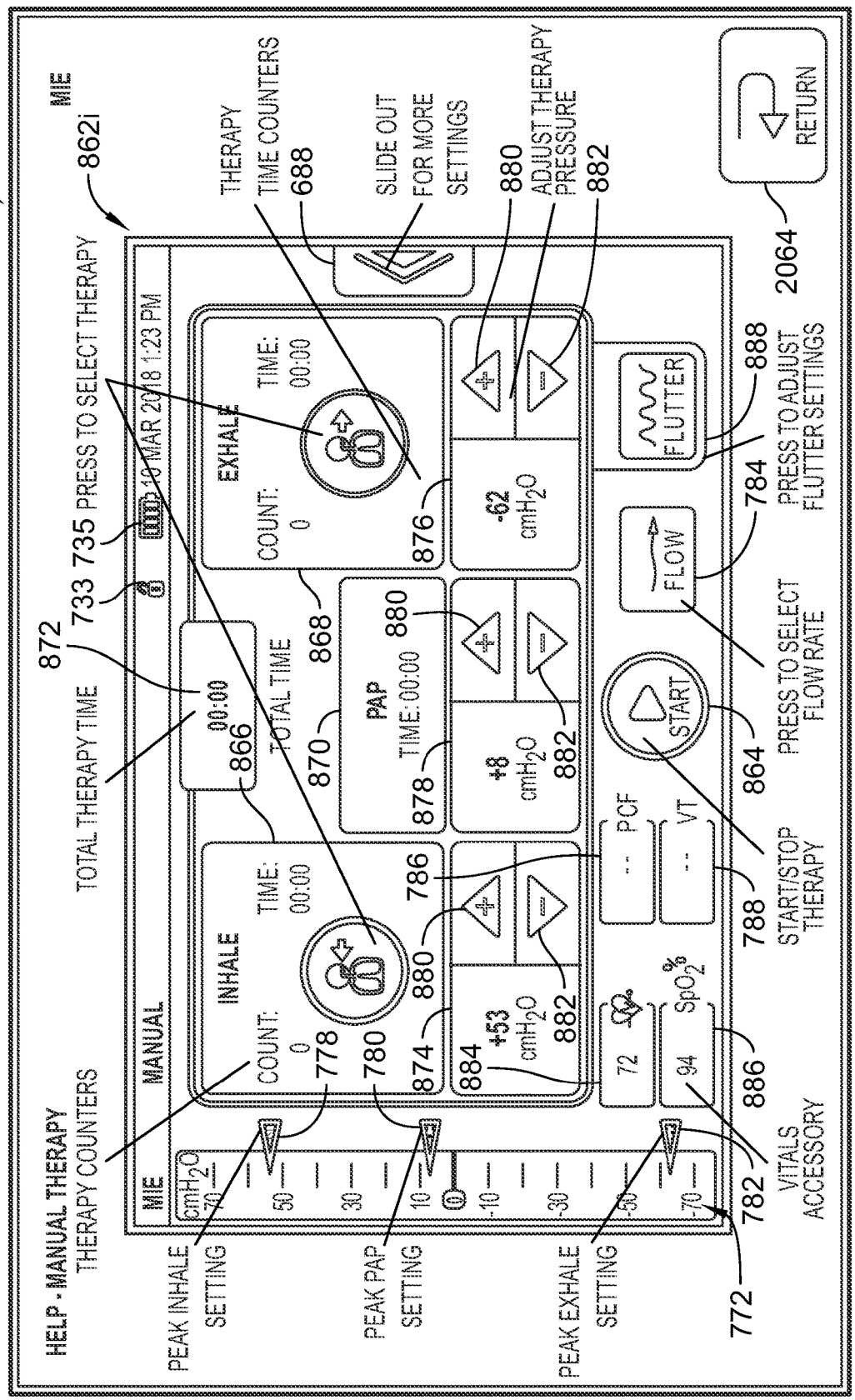
Figure 272:
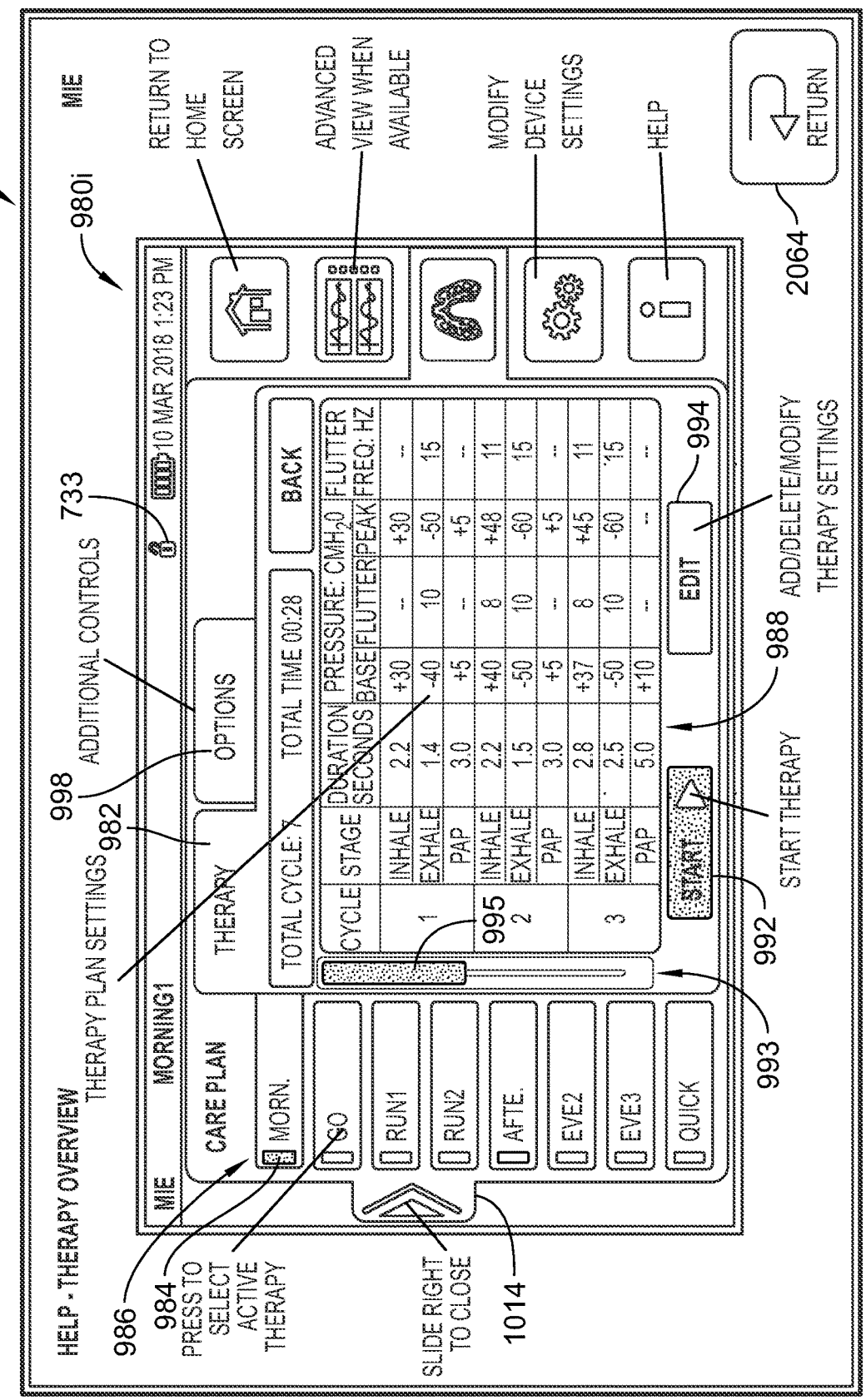
Figure 273:
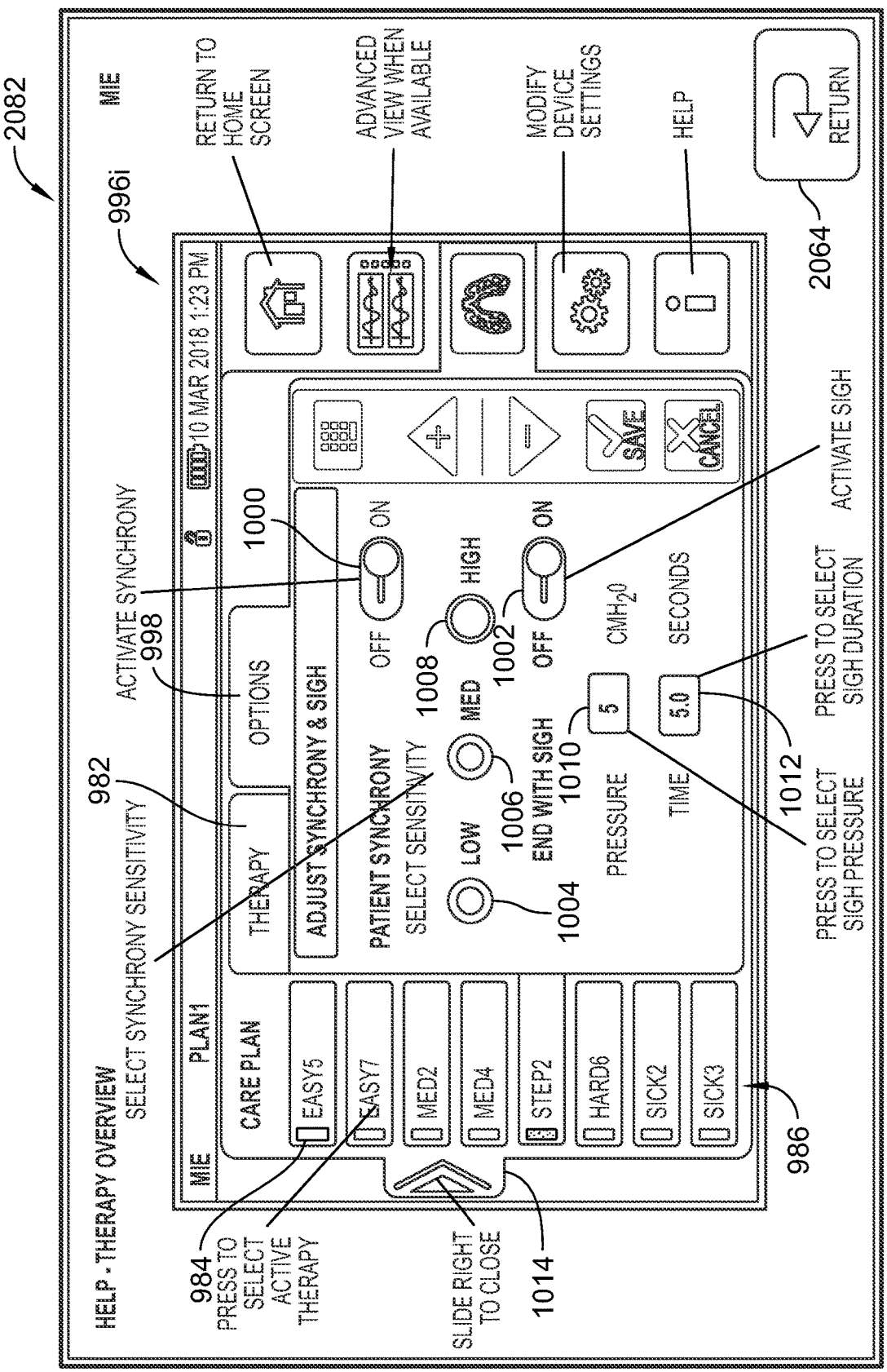
Figure 274:
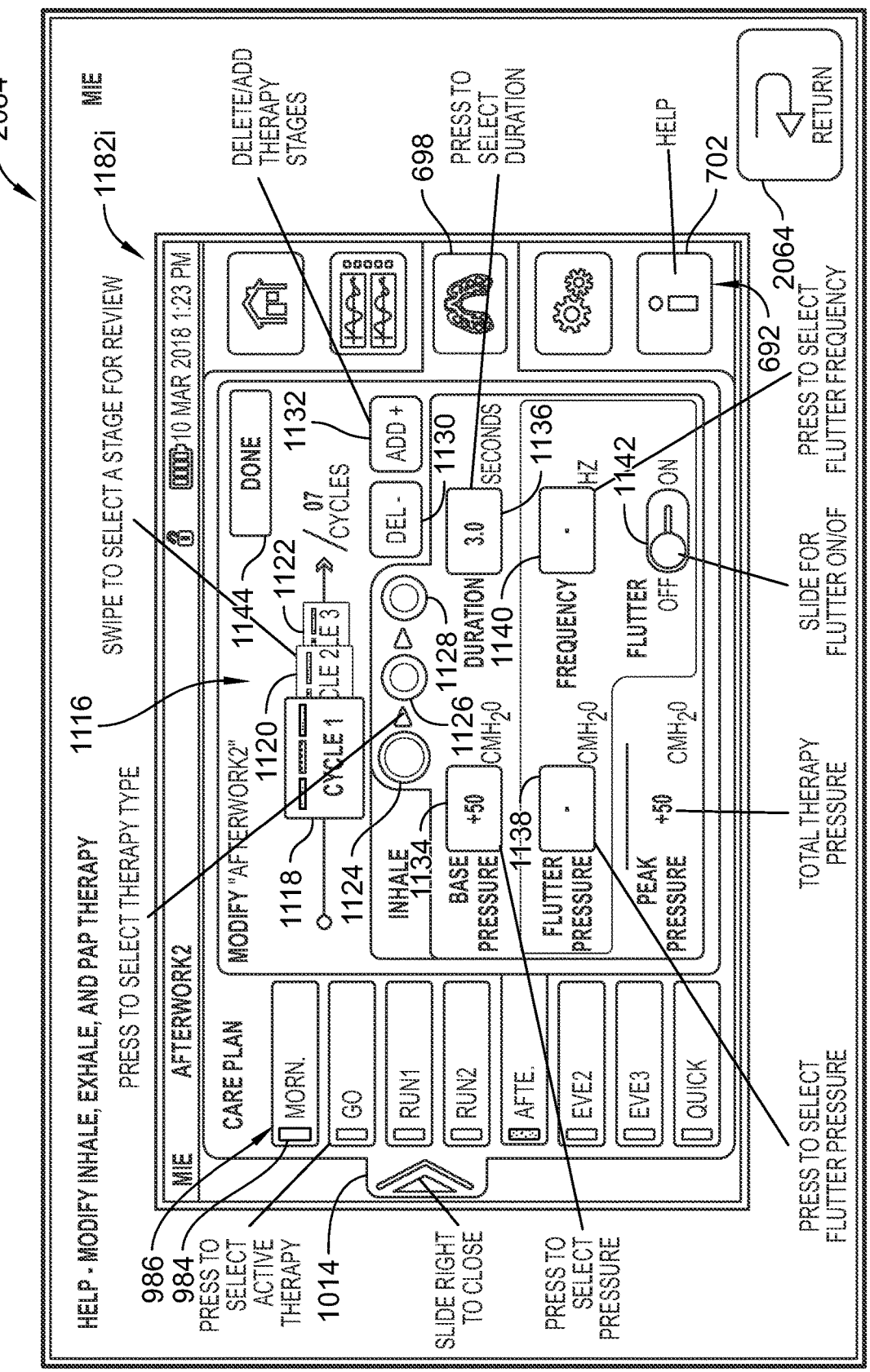

FIG. 116 is a screen shot of a first new automatic MIE therapy start screen, similar to FIG. 31, that appears on the GUI if a start button of the second create new therapy screen of FIG. 115 is selected while the respiratory therapy apparatus is operating under battery power and the battery charge is greater than 20% of a full battery charge, the first new automatic MIE therapy start screen showing a graph with the default parameters indicated and a pause button that can be selected to pause the therapy;

FIG. 117 is a screen shot of a second new automatic MIE therapy start screen, similar to FIG. 116, that appears on the GUI if a back button of the second create new therapy screen of FIG. 115 is selected, the second new automatic MIE therapy start screen showing the graph with the default parameters indicated and having a start button that can be selected to start the therapy;

FIG. 118 is a screen shot of an edit therapy settings screen that appears on the GUI in response to selection of an edit button of the second create new therapy screen of FIG. 66 or FIG. 115 if the clinical access feature of the respiratory therapy apparatus is turned on or enabled;

FIG. 119 is a screen shot of a delete preset screen that appears on the GUI in response to selection of a delete button on the edit new therapy settings screen of FIG. 118, the delete preset screen having a proceed button that is selectable to delete the presets shown in the table of FIG. 66 of FIG. 115, respectively, and a cancel button that is selectable to abort the deletion and return back to the screen of FIG. 66 or FIG. 115, respectively;

FIG. 120 is a screen shot of an alternative main automatic MIE therapy screen, similar to FIG. 29, that appears on the GUI in response to the automatic button of the main MIE therapy selection screen of FIG. 19 being selected, but having a foot switch control field with plus and minus indicators that are highlighted to indicate a status of an input from a foot switch control of the respiratory therapy apparatus;

FIG. 121 is a screen shot of a main automatic OLE therapy screen that appears on the GUI in response to selection of the automatic button of the main OLE therapy selection screen of FIG. 20, the main automatic OLE therapy screen showing a therapy duration clock that indicates a length of time that the selected automatic OLE therapy is programmed to occur;

FIG. 122 is a screen shot of an automatic OLE therapy start screen that appears on the GUI if a start button of the main automatic OLE therapy screen of FIG. 121 is selected while the respiratory therapy apparatus is operating under battery power and the battery charge is greater than 20% of a full battery charge, and in response to the automatic OLE therapy beginning, the start button being converted graphically to a pause button that can be selected to pause the therapy;

FIG. 123 is a screen shot of a first automatic OLE therapy in process screen that appears on the GUI during the automatic OLE therapy showing a graphical therapy progress indicator moving along a graphical waveform of the therapy, showing the graph being filled in up to the progress indicator to indicate an amount of the current therapy that has been completed, and showing the therapy duration clock having counted down from its beginning value;

FIG. 124 is a screen shot of a second automatic OLE therapy in process screen that appears on the GUI during automatic OLE therapy, similar to FIG. 123, but showing the progress indicator having advanced into a CHFO portion of the therapy from a CPEP portion of the therapy and showing the therapy duration clock having counted down further;

FIG. 125 is a screen shot of an automatic OLE therapy paused screen that appears on the GUI in response to the pause button of the screen of FIG. 123 or the screen of FIG. 124 being pressed;

FIG. 126 is a screen shot of a cough pause screen that appears on the GUI in response to a cough pause portion of the automatic OLE therapy occurring if the cough pause function of the respiratory therapy apparatus has been enabled and if the interval at which the cough pause is to occur has been reached;

FIG. 127 is a screen shot of a third automatic OLE therapy in process screen that appears on the GUI during automatic OLE therapy, similar to FIG. 124, but showing the progress indicator having advanced to a last CHFO portion of the automatic OLE therapy, and showing the therapy duration clock nearing and end of the count down;

FIG. 128 is a screen shot of a first example of an automatic OLE therapy complete screen that appears on the GUI at the end of the automatic OLE therapy session, the first example of the OLE therapy complete screen showing a variety of statistical data and other information pertaining to the automatic OLE therapy that has just been completed including a nebulizer duration indicating an amount of time that a nebulizer was turned on during the automatic OLE therapy;

FIG. 129 is a screen shot of a first advanced view screen for automatic OLE therapy that appears on the GUI in response to selection of the graph icon of a vertical menu of icons substantially the same as the menu of icons shown on the menu screen of FIG. 39, the first advanced view screen having first and second graphs for the automatic OLE therapy that are traced in substantially real time during the automatic OLE therapy, the first graph being for a trace of pressure, in cmH$_2$O, over time, and the second graph being for a trace of air flow, in liters per minute (LPM), over time;

FIG. 130 is a screen shot of a second advanced view screen for automatic OLE therapy that appears on the GUI in response to selection of the start button of the first advanced view screen of FIG. 129 if a filter unit usage count is below a threshold number of uses and if the battery charge is greater than 20% of a full charge, the second advanced view screen showing the start button converted to a pause button;

FIG. 131 is a screen shot of a second example of an automatic OLE therapy complete screen that appears on the GUI at the end of the automatic OLE therapy session, the second example of the OLE therapy complete screen showing the statistical data and other information pertaining to the automatic OLE therapy that has just been completed including indicating the nebulizer duration and also showing vitals data relating to the patient's heart rate and blood oxygen saturation percentage;

FIG. 132 is a screen shot of a second cough pause screen, similar to the cough pause screen of FIG. 126, that appears on the GUI in response to a cough pause portion of the automatic OLE therapy occurring if the cough pause function of the respiratory therapy apparatus has been enabled and if the interval at which the cough pause is to occur has been reached;

FIG. 133 is a screen shot of an alternative main automatic OLE therapy screen that appears on the GUI in response to selection of the automatic button of the main OLE therapy selection screen of FIG. 20, the alternative main automatic OLE therapy screen showing a nebulizer portion of the automatic OLE therapy programmed to occur between a first CHFO portion of the therapy and a second CPEP portion of the therapy;

FIG. 134 is a screen shot of a first care plan screen for automatic OLE therapy that appears on the GUI after the lung icon of the vertical menu of icons substantially the same as the menu of icons shown on the menu screen of FIG. 39 is selected, the first care plan screen for automatic OLE therapy having a therapy tab selected for a first care plan, and a table of the parameters for various CPEP, CHFO, and nebulizer (NEB) stages of the first care plan being shown in the table;

FIG. 135 is a screen shot of an access limited screen that appears on the GUI in response to selection of an edit button of the first care plan screen of FIG. 134 if a clinical access feature of the respiratory therapy apparatus is turned off or disabled;

FIG. 136 is a screen shot of an edit therapy settings screen that appears on the GUI in response to selection of the edit button of the first care plan screen of FIG. 134 if the clinical access feature of the respiratory therapy apparatus is turned on or enabled;

FIG. 137 is a screen shot of a first modify therapy screen that appears on the GUI in response to selection of a modify button on the edit therapy settings screen of FIG. 136, the first modify screen showing that a CPEP portion of stage 1 of plan 1 of the automatic OLE therapy is selected for parameter adjustment as indicated by enlargement of a stage 1 tile of a set of horizontally arranged, overlapping tiles in the top region of the first modify therapy screen;

FIG. 138 is a screen shot of a second modify therapy screen that appears on the GUI in response to selection of a stage 2 tile of the horizontally arranged, overlapping tiles of the first modify therapy screen of FIG. 137, the second modify screen showing that a CHFO portion of stage 2 of plan 1 of the automatic OLE therapy is selected for parameter adjustment as indicated by enlargement of the stage 2 tile;

FIG. 139 is a screen shot of a third modify therapy screen that appears on the GUI in response to selection of a stage 3 tile of the horizontally arranged, overlapping tiles of the second modify therapy screen of FIG. 138, the third modify therapy screen showing that a NEB portion of stage 3 of plan 1 of the automatic OLE therapy is selected for parameter adjustment as indicated by enlargement of the stage 3 tile;

FIG. 140 is a screen shot of a second care plan screen for automatic OLE therapy that appears on the GUI after an options tab is selected on the first care plan screen of FIG. 134, the second care plan screen having a first on/off slider input for turning on and off the cough pause feature of the respiratory therapy apparatus and having fields for entering the cough pause interval and the cough pause duration;

FIG. 141 is a screen shot of a cough pause settings screen for automatic OLE therapy, similar to FIG. 140, but showing the slider moved to the on position, the cough pause interval set to begin every five minutes during the automatic OLE therapy, and the cough pause duration for each occurrence of the cough pause function set for 40 seconds;

FIG. 142 is a screen shot of a fourth modify therapy screen that appears on the GUI in response to the cough pause interval field of the cough pause settings screen of FIG. 141 having been selected for adjustment and showing keyboard, up arrow, down arrow, save, and cancel icons being illuminated for use in adjusting the cough pause interval;

FIG. 143 is a screen shot of a fifth modify therapy screen that appears on the GUI after the keyboard icon of FIG. 142 is selected, the graphical keyboard being usable to change the cough pause interval value to a new value;

FIG. 144 is a screen shot of a sixth modify therapy screen that appears on the GUI in response to the cough pause duration field of the cough pause settings screen of FIG. 141 having been selected for adjustment and showing the keyboard, up arrow, down arrow, save, and cancel icons being illuminated for use in adjusting the cough pause duration;

FIG. 145 is a screen shot of a seventh modify therapy screen that appears on the GUI after the keyboard icon of FIG. 142 is selected, the graphical keyboard being usable to change the cough pause duration value to a new value;

FIG. 146 is a screen shot of an eighth modify therapy screen that appears on the GUI in response to a base pressure field of the second modify therapy screen of FIG. 138 having been selected for adjustment and showing keyboard, up arrow, down arrow, save, and cancel icons being illuminated for use in adjusting the base pressure;

FIG. 147 is a screen shot of a ninth modify therapy screen that appears on the GUI after the keyboard icon of FIG. 146 is selected, the graphical keyboard being usable to change the base pressure to a new value;

FIG. 148 is a screen shot of a tenth modify therapy screen that appears on the GUI in response to a duration field of the second modify therapy screen of FIG. 138 having been selected for adjustment and showing the keyboard, up arrow, down arrow, save, and cancel icons being illuminated for use in adjusting the duration;

FIG. 149 is a screen shot of an eleventh modify therapy screen that appears on the GUI after the keyboard icon of FIG. 148 is selected, the graphical keyboard being usable to change the duration value to a new value;

FIG. 150 is a screen shot of a delete stage screen that appears on the GUI in response to selection of a delete button on the first, second or third modify therapy screens of FIGS. 137-139, respectively, the delete stage screen having a proceed button that is selectable to delete the selected stage and a cancel button that is selectable to abort the deletion and return to the previous screen;

FIG. 151 is a screen shot of a twelfth modify therapy screen that appears on the GUI in response to selection of the proceed button of FIG. 150, the twelfth modify therapy screen showing that a CPEP stage has been deleted from corresponding to stage 1 and a CHFO which used to be stage 2 of the automatic OLE therapy now corresponds to the stage 1 of the automatic OLE therapy;

FIG. 152 is a screen shot of a next stage screen that appears on the GUI in response to selection of an add/next stage button shown on the various modify therapy screens of FIGS. 137-139 and 151, the next stage screen initially being a duplicate of the stage in which the add/next stage button was selected;

FIG. 153 is a screen shot of a stage menu screen that appears on the GUI in response to a down arrow icon of a therapy portion tab of the various modify therapy screens of FIGS. 137-139, 151 and 152 being selected, the stage menu screen including CPEP, CHFO and NEB options listed on a resulting menu;

FIG. 154 is a screen shot of a stage 2 change screen that appears on the GUI in response to the CHFO option on the menu of FIG. 153 having been selected to change stage 2 of the automatic OLE therapy from being a CPEP stage to being a CHFO stage;

FIG. 155 is a screen shot of a stage 3 screen that appears on the GUI in response to swiping to the left on the stage 2 tile on FIG. 154, the stage 3 screen of FIG. 155 showing the settings for the current stage 3 of the automatic OLE therapy;

FIG. 156 is a screen shot of another stage menu screen, substantially the same as the stage menu screen of FIG. 153 but that appears on the GUI in response to selection of the down arrow icon of the stage 3 screen of FIG. 155, and also including CPEP, CHFO and NEB options listed on a resulting menu;

FIG. 157 is a screen shot of a stage 3 change screen that appears on the GUI in response to the NEB option on the menu of FIG. 156 having been selected to change stage 3 of the automatic OLE therapy from being a CHFO stage to being a NEB stage;

FIG. 158 is a screen shot of another first care plan screen for automatic OLE therapy, similar to FIG. 134, that appears on the GUI after a done button of the stage 3 change screen of FIG. 157 is selected, the first care plan screen for automatic OLE therapy of FIG. 158 having a table showing the parameters for various CPEP, CHFO, and NEB stages of the first care plan including the changed stages and parameters;

FIG. 159 is a screen shot of an empty preset screen that appears on the GUI if the lung icon of the menu screen of FIG. 39 is selected from the vertical menu of icons and there are no care plans with any parameters entered for operation of the automatic OLE therapy;

FIG. 160 is a screen shot of a first create new therapy screen that appears on the GUI in response to selection of the create button of the empty preset screen of FIG. 159 if the clinical access feature of the respiratory therapy apparatus is turned on or enabled, the first create new therapy screen showing that a CPEP stage is a default stage for stage 1 of plan 1 of a new care plan for the automatic OLE therapy and showing the parameter fields populated with default parameter settings and that the nebulizer is turned on;

FIG. 161 is a screen shot of a second create new therapy screen that appears on the GUI in response to selection of a done button on the first create new therapy screen of FIG. 160, the second create new therapy screen having a therapy tab selected for the new care plan and a table of the parameters for the CPEP stage as entered on the first create new therapy screen of FIG. 160;

FIG. 162 is a screen shot of a first new automatic OLE therapy start screen that appears on the GUI if a start button of the second create new therapy screen of FIG. 161 is selected while the respiratory therapy apparatus is operating under battery power and the battery charge is less than 20% of a full battery charge, the first new automatic OLE therapy start screen showing a graph with the default parameters indicated and a start button that can be selected to start the therapy despite the battery power being less than 20%;

FIG. 163 is a screen shot of a second new automatic OLE therapy start screen that appears on the GUI if the start button of the second create new therapy screen of FIG. 161 is selected while the respiratory therapy apparatus is operating under battery power and the battery charge is greater than 20% of a full battery charge, the second new automatic OLE therapy start screen showing a graph with the default parameters indicated and a pause button that can be selected to pause the therapy which has already started;

FIG. 164 is a screen shot of an edit new therapy settings screen that appears on the GUI in response to selection of an edit button of the second create new therapy screen of FIG. 161;

FIG. 165 is a screen shot of a delete preset screen that appears on the GUI in response to selection of a delete button on the edit new therapy settings screen of FIG. 164, the delete preset screen having a proceed button that is selectable to delete the presets shown in the table of the second create new therapy screen of FIG. 161 and a cancel button that is selectable to abort the deletion and return back to the second create new therapy screen of FIG. 161;

FIG. 166 is a screen shot of a main manual OLE therapy screen that appears on the GUI in response to the manual button of the main OLE therapy selection screen of FIG. 20 being selected;

FIG. 167 is a screen shot of a manual OLE therapy preparation screen that appears on the GUI in response to a start button being selected on the main manual OLE therapy screen of FIG. 166, the manual OLE therapy preparation screen showing the start button being converted to a stop button and showing CPEP and CHFO pressure parameters being grayed out during a preparation operation of the manual OLE therapy;

FIG. 168 is a screen shot of a manual OLE therapy ready screen that appears on the GUI after the preparation operation, the manual OLE therapy ready screen having the CPEP and CHFO parameters illuminated;

FIG. 169 is a screen shot of a manual OLE therapy CPEP on screen showing a CPEP icon illuminated and filled in with a surrounding border highlighted after a user presses the CPEP icon for delivery of CPEP to the user's lungs by the respiratory therapy apparatus and showing the CHFO icon and a nebulizer field being grayed out during the delivery of CPEP to the user;

FIG. 170 is a screen shot of a manual OLE therapy CPEP off screen showing the CPEP and CHFO icons indicating an off state and ready for use after the user presses the CPEP icon of FIG. 169 to turn off the delivery of CPEP, and showing a nebulizer icon in the nebulizer field being illuminated and filled in with a surrounding border highlighted after a user presses the nebulizer icon for delivery of nebulized medication to the user's lungs by the respiratory therapy apparatus;

FIG. 171 is a screen shot of a manual OLE therapy CHFO on screen showing a CHFO icon illuminated and filled in with a surrounding border highlighted after a user presses the CHFO icon for delivery of CHFO to the user's lungs by the respiratory therapy apparatus, showing the nebulizer icon and field still being illuminated and filled in with the surrounding border highlight to indicate that the nebulizer is still turned on, and showing the CPEP icon grayed out during the delivery of CHFO and nebulized medication to the user;

FIG. 172 is a screen shot of a manual OLE therapy CHFO off screen showing the CPEP and CHFO icons indicating an off state and ready for use after the user presses the CHFO icon of FIG. 171 to turn off the delivery of CHFO, and showing the nebulizer icon in the nebulizer field being illuminated and filled in with a surrounding border highlighted to indicate that the nebulizer is still turned on;

FIG. 173 is a screen shot of a manual OLE CPEP pressure adjustment screen that appears on the GUI in response to the user selecting a CPEP numerical value field that appears beneath the CPEP button of FIGS. 168-172, the manual CPEP pressure adjustment screen including a graphical numeric keypad on which the user selects a new numerical value for the CPEP pressure;

FIG. 174 is a screen shot of a manual OLE CHFO pressure adjustment screen that appears on the GUI in response to the user selecting a CHFO numerical value field that appears beneath the CHFO button of FIGS. 168-172, the manual CHFO pressure adjustment screen including a graphical numeric keypad on which the user selects a new numerical value for the CHFO pressure;

FIG. 175 is a screen shot of a select CHFO frequency selection screen that appears on the GUI in response to the user selecting a frequency icon that appears beneath the CHFO button and CHFO numerical value field, the CHFO frequency selection screen having low, medium, and high frequency buttons that are selectable for setting the CHFO frequency;

FIG. 176 is a screen shot of a settings screen, substantially the same as FIG. 22, that appears on the GUI in response to the settings icon being selected from the menu of various OLE screens such as those of FIGS. 134, 140, 141, 158, 159, and 161, the settings screen including a window of device information pertaining to the respiratory therapy apparatus;

FIG. 177 is a screen shot of a data screen that appears on the GUI in response to a data button of the settings screen of FIG. 22 or FIG. 176 being selected, the data screen including buttons for reviewing and exporting a therapy log, importing and exporting device settings, reviewing and exporting an error log, upgrading firmware, and importing health level seven (HL7) information, with all buttons except for the therapy log review button and the error log review button being grayed out;

FIG. 178 is a screen shot of a connect screen that appears on the GUI in response to a connect button of the settings screen of FIG. 22 or FIG. 176 being selected, the connect screen having Bluetooth and WiFi tabs, the Bluetooth tab being selected and having a Bluetooth slider for turning Bluetooth functionality of the respiratory therapy apparatus on and off;

FIG. 179 is a screen shot of a device screen that appears on the GUI in response to a device button of the settings screen of FIG. 22 or FIG. 176 being selected, the device screen having date-time, language, and controls tabs, the date-time tab being selected and having user inputs for setting a date and time for the respiratory therapy apparatus;

FIG. 180 is a screen shot of a language screen that appears on the GUI in response to the language tab of the device screen of FIG. 179 being selected, the language screen having one or more language buttons for languages that are available for the textual information of the screens of FIGS. 18-274 of the respiratory therapy apparatus;

FIG. 181 is a screen shot of a controls screen that appears on the GUI in response to the controls tab of the device screen of FIG. 179 being selected, the controls screen having a slider bar for adjusting screen brightness, a barcode slider for turning barcode reading functionality of the respiratory therapy apparatus on and off, a clinical access slider for turning clinical access functionality of the respiratory therapy apparatus on and off, and up and down arrows for setting a pressure ceiling value for the respiratory therapy apparatus;

FIG. 182 is a screen shot of a modify date-time screen that appears on the GUI in response to a modify button of the device screen of FIG. 179 being selected, the modify date-time screen having a table of selectable times zones;

FIG. 183 is a screen shot of is a confirm language screen that appears on the GUI in response to selection of one of the language buttons of the language screen of FIG. 180;

FIG. 184 is a screen shot of a first access advanced features screen that appears on the GUI in response to an attempt to move the clinical access slider from the off position to the on position, the first access advanced features screen having a graphical numeric keypad for entering a key code to unlock access to advanced features;

FIG. 185 is a screen shot of a second access advanced features screen, substantially the same as FIG. 184, but showing a key code having been typed into a key code field using the graphical numeric keypad;

FIG. 186 is a screen shot of is a clinical access on screen, substantially the same as FIG. 181, but showing the clinical access slider moved to the on position in response to selection of an enter button of the second access advanced feature screen of FIG. 185 after a valid key code has been entered in the key code field;

FIG. 187 is a screen shot of an import/export/upgrade enabled screen, similar to FIG. 177, but showing the import buttons, the export buttons, and the upgrade button no longer being grayed out to indicate that the respiratory therapy apparatus is successfully communicating with one or more external devices that result in the import, export, and upgrade functionalities being possible, the successful communication with the external device also being indicated by a memory stick icon at the top of the import/export/upgrade enabled screen;

FIG. 188 is a screen shot of a loading screen that appears on the GUI in response to selection of any of the export buttons of FIG. 187, the loading screen indicating that the respiratory therapy apparatus is checking to confirm that the external device has sufficient memory to receive the therapy log, device settings, or error log data to be exported;

FIG. 189 is a screen shot of an insufficient memory screen that appears on the GUI if the external device does not have sufficient memory to receive the therapy log, device settings, or error log data to be exported;

FIG. 190 is a screen shot of a pressure ceiling confirm screen that appears on the GUI in response to selection of the device settings import button of FIG. 187 if the clinical access function of the respiratory therapy apparatus is turned on or enabled;

FIG. 191 is a screen shot of a first error log review screen that appears on the GUI in response to selection of the error log review button of FIG. 177 or FIG. 187, the first error log review screen having a list of dates and times at which recent errors have occurred in the respiratory therapy apparatus;

FIG. 192 is a screen shot of a second error log review screen that appears on the GUI in response to selection of one of the error log dates and times from the list of the first error log review screen of FIG. 191, the second error log review screen showing an error code corresponding to the selected error log date and time;

FIG. 193 is a screen shot of a first therapy log review screen that appears on the GUI in response to selection of the therapy log review button of FIG. 177 or FIG. 187, the first therapy log review screen having a list of dates and times at which recent therapies have occurred using the respiratory therapy apparatus;

FIG. 194 is a screen shot of a second therapy log review screen that appears on the GUI in response to selection of one of the therapy log dates and times from the list of the first error log review screen of FIG. 193, the second therapy log review screen showing information about the therapy corresponding to the selected therapy log date and time;

FIG. 195 is a screen shot of an alternative second therapy log review screen, similar to FIG. 194, but omitting a scroll icon due to less than seven recent therapies being listed on the list of recent therapies;

FIG. 196 is a screen shot of a therapy log export in process screen that appears on the GUI after the respiratory therapy apparatus confirms that the external device has sufficient memory to receive the therapy log data and begins the therapy log export process;

FIG. 197 is a screen shot of a therapy log export complete screen that appears on the GUI after the therapy log data has been exported to the external device;

FIG. 198 is a screen shot of a therapy log export interrupted screen that appears on the GUI if any interruption occurs during the therapy log export process;

FIG. 199 is a screen shot of a device settings export in process screen that appears on the GUI after the respiratory therapy apparatus confirms that the external device has sufficient memory to receive the device settings data and begins the device settings export process;

FIG. 200 is a screen shot of a device settings export complete screen that appears on the GUI after the device settings data has been exported to the external device;

FIG. 201 is a screen shot of a device settings export interrupted screen that appears on the GUI if any interruption occurs during the device settings export process;

FIG. 202 is a screen shot of an error log export in process screen that appears on the GUI after the respiratory therapy apparatus confirms that the external device has sufficient memory to receive the error log data and begins the error log export process;

FIG. 203 is a screen shot of an error log export complete screen that appears on the GUI after the error log has been exported to the external device;

FIG. 204 is a screen shot of an error log export interrupted screen that appears on the GUI if any interruption occurs during the error log export process;

FIG. 205 is the same as the screen shot of FIG. 190;

FIG. 206 is a screen shot of a device settings import in process screen that appears on the GUI after the respiratory therapy apparatus confirms that it has sufficient memory to receive the device settings data and begins the device settings import process;

FIG. 207 is a screen shot of a device settings import complete screen that appears on the GUI after the device settings data has been imported from the external device to the respiratory therapy apparatus;

FIG. 208 is a screen shot of a device settings import interrupted screen that appears on the GUI if any interruption occurs during the device settings import process;

FIG. 209 is a screen shot of a connect AC power screen that appears on the GUI in response to selection of the upgrade button of FIG. 187 if AC power is not already connected to the respiratory therapy apparatus;

FIG. 210 is a screen shot of a firmware download in process screen that appears on the GUI after the upgrade button of FIG. 177 or FIG. 187 has been selected and the respiratory therapy apparatus confirms that it has been connected to AC power;

FIG. 211 is a screen shot of a firmware download complete screen that appears on the GUI after the new firmware has been downloaded from the external device to the respiratory therapy apparatus;

FIG. 212 is a screen shot of a firmware download interrupted screen that appears on the GUI if any interruption occurs during the firmware download process;

FIG. 213 is a screen shot of a firmware upgrade file present screen that appears on the GUI in response to a thumb drive with a valid firmware upgrade file stored in memory being connected to a display control board (DCB) universal serial bus (USB) port of the respiratory therapy apparatus;

FIG. 214 is a screen shot of an HL7 file present screen that appears on the GUI in response to a thumb drive with a valid HL7 file stored in memory being connected to a main control board (MCB) USB port of the respiratory therapy apparatus;

FIG. 215 is a screen shot of a device settings file present screen that appears on the GUI in response to a thumb drive with a valid device settings file stored in memory being connected to the MCB USB port of the respiratory therapy apparatus;

FIG. 216 is a screen shot of a firmware upgrade status screen that appears on the GUI in response to the conclusion of a restart operation of the respiratory therapy apparatus that occurs after the firmware upgrade operation, the firmware upgrade status screen showing a list of successful and failed upgrades for Bluetooth, near field communication (NFC), MCB, and DCB circuitry of the respiratory therapy apparatus;

FIG. 217 is a screen shot of an HL7 import in process screen that appears on the GUI after an HL7 import button of the HL7 file present screen of FIG. 214 is selected to begin the HL7 import process;

FIG. 218 is a screen shot of an HL7 import complete screen that appears on the GUI after the HL7 data has been imported from the external device to the respiratory therapy apparatus;

FIG. 219 is a screen shot of an HL7 import interrupted screen that appears on the GUI if any interruption occurs during the HL7 import process;

FIG. 220 is the same as the screen shot of FIG. 178;

FIG. 221 is a screen shot of a first Bluetooth on screen that appears on the GUI in response to the Bluetooth slider being moved from the off position to the on position while the clinical access functionality of the respiratory therapy apparatus is turned off, the first Bluetooth on screen showing a list of devices that are paired in Bluetooth communication with the respiratory therapy apparatus;

FIG. 222 is a screen shot of a second Bluetooth on screen that appears on the GUI in response to the Bluetooth slider being moved from the off position to the on position while the clinical access functionality of the respiratory therapy apparatus is turned on, the second Bluetooth on screen showing an SpO2 tab and a barcode tab and the SpO2 tab being selected;

FIG. 223 is a screen shot of a Bluetooth scan screen that appears on the GUI in response to a scan button of the second Bluetooth on screen of FIG. 222 being selected, the Bluetooth scan screen including a progress icon to show the progress of the Bluetooth scanning process;

FIG. 224 is a screen shot of a scan results screen that appears on the GUI after the Bluetooth scanning process is complete, the scan results screen showing a list of available SpO2 devices that are in Bluetooth communication range of the respiratory therapy apparatus;

FIG. 225 is a screen shot of a device selected screen that appears on the GUI after one of the devices has been selected from the list of available SpO2 devices of FIG. 224 for Bluetooth pairing with the respiratory therapy apparatus;

FIG. 226 is a screen shot of a pair new device screen that appears on the GUI after selection of the device on the device selected screen of FIG. 225;

FIG. 227 is a screen shot of a device paired screen that appears on the GUI in response to a proceed button of the pair new device screen of FIG. 226 being selected, the device paired screen having a check mark in a paired column next to the device that was selected for Bluetooth pairing;

FIG. 228 is a screen shot of a Bluetooth scanning disabled screen that appears on the GUI in response to the Bluetooth scanning operation becoming disabled during the Bluetooth scan, the Bluetooth scanning disabled screen having a manual setup button activated to permit manual setup of Bluetooth communications with an external device;

FIG. 229 is a screen shot of a manual setup screen that appears on the GUI in response to the manual setup button of any of the screens of FIG. 224, 225, 227 or 228 being selected, the manual set up screen including a graphical keyboard that is used to enter a media access control (MAC) address in a MAC address field for an external device to be Bluetooth paired with the respiratory therapy apparatus;

FIG. 230 is a screen shot of a MAC address entered screen showing a MAC ID that was entered in the MAC address field of FIG. 229 at the bottom of the MAC address entered screen, the MAC address entered screen appearing on the GUI after selection of an enter button of the manual setup screen of FIG. 229;

FIG. 231 is a screen shot of a third Bluetooth on screen that appears on the GUI in response to the barcode tab of the second Bluetooth on screen of FIG. 222 being selected, the third Bluetooth on screen having a progress icon to show the progress of an automatic scan for barcode scanners that occurs in response to selection of the barcode tab;

FIG. 232 is a screen shot of a barcode scan results screen that appears on the GUI after the Bluetooth scanning process is complete, the scan results screen showing a list of available barcode scanner devices that are in Bluetooth communication range of the respiratory therapy apparatus;

FIG. 233 is a screen shot of a device selected screen that appears on the GUI after one of the barcode scanner devices has been selected from the list of available barcode scanner devices of FIG. 232 for Bluetooth pairing with the respiratory therapy apparatus;

FIG. 234 is a screen shot of a device paired screen that appears on the GUI in response to a proceed button of a pair new device screen, similar to that of FIG. 226, being selected after selection of the barcode scanner device on the device selected screen of FIG. 233, the device paired screen having a check mark in a paired column next to the barcode scanner device that was selected for Bluetooth pairing;

FIG. 235 is a screen shot of an alternative scan results screen that appears on the GUI after a Bluetooth scanning process is completed in response to selection of a scan button on any of the screens of FIGS. 232-234, the alternative scan results screen showing a list of available barcode scanner devices that are in Bluetooth communication range of the respiratory therapy apparatus;

FIG. 236 is a screen shot of a first WiFi on screen that appears on the GUI in response to the selection of the WiFi tab of FIG. 220 and in response to a WiFi slider being moved from an off position to the on position, the first WiFi on screen having a scan button that becomes active in response to movement of the WiFi slider to the on position;

FIG. 237 is a screen shot of a WiFi scan screen that appears on the GUI in response to the scan button of the first WiFi on screen of FIG. 236 being selected, the WiFi scan screen including a progress icon to show the progress of the WiFi scanning process;

FIG. 238 is a screen shot of a scan results screen that appears on the GUI after the WiFi scanning process is complete, the scan results screen showing a list of available wireless access points (WAP's) that are in WiFi communication range of the respiratory therapy apparatus and showing WiFi signal strength icons for each of the WAP's;

FIG. 239 is a screen shot of a WAP selected screen that appears on the GUI after one of the WAP's has been selected from the list of available WAP's of FIG. 238 for WiFi communication with the respiratory therapy apparatus;

FIG. 240 is a screen shot of an enterprise setup screen that appears on the GUI in response to selection of the WAP on the WAP selected screen of FIG. 239, the enterprise setup screen including fields for entry of enterprise setup information regarding the selected WAP;

FIG. 241 is a screen shot of an enter user ID screen that appears on the GUI in response to selection of an enter ID field in the enterprise setup screen of FIG. 240, the enter user ID screen having a graphical keyboard usable to enter a user ID for connection to a WiFi network associated with the WAP selected on the WAP selected screen of FIG. 239;

FIG. 242 is a screen shot of an enter password screen that appears on the GUI in response to selection of a password field in the enterprise setup screen of FIG. 240, the enter password screen having a graphical keyboard usable to enter a password for connection to the WiFi network associated with the WAP selected on the WAP selected screen of FIG. 239;

FIG. 243 is a screen shot of an authentication in progress screen that appears on the GUI in response to selection of a proceed button on the enterprise setup screen of FIG. 240 after the user has entered user ID and password information in the user ID and password fields, the authentication in progress screen having an authentication progress icon to show the progress of the authentication process;

FIG. 244 is a screen shot of a successful authentication screen that appears on the GUI in response to a successful authentication between device 10 and the WiFi network associated with the selected WAP, the successful authentication screen having a check mark next to the WAP that was selected on the screen of FIG. 239;

FIG. 245 is a screen shot of an unable to connect screen that appears on the GUI in response to the respiratory therapy apparatus being unable to connect to the WiFi network associated with the WAP selected on the screen of FIG. 239;

FIG. 246 is a screen shot of a WiFi status screen that appears on the GUI after selection of a status tab that appears after successful authentication and connection to the WiFi network associated with the WAP selected on the screen of FIG. 239, the WiFi status screen including information regarding the WiFi network to which the respiratory therapy apparatus is connected;

FIG. 247 is a screen shot of a first WiFi settings screen that appears on the GUI after selection of a settings tab on the WiFi status screen of FIG. 246, the WiFi settings screen including a first slider to select between having a static IP address assigned to the respiratory therapy apparatus and having an IP address assigned to the respiratory therapy apparatus based on a Dynamic Host Configuration Protocol (DHCP), the first slider being in a static position, and the setting screen including a second slider to select between communication with first or second servers of the WiFi network, the second slider being in a first position;

FIG. 248 is a screen shot of a second WiFi settings screen, similar to FIG. 247, but having the first slider moved to the DHCP position from the static position;

FIG. 249 is a screen shot of a third WiFi settings screen, similar to FIG. 248, but having the second slider moved to a second position;

FIG. 250 is a screen shot of a fourth WiFi settings screen, similar to FIG. 247, but having the second slider moved to the second position;

FIG. 251 is a screen shot of a first settings adjustment screen that appears on the GUI in response to selection of a subnet field beneath the first slider of FIG. 247, the first settings adjustment screen having a graphical numeric keyboard for editing an IP address of a subnet, and the subnet field being highlighted to indicate that it is the field that will be edited using the graphical numeric keyboard;

FIG. 252 is a screen shot of a second settings adjustment screen that appears on the GUI in response to selection of a port field beneath the second slider of FIG. 247, the second settings adjustment screen having a graphical numeric keyboard for editing a port address of the server selected using the second slider, and the port field being highlighted to indicate that it is the field that will be edited using the graphical numeric keyboard FIG. 253 is a screen shot of a fifth WiFi settings screen, similar to FIG. 247, but having zeroes in all fields beneath the first and second sliders and having a test connection button shown in FIG. 247 omitted to indicate that no WAP is available for communication with the respiratory therapy apparatus;

FIG. 254 is a screen shot of a sixth WiFi settings screen, similar to FIG. 247, but having all fields beneath the first and second sliders populated with relevant IP address and port address information and showing the test connection button available for use;

FIG. 255 is a screen shot of a connection test in progress screen that appears on the GUI in response to selection of the test connection button of FIG. 254, the connection test in progress having a test progress icon to show the progress of the connection test;

FIG. 256 is a screen shot of an unable to connect screen, similar to FIG. 245, that appears on the GUI in response to the respiratory therapy apparatus being unable to connect to the WiFi network associated with the information on the screen of FIG. 254;

FIG. 257 is a screen shot of a first connection results screen that appears on the GUI after the connection test is completed, the first connection results screen indicating that a network connection was successful but a server connection was unsuccessful;

FIG. 258 is a screen shot of a second connection results screen that appears on the GUI after the connection test is completed, the second connection results screen indicating that the network connection was successful and that the server connection was unsuccessful;

FIG. 259 is a screen shot of a first long term evolution (LTE) on screen that appears on the GUI in response to selection of an LTE tab that is provided in lieu of the WiFi tab of FIG. 220 if the respiratory therapy apparatus is configured for connection to an LTE network rather than a WiFi network, the first LTE on screen having a 4G slider in an off position;

FIG. 260 is a screen shot of a second LTE on screen, similar to FIG. 259, but having the 4G slider moved from the off position to the on position, the second LTE on screen including an LTE progress icon to indicate the progress of a search for an LTE network;

FIG. 261 is a screen shot of a no carrier found screen that appears on the GUI if no LTE carrier is found after the 4G slider is moved to the on position;

FIG. 262 is a screen shot of a carrier found screen that appears on the GUI if an LTE carrier is found after the 4G slider is moved to the on position, the carrier found screen having information about the LTE carrier automatically populated in a carrier name field, an international mobile equipment identity (IMEI) field, and a subscriber identity module (SIM) card ID field;

FIG. 263 is a screen shot of a help category screen that appears on the GUI in response to selection of the information or help icon on the menu screen of FIG. 21 or FIG. 39, the help category screen having a list of categories for which help is available;

FIG. 264 is a screen shot of an automatic OLE therapy help screen that appears on the GUI in response to selection of an automatic therapy button on the help category screen of FIG. 263 if navigated to from the main OLE therapy selection screen of FIG. 20;

FIG. 265 is a screen shot of a manual OLE therapy help screen that appears on the GUI in response to selection of a manual therapy button on the help category screen of FIG. 263 if navigated to from the main OLE therapy selection screen of FIG. 20;

FIG. 266 is a screen shot of an OLE therapy overview help screen that appears on the GUI in response to selection of a therapy overview button on the help category screen of FIG. 263 if navigated to from the main OLE therapy selection screen of FIG. 20;

FIG. 267 is a screen shot of an example of a return from help screen showing a predecessor screen that is returned to if the return button of the help category screen of FIG. 263 is selected, if the help category screen was originally navigated to in response to selection of the help icon of the options tab of the cough pause settings screen for automatic OLE therapy of FIG. 141;

FIG. 268 is a screen shot of an OLE therapy options help screen that appears on the GUI in response to selection of a therapy options button on the help category screen of FIG. 263 if navigated to from the main OLE therapy selection screen of FIG. 20;

FIG. 269 is a screen shot of an OLE modify therapy help screen that appears on the GUI in response to selection of a modify therapy overview button on the help category screen of FIG. 263 if navigated to from the main OLE therapy selection screen of FIG. 20, or in response to selection of the information or help icon on the first modify therapy screen of FIG. 137;

FIG. 270 is a screen shot of an automatic MIE therapy help screen that appears on the GUI in response to selection of the automatic therapy button on the help category screen of FIG. 263 if navigated to from the main MIE therapy selection screen of FIG. 19;

FIG. 271 is a screen shot of a manual MIE therapy help screen that appears on the GUI in response to selection of the manual therapy button on the help category screen of FIG. 263 if navigated to from the main MIE therapy selection screen of FIG. 19;

FIG. 272 is a screen shot of an MIE therapy overview help screen that appears on the GUI in response to selection of the therapy overview button on the help category screen of FIG. 263 if navigated to from the main MIE therapy selection screen of FIG. 19;

FIG. 273 is a screen shot of an MIE therapy options help screen that appears on the GUI in response to selection of the therapy options button on the help category screen of FIG. 263 if navigated to from the main MIE therapy selection screen of FIG. 19; and FIG. 274 is a screen shot of an MIE modify therapy help screen that appears on the GUI in response to selection of the modify therapy overview button on the help category screen of FIG. 263 if navigated to from the main OLE therapy selection screen of FIG. 19, or in response to selection of the information or help icon on the add cycle screen of FIG. 101.

DETAILED DESCRIPTION

Figure 1:
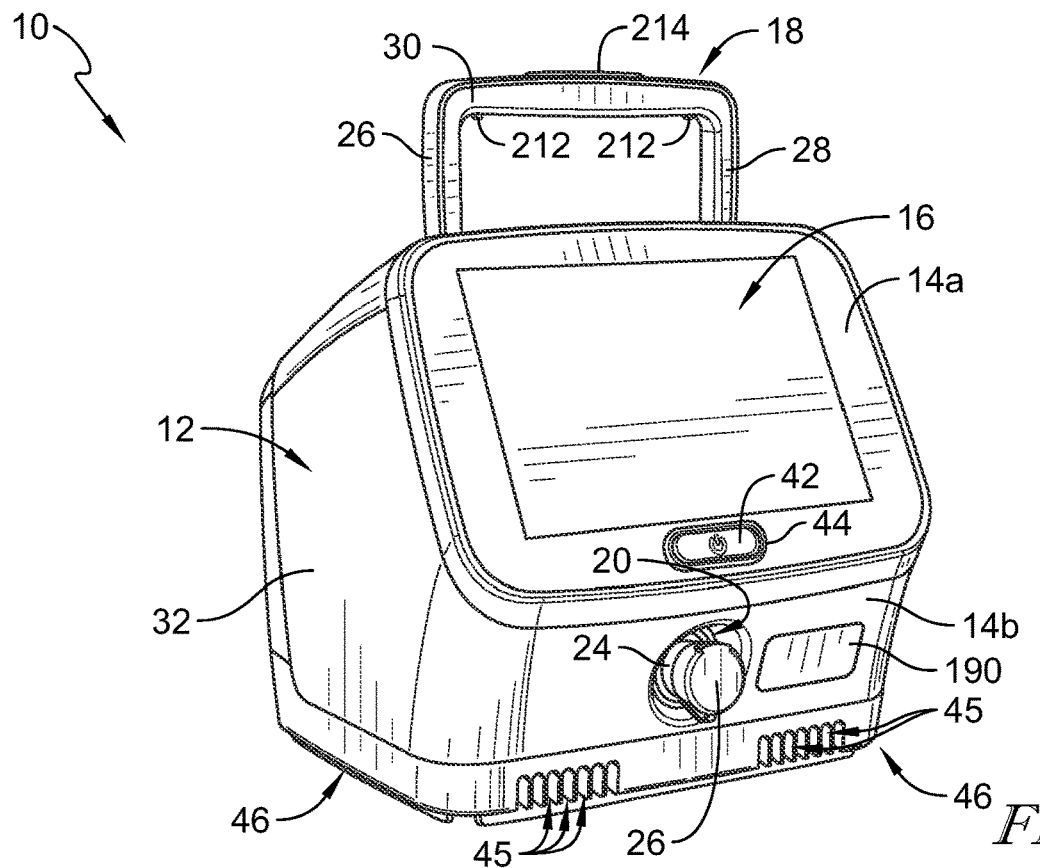
FIG. 1 is a perspective view of a respiratory therapy apparatus in a first configuration according to the present disclosure, showing the respiratory therapy apparatus having an outlet port extending from a recessed portion of a lower front wall of a housing, a display screen of a graphical user interface (GUI) on an upper front wall of the housing above the outlet port, and a U-shaped carrying handle extending upwardly from a top wall of the housing.
Figure 2:
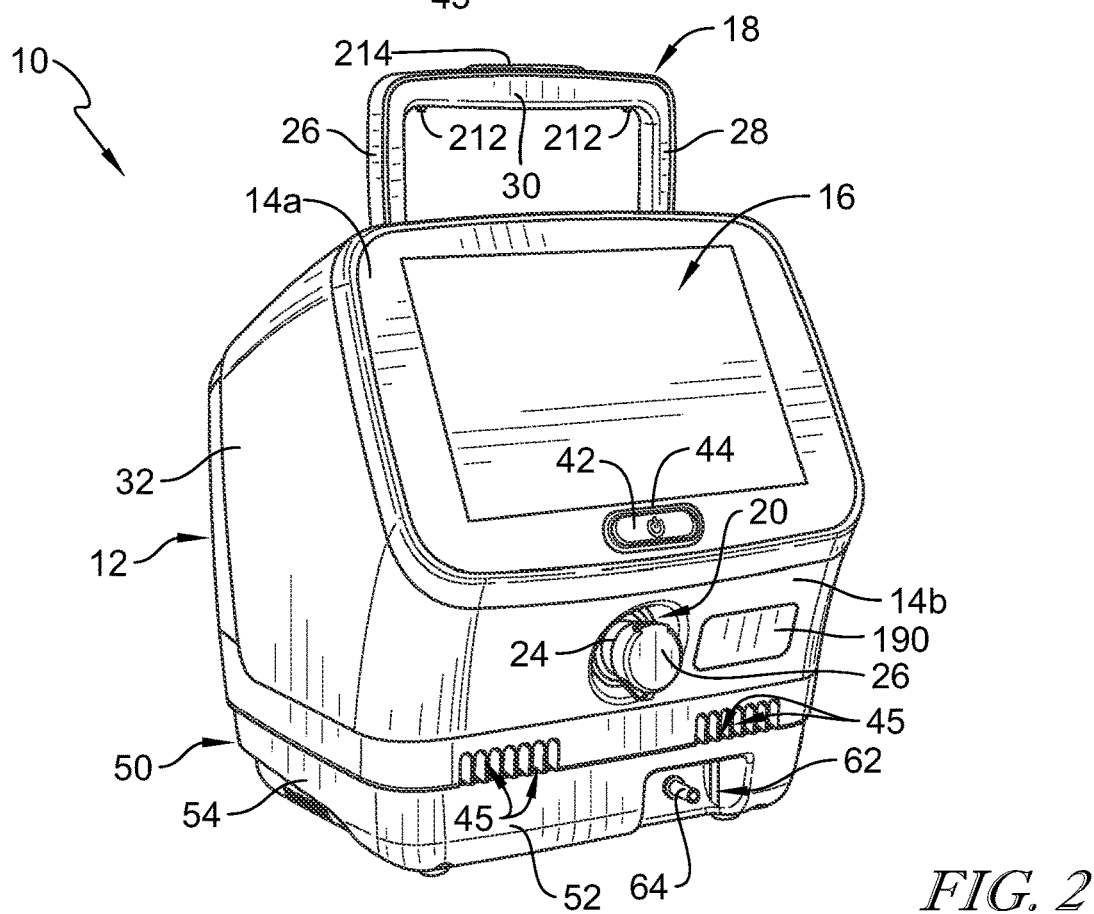
FIG. 2 is a perspective view, similar to FIG. 1, of the respiratory apparatus in a second configuration due to the addition of a nebulizer tray to a bottom of the housing of the respiratory therapy apparatus of the first configuration, the nebulizer tray underlying a vast majority of a bottom wall of the housing and a nebulizer port extending from a recessed portion of a front wall of the nebulizer tray.

A respiratory therapy device or apparatus 10, shown in FIGS. 1 and 2, includes a housing 12 having a sloped upper front wall portion 14*a* on which a display screen or graphical user interface (GUI) 16 is accessible to enter user inputs into device 10 and to see displayed information regarding the operation of device 10 as shown in the screen shot examples of FIGS. 18-274 which are discussed in greater detail below. The terms GUI and display screen are used interchangeably herein. Housing 12 of device 10 also has a sloped bottom front wall portion 14*b* which slightly curves downwardly and rearwardly from the bottom of upper wall portion 14*a*. A port 24 of housing 12 extends from an annular recess 20 provided in front wall portion 14*b* as shown in FIGS. 1 and 2. Port 24 is sometimes referred to herein as a pneumatic port or an outlet port, for example. A cap 26 is shown in FIGS. 1 and 2 in a closed position covering an opening of port 24.

A handle 18 is coupled to a top of housing 12 and is gripped by a person to carry device 10. Handle 18 is pivotable relative to housing 12 between a use position, shown in FIGS. 1 and 2, in which handle 18 extends upwardly from housing 12, and a storage in which handle 18 is folded downwardly against the top of housing 12. Handle 18 has a first side portion 26, a second side portion 28 that is spaced from and substantially parallel with side portion 26, and a hand grip portion 30 that interconnects first ends of side portions 26, 28. Second ends of side portions 26, 28 of handle 18 are pivotably coupled to the top of housing 12. Thus, handle 18 is generally U-shaped in the illustrative example.

Figure 3:
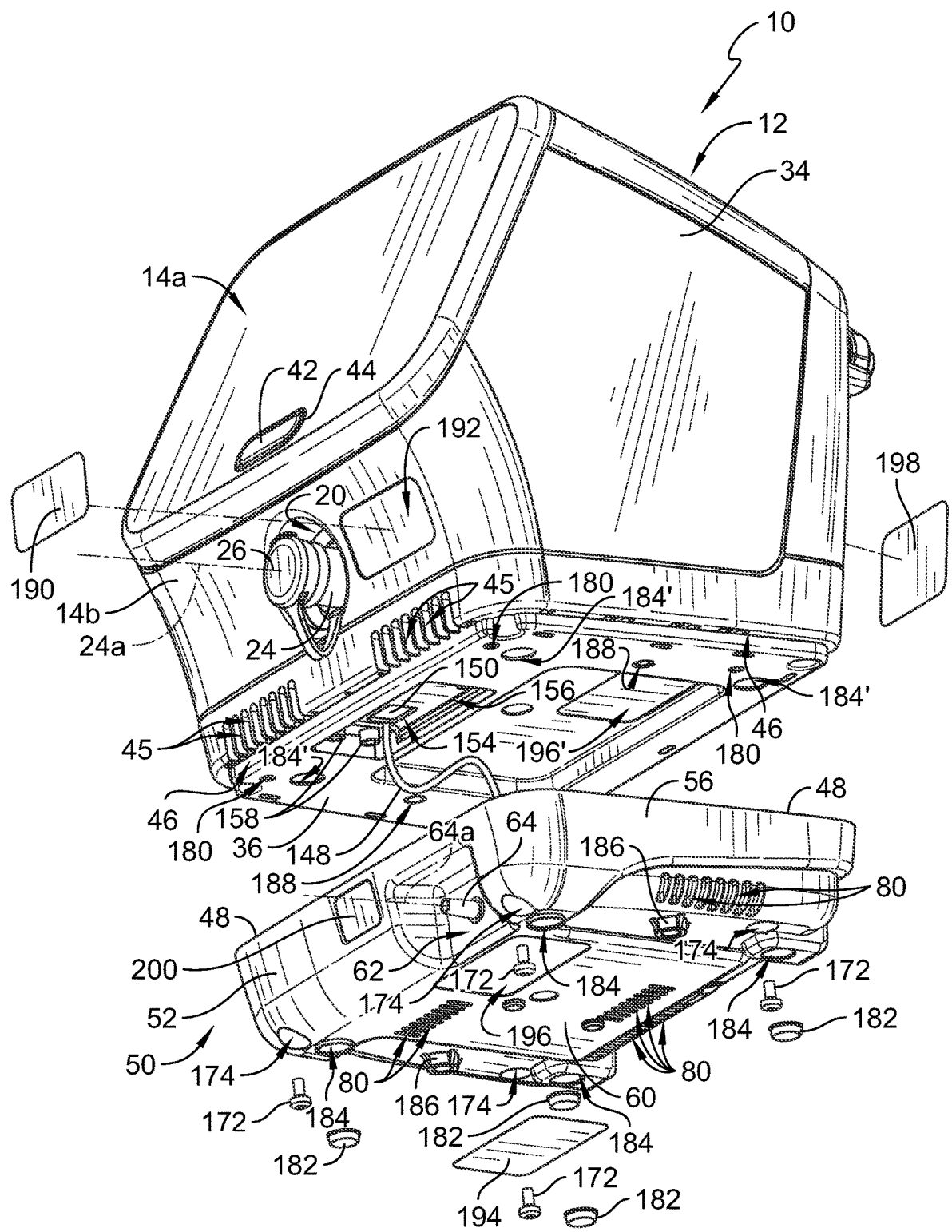
FIG. 3 is an exploded view showing the nebulizer tray exploded away from the bottom wall of the housing and showing an electrical cable arranged for insertion through an opening in the bottom wall into an interior region of the housing.

Housing 12 includes a first side wall 32, shown in FIGS. 1 and 2, a second side wall 34, shown in FIG. 3, and a bottom wall 36, also shown in FIG. 3. Housing 12 further includes a top wall 38, shown in FIGS. 6 and 7A, and a back wall 40, also shown in FIGS. 6 and 7A. Device 10 includes a main on/off button 42 that is accessible in an oblong opening 44 provided on upper front wall portion 14*a* of housing 12 beneath GUI 16 and about midway between side walls 32, 34 of housing 12. On/off button 42 is pressed sequentially to turn device 10 on and off. A lower region of lower wall portion 14*b* and back wall 40 each have a plurality of ventilation holes 45 which permit air to flow into and out of an interior region of housing 12. In the illustrative example, holes 45 are formed as slots.

As will be discussed in further detail below, device 10 is operable to provide multiple types of respiratory therapies to a patient. In some embodiments, device 10 is operable to provide manual and automatic modes of mechanical insufflation/exsufflation (MIE) therapy to patient. MIE therapy is sometimes referred to cough assist therapy by those skilled in the art. In other embodiments, device 10 is operable to provide manual and automatic modes of oscillatory lung expansion (OLE) therapy to a patient. In still other embodiments, device 10 is operable to provide manual and automatic MIE therapy and manual and automatic OLE therapy to a patient. Each of the manual and automatic OLE therapies may include one or more stages of continuous positive expiratory pressure (CPEP) therapy and/or one or more stages of continuous high frequency oscillation (CHFO) therapy to the patient, at the option of the user of device 10. It is within the scope of the present disclosure for device 10 to be configured to provide other types of respiratory therapies to a patient.

When used as for MIE therapy (manual or automatic), device 10 provides a noninvasive therapy that is an alternative to invasive suctioning. Device 10 is designed for use by patients, caregivers, and healthcare providers, such as respiratory therapists. Thus, the term "user" or "users" as used herein encompasses each of these types of people unless specifically noted otherwise. Device 10, when providing MIE therapy, simulates a cough to remove secretions in patients with a compromised peak cough flow. During MIE therapy, device 10 supplies positive insufflatory pressure (inhale) to the patient's airway with the intended goal of inflating the lungs. Device 10 then rapidly shifts to supply negative exsufflatory pressure (exhale) with the intended goal of rapidly deflating the lungs to simulate a high expiratory flow which stimulates an effective cough. After exhale, device 10 moves into a paused state and maintains a positive pressure flow to the patient, if so programed. This is referred to as Positive Airway Pressure (PAP) on Pause. An optional sigh stage can also be included after the MIE therapy to inflate the patient's lungs after the last exhale of the MIE therapy.

When used for OLE therapy (manual or automatic), device 10 provides a therapy that enhances secretion removal and helps prevent or resolve patchy atelectasis of the patient. As noted above, device 10 is configurable to deliver the OLE therapy in two modes: a CHFO mode which is a pneumatic form of chest physiotherapy that delivers medicated aerosol while oscillating the airways with continuous pulses of positive pressure, and a CPEP mode which supplies continuous positive pressure to help hold open and expand the airways. Together with the CPEP and/or CHFO modes of OLE therapy, device 10 is also operable to deliver aerosolized medications using a nebulizer and to deliver supplemental oxygen from an external oxygen source. The nebulizer used with device 10 is configured to aerosolize medication approved for nebulization and prescribed by a physician.

If device 10 is to be operated with the nebulization feature, such as during OLE therapy, then an optional nebulizer tray 50 is attached to a bottom of housing 12 as shown in FIG. 2. When attached to housing 12, the nebulizer tray 50 covers a vast majority of bottom wall 36 of housing 12. Bottom wall 36 has a perimeter recess 46 formed at the junction between bottom wall 36 and each of lower wall portion 14b, side walls 32, 34, and back wall 40 of housing 12. An upper edge 48 of nebulizer tray 50 is received in the perimeter recess 46 when the nebulizer tray 50 is attached to the bottom of housing 12. Nebulizer tray 50 includes a front wall 52, a first side wall 54, a second side wall 56, a back wall 58, and a bottom wall 60 as shown best in FIGS. 4 and 5. Tray 50 is molded from a plastics material as a single, monolithic component.

Front wall 52 of tray 50 has a recess 62 and a nebulizer tube port 64 extends from the front wall 52 within the recess 62. A port axis 24a of port 24 is substantially parallel with a port axis 64a of port 64 as shown, for example, in FIG. 3. By having port 24 situated primarily within recess 20 and by having port 64 situated within recess 62, ports 24, 64 are protected from impacts from falling objects. Furthermore, due to the concavity or sloped shape of lower front wall portion 14b, the junction between upper front wall portion 14a and lower front wall portion 14b just below button 42 overhangs the distal ends of ports 24, 64 to provide even further protection from falling objects. When respiratory therapy device 10 is viewed from the front, recess 62 and port 64 are offset downwardly and to the right of recess 20 and port 24. This location of ports 24, 64 makes it easier for a right-handed user to attach and detach nebulizer tubing from port 64 while a patient circuit is attached to port 24. If port 64 were located vertically beneath port 24, which is a possible configuration in alternative embodiments, then the patient circuit attached to port 24 would have a tendency to obstruct or possibly interfere with attachment and detachment of nebulizer tubing to port 64.

Figure 4:
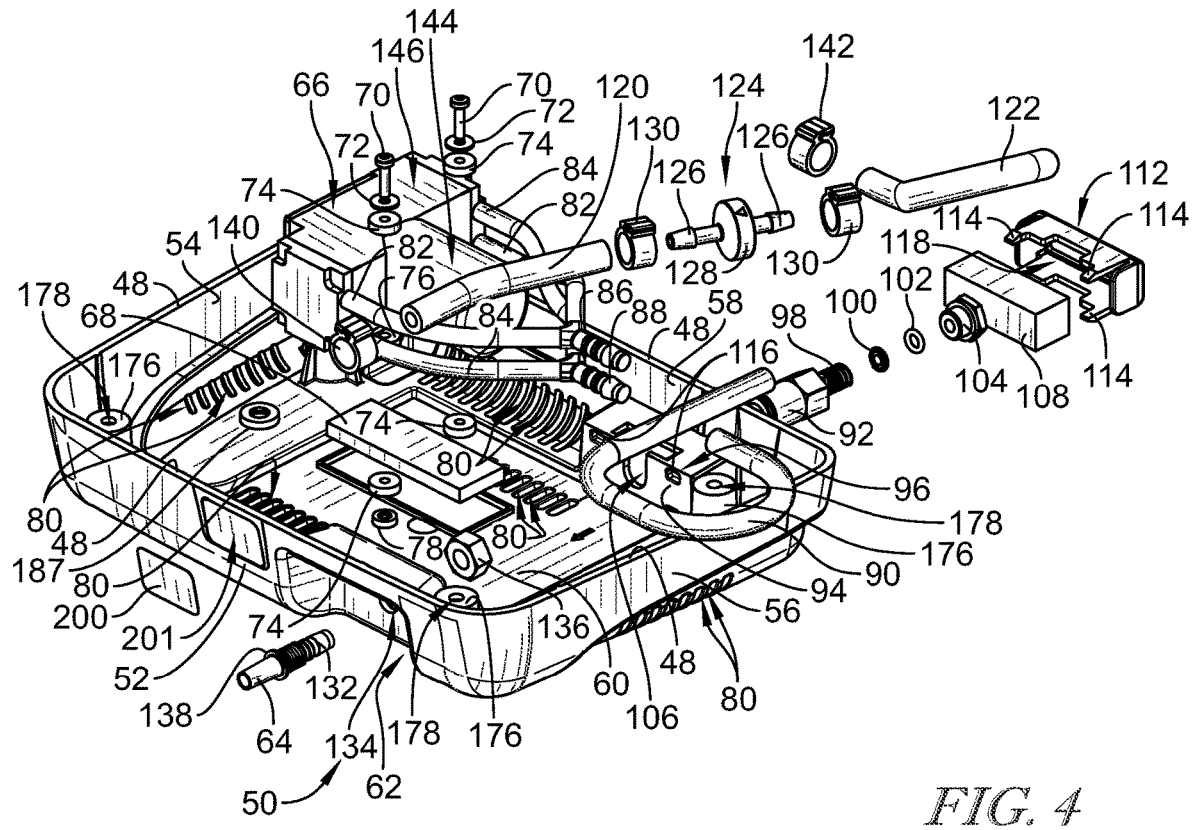
FIG. 4 is an exploded view of the nebulizer tray showing a tray shell of the nebulizer tray, a nebulizer pump situated above the tray shell, and pneumatic tubing having portions extending from the nebulizer pump and portions exploded away from the tray shell.
Figure 5:
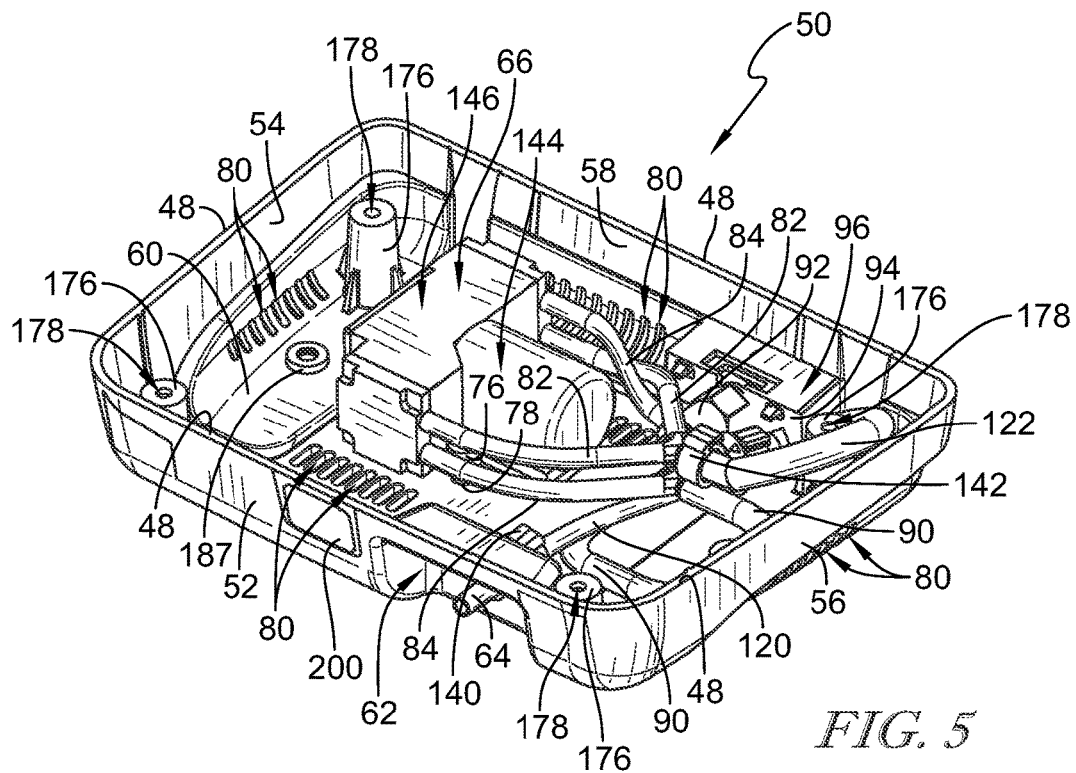
FIG. 5 is a perspective view of the nebulizer tray of FIG. 4, showing the nebulizer pump and pneumatic tubing assembled together within the tray shell of the nebulizer tray.

As shown in FIGS. 4 and 5, a nebulizer pump 66 is carried by bottom wall 60 of tray 50. In the illustrative example, a rectangular piece of foam padding 68, shown in FIG. 4, is interposed between pump 66 and bottom wall 60. A pair of screws 70 are inserted through corresponding flat washers 72 and corresponding pairs of rubber grommets 74 that are located above and below respective mounting ears 76 of pump 66 (only one ear 76 of pump 66 can be seen in FIGS. 4 and 5). Lower ends of screws 70 thread into screw receiving bosses 78 that are molded integrally with bottom wall 60 of tray 50 (only one boss 78 can be seen in FIGS. 4 and 5). Tray 50 includes a multitude of ventilation holes 80 formed in walls 54, 56, 58, 60. In the illustrative example, holes 80 are formed as slots. Heat generated by pump 66 is ventilated to ambient atmosphere through holes 80.

Still with reference to FIGS. 4 and 5, a pair of pump outlet tubes 82 and a pair of pump inlet tubes 84 extend from pump 66. Ends of tubes 82 that are spaced from pump 66 meet at, and are connected to, two branches of a first pneumatic Y-connector 86 and ends of tubes 84 that are spaced from pump 66 meet at, and are connected to, two branches of a second pneumatic Y-connector 88. A main inlet tube 90 has one end connected to a trunk of Y-connector 88 and an opposite end connected to an inlet fitting 92 that couples to a rear wall 94 of a filter receiving box 96 that is molded integrally with tray 50. An interior region of inlet fitting 92 receives a compression spring 98, a circular inlet filter 100, and a rubber O-ring 102 shown in FIG. 4. An inlet nut and bushing 104 threads into an end of fitting 92 that is adjacent to rear wall 94. More particularly, a threaded portion of nut and bushing 104 threads into a bore of fitting 92 through a notch 106 formed in rear wall 96 of box 96 so that a portion of rear wall 94 adjacent to notch 106 is clamped between an end surface of fitting 92 and a head portion of nut and bushing 104. As nut and bushing 104 is threaded into fitting 92, O-ring 100 is pressed against filter 100 and filter is pressed against compression spring 98 to compress spring 98 in the interior region of fitting 92.

An inlet filter 108 is received in a recess 110 (see FIG. 7A) defined by box 96 in the back wall 58 of tray 50. Filter 108 comprises a rectangular block of foam in the illustrative embodiment. A long dimension of the foam block comprising filter 108 is oriented substantially horizontally when respiratory therapy device 10 having tray 50 is supported on a horizontal surface in its proper orientation. A filter cover 112 includes a set of snap fingers 114 having ramped distal ends that snap into and through respective apertures 116 formed in rear wall 94 of box 96 so that cover 112 retains filter 108 within recess 110. Cover 112 has a pocket 118 in which inlet filter 108 is situated when cover is snapped into place in box 96. When retained in recess 110 by cover 112, filter 108 abuts the headed portion of nut and bushing 104.

As also shown in FIGS. 4 and 5, tray 50 houses a first outlet tube segment 120 and a second outlet tube segment 122. Segments 120, 122 are pneumatically coupled together by a diaphragm check valve 124. In this regard, barbed couplers 126 extending outwardly from a central disc-shaped portion 128 of check valve 124 are inserted into respective open ends of tubes 120, 122 and hose clamps 130 provide additional clamping force to secure the ends of tubes 120, 122 onto the respective barbed couplers 126. An end of tube 120 that is spaced from check valve 124 attaches to a tube fitting portion 132 that is formed integrally with tube port 64 and that extends through an aperture 134 formed in a portion of front wall 52 that defines the recess 62.

A nut 136 threads onto a threaded region of tube fitting portion 132 so that a portion of the front wall 52 around aperture 134 is clamped between nut 136 and an annular flange 138 formed at the junction between tube port 64 and tube fitting portion 132. A hose clamp 140 provides additional clamping force to secure the respective end of tube 120 onto tube fitting portion 132. An end of tube 122 that is spaced from check valve 124 attaches to a trunk of Y-connector 86. Yet another hose clamp 142 provides additional clamping force to secure the respective end of tube 122 onto the trunk of Y-connector 86. In use, a motor 144 of pump 66 operates to draw ambient air through filter 108 and fitting 92 into tube 90 and then through Y-connector 88 and inlet tubes 84 into an interior of a manifold block 146 of pump 66. The motor 144 of pump 66 compresses the air entering manifold block 146 and then compressed or pressurized air is expelled from manifold block 146 and moved through outlet tubes 82, Y-connector 86, tubes 120, 122 and filter 124, and nebulizer port 64 into a nebulizer hose attached to port 64.

Figure 16A:
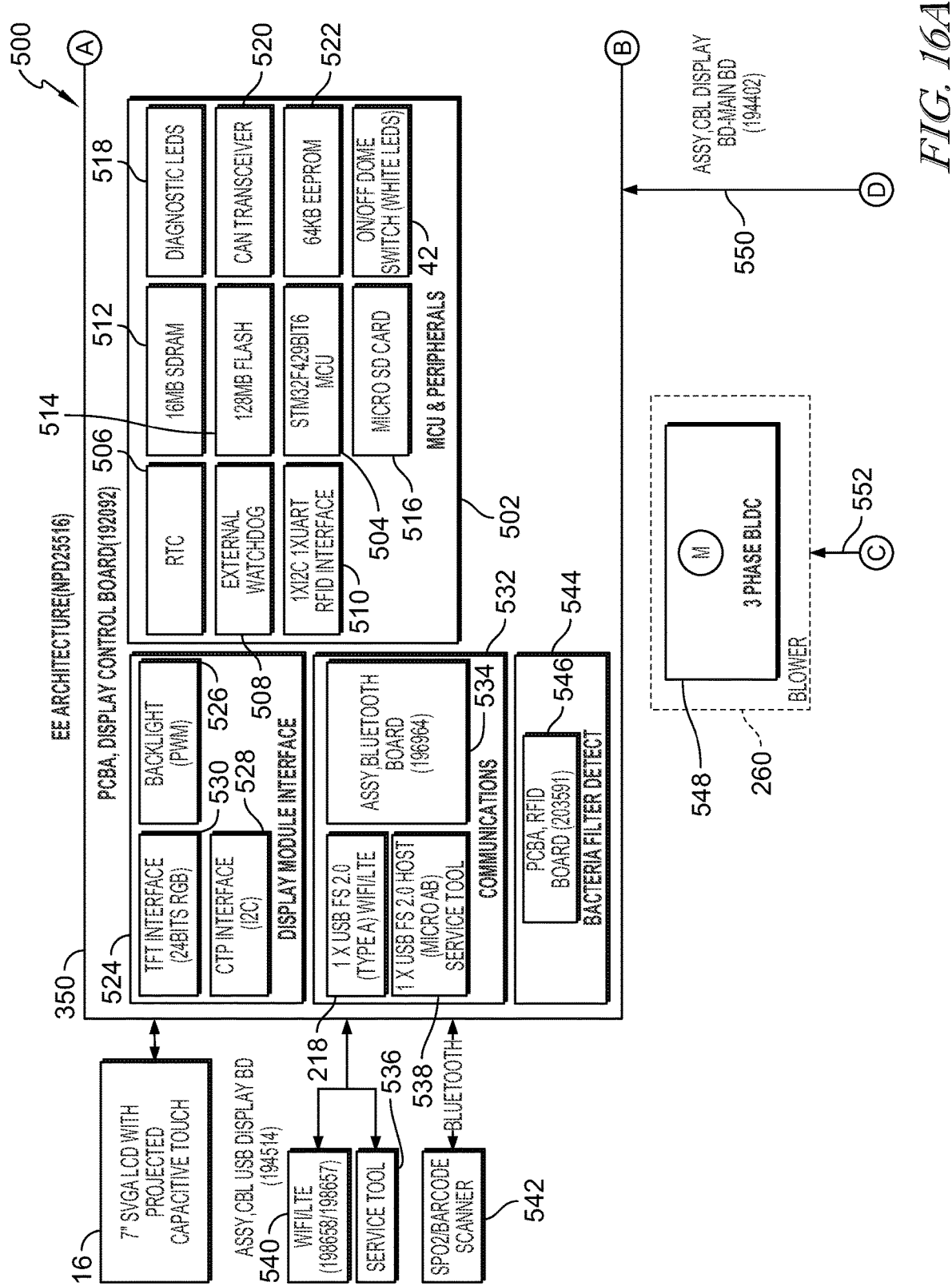
FIGS. 16A-16D together form a block diagram of the electrical architecture of the respiratory therapy apparatus of the present disclosure.
Figure 16B:
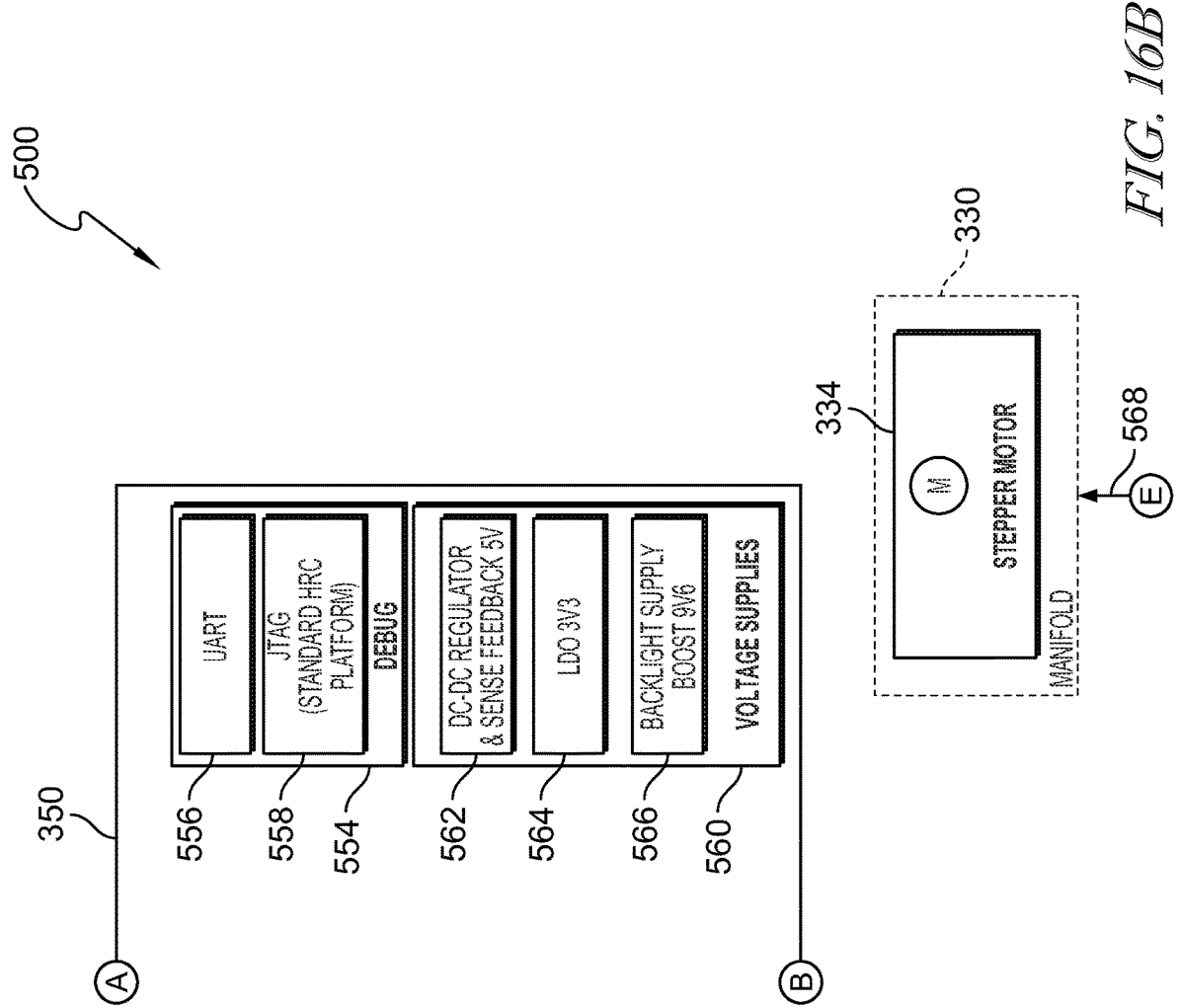
Figure 16C:
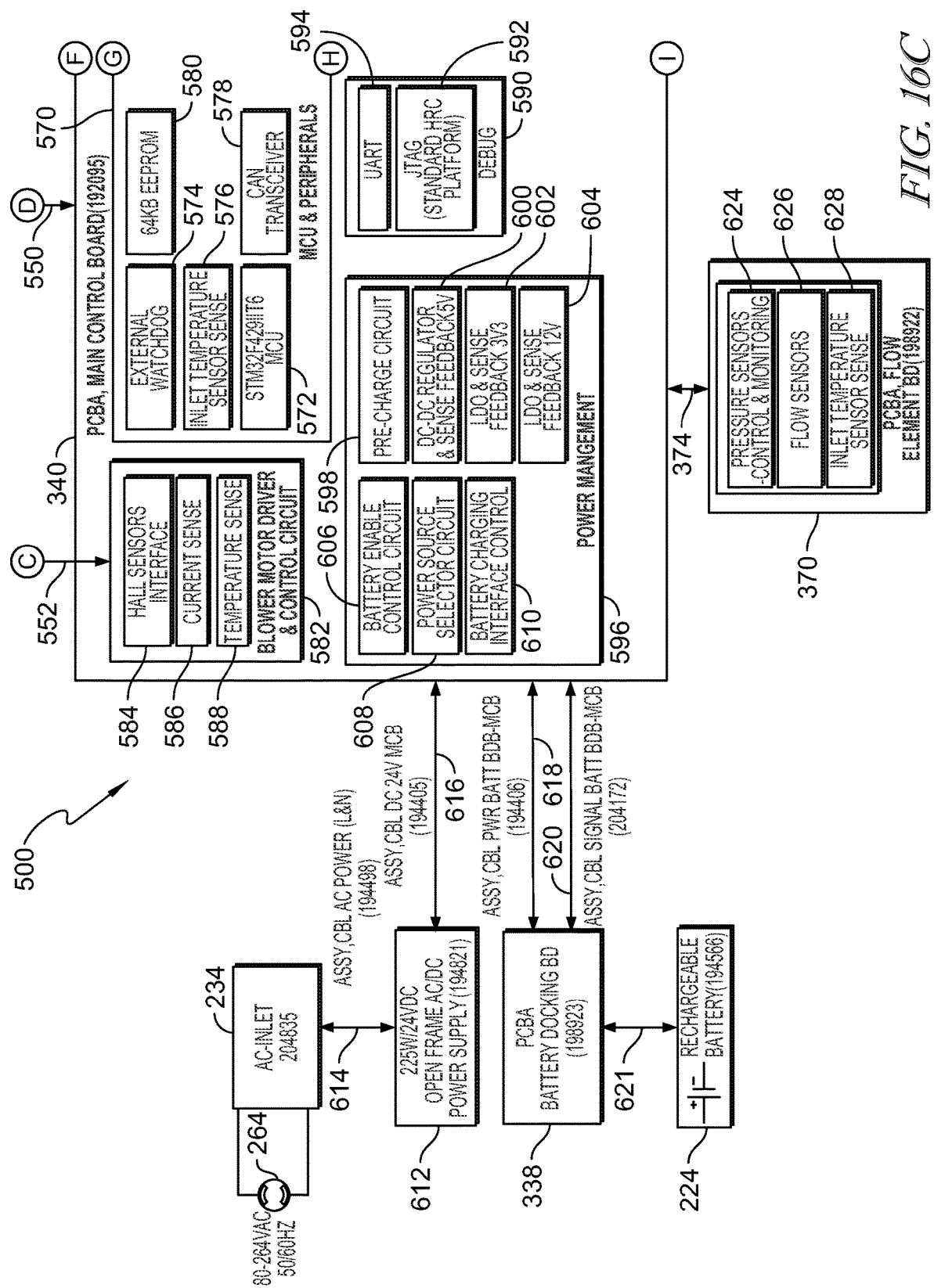
Figure 16D:
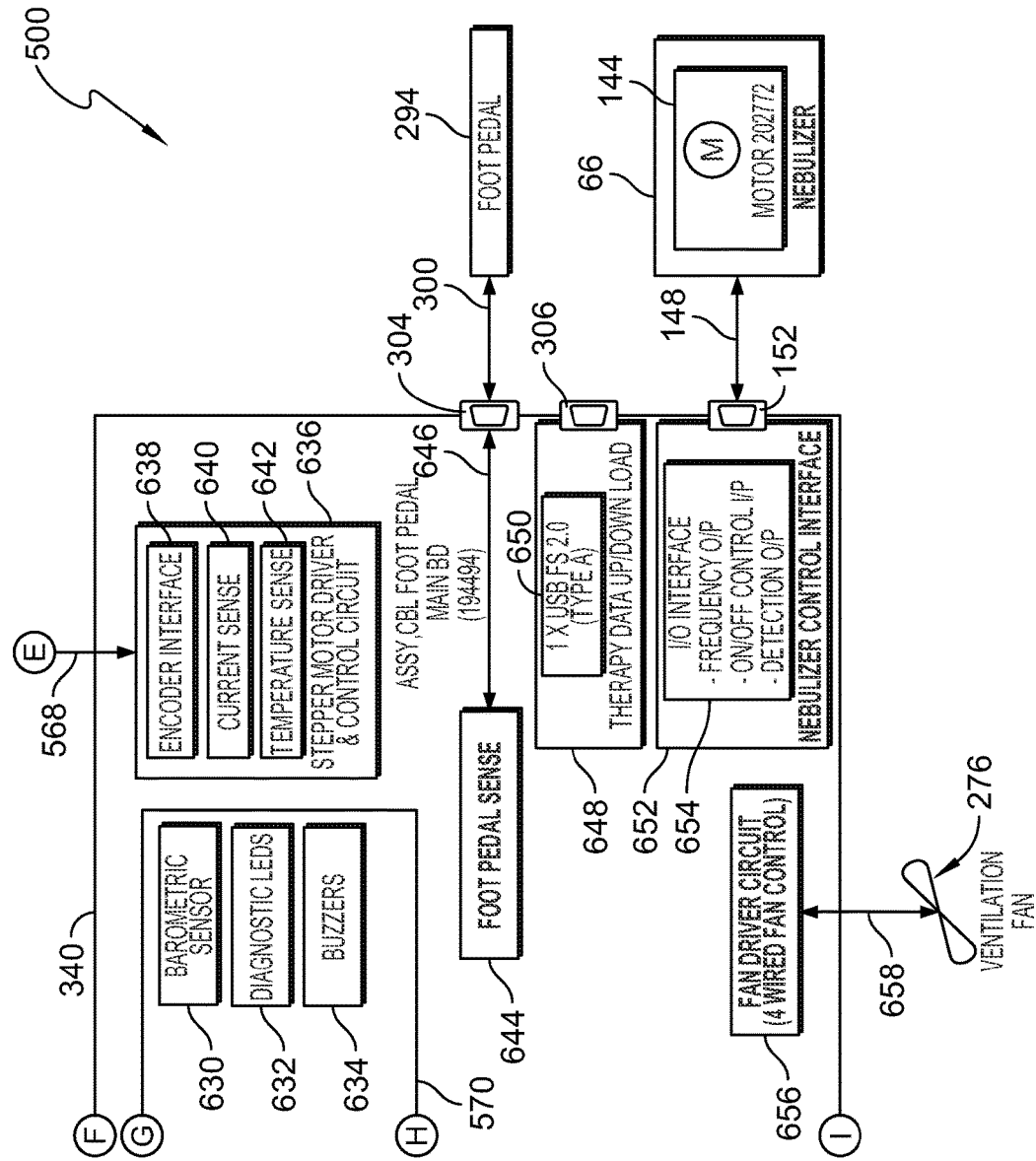

Referring once again to FIG. 3, an electrical cable 148 extends from pump 66 and has an electrical connector 150 that attaches to a mating electrical connector 152, shown diagrammatically in FIG. 16D. Connector 152 is accessible through an opening 154 provided in a rectangular recess 156 formed in bottom wall 36 of housing 12 of respiratory therapy device 10. In the configuration of respiratory therapy device 10 in which tray 50 is omitted, a rectangular cover (not shown) fits within recess 156 and is attached to cylindrical bosses 158 with suitable fasteners such as screws. Electrical power is provided to operate pump 66 of nebulizer tray 50 via cable 148. Circuitry, which is discussed below in connection with FIGS. 16A-17C, located within the interior region of housing 12 of device 10 controls when pump 66 is turned on and off to provide pneumatic pressurization to a nebulizer 160 shown in FIG. 9 via tubing 162, a portion of which is shown in FIG. 9 and a portion of which is shown in FIG. 7B.

Figure 7A:
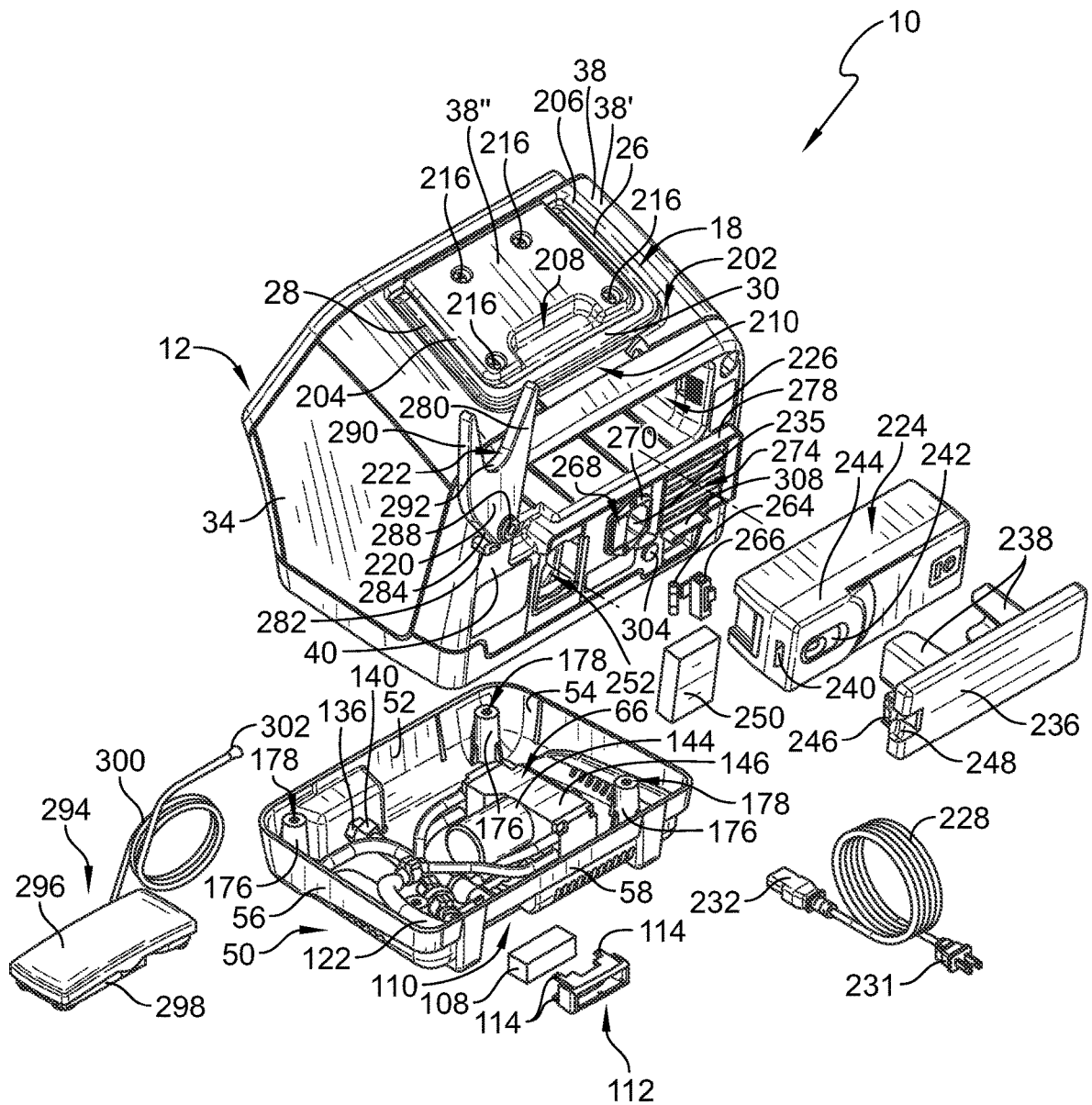
FIG. 7A is an exploded perspective view showing the generally V-shaped hose support plate rotated about 90 degrees from the storage position to a use position having a V-shaped notch of the plate situated for receiving a hose therein, a battery and battery cover exploded away from a rectangular battery-receiving recess provided in the back wall of the housing, the nebulizer tray exploded away from the bottom wall of the housing and a foot switch situated to the left of the nebulizer tray.
Figure 7B:
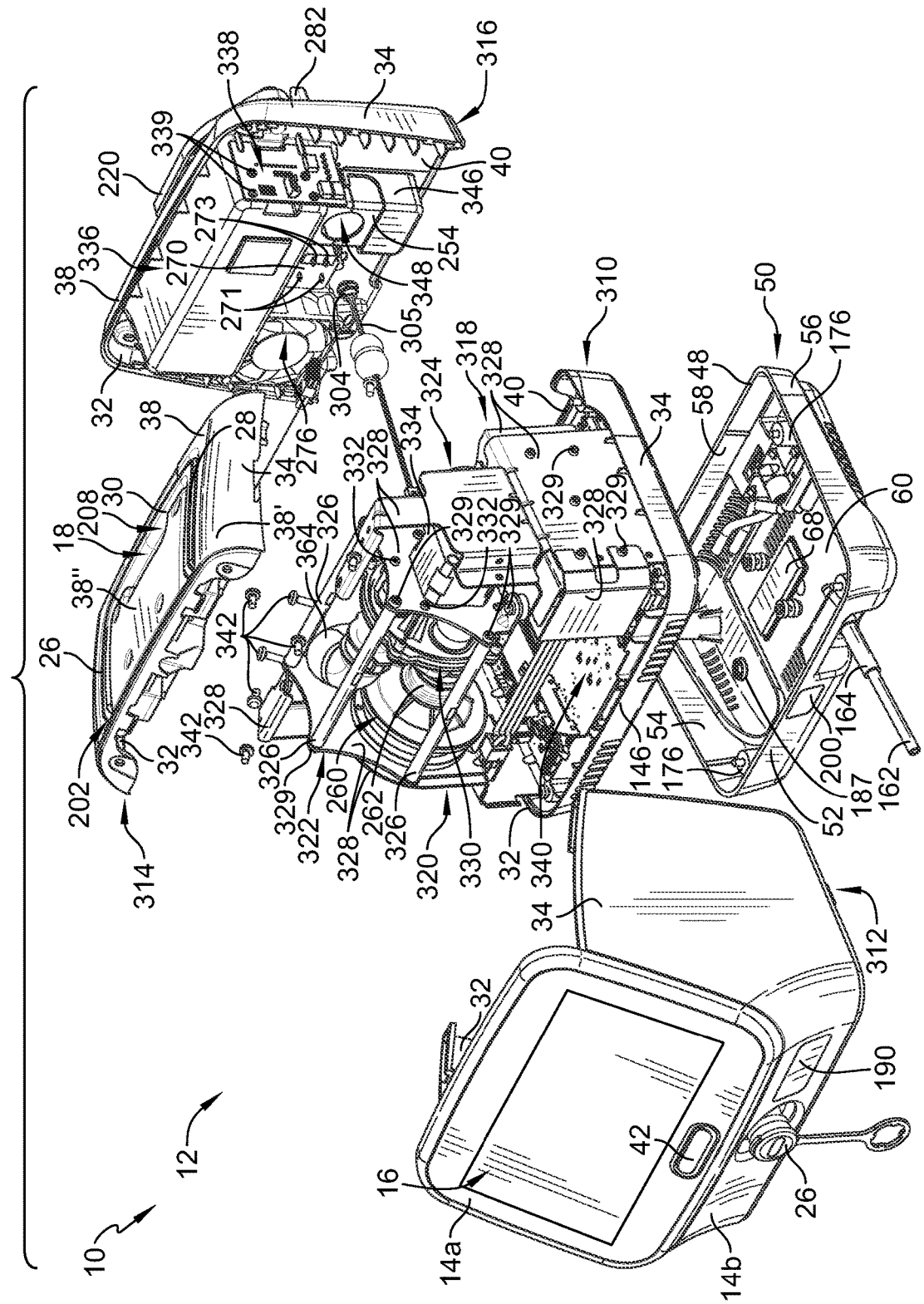
FIG. 7B is an exploded perspective view showing portions of the housing exploded away to show a chassis supporting a manifold and valve assembly and supporting a blower above the bottom wall of the housing.
Figure 9:
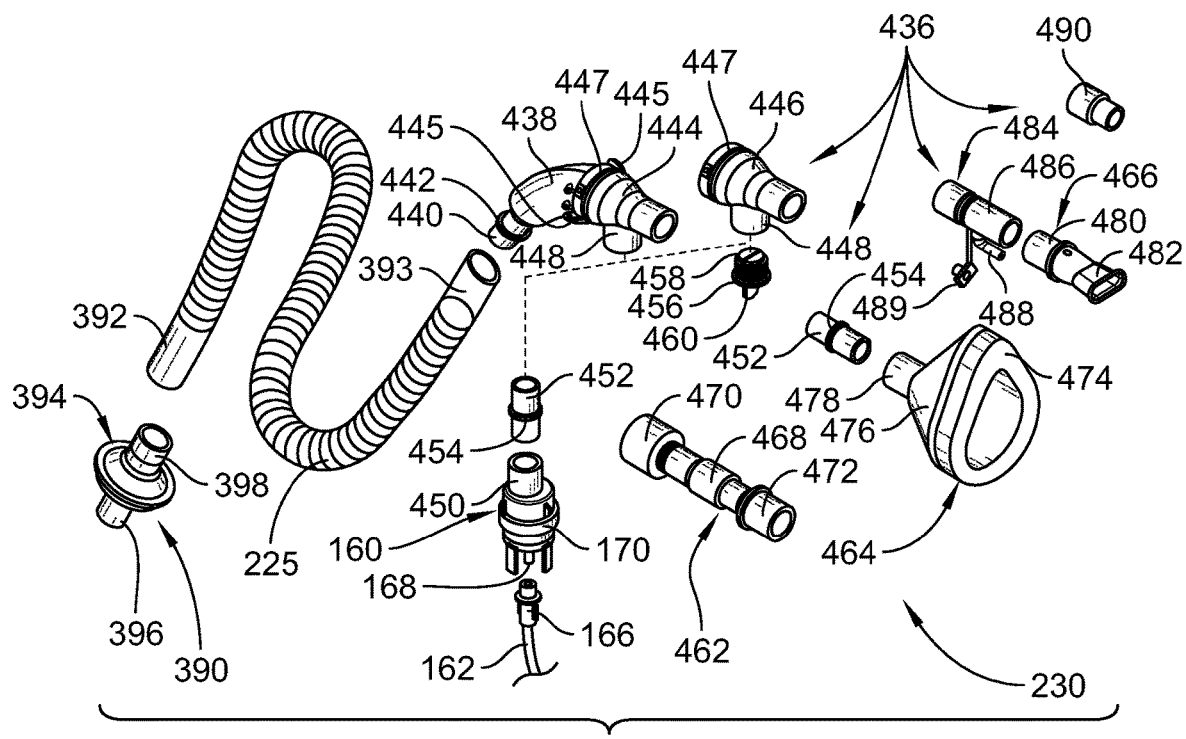
FIG. 9 is an exploded view showing a patient interface circuit including a flexible, corrugated hose, a filter unit exploded away from a first end of the hose and a variety of patient interface components exploded away from a second end of the hose.

A first connector 164 at a proximal end of tubing 162 attaches to port 64 as shown in FIG. 7B and a second connector 166 at a distal end of tubing 162 attaches to a pneumatic inlet 168 of nebulizer 160 as shown in FIG. 9. Pressurized air from pump 66 passes through port 64, connector 164, tubing 162, connector 166, and inlet 168 into an interior region of a nebulizer cup 170 of nebulizer 160 to atomize or nebulize a liquid medicine contained within cup 170 for eventual delivery to the patient's airway.

Referring again to FIG. 3, a set of four screws 172 are provided for attaching nebulizer tray 50 to housing 12 of respiratory therapy apparatus 10. Screws 172 are inserted through openings 174 into interior regions of upstanding pylons 176 (see FIGS. 5 and 7A) that extend upwardly from bottom wall 60 of tray 50 near the corner regions of tray 50. The threaded portions of screws 172 extend though apertures 178 formed at the top of pylons 176 and are screwed into threaded apertures 180 formed in bottom wall 36 of housing 12 with the heads of screws 172 being retained within the interior regions of respective pylons 176 and clamping the tops of pylons 176 against the bottom wall 36 of housing 12.

A set of four rubber feet 182 are adhered to bottom wall of 60 of nebulizer tray 50. In particular, feet 182 are disc-shaped and are received in shallow circular depressions 184 formed in bottom wall 60, as shown in FIG. 3, but are thick enough to protrude downwardly from the depressions 184. In configurations of device 10 in which nebulizer tray 50 is omitted, feet 182 are received in depressions 184' formed in bottom wall 36 of housing 12. Feet 182 inhibit respiratory therapy device 10 from slipping on an underlying surface, such as a table surface for example. If desired, respiratory therapy device 10 can be mounted to a support surface or shelf of a mobile stand (not shown). See, for example, the mobile stand in FIGS. 52 and 53 and the related description of U.S. Pat. No. 8,460,223 which is hereby incorporated by reference herein to the extent not inconsistent with the present disclosure which shall control as to any inconsistencies.

To mount respiratory therapy device 10 in the configuration with nebulizer tray 50 to the mobile stand, a pair of suitable fasteners such as screws (not shown), are inserted through holes formed in the shelf of the mobile stand and into respective threaded bosses 186 formed in the bottom wall 60 of nebulizer tray 50 as shown in FIG. 3. Illustrative tray 50 also has internal bosses 187 formed above bottom wall 60 of tray as shown in FIGS. 4 and 5 (only one of bosses 187 can be seen) and aligned with bosses 186 so that the screws have additional material to thread into. In configurations of device 10 in which tray 50 is omitted, the fasteners are inserted through the holes formed in the shelf of the mobile stand and into respective threaded apertures 188 formed in the bottom wall 36 of housing 12 as also shown in FIG. 3. If desired, device 10 can be mounted to stationary shelves or surfaces in a similar manner using fasteners, such as screws, that are threaded into bosses 186 or apertures 188, depending upon the configuration of device 10 with or without tray 50.

In the illustrative example, a product label 190 is received in a complimentarily shaped depression 192 formed in lower front wall portion 14b of housing 12 adjacent to the recess 20 that contains port 24 as shown in FIG. 3. The product label 190 includes the product name and/or manufacturer name for device 10 in some embodiments. Also in the illustrative example, a unique device identifier (UDI) label 194 is received in a complimentarily shaped depression 196 formed in bottom wall 60 of tray 50 and/or in a complimentarily shaped depression 196' formed in bottom wall 36 of housing 12. The contents of UDI labels are established by governmental bodies such as the U.S. Food & Drug Administration (FDA), for example.

In the illustrative example, a safety label 198 is received in a complementarily shaped depression (not shown, but similar to depressions 192, 196, 196') of back wall 40 of housing 12. The safety label 198 includes safety information pertaining to device 10 along with Underwriters Laboratories (UL) and/or CE certification marks, for example. As also shown in FIG. 4, a nebulizer label 200 is received in a complimentarily shaped depression 201 formed in front wall 52 of tray 50 adjacent to the recess 62 that contains port 64. The nebulizer label 200 indicates to a user that port 64 provides pressurized air for a nebulizer, such as illustrative nebulizer 160 shown in FIG. 9.

Figure 6:
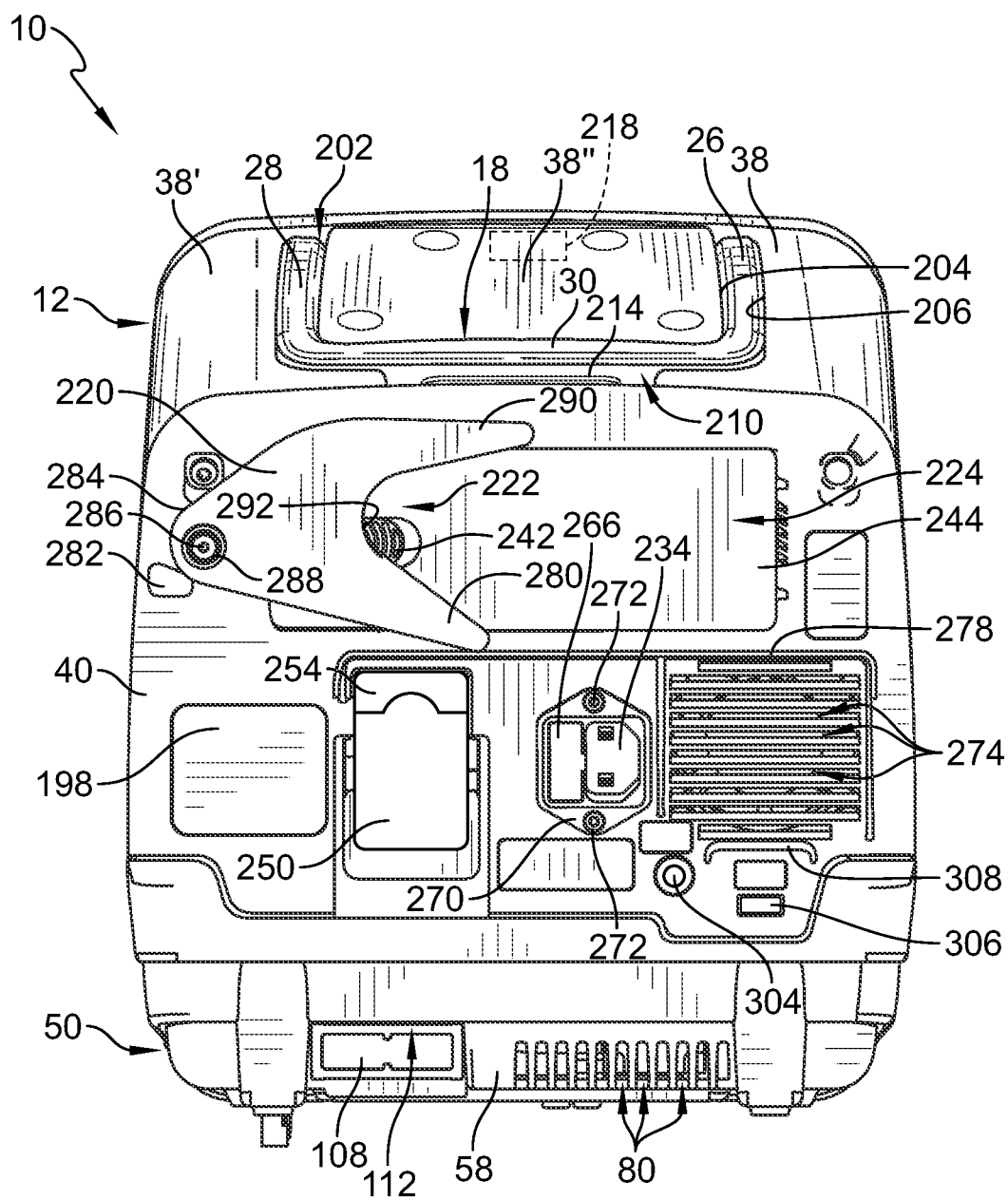
FIG. 6 is a rear elevation view of the respiratory therapy apparatus of FIG. 2 showing the U-shaped handle in a storage position within a recess formed in the top wall of the housing and showing a generally V-shaped hose support plate in a storage position behind a back wall of the housing.

Referring now to FIG. 6, handle 18 is shown lowered into its storage position against top wall 38 of housing 12 of respiratory therapy device 10. Top wall 38 includes a first top wall portion 38' formed to include a recess 202 and a second top wall portion 38" selectively receivable in the recess 202. A U-shaped handle receiving space is formed by a portion of recess 202 between an outer edge 204 of the second top wall portion 38" and a recess defining edge 206 of the first top wall portion 38' that defines the recess 202. Thus, handle 18 is received in the handle receiving space of recess 202 when the handle 18 is situated in a storage position. As shown in FIG. 6, for example, handle 18 and second top wall portion 38" fill substantially all of recess 202 when handle is in the storage position.

Ends of side portions 26, 28 of handle 18 adjacent to the front of device 10 are pivotably coupled to first top wall portion 38' for rotation about a pivot axis. Second top wall portion 38" has a finger receiving depression 208, shown in FIGS. 7A and 7B, that is sized to receive one or more of a user's fingers to facilitate movement of the handle 18 from the storage position to the use position. In the illustrative, example the first top wall portion 38' also has a finger receiving depression 210, shown in FIGS. 6 and 7A, that is sized to receive one or more of a user's fingers to facilitate movement of the handle 18 from the storage position to the use position. As shown in FIGS. 1 and 2, hand grip portion 30 of handle 18 has a pair of small protrusions or nubs 212 that snap into complementarily shaped depressions (not shown) in edge 204 of second top wall portion 38" to help secure handle 18 in the storage position. With just a slight amount of upward force on hand grip portion 30, nubs 212 are able to snap out of the corresponding depressions so that handle 18 can be moved to the use position.

A ridge 214, shown in FIGS. 1 and 2, is formed in a central region of hand grip portion 30 of handle 18 and is accessible within recess 210, as shown in FIG. 6, when handle 18 is in the storage position. Ridge 214 abuts a surface of first top wall portion 38' that defines a bottom of recess 210. This abutment results in handle 18 stopping in the proper orientation when in the storage position. Finger receiving depression 208 is deeper than depression 210 so that a user is able to insert a portion of the user's finger tips underneath hand grip portion 30 to initially lift handle 18 out of the storage position for movement toward the use position.

As shown in FIG. 7A, a set of four fasteners 216, illustratively screws, are provided and are configured to removably couple the second top wall portion 38" to the first top wall portion 38'. In other embodiments, more or less than four fasteners 216 are used to removably couple top wall portion 38" to top wall portion 38'. Thus, at least one fastener 216 is used to couple top wall portion 38" to top wall portion 38' according to the present disclosure. Top wall portions 38', 38" are configured so that upper surfaces are generally coplanar when portion 38" is attached to portion 38'. Furthermore, the top wall 38 formed by portions 38', 38" of housing 12 is inclined downwardly at an angle (e.g., slopes downwardly) from a front of the housing 12 to a back of the housing 12 when the housing 12, with or without tray 50 being attached, is supported on a horizontal surface.

As mentioned above, respiratory therapy apparatus 10 includes GUI 16. As will be described in further detail below, respiratory therapy apparatus 10 also includes control circuitry and GUI 16 provides user inputs that are configured for controlling firmware updates to the control circuitry. According to the illustrative embodiment, the firmware updates are provided to the control circuitry via a firmware upgrade port 218 that is situated beneath top wall portion 38" as shown in FIG. 6 (in dotted line). Thus, to access firmware upgrade port 218 for uploading firmware updates, top wall portion 38" is detached and removed from top wall portion 38' thereby exposing firmware upgrade port 218 within recess 202. In some embodiments, firmware upgrade port 218 comprises a universal serial bus (USB) port and the firmware updates are provided on a USB drive that couples to the USB port 218.

Referring once again to FIG. 6, a generally V-shaped hose support plate 220 is shown in a storage position behind back wall 40 of housing 12. Plate 220 is coupled to back wall 40 of housing 12 for pivoting movement between the storage position shown in FIG. 6 and a deployed position, shown in FIG. 7A, in which a portion of the plate 220 extends above top wall 38 of the housing 12 so that a hose receiving notch 222 of the plate is situated above top wall 38 of housing 12. A hose 225 of a configurable patient circuit 230, shown in FIG. 9 is receivable in the hose receiving notch 222 when plate 220 is in the deployed position. Thus, plate 220 supports slack in hose 225 during operation of device 10 to provide respiratory therapy to the patient if the patient is located in suitably close proximity to housing 12.

As shown in FIG. 7A, when plate 220 is in the deployed position, a battery 224 is insertable into, and removable from, a battery compartment 226 formed in back wall 40 of housing 12. When battery 224 is received in battery compartment 226 and plate 220 is moved to the storage position, plate 220 blocks a portion of the battery compartment and a front surface of plate 220 confronts a portion of battery 224 received in the battery compartment 226. In some uses of device 10, battery 224 is omitted and power is provided to device 10 by an alternating current (AC) power cable 228, shown in FIG. 7A, having at one end thereof an AC power plug 231 with prongs that plug into a standard AC power receptacle (not shown), and having at an opposite end thereof a power connector 232 that attaches to a mating power connector 234 provided on back wall 40 of housing 12 as shown in FIG. 6, for example. Power connector 234 has a recess 235, shown best in FIG. 7A, into which connector 232 is inserted. If battery 224 is installed in compartment and AC power is provided to operate device 10 via power cable 228, then battery 224 is charged by the power from power cable 228.

When battery 224 is removed from compartment 226, a battery compartment cover 236 is insertable into compartment 226 to cover the opening to compartment 226. A pair of standoffs 238 are molded integrally with cover 226. When cover 236 is inserted into compartment 226, distal ends of standoffs 238 bottom out against a portion of back wall 40 that defines a depth of compartment 226 to properly position cover 236 at the opening of compartment 226. When cover 236 is received in compartment 226 and plate 220 is in the storage position, the front surface of plate 220 confronts a portion of cover 236 received in the battery compartment 226.

Battery 224 includes a retractable latch 240 and a spring loaded button 242 as shown in FIG. 7A. Button 242 is coupled to latch 240 and is spring biased into a locking position in which latch 240 extends from an end of a battery housing 244 of battery 224 for receipt in a latch receiving pocket (not shown) formed in a portion of back wall 40 that defines one of the sides of battery compartment 226. Button 242 is moved relative to battery housing 244 from the locking position to a releasing position to retract latch 240 from the pocket which permits removal of battery 224 from battery compartment 226. Cover 236 also has a latch 246 which is received in the same pocket as latch 240 to lock cover 236 battery compartment 226. Latch 246 is molded integrally with a flexible finger 248 that is moved manually to retract latch 246 from the pocket to permit removal of cover 236 from battery compartment 226.

As shown in FIGS. 6 and 7A, device 10 includes an air inlet filter 250 which in the illustrative embodiment comprises a rectangular block of foam. A long dimension of the foam block comprising filter 250 is oriented substantially vertically when respiratory therapy device 10 is supported on a horizontal surface in its proper orientation. Air inlet filter 250 is received in a recess 252, shown in FIG. 7A, defined in the back wall 40 of housing 12 beneath battery compartment 226. A filter cover 254, shown in FIG. 6, which is similar to filter cover 112, but appropriately sized for filter 250, is received in recess 252 to retain filter 108 within recess 110. As will be discussed in further detail below, device 10 includes a blower 260, shown in FIG. 7B, which is operated in connection with the provision of respiratory therapy to a patient. In use, blower 260 operates to draw ambient air through filter 250 and into a conduit (not shown) that leads to an inlet 262 of blower 260. According to the present disclosure, therefore, either of blower 260 and nebulizer pump 66 are considered to be a first pressure source and the other of blower 260 and nebulizer pump 66 are considered to be a second pressure source.

Device 10 further includes a fuse 264 and fuse cover 266 as shown in FIG. 7A. In the illustrative embodiment, fuse 264 comprises a 4 Amp (A), 250 Volt (V) fuse but other types of fuses may be used in other embodiments. Fuse cover 266 snaps into a fuse receiving recess 268 provided adjacent to recess 235. In the illustrative embodiment, receptacles 268, 235 are molded into a single plastic power receptacle component 270, such as a model no. 719 W-00/02 Power Entry Connector Receptacle available from Qualtek Electronics Corporation of Mentor, Ohio, which mounts to rear wall 40 of housing 12 with suitable fasteners such as screws 272 as shown in FIGS. 6 and 7A.

A set of vent slots 274 are formed in back wall 40 of housing adjacent to receptacle component 270 as shown in FIGS. 6 and 7A. A ventilation fan 276, shown in FIG. 7B, is situated in the interior region of housing 12 behind vent slots 274. Fan 276 operates to cool the interior region of housing 12 by blowing air from inside interior region of housing 12 out to ambient atmosphere through vent slots 274. A ridge or ledge 278 is formed integrally with back wall 40 and includes a substantially horizontal portion that protrudes outwardly from housing 12 above each of receptacles 235, 252, 268 and vent slots 274 as shown in FIG. 7A. Ridge 278 also has a substantially vertical portion that protrudes outwardly from housing 12 adjacent to vent slots 274.

When hose support plate 220 is in the storage position, a first prong 280 of hose support plate contacts ledge 278 to prevent plate 220 from pivoting downwardly relative to back wall 40 of housing 12 past the storage position. Thus, ledge 278 serves as a stop that is contacted by prong 280 of plate 220 when plate 220 is in the storage position. A post 282 also is formed integrally with back wall 40 and protrudes from housing 12 to serve as another stop for plate 220. When plate 220 is in the deployed position, an edge 284 of plate contacts post 282 so that plate 220 does not pivot past the deployed position. As plate 220 moves between the storage and deployed positions, plate 220 pivots about a substantially horizontal pivot axis 286, shown in FIG. 6, defined by a pivot coupler 288.

Plate 220 includes a second prong 290 that cooperates with prong 280 to define the V-shaped notch 222 of plate 222. A rounded edge 292 of plate 220 generally conforms to a size of hose 225 so that hose 225 nests upon edge 292 of plate 222 when hose 225 is placed within notch 222 with plate 220 in the deployed position. Edge 292 blends smoothly into edges of respective prongs 280, 290 which form the V-shape of notch 222. Plate 220 has an irregular or non-symmetric shape so that when plate 220 is moved to the deployed position from the storage position, a center of gravity of plate 220 moves past an imaginary vertical plane (not shown) passing through axis 286 so that the edge 284 of plate 220 is gravity biased into contact with post 282 when plate 220 is in the deployed position.

As shown in FIG. 7A, apparatus 10 includes a foot switch 294 having a foot pedal 296 coupled to a foot switch base 298 and an electrical cord 300 that extends from base 298 and terminates at an electrical connector 302. A mating electrical connector 304 is provided on back wall 40 of housing 12 beneath vent slots 274 as shown best in FIG. 6. When connectors 302, 304 are coupled together, foot switch 294 is usable to start and stop (or pause) the delivery of respiratory therapy to the patient by the respiratory therapy device 10. In this regard, foot pedal 296 rocks relative to base 298 to send signals to the control circuitry of device 10. In some embodiments, foot pedal 296 is spring biased to a raised home position and each successive rocking motion of the foot pedal 296 relative to base 298 from the home position to a depressed position by a user's foot results in a signal being sent from foot switch 294 to device 10. Successive movement of the foot pedal 296 to the depressed position starts and stops (or pauses) the respiratory therapy. In other embodiments, foot pedal 296 can be rocked in forward and rearward directions from the home position. For example, if a user places a foot over the upper surface of pedal 296 and presses one side of pedal 296 downwardly with the user's toes, this movement corresponds to the forward direction, and if the user presses the other side of pedal 296 downwardly with the user's heel, this movement corresponds to the rearward direction.

As shown in FIG. 6, a data port 306 is also provided on back wall 40 of housing 12 beneath vent slots 274. In some embodiments, data port 306 comprises a USB port 306 to which external devices couple. For example, a USB drive, sometimes referred to as a thumb drive, is coupleable to data port 306 for wired import and export of data to or from the control circuitry of device 10 or for wired import and export of data to or from other computer devices that have USB cables that couple to port 306. In still other embodiments, patient monitors such as pulse oximeters, heart rate monitors, and the like are coupleable to data port 306 via USB cables to provide patient physiological data to the control circuitry of device 10. A ledge 308 is integrally molded with back wall 40 and protrudes therefrom above data port 306 to provide some degree of protection to devices, modules, memory sticks, etc. that are coupled to data port 306 from falling objects.

Figure 8:
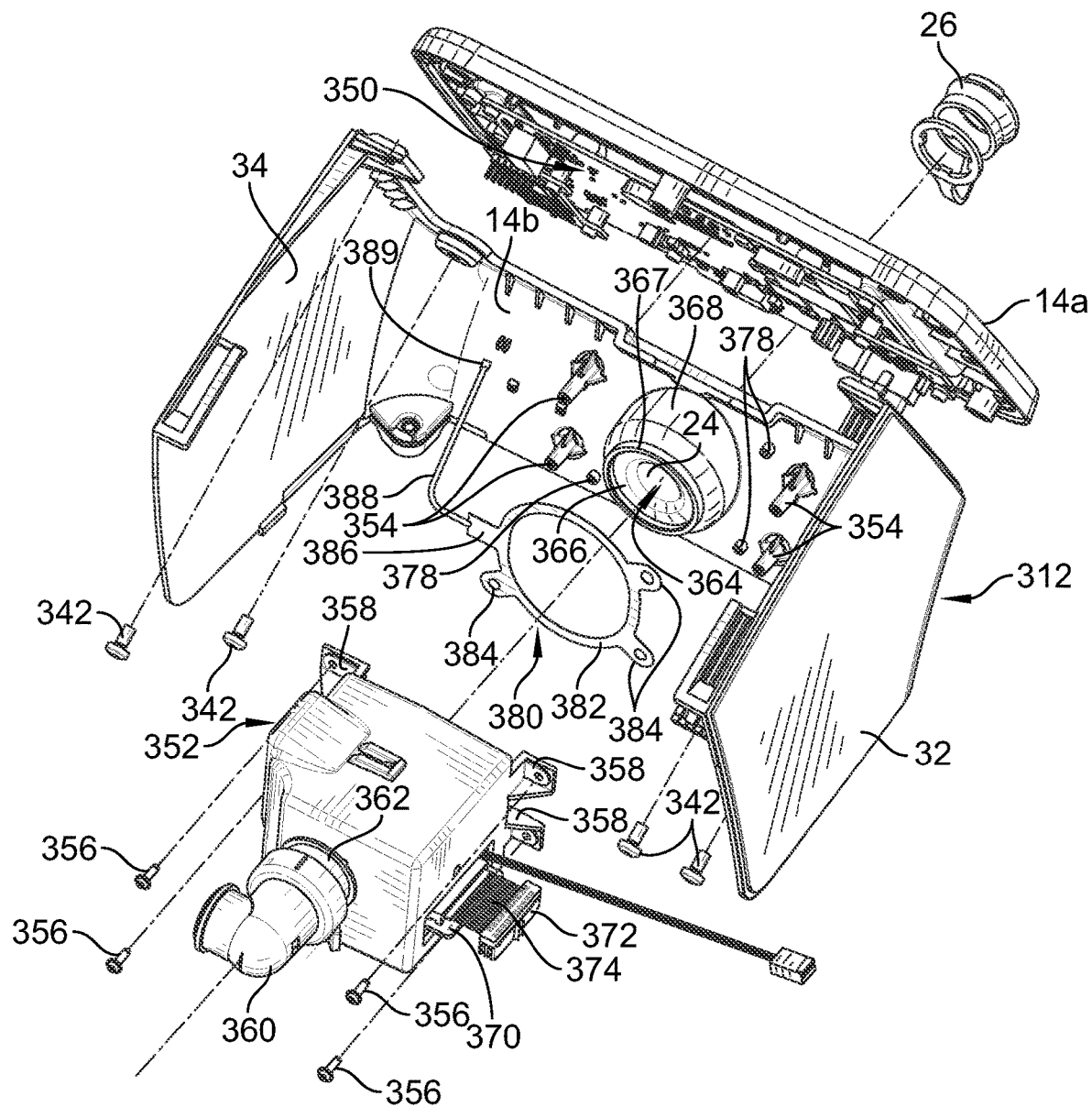
FIG. 8 is an exploded perspective view showing first and second sidewalls of the housing attached to the lower front wall portion of the housing, a generally cylindrical recess defining portion protruding into an interior region of the housing, a generally annular antenna aligned with the generally cylindrical recess defining portion, a flow control assembly aligned with the generally annular antenna, and a display circuit board attached to the underside of the upper front wall of the housing.

Referring now to FIG. 7B, components forming housing 12 are shown exploded away to reveal many of the components of device 10 that are situated inside the interior region of housing 12. Tray 50 is also shown in FIG. 7B, but with many of its components removed. As shown in FIG. 7B, lower front wall portion 14*b* is molded integrally with most of first and second sidewalls 32, 34 to form a single unitary or monolithic front component 312 of housing 12. Upper front wall portion 14*a* is molded separately from component 312 and attaches thereto with suitable fasteners such as screws 313 as shown in FIG. 8.

Referring again to FIG. 7B, bottom wall 36 of housing 12 is molded integrally with bottom regions of walls 14*b*, 32, 34, 40 to form a unitary or monolithic bottom tray 310 of housing 12. Top wall 38, particularly top wall portion 38' is molded integrally with top regions of first and second side walls 32, 34 to form a unitary or monolithic top cover 314 of housing 12. Finally, back wall 40 is molded integrally with rear regions of side walls 32, 34 and top wall 38 to form a unitary or monolithic rear component 316 of housing.

Device 10 includes a chassis 318 that supports components of a pneumatic system 320 within the interior region of housing 12 of respiratory therapy apparatus 10. Thus, the pneumatic system 320 is carried by the housing 12. Chassis 318 is supported by bottom tray 310 and extends upwardly from the bottom wall 36 of housing 12. Chassis 318 includes a first tower 322, a second tower 324, and a set of rods 326 that interconnect towers 322, 324 as shown in FIG. 7B. Each tower 322, 324 comprises multiple interconnected bent plates 328. A number of screws 329 interconnect the various bent plates 328 forming the towers 322, 324 and also to connect the towers 322, 324 to rods 326.

Blower 260 of the pneumatic system 320 is attached to the first tower 322 by suitable fasteners such as screws (not shown). A manifold and rotary valve assembly 330 of the pneumatic system 320 is attached to the second tower 324 by suitable fasteners such as screws 332. A conduit 364 interconnects an outlet of blower 260 with an inlet of the manifold and rotary valve assembly 330. A stepper motor 334 which is operable to rotate and oscillate a rotary plate of the manifold and rotary valve assembly 330 is also coupled to and supported by the second tower 324 of chassis 318. Additional details of the construction and operation of blower 260 and manifold and rotary valve assembly 330 of pneumatic system 320 is shown and described in U.S. Patent Application Publication No. 2018/0085541 A1 (see particularly, FIGS. 40 and 72 and the related discussion) which is hereby incorporated by reference herein, in its entirety, to the extent not inconsistent with the present disclosure which shall control as to any inconsistencies.

Figure 78:
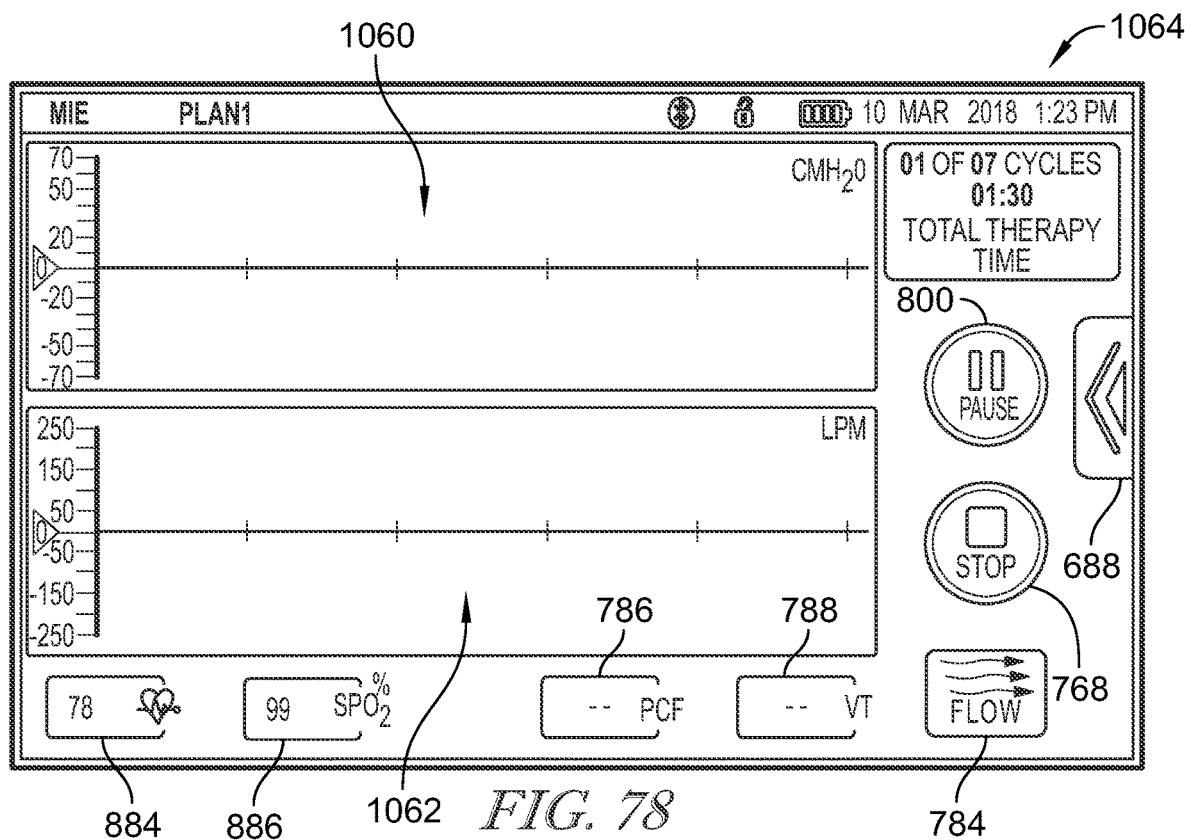
FIG. 78 is a screen shot of a second advanced view screen for automatic MIE therapy that appears on the GUI in response to selection of the start button of the first advanced view screen of FIG. 77 if a filter unit usage count is below a threshold number of uses and if the battery charge is greater than 20% of a full charge, the second advanced view screen showing the start button converted to a pause button.

Still with reference to FIG. 7B, a main control board (MCB) 340 of the control circuitry of the respiratory therapy apparatus is supported by chassis 318 above bottom wall 36 of bottom tray 310 of housing 12. Aspects of MCB 340 are discussed in further detail below in connection with FIGS. 16A-17C. Main control board 340 is sometimes referred to herein as printed circuit board assembly (PCBA) 340. A number of screws 342 for interconnecting bottom tray 310, front component 312, top cover 314, and rear component 316 together are shown in FIG. 78 above chassis 318. Similar screws 342 for coupling upper front wall portion 14*a* to front component 312 are shown in FIG. 8. A display control board (DCB) 350 is mounted to the back of upper front wall portion 14*a* as also shown in FIG. 8. Aspects of DCB 350 are discussed in further detail below in connection with FIGS. 16A-17C. Display control board 340 is sometimes referred to herein as printed circuit board assembly (PCBA) 350.

As shown in FIG. 7B, a large rectangular box 336 is molded integrally with back wall 40 of rear component 316 of housing 12. Box 336 is open at the back of housing 12 and provides the battery compartment 226 that receives battery 224 or battery compartment cover 226 if battery 224 is omitted. A battery docking board 338 is mounted to a substantially vertical wall of box 336 with suitable fasteners such as screws 339 as shown in FIG. 7B. When battery 224 is inserted into compartment 226 of box 336, electrical contacts of battery 224 interface with mating electrical contacts that are exposed within compartment 226 and that are electrically coupled to circuit components of battery docking board 338.

Filter housing 254 nests within a box-shaped receptacle 346 that is also formed integrally with back wall 40 of rear component 316 of housing 12 as shown in FIG. 7B. A suitably sized space is provided between a top of receptacle 346 and a bottom wall of box 336 so that the conduit leading to the inlet of blower 260 is able to couple to filter housing 254 at a circular opening 348 thereof. As can also be seen in FIG. 7B, a pair of AC contacts 271 and a pair of fuse contacts 273 extend from a back of power receptacle component 270 within the interior region of housing 12. An electrical cable 305 which leads from connector 304 to MCB 340 is also shown in FIG. 7B but is shown disconnected from MCB 340.

Referring now to FIG. 8, a flow control module 352 is shown exploded away from front component 312 of housing 12. Lower front wall portion 14*b* has a set of four pylons 354 integrally molded therewith and extending therefrom in a cantilevered manner within an interior region of housing 12. A set of four screws 356 are used to attach respective ears 358 of flow control module 352 to the distal ends of pylons 354. An elbow conduit connector 360 is coupled to an inlet 362 of flow control module 352. A conduit (not shown) is routed from an outlet of manifold and rotary valve assembly 330 to elbow connector 360. When mounted to pylons 354 by screws 356, an outlet (not shown) of flow control module 352 interfaces with a flow passage 364 through port 24. A surface of flow control module 352 around its outlet sealingly engages a distal end 366 of a generally cylindrical wall 368 that is integrally molded with lower front wall portion 14*b* and that extend therefrom into the interior region of housing 12. An annular ridge 367 protrudes from the distal end 366 of cylindrical wall 368 to enhance the sealing engagement between flow control module 352 and distal end 366. In some embodiments, one or more seals or gaskets are interposed between module 352 and distal end 366 to further enhance the sealing engagement therebetween.

Flow control module 352 contains one or more pressure sensors and flow sensors to sense pressure and/or flow of pressurized air exiting or entering outlet port 24 via the patient circuit 230. The pressure sensors and flow sensors are provided on a flow element board 370 of module 352. An electrical coupler 372 is situated at an end of a ribbon cable 374 extending from flow element board 370 as shown, for example, in FIG. 8. Coupler 372 couples to a mating coupler 376 shown diagrammatically in FIG. 17B. Additional details of flow control module 352 are shown and described in U.S. Patent Application Publication No. 2018/0243518 A1 (see particularly, FIGS. 9-12 and the related discussion) which is hereby incorporated by reference herein, in its entirety, to the extent not inconsistent with the present disclosure which shall control as to any inconsistencies.

Still referring to FIG. 8, a radio frequency identification (RFID) antenna 380 is provided in device 10 and is mounted to antenna bosses 378 that are formed integrally with lower front wall portion 14b of housing 12 and that protrude therefrom in a cantilevered manner. More particularly, antenna 380 has an annular portion 382 and a set of three ears 384 extending generally radially outwardly from annular portion 382. Ears 384 are coupled to bosses 378 with suitable fasteners such as screws (not shown, but similar to screws 356, for example). RFID antenna 380 also as a tab 386 extending from annular portion 382 and an electrical line or cable 388 that extends from tab 386 as shown in FIG. 8. A terminal end of electrical line 388 has an electrical connector 389 that attaches to an RFID reader of the control circuitry of device 10 as will be discussed in further detail below in connection with FIGS. 16A-17C.

Referring now to FIG. 9, pneumatic patient circuit 230 has a filter unit 390 that couples to a proximal end 392 of hose 225. With regard to the discussion of the components of patient circuit 230, the term "proximal" will be used to denote an end or end region of the component that is closest to housing 12 of respiratory therapy apparatus 10 and the term "distal" will be used to denote an end or end region of the component that is farthest from housing 12. In some embodiments, hose 225 is a corrugated breathing hose that is about 120 centimeters (cm) (about 47 inches) long with a 22 millimeter (mm) inside diameter. Filter unit 390 includes a filter housing 394 that, in turn, includes a substantially cylindrical first tubular portion 396 that includes the proximal end of filter housing 394 and a substantially cylindrical second tubular portion 398 that includes the distal end of filter housing 394.

First tubular portion 396 of filter housing 394 press fits over port 24 when cap 26 is removed from port 24 to expose the flow passage 364 through port 24. Proximal end 392 of hose 225 is also substantially cylindrical and press fits over the second tubular portion 398 of filter housing 394. If a smaller diameter hose (not shown) is used in patient circuit 230 in lieu of hose 225, then a cylindrical tubular portion 397 supported inside tubular portion 398 by an annular support ring 399 receives the proximal end of the smaller diameter hose therein with a press fit. In the illustrative example, tubular portion 397 and support ring 399 are molded integrally with tubular portion 398.

Figure 10:
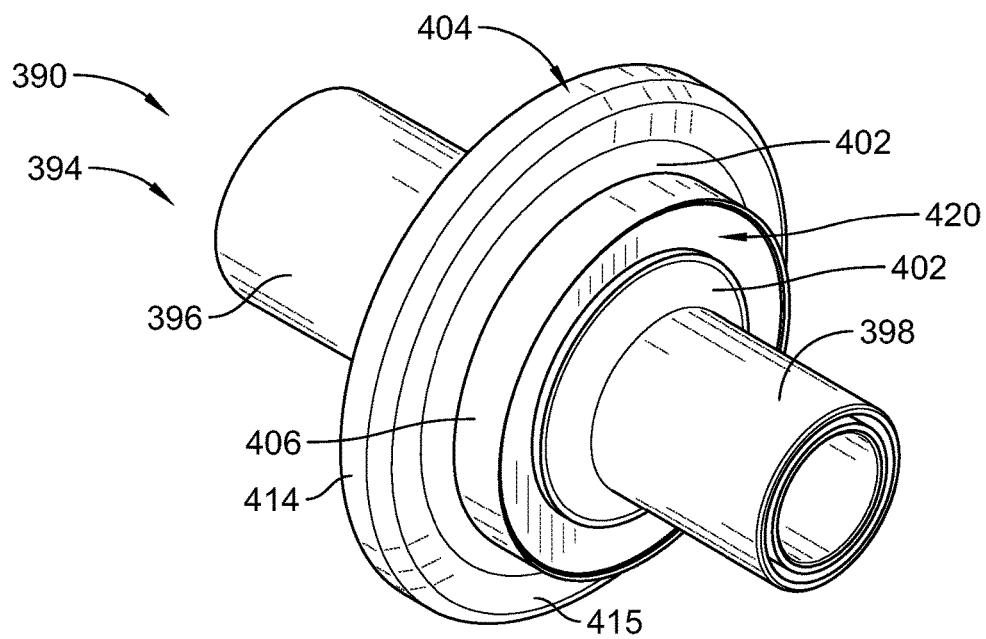
FIG. 10 is a perspective view of the filter unit showing the filter unit having a filter housing with first and second cylindrical tubular portions extending in opposite directions from an annular central filter receiving portion.
Figure 11:
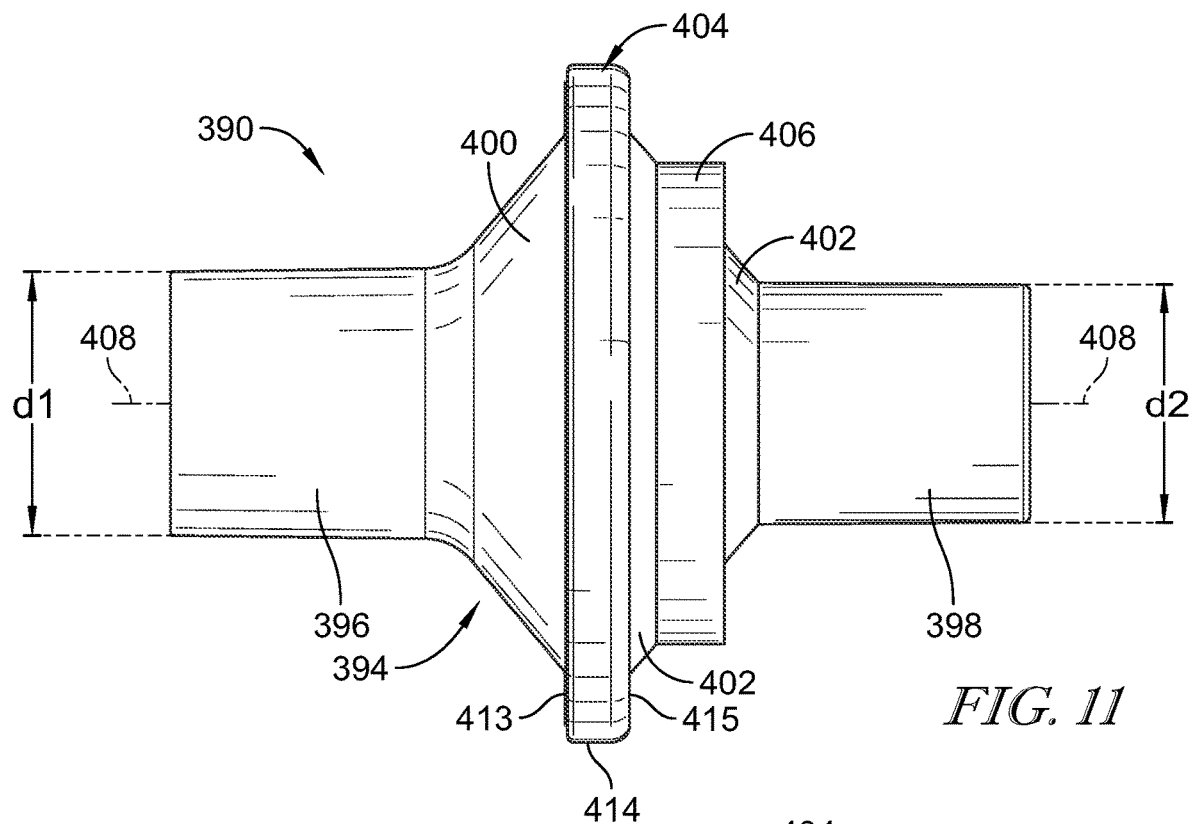
FIG. 11 is a side elevation view of the filter unit of FIG. 10 showing a first and second frustoconical portions extending from the annular central filter receiving portion to the respective first and second cylindrical tubular portions and showing an annular shoulder extending from the first frustoconical portion about midway between the annular central filter receiving portion and the first cylindrical tubular portion.
Figure 12:
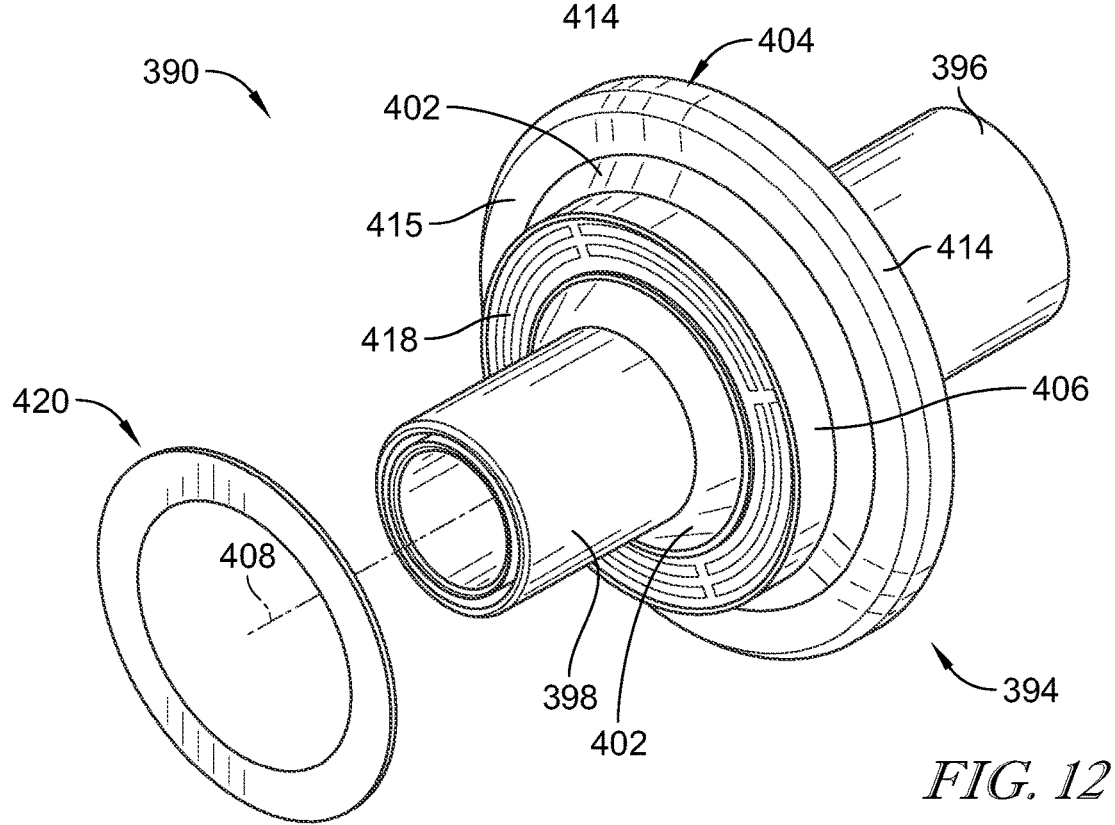
FIG. 12 is a perspective view of the filter unit of FIGS. 10 and 11 showing a transponder ring exploded way from an annular shoulder surface of the annular shoulder of the filter housing.

Filter housing 394 further includes a first substantially frustoconical portion 400, shown best in FIG. 11, extending from the first tubular portion, and a second substantially frustoconical portion 402, shown in FIGS. 10-12, extending from the second tubular portion 398. First and second substantially frustoconical portions 400, 402 meet at a joint defining an annular apex 404 of the filter housing 394. Housing 394 further includes a shoulder wall portion 406 that is formed on the second substantially frustoconical portion 402. As shown in FIG. 11, first and second tubular portions 396, 398 are aligned along a common axis 408 with an outer diameter d1 of first tubular portion 396 being larger than an outer diameter d2 of second tubular portion 398. In some embodiments, diameter d1 is about 25 mm and diameter d2 is about 22 mm within a ±0.2 mm tolerance range. External and internal diameters and tapers of tubular portions 396, 398 are in compliance with ISO Standard 5356-1 in some embodiments.

Figure 13A:
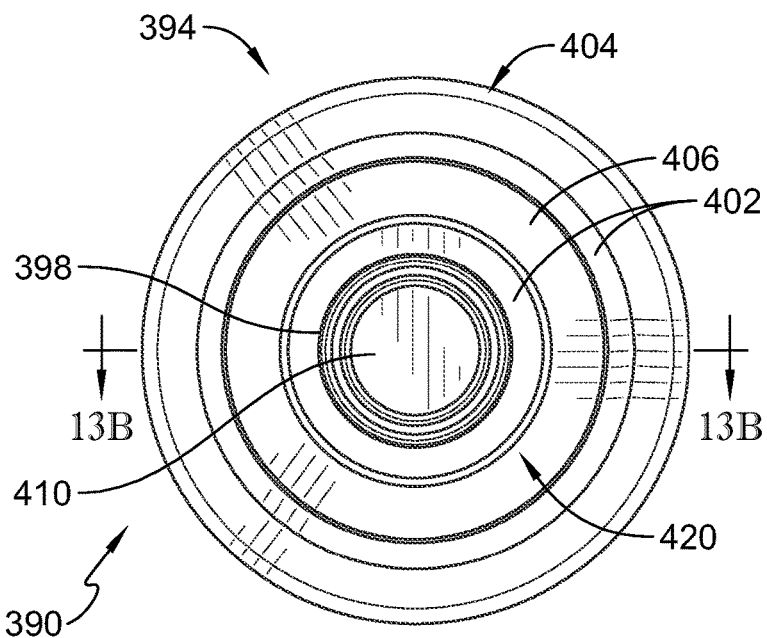
FIG. 13A is a front elevation view of the filter unit of FIGS. 10 and 11 showing the first cylindrical tubular portion, the transponder ring attached to the shoulder surface, and showing through a flow passage of first cylindrical tubular portion a central region of a filter that is contained within the annular central filter receiving portion of the filter unit.
Figure 13B:
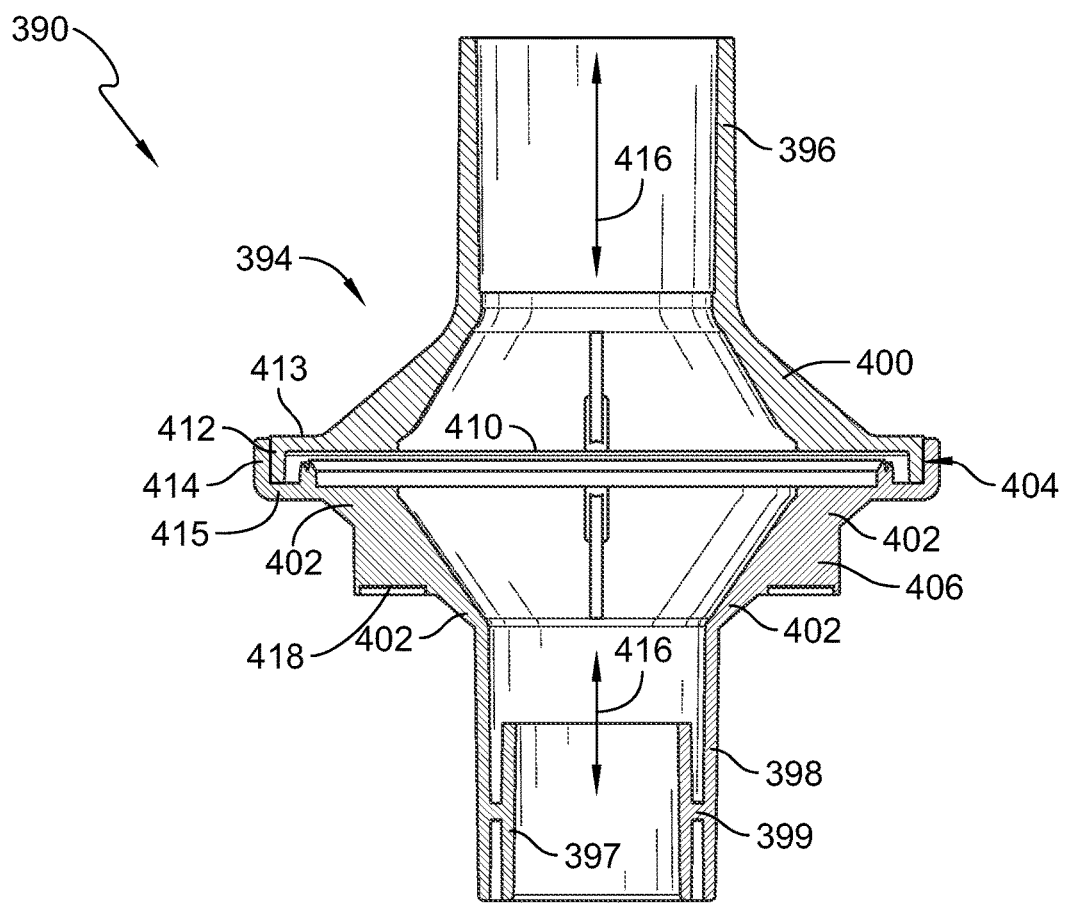
FIG. 13B is a cross sectional view of the filter unit, taken along line 13B-13B of FIG. 13A, showing the filter extending across the annular central filter receiving portion between the first and second frustoconical portions of the filter housing.
Figure 14:
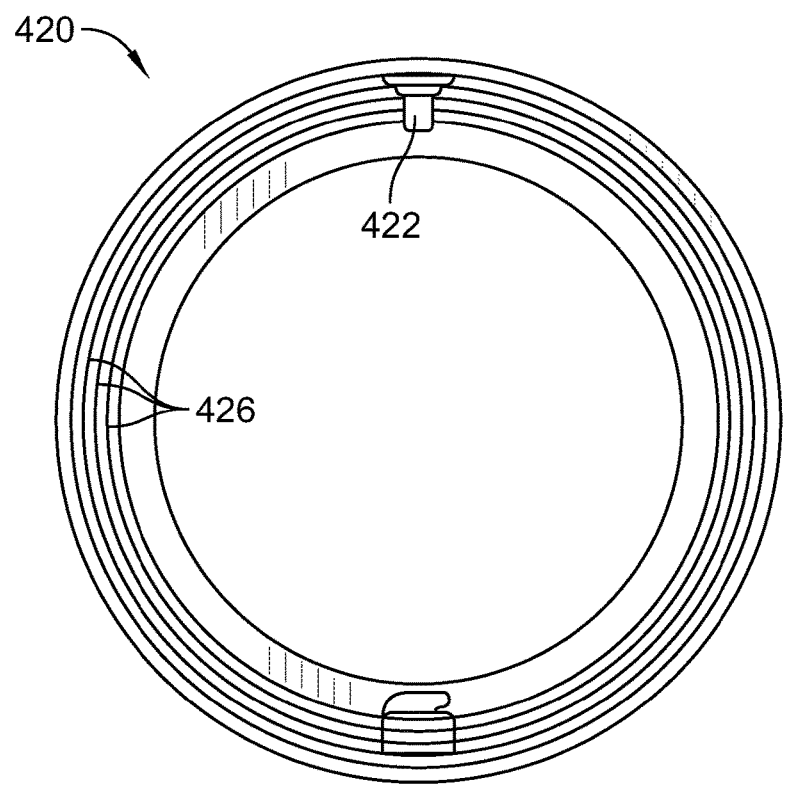
FIG. 14 is a front elevation view of the transponder ring of FIG. 12.

Filter unit 390 further includes a filter 410, shown in FIGS. 13A and 13B that is carried by filter housing 394. Filter 410 is round in shape and has its outer periphery clamped between housing shell pieces that are coupled together to form filter housing 394. One of the shell pieces of housing 394 includes first tubular portion 396, first frustoconical portion 400, an inner cylindrical flange 412 of annular apex 404, and a first annular wall 413 interconnecting portion 400 and flange 412 as shown, for example, in FIG. 13B. The other of the shell pieces of housing 394 includes second tubular portion 398, second frustoconical portion 402, shoulder wall portion 406, an outer cylindrical flange 414 of annular apex 404, and a second annular wall 415 interconnection portion 402 and flange 414 as also shown in FIG. 13B. Annular flange 412 nests within annular flange 414 and is coupled thereto with adhesive, radio frequency (RF) welding, or sonic welding, for example.

In some embodiments, housing 394 is made from styrene acrylonitrile resin but other materials of suitable strength and durability may be used if desired. Illustrative filter unit 390 is available from A-M Systems, LLC of Sequim, Washington as part no. 1192300. In some embodiments, filter 412 includes a white TECHNOSTAT® filter screen material which is a hydrophobic material having bidirectional airflow capability, a bacterial filter efficiency (BFE) of greater than 99%, and a viral filter efficiency (VFE) of greater than 99%. Filter unit 390 also has a low flow resistance of 1.5 centimeters of water (cm H2O) at 60 liters per minute (LPM). Thus, filter unit 390 has a flow passage 416 therethrough as indicated by the bidirectional arrows 416 in FIG. 13B.

Filter unit 390 includes a transponder ring 420, shown in FIGS. 10, 12, 13A, and 14, that is mounted to an annular shoulder surface 418 of shoulder wall portion 406, shown in FIGS. 12 and 13B. Transponder ring 420 includes a transponder chip 422 which is embedded therein as shown diagrammatically in FIGS. 14 and 15. In some embodiments, transponder chip 422 is a model no. SRF55V 10P HC integrated circuit chip available from Infineon Technologies AG of Neubiberg, Germany. However, other transponder chips may be used in other embodiments.

Transponder ring 420 of the illustrative embodiment has a number of annular ring layers that are laminated together. In particular, illustrative transponder ring 420 includes a layer of face material 424, an antenna 426, a substrate layer 428, an adhesive layer 430, and a backing layer 432. In the illustrative example, the layer of face material 424 comprises a white polyethylene terephthalate (PET) material that is about 50 microns in thickness. The antenna 426 comprises a layer of copper material forming a multitude of annular coils as shown diagrammatically in FIG. 14. In some embodiments, antenna 426 is a SMARTRAC™ 140_9 antenna available from Smartrac N.V. of Amsterdam, Netherlands.

Figure 15:
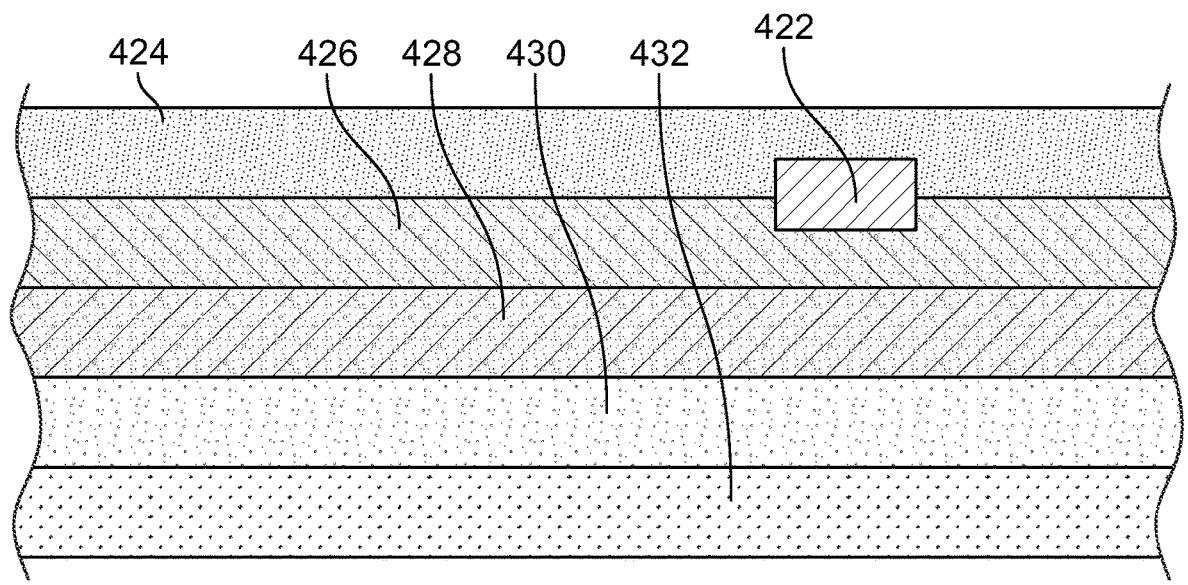
FIG. 15 is a cross section of a portion of the transponder ring of FIGS. 12 and 14 showing a layer of face material at the top of the Fig., a copper antenna beneath the face material with an integrated circuit transponder chip sandwiched between the face material and the copper antenna, a substrate layer of polyethylene terephthalate (PET) material beneath the copper antenna, an adhesive layer beneath the substrate layer, and a backing layer beneath the adhesive layer.

As shown in FIG. 15, transponder chip 422 is sandwiched between the layer of face material 424 and the antenna 426. The substrate layer 428 is made of PET material in some embodiments. The adhesive layer 430 comprises an RA-2 adhesive in some embodiments. The backing layer 432 includes a siliconized paper or a backing paper with a silicon liner in some embodiments. The adhesive layer 430 is provided on the substrate and the backing layer 432 is attached to the adhesive layer such that the adhesive layer 430 is situated between the backing layer 432 and the substrate layer 428. During manufacture of filter unit 390, backing layer 432 is peeled off leaving adhesive layer 430 exposed. Transponder ring 420 without the backing layer 432 is then attached to shoulder surface 418 of shoulder wall portion 406 of filter housing 394. When transponder ring 420 is attached to filter unit 390, antenna 426 surrounds flow passage 416 in a similar manner that antenna 380, shown in FIG. 8, surrounds flow passage 364.

Figure 17A:
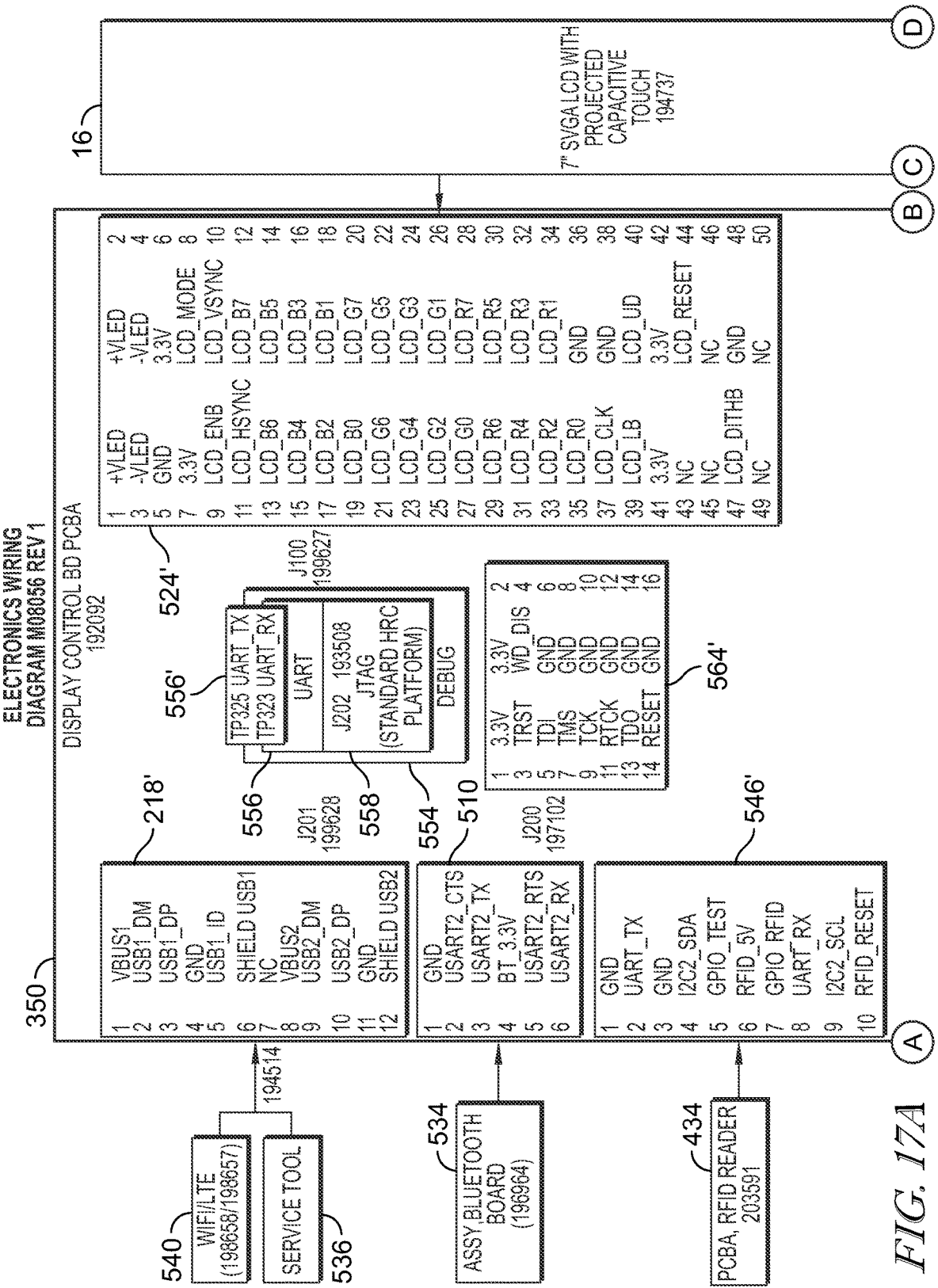
FIGS. 17A-17C together form a block diagram of the electronics wiring of the respiratory therapy apparatus of the present disclosure.

An RFID reader 434, shown diagrammatically in FIG. 17A, provides power to antenna 380 to emit energy to antenna 426 to power transponder chip 422. By providing antennas 380, 426 with annular shapes of similar sizes, the orientation of transponder chip 422 relative to antenna 380 does not matter when filter unit 390 is attached to outlet port 24 of housing 12 of respiratory therapy device 10. That is, filter unit 390 can be attached to port 24 in any orientation about axis 408 and successful communication between reader 434 and transponder chip 422 via antennas 380, 426 is still possible.

Transponder chip 422 stores a usage count that indicates the number of times that filter unit 390 has been used for prior therapy sessions. As will be described in further detail below in connection with FIGS. 29, 78, 84, and 130, when filter unit 390 is attached to port 24 and respiratory therapy device 10 is activated to deliver respiratory therapy to the patient, reader 434 reads the usage count stored in transponder chip 422 to confirm that the usage count is equal to or below a threshold number, such as 70 or 90 uses just to give a couple arbitrary examples. After respiratory therapy has been delivered to the patient for a threshold amount of time, reader 434 sends a signal to transponder chip 422 via antennas 380, 426 with new data corresponding the usage count incremented by one. The threshold amount of time may be 2 minutes or 5 minutes just to a couple arbitrary examples.

Referring once again to FIG. 9, pneumatic patient circuit 230 includes a variety of patient interfaces 436. For example, patient interfaces include a handset 438 having a tubular connector 440 that is inserted into a distal end 393 of hose 225 until a stop ring 442 abuts a distal terminal surface of end 393. Handset 438 is configured for selective attachment of an expiratory valve funnel 444 or an occlusion valve funnel 446. Each of funnels 444, 446 has a large open proximal end that attaches to a distal open end of handset 438. Each of funnels 444, 446 also has a small open distal end for coupling to other components of patient interfaces 436 as will be discussed below.

Expiratory valve funnel 444 has a pair of expiratory ports to atmosphere for entrainment of ambient during inhalation of the respective patient and through which some exhaled air from the patient is permitted to escape to atmosphere. Thus, the expiratory ports prevent the accumulation of carbon dioxide in funnel 444 and handset 438 during the therapy session. In the illustrative example, the expiratory ports are formed as passages through finger tabs 445 that extend radially outwardly from a locking ring portion 447 that is formed integrally with the rest of funnel 444. Thus, tabs 445 are used to rotate funnel 444 between a locked position in which funnel 444 is secured to handset 438 and an unlocked position in which funnel 444 is able to be manually separated away from handset 438.

Occlusion valve funnel 446 does not have any additional openings to atmosphere and is used when respiratory therapy device 10 is being operated in combination with a mechanical ventilator or life support ventilator (not shown) which provides for any needed communication to ambient atmosphere during the patient's inhalation and exhalation. Funnel 446 is rotated in its entirety relative to handset 438 between locked and unlocked and unlocked positions in a similar manner as described above in connection with funnel 444. Thus, funnel 446 also has locking ring portion 447 formed integrally therewith but finger tabs 445 are omitted from funnel 446. Each of funnels 444, 446 includes an indicia on locking ring portion 447 that aligns with a lock indicia on handset 438 when the respective funnel 444, 446 is locked to handset 438 and that aligns with an unlock indicia on handset 438 when the respective funnel 444, 446 is unlocked from handset 438.

As shown in FIG. 9, each of funnels 444, 446 has a nebulizer port 448 to which an outlet port 450 of nebulizer 160 couples directly or by use of an adapter 452. The nebulizer port 448 is situated between the proximal and distal ends of the respective funnel 444, 446 and defines a passage that is generally perpendicular to the main passage through funnels 444, 446 between the proximal and distal ends thereof. In some embodiments, adapter 452 is a 22 mm×22 mm adapter that has a 22 mm outside diameter at one end and a 22 mm inside diameter at the opposite end. An annular ridge or flange 454 separates the end regions of adapter 452. The end regions of adapter 452 are in compliance with ISO Standard 5356-1 in some embodiments. A nebulizer port plug 456 is provided for closing nebulizer port 448 of funnels 444, 446 when nebulizer 160 is not being used with funnels 444, 446. Plug 456 includes a stopper region 458 that press fits into port 448 and a finger grip tab 460 that a user grips to insert plug 456 into port 456 and to remove plug 456 from port 456.

A tracheostomy adapter 462, a respiratory mask 464, and a mouthpiece 466 are among the components of patient interfaces 436 that are selectively attachable to distal ends of funnels 444, 446 or to distal end region 393 of hose 225 to form various configurations of patient interfaces 436 of respiratory therapy apparatus 10. In the illustrative example, tracheostomy adapter 462 includes a flex-adapter 468, a proximal adapter 470 attached to the proximal end of flex-adapter 468, and a distal adapter 472 attached to the distal end of flex-adapter 468. Adapter 470 is configured to attach to distal ends of funnels 444, 446 and adapter 472 is configured to attach to a tracheostomy tube (not shown) of the patient. Flex-adapter 468 is resiliently flexible to accommodate movement by the patient when tracheostomy adapter 462 is being used.

Illustrative respiratory mask 464 includes a flexible, resilient facial cushion or cuff 474 that is sized and configured to surround a patient's nose and mouth when mask 464 is pressed against the patient's face. Facial cushion 474 is sometimes made from soft rubber or foam. Mask 464 also includes a mask frame 476 that is a more rigid component of mask 464 such as being made from a generally rigid plastics material. Mask frame 476 is generally funnel-shaped and tapers from its larger distal end to its smaller proximal end. In some embodiments, one or more straps or harnesses (not shown) are attached to mask frame 476 to hold the mask 464 on the patient's head with cushion 474 held in substantially airtight manner against the patient's face. Mask 464 further includes a pneumatic port 478 that, in the illustrative example, is molded integrally with the proximal end of mask frame 476. Port 478 of mask 464 is cylindrical in shape and is pneumatically coupled to the distal end of the respective funnel 444, 446 or to distal end region 393 of hose 225, either directly or with the use of illustrative adapter 452 (or a different type of adapter), as needed, at the discretion of the user.

Mouthpiece 466 includes a cylindrical proximal end 480 and a somewhat flattened distal end 482 that a user places inside their mouth when in use. In the illustrative example, proximal end 480 of mouthpiece 466 is shown adjacent to an oxygen bleed-in adapter 484. Oxygen bleed-in adapter 484 includes a main cylindrical portion 486 and an L-shaped tube 488 of smaller diameter than portion 484 that extends from a middle region of main cylindrical portion 486. A distal end of L-shaped tube 488 is configured for attachment to an oxygen line that supplies oxygen to an interior region of main cylindrical portion 486 through an internal passage of L-shaped tube 488. A cover cap 489 is tethered to portion 486 and attaches to the distal end of tube 488 when no oxygen line is attached to tube 488. Oxygen bleed-in adapter 484 can also be used with mask 464 or tracheostomy adapter 464 at the discretion of the user. An additional adapter 490 is shown in FIG. 9 and may be used, as needed, with mouthpiece 466, mask 464, or adapter 462 for coupling to other components of patient circuit 230. In some embodiments, adapter 490 is a 22 mm/15F-15F adapter that has a 22 mm outside diameter at one end and a 15 mm inside diameter at the opposite end.

It should be appreciated that FIG. 9 shows a variety of components that can be mixed and matched at the discretion of the user, and as needed, to create numerous different types of patient interfaces 436 of pneumatic patient circuit 230. Those skilled in the art will also appreciate that other patient interface components such as T-connectors, elbow connectors, swivel connectors, and the like, as well as other types of adapters may be used in addition to, or in lieu of, the components of patient interfaces 436 discussed herein in connection with FIG. 9. Thus, the terms "patient circuit" and/or "patient interface" used herein is intended to cover the full gamut of components that may serve as conduits from a main unit (e.g., housing 12 of device 10, a ventilator, a CPAP machine, etc.) to a patient's airway.

With regard to hose 225, shown in FIG. 9, it has been specially designed to have longer non-corrugated proximal and distal end regions 392, 393 than typical off-the-shelf corrugated hoses used with respiratory therapy devices. This is because the corrugated region of hose 225 between end regions 393, 393 is thinner in cross section, and therefore weaker, than the non-corrugated end regions 392, 393. It was determined that users tend to grab the weaker corrugated region when dismantling the off-the-shelf corrugated hoses such as detaching the hoses from the filter unit 390 or detaching the hose from components of the patient interface such as handset 438. This leads to breaking or tearing a hole in the corrugated region of the off-the-shelf hose. By lengthening the stronger, non-flexible end regions 392, 393 of hose 225, users are more apt to grab the end regions 392, 393 during disassembly of the patient circuit 230 while not compromising the flexibility of the hose 225 in the corrugated region.

In the illustrative embodiment, the overall length of hose 225 is 1,200 mm±13.0 mm and length of each non-corrugated end region 392, 393 is 76.2 mm±5.0. Thus, the length of the corrugated region of hose 225 is about 1050 mm±18.0 mm (1,200 mm−76.2 mm−76.2 mm=1,047.6 mm). The outside diameter of the end regions 392, 393 of hose 225 is 23.37 mm and the inside diameter is 21.1 mm. End regions 392, 393 are constructed in compliance with ISO standard 5367 in some embodiments, including the tolerance ranges thereof. In the illustrative example, the width of the corrugations is about 3.45 mm and the spacing between corrugations is about 7.62 mm. Tubular portion 398 of filter unit 398 is inserted into end region 392 of hose 225 and tubular connector 440 of handset 398 is among the components of patient interface 436 that are inserted into end region 393 of hose 225. However, end regions 392, 393 of hose 225 are at least twice as long as tubular portion 398 and tubular connector 440 in some embodiments. Thus, about 50% of end regions 392, 393 remain unoccupied by any portions of filter unit 390 and the patient interface components 436 that are inserted therein.

When words of degree, such as "about," "substantially," and "generally" are used herein in connection with a characteristic or measurement, they are intended to mean at least within manufacturing tolerance ranges and up to ±10% of the recited characteristic. So, about 90 degrees would cover a range of 81 degrees to 99 degrees; substantially 75% would cover 67.5% to 82.5%; and substantially vertical would cover ±9 degrees from vertical (e.g., vertical is 90 degrees from horizontal, and vice versa), just to give a few examples.

Based on the dimensions in the preceding paragraph, therefore, various ratios of dimensions can be determined. For example, the ratio of the length of each end region 392, 393 to its outside diameter is about 3.26 (e.g., 76.2÷23.37=3.26); the ratio of the total length of hose 225 to the length of its corrugated region is about 1.145 (e.g., 1200 mm÷1047.6 mm=1.145), and the ratio of non-corrugated regions 392, 393 to the overall length of hose 225 is about 0.127 (e.g., (76.2 mm+76.2 mm)÷1200 mm=0.127). Stated another way, the length of each end region 392, 393 is more than three times its outside diameter. Also, the non-corrugated end regions 392, 393 constitute about 12.7% of the overall length of hose 225 (e.g., 0.127 ratio×100). All other comparisons between the numerical data in the preceding paragraph in a similar manner are within the scope of the present disclosure for setting forth the geometric aspects of hose 225. In some embodiments, hose 225 is made from a polyolefin plastomer (POP) material.

Additional views of hose 225, filter unit 390, handset 438, funnel 444, funnel 446, and plug 456 of pneumatic patient circuit 230 are provided in U.S. Design application No. 29/712,899, which was filed on Nov. 12, 2019, which issued as U.S. Design Pat. No. 985,758, and which is hereby incorporated by reference herein in its entirety.

Referring now to FIGS. 16A-16D, control circuitry 500 is shown diagrammatically along with other electrical components of respiratory therapy device 10. In general, any printed circuit board assemblies (PCBA's) and the elements on the PCBA's of FIGS. 16A-16D are considered to be part of the control circuitry 500 of device 10. Some of these have been mentioned previously herein. For example, display control board 350, main control board 340, battery docking board 338, and flow element board 370 have been mentioned above and form part of control circuitry 500 of device 10. The RFID reader 434 shown in FIG. 17A is another example of a part of control circuitry 500 that has been mentioned previously herein. In general, components of device 10 that are connected to the PCBA's to be controlled electrically in some respect are not considered to be part of control circuitry 500. Such components include, for example, blower 260, stepper motor 334, ventilation fan 276, and nebulizer motor 144. As to other components such as rechargeable battery 224, foot pedal 294, and other elements that are selectively connectable to and disconnectable from the respective PCBA's, these may be considered part of control circuitry 500 in some instances but not in others depending upon the context of the discussion.

With reference to FIG. 16A, display control board (DCB) 350 of control circuitry 500 includes a microcontroller unit (MCU) and peripherals section 502 that includes a microcontroller unit (MCU) 504. In the illustrative example, MCU 504 is a model no. STM32F429BIT6 microcontroller available from STMicroelectronics N.V. of Amsterdam, Netherlands. Section 502 of control circuitry 500 also includes a real time clock (RTC) circuitry 506, external watchdog circuitry 508, RFID interface circuitry 510 including an I2C interface and a universal asynchronous transmitter/receiver (UART), a 16 Megabyte (MB) synchronous dynamic random access memory (SDRAM) 512, a 128 MB flash memory 514, a micro secure digital (SD) card 516, diagnostic light emitting diodes (LED's) 518, a controller area network (CAN) transceiver 520, a 64 kilobyte (KB) electronically erasable programmable read only memory (EEPROM) 522, and the on/off switch 42.

Display control board 350 also includes a display module interface section 524 having a pulse width modulated (PWM) backlight 526, a capacitive touch panel (CTP) interface 528 that communicates according to the I2C protocol, and a thin film transistor (TFT) interface 530 that provides for 24 bit red, green blue (RGB) color control of display pixels. As shown diagramatically in FIG. 16A, display screen 16 of the illustrative example is a 7 inch super video graphics array (SVGA) liquid crystal display (LCD) with projected capacitive touch. Screen 16 electrically couples to both interfaces 528, 530.

Figure 40:
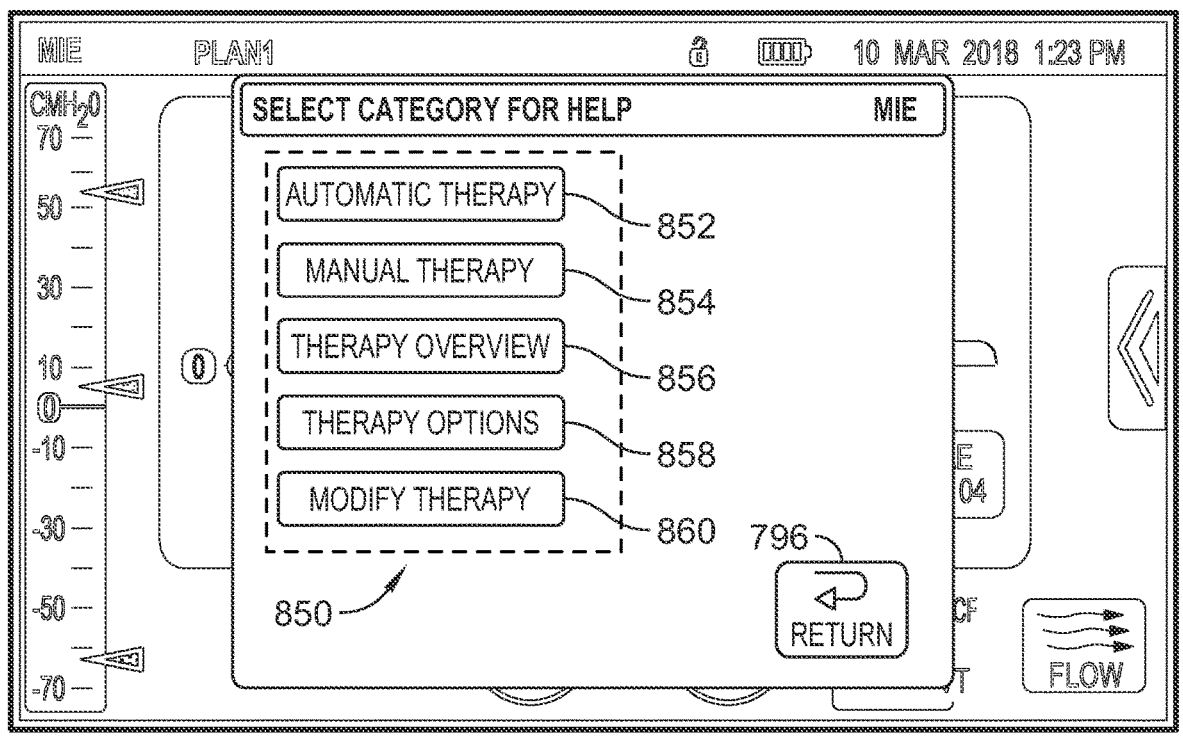
FIG. 40 is a screen shot of a help menu screen that appears on the GUI in response to the help or information icon being selected on the menu screen of FIG. 39, the help menu screen including a menu of buttons or icons that are selectable to navigate to help screens for automatic therapy, manual therapy, a therapy overview, therapy options, and modify therapy.

Still referring to FIG. 16A, display control board 350 further includes a communications section 532 having a Bluetooth board assembly 534, a 1×USB full speed (FS) 2.0 (Type A) WiFi/LTE connector 218, and a 1×USB FS 2.0 host (micro AB) service tool connector 538. A WiFi/LTE module 540 is shown in FIG. 40 and is configured for connection to connector 218. More particularly, module 540 is just a WiFi module in some embodiments, is just an LTE module in other embodiments, and is a combined WiFi/LTE module in other embodiments. When connected to connector 218, module 540 provides device 10 with the type of wireless communication (WiFi and/or LTE) capability that its name implies. The present disclosure contemplates that module 540 is an option that device 10 may or may not have. If module 540 is included with device 10, then various configurations screens are used to set up device 10 for WiFi or LTE wireless communications as will be discussed below.

As noted above, connector 218 also serves as the firmware upgrade port for device 10. Thus, top wall portion 38″ is removed from top wall portion 38′ as described above, to provide access to connector 218 for connection of module 540. Furthermore, once module 540 is attached to connector 218, top wall portion 38″ is reattached to top wall portion 38′ with module 540 being located underneath top wall portion 38″. FIG. 16A shows a service tool 536 which corresponds to the device that attaches to connector 218 to upgrade the firmware of control circuitry 500 of respiratory therapy device 10. Thus, if module is 540 is attached to connector 218, it is removed temporarily to permit attachment of service tool 536 to connector 218 during the firmware upgrade process.

An SpO2/barcode scanner 542 is also shown diagrammatically in FIG. 16A and communicates according to the Bluetooth protocol with Bluetooth board assembly 534 in the illustrative example. Although a SpO2/barcode scanner 542 is shown diagrammatically as a single block in FIG. 16A, it should be understood that these are separate components and that Bluetooth board assembly 534 is able to communicate wirelessly with a pulse oximeter (e.g., SpO2 device) and a separate bar code scanner. Furthermore, while a pulse oximeter is discussed herein as communicating wirelessly with control circuitry 500 of device 10, it should be understood that the same principles apply to other types of patient physiological monitors having Bluetooth communication capability. Examples of other such physiological monitors include heart monitors (e.g., electrocardiograms (ECG's)) including heartrate monitors, respiration rate monitors, blood pressure monitors, temperature sensors, blood glucose monitors, neurological monitors (e.g., electroencephalograms (EEG's)), and blood gas monitors including capnographs, just to name a few.

As also shown diagrammatically in FIG. 16A, DCB 350 of control circuitry 500 includes a bacterial filter detect section 544 that, in turn, includes an RFID board 546. RFID board 546 couples to the RFID reader 434 shown in FIG. 17A in some embodiments or includes RFID reader 434 in other embodiments. As noted above, terminal end 389 of electrical line 388 extending from tab 386 of RFID antenna 380 attaches to RFID reader 434 of the control circuitry 500 of device 10 for communication with the antenna 426 and transponder chip 422 of filter unit 390. FIG. 16A further shows, diagrammatically, that blower 260 includes a 3 phase brushless direct current (BLDC) motor 548 and that a cable assembly 550 interconnects DCB 350 with MCB 340. A portion of a blower motor cable 552 is also shown diagrammatically in FIG. 16A.

Referring now to FIG. 16B, DCB 350 also includes a debug section 554 having a UART 556 and a Joint Test Action Group JTAG circuit 558. DCB 350 further includes a voltage supplies section 560 that includes a DC-DC regulator and sense feedback 5V circuit and/or chip 562, a 3.3 V low drop out (LDO) circuit and/or chip 564, and a 9.6 V backlight supply boost circuit and/or chip 566. A portion of a stepper motor cable 568 is also shown diagrammatically in FIG. 16B.

Referring now FIG. 16C, main control board (MCB) 340 of control circuitry 500 includes a microcontroller unit (MCU) and peripherals section 570 that includes a microcontroller unit (MCU) 572. In the illustrative example, MCU 572 is a model no. STM32F429IIT6 microcontroller available from STMicroelectronics N.V. of Amsterdam, Netherlands. Section 570 of MCB 340 also includes external watchdog circuitry 574, an inlet temperature sensor sense circuit 576, a controller area network (CAN) transceiver 578, and a 64 KB EEPROM 580. A portion of cables 550, 552 are also shown in FIG. 16C.

MCB 340 of control circuitry 500 also includes a blower motor driver and control circuit 582 which, in turn, includes a hall sensors interface 584 to receive signals from Hall effect sensors of blower motor 548 of blower 260 via respective conductors of cable 552. The signals from the Hall effect sensors indicate the speed at which blower motor 548 is operating. Circuit 582 also includes current sense circuitry 586 and temperature sense circuitry 588 to determine the current draw and temperature, respectively, of blower motor 584. MCB 340 also includes a debug section 590 having a UART 594 and a JTAG circuit 592.

Still referring to FIG. 16C, MCB 340 of control circuitry 500 includes a power management section 596 which, in turn, includes a pre-charge circuit 598, a DC-DC regulator and sense feedback 5V circuit and/or chip 600, a 3.3 V LDO and sense feedback circuit and/or chip 602, and a 12 V LDO and sense feedback circuit and/or chip 604. Power management section 596 also includes a battery enable control circuit 606, a power source selector circuit 608 that determines whether AC power or battery power is to power device 10 at any given time, and a battery charging interface control circuit and/or chip 610. The AC inlet 234 of apparatus 10 is coupled to a 225 Watt (W)/24 VDC open frame AC/DC power supply 612 of control circuitry 500 by an AC power cable assembly 614 having live and neutral (L&N) lines, as shown diagrammatically in FIG. 16C. AC/DC power supply 612 is, in turn, coupled to power management section 596 of MCB 340 by a 24 VDC cable assembly 616. As also shown diagrammatically in FIG. 16C, battery docking board 338 to which rechargeable battery 224 is removably coupled, electrically couples to MCB 340 by a power cable assembly 618 and a signal or data cable assembly 620. Electrical contacts 621 between battery 224 and battery docking board 338 are also shown diagrammatically in FIG. 16C.

Flow element board 370 is shown in FIG. 16C coupled to MCB 340 by a diagrammatic cable 622. Flow element board 370 includes pressure sensors 624 for control and monitoring of the therapy delivered by device 10 via port 24, flow sensors 626, and an inlet temperature sensor sense circuit or chip 628 that senses the temperature air entering inlet 362 of flow control module 352. Because respiratory therapy apparatus 10 is operable to produce positive pressure and negative pressure at port 24 depending upon the position of the rotary plate of the manifold and rotary valve assembly 330, it should be appreciated that air may exit through port 24 from housing 12 during application of positive pressure to the patient's airway and air may enter into housing 12 through port 24 during application of negative pressure to the patient's airway. Similarly, air travels in a first direction through flow control module 352 toward port 24 when positive pressure is applied to the patient's airway and air travels in an opposite, second direction through flow control module 352 away from port 24 when negative pressure is applied to the patient's airway. Thus, outlet port 24 sometimes serves as an inlet port 24 and inlet 362 of flow control module 352 is sometimes the outlet of flow control module 352. Thus, the use of the terms "outlet" and "inlet" herein are generally based on the situation when positive pressure is being applied to the patient's airway by apparatus 10.

Referring now FIG. 16D, section 570 of MCB340 also includes a barometric sensor 630, diagnostic LED's 632, and one or more buzzers 634 for audibly signaling device status or alarm conditions. MCB 340 further includes a stepper motor driver and control circuit 636 that, in turn, includes an encoder interface 638, a current sense circuit and/or chip 640, and a temperature sense circuit and/or chip 642. Stepper motor cable 568 couples to circuit 636 as shown diagrammatically in FIG. 16D. Encoder interface 638 receives a signal on cable 568 indicative of the position of an output shaft of the stepper motor 334 which corresponds to the position of the rotary plate of the manifold and rotary valve assembly 330. Current sense circuitry 640 and temperature sense circuitry 642 are operable to determine the current draw and temperature, respectively, of stepper motor 334.

With continued reference to FIG. 16D, MCB 340 of control circuitry 500 includes foot pedal sense circuitry 644 that is electrically coupled to connector 304 by a foot pedal cable assembly 646. Circuitry 644 senses whether foot pedal 294 is coupled to connector 304 by electrical cord 300. MCB 340 also includes a therapy data up/down load section 648 coupled to connector 306, which illustratively is a 1×USB FS 2.0 (Type A) connector as indicated by block 650. Therapy data and settings are downloaded and uploaded to devices coupled to connector 306 under the control of section 648.

MCB 340 further includes a nebulizer control interface section 652 that is coupled to nebulizer 66 via connector 152 and cable 148 and that has input/output (I/O) interface circuitry 654. Circuitry 654 receives an on/off control input (I/P) from section 570 and communicates the input to nebulizer 66 to turn motor 144 on and off. Circuitry 654 also transmits a frequency output (O/P) and a detection O/P to section 570. As also shown diagrammatically in FIG. 16D, MCB 340 of control circuitry 500 includes a fan driver circuit 656 that electrical couples with ventilation fan 276 via a 4 wired fan control cable 658.

Figure 17B:
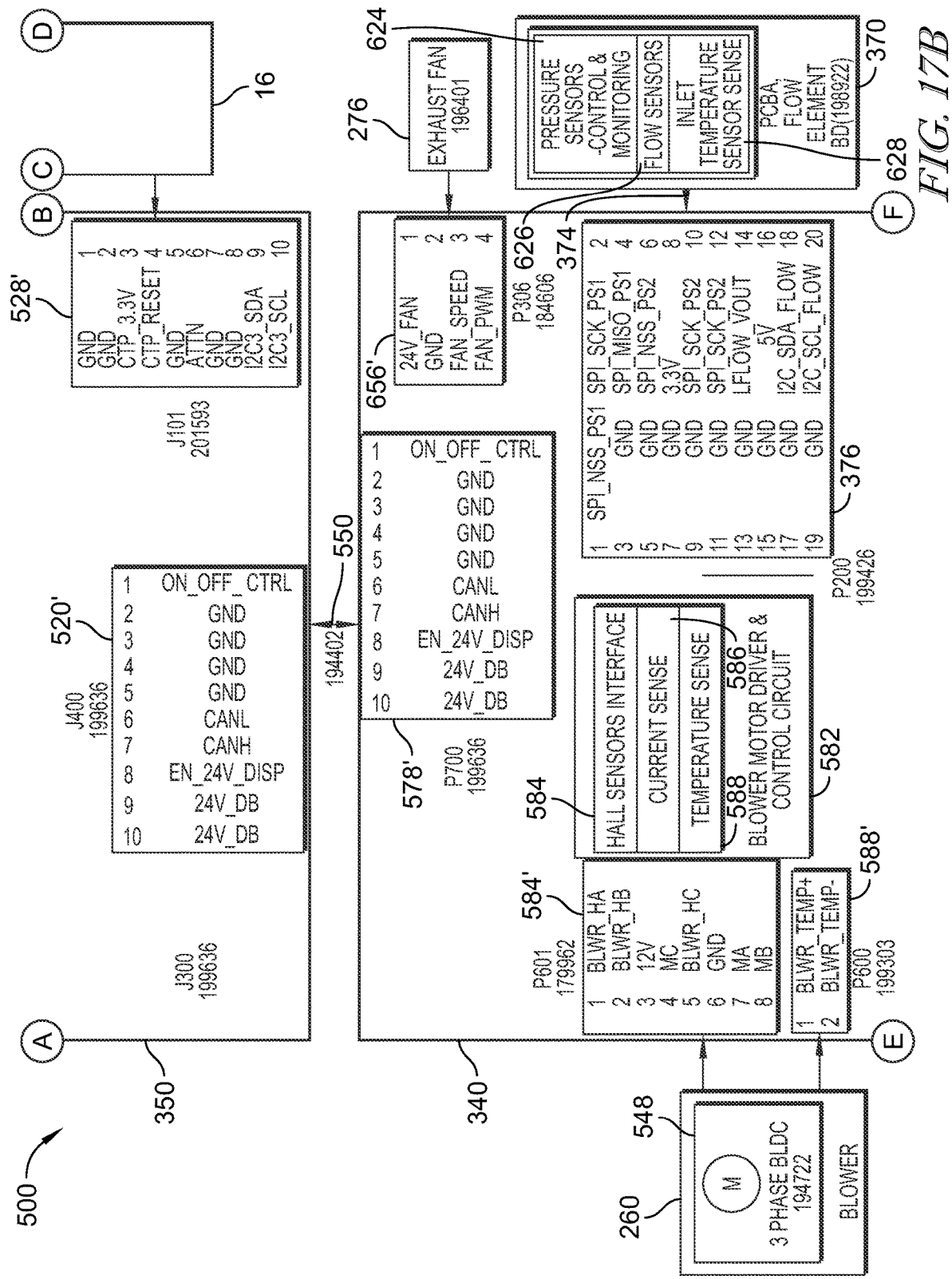
Figure 17C:
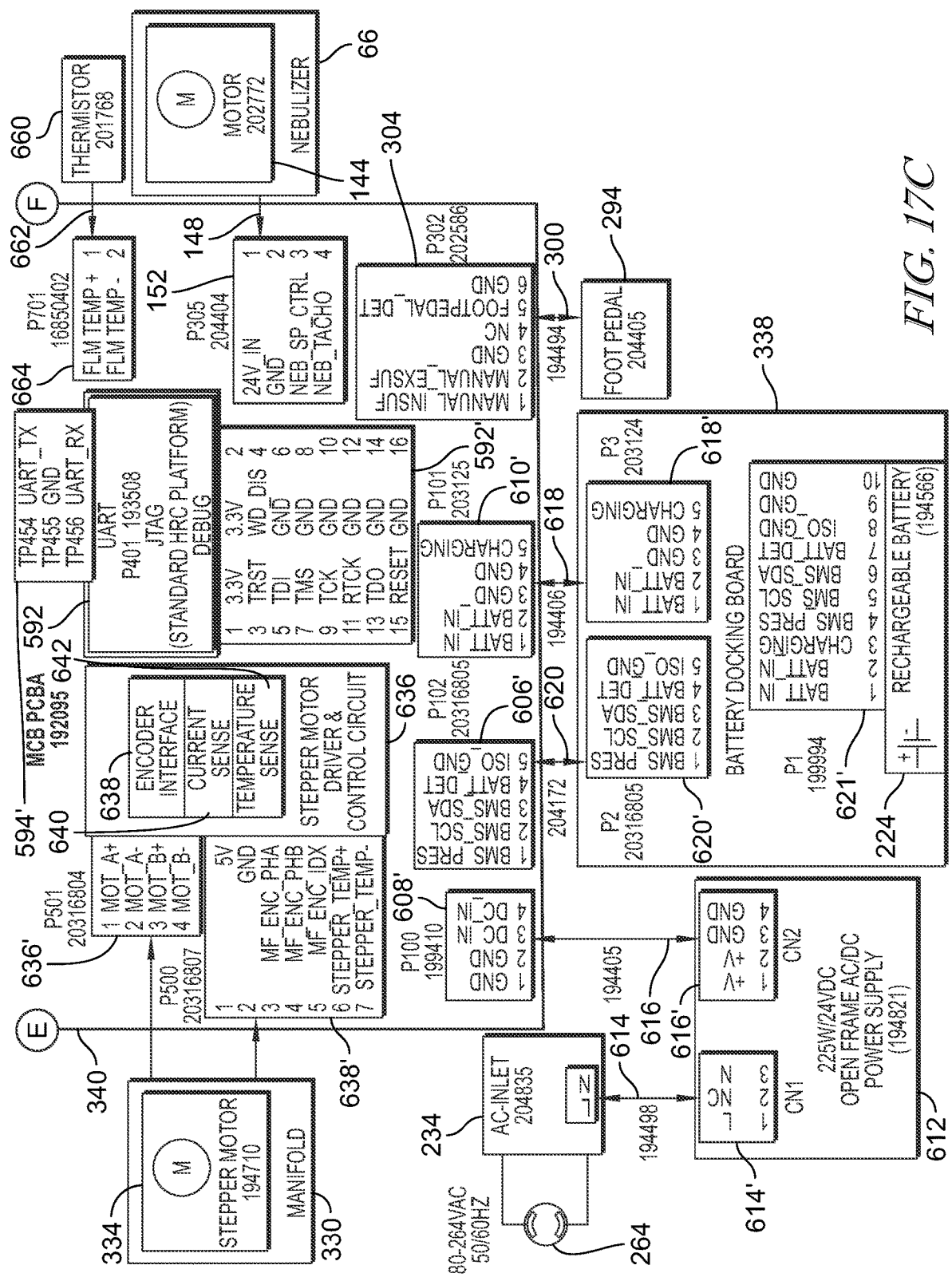

Referring now to FIGS. 17A-17C, an electrical wiring diagram for the control circuitry 500 of respiratory therapy apparatus 10 is shown. FIGS. 17A-17C show similar components as FIGS. 16A-16D, but has particular jumpers or electrical connectors of control circuitry 500 shown. In general, the same reference numbers are used for the electrical connectors in FIGS. 17A-17C as their corresponding sections, circuits, or components, as the case may be, of FIGS. 16A-16D but with the prime symbol, "'" added. Thus, for example, in FIG. 17A, reference number 546' refers to an electrical connector of RFID board 546 and reference number 556' refers to an electrical connector of UART 556. One exception is if a particular electrical connector was mentioned previously herein. A first example of this exception is connector 376, shown in FIG. 17B, which has been referred to previously in this disclosure. Another example of this exception is connector 304, shown in FIG. 17C, which has been mentioned previously in this disclosure. As shown in FIG. 17C, a thermistor 660 is provided in nebulizer 66 to measure a temperature of motor 144. An electrical line 662 electrically couples thermistor 660 to a thermistor coupler 664 of MCB 340.

In some embodiments, thermistor 660 or another temperature sensor like thermistor 660 is situated within the interior region of housing 12 and serves as a sort of supervisory temperature sensor for all of the heat producing elements, such as blower motor 548, stepper motor 334, nebulizer motor 144, the motor of exhaust fan 276, and the various circuit components of control circuitry 500. That is, the supervisory temperature sensor monitors the overall heat condition of apparatus 10. Such a supervisory temperature sensor is coupled to an upper surface of bottom wall 36, for example. In embodiments having the supervisory temperature sensor, others of the temperature sensors disclosed herein, such as thermistor 660, are omitted. If the temperature sensed by the supervisory temperature sensor meets or exceeds a predetermined maximum temperature threshold, then one or more components such as blower motor 548, stepper motor 334, and nebulizer motor 144, are turned off. Control circuitry 500 may continue to operate, however, so that an appropriate over temperature alert message is displayed on GUI 16.

Referring now to FIGS. 18-274, examples are given of screen shots of a plurality of navigable control screens that appear on the GUI 16 of the respiratory therapy apparatus 10 and that are usable to control features and functions of the respiratory therapy apparatus 10. The screen shots shown in FIG. 18-274 include various numerical values and other information that is provided to illustrate the general concepts of the operation of device 10. Furthermore, it should be understood that GUI 16 is used to provide inputs to control circuitry 500 and to display information stored in or determined by control circuitry 500 during the operation of device 10. Thus, the features and functions disclosed below in connection with the screen shots of FIGS. 18-274 constitute a description of the software that is stored in and executed by control circuitry 500 of device 10.

Referring now to FIG. 18, a main therapy selection screen 670 has a selectable mechanical insufflation/exsufflation (MIE) button or icon 672 and a selectable oscillatory lung expansion (OLE) button or icon 674. The terms buttons and icons are used interchangeably herein and, in connection with FIGS. 18-274, are referring to portions of GUI 16 that are touched by a user to make a selection or to provide an input to control circuitry 500 to perform a function. In response to selection of button 672 on screen 670, a main MIE therapy selection screen 676 appears on GUI 16 as shown in FIG. 19. Main MIE therapy selection screen 676 includes a selectable automatic button 678 and a selectable manual button 680 for selecting automatic and manual modes of MIE therapy, respectively. If button 672 is selected on screen 676, the GUI 16 goes back to showing screen 670.

In response to selection of button 674 on screen 670, a main OLE therapy selection screen 682 appears on GUI 16 as shown in FIG. 20. Main OLE therapy selection screen 682 includes a selectable automatic button 684 and a selectable manual button 686 for selecting automatic and manual modes of OLE therapy, respectively. If button 674 is selected on screen 682, the GUI 16 goes back to showing screen 670. Each of screens 670, 676, 682 includes a menu open icon 688 on the right hand side of the respective screen. In response to selection of icon 688 on any of screens 670, 676, 682, GUI 16 displays a menu screen 690 as shown in FIG. 21. In the illustrative example of FIG. 21, icon 688 was selected on screen 676 and so portions of screen 676 are still visible on screen 690 but are grayed out and inactive (i.e., unable to be selected). Screen 690 includes a vertical menu of icons 692 along a right hand side of GUI 16. The illustrative vertical menu of icons 692 includes, from top to bottom, a home icon 694, a graph icon 696, a lung icon 698, a settings icon 700, and an information or help icon 702. The screens that result in response to selection of any of icons 694, 696, 698, 700, 702 are discussed in further detail below.

In response to selection of settings icon 700 on screen 690 of FIG. 21, a settings screen 704 appears on the GUI 16 as shown in FIG. 22. Settings screen 704 includes a window 706 of device information pertaining to the respiratory therapy apparatus 10. In the illustrative example, window 706 includes the following device information: model number of device 10, serial number of device 10, main control board (MCB) software (SW) version, MCB bootload version, display control board (DCB) SW version, DCB bootload version, Federal Communications Commission (FCC) identification (ID) number, radio frequency (RF) identification (ID) firmware (FW) version, Bluetooth FW version, total therapy run time, and total nebulization time. Also in the illustrative example, a series of "X's" are given as placeholder text for each of the items listed in window 706. However, it should be appreciated that the appropriate information (e.g., alphanumeric text, numeric text, etc.) is given for each of these in an actual implementation of device 10.

In some embodiments, settings icon 700 and home icon 694 remain active on screen 704 of FIG. 22 and icons 696, 698, and 702 are inactive and grayed out. Selection of home icon 694 on screen 704 returns the user back to screen 690 of FIG. 21. A menu close tab 708 is provided to the left of vertical menu of icons 692 in FIG. 21 and is selectable to return the user back to whichever of screens 670, 676, 682 was the one on which the menu open icon 688 was selected to begin with. When screen 704 of FIG. 22 first appears on GUI 16 in response to selection of setting icon 700, an about button 710 under a Settings heading is highlighted and has a graphical box 712 colored green. Window 706 is associated with the about button 710.

A device button 714, a data button 716, and a connect button 718 also appear beneath the Settings heading and are selectable to navigate to other information and controls pertaining to the operation of device 10 as will be discussed in further detail below. Each of buttons 714, 716, 718 has its own respective graphical box 712 that changes from a color such as black or gray to indicate that the button 714, 716, 718 has not been selected, to green to indicate that the respective button 714, 716, 718 has been selected. A close settings tab 720 appears to the left of the buttons 716, 718 in FIG. 22 and is selectable to return to screen 690 of FIG. 21. Screen 704 also includes a clinical access unlocked button 721 having a lock image in an unlocked state to indicate that a clinical access function of device 10 is unlocked.

Figure 23:
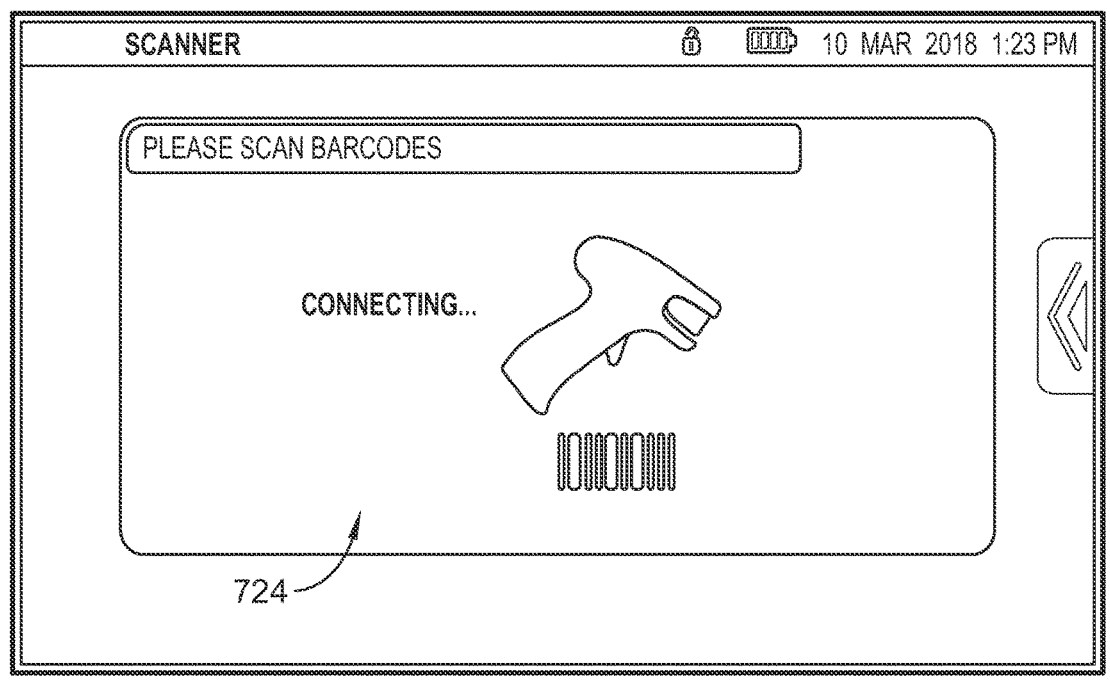
FIG. 23 is a screen shot of a bar code scanner connecting screen that appears on the GUI in response to selection of the automatic button or manual button on either of the screens of FIGS. 19 and 20 if a bar code reader feature of the respiratory therapy apparatus is turned on or enabled.

If any of buttons 678, 680 of screen 676 of FIG. 19 or buttons 684, 686 of screen 682 of FIG. 20 are selected and a bar code scanning function of device 10 is turned on, then a bar code scanner connecting screen 722 appears on the GUI 16 as shown in FIG. 23. Screen 722 includes a window 724 having the text "CONNECTING . . . " flashing therein to indicate that control circuitry 500 of device 10 is attempting to connect to a bar code scanner. In the illustrative example, the text "CONNECTING . . . " flashes once per second during the search process. Also in the illustrative example, a generic bar code scanner icon and a generic bar code appear within window 724 to convey to the user that device 10 is attempting to establish wireless communication with a bar code scanner.

Figure 24:
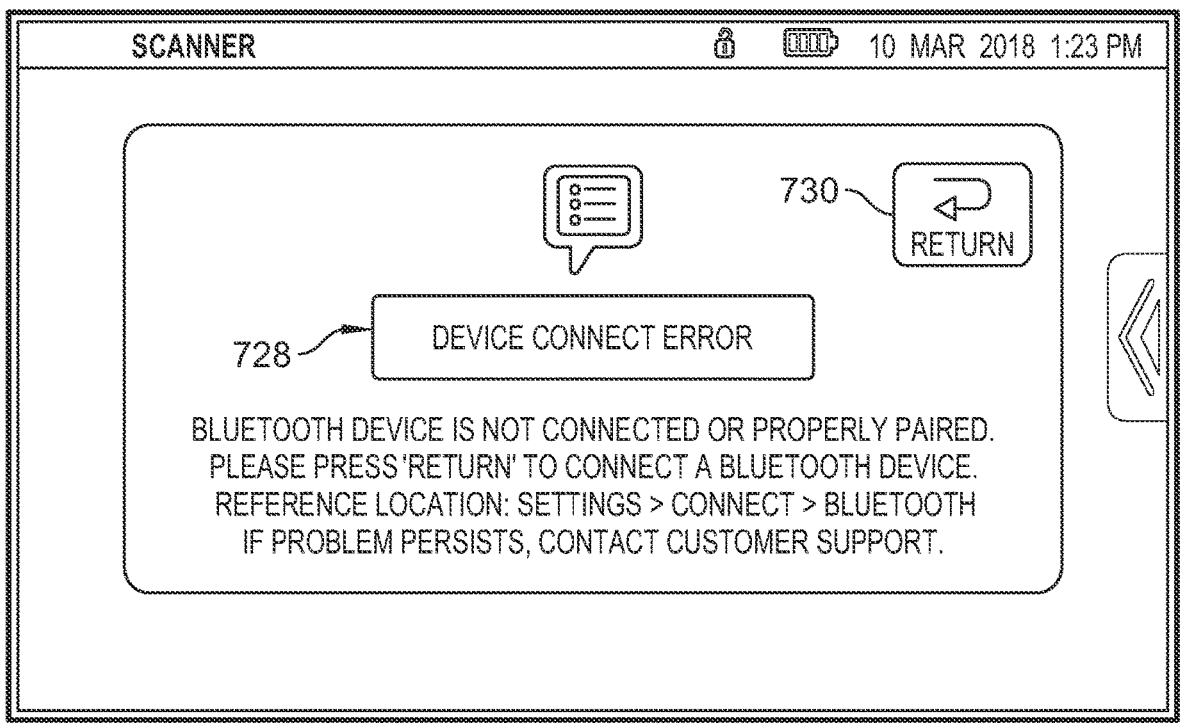
FIG. 24 is a screen shot of a device connect error screen that appears on the GUI if no connection with a bar code scanner occurs within a threshold period of time.

If no connection with a bar code scanner occurs within a threshold period of time, such as about fifteen seconds in some embodiments, then a device connect error screen 726 appears on GUI 16 as shown in FIG. 24. Screen 726 includes a box 728 with the text "DEVICE CONNECT ERROR" therein. Beneath box 728, the following explanatory text is provided: "BLUETOOTH DEVICE IS NOT CONNECTED OR PROPERLY PAIRED. PLEASE PRESS 'RETURN' TO CONNECT A BLUETOOTH DEVICE. REFERENCE LOCATION: SETTINGS>CONNECT>BLUETOOTH. IF PROBLEM PERSISTS, CONTACT CUSTOMER SUPPORT." Screen 726 includes a return button 730 that is selected by the user to navigate to the settings screen 704 to begin the process of navigating to the reference location indicated in the explanatory text of screen 726.

Figure 25:
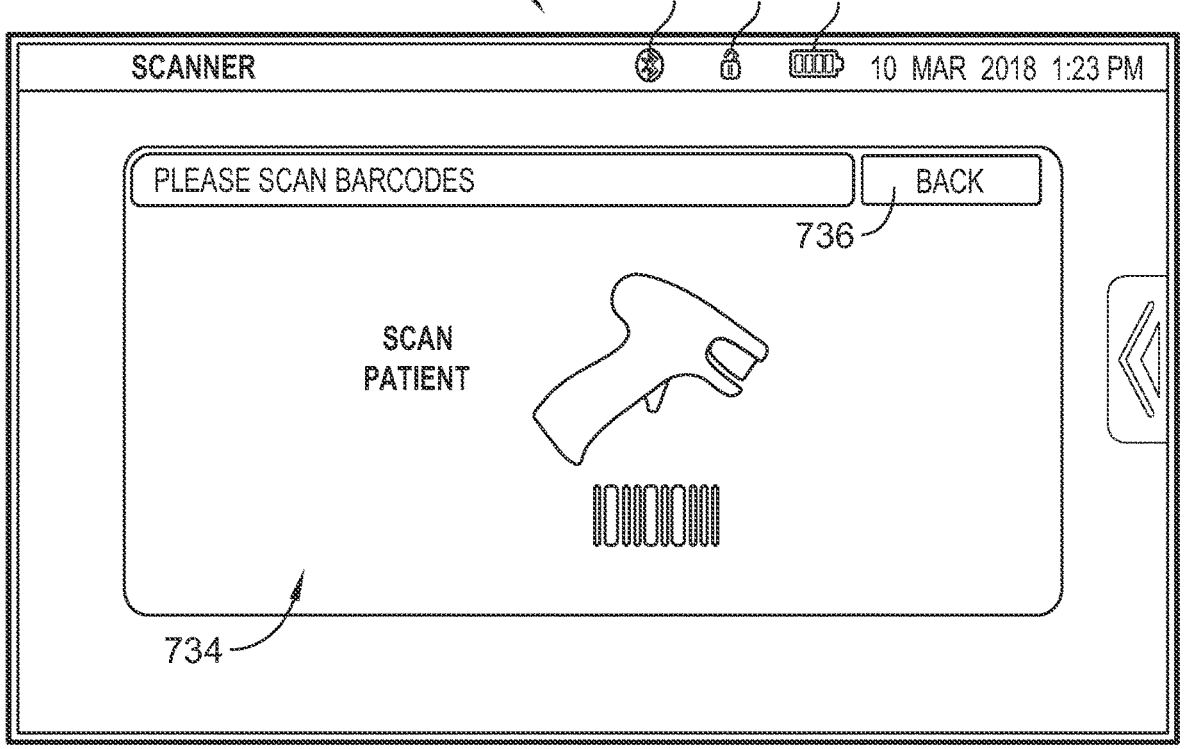
FIG. 25 is a screen shot of a scan patient screen that appears on the GUI in response to the respiratory therapy apparatus establishing wireless communications with the bar code scanner.

If wireless connection with a bar code scanner by the control circuitry 500 of device 10 occurs within the threshold period of time, then a scan patient screen 732 appears on the GUI as shown in FIG. 25. Screen 732 includes a window 734 having the text "SCAN PATIENT" flashing therein to indicate that the caregiver with the bar code scanner should scan a bar code of a patient identification token, such as a wristband, for example. In the illustrative example, the text "SCAN PATIENT" flashes once per second until a scan is detected. Also in the illustrative example, a generic bar code scanner icon and a generic bar code appear within window 734 to convey to the user that the bar code scanner should be used.

A Bluetooth icon 731 appears in a header region of screen 732 next to clinical access unlock icon 733 and battery charge state icon 735 as shown in FIG. 25. Icon 731 indicates that control circuitry 500 is successfully communicating via Bluetooth technology with another device. A back button 736 also appears in window 734 of screen 732. Selection of button 736 returns the user back to screen 676 or screen 682 depending upon which screen had the respective button 678, 680, 684, 686 resulting in the initiation of the bar code scanning process. In some embodiments, control circuitry 500 times out after a threshold amount of time such as fifteen or thirty seconds, for example, and returns the user to screen 676 or screen 682, as the case may be, if no bar code is scanned with the bar code scanner.

Figure 26:
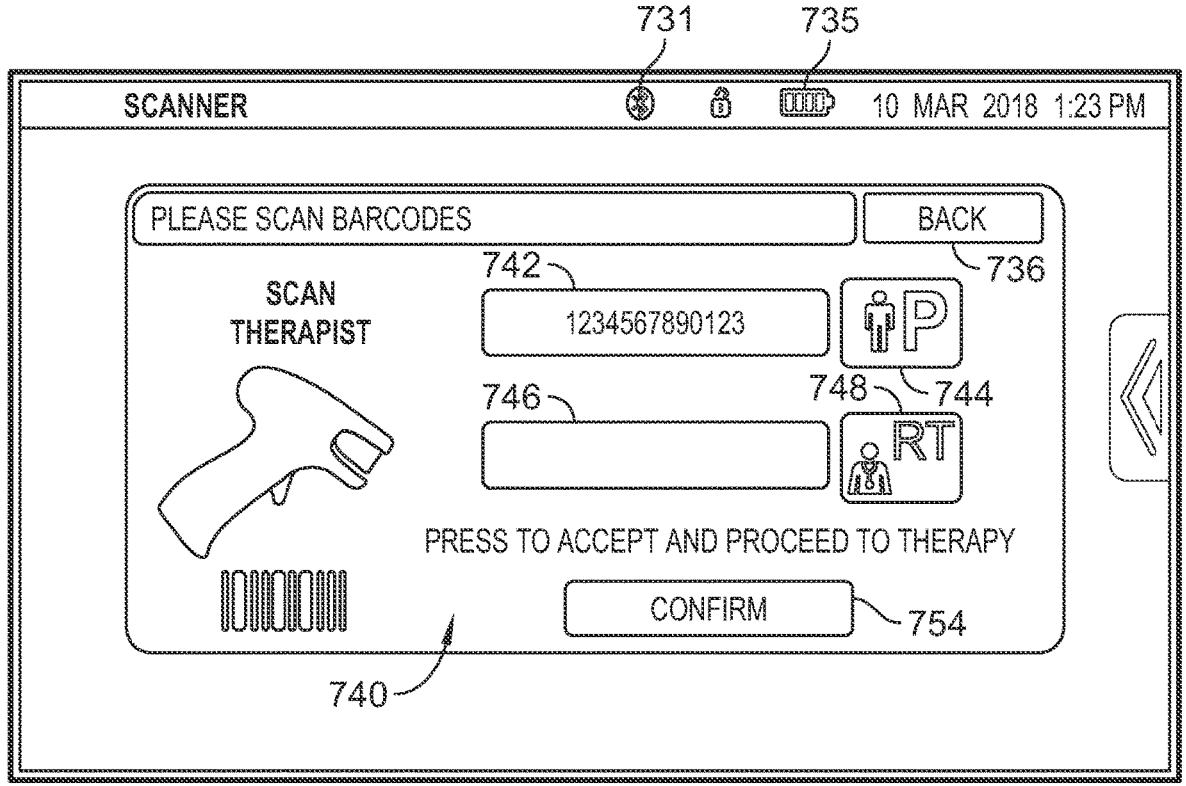
FIG. 26 is a screen shot of a scan therapist screen that appears on the GUI in response to a bar code identifying a patient being scanned successfully.

In response to a patient bar code being scanned successfully, GUI 16 displays a scan therapist screen 738 as shown in FIG. 26. Screen 738 includes a window 740 having the text "SCAN THERAPIST" flashing therein to indicate that the caregiver with the bar code scanner should scan a bar code of a therapist identification token, such as an employee ID card, for example. In the illustrative example, the text "SCAN THERAPIST" flashes once per second until a scan is detected. Also in the illustrative example, a generic bar code scanner icon and a generic bar code appear within window 740 to convey to the user that the bar code scanner should be used. Window 740 also includes back button 736 which operates in the same manner as described above in connection with screen 732 of FIG. 25.

Window 740 of screen 738 of FIG. 26 includes a patient ID field 742 in which the patient ID appears based on the scanned patient bar code. A patient icon 744 is shown in window 740 to the right of field 742 with the letter "P" therein to indicate that field 742 relates to the patient. A caregiver ID field 746 appears in window 740 beneath field 742 and is blank because a caregiver ID has not yet been scanned with the bar code scanner. The caregiver having the bar code scanner may scan themselves if they are the caregiver charged with delivering respiratory therapy to the patient using device 10 or the caregiver having the bar code scanner may scan another caregiver charged with this task. Window 740 includes a caregiver icon 748 to right of field 746 with the letters "RT" therein to indicate that field 746 relates to a respiratory therapist which is the type of caregiver that typically administers respiratory therapy to a patient using device 10.

Figure 27:
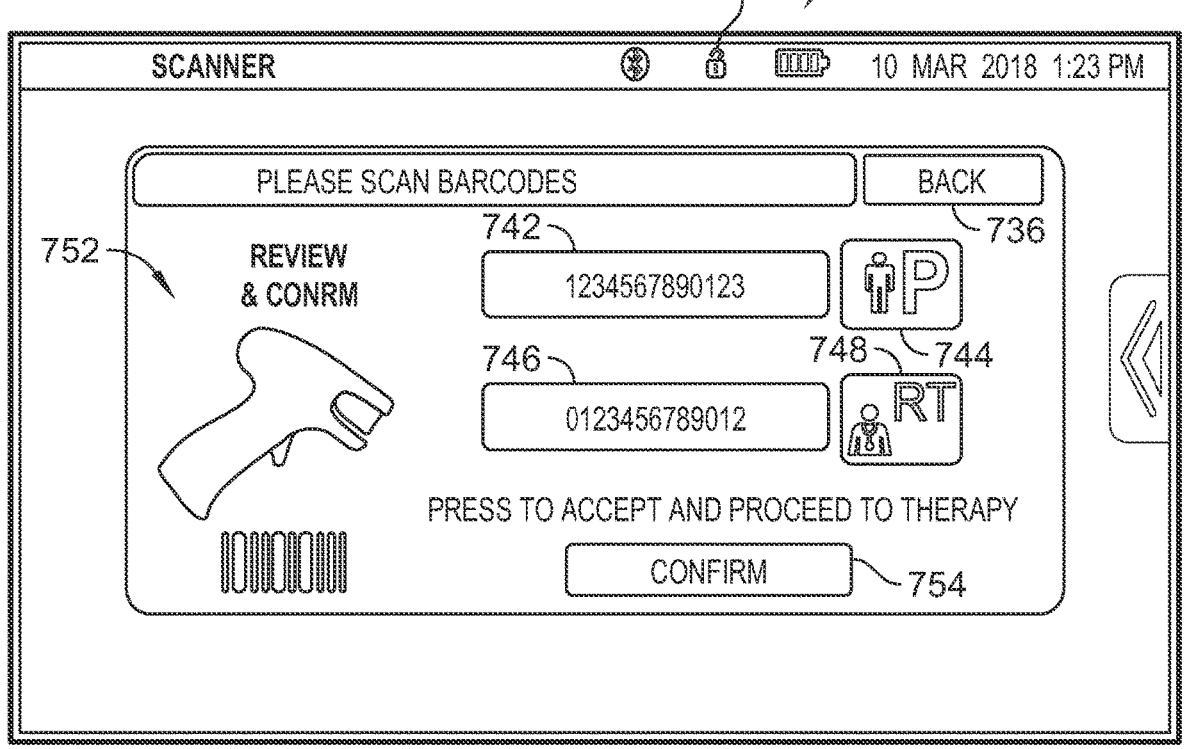
FIG. 27 is a screen shot of a review and confirm screen that appears on the GUI in response to a bar code identifying a respiratory therapist being scanned successfully, the review and confirm screen including text boxes in which alphanumeric identification (ID) codes for the patient and the respiratory therapist appear and a confirm button that is selected to confirm the successful scan of the patient and the respiratory therapist.

In response to a caregiver bar code being scanned successfully, GUI 16 displays a review and confirm screen 750 as shown in FIG. 27. Screen 738 includes a window 752 having the text "REVIEW & CONFIRM" flashing therein to indicate that the patient ID and caregiver ID should be confirmed. In the illustrative example, the text "REVIEW & CONFIRM" flashes once per second until a confirm button 754 is selected. Button 754 is inactive, such as in FIG. 26, until a caregiver bar code is scanned at which point button 754 becomes active, such as in FIG. 27. Thus, on screen 738 of FIG. 26, button 754 is grayed out and then becomes highlighted on screen 750 of FIG. 27 after the caregiver bar code is scanned. Similar to before, the generic bar code scanner icon and the generic bar code appear within window 752 to convey to the user that the bar code scanning process is not yet complete. Window 740 also includes back button 736 which operates in the same manner as described above in connection with screen 732 of FIG. 25.

Figure 28:
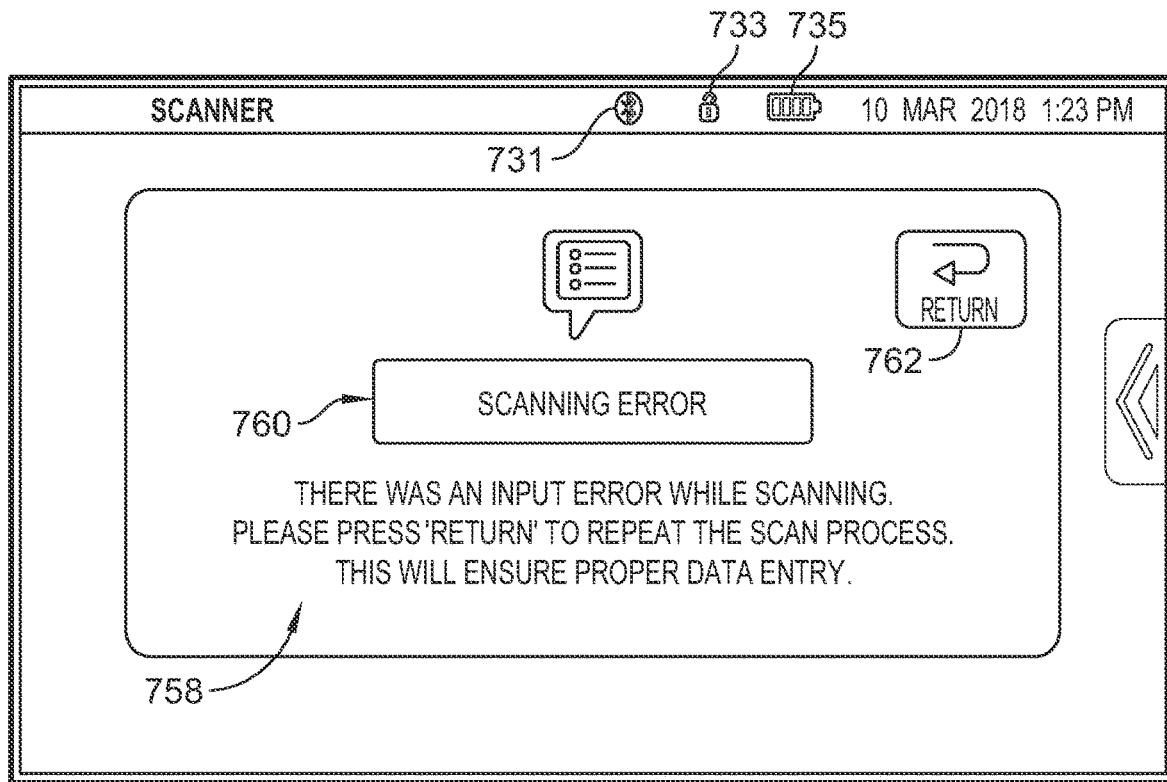
FIG. 28 is a screen shot of a scanning error screen that appears on the GUI in response to the first alphanumeric ID code matching the second alphanumeric ID code due to inadvertent duplicate scanning of the same ID code.

As also shown in FIG. 27, the caregiver ID appears in field 746 based on the scanned caregiver bar code. After the user, typically the caregiver, reviews and confirms the information in fields 742, 746, the user selects button 754 to advance to a main therapy screen corresponding to whichever of buttons 678, 680, 684, 686 of screens 676, 682 of FIGS. 19 and 20 was selected initially to start the bar code scanning process. However, if an error is detected by control circuitry 500 in connection with the patient and caregiver ID's appearing in fields 742, 746, then GUI 16 displays a scanning error screen 756 as shown in FIG. 28. For example, if the first alphanumeric ID code appearing in field 742 matches the second alphanumeric ID code appearing in field 746, then it is likely that inadvertent duplicate scanning of the same ID code has taken place. That is, the user may have scanned the patient ID twice or scanned the caregiver ID twice. This error situation results in screen 756 of FIG. 28 being displayed with a window 758 that, in turn, includes a box 760 with the text "SCANNING ERROR" therein. Beneath box 760, the following explanatory text is provided: "THERE WAN INPUT ERROR WHILE SCANNING. PLEASE PRESS 'RETURN' TO REPEAT THE SCAN PROCESS. THIS WILL ENSURE PROPER DATA ENTRY." Screen 726 includes a return button 762 that is selected by the user to navigate back to the scan patient screen 734 of FIG. 25 to begin the process of bar code scanning once again.

Assuming that automatic button 678 was selected initially on main MIE therapy selection screen 676 of FIG. 19 prior to the bar code scanning process, then after successful completion of the bar code scanning process and selection of confirm button 754 on screen 750 of FIG. 27, a main automatic MIE therapy screen 764 appears on GUI 16 as shown in FIG. 29. Alternatively, screen 764 appears on GUI 16 in response to selection of automatic button 678 on screen 676 of FIG. 19 if the clinical access function of device 10 is turned off such that the bar code scanning process illustrated in FIGS. 23-28 is omitted. In the illustrative example of screen 764, it is assumed that operational parameters for MIE therapy have been stored previously in control circuitry 500. Thus, in the illustrative example, screen 764 defaults to showing details of plan 1 settings for the automatic mode of MIE therapy.

As shown in FIG. 29, screen 764 includes a start button 766 which is selected to start the associated automatic MIE therapy and a stop button 768 which is selected to stop the associated MIE therapy. Button 768 is grayed out on screen 764 because the therapy is not currently being delivered. Screen 764 also has an information graph 770 and an information bar 772 in the form of a digital manometer. Graph 770 displays numerical parameters for the associated portions of the automatic MIE therapy including inhale pressure (+53 cmH2O in the illustrative example), exhale pressure (−62 cmH2O in the illustrative example), inhale time (2.8 second in the illustrative example), exhale time (2.5 seconds in the illustrative example), a therapy progress indicator 774 which moves along the curve shown in graph 770 during the associated therapy, pause pressure (+6 cmH2O in the illustrative example), pause time (3.2 seconds in the illustrative example, and a cycle box 776 showing a running total of the number of cycles completed during the associated therapy (1 of 4 cycles in the illustrative example).

Bar 772 of screen 764 of FIG. 29 includes an upper arrow 778 serving as an inhale pressure marker, a middle arrow 780 serving as a pause pressure marker, and a lower arrow 782 serving as an exhale pressure marker. In some embodiments, the inhale portions, exhale portions, and pause portions of MIE therapy are color coded. In some embodiments, for example, the inhale portions of MIE therapy are color coded blue, the exhale portions of MIE therapy are color coded orange, and the pause portions of MIE therapy are color coded green. Thus, with reference to the screen 764 example of FIG. 29, the text "INHALE +53" is blue, the text "EXHALE −62" is orange, and the text "PAP +6" is green. Similarly, some or all of upper arrow 778 is blue, some or all of middle arrow 780 is green, and some or all of lower arrow 782 is orange. Screen 764 further includes a flow button 784 in the lower right hand corner, a peak cough flow ($P_{CF}$) field 786 to the left of button 784, and a tidal volume ($V_t$) field 788 beneath field 786. Various ones of FIGS. 29-274 use the text "PCF" and "VT" in lieu of "$P_{CF}$" and "$V_t$" for purposes of meeting drawing requirements of the USPTO. Similarly, "CMH2O" or "CMH$_2$O" are used in lieu of "cm H$_2$O" throughout FIGS. 29-274 for the same reason.

In response to selection of start button 766 on screen 764 of FIG. 29, the control circuitry of device 10 performs an RFID count check to confirm that filter unit 390 is equal to or below its usage count limit. As discussed above, reader 434 reads the usage count stored in transponder chip 422 of filter unit 390 to confirm that the usage count is equal to or below the threshold number of uses, such as 70 or 90 uses. If the usage count is greater than the usage count limit, then an error message is displayed on GUI 16 instructing the user to replace the old filter unit 390 with a new one. Until the filter unit 390 meets the usage count requirement (i.e., is equal to or below the threshold limit), device 10 is prevented from delivering any respiratory therapy to any patients in some embodiments.

Figure 30:
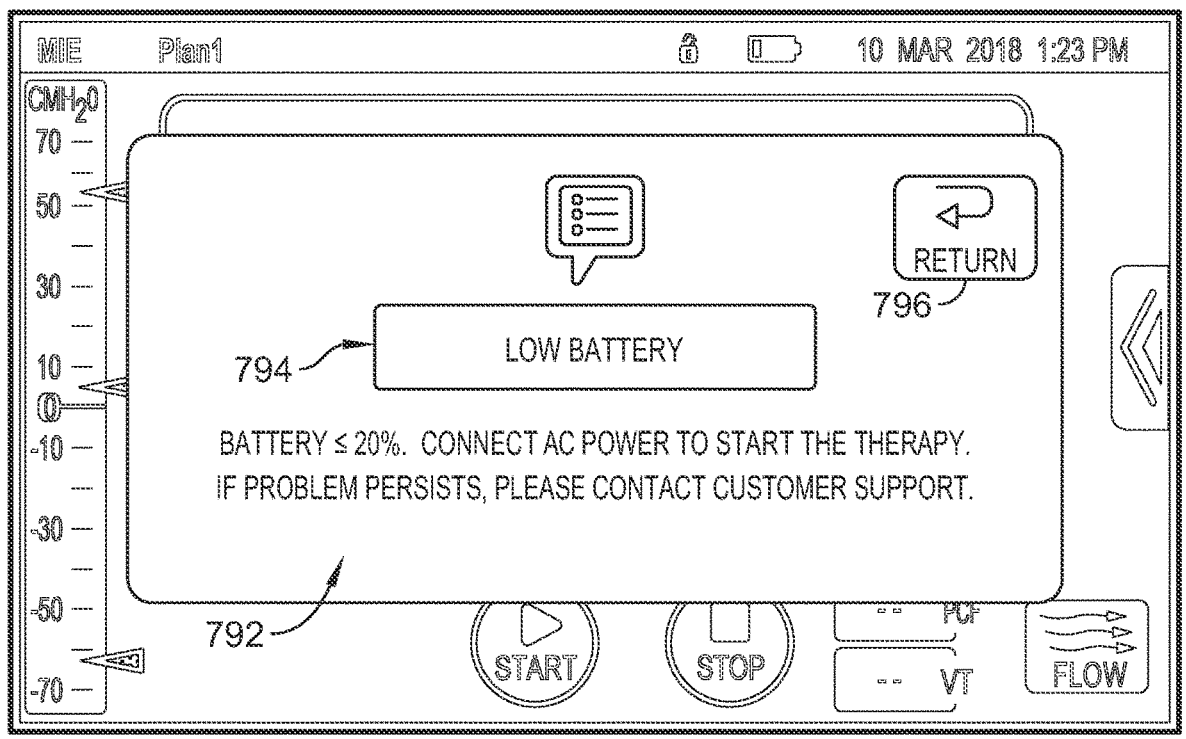
FIG. 30 is a screen shot of a low battery screen that appears on the GUI if a start button of the main automatic MIE therapy screen of FIG. 29 is selected while the respiratory therapy apparatus is operating under battery power and the battery charge is less than or equal to 20% of a full battery charge.

In response to selection of start button 766 on screen 764 of FIG. 29, the control circuitry of device 10 also checks for the amount of battery charge of battery 224 if device 10 is operating under battery power. If the battery charge amount is less than or equal to 20% of a full battery charge, then a low battery screen 790 appears on GUI 16 as shown in FIG. 30. Low battery screen 790 includes a window 792 having a text box 794 with the text "LOW BATTERY" therein. Beneath box 794 is the explanatory text, "BATTERY ≤20%. CONNECT AC POWER TO START THE THERAPY. IF PROBLEM PERSISTS, PLEASE CONTACT CUSTOMER SUPPORT." A return button 796 is also provided in window 792. Selection of button 796 returns the user back to screen 764 of FIG. 29. If device 10 is operating under AC power (e.g., plug 231 of cord 228 is plugged into an AC power outlet to power device 10), then the battery charge check is skipped.

If filter unit 390 passes the RFID count check and if the battery charge check is passed (or device 10 is being operated under AC power) after start button 766 is pressed on screen 764, then an automatic MIE therapy start screen 798 appears on GUI 16 as shown, for example, in FIG. 31. Screen 798 of FIG. 31 is basically the same as screen 764 of FIG. 29 except that start button 766 of screen 764 is converted graphically to a pause button 800 on screen 798. Also, stop button 768 of screen 798 is no longer grayed out and becomes active and menu tab 688, which is active on screen 764 of FIG. 29, becomes grayed out and inactive on screen 798 of FIG. 31.

Figure 32:
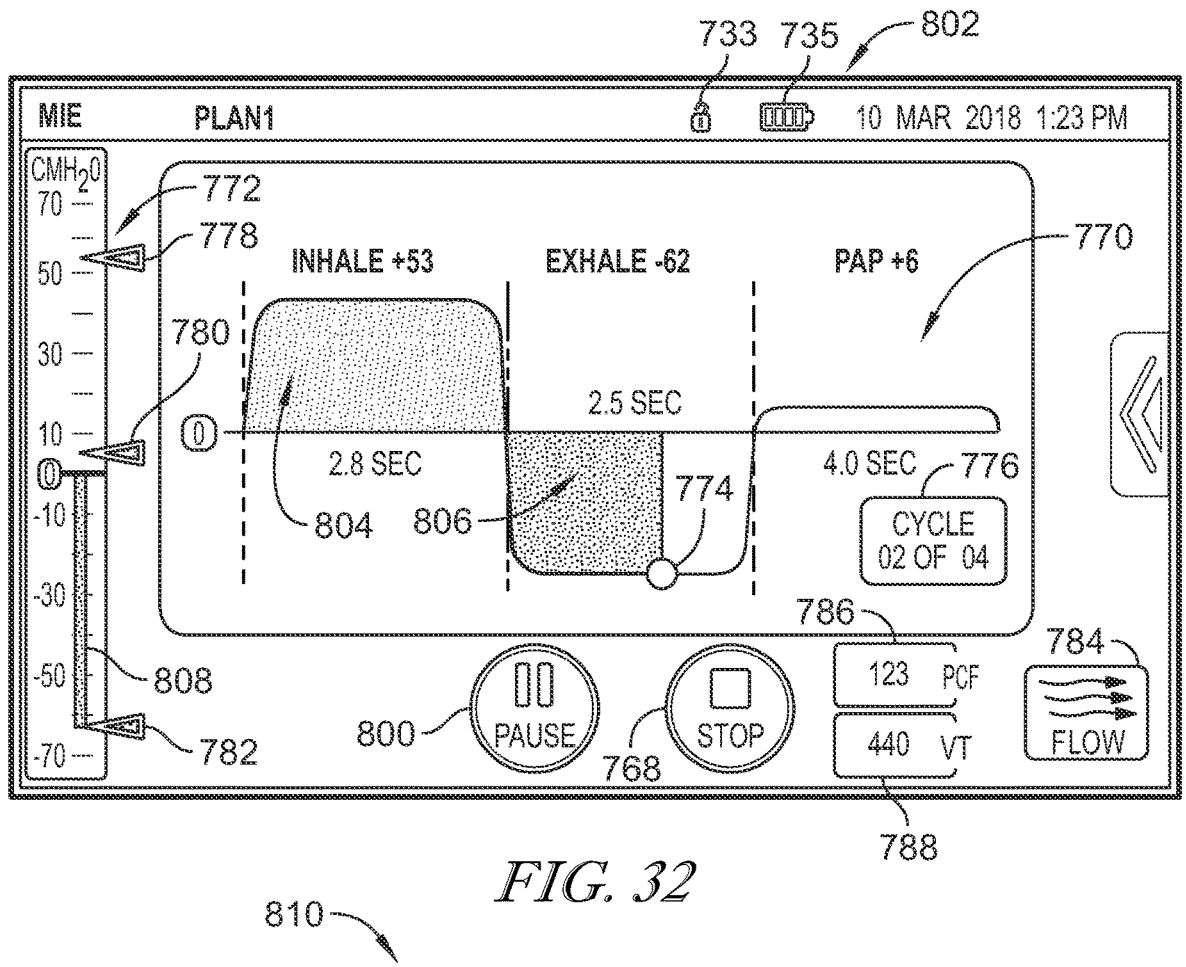
FIG. 32 is a screen shot of an automatic MIE therapy in process screen that appears on the GUI during the automatic MIE therapy showing a graphical therapy progress indicator moving along a graphical waveform of one cycle of the therapy and showing the graph being filled in up to the progress indicator to indicate an amount of the current therapy cycle that have been completed.

Referring now to FIG. 32, an automatic MIE therapy in process screen 802 is shown at an arbitrary point in time during the delivery of automatic MIE therapy by device 10. As shown in FIG. 32, the graphical therapy progress indicator 774 has moved along the graphical waveform of graph 770 to indicate the current therapy progress. As shown in box 776, the therapy being delivered is currently on the second cycle of four cycles. For the current cycle, graph 770 is filled in up to the progress indicator 774 to indicate an amount of the current therapy cycle that has been completed. Thus, an inhale region 804 is filled in, in blue in some embodiments, and a portion of exhale region 806 is filled in, in orange in some embodiments, up to the progress indicator 774. Thus, progress indicator 774 travels on graph 770 from left to right until it reaches the right end of the depicted cycle and then starts over again at the left end of graph 770 for the next cycle. Box 776 is incremented to next cycle at that point as well.

As also shown in FIG. 32, an exhale segment 808 is superimposed on bar 772 from 0 cmH$_2$O down to lower arrow 782 to indicate that the therapy is currently in the exhale phase. In some embodiments, bar 808 is color coded orange to match the color of region 806. Screen 802 also shows a peak cough flow value of 123 liters per minute (L/min) in box 786 and a tidal volume of 440 milliliters (mL) in box 788. Thus, at the instant in time to which screen 802 of FIG. 32 pertains, control circuitry 500 of device 10 has accumulated enough data during the delivery of the automatic MIE therapy to be able to calculate the peak cough flow and tidal volume values and populate boxes 786, 788 with the calculated values.

Figure 33:
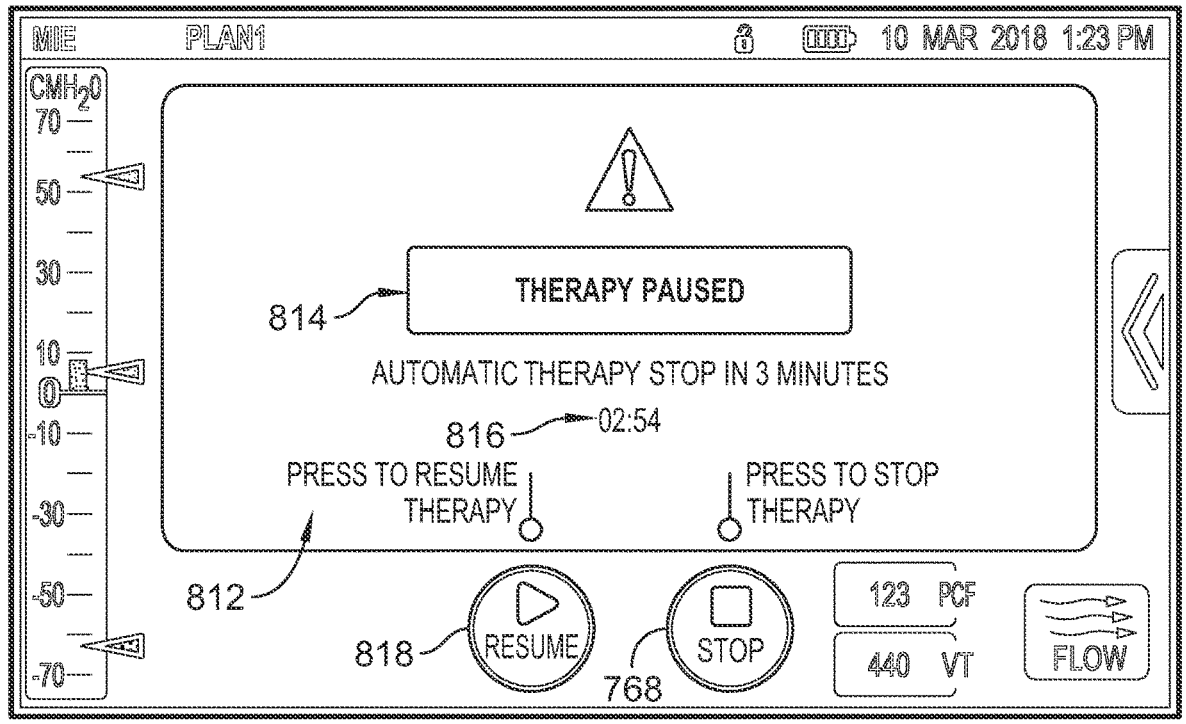
FIG. 33 is a screen shot of an automatic MIE therapy paused screen that appears on the GUI in response to the pause button of the screen of FIG. 32 being pressed.

In response to pause button 800 being pressed during automatic MIE therapy, an automatic MIE therapy paused screen 810 appears on GUI 16 as shown in FIG. 33. Screen 810 includes a window 812 having a box 814 with the text "THERAPY PAUSED" therein. Beneath box 814 is explanatory text which, in the illustrative example, states "AUTOMATIC THERAPY STOP IN 3 MINUTES." A timer 816 is shown beneath the explanatory text in window 812 to indicate, in some embodiments, how long the therapy has been paused or, in other embodiments, how much time is left until the therapy is automatically stopped. Thus, timer 816 counts up in some embodiments and counts down in other embodiments. After pause button 800 is selected, it converts to a resume button 818 as shown in FIG. 33. Thus, the user is able to select stop button 768 on screen 810 to stop the therapy altogether without having to wait for the three minute pause period to elapse, or the user can select the resume button 818 to resume the automatic MIE therapy.

Figure 34:
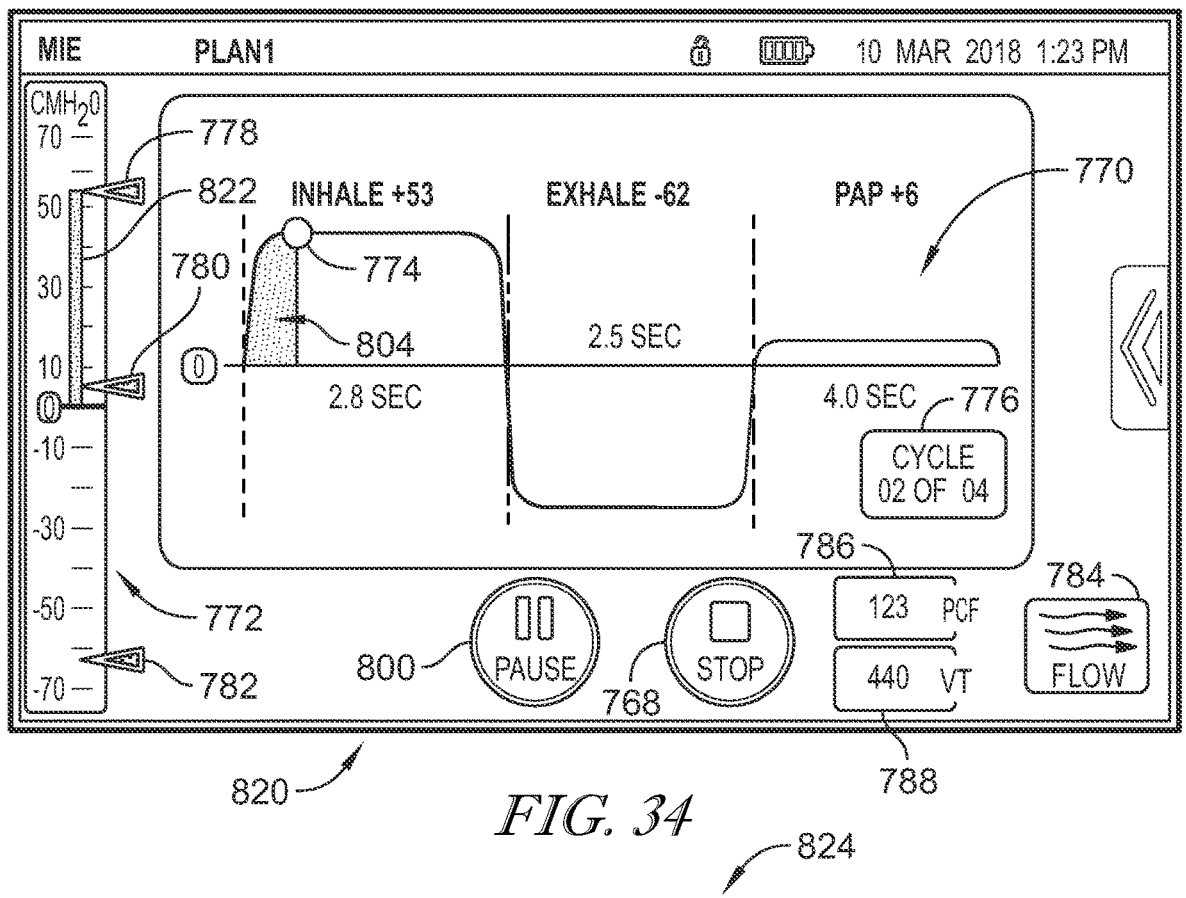
FIG. 34 is a screen shot of a resume automatic MIE therapy screen that appears on the GUI after a resume button of the screen of FIG. 33 is pressed, showing that pressing the resume button restarts the current cycle of therapy from the beginning of the cycle.

In response to resume button 818 being selected on screen 810 of FIG. 33, a resume automatic MIE therapy screen 820 appears on the GUI 16 as shown, for example, in FIG. 34. In the illustrative embodiment, selection of the resume button 818 restarts the current cycle of therapy from the beginning of the cycle. For example, box 776 of screen 802 of FIG. 32 shows that the automatic MIE therapy was in the second cycle of four cycles when pause button 800 was selected. Thus, when resume button 818 of screen 810 of FIG. 33 is selected, the second cycle begins anew. It will be appreciated, therefore, that screen 820 shown in FIG. 34 represents an instant in time after a beginning portion of the restarted second cycle has transpired. As also shown in FIG. 34, an inhale segment 822 is superimposed on bar 772 from 0 cmH$_2$O up to upper arrow 778 to indicate that the therapy is currently in the inhale phase. In some embodiments, bar 822 is color coded blue to match the color of region 804.

Figure 35:
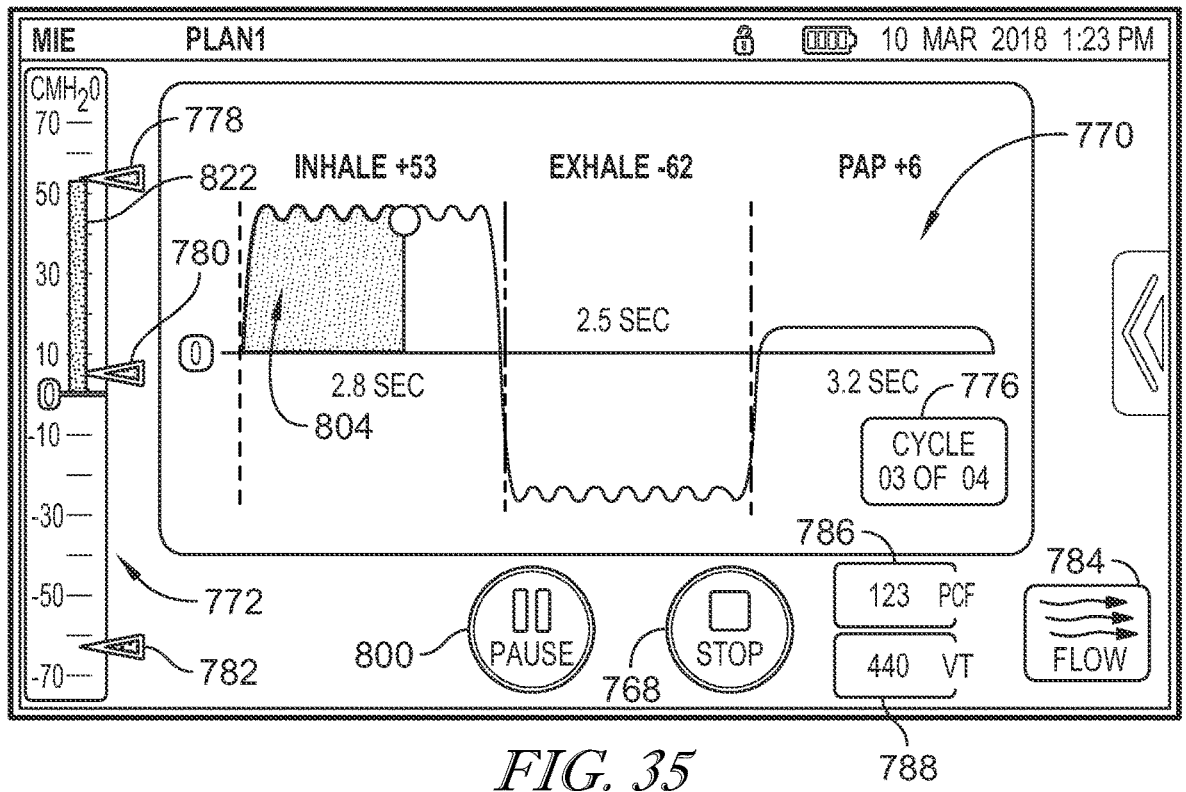
FIG. 35 is a screen shot of another automatic MIE therapy screen of another cycle of automatic MIE therapy showing that the respiratory therapy apparatus is programmed to superimpose oscillations on the baseline pressures of the inhale and exhale portions of the automatic MIE therapy.

Referring now to FIG. 35, another automatic MIE therapy screen 824 of another cycle of automatic MIE therapy is shown and has box 776 indicating that the automatic MIE therapy has progressed to a third cycle of four cycles. Graph 770 shows that the respiratory therapy apparatus 10 is programmed to superimpose high frequency oscillations on the baseline pressures of the inhale and exhale portions of the automatic MIE therapy. Inclusion of high frequency oscillations on a baseline pressure is sometimes referred to herein as "flutter" or the "flutter feature" or the "flutter function." In the third cycle, the pause airway pressure is programmed to have a duration of 3.2 seconds rather than 4.0 seconds. Otherwise, screen 824 of FIG. 35 is similar to screens 802, 820 of FIGS. 32 and 34, respectively, and so like reference numbers are used in FIG. 35 for the like features.

Figure 36:
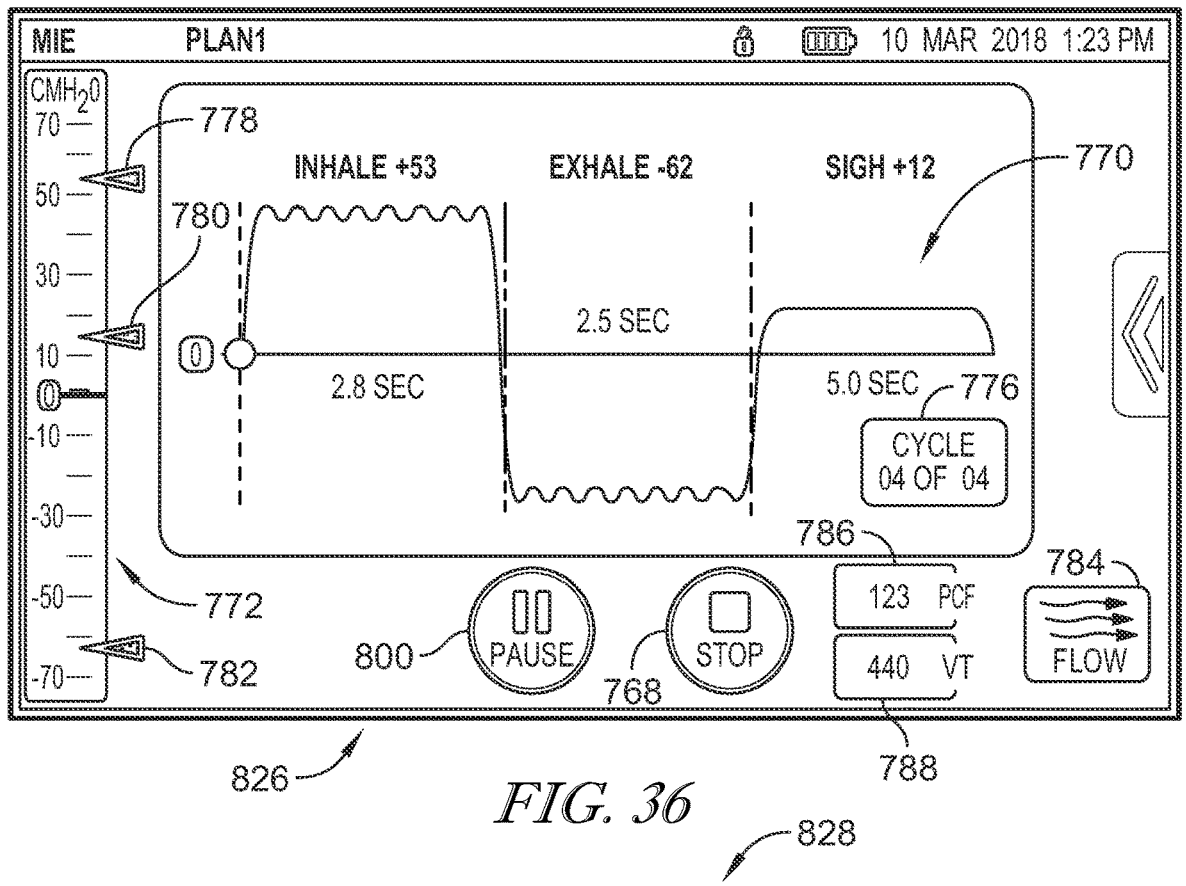
FIG. 36 is a screen shot of another automatic MIE therapy screen of a final cycle of automatic MIE therapy similar to the automatic MIE therapy cycle of FIG. 35 but having a sigh phase of positive pressure at the very end of the cycle rather than a positive airway pressure (PAP) phase.

Referring now to FIG. 36, yet another automatic MIE therapy screen 826 of a final cycle of automatic MIE therapy similar to the automatic MIE therapy screen 824 of FIG. 35 but having a sigh phase of positive pressure at the very end of the cycle rather than a positive airway pressure (PAP) phase. In the illustrative example, the sigh phase is programmed to have a positive pressure of 12 cmH$_2$O for 5.0 seconds. As also shown in FIG. 36, box 776 indicates that the fourth cycle of four total cycles is occurring and middle arrow 780 has been elevated on bar 772 to match the programmed sigh pressure of 12 cmH$_2$O. In some embodiments, the sigh phase portions of graph 770 and middle arrow 780 are color coded green which is the same color coding as the PAP phase.

Figure 37:
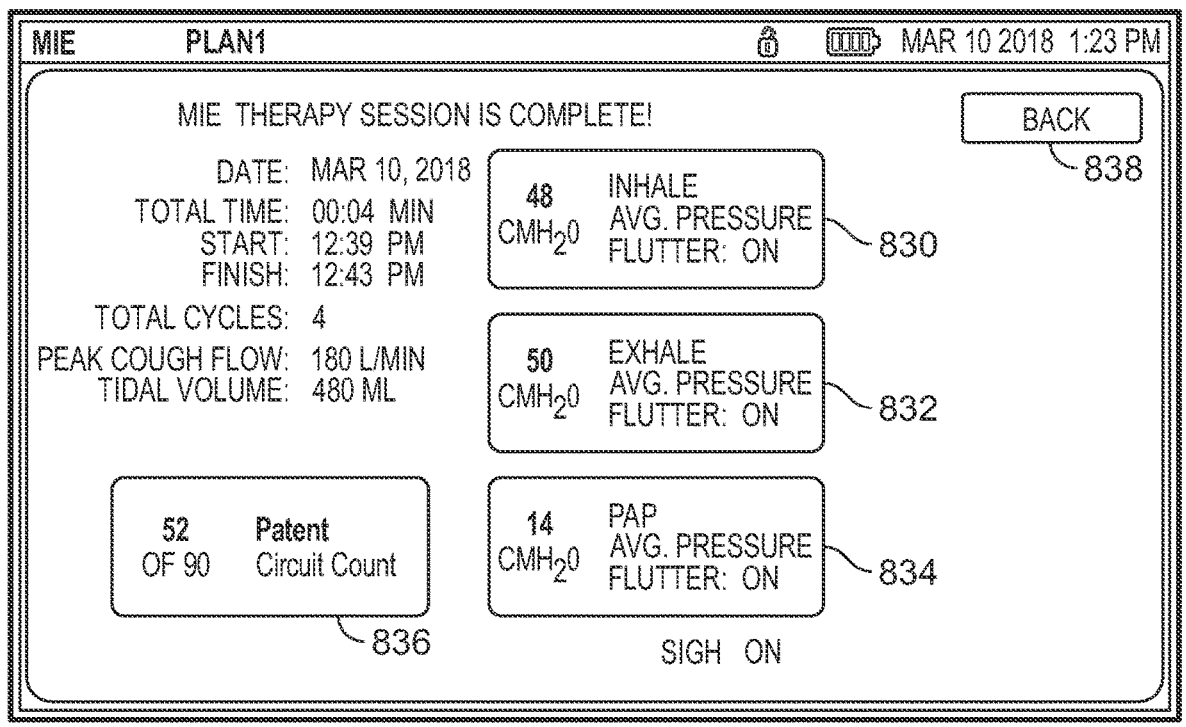

After the automatic MIE therapy session is complete or in response to the stop button 768 being selected during the automatic MIE therapy, an automatic MIE therapy complete screen 828 appears on GUI 16 as shown, for example, in FIG. 37. MIE therapy complete screen 828 displays a variety of statistical data and other information pertaining to the automatic MIE therapy that has just been completed, or stopped. For example, screen 828 includes an inhale field 830, an exhale field 832, and a PAP field 834. Each of fields 830, 832, 834 includes text indicating the average pressure and whether the flutter feature was on or off for the corresponding phase (e.g., inhale, exhale, and PAP). Screen 828 also includes a patient circuit count field 836 which indicates the number of uses of the filter unit 390 that was attached to port 24 during the therapy session. As shown in the illustrative example, the usage count of the filter unit 390 has been incremented to 52 uses out of a maximum number of 90 uses. That is, the usage count number in field 836 is the new usage count number for filter unit 390 after the completion of the therapy session resulting in display of screen 828 on GUI 16.

Beneath field 834, screen 828 includes text indicating that the sigh function at the end of the automatic MIE therapy was turned on. Above field 836 the following information is provided on screen 828: date of the therapy, total time of the therapy, the start time of the therapy, the finish time of the therapy, the total number of cycles completed during the therapy, the peak cough flow during the therapy, and the tidal volume during the therapy. Screen 828 also includes a back button 838, the selection of which returns the user to screen 764 of FIG. 29.

Figure 38:
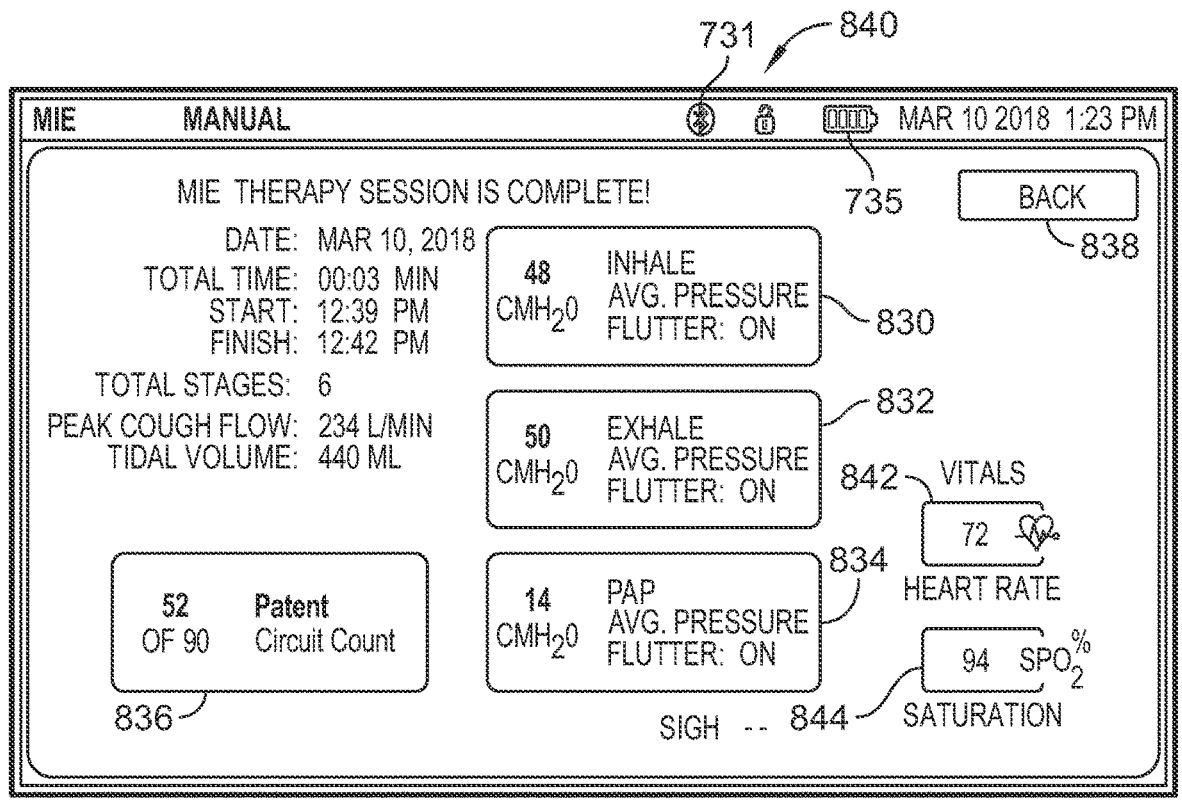
FIG. 38 is a screen shot of a manual MIE therapy complete screen that appears on the GUI at the end of a manual MIE therapy session, the manual MIE therapy complete screen showing the statistical data and other information pertaining to manual MIE therapy that has just been completed including indicating that the sigh function at the end of the automatic MIE therapy was turned off and showing vitals data relating to the patient's heart rate and blood oxygen saturation percentage.

Referring now to FIG. 38, an example of a manual MIE therapy complete screen 840 is shown. Screen 840 is similar to screen 828 with just a few exceptions. One exception is that the sigh pressure was not turned on as indicated by the double dashes adjacent to the word "SIGH" beneath field 834. Another exception is that total stages are given in the data above field 836 rather than total cycles. Yet another exception is that screen 840 has a heart rate field 842 with a numerical value therein in beats per minute for the patient's heart rate during the therapy session and a saturation field 844 with a numerical value there for the patient's blood oxygen saturation percentage during the therapy session. In some embodiments, the numerical values in fields 842, 844 are averages for the duration of the therapy session, and in other embodiments, the numerical values in fields 842, 844 are the numerical values measured at the end of the therapy session.

Fields 842, 844 appear on screens 828, 840 after the therapy session if a patient physiological monitor was communicating wirelessly with control circuitry 500, such as via Bluetooth communications as indicated by icon 731 in FIG. 38, during the therapy session. In some embodiments, a single pulse oximeter provides both the patient's heart rate and the patient's blood oxygen saturation percentage to control circuitry 500 of device 10. If WiFi or LTE communication capability of control circuitry 500 is turned on, as will be discussed in further detail below, then upon the end of the therapy session, the control circuitry 500 operates to transmit the data shown on screen 828 or screen 840, as the case may be, to one or more remote computer devices assuming that the control circuitry 500 is successfully communicating with a wireless access point (WAP). A WiFi icon (see FIGS. 236-262 for an example) is displayed on the header of screen 828 or screen 840 during the wireless data transmission process.

If tab 688 is selected on screen 764 of FIG. 29, a menu screen 846, similar to menu screen 690 of FIG. 21 but having screen 764 features grayed out in the background, appears on the GUI 16 as shown in FIG. 39. Like screen 690 of FIG. 21, screen 846 of FIG. 39 includes menu bar 692 with icons 694, 696, 698, 700, 702 and menu close tab 708. In response to the help or information icon 702 being selected on the menu screen 846 of FIG. 39, a help menu screen 848 appears on the GUI 16 as shown in FIG. 40. Help menu screen 848 includes a menu 850 of buttons or icons that are selectable to navigate to other help screens as will be described in further detail below. The buttons on menu 850 in the illustrative example include an automatic therapy button 852, a manual therapy button 854, a therapy overview button 856, a therapy options button 858, and a modify therapy button 860. Screen 848 also has the return button 796 the selection of which returns the user to screen 764 of FIG. 29.

Figure 41:
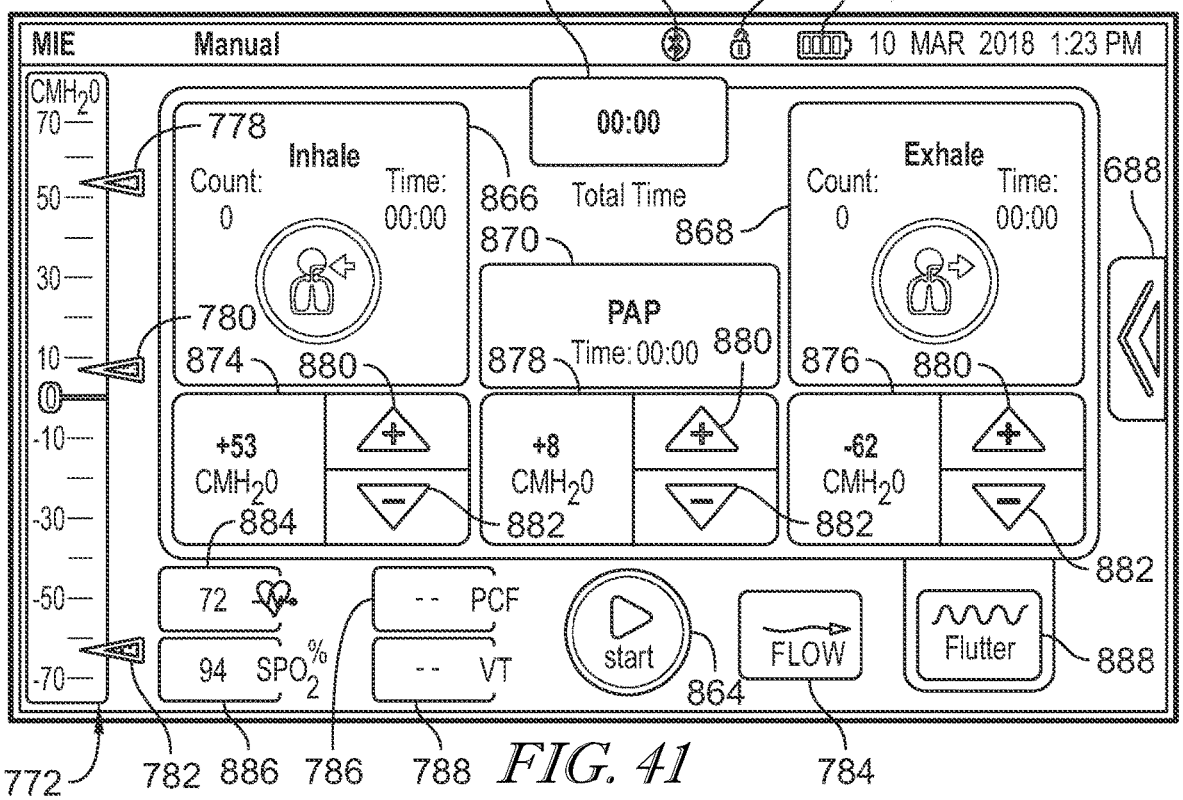
FIG. 41 is a screen shot of a main manual MIE therapy screen that appears on the GUI in response to the manual button of the main MIE therapy selection screen of FIG. 19 being selected.

Referring now to FIG. 41, a main manual MIE therapy screen 862 appears on GUI 16 in response to manual button 680 of the main MIE therapy selection screen 676 of FIG. 19 being selected. However, the bar code scanning process shown on screens 722, 726, 732, 738, 750, 756 of FIGS. 23-28 also occurs, as appropriate, prior to display of screen 862 if the bar code scanning function of device 10 is turned on. The discussion above of screens 722, 726, 732, 750, 756 of FIGS. 23-28 after selection of button 678 of screen 676 is equally applicable with regard to selection of button 680 of screen 676 and thus, does not need to be repeated.

Main manual MIE therapy screen 862 of FIG. 41 includes a start button 864, an inhale button 866, an exhale button 868, and a positive air pressure (PAP) field 870 between buttons 866, 868. Within inhale button 866 is a count number beneath the text "Count:" that indicates the number of times the inhale button has been selected during the manual MIE therapy session and a timer beneath the text "Time:" to indicate the amount of time the current or most recent inhale phase has occurred during the manual MIE therapy session. A patient-and-lung indicia is shown inside a circle within inhale button 866 with an arrow pointing toward the mouth of the patient-and-lung indicia to indicate that button 866 pertains to the inhale phase of the manual MIE therapy.

Similarly, within exhale button 868 is a count number beneath the text "Count:" that indicates the number of times the exhale button has been selected during the manual MIE therapy session and a timer beneath the text "Time:" to indicate the amount of time the current or most recent exhale phase has occurred during the manual MIE therapy session. The patient-and-lung indicia is also shown inside a circle within exhale button 868 but with an arrow pointing away from the mouth of the patient-and-lung indicia to indicate that button 868 pertains to the exhale phase of the manual MIE therapy. The PAP field 870 includes a timer to the right of the text "Time:" to indicate the amount of time that the current or most recent PAP phase has occurred during the manual MIE therapy.

Still referring to screen 862 of FIG. 41, a main timer 872 is shown above field 870 and between buttons 866, 868. Timer 872 indicates the overall time of the manual MIE therapy session. Timer 872 and the timers in buttons 866, 868 and in field 870 are each in a minutes:seconds format and are each shown to be 00:00 in FIG. 41 since the manual MIE therapy session has not yet started. Screen 862 has an inhale pressure information and adjustment field 874 beneath button 866, an exhale pressure information and adjustment field 876 beneath button 868, and a PAP information and adjustment field 878 beneath PAP field 870. Each of fields 874, 876, 878 indicates the baseline pressure that is programmed for the corresponding phase of the manual MIE therapy. In the illustrative example, field 874 indicates that the baseline inhale pressure is programmed for +53 cmH$_2$O, field 876 indicates that the baseline exhale pressure is programmed for −62 cmH$_2$O, and field 878 indicates that the PAP pressure is programmed for +8 cmH$_2$O.

Each of fields 874, 876, 878 includes an up arrow icon 880 and a down arrow icon 882 which are touched successively to increment or decrement, respectively, the corresponding pressure value by 1 cmH$_2$O. Alternatively, each of arrow icons 880, 882 can be selected and held continuously and the respective pressure value will be incremented or decremented, respectively, by 1 cmH$_2$O for every second held, up to five seconds, after which the pressure value will be incremented or decremented, respectively, by 1 cmH$_2$O for every ½ second held. If an upper pressure limit or lower pressure limit is reached for any of the pressure values in fields 874, 876, 878, then the up arrow icon 880 or down arrow icon 882, as the case may be, becomes inactive and continued selection of the particular arrow icon 880, 882 has no effect.

Some portions of screen 862 of FIG. 41 are similar to like portions of the screens of FIGS. 25-36 and so like reference numbers are used to denote these like portions and the descriptions of these like portions above is equally applicable to screen 862 of FIG. 41 and to subsequent Figs. herein. As shown in the header area of screen 862, Bluetooth icon 731 appears which indicates that control circuitry 500 of device 10 is in wireless communication with some other device. In the illustrative example, circuitry 500 of device 10 is in communication with a pulse oximeter and so a heart rate field 884 and a blood oxygen saturation field 886 (aka saturation field 886 or SPO$_2$ field 886) appear on screen 862 between bar 772 and fields 786, 788. Also in the illustrative example, field 884 indicates that the patient's heart rate (HR) is 72 beats per minute (BPM) and the patient's blood oxygenation is 94%. Thus, values from the pulse oximeter are received by circuitry 500 and displayed on GUI 16 prior to the manual MIE therapy session even beginning in the depicted example. Screen 862 further includes a flutter button 888 to the right of the flow button 784. Flutter button 888 is pressed to control a flutter feature of device 10 as will be discussed below in connection with FIGS. 52-62.

Figure 42:
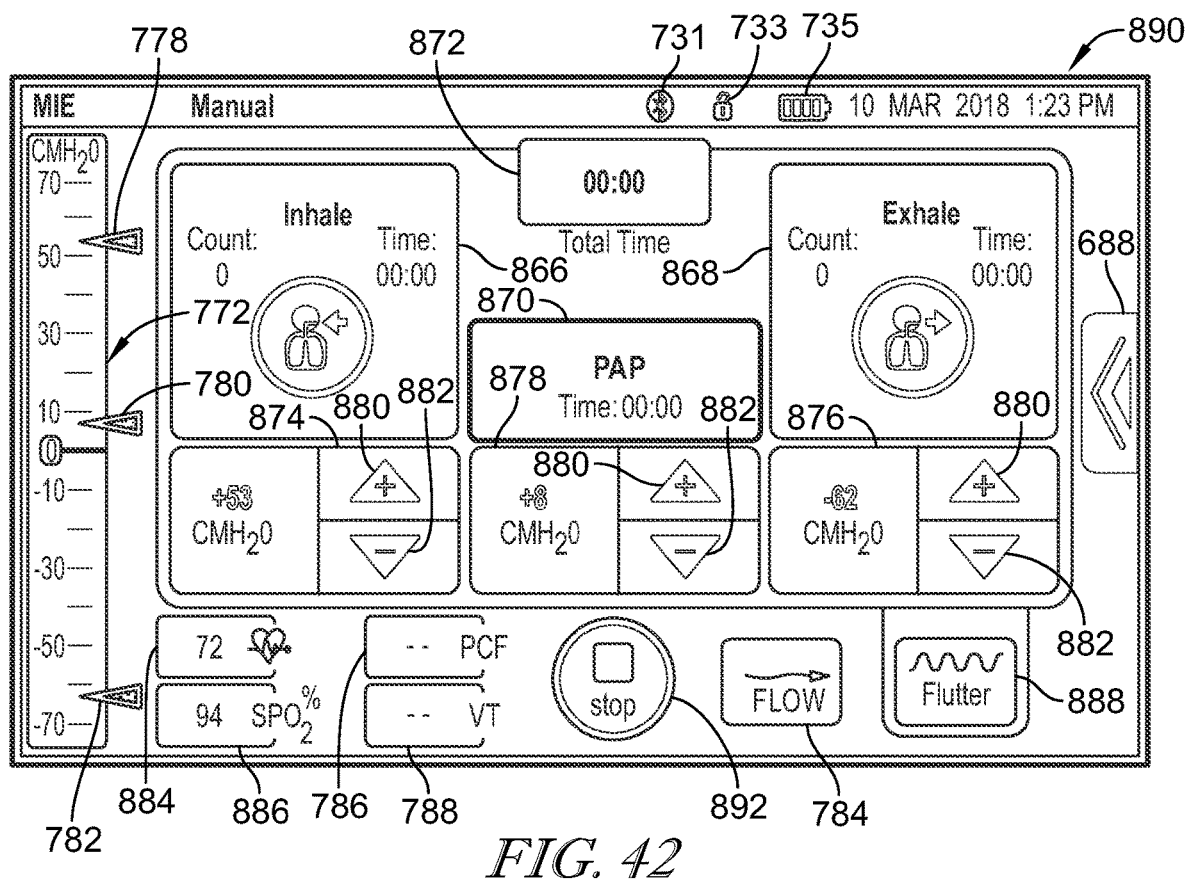
FIG. 42 is a screen shot of a manual MIE therapy preparation screen that appears on the GUI in response to a start button being selected on the main manual MIE therapy screen of FIG. 41, the manual MIE therapy preparation screen showing the start button being converted to a stop button and showing inhale and exhale icons being grayed out during a preparation operation of the manual MIE therapy.

Referring now to FIG. 42, a manual MIE therapy preparation screen 890 appears on GUI 16 in response to start button 864 being selected on main manual MIE therapy screen 862 of FIG. 41, and assuming that filter unit 390 attached to port 24 passes the RFID count check and that battery power is greater than 20% of a full battery charge in the event that device 10 is operating under battery power rather than being plugged in to an AC power outlet. If the RFID count check of filter unit 390 fails or if battery power is less than 20% of a full battery charge, again assuming device 10 is not plugged into an AC power outlet, then an appropriate alert message (e.g., screen 790 of FIG. 30) is shown on GUI 16 in this regard. Screen 890 of FIG. 42 is very similar to screen 862 of FIG. 41 expect that the start button 864 of screen 862 is converted to a stop button 892 on screen 890. Furthermore, the inhale and exhale icons 866, 868 remain grayed out on screen 890 during a preparation operation of the manual MIE therapy in which the pneumatic system 320 is turned on and configured to provide the PAP pressure at outlet port 24 of device 10.

Figure 43:
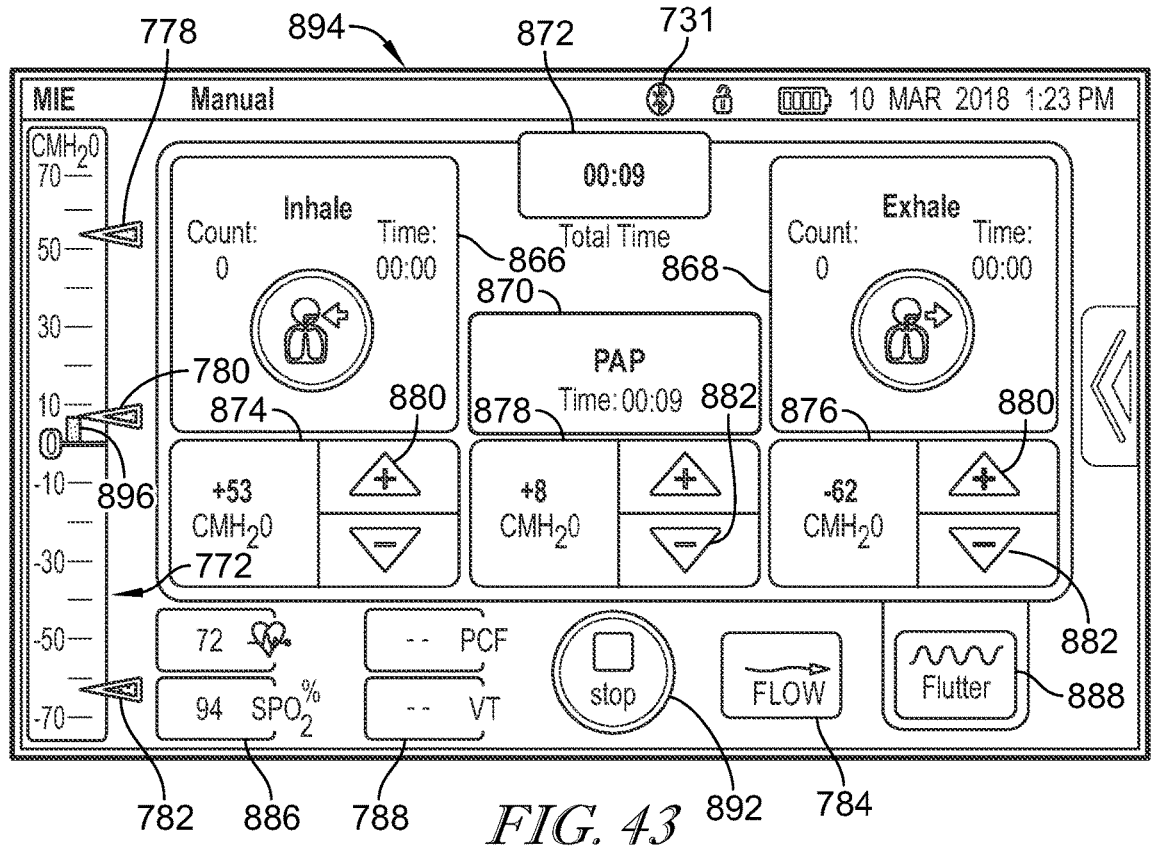
FIG. 43 is a screen shot of a manual MIE therapy ready screen that appears on the GUI after the preparation operation, the manual MIE therapy ready screen having the inhale and exhale icons illuminated and ready for use, and a positive airway pressure (PAP) field being illuminated to indicate that a PAP is being applied to a user's airway by the respiratory therapy apparatus.

Referring now to FIG. 43, a manual MIE therapy ready screen 894 appears on GUI 16 after the preparation operation. Manual MIE therapy ready screen 894 has the patient-and-lung indicia within the inhale and exhale buttons 866, 868 illuminated to indicate that buttons 866, 868 are ready for use. The indicia illumination is indicated in FIG. 43 by the use of thicker lines but in a real world embodiments, the indicia of buttons 866, 868 change from being grayed out to appearing with white lines and with the background of screen 894 being black in color. Also in screen 894, positive airway PAP field 870 is illuminated to indicate that the PAP is being applied to a patient's airway by the respiratory therapy apparatus 10. In FIG. 43, the illumination of field 870 is indicated by a bolded line at the border around field 870. In real world embodiments, the border around field 870 changes from being grayed out to being shown in green. As also shown on screen 894 of FIG. 43, a PAP segment 896 is superimposed on bar 772 from 0 cmH$_2$O up to upper arrow 780 to indicate that the therapy is currently in the PAP phase. In some embodiments, bar 896 is color coded green to match the color of the border of field 870.

Figure 44:
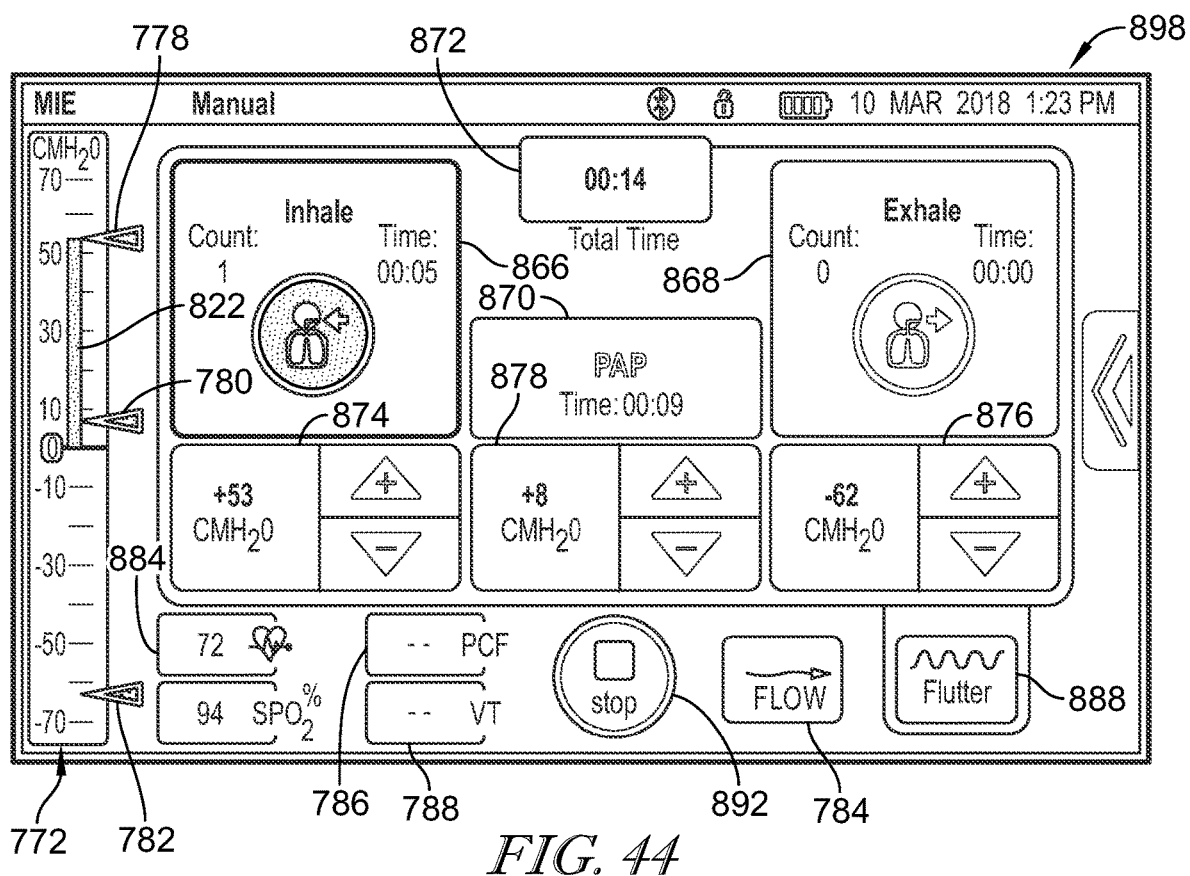
FIG. 44 is a screen shot of a manual MIE therapy inhale screen showing the inhale icon illuminated and filled in with a surrounding border highlighted while a user presses and holds the inhale icon for delivery of positive pressure to the user's lungs by the respiratory therapy apparatus and showing the exhale icon and the PAP field being grayed out while the user presses and holds the inhale icon.

Referring now to FIG. 44, a manual MIE therapy inhale screen 898 appears on GUI 16 after buttons 866, 868 become active on screen 894 of FIG. 43 and after a user selects and holds the inhale button 866 for delivery of positive pressure to the user's lungs by the respiratory therapy apparatus 10. While the user selects (e.g., presses or touches) and holds button 866, button 866 is illuminated to indicate that the inhale pressure is being applied to the patient's airway by the respiratory therapy apparatus 10. Button 868 and field 870 are grayed out while button 866 is pressed in the illustrative example. In this regard, the text "PAP" in field 870 changes from green to gray as indicated by the difference between the manner in which the text "PAP" is shown in FIG. 44 as compared to FIGS. 41-43.

In FIG. 44, the illumination of button 866 is indicated by a bolded line at the border around button 866. In some real world embodiments, the border around button 866 changes from being grayed out to being shown in blue when button 866 is pressed and held. Furthermore, the area between the circle and the patient-and-lung indicia in button 866 becomes filled in with blue while button 866 is pressed and held in some embodiments. As also shown on screen 898 of FIG. 44, inhale segment 822 is superimposed on bar 772 from 0 cmH$_2$O up to upper arrow 778 to indicate that the therapy is currently in the inhale phase. Main timer 872 of FIG. 44 shows a time of 00:14 (i.e., 14 seconds) which matches the PAP time of nine seconds shown in timer 872 and field 870 of FIG. 43 plus the inhale time of five seconds shown in button 866 of FIG. 44. Furthermore, the count in button 866 of screen 898 has been incremented from zero, as shown in FIGS. 41-43, to one.

Figure 45:
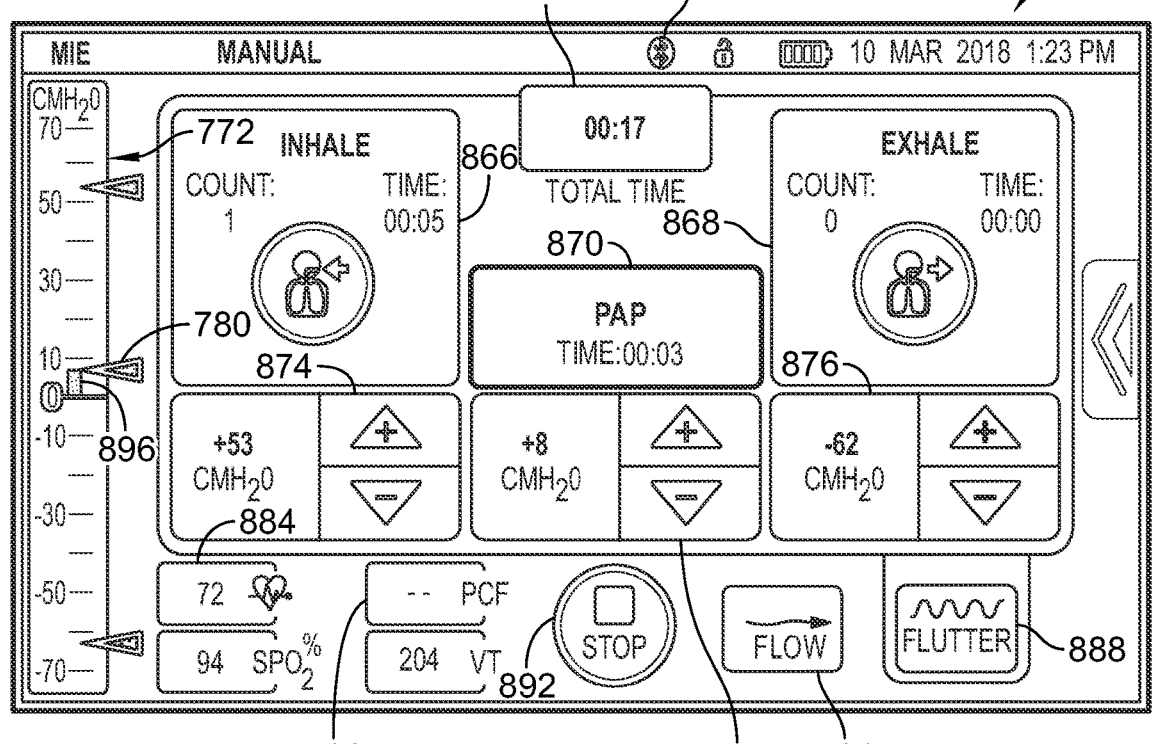
FIG. 45 is a screen shot of a manual MIE therapy inhale release screen showing the inhale and exhale icons once again being illuminated and ready for use, and the PAP field once again being illuminated to indicate that PAP is once again being applied to a user's airway by the respiratory therapy apparatus.

Referring now to FIG. 45, a manual MIE therapy inhale release screen 900 appears on GUI 16 in response to the user releasing button 866 on screen 898 of FIG. 44. Screen 900 is basically the same as screen 894 of FIG. 43 except that main timer 872 now shows a total time of seventeen seconds which matches the previous time, fourteen seconds, of screen 898 shown in FIG. 44 plus the three seconds of PAP time shown in field 870 of screen 900 of FIG. 45. FIG. 45 also shows the inhale and exhale icons 866, 868 once again being illuminated and ready for use. It should be understood that the PAP phase corresponding to screens 894, 900 of FIGS. 43 and 45 do not require the user to press, or press and hold, PAP field 870. That is, during the delivery of manual MIE therapy, the PAP phase is the default phase in which respiratory therapy apparatus 10 operates when neither of buttons 866, 868 is pressed.

Figure 46:
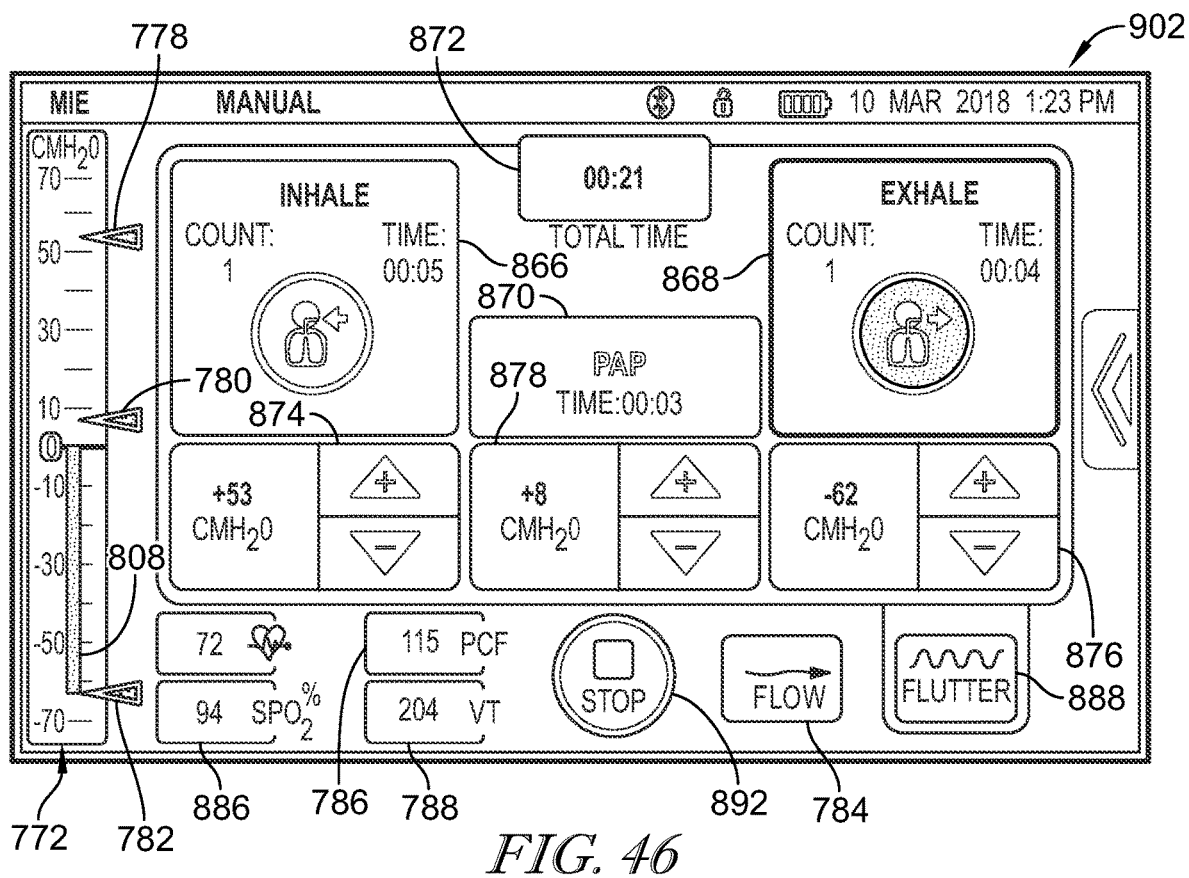
FIG. 46 is a screen shot of a manual MIE therapy exhale screen showing the exhale icon illuminated and filled in with a surrounding border highlighted while a user presses and holds the exhale icon for delivery of negative pressure to the user's lungs by the respiratory therapy apparatus and showing the inhale icon and the PAP field being grayed out while the user presses and holds the exhale icon.

Referring now to FIG. 46, a manual MIE therapy exhale screen 902 appears on GUI 16 after buttons 866, 868 become active on screen 900 of FIG. 45 and after the user selects and holds the exhale button 868 for delivery of negative pressure to the user's lungs by the respiratory therapy apparatus 10. While the user selects (e.g., presses or touches) and holds button 868, button 868 is illuminated to indicate that the exhale pressure is being applied to the patient's airway by the respiratory therapy apparatus 10. Button 866 and field 870 are grayed out while button 868 is pressed in the illustrative example. In this regard, the text "PAP" in field 870, once again, changes from green to gray as indicated by the difference between the manner in which the text "PAP" is shown in FIG. 46 as compared to FIGS. 41-43 and 45.

In FIG. 46, the illumination of button 868 is indicated by a bolded line at the border around button 868. In some real world embodiments, the border around button 868 changes from being grayed out to being shown in orange when button 868 is pressed and held. Furthermore, the area between the circle and the patient-and-lung indicia in button 868 becomes filled in with orange while button 868 is pressed and held in some embodiments. As also shown on screen 902 of FIG. 46, exhale segment 808 is superimposed on bar 772 from 0 cmH$_2$O down to lower arrow 782 to indicate that the therapy is currently in the exhale phase. Main timer 872 of FIG. 46 shows a time of 00:21 (i.e., 21 seconds) which matches the previous time, seventeen seconds, of screen 900 shown in FIG. 45 plus the four seconds of exhale time shown in button 868 of screen 902 of FIG. 46. Furthermore, the count in button 868 of screen 902 has been incremented from zero, as shown in FIGS. 41-45, to one.

Figure 47:
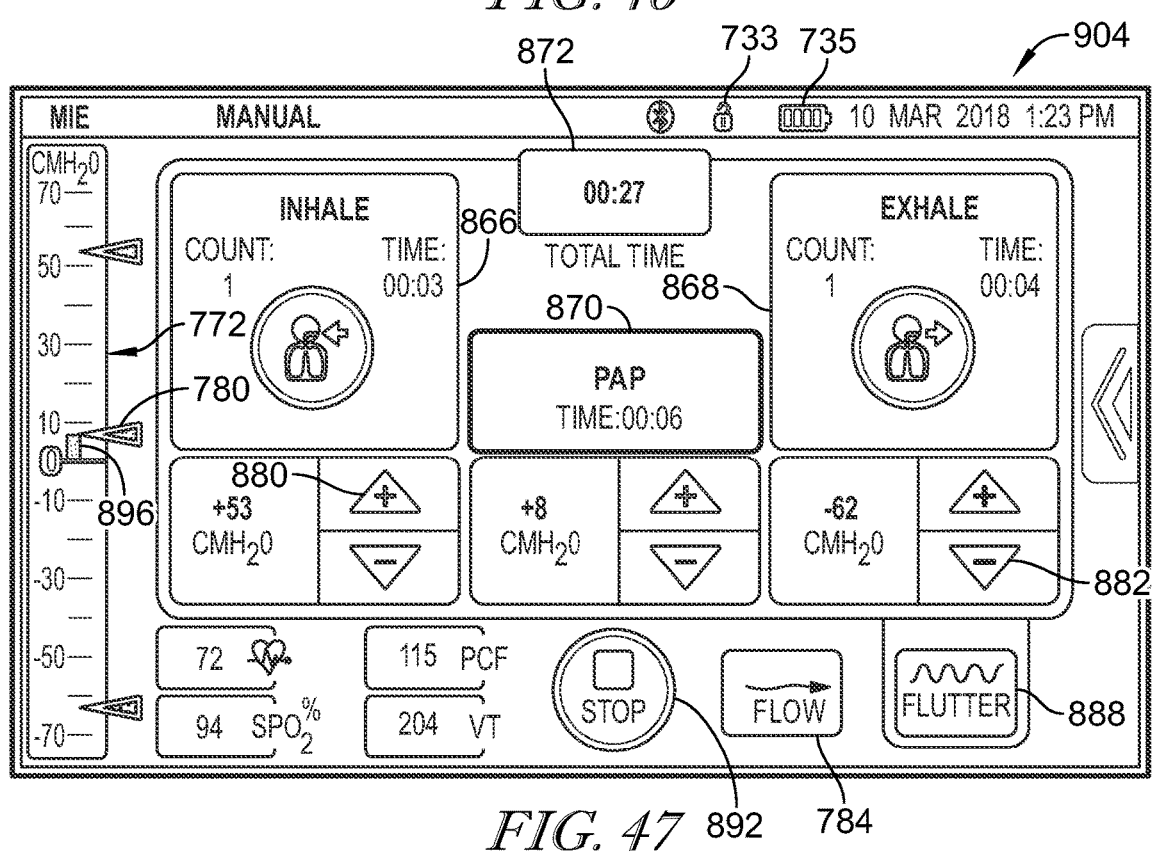
FIG. 47 is a screen shot of a manual MIE therapy exhale release screen showing the inhale and exhale icons once again being illuminated and ready for use, and the PAP field once again being illuminated to indicate that PAP is once again being applied to a user's airway by the respiratory therapy apparatus.

Referring now to FIG. 47, a manual MIE therapy exhale release screen 904 appears on GUI 16 in response to the user releasing button 868 on screen 902 of FIG. 46. Screen 904 is basically the same as screen 894 of FIG. 43 and screen 900 of FIG. 45 except that main timer 872 now shows a total time of twenty seven seconds which matches the previous time, twenty one seconds, of screen 902 shown in FIG. 46 plus the six seconds of PAP time shown in field 870 of screen 904 of FIG. 47. FIG. 47 also shows the inhale and exhale icons 866, 868 once again being illuminated and ready for use. As noted previously, during the delivery of manual MIE therapy, the PAP phase is the default phase in which respiratory therapy apparatus 10 operates when neither of buttons 866, 868 is pressed. Segment 896, once again, appears on bar 772 of screen 904 of FIG. 47 after exhale button 868 of screen 902 of FIG. 46 is released.

Figure 48:
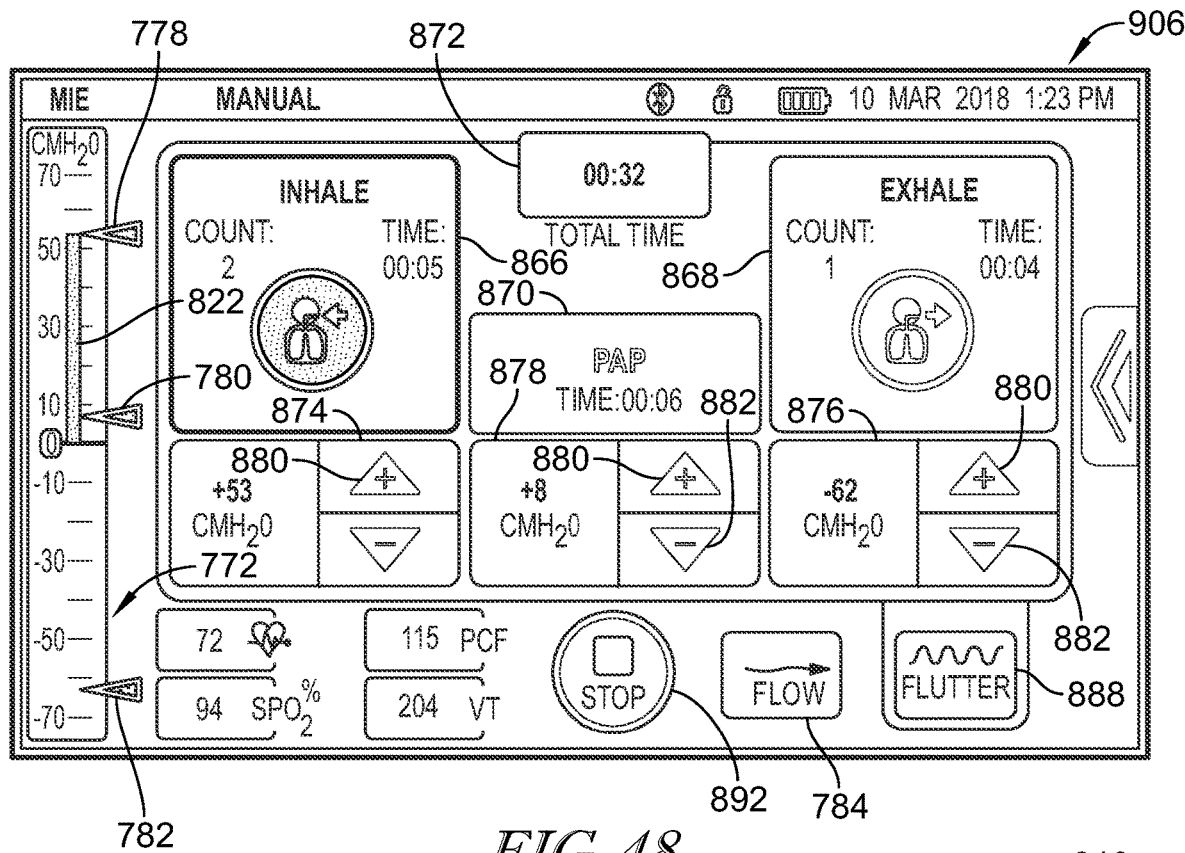
FIG. 48 is a screen shot of another manual MIE therapy inhale screen, similar to FIG. 44, showing the inhale icon once again illuminated and filled in with a surrounding border highlighted while a user once again presses and holds the inhale icon for delivery of positive pressure to the user's lungs by the respiratory therapy apparatus for a second cycle of mechanical insufflation.

Referring now to FIG. 48, another manual MIE therapy inhale screen 906, similar to screen 898 of FIG. 44, appears on GUI 16 after buttons 866, 868 become active on screen 904 of FIG. 47 and after a user, once again, selects and holds the inhale button 866 for delivery of positive pressure to the user's lungs by the respiratory therapy apparatus 10. The discussion above of screen 898 of FIG. 44 is equally applicable to screen 906 of FIG. 48 and is not repeated. However, main timer 872 of FIG. 48 shows a time of 00:32 (i.e., thirty two seconds) which matches the previous time of twenty seven seconds shown in timer 872 of FIG. 47 plus the current inhale time of five seconds shown in button 866 of FIG. 48. Furthermore, the count in button 866 of screen 906 has been incremented from one, as shown in FIGS. 44-47, to two.

During the manual MIE therapy of device 10, the cycle of manually pressing and holding inhale button 866, then releasing button 866, then pressing and holding exhale button 868, and then releasing button 868, with PAP phases occurring automatically between the inhale and exhale phases, as shown for illustrative purposes in FIGS. 43-48, can be repeated by the user as many times as the user wishes. After the user has completed the manual MIE therapy, the user presses stop button 892. After stop button 892 is pressed, GUI 16 displays the manual MIE therapy complete screen 840 of FIG. 38 which was discussed above.

Figure 49:
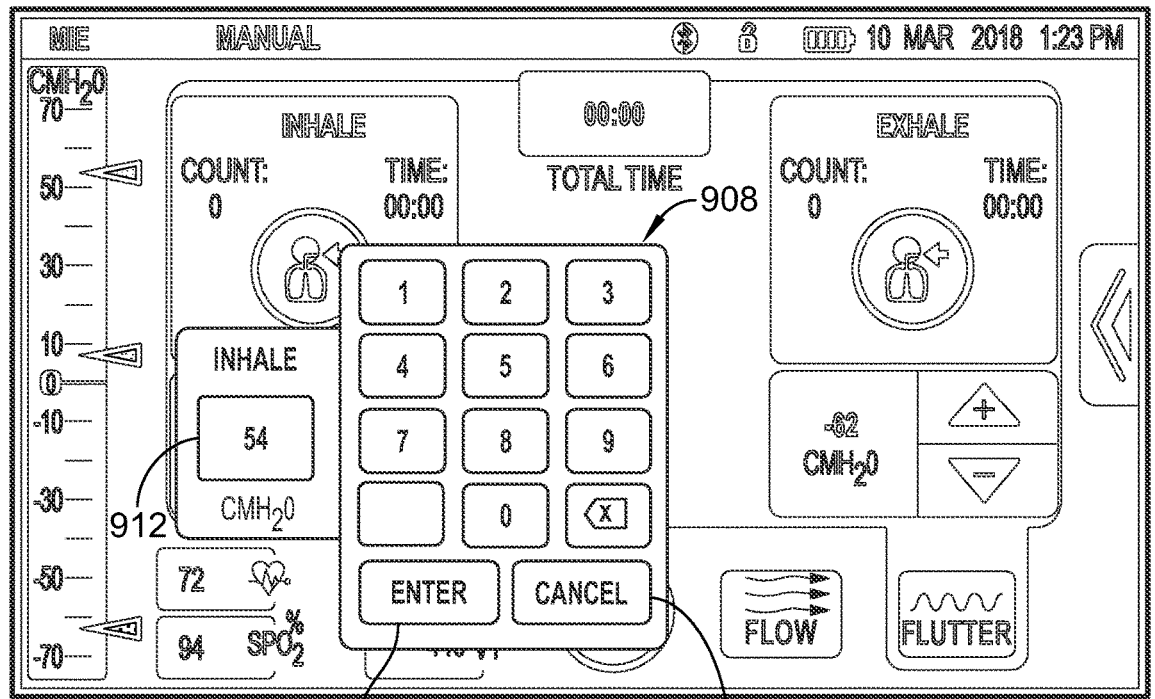
FIG. 49 is a screen shot of a manual MIE inhale pressure adjustment screen that appears on the GUI in response to the user selecting an inhale numerical value icon that appears beneath the inhale button of FIGS. 41-48, the manual inhale pressure adjustment screen including a graphical numeric keypad on which the user selects a new numerical value for the inhale pressure.
Figure 50:
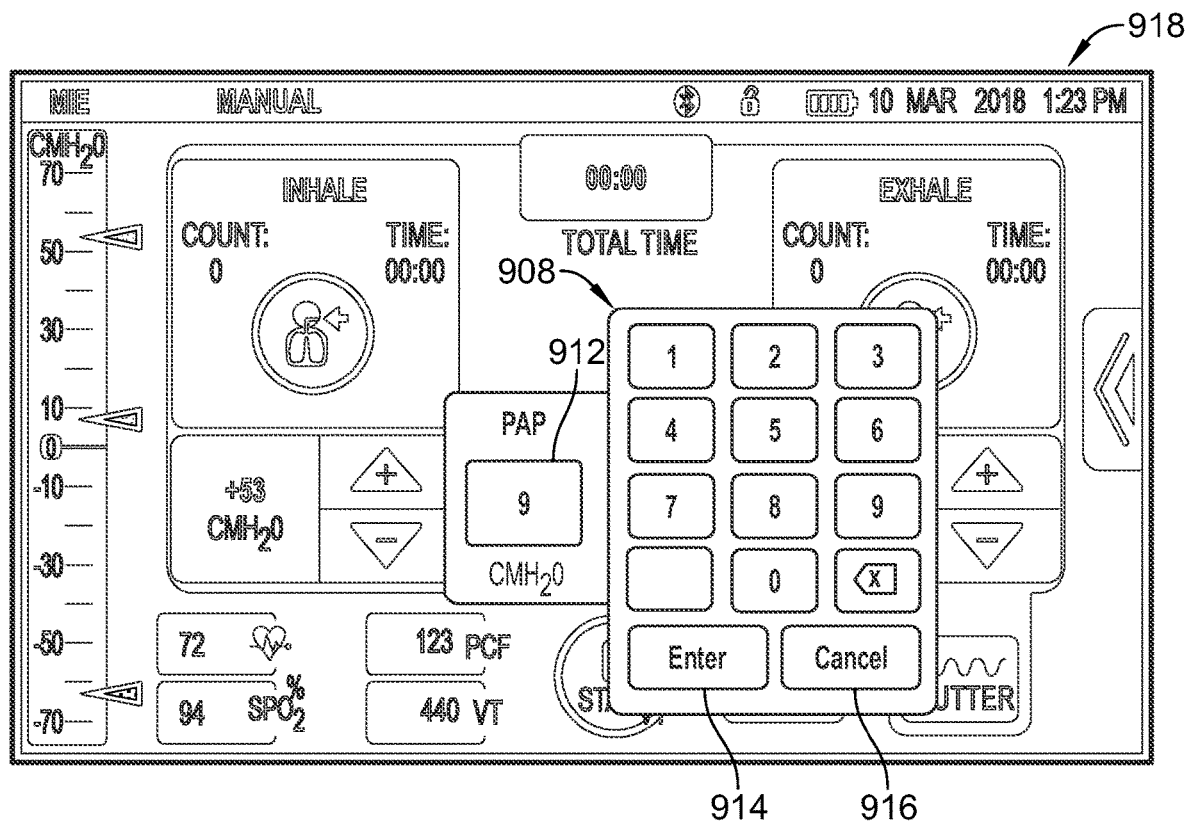
FIG. 50 is a screen shot of a manual MIE PAP pressure adjustment screen that appears on the GUI in response to the user selecting a PAP numerical value icon that appears beneath the PAP field of FIGS. 41-48, the manual PAP pressure adjustment screen including a graphical numeric keypad on which the user selects a new numerical value for the PAP pressure.
Figure 51:
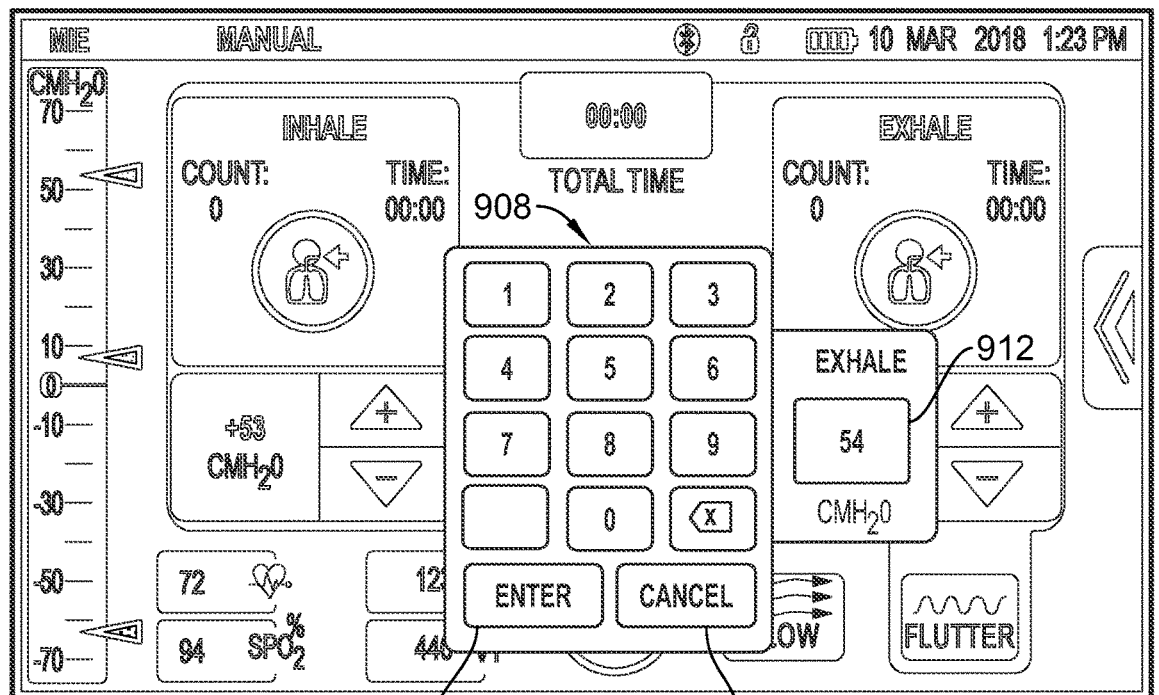
FIG. 51 is a screen shot of a manual MIE exhale pressure adjustment screen that appears on the GUI in response to the user selecting an exhale numerical value icon that appears beneath the exhale button of FIGS. 41-48, the manual exhale pressure adjustment screen including a graphical numeric keypad on which the user selects a new numerical value for the exhale pressure.

As discussed above, up arrow buttons 880 and down arrow buttons 882 can be used to adjust the baseline inhale, exhale, and PAP pressures, respectively, of the manual MIE therapy. The present disclosure also contemplates an alternative manner of adjusting these pressures as shown in FIGS. 49-51. In particular, instead of selecting arrow icons 880, 882 in fields 874, 876, 878, the user touches or presses the numerical pressure values appearing in fields 874, 876, 878. In the illustrative example, arrow icons 880, 882 appear in the right half of respective fields 874, 876, 878 and the numerical pressure values appear in the left half of respective fields 874, 876, 878. Selection of the numerical pressure value in one of fields 874, 876, 878 results in a graphical numerical keyboard 908 appearing on GUI 16 for direct entry of a new pressure value.

As shown in FIG. 49, a manual MIE inhale pressure adjustment screen 910 appears on the GUI 16 in response to the user selecting the inhale numerical value in field 874. The graphical numeric keypad 908 of screen 910 is then used to type in a new numerical value for the inhale pressure. A typed value window 912 overlies the region wherein the inhale pressure value of field 874 was shown previously. After the user types in the new inhale pressure value, an enter button 914 of graphical numeric keyboard 908 is selected to save the new inhale pressure value for subsequent use during future manual MIE therapy sessions. If the user decides not to enter a new inhale pressure value, then a cancel button 916 of keyboard 908 is selected and the previous inhale pressure value is used for future manual MIE therapy sessions.

In a similar manner, a manual MIE PAP pressure adjustment screen 918, shown in FIG. 50, appears on the GUI 16 in response to the user selecting the PAP numerical value in field 878. The graphical numeric keypad 908 of screen 918 is then used to type in a new numerical value for the PAP pressure. In screen 918, the typed value window 912 overlies the region wherein the PAP pressure value of field 878 was shown previously. After the user types in the new PAP pressure value, enter button 914 of graphical numeric keyboard 908 is selected to save the new PAP pressure value for subsequent use during future manual MIE therapy sessions. If the user decides not to enter a new PAP pressure value, then cancel button 916 of keyboard 908 is selected and the previous PAP pressure value is used for future manual MIE therapy sessions.

Also in a similar manner, a manual MIE exhale pressure adjustment screen 920, shown in FIG. 51, appears on the GUI 16 in response to the user selecting the exhale numerical value in field 876. The graphical numeric keypad 908 of screen 920 is then used to type in a new numerical value for the exhale pressure. In screen 920, the typed value window 912 overlies the region wherein the exhale pressure value of field 876 was shown previously. After the user types in the new exhale pressure value, enter button 914 of graphical numeric keyboard 908 is selected to save the new exhale pressure value for subsequent use during future manual MIE therapy sessions. If the user decides not to enter a new exhale pressure value, then cancel button 916 of keyboard 908 is selected and the previous exhale pressure value is used for future manual MIE therapy sessions.

Figure 52:
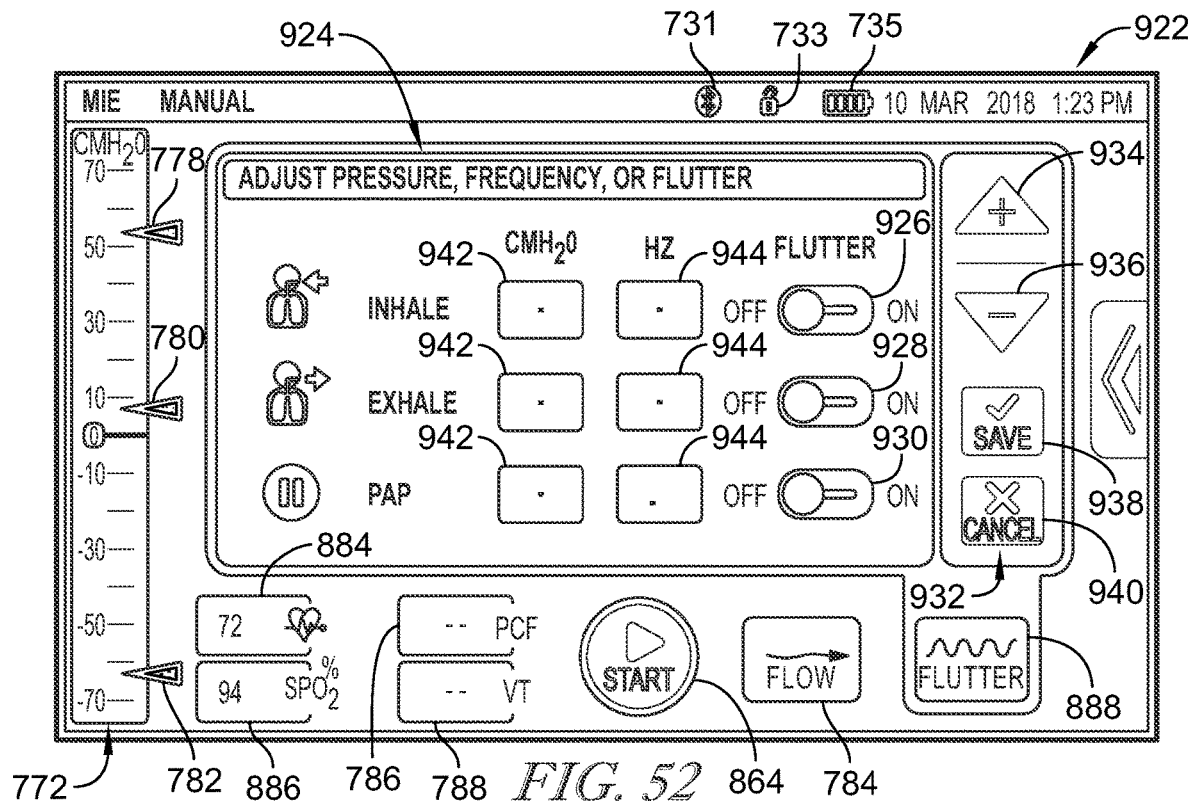
FIG. 52 is a screen shot of a manual MIE flutter on/off screen that appears on the GUI in response to a flutter icon of FIG. 41 being selected, the manual MIE flutter on/off screen including first, second, and third slider inputs that are used to turn a flutter feature of the respiratory therapy apparatus on and off for the inhale, exhale, and PAP portions, respectively, of the manual MIE therapy.

During manual MIE therapy, the flutter button 888 is inactive and grayed out. However, prior to the start button 864 being selected on the main manual MIE therapy screen 862 of FIG. 41, button 888 is active and can be selected to program the flutter function of the manual MIE therapy. Thus, in response to flutter button 888 being selected on screen 862 of FIG. 41, a manual MIE flutter on/off screen 922 appears on the GUI 16 as shown in FIG. 52. Screen 922 includes an adjust pressure, frequency, or flutter window 924. Window 924 of screen 922 includes first, second, and third slider inputs 926, 928, 930 that are used to turn a flutter feature of the respiratory therapy apparatus 10 on and off for the inhale, exhale, and PAP portions, respectively, of the manual MIE therapy.

With continued reference to FIG. 52, window 924 further includes an icon menu 932 to the right of slider inputs 926, 928, 930 that includes an up arrow button 934, a down arrow button 936, a save button 938, and a cancel button 940. To the left of each slider input 926, 928, 930 is a pressure value box or field 942 and a frequency value box or field 944. The upper pair of boxes 942, 944 and slider input 926 relate to the inhale portion of the manual MIE therapy, the middle pair of boxes 942, 944 and slider input 928 relate to the exhale portion of the manual MIE therapy, and the lower pair of boxes 942, 944 and slider 930 relate to the PAP portion of manual MIE therapy.

Figure 53:
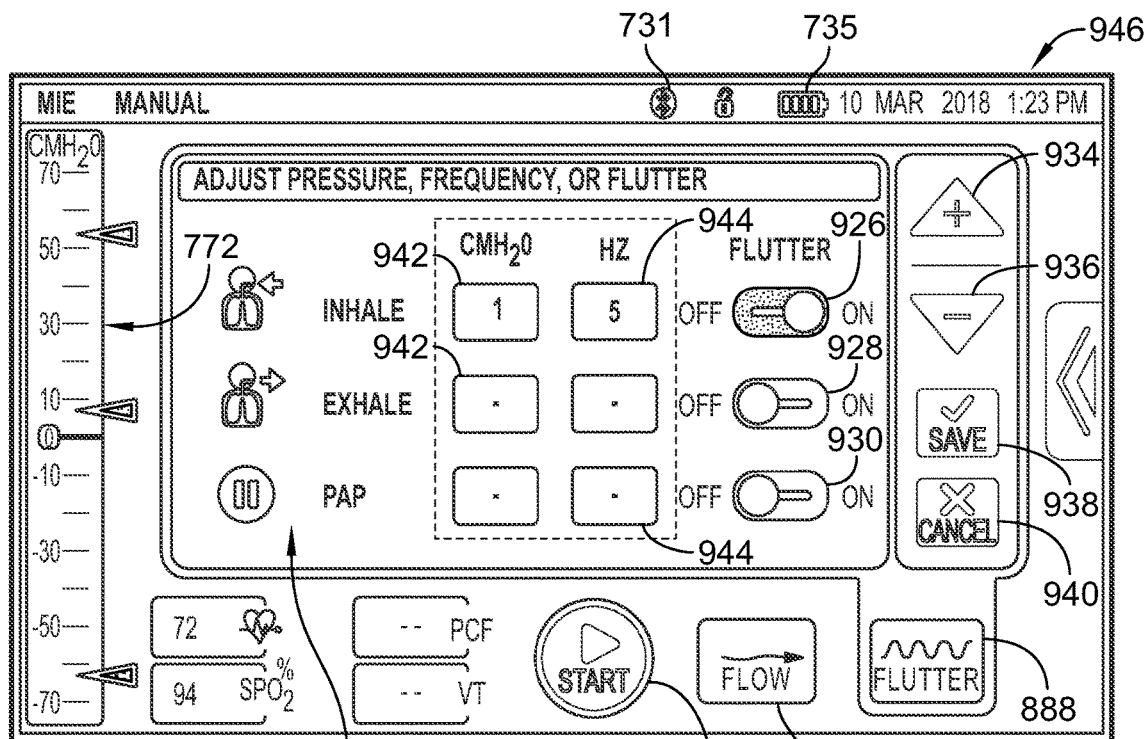
FIG. 53 is a screen shot of a first manual MIE flutter parameter adjustment screen showing default flutter pressure and flutter frequency values populated in respective fields for the inhale portion of the manual MIE therapy in response to the first slider input being moved to an on position.

Referring now to FIG. 53, a first manual MIE flutter parameter adjustment screen 946 appears on GUI 16 in response to first slider input 926 being moved by the user from an off position shown in FIG. 52, to an on position shown in FIG. 53. In response to movement of first slider input 926 to the on position in FIG. 53, a default flutter pressure value and a default flutter frequency value are populated in respective fields 942, 944 for the inhale portion of the manual MIE therapy. In the illustrative example, the default flutter pressure value in field 942 is 1 cmH$_2$O and the default flutter frequency value is 5 Hz. On screen 946 of FIG. 53, slider inputs 928, 930 remain in the respective off positions and so dashes "-" appear in respective fields 942, 944 for the exhale and PAP portions of the MIE therapy.

Figure 54:
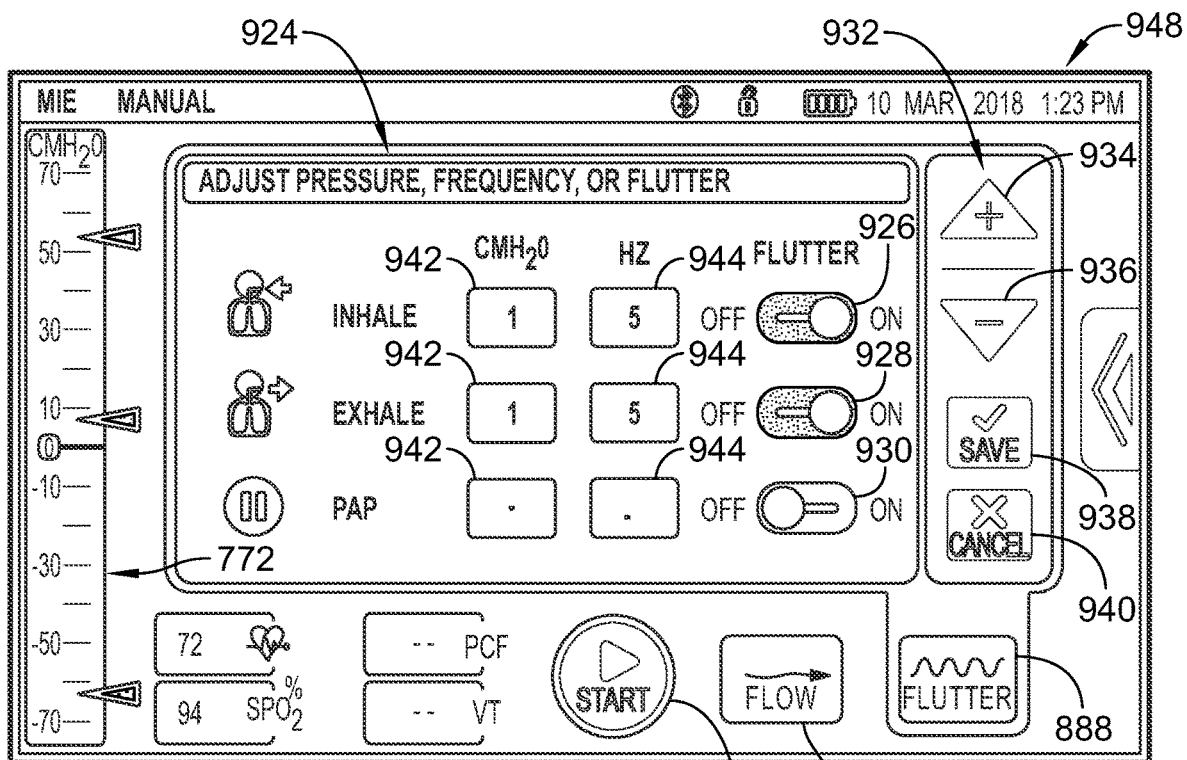
FIG. 54 is a screen shot of a second manual MIE flutter parameter adjustment screen showing default flutter pressure and flutter frequency values populated in respective fields for the exhale portion of the manual MIE therapy in response to the second slider input being moved to an on position.

Referring now to FIG. 54, a second manual MIE flutter parameter adjustment screen 948 appears on GUI 16 in response to the second slider input 928 being moved to the on position from the off position. Thus, in FIG. 54, the first and second slider inputs 926, 928 are both in the on position. In response to movement of second slider input 928 to the on position in FIG. 54, the default flutter pressure value of 1 cmH$_2$O and the default flutter frequency value of 5 Hz are populated in respective fields 942, 944 for the exhale portion of the manual MIE therapy. On screen 948 of FIG. 54, slider input 930 remains in the respective off positions and so dashes "-" appear in respective fields 942, 944 for the PAP portion of the MIE therapy.

Figure 55:
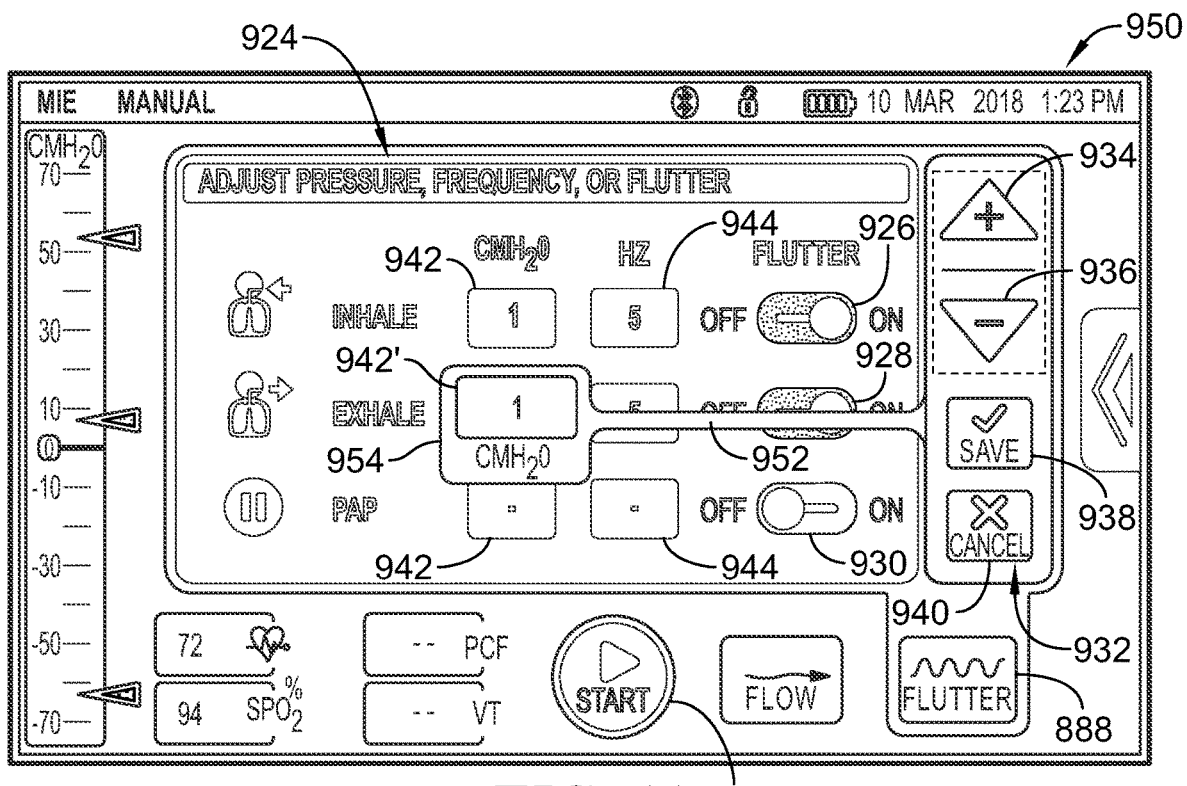
FIG. 55 is a screen shot of a third manual MIE flutter parameter adjustment screen showing the exhale flutter pressure field having been selected for adjustment and showing up arrow, down arrow, save, and cancel icons being illuminated for use in adjusting the exhale flutter pressure.

Referring now FIG. 55, a third manual MIE flutter parameter adjustment screen 950 appears on GUI 16 in response to the exhale flutter pressure field 942 having been selected for adjustment such that an enlarged field 942' appears over the region on screen 950 where exhale flutter pressure field 942 appeared previously. A connector segment 952 extends from a bubble 954 around field 942' to menu 932 to indicate that up arrow icon 934, down arrow icon 936, save icon 938, and cancel icon 940 are activated for use in connection with exhale flutter pressure adjustment. Up arrow icon 934 and down arrow icon 936 are touched successively to increment or decrement, respectively, the corresponding exhale flutter pressure value by 1 cmH$_2$O. Alternatively, each of arrow icons 934, 936 can be selected and held continuously and the respective exhale flutter pressure value will be incremented or decremented, respectively, by 1 cmH$_2$O for every second held, up to five seconds, after which the exhale flutter pressure value will be incremented or decremented, respectively, by 1 cmH$_2$O for every ½ second held. If an upper pressure limit or lower pressure limit is reached for the exhale flutter pressure value in field 942', then the up arrow button 934 or down arrow button 936, as the case may be, becomes inactive and continued selection of the particular arrow button 934, 936 has no effect.

Figure 56:
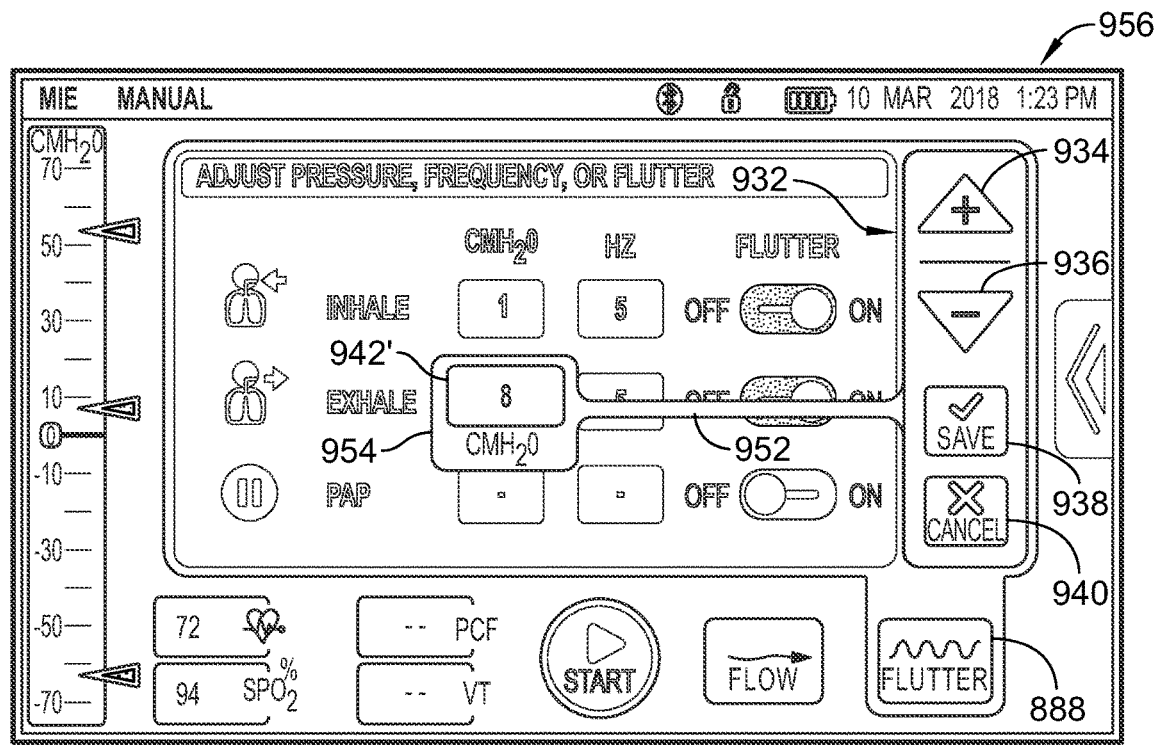
FIG. 56 is a screen shot of a fourth manual MIE flutter parameter adjustment screen showing the exhale flutter pressure field indicating a new pressure value in response to use of the up arrow icon of FIG. 55 to increase the exhale flutter pressure from the default flutter pressure of 1 cmH$_2$O to the new exhale flutter pressure of 8 cmH2O.
Figure 57:
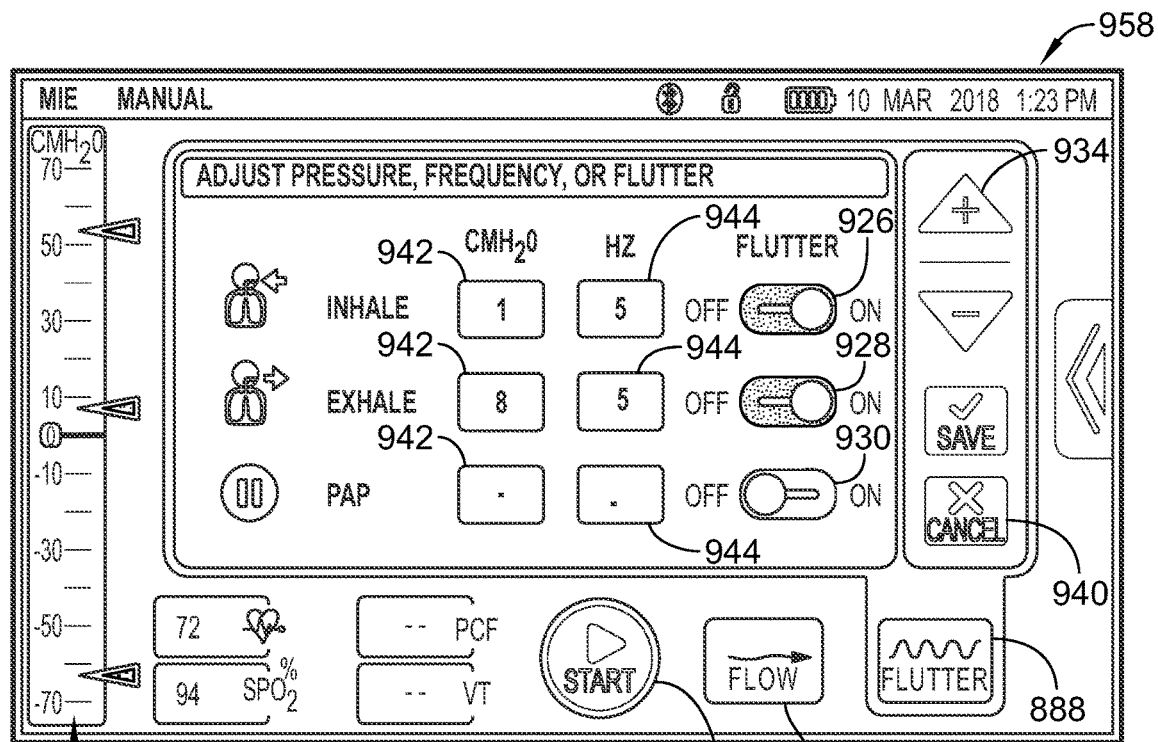
FIG. 57 is a screen shot of a fifth manual MIE flutter parameter adjustment screen showing the new exhale flutter pressure in the respective field after the save icon of the fourth manual MIE flutter parameter adjustment screen of FIG. 56 has been selected.

After the user has incremented or decremented to the desired exhale flutter pressure value in field 942' using arrow buttons 934, 936, save button 938 of menu 932 is selected to save the new exhale flutter pressure value for subsequent use during future manual MIE therapy sessions. If the user decides not to enter a new exhale flutter pressure value, then cancel button 940 of menu 932 is selected and the previous exhale flutter pressure value is used for future manual MIE therapy sessions. As shown in FIG. 56, a fourth manual MIE flutter parameter adjustment screen 956 appears on GUI 16 after the user has incremented the exhale flutter pressure value in field 942' to 8 cmH$_2$O using up arrow button 934. With reference to FIG. 57, a fifth manual MIE flutter parameter adjustment screen 958 appears on GUI 16 after the user selects the save icon 938 on screen 956 of FIG. 56. Screen 958 shows the new exhale flutter pressure of 8 cmH$_2$O in the respective field 942 for the exhale flutter pressure value thereby indicating that the new exhale flutter pressure value has successfully been saved in control circuitry 500.

Figure 58:
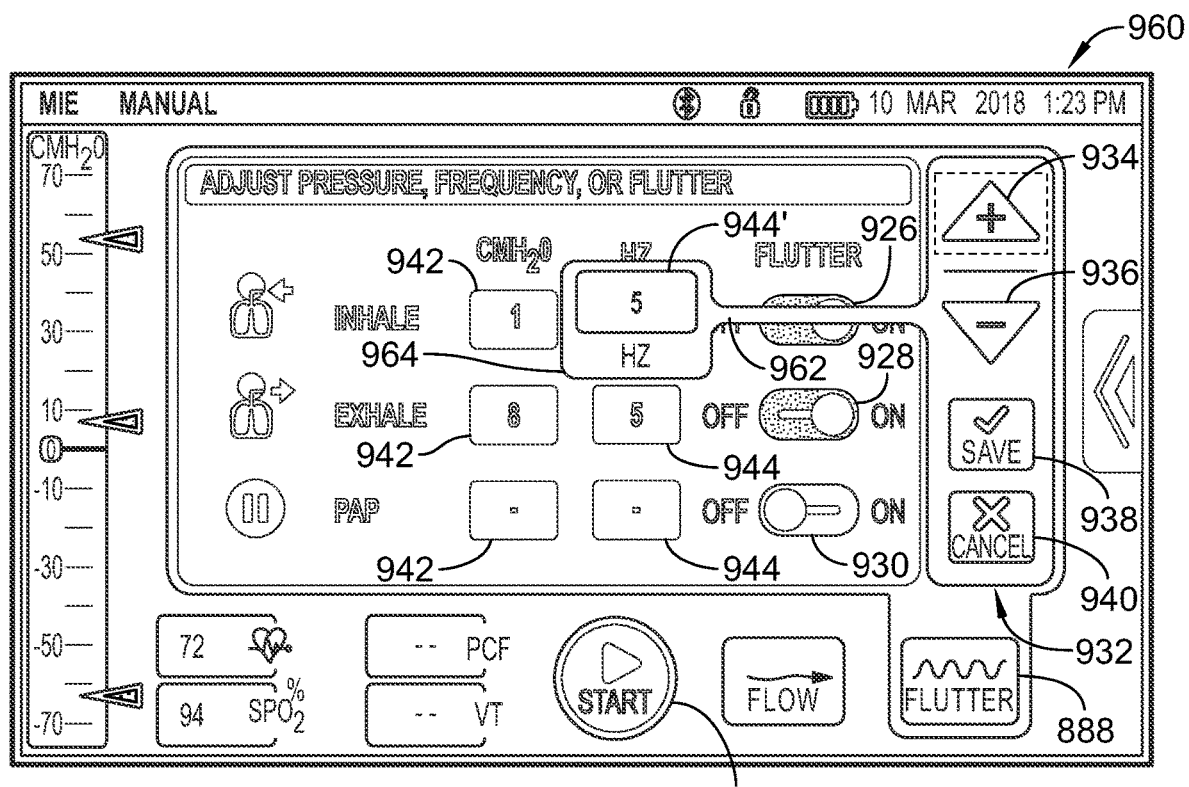
FIG. 58 is a screen shot of a sixth manual MIE flutter parameter adjustment screen showing the inhale flutter frequency field having been selected for adjustment and showing up arrow, down arrow, save, and cancel icons being illuminated for use in adjusting the exhale flutter frequency.

Referring now to FIG. 58, a sixth manual MIE flutter parameter adjustment screen 960 appears on GUI 16 in response to the inhale flutter frequency field 944 having been selected for adjustment such that an enlarged field 944' appears over the region on screen 960 where inhale flutter frequency field 944 appeared previously. A connector segment 962 extends from a bubble 964 around field 944' to menu 932 to indicate that up arrow icon 934, down arrow icon 936, save icon 938, and cancel icon 940 are activated for use in connection with inhale flutter frequency adjustment. Up arrow icon 934 and down arrow icon 936 are touched successively to increment or decrement, respectively, the corresponding inhale flutter frequency value by 1 Hz. Alternatively, each of arrow buttons 934, 936 can be selected and held continuously and the respective inhale flutter frequency value will be incremented or decremented, respectively, by 1 Hz for every second held, up to five seconds, after which the inhale flutter frequency value will be incremented or decremented, respectively, by 1 Hz for every ½ second held. If an upper frequency limit or lower frequency limit is reached for the inhale flutter frequency value in field 944', then the up arrow button 934 or down arrow button 936, as the case may be, becomes inactive and continued selection of the particular arrow button 934, 936 has no effect.

Figure 59:
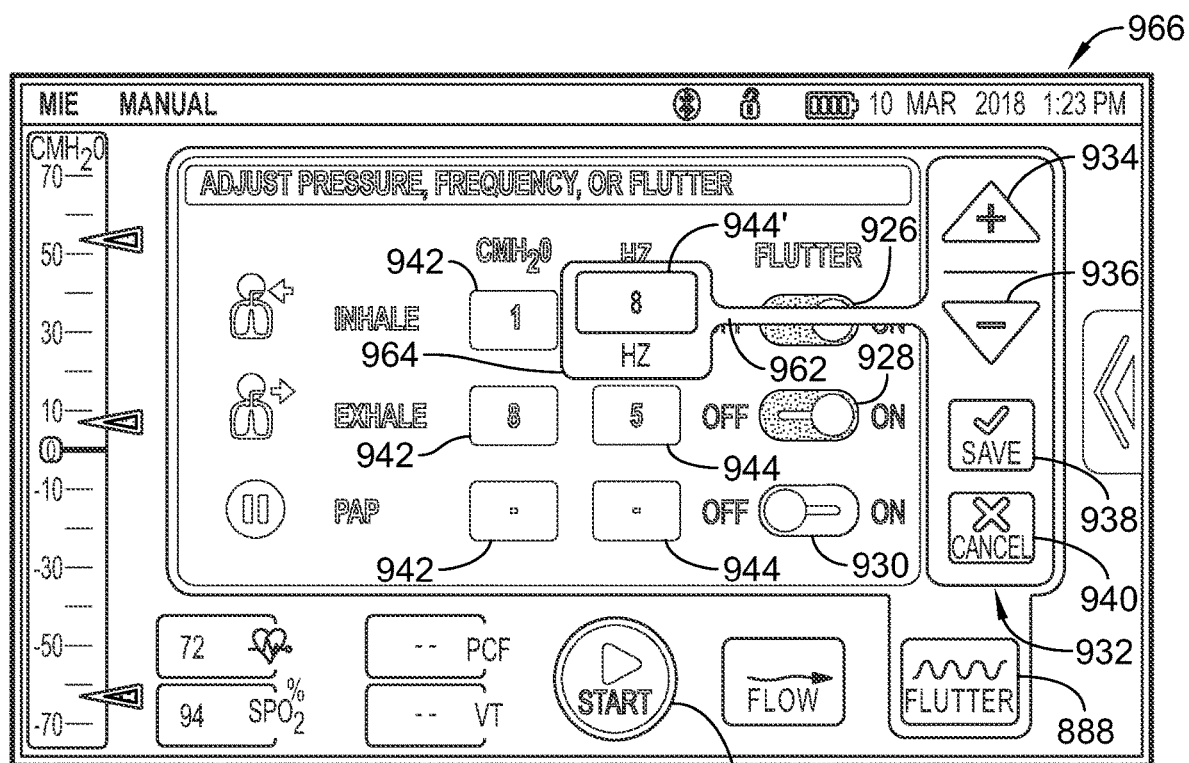
FIG. 59 is a screen shot of a seventh manual MIE flutter parameter adjustment screen showing the inhale flutter frequency field indicating a new frequency value in response to use of the up arrow icon of FIG. 58 to increase the inhale flutter frequency from the default flutter frequency of 5 Hz to the new inhale flutter frequency of 8 Hz.
Figure 60:
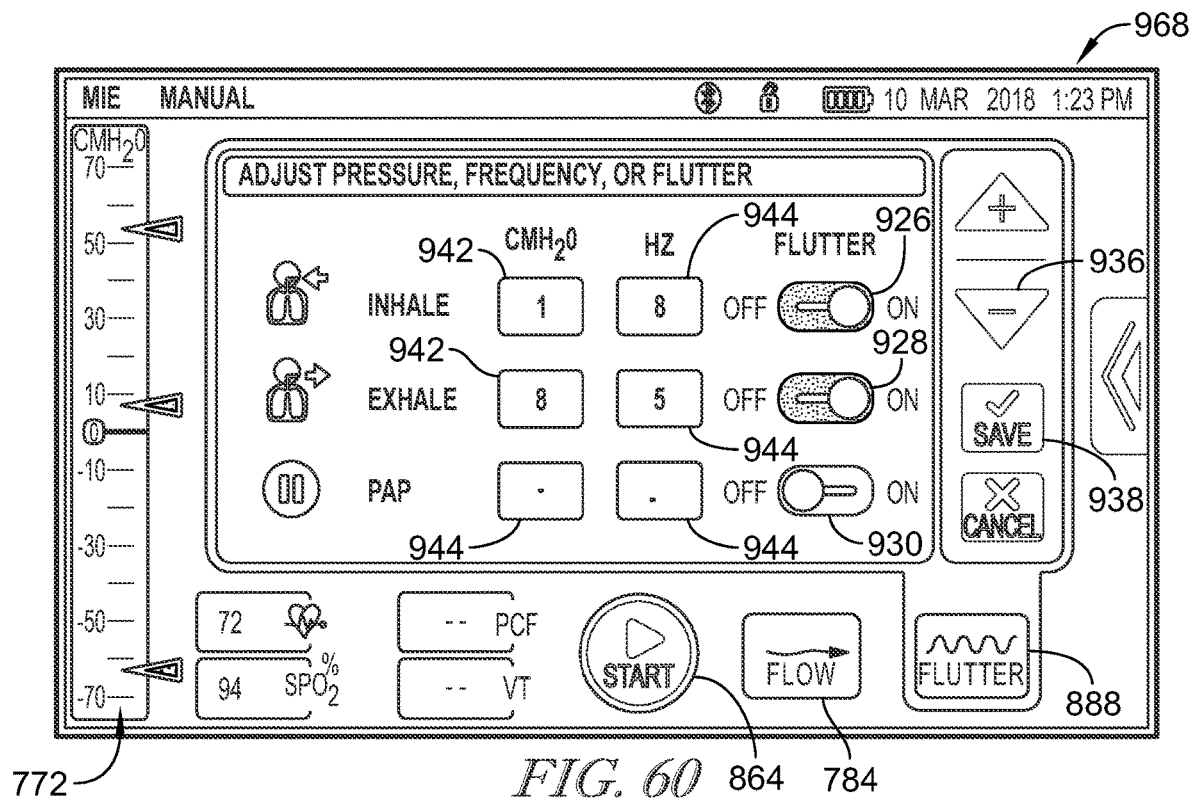
FIG. 60 is a screen shot of an eighth manual MIE flutter parameter adjustment screen showing the new inhale flutter frequency in the respective field after the save icon of the seventh manual MIE flutter parameter adjustment screen of FIG. 59 has been selected.

After the user has incremented or decremented to the desired inhale flutter frequency value in field 944' using arrow buttons 934, 936, save button 938 of menu 932 is selected to save the new inhale flutter frequency value for subsequent use during future manual MIE therapy sessions. If the user decides not to enter a new inhale flutter frequency value, then cancel button 940 of menu 932 is selected and the previous inhale flutter frequency value is used for future manual MIE therapy sessions. As shown in FIG. 59, a seventh manual MIE flutter parameter adjustment screen 966 appears on GUI 16 after the user has incremented the inhale flutter frequency value in field 944' to 8 Hz using up arrow button 934. With reference to FIG. 60, an eighth manual MIE flutter parameter adjustment screen 968 appears on GUI 16 after the user selects the save icon 938 on screen 966 of FIG. 59. Screen 968 shows the new inhale flutter frequency of 8 Hz in the respective field 942 for the inhale flutter frequency value thereby indicating that the new inhale flutter frequency value has successfully been saved in control circuitry 500.

The discussion above regarding screens 950, 956, 958 of FIGS. 55-57 in connection with adjusting the exhale flutter pressure value is equally applicable to adjusting the inhale flutter pressure value and the PAP flutter pressure value. The only difference is that the field 942 of the respective inhale portion or PAP portion of the manual MIE therapy is selected to begin the flutter pressure adjustment process. Similarly, the discussion above regarding screens 960, 966, 968 of FIGS. 58-60 in connection with adjusting the inhale flutter frequency value is equally applicable to adjusting the exhale flutter frequency value and the PAP flutter frequency value. The only difference is that the field 944 of the respective exhale portion or PAP portion of the manual MIE therapy is selected to begin the flutter frequency adjustment process.

Figure 61:
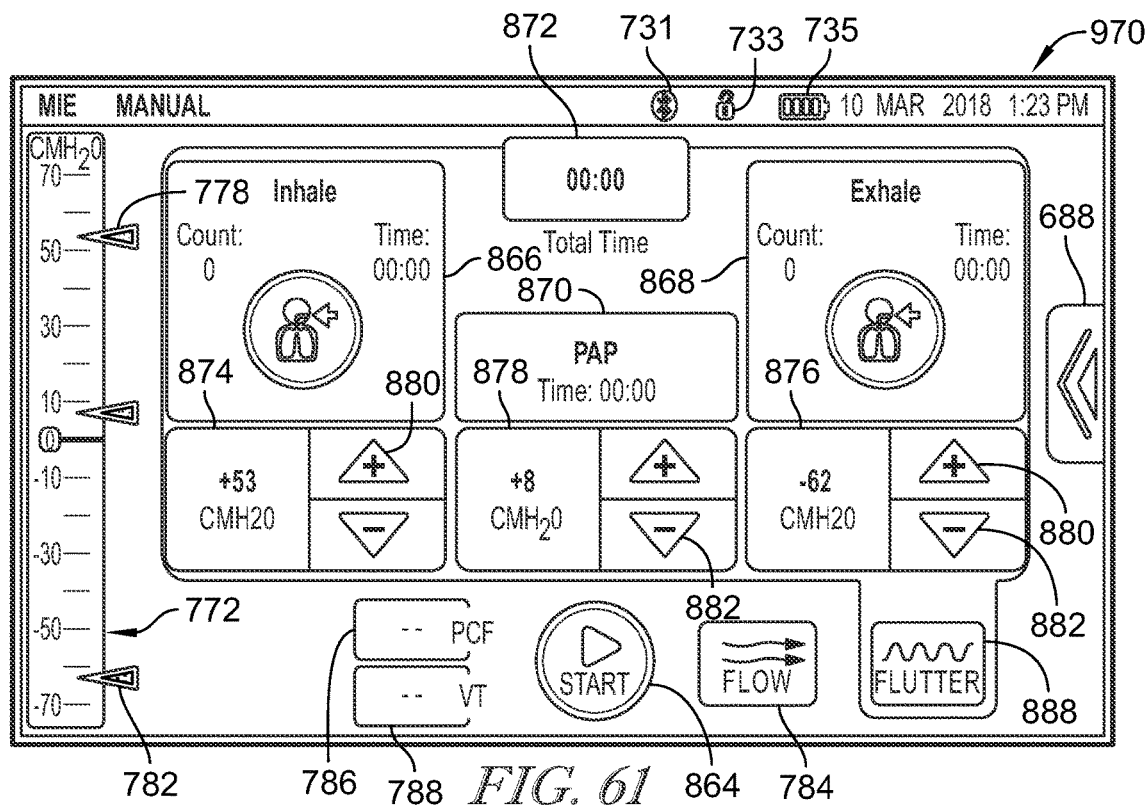
FIG. 61 is a screen shot of a first manual MIE flow control adjustment screen showing a flow button indicating a medium level of air flow of the respiratory therapy apparatus with two wavy arrows in the flow button after the flow button of FIG. 41, indicating a low level of air flow with one wavy arrow, has been selected.

Referring now to FIG. 61, a first manual MIE flow control adjustment screen 970 appears on GUI 16 in response to selection of flow button 784 on screen 968 of FIG. 60 or in response to selection of flow button 784 on screen 862 of FIG. 41. Screen 970 of FIG. 61 is basically the same as screen 862 of FIG. 41 except that button 784 of screen 970 indicates a medium level of air flow for the manual MIE therapy with two wavy arrows in the flow button 784 as compared to button 784 of screen 862 of FIG. 41 which indicates a low level of air flow with one wavy arrow. Fields 884, 886 of screen 862 of FIG. 41 are absent from screen 970 of FIG. 61 which indicates that control circuitry 500 of device 10 is not in wireless communication with any patient physiological monitor even though the Bluetooth communication capability of device 10 is enabled as indicated by the Bluetooth icon 731 appearing in the header of screen 970.

Figure 62:
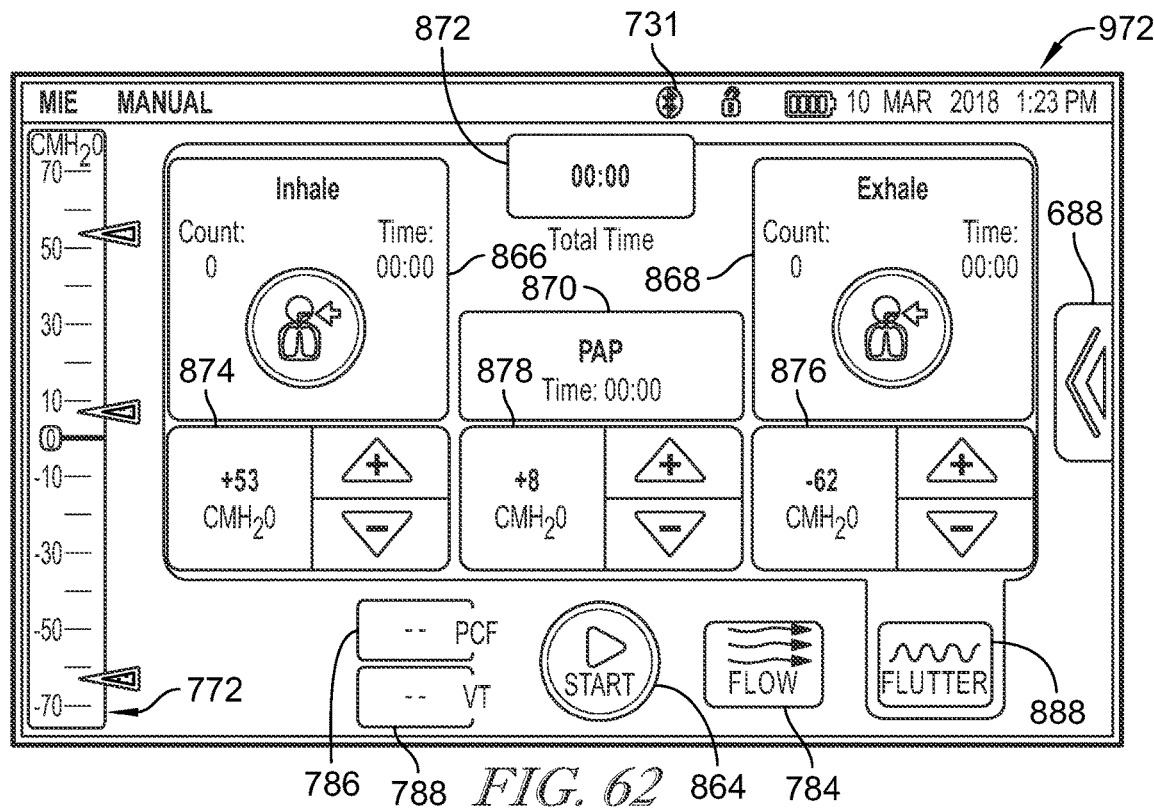
FIG. 62 is a screen shot of a second manual MIE flow control adjustment screen showing the flow button indicating a high level of air flow of the respiratory therapy apparatus with three wavy arrows in the flow button after the flow button of FIG. 61, indicating a medium level of air flow with two wavy arrows, has been selected.

As shown in FIG. 62, a second manual MIE flow control adjustment screen 972 appears on GUI 16 in response to selection of flow button 784 on screen 970 of FIG. 61. Flow button 784 of screen 972 of FIG. 62 indicates a high level of air flow for the manual MIE therapy of the respiratory therapy apparatus 10 with three wavy arrows in the flow button 784. If flow button 784 is selected on screen 972 of FIG. 62, then flow button 784 will, once again, have one wavy arrow to indicate a low level of air flow. So, it should be appreciated that, prior to selection of start button 864 for the manual MIE therapy, successive presses of flow button 784 toggles the air flow setting between low, medium, and high levels of air flow.

Figure 63:
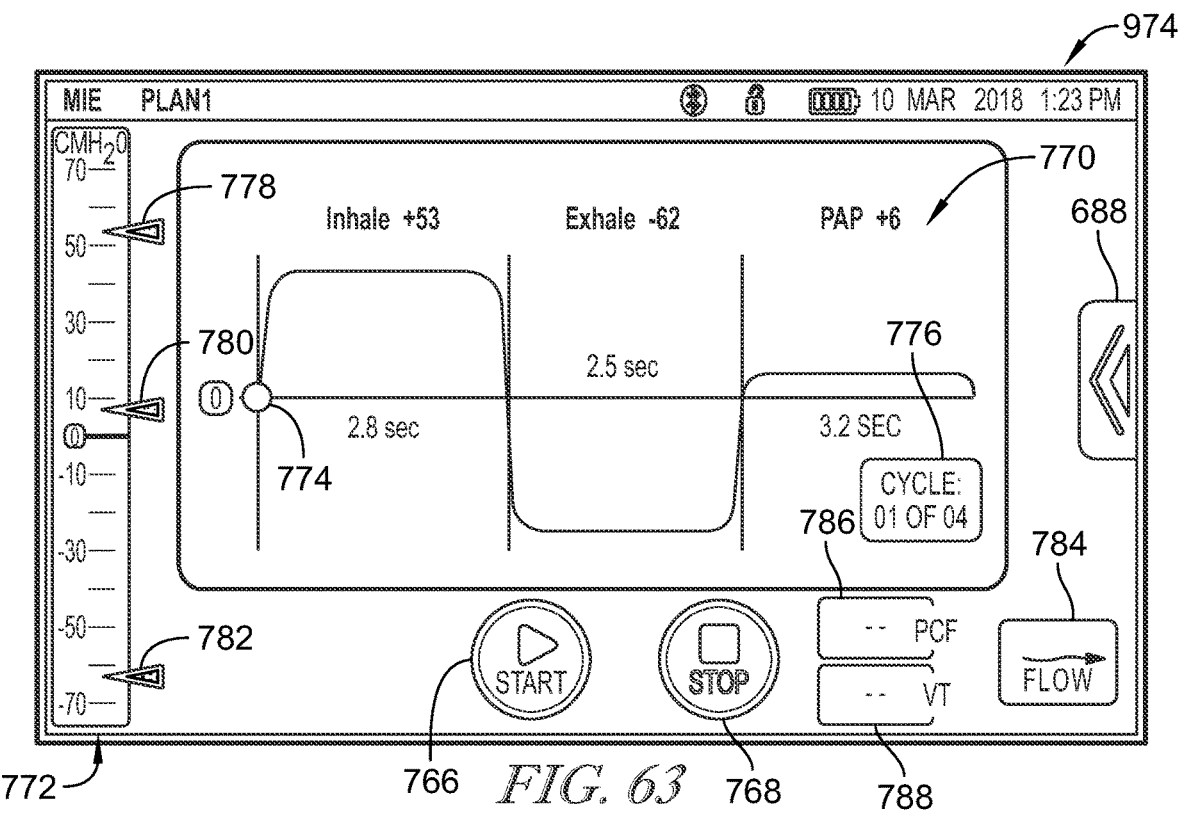
FIG. 63 is a screen shot of a first automatic MIE flow control adjustment screen showing a flow button indicating a low level of air flow of the respiratory therapy apparatus with one wavy arrow in the flow.
Figure 64:
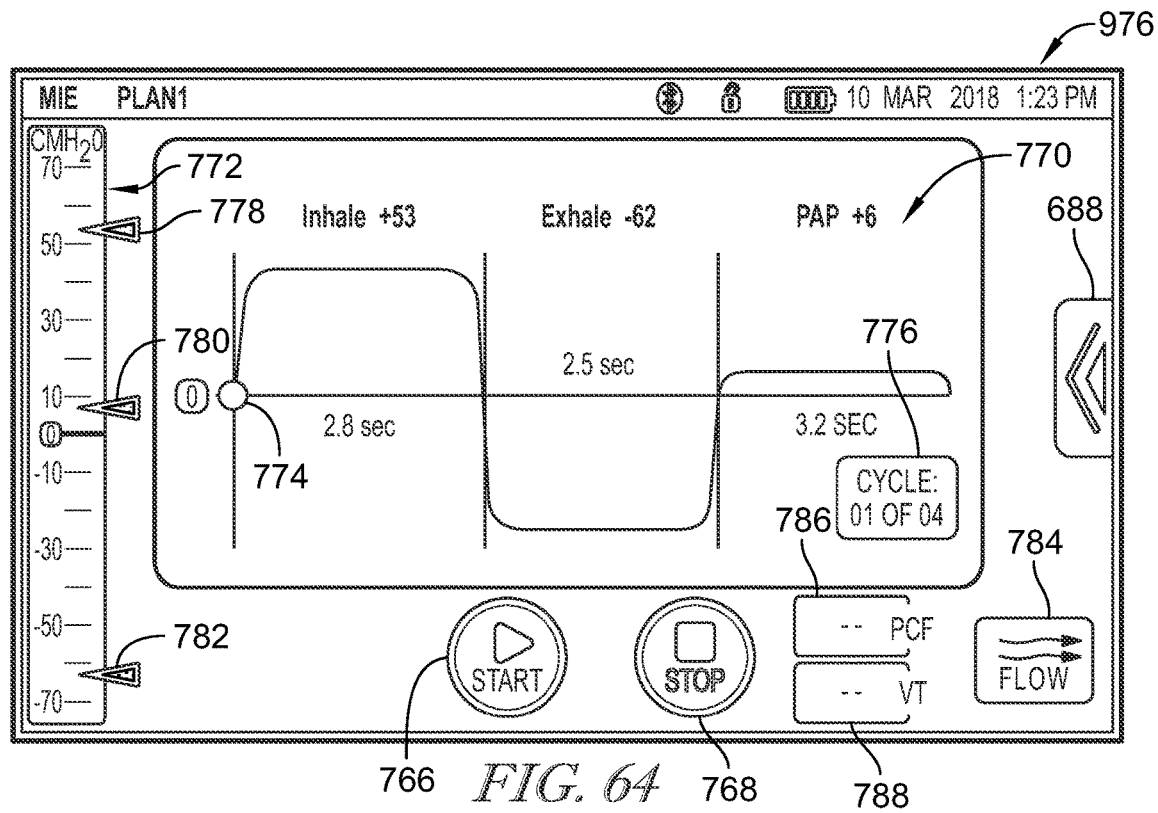
FIG. 64 is a screen shot of a second automatic MIE flow control adjustment screen showing the flow button indicating a medium level of air flow of the respiratory therapy apparatus with two wavy arrows in the flow button after the flow button of FIG. 63 has been selected.
Figure 65:
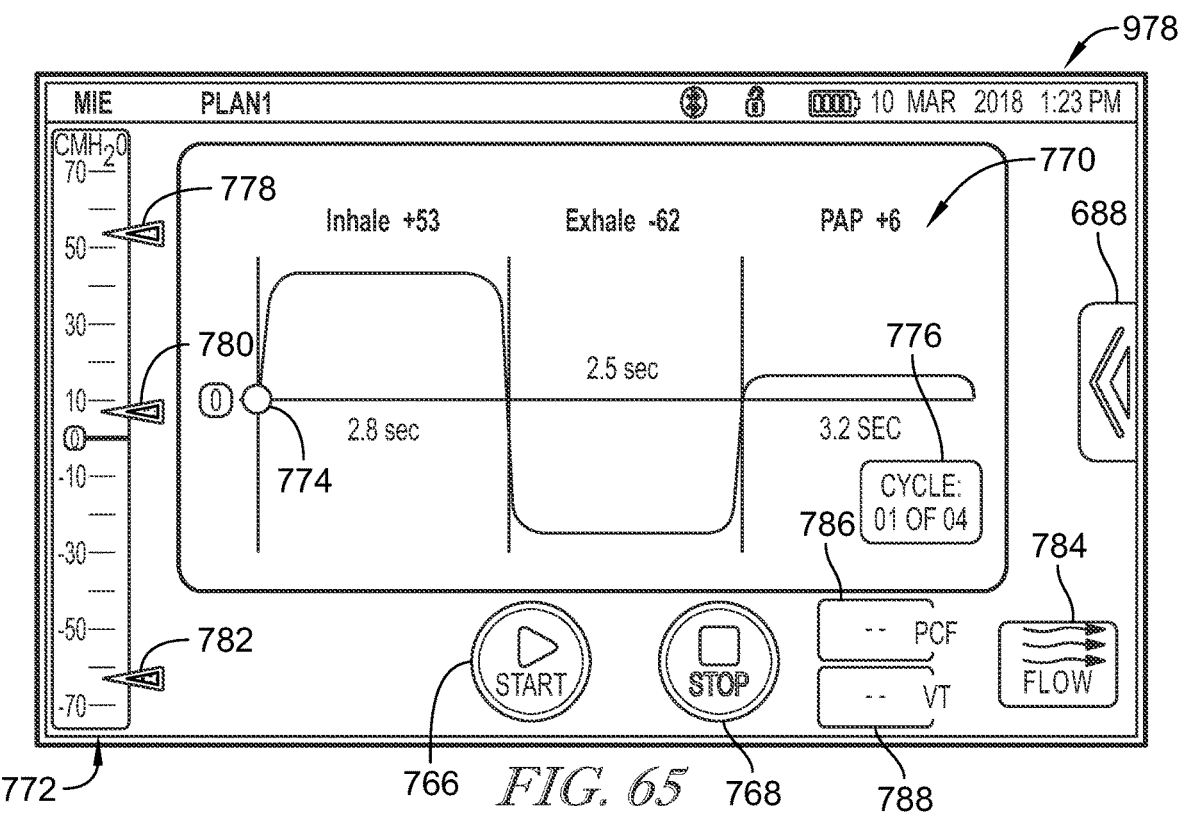
FIG. 65 is a screen shot of a third automatic MIE flow control adjustment screen showing the flow button indicating a high level of air flow of the respiratory therapy apparatus with three wavy arrows in the flow button after the flow button of FIG. 64 has been selected.

Referring now to FIGS. 63-65, a similar air flow level adjustment scheme is depicted for the automatic MIE therapy. Thus, in FIG. 63, a first automatic MIE flow control adjustment screen 974 appears on GUI 16 in response to selection of flow button 784 on screen 764 of FIG. 29 prior to selection of start button 766. Screen 974 of FIG. 63 is basically the same as screen 764 of FIG. 29 except that button 784 of screen 974 indicates a low level of air flow for the automatic MIE therapy with one wavy arrow in the flow button 784 as compared to button 784 of screen 764 of FIG. 29 which indicates a high level of air flow with three wavy arrow. Thus, screen 974 of FIG. 63 appears on GUI 16 in response to selection of button 784 on screen 764 of FIG. 29. As shown in FIG. 64 a second automatic MIE flow control adjustment screen 976 appears on GUI 16 in response to selection of button 784 on screen 974 of FIG. 63. Screen 976 of FIG. 64 is the same as screen 974 of FIG. 63 except that button 784 has two wavy arrows to indicate a medium level of air flow.

With regard to the low, medium, and high levels of air flow of the MIE therapy of device 10, it should be appreciated that a number of factors contribute to the actual flow rate at any given time. Such factors include, for example, the pressure at which the flow is to occur, the tidal volume of the patient using device 10, the patient's lung compliance, and the patient's lung resistance. However, in general, the speed at which blower 260 operates is determined, at least in part, by the flow rate setting established by the high, medium, and low settings of button 784. In some embodiments, device 10 is calibrated or designed so that, when hose 225 and filter unit 390 are attached to outlet port 24 with distal end 393 of hose 225 blocked with a plug, the speed of blower 260 is established so that, from a starting point of 0 cm H2O, it takes 0.3 seconds±0.2 seconds to reach within 3 cmH2O of a baseline pressure of 70 cmH2O in connection with the high flow setting; the speed of blower 260 is established so that, from a starting point of 0 cm H2O, it takes 0.7 seconds±0.2 seconds to reach within 3 cmH2O of a baseline pressure of 70 cmH2O in connection with the medium flow setting; and the speed of blower 260 is established so that, from a starting point of 0 cm H2O, it takes 1.1 seconds±0.2 seconds to reach within 3 cmH2O of a baseline pressure of 70 cmH2O in connection with the low flow setting.

The high, medium, and low air flow speed settings of blower 260 correspond, for example, to a pulse-width-modulation duty cycle or average applied voltage for the blower 260. In other words, once calibrated as described above for the high, medium, and low air flow settings under the given test or calibration conditions, the calibrated blower speed voltages are supplied to blower 260 when in use for MIE therapy regardless of what the baseline pressure may be, regardless of what the patient's lung physiology may be, and regardless of which type of patient interface 436 is used in the patient circuit 230. It has been found that, in accordance with the above described calibration of high, medium, and low flow settings, starting from 0 cmH2O and increasing pressure up to 70 cmH2O for a patient having lungs with 500 milliliters (mL) of tidal volume, 25 mL/millibar (mbar) compliance, and 20 mbar/L/s resistance, the resulting low flow is about 50 standard liters per minute (SLPM), the resulting medium flow is about 60 SLPM, and the resulting high flow is about 70 SPLM, just to give one example.

As shown in FIG. 65 a third automatic MIE flow control adjustment screen 978 appears on GUI 16 in response to selection of button 784 on screen 976 of FIG. 64. Screen 978 of FIG. 65 is the same as screen 976 of FIG. 64 except that button 784 has three wavy arrows to indicate a high level of air flow. Furthermore, screen 978 of FIG. 65 is a duplicate of screen 764 of FIG. 29 since flow button 784, once again, has three wavy arrows therein. So, it should be appreciated that, prior to selection of start button 766 for the automatic MIE therapy, successive presses of flow button 784 toggles the air flow setting between low, medium, and high levels of air flow.

In some embodiments, after start button 864 is selected to initiate the manual MIE therapy, button 784 becomes inactive and cannot be selected to change the air flow level during the inhale and exhale phases of the manual MIE therapy, but button 784 does become active and can be selected to change the air flow level during the PAP phase of the manual MIE therapy. In contrast, after start button 766 is selected to initiate the automatic MIE therapy, button 784 becomes inactive and cannot be selected to change the air flow level during all three of the inhale, exhale, and PAP phases of the automatic MIE therapy.

Referring now to FIG. 66, a first care plan screen 980 for automatic MIE therapy appears on GUI 16 in response to selection of the lung icon 698 of the vertical menu of icons 692 of screen 846 of FIG. 39. The first care plan screen 980 for automatic MIE therapy defaults to having a therapy tab 982 selected for a first care plan as indicated by highlighting in a first care plan button 984 of a menu 986 of care plan buttons. Screen 980 of FIG. 66 also displays a table 988 of the parameters for inhale, exhale, and PAP portions of each cycle of the automatic MIE therapy. From left to right in FIG. 66, table 66 includes columns for cycle number, stage of the respective cycle, baseline pressure for each stage, flutter pressure for each stage, peak pressure for each stage, and flutter frequency of each stage. Text above table 988 indicates that plan 1 of the automatic MIE therapy has seven total stages and lasts a total time of 00:52 seconds. A back button 990 is also shown above table 988 in FIG. 66 and is selectable to return the user to screen 764 of FIG. 29.

Screen 980 of FIG. 66 further includes a start button 992 and an edit button 994 located beneath table 988. Start button 992 is selectable to begin the automatic MIE therapy according to the parameters in table 988 of selected plan 1. Edit button 994 is selectable to edit the parameters of the selected plan 1 shown in table 988 as will be discussed below in connection with FIGS. 90-110. If another button of the menu 986 of care plan buttons (e.g., plan 2 button, plan 3 button, plan 4 button, etc.) is selected, then table 988 shows the parameters for the selected care plan and the start and edit buttons 992, 994 pertain to the selected care plan. A scroll bar 993 to the left of table 988 includes a scroll slider 995 that is touched and dragged downwardly to reveal other cycles on table 988. In the illustrative example of FIG. 66, cycles 1-3 are shown on table 988 and so scroll slider 995 is used to reveal cycles 4-7, as desired, on table 988.

Figure 67:
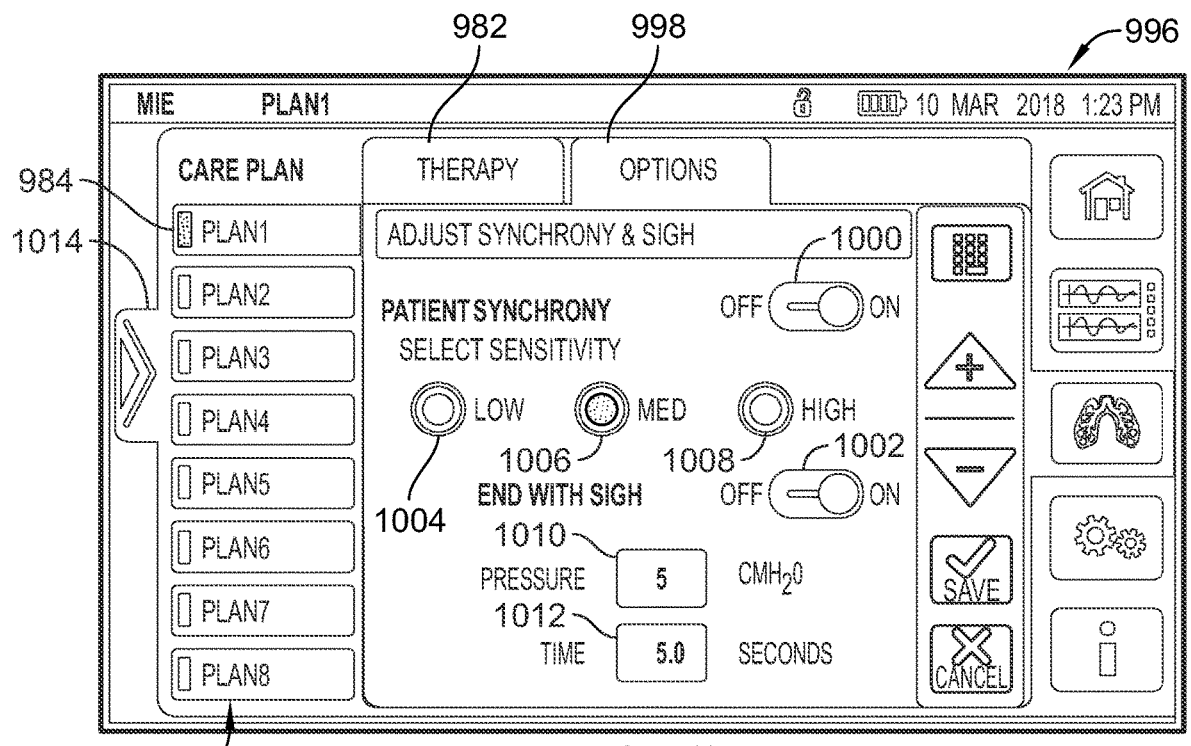
FIG. 67 is a screen shot of a second care plan screen for automatic MIE therapy that appears on the GUI after an options tab is selected on the first care plan screen of FIG. 66, the second care plan screen having a first on/off slider input for a patient synchrony feature of the respiratory therapy apparatus, radio buttons for selection of low, medium, and high sensitivities for the synchrony feature, a second on/off slider input for the sigh function of the automatic MIE therapy, and fields for entering the sigh pressure and time duration of the sigh function.

Referring now to FIG. 67, a second care plan screen 996 for automatic MIE therapy appears on GUI 16 in response to an options tab 998 being selected on the first care plan screen 980 of FIG. 66. The second care plan screen 996 has a first on/off slider input 1000 for a patient synchrony feature of the respiratory therapy apparatus 10; radio buttons 1004, 1006, 1008 for selection of low, medium, and high sensitivities for the synchrony feature, respectively; a second on/off slider input 1002 for the sigh function of the automatic MIE therapy, and fields 1010, 1012 for entering the sigh pressure and time duration of the sigh function, respectively.

In the example of FIG. 67, both slider inputs 1000, 1002 are in the on position, radio button 1006 is selected for medium sensitivity of the patient synchrony feature (aka an inspiratory trigger to start the automatic MIE therapy), the sigh pressure shown in field 1010 is 5 cmH$_2$O, and the sigh function time duration is 5.0 seconds. Screen 980 of FIG. 66 and screen 996 of FIG. 67 each include an arrow tab 1014 that appears to the left of menu 986 and that is selectable, such as by touching and swiping to the right, to close the respective screen 980, 996, as the case may be.

With regard to the patient synchrony feature of device 10, whenever the patient begins to inspire (e.g., breathe in), a pressure drop occurs relative to current pressure such as 0 cmH2O at the beginning of MIE therapy or such as the PAP pressure during delivery of the MIE therapy. In some embodiments, when low button 1004 is selected for the patient synchrony sensitivity, a pressure drop of about 3.0 cmH$_2$O is required to trigger the inhale or insufflation phase of the MIE therapy; when medium button 1006 is selected for the patient synchrony sensitivity, a pressure drop of about 2.0 cmH$_2$O is required to trigger the inhale or insufflation phase of the MIE therapy; and when the high button 1008 is selected for the patient synchrony sensitivity, a pressure drop of about 0.5 cmH$_2$O is required to trigger the inhale or insufflation phase of the MIE therapy.

An air flow increase also occurs as a result of the patient's inspiration. Thus, in some embodiments, in addition to requiring the pressure drops listed above to occur for triggering the insufflation phase of MIE therapy, an air flow increase is also required to be detected such as an air flow increase of about 16.0 liters per minute (LPM) when low button 1004 is selected, an air flow increase of about 12.0 LPM when medium button 1006 is selected, and an air flow increase of about 8.0 LPM when high button 1008 is selected. In some embodiments, control circuitry 500 of device 10 samples the pressure and air flow every 10 milliseconds (ms) using flow control module 352 and keeps a running average of pressure and air flow for 10 samples over a period of 100 ms. It is the running average of pressure and air flow in such embodiments that are compared to the pressure drop and air flow increase thresholds given above to determine whether the criteria for an inspiratory trigger is met. In other embodiments, different thresholds are used for pressure drop and/or air flow increase at the discretion of the device designer.

Figure 68:
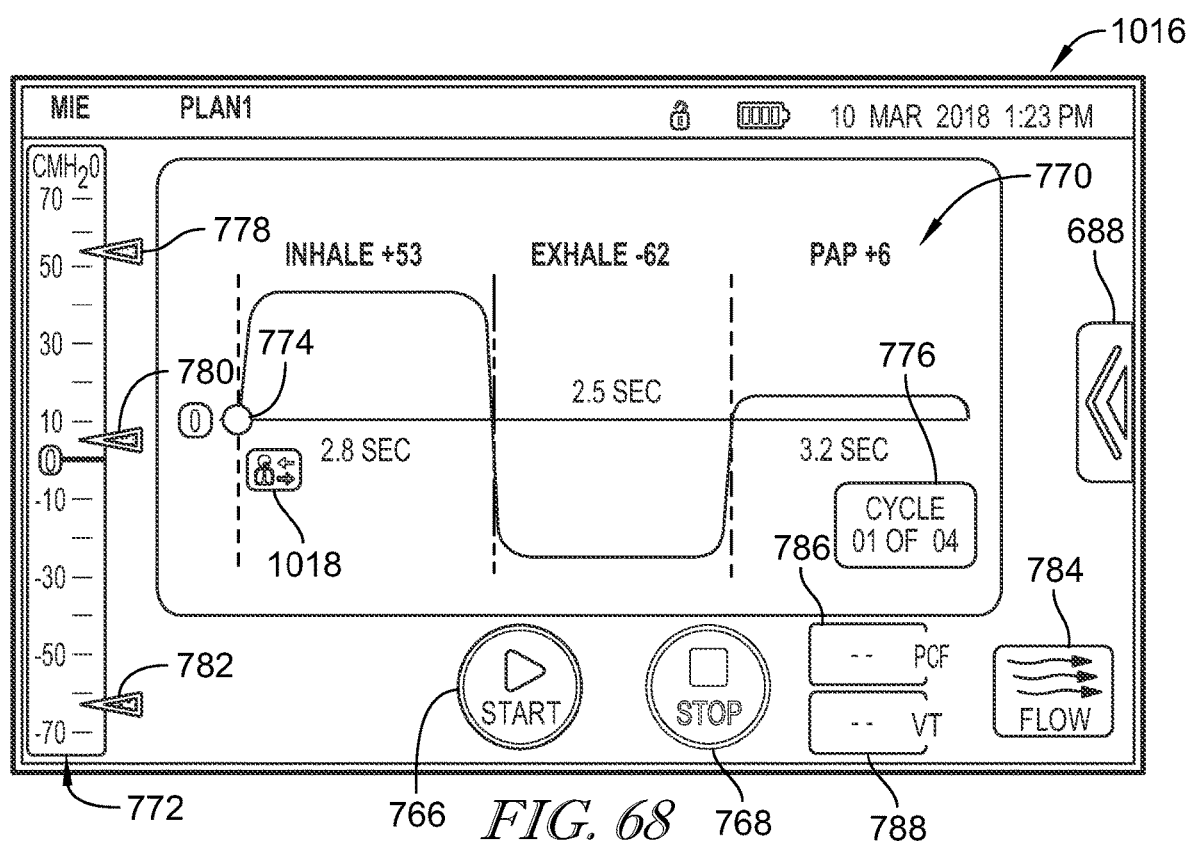
FIG. 68 is a screen shot of a synchrony function on screen, similar to FIG. 65, but having a synchrony function on icon beneath the inhale portion of the graphical waveform of one cycle of the automatic MIE therapy.
Figure 69:
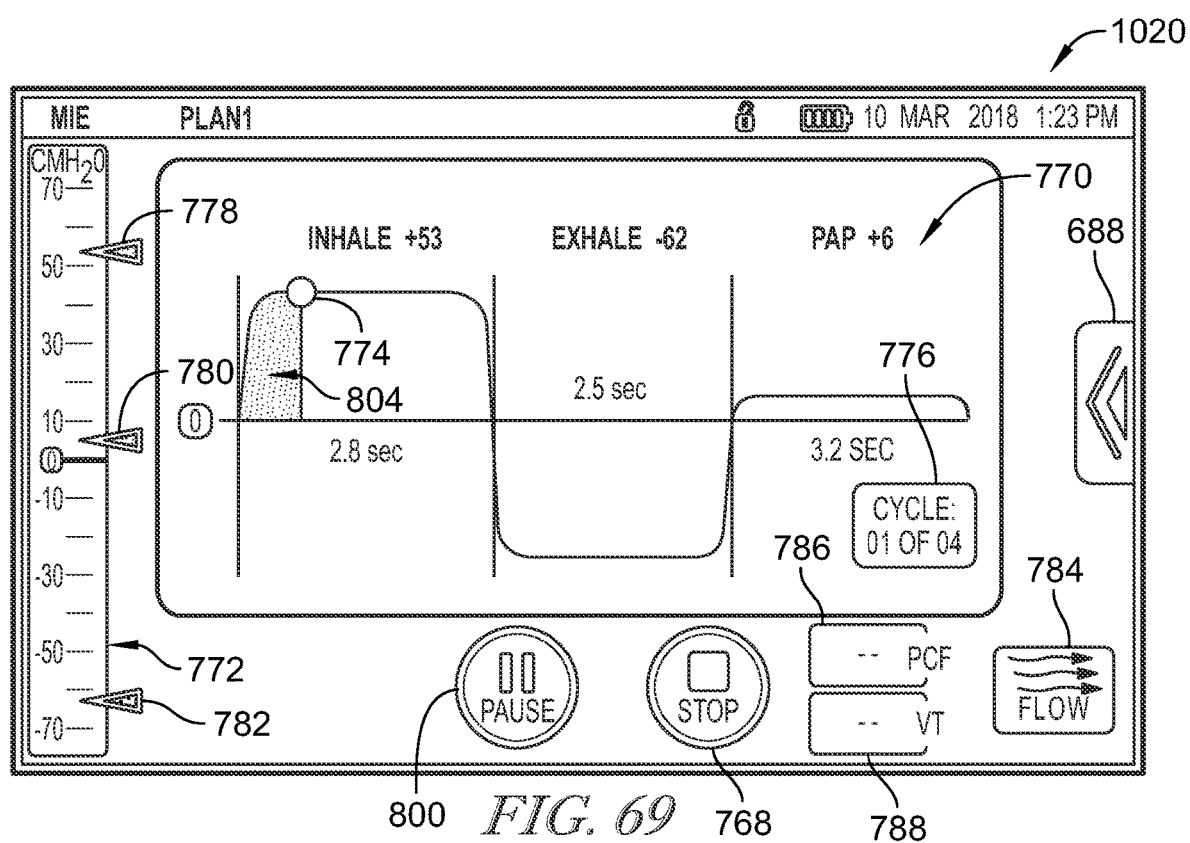
FIG. 69 is a screen shot of an automatic MIE therapy started screen, similar to FIG. 68, but showing the synchrony function on icon removed because a user inhalation has been detected to start the automatic MIE therapy and showing the start button converted to a pause button.

Referring now to FIG. 68, a screen shot of a synchrony function on screen 1016, similar to FIG. 65, but having a synchrony function on icon 1018 beneath the inhale portion of the graphical waveform 770 which is depicted according to the parameters of cycle one of four of plan 1 of the automatic MIE therapy. Icon 1018 is shown as a result of slider input 1000 of screen 996 of FIG. 67 being in the on position. In some embodiments, icon 1018 blinks on screen 1016 of FIG. 68, such as being repeatedly on for one second and off for one second, to inform the patient to inhale at a sufficient breath volume to begin the automatic MIE therapy session. If a sufficient patient inhale is detected, then the automatic MIE therapy begins as shown in FIG. 69 in which an automatic MIE therapy started screen 1020 is shown. The synchrony function on icon 1018 of screen 1016 of FIG. 68 is removed from screen 1020 of FIG. 69 because the patient inhalation was detected to start the automatic MIE therapy. Screen 1020 also shows that the start button 766 of screen 1016 of FIG. 68 is converted to pause button 800 after the automatic MIE therapy begins.

Figure 70:
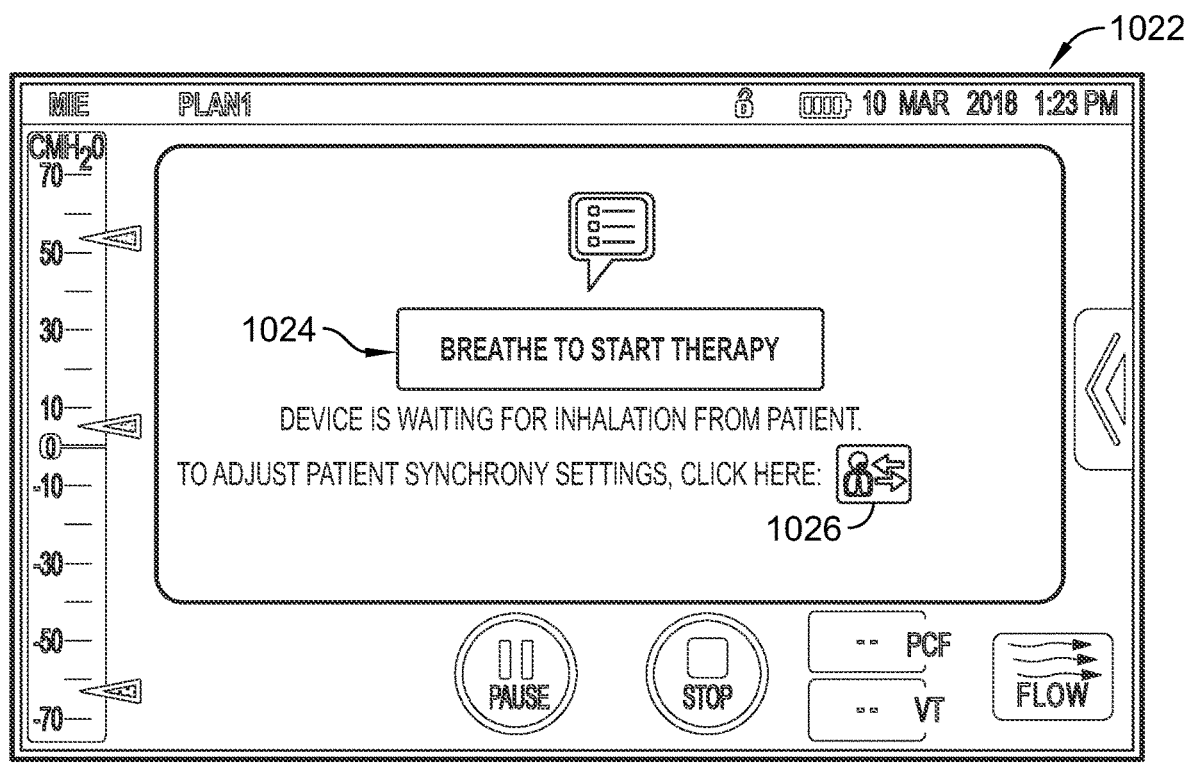
FIG. 70 is a screen shot of a breathe to start therapy screen that appears on the GUI in response to the respiratory therapy apparatus failing to detect the user's breath for ten seconds or more during startup of the automatic MIE therapy, the breathe to start therapy screen including a patient synchrony icon that is selectable to adjust the sensitivity setting of the synchrony function.

Referring now to FIG. 70, a breathe to start therapy screen 1022 appears on GUI 16 in response to the respiratory therapy apparatus 10 failing to detect the user's breath for ten seconds or more during startup of the automatic MIE therapy. Screen 1022 includes a text box 1024 with the text "BREATH TO START THERAPY" therein. Beneath box 1024 is explanatory text that states, "DEVICE IS WAITING FOR INHALATION FROM PATIENT. TO ADJUST PATIENT SYNCHRONY SETTINGS, CLICK HERE:" with a patient synchrony icon 1026 appearing thereafter. Icon 1026 is selectable to return the user back to screen 996 of FIG. 67 so that the user can adjust the sensitivity setting of the patient synchrony function, such as by reducing the patient synchrony setting to the low sensitivity level via selection or radio button 1004, for example. Alternatively, the user can take a sufficiently deep breath while viewing screen 1022 of FIG. 70 to start the automatic MIE therapy session.

Figure 71:
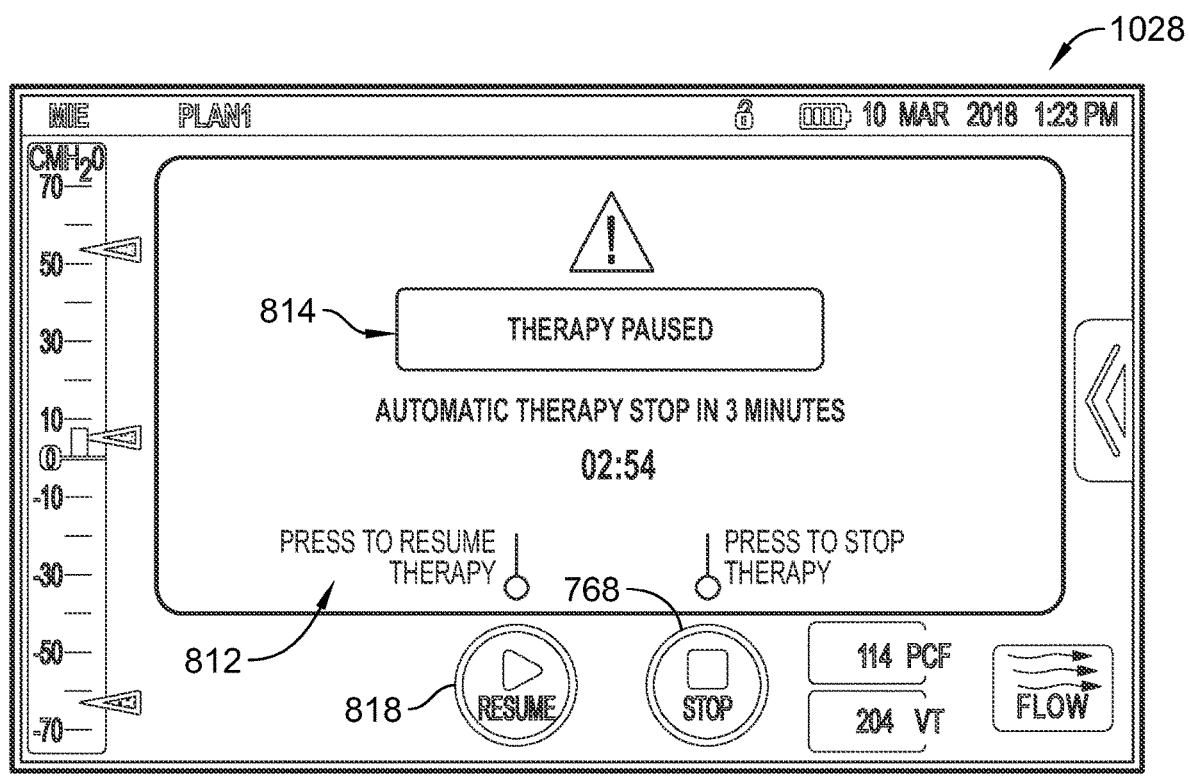
FIG. 71 is a screen shot of a therapy paused screen that appears on the GUI if fifteen seconds elapses without the respiratory therapy apparatus detecting a breath or without the user selecting the patient synchrony icon of FIG. 70, or that appears in response to the user selecting the pause button during the automatic MIE therapy, the therapy paused screen including a resume button that is selectable to resume the automatic MIE therapy and a stop button that is selectable to stop the automatic MIE therapy altogether.

Referring now to FIG. 71, a therapy paused screen 1028 appears on GUI 16 if a threshold period of time, such as fifteen seconds, elapses without the respiratory therapy apparatus 10 detecting a breath or without the user selecting the patient synchrony icon of FIG. 70, or that appears in response to the user selecting the pause button during the automatic MIE therapy. Screen 1028 of FIG. 71 is basically the same as screen 810 of FIG. 33 and so the same reference numbers are used to denote like portions. For example, the therapy paused screen 1028 includes resume button 818 that is selectable to resume the automatic MIE therapy and stop button 768 that is selectable to stop the automatic MIE therapy altogether. When the patient synchrony function is turned on, after each cycle of automatic MIE therapy the patient synchrony icon 1018 reappears on graph 770 like shown in FIG. 68 until the patient inhales sufficiently to begin the next cycle of automatic MIE therapy or until screen 1022 of FIG. 70 is shown as a result of a failure to detect a sufficient patient inhalation for the threshold period of time at the beginning of the next cycle.

Figure 72:
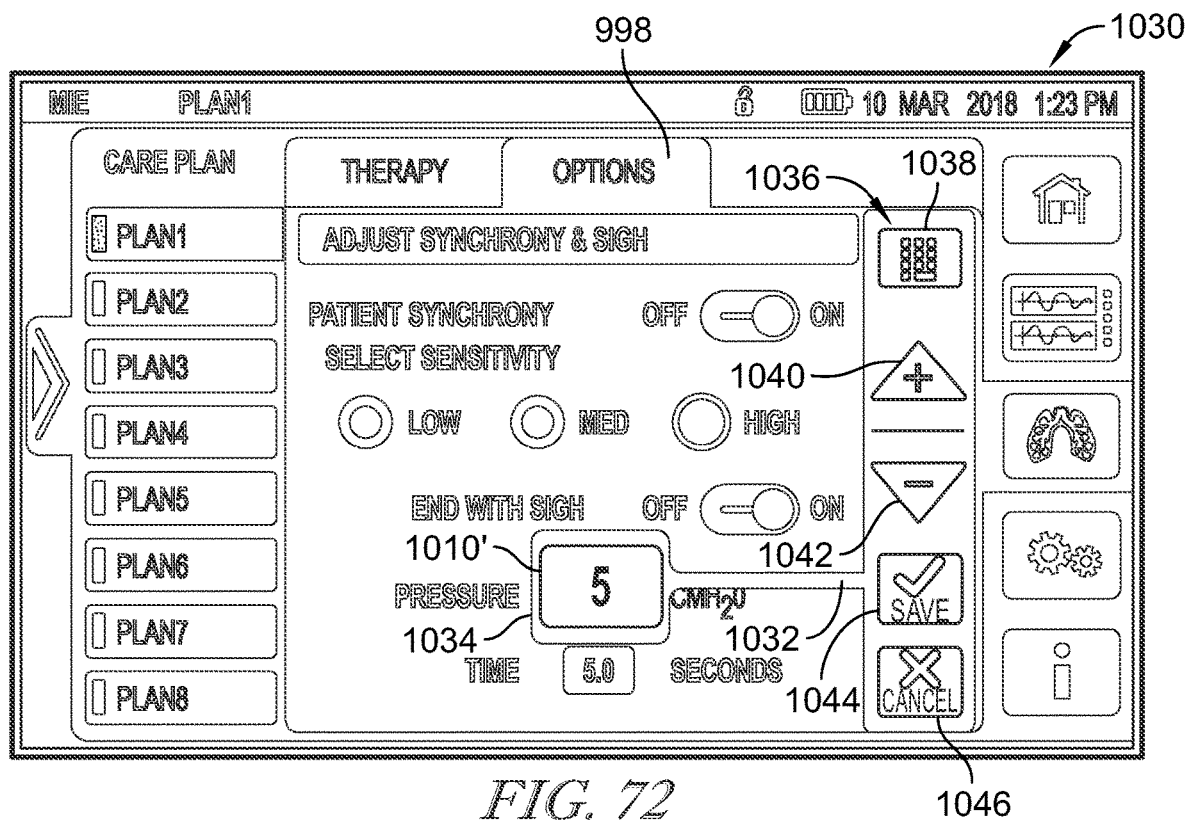
FIG. 72 is a screen shot of a first automatic MIE sigh pressure parameter adjustment screen showing a sigh pressure field having been selected for adjustment and showing keyboard, up arrow, down arrow, save, and cancel icons being illuminated for use in adjusting the sigh pressure.

Referring now to FIG. 72, a first automatic MIE sigh pressure parameter adjustment screen 1030 appears on GUI 16 in response to sigh pressure field 1010 of screen 996 of FIG. 67 having been selected for adjustment such that an enlarged field 1010' appears over the region on screen 1030 where sigh field 1010 appeared previously. A connector segment 1032 extends from a bubble 1034 around field 1010' to a menu of icons 1036 to indicate that a keyboard icon 1038, an up arrow icon 1040, a down arrow icon 1042, a save icon 1044, and a cancel icon 1046 are activated for use in connection with sigh adjustment. Up arrow icon 1040 and down arrow icon 1042 are touched successively to increment or decrement, respectively, the corresponding sigh pressure value by 1 $cmH_2O$. Alternatively, each of arrow icons 1040, 1042 can be selected and held continuously and the sigh pressure value will be incremented or decremented, respectively, by 1 $cmH_2O$ for every second held, up to five seconds, after which the sigh pressure value will be incremented or decremented, respectively, by 1 $cmH_2O$ for every ½ second held. If an upper pressure limit or lower pressure limit is reached for the sigh pressure value in field 1010', then the up arrow button 1040 or down arrow button 1042, as the case may be, becomes inactive and continued selection of the particular arrow button 1040, 1042 has no effect.

Figure 73:
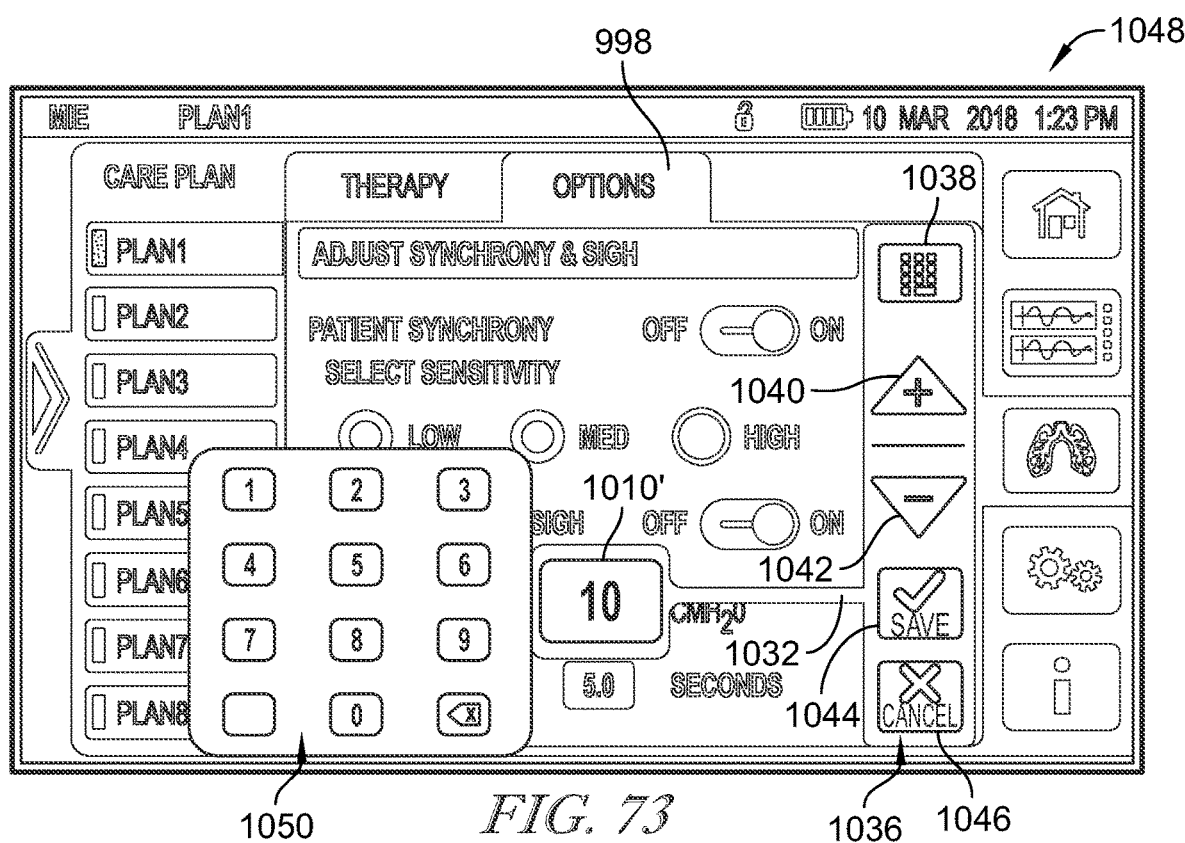
FIG. 73 is a screen shot of a second automatic MIE sigh pressure parameter adjustment screen showing a graphical keyboard appearing on the GUI after the keyboard icon of FIG. 72 is selected, the graphical keyboard being used to change the sigh pressure from the default setting of 5 cmH$_2$O to 10 cmH$_2$O.

As shown in FIG. 73, a second automatic MIE sigh pressure parameter adjustment screen 1048 appears on GUI 16 in response to keyboard icon 1038 of FIG. 72 being selected. Screen 1048 includes a graphical keyboard 1050 that is located just to the left of bubble 1034 and that is usable to directly type the new sigh pressure value into field 1010'. In the illustrative example of screen 1048 of FIG. 73, the sigh pressure value has been changed from the default setting of 5 $cmH_2O$ to 10 $cmH_2O$. After the user has incremented or decremented to the desired sigh pressure value in field 1010' using arrow buttons 1040, 1042 or after the user has typed the desired sigh pressure value in field 1010' using graphical keyboard 1050, save button 1044 of menu 1036 is selected to save the new sigh pressure value for subsequent use during future automatic MIE therapy sessions. If the user decides not to enter a new sigh pressure value, then cancel button 1046 of menu 1036 is selected and the previous sigh pressure value is used for future automatic MIE therapy sessions.

Figure 74:
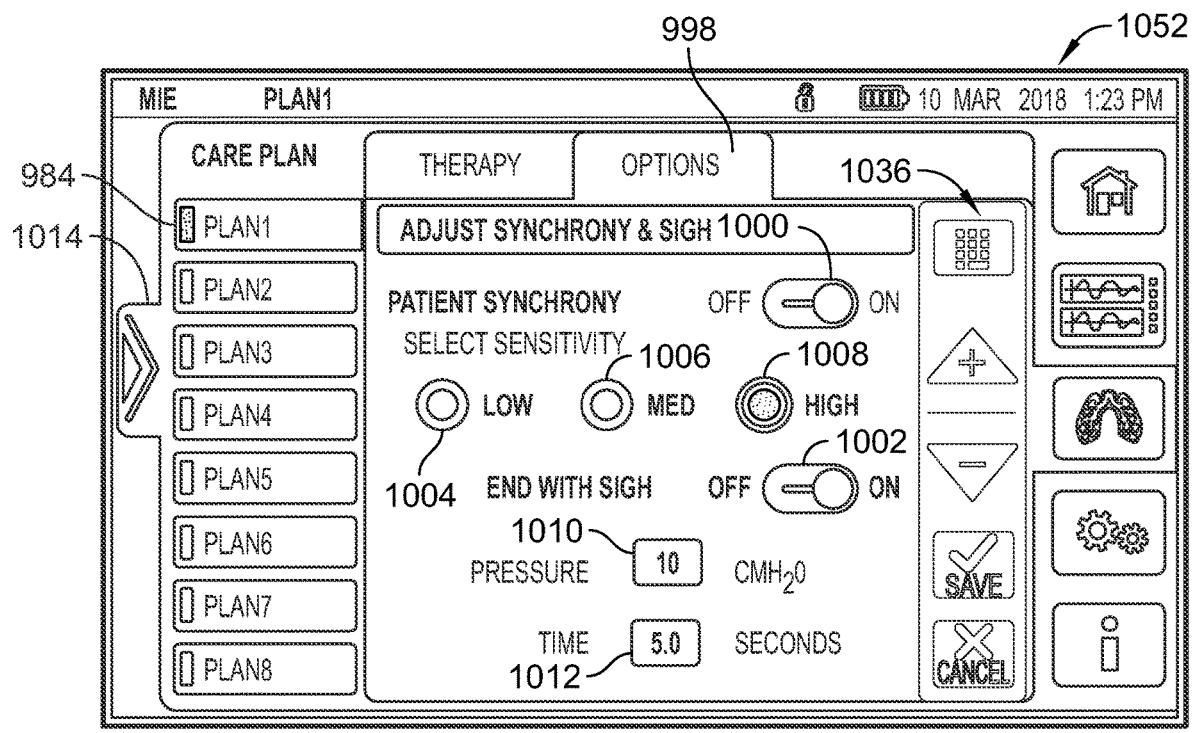
FIG. 74 is a screen shot of a third automatic MIE sigh pressure parameter adjustment screen showing the new sigh pressure in the respective field after the save icon of the second automatic MIE sigh pressure parameter adjustment screen of FIG. 73 has been selected.

As shown in FIG. 74, a third automatic MIE parameter adjustment screen 1052 appears on GUI 16 after the user has adjusted the sigh pressure value in field 1010' to 10 $cmH_2O$ using graphical keyboard 1050 on screen 1048 and in response to selection of the save button 1044 on screen 1048 of FIG. 73. Screen 1052 of FIG. 74 shows the new sigh pressure value of 10 $cmH_2O$ in field 1010. Also, after the save button 1044 is selected, the icons of menu 1036 become grayed out and inactive. Screen 1052 of FIG. 74 also shows that the sensitivity of the patient synchrony feature of device 10 has been adjusted to the high setting due to selection of radio button 1008.

With regard to the sigh pressure time shown in field 1012 of FIGS. 67 and 74, it can be selected and adjusted in a manner similar to that described above in connection with adjustment of the sigh pressure in field 1010. That is, selection of field 1012 results in an enlarged field over field 1012 being shown with a segment connecting the enlarged field to the menu 1036 of icons 1038, 1040, 1042, 1044, 1046. The up arrow 1040 and down arrow 1042 then can be touched successively to increment or decrement, respectively, the corresponding sigh pressure time by 0.1 seconds. Alternatively, each of arrow icons 1040, 1042 can be selected and held continuously and the respective sigh pressure time will be incremented or decremented, respectively, by 0.1 seconds for every second held, up to five seconds, after which the sigh pressure time will be incremented or decremented, respectively, by 0.1 seconds for every ½ second held. If an upper sigh pressure time limit or lower sigh pressure time limit is reached for the sigh pressure time, then the up arrow button 1040 or down arrow button 1042, as the case may be, becomes inactive and continued selection of the particular arrow button 1040, 1042 has no effect. In connection with adjusting the sigh pressure time, after menu 1036 becomes active in response to selection of field 1012, keyboard icon 1038 of menu 1036 can be selected and the new sigh pressure time typed in directly, if desired.

Figure 75:
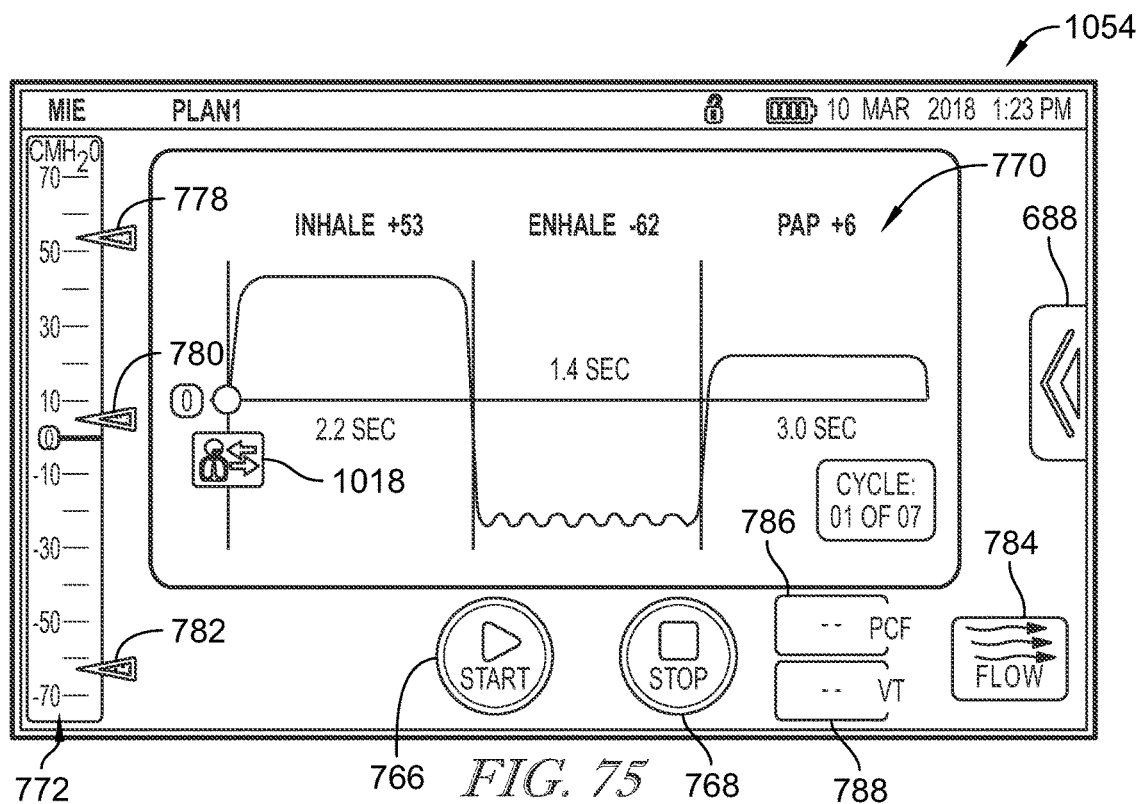
FIG. 75 is a screen shot of an exhale flutter screen for automatic MIE therapy, similar to FIG. 68, but showing the exhale portion of the graph of the first cycle of automatic MIE therapy having a flutter function during the exhale portion of the automatic MIE therapy.

Referring now to FIG. 75, an exhale flutter screen 1054 for automatic MIE therapy, similar to FIG. 68, is shown with an exhale portion of the graph 770 of the first cycle of seven cycles of automatic MIE therapy having a flutter function depicted. Screen 1054 appears on GUI 16, for example, after start button 992 of FIG. 66 is selected and after the RFID count check and battery charge check are performed by the control circuitry 500 of device 10. However, prior to screen 1054 appearing on GUI 16, an exhale flutter frequency and pressure, such as 15 Hz and 10 $cmH_2O$ just to pick a couple possible arbitrary values, will have been selected as described below in connection with FIGS. 92-108, for example.

Figure 76:
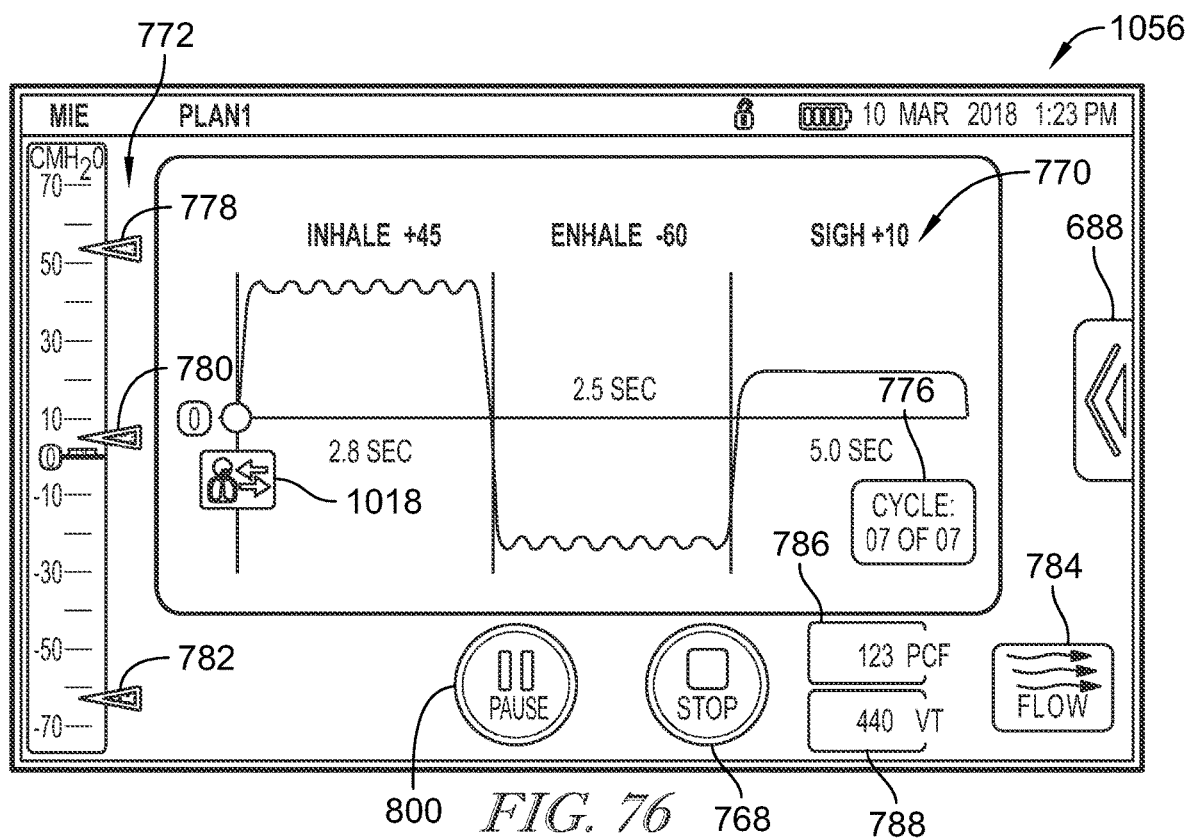
FIG. 76 is a screen shot of an inhale and exhale flutter screen for automatic MIE therapy, similar to FIGS. 68 and 75, but showing the inhale portion and the exhale portion of the graph of the seventh cycle of automatic MIE therapy having a flutter function during the inhale portion and the exhale portion of the automatic MIE therapy, the inhale and exhale flutter screen for automatic MIE therapy also showing numerical values for the peak cough flow ($P_{CF}$) data and tidal volume ($V_t$) of the user.

Referring now to FIG. 76, an inhale and exhale flutter screen 1056 for automatic MIE therapy, similar to FIGS. 68 and 75, is shown with the inhale portion and the exhale portion of the graph 770 of the seventh cycle of automatic MIE therapy having a flutter function during the inhale portion and the exhale portion of the automatic MIE therapy. Screen 1056 also shows numerical values for the peak cough flow ($P_{CF}$) data and tidal volume ($V_t$) of the user. At the end of cycle seven of plan 1 of automatic MIE therapy, a sigh phase at 10 $cmH_2O$ for a duration of 5.0 seconds, as programmed on screens 1030, 1048 of FIGS. 72 and 73, respectively, and as shown on screen 1052 of FIG. 74 occurs as indicated on graph 770 of screen 1056 of FIG. 76.

Figure 77:
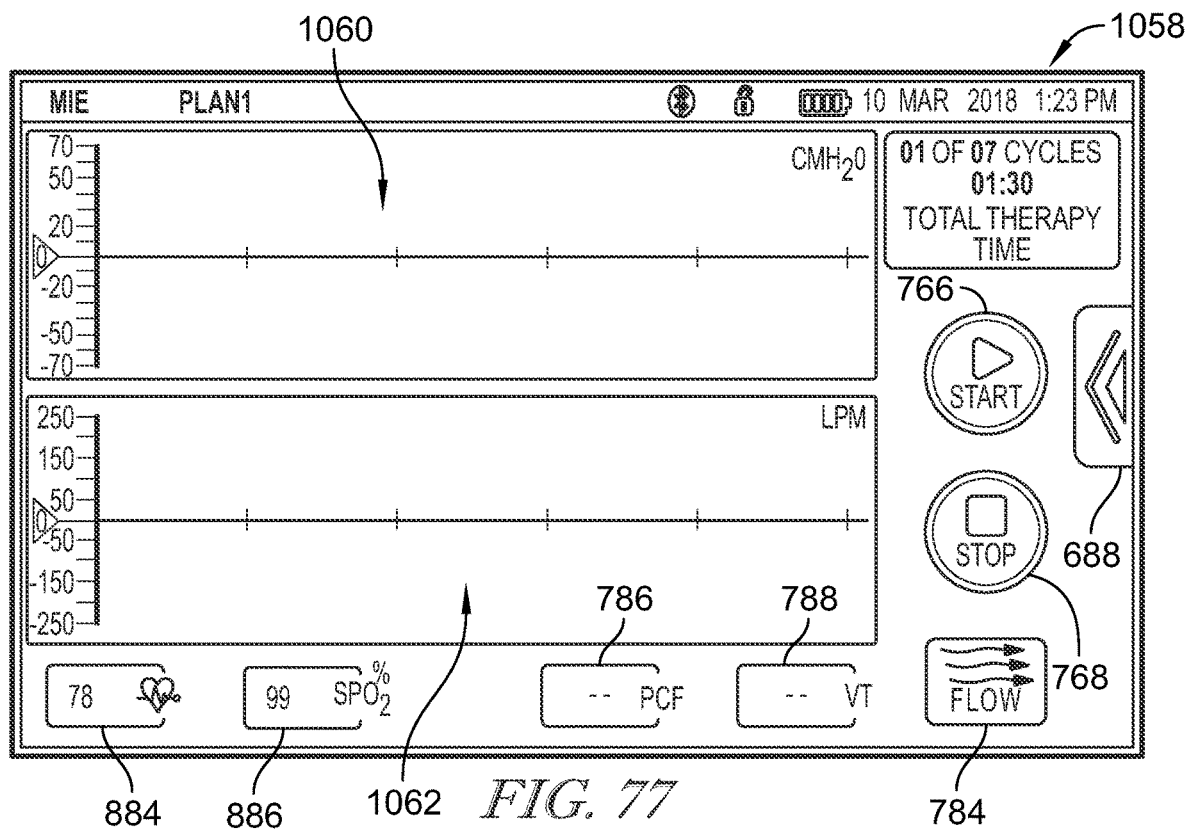
FIG. 77 is a screen shot of a first advanced view screen for automatic MIE therapy that appears on the GUI in response to selection of the graph icon of the vertical menu of icons of the menu screen of FIG. 39, the first advanced view screen having first and second graphs for the automatic MIE therapy that are traced in substantially real time during the automatic MIE therapy, the first graph being for a trace of pressure, in cmH$_2$O, over time, and the second graph being for a trace of air flow, in liters per minute (LPM), over time.

Referring now to FIG. 77, a first advanced view screen 1058 for automatic MIE therapy appears on GUI 16 in response to selection of the graph icon 696 of the vertical menu 692 of icons of the menu screen of FIG. 39. The first advanced view screen 1058 of FIG. 77 has a first graph 1060 and a second graph 1062 for the automatic MIE therapy that are traced in substantially real time during the automatic MIE therapy. During the advanced view of the automatic MIE therapy, first graph 1060 shows a trace of pressure, in cmH$_2$O, over time, and second graph 1062 shows a trace of air flow, in liters per minute (LPM), over time.

In the upper right hand corner of screen 1058, informational text is shown and, in the illustrative example, states "01 OF 07 CYCLES" and "01:30 TOTAL THERAPY TIME." Other portions of screen 1058 are the same as portions of other screens described above and so the same reference numbers are used for these without repeating the descriptions. After start button 766 is selected on screen 1058, a second advanced view screen 1064 for automatic MIE therapy appears on GUI 16 as shown in FIG. 78 assuming the filter unit usage count is below the threshold number of uses and assuming the battery charge is greater than 20% of a full charge. Screen 1064 shows that the start button 766 of screen 1058 of FIG. 77 is converted to pause button 800.

Figure 79:
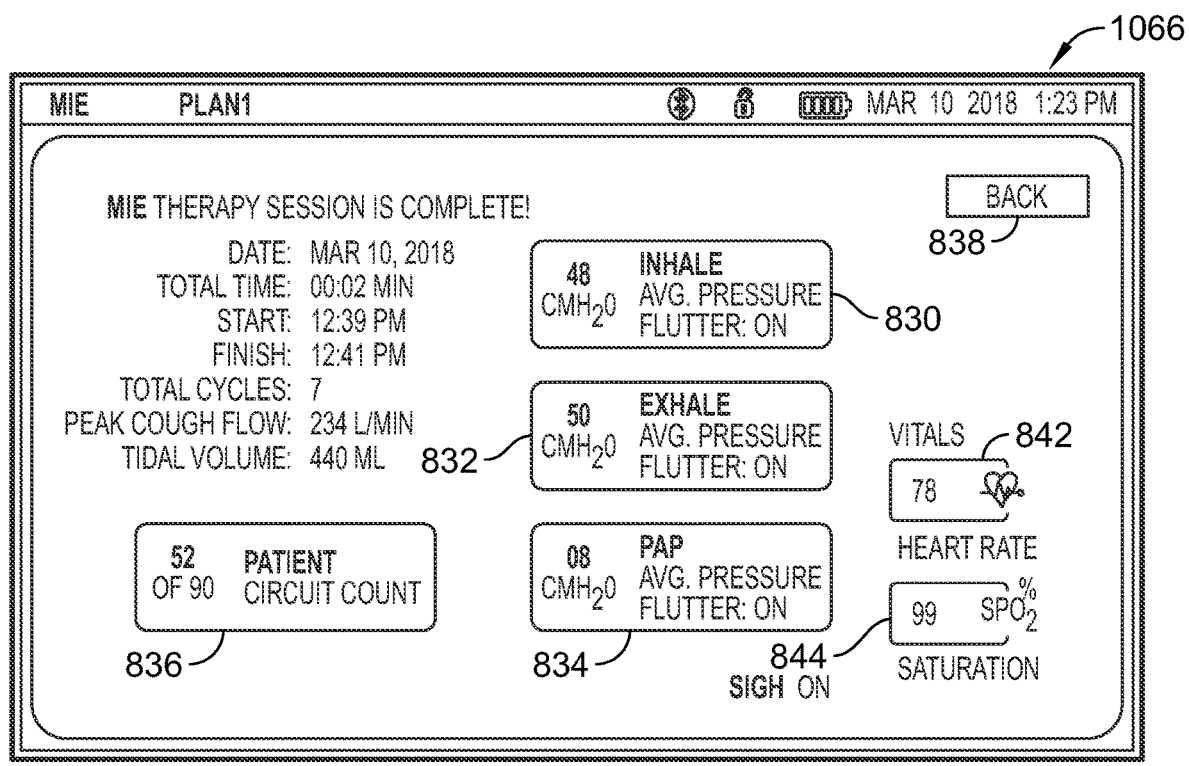
FIG. 79 is a screen shot of an advanced MIE therapy complete screen that appears on the GUI in response to selection of the stop button of the second advanced view screen of FIG. 78, the advanced MIE therapy complete screen showing a variety of statistical data and other information pertaining to the automatic MIE therapy, substantially the same as the MIE therapy complete screen of FIG. 37, but also showing vitals data relating to the patient's heart rate and blood oxygen saturation percentage.

Referring now to FIG. 79, an advanced MIE therapy complete screen 1066 appears on GUI 16 in response to completion of the advanced MIE therapy or selection of stop button 768 of screen 1064 of FIG. 78. Advanced MIE therapy complete screen 1066 is substantially the same as the MIE therapy complete screen 828 of FIG. 37 and so similar references numbers are used to denote like portions without repeating the descriptions. Thus, similar to screen 828 of FIG. 37, screen 1066 of FIG. 79 displays a variety of statistical data and other information pertaining to the automatic MIE therapy that was just completed. However, unlike screen 828 of FIG. 37, screen 1066 of FIG. 79 also includes fields 842, 844, similar to those of screen 840 of FIG. 38, showing vitals data relating to the patient's heart rate and blood oxygen saturation percentage. Furthermore, in response to selection of back button 838 on screen 1066 of FIG. 79, the user is returned to screen 1058 of FIG. 77.

Figure 80:
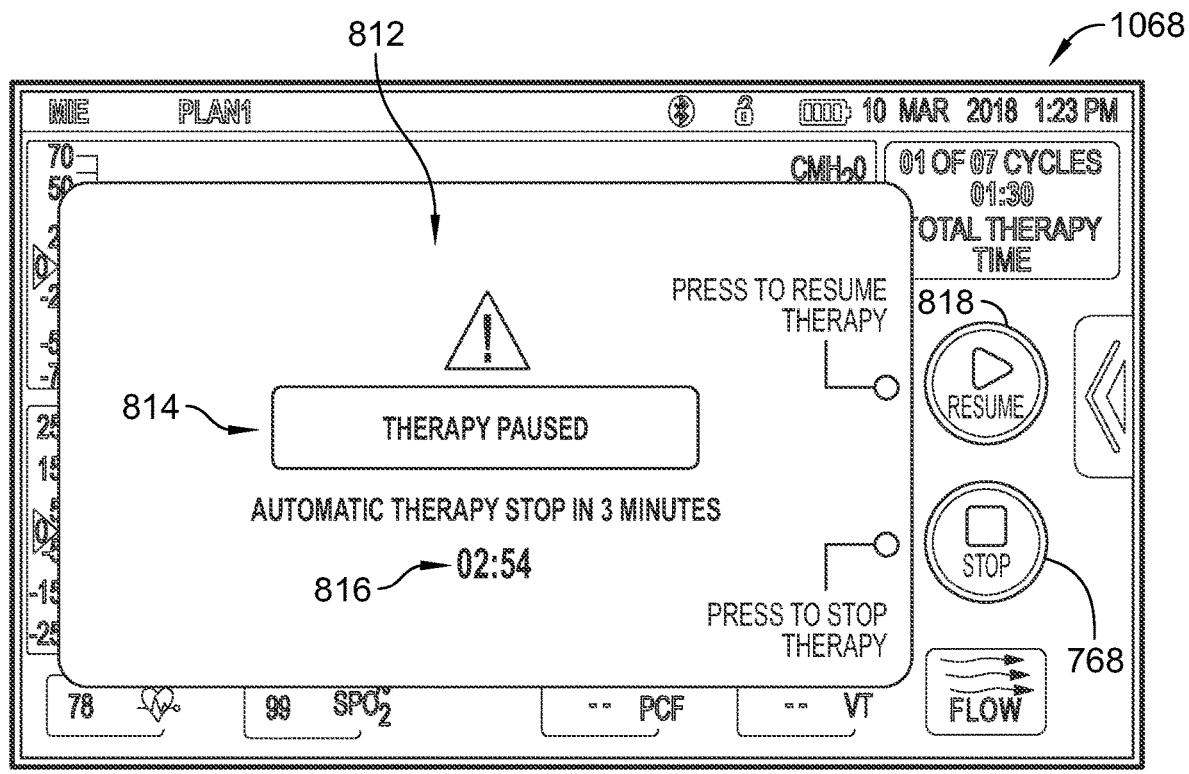
FIG. 80 is a screen shot of a therapy paused screen, similar to FIG. 33, that appears on the GUI in response to selection of the pause button of the second advanced view screen of FIG. 78.

Referring now to FIG. 80, a therapy paused screen 1068, similar to screen 810 of FIG. 33 and screen 1028 of FIG. 71, appears on GUI 16 in response to selection of the pause button 800 of the second advanced view screen 1064 of FIG. 78. The same reference numbers are used in FIGS. 33, 71 and 80 to denote like portions without repeating the descriptions. However, in FIG. 80, resume button 818 and stop button 768 appear on screen 1068 to the right of window 812 rather than being beneath window 812 like in screens 810, 1028 of FIGS. 33 and 71, respectively.

Figure 81:
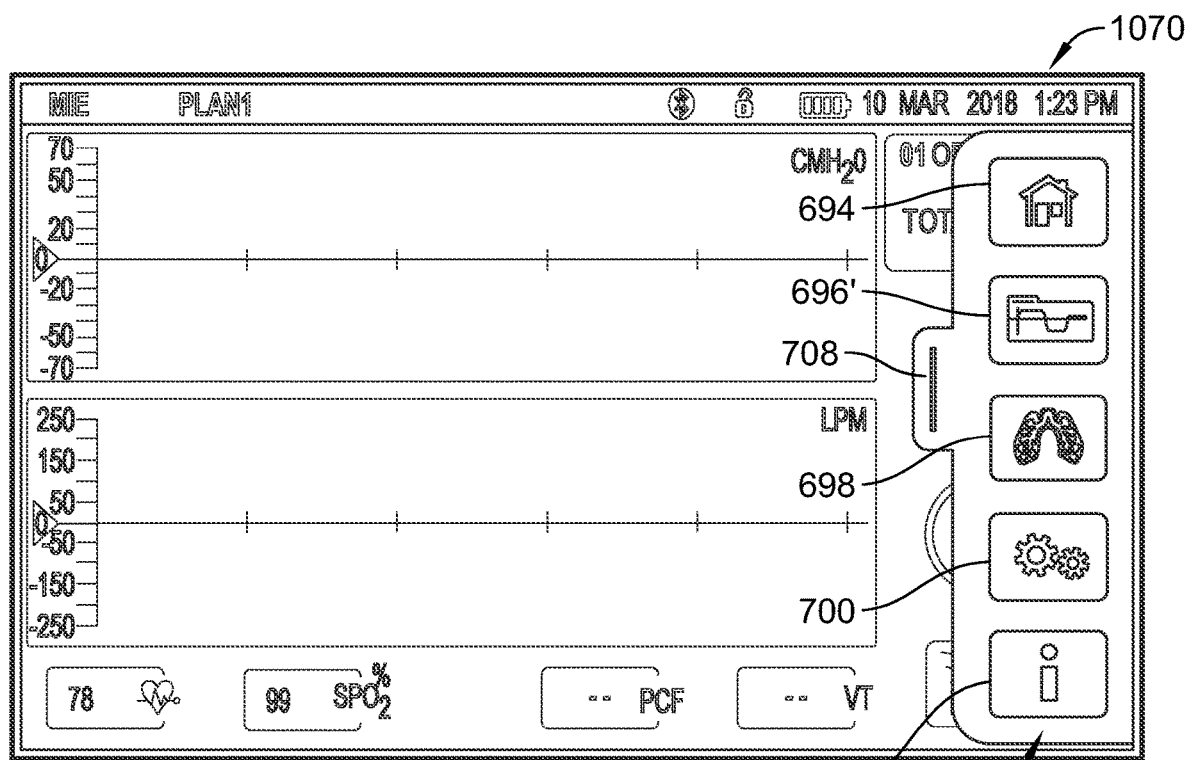
FIG. 81 is a screen shot of an advanced view menu screen that appears on the GUI in response to selection of an arrow icon at the right side of the first advanced view screen of FIG. 77, the advanced view menu screen including a vertical menu of icons similar to the icons of FIG. 39, but with the graph icon linking to the single graph format for the automatic MIE therapy.

As shown in FIG. 81, an advanced view menu screen 1070 appears on GUI 16 in response to selection of arrow icon 688 at the right side of the first advanced view screen 1058 of FIG. 77. Advanced view menu screen 1070 includes a vertical menu of icons 1072 similar to the icons of menu 692 of screen 846 of FIG. 39, but with a basic graph icon 696' linking to the single graph format for the automatic MIE therapy. Thus, icons 694, 698, 700, 702 of menu of icons 1072 and close tab 708 of screen 1070 of FIG. 81 are the same as those of screen 846 of FIG. 39 and so the descriptions of those are not repeated.

Figure 82:
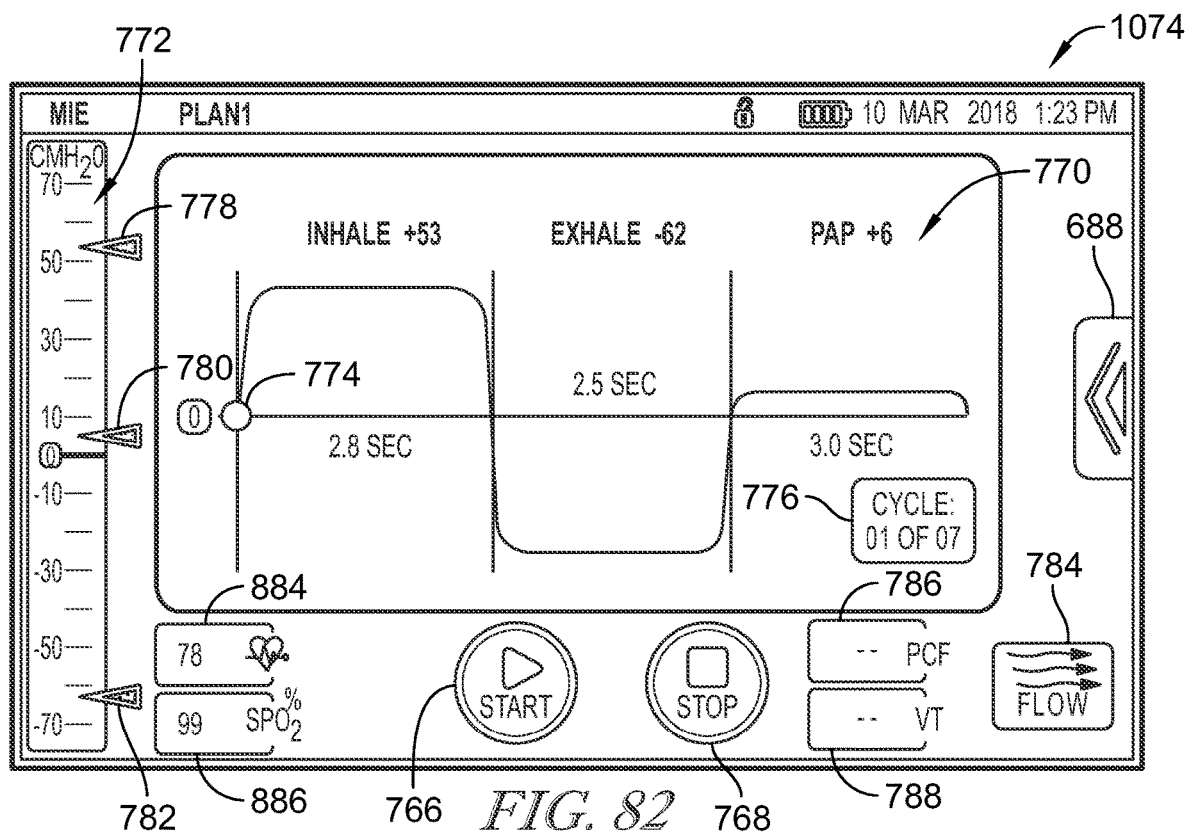
FIG. 82 is a screen shot of another main automatic MIE therapy screen, similar to FIG. 29, that appears on the GUI in response to selection of the graph icon of the vertical menu of icons of FIG. 81, but also showing vitals data relating to the patient's heart rate and blood oxygen saturation percentage.

In response to selection of basic graph icon 696' on the menu of icons 1072 of FIG. 81, another main automatic MIE therapy screen 1074, similar to screen 764 of FIG. 29, appears on the GUI 16 as shown in FIG. 82. However, screen 1074 of FIG. 82 also shows vitals data in fields 884, 886 relating to the patient's heart rate and blood oxygen saturation percentage. Furthermore, the PAP phase of graph 770 of screen 1074 is 3.0 seconds rather than 3.2 seconds as shown in FIG. 29 and box 776 of screen 1074 indicates that the graph 770 pertains to cycle 1 of 7 rather than 1 of 4 as shown in FIG. 29. Otherwise, the same reference numbers as shown in FIG. 29 are used in FIG. 82 to denote like portions and the descriptions are not repeated.

Figure 83:
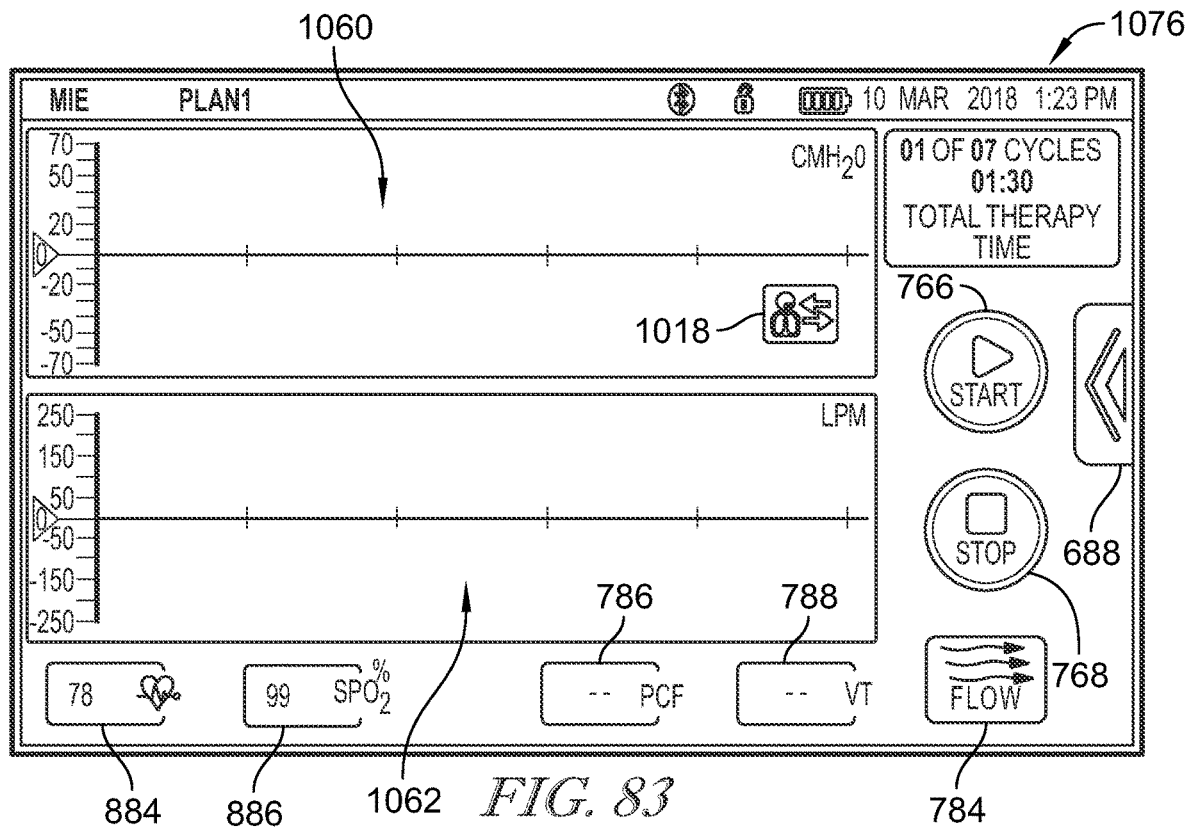
FIG. 83 is a screen shot of a third advanced view screen for automatic MIE therapy that appears on the GUI in response to selection of the graph icon of the vertical menu of icons of the menu screen of FIG. 39, the third advanced view screen being substantially the same as the first advanced view screen of FIG. 77, but having a patient synchrony icon on the pressure graph to indicate that a synchrony function of the respiratory therapy apparatus is enabled.

Referring now to FIG. 83, a third advanced view screen 1076 for automatic MIE therapy appears on GUI 16 in response to selection of the graph icon 696 of the vertical menu of icons 692 of the menu screen of FIG. 39. Third advanced view screen 1076 is substantially the same as the first advanced view screen 1058 of FIG. 77, but has the patient synchrony icon 1018 on the pressure graph 1060 to indicate that the patient synchrony function of the respiratory therapy apparatus 10 is enabled for the automatic MIE therapy. Otherwise, the same reference numbers as shown in FIG. 77 are used in FIG. 83 to denote like portions and the descriptions are not repeated.

Figure 84:
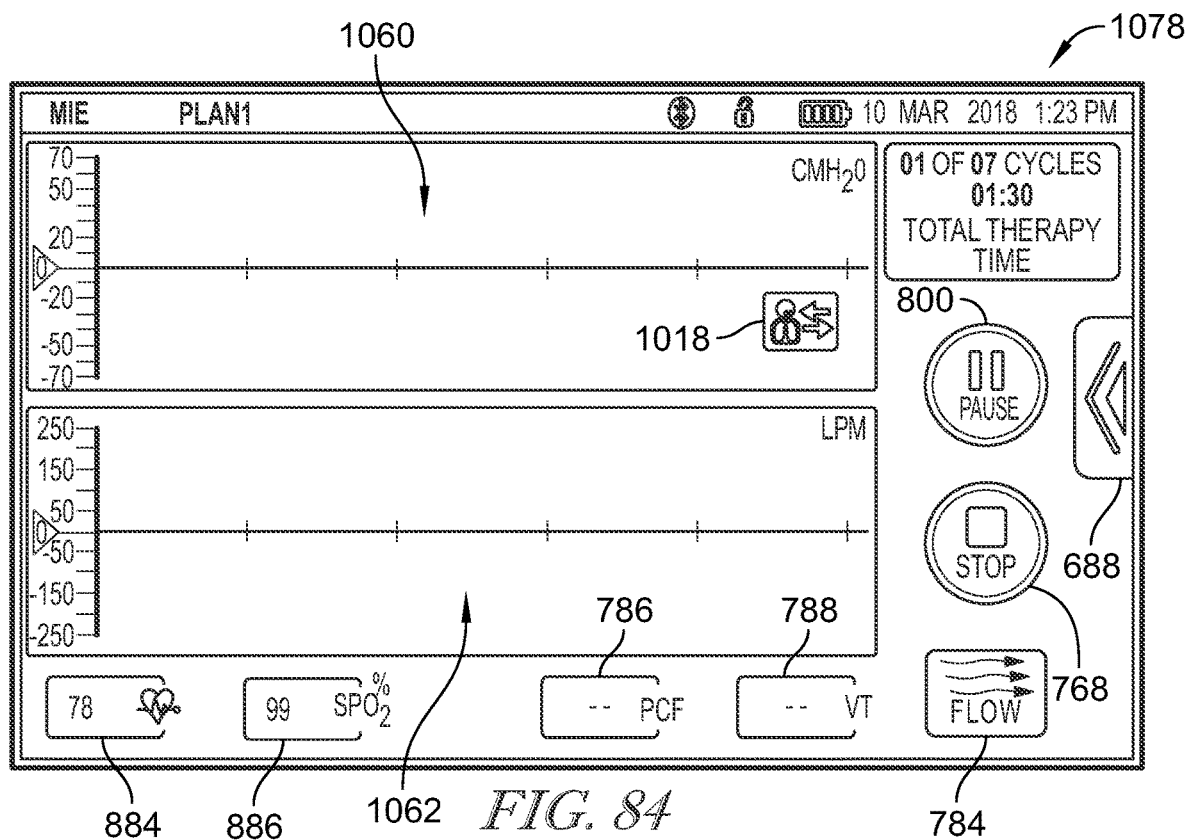
FIG. 84 is a screen shot of a fourth advanced view screen for automatic MIE therapy, substantially the same as FIG. 78, that appears on the GUI in response to selection of the start button of the third advanced view screen of FIG. 83 if a filter unit usage count is below a threshold number of uses and if the battery charge is greater than 20% of a full charge, the fourth advanced view screen showing the start button converted to a pause button and showing the patient synchrony icon.

Referring now to FIG. 84, a fourth advanced view screen 1078 for automatic MIE therapy, substantially the same as FIG. 78, appears on GUI 16 in response to selection of the start button 766 of the third advanced view screen 1076 of FIG. 83 if the filter unit usage count is below the threshold number of uses and if the battery charge is greater than 20% of a full charge. The fourth advanced view screen 1078 of FIG. 84 shows the start button 766 of screen 1076 of FIG. 83 converted to pause button 800 and continues to show the patient synchrony icon 1018. Otherwise, the same reference numbers as shown in FIG. 78 are used in FIG. 84 to denote like portions and the descriptions are not repeated.

Figure 85:
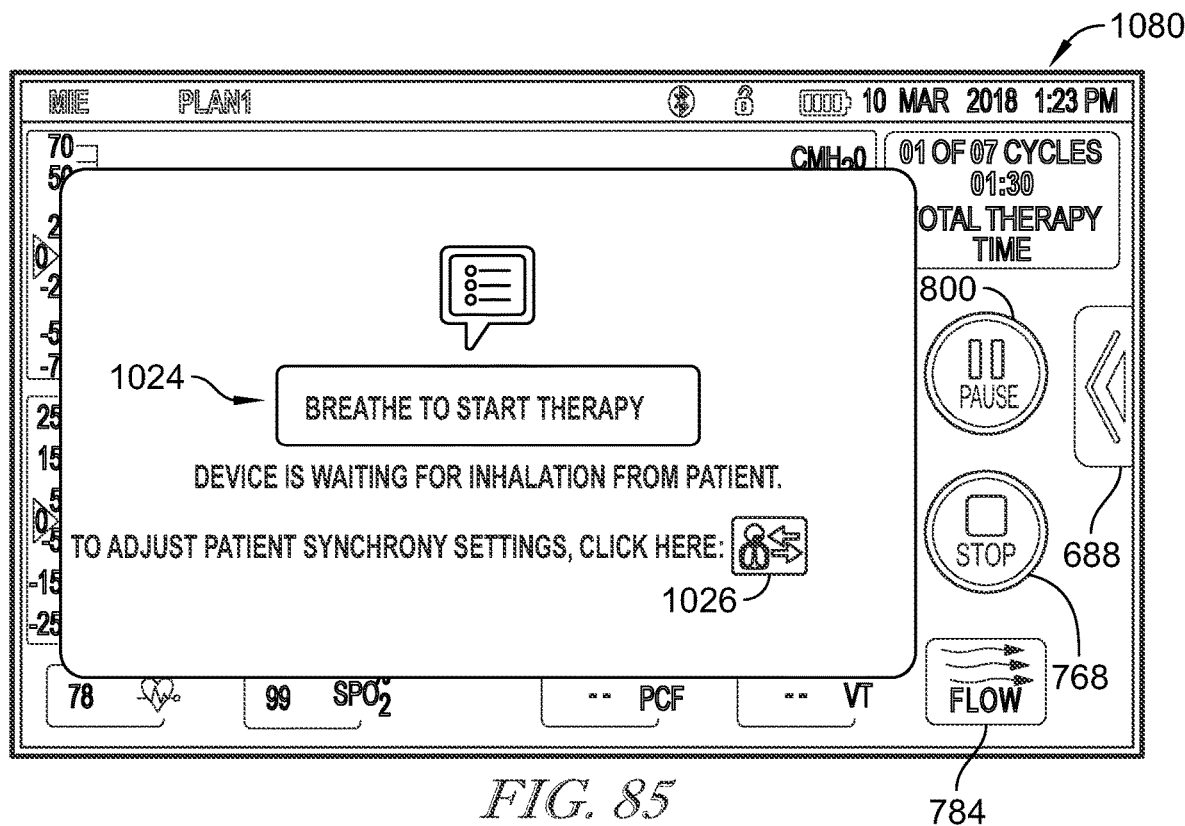
FIG. 85 is a screen shot of a breathe to start therapy screen, similar to FIG. 70, that appears on the GUI in response to the respiratory therapy apparatus failing to detect the user's breath for fifteen seconds or more during startup of the advanced automatic MIE therapy, the breathe to start therapy screen including a patient synchrony icon that is selectable to adjust the sensitivity setting of the synchrony function.

Referring now to FIG. 85, a breathe to start therapy screen 1080, similar to FIG. 70, appears on GUI 16 in response to the respiratory therapy apparatus 10 failing to detect the user's breath for fifteen seconds or more during startup of the advanced automatic MIE therapy. Similar to screen 1022 of FIG. 70, screen 1080 of FIG. 85 includes text box 1024 with the text "BREATH TO START THERAPY" therein. Beneath box 1024 is explanatory text that states, "DEVICE IS WAITING FOR INHALATION FROM PATIENT. TO ADJUST PATIENT SYNCHRONY SETTINGS, CLICK HERE:" with patient synchrony icon 1026 appearing thereafter. Selection of icon 1026 on screen 1080 navigates the user to a screen discussed below in connection with FIG. 88 so that, if desired, the user can adjust the sensitivity setting of the patient synchrony function. Alternatively, the user can take a sufficiently deep breath while viewing screen 1080 of FIG. 85 to start the automatic MIE therapy session.

Figure 86:
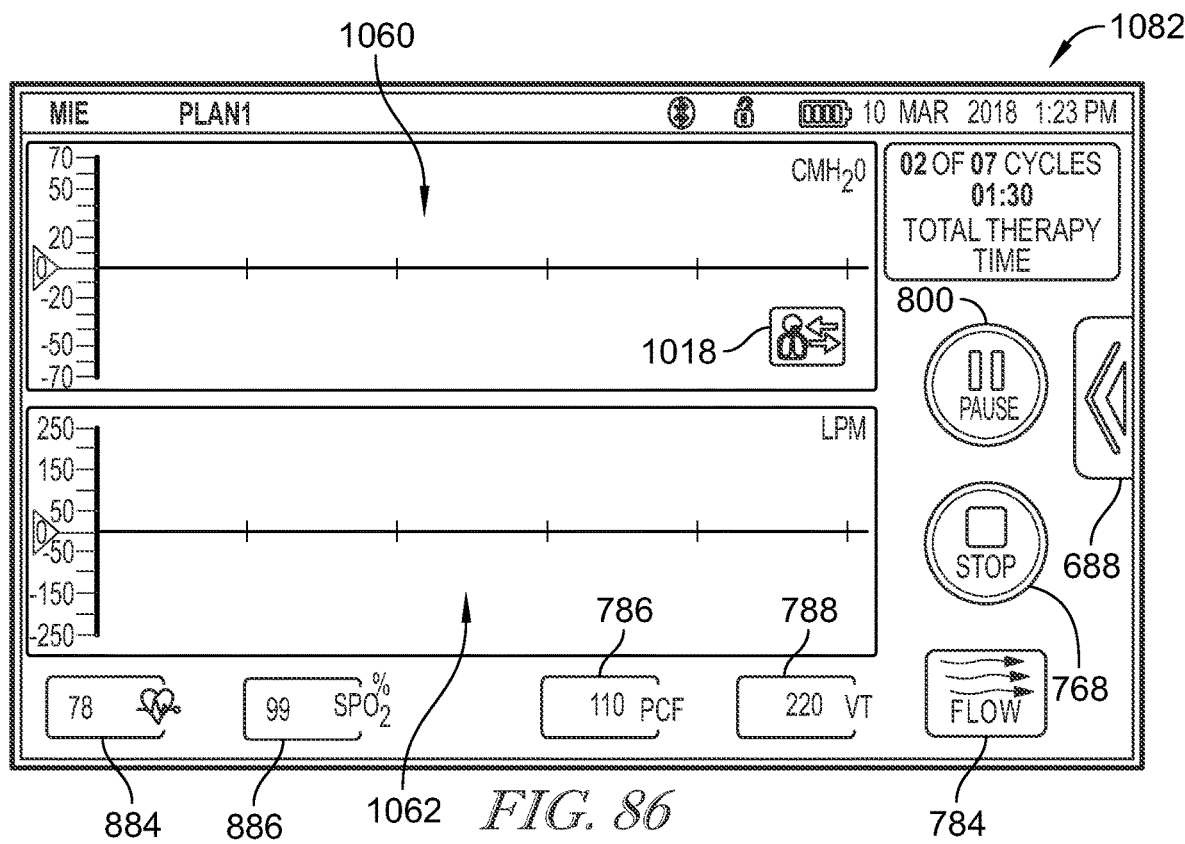
FIG. 86 is a screen shot of a fifth advanced view screen for automatic MIE therapy, substantially the same as the fourth advanced view screen of FIG. 84, but showing that the MIE therapy has progressed to a second therapy cycle of seven total therapy cycles as indicated in a window in the upper right hand corner of the screen and also showing numerical data for peak cough flow ($P_{CF}$) and tidal volume ($V_t$)

As the automatic MIE therapy progresses with the advanced view, a fifth advanced view screen 1082 for automatic MIE therapy, substantially the same as the fourth advanced view screen 1078 of FIG. 84, appears on GUI 16 as shown in FIG. 86. Screen 1082 indicates that the automatic MIE therapy has progressed to a second therapy cycle of seven total therapy cycles in the window in the upper right hand corner of screen 1082. Screen 1082 of FIG. 86 also shows numerical data for peak cough flow ($P_{CF}$) and tidal volume ($V_t$) in fields 786, 788. With regard to screens 1078, 1082 of FIGS. 84 and 86, respectively, the patient synchrony icon 1018 flashes, such as being on for one second then being off for one second, for up to 10 seconds at the beginning of each therapy cycle. Furthermore, during the advanced view automatic MIE therapy, the pressure and flow values of graphs 1060, 1062, respectively, fill into graphs 1060, 1062 from left to right until the X-axis (e.g., time axis) of the graphs 1060, 1062 is fully covered and then graphs 1060, 1062 are cleared and continue to plot, once again, from left to right.

Figure 87:
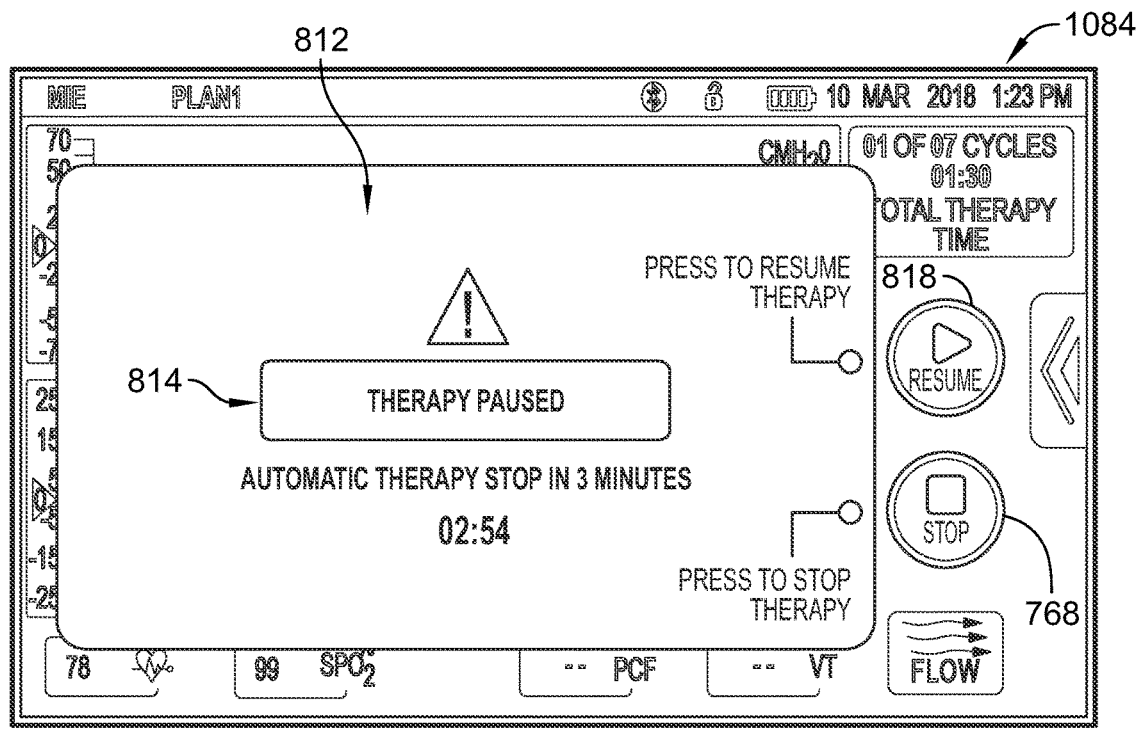
FIG. 87 is a screen shot of an advanced therapy paused screen of automatic MIE therapy, substantially the same as FIG. 71, that appears on the GUI in response to selection of the pause button of the fourth advanced view screen of FIG. 84.

Referring now to FIG. 87, an advanced therapy paused screen 1084 of automatic MIE therapy, substantially the same as FIG. 71, appears on GUI 16 in response to selection of pause button 800 of the fourth advanced view screen 1078 of FIG. 84 or the fifth advanced view screen 1082 of FIG. 86, for example. Alternatively, therapy paused screen 1084 appears on GUI 16 if a threshold period of time, such as twenty seconds, elapses without the respiratory therapy apparatus 10 detecting a breath or without the user selecting the patient synchrony icon 1026 of FIG. 85. Screen 1084 of FIG. 87 is basically the same as screen 1028 of FIG. 71 and so the same reference numbers are used to denote like portions. However, resume button 818 and stop button 768 are to the right of window 812 on screen 1084 of FIG. 87 rather than beneath window 812 like screen 1028 of FIG. 71.

Figure 88:
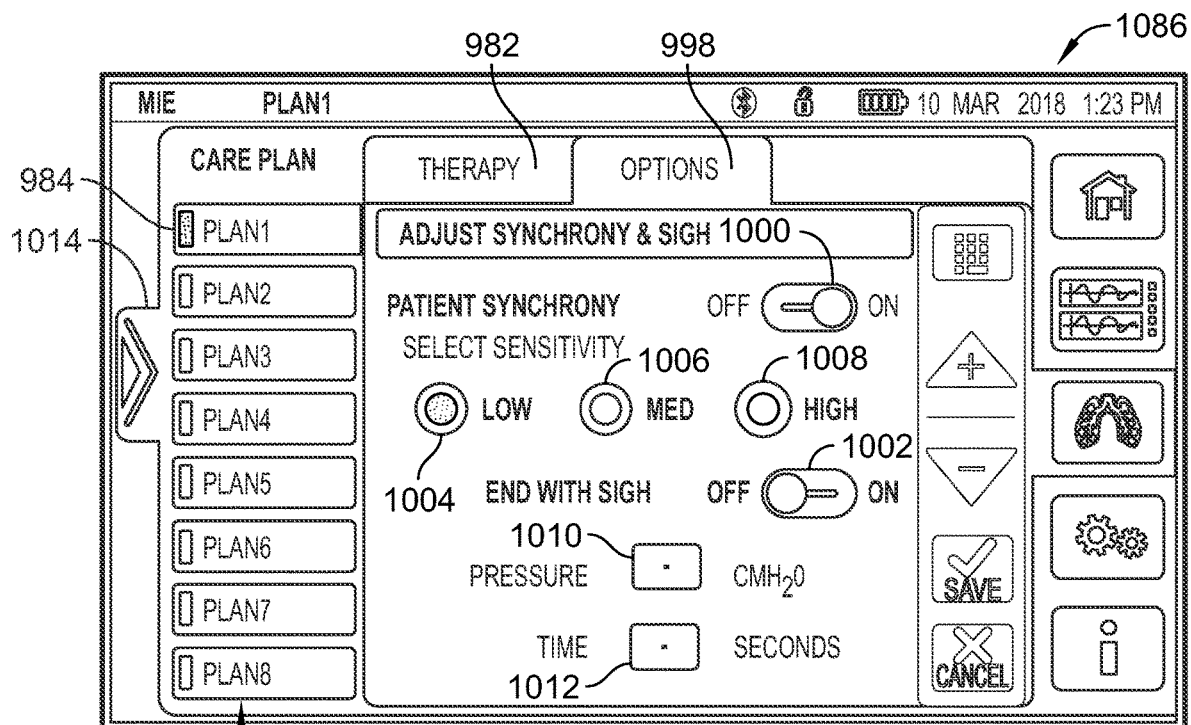
FIG. 88 is a screen shot of a synchrony and sigh adjustment screen for automatic MIE therapy, similar to FIG. 67, that appears on the GUI in response to selection of the patient synchrony icon of FIG. 85.

Referring now FIG. 88, a synchrony and sigh adjustment screen 1086 for automatic MIE therapy, similar to screen 996 of FIG. 67, appears on GUI 16 in response to selection of the patient synchrony icon 1026 of screen 1080 of FIG. 85. Because screen 1086 of FIG. 88 is basically the same as screen 996 of FIG. 67, the same reference numbers are used to denote like portions and the descriptions for these does not need to be repeated. However, on screen 1086 of FIG. 88, the second slider input 1002 is shown in the off position such that the sigh phase at the end of the last cycle of the corresponding automatic MIE therapy does not occur. Accordingly, dashes "-" appear in fields 1010, 1012 since there are no pressure and time values programmed for the sigh phase. Also, radio button 1004 is shown as being selected in FIG. 88 to indicate that the low level of patient synchrony sensitivity will be used during the corresponding automatic MIE therapy.

The discussion above of FIGS. 66-88 with regard to Plan 1 of automatic MIE therapy is equally applicable to Plan 2, Plan 3, Plan 4, etc. of care plan menu 986. The user simply selects the particular plan number tab on menu 986 and proceeds as described above to operate and adjust the settings for the selected plan. According to the present disclosure, a user can also rename any of the care plans so that the renamed care plan text appears in the corresponding care plan tab of menu 986. To change a care plan name, the user touches and holds the desired care plan tab to be renamed on menu 986 for a threshold amount of time, such as four seconds or more in some embodiments, and then a plan name entry screen 1088, shown in FIG. 89, will appear on the GUI 16. Plan name entry screen 1088 includes a graphical keyboard 1090 that is used to enter a plan name for the selected care plan tab.

Figure 89:
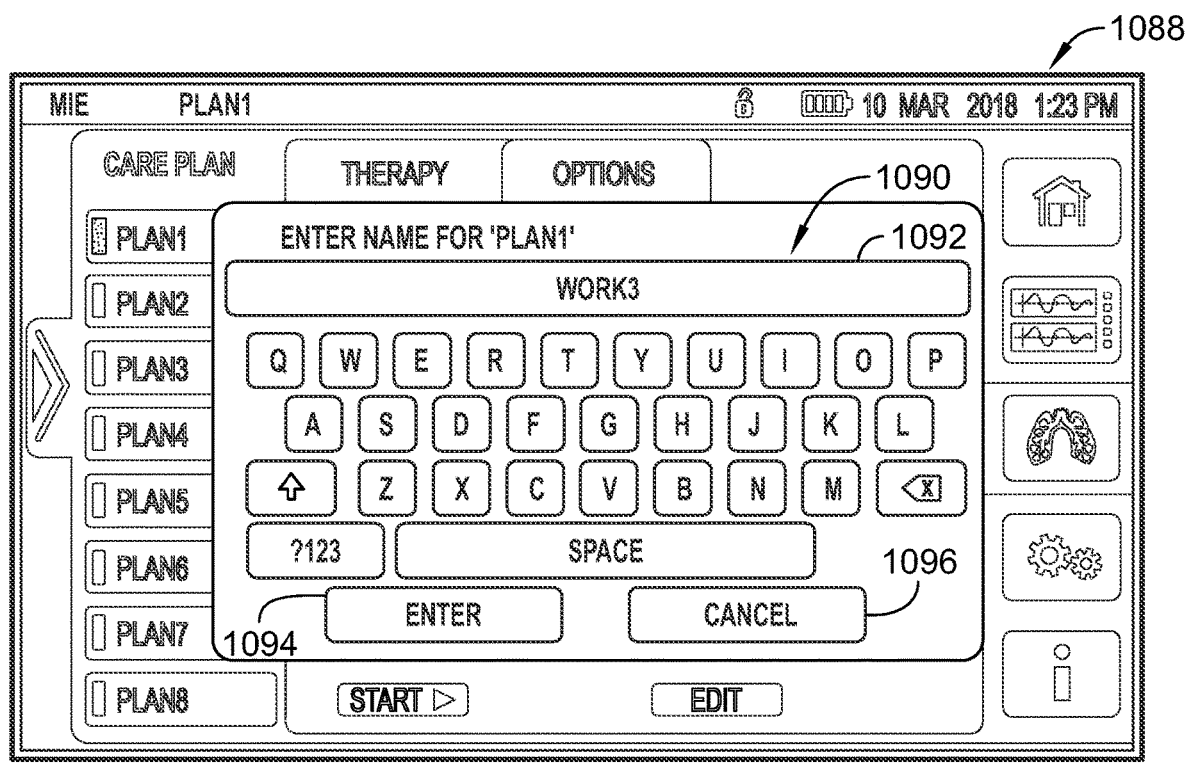
FIG. 89 is a screen shot of a plan name entry screen that appear on the GUI in response to selection of a care plan tab from among a vertical menu of care plan tabs shown along a left hand side of the first care plan screen of FIG. 66, the plan name entry screen including a graphical keyboard that is used to enter a plan name for the selected care plan tab.

Referring still to FIG. 89, a text box 1092 appears above the alphanumeric keys of keyboard 1090 to show the care plan name that is being typed in with graphical keyboard 1090. As indicated by the text above text box 1092, plan 1 has been selected for renaming and the text "WORK3" has been typed using keyboard 1090. After the user types in the new care plan name using keyboard 1090 of screen 1088, an enter button 1094 of graphical keyboard 1090 is selected to save the new care plan name for display in the respective tab which is the tab for plan 1 in the illustrative example. If the user decides not to enter a new care plan name, then a cancel button 1096 of keyboard 1090 is selected and the previous care plan name continues to be used.

Figure 90:
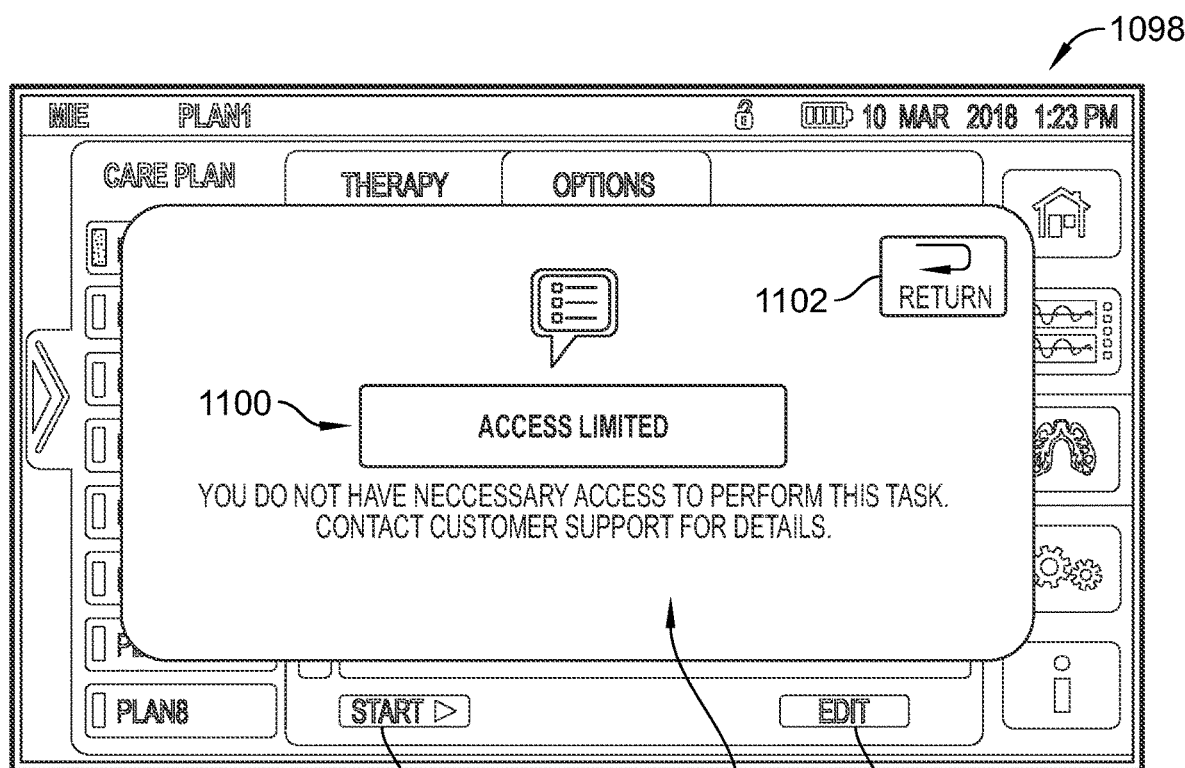
FIG. 90 is a screen shot of an access limited screen that appears on the GUI in response to selection of an edit button of the first care plan screen of FIG. 66 if a clinical access feature of the respiratory therapy apparatus is turned off or disabled.

Referring now to FIG. 90, an access limited screen 1098 appears on GUI 16 in response to selection of edit button 994 of the first care plan screen 980 of FIG. 66 if a clinical access feature of the respiratory therapy apparatus 10 is turned off or disabled. Screen 1098 includes a window 1099 having a text box 1100 with the text "ACCESS LIMITED" therein. Beneath box 1100 is the explanatory text, "YOU DO NOT HAVE NECESSARY ACCESS TO PERFORM THIS TASK. CONTACT CUSTOMER SUPPORT FOR DETAILS." A return button 1102 is also provided in window 1099 of screen 1098 of FIG. 90. Selection of button 1102 returns the user back to screen 980 of FIG. 66.

Figure 91:
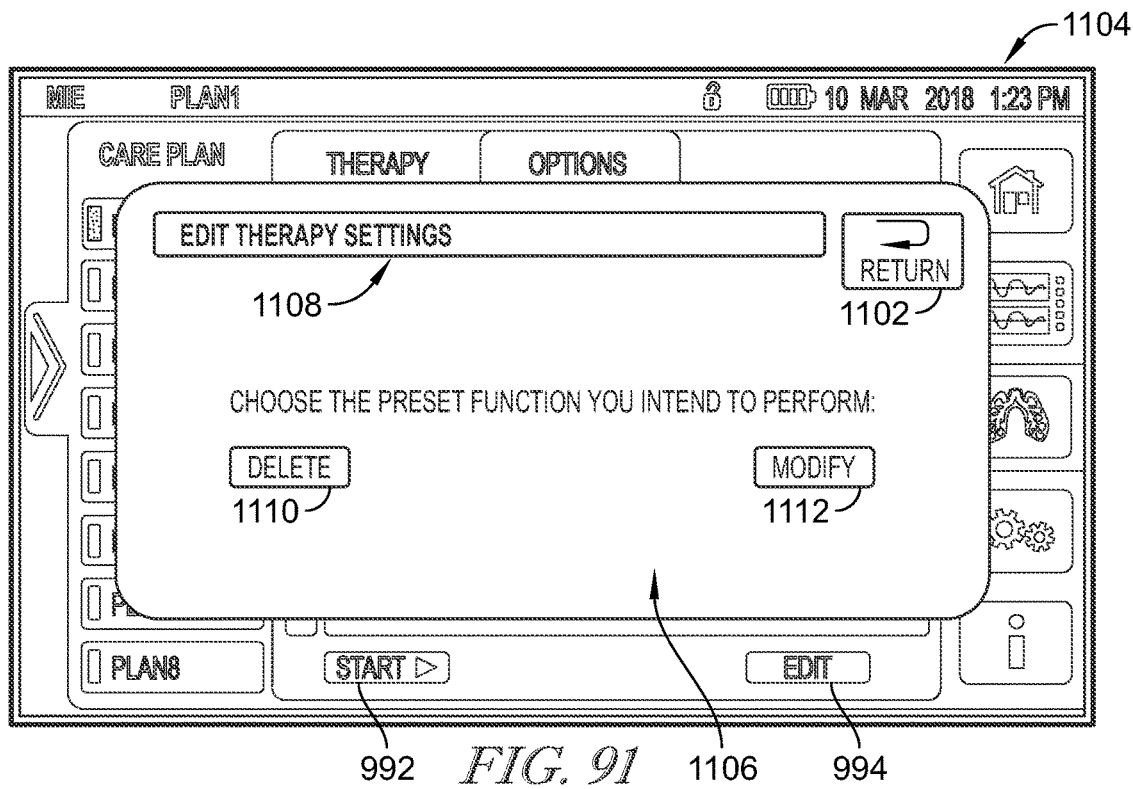
FIG. 91 is a screen shot of an edit therapy settings screen that appears on the GUI in response to selection of the edit button of the first care plan screen of FIG. 66 if the clinical access feature of the respiratory therapy apparatus is turned on or enabled.

Referring now to FIG. 91, an edit therapy settings screen 1104 appears on GUI 16 in response to selection of edit button 994 of the first care plan screen 980 of FIG. 66 if the clinical access feature of the respiratory therapy apparatus 10 is turned on or enabled. Screen 1104 includes a window 1106 having a text box 1108 with the text "EDIT THERAPY SETTINGS" therein. Beneath box 1108 is the explanatory text, "CHOOSE THE PRESET FUNCTION YOU INTEND TO PERFORM:." Beneath the explanatory text in window 1106 is a delete button 1110 and a modify button 1112. Selection of button 1110 begins the process of deleting the selected care plan (e.g., plan 1 in the illustrative example) as will be discussed in further detail below in connection with FIGS. 118 and 119. Selection of button 1112 starts the process for editing the selected care plan. Window 1106 of screen 1104 of FIG. 91 also includes return button 1102 the selection of which returns the user back to screen 980 of FIG. 66.

Figure 92:
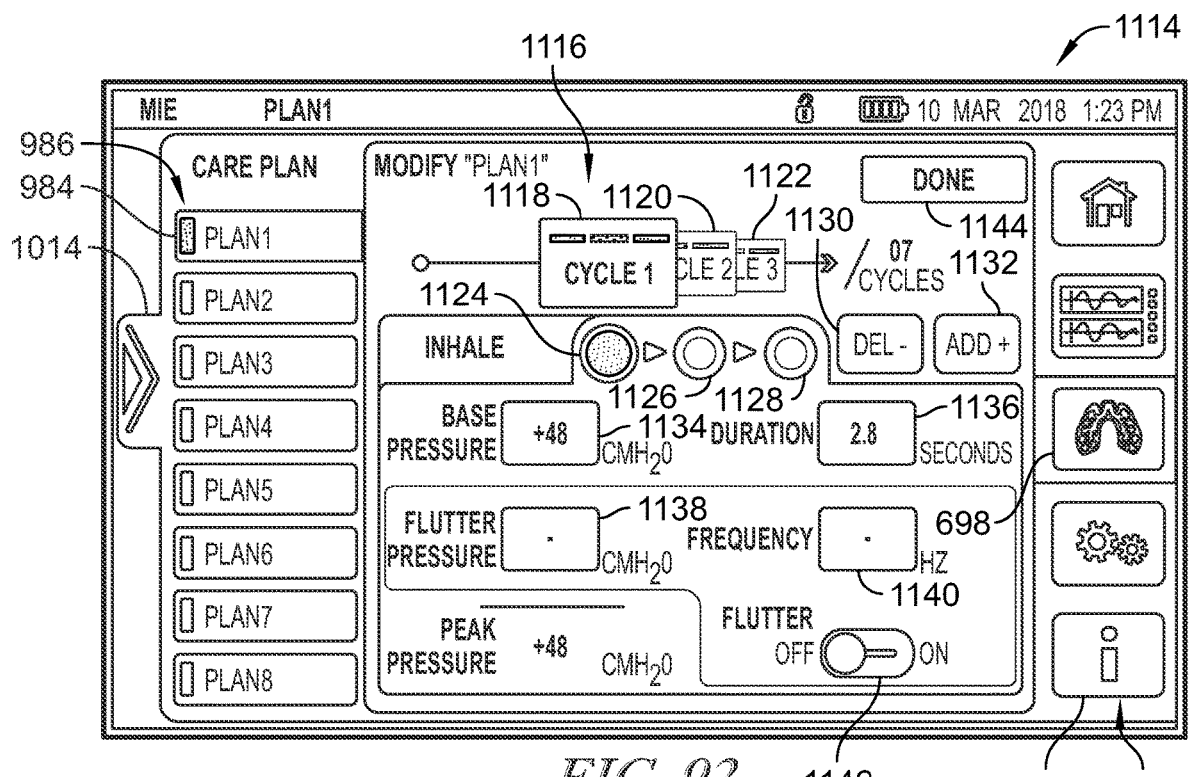
FIG. 92 is a screen shot of a first modify therapy screen that appears on the GUI in response to selection of a modify button on the edit therapy settings screen of FIG. 91, the first modify screen showing that the inhale portion of cycle 1 of plan 1 of the automatic MIE therapy is selected for parameter adjustment as indicated by highlighting of a first radio button of a set of first, second, and third radio buttons.

Referring now to FIG. 92, a first modify therapy screen 1114 appears on GUI 16 in response to selection of modify button 1112 on the edit therapy settings screen 1104 of FIG. 91. First modify screen 1114 shows that the inhale portion of cycle 1 of plan 1 of the automatic MIE therapy is selected for parameter adjustment. In particular, plan 1 button 984 of menu 986 is highlighted and the text "MODIFY 'PLAN 1'" appears in the upper left corner of a window 1116 of screen 1114. Furthermore, a cycle 1 tile 1118 of a set of overlapped tiles including a cycle 2 tile 1120 and a cycle 3 tile 1122 is enlarged near the top of window 1116 to indicate that the parameters in window 1116 pertain to cycle 1 of plan 1. In some embodiments, each care plan for MIE therapy can have up to 20 cycles. As shown to the right of tile 1122, the illustrative example of care plan 1 has seven cycles.

Beneath tiles 1118, 1120, 1122, window 1116 of screen 1114 of FIG. 92 includes first, second, and third radio buttons 1124, 1126, 1128. The first radio button 1124 corresponds to the inhale phase or stage of the selected cycle, the second radio button 1126 corresponds to the exhale phase or stage of the selected cycle, and the third radio button 1128 corresponds to the PAP phase or stage of the selected cycle. In the illustrative example, button 1124 is selected to indicate that the parameters for the inhale phase of cycle 1 of plan 1 appear in window 1116. The word "INHALE" appears in window 1116 to the left of button 1124. To the right of button 1128 is a delete button 1130 and an add button 1132.

Still referring to FIG. 92, window 1116 includes a base pressure box or field 1134 in which the baseline inhale pressure is shown, a duration field or box 1136 in which the duration of the inhale phase is shown, a flutter pressure field or box 1138 in which the flutter pressure for the inhale phase is shown, a frequency box or field 1140 in which the flutter frequency for the inhale phase is shown, and a flutter slider input 1142 that is used to turn the flutter feature of the inhale phase on and off. In the illustrative example, the inhale baseline pressure in field 1134 is +48 $cmH_2O$, the duration of the inhale phase in field 1136 is 2.8 seconds, and the flutter slider input 1142 is in the off position resulting in dashes "-" appearing in fields 1138, 1140.

Beneath flutter pressure field 1138 is a calculated peak pressure value, which in the illustrative example is +48 cmH$_2$O. The peak pressure value is the sum of the pressure values in fields 1134, 1138. Screen 1114 of FIG. 92 further includes a done button 1144 in the upper right corner of window 1116. Selection of done button 1144 returns the user back to screen 980 of FIG. 66 but with the various new parameters for plan 1 shown on table 988. On screen 1146 in some embodiments, icons 698 and 702 of menu 692 are active and can be selected by the user, but the other icons of menu 692 are inactive and grayed out.

Figure 93:
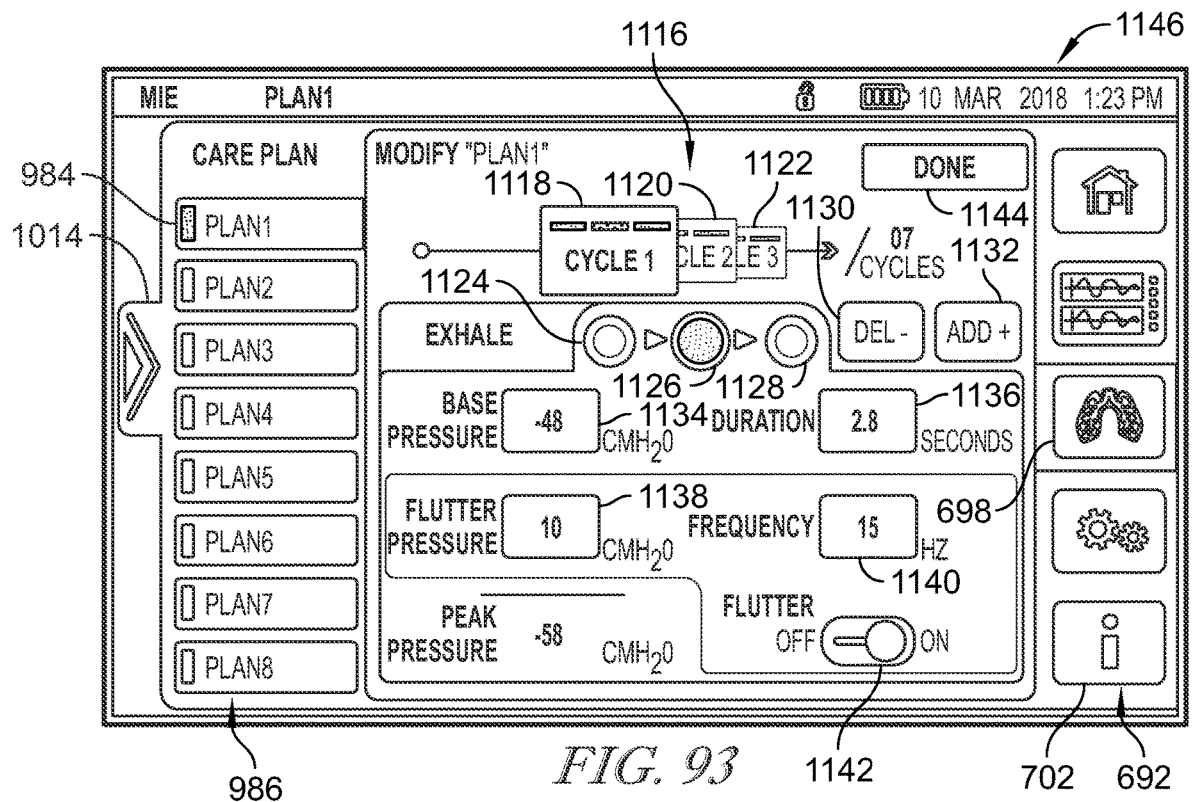
FIG. 93 is a screen shot of a second modify therapy screen that appears on the GUI in response to selection of the second radio button from among the first, second, and third radio buttons, the second radio button corresponding to the exhale portion of the selected cycle and plan number of the automatic MIE therapy.

Referring now to FIG. 93, a second modify therapy screen 1146 appears on GUI 16 in response to selection of the second radio button 1126 from among the first, second, and third radio buttons 1124, 1126, 1128. The second radio button corresponds to the exhale portion of the selected cycle and plan number of the automatic MIE therapy as indicated by the text "EXHALE" appearing to the left of button 1124. Portions of screen 1146 of FIG. 93 that are substantially the same as like portions of screen 1114 of FIG. 92 are denoted with like reference numbers and the descriptions are not repeated. However, fields 1134, 1136, 1138, 1140 and flutter slider input 1142 pertain to the exhale portion of the automatic MIE therapy and not the inhale portion.

Slider input 1142 of screen 1146 is in the on position and, in the illustrative example, the flutter pressure in box 1138 is 10 cmH2O which means the flutter pressure goes 10 cmH$_2$O above and below the baseline pressure of −48 cmH$_2$O shown in box 1134. Accordingly, the peak pressure shown beneath flutter pressure field 1138 in FIG. 93 is −58 cmH$_2$O which is the most negative pressure (e.g., the negative peak) that is programmed to occur during the exhale phase in the illustrative example. Also in the illustrative example of screen 1146 of FIG. 93, field 1136 indicates an exhale phase duration of 2.8 seconds and field 1140 indicates a flutter frequency of 15 Hz.

Figure 94:
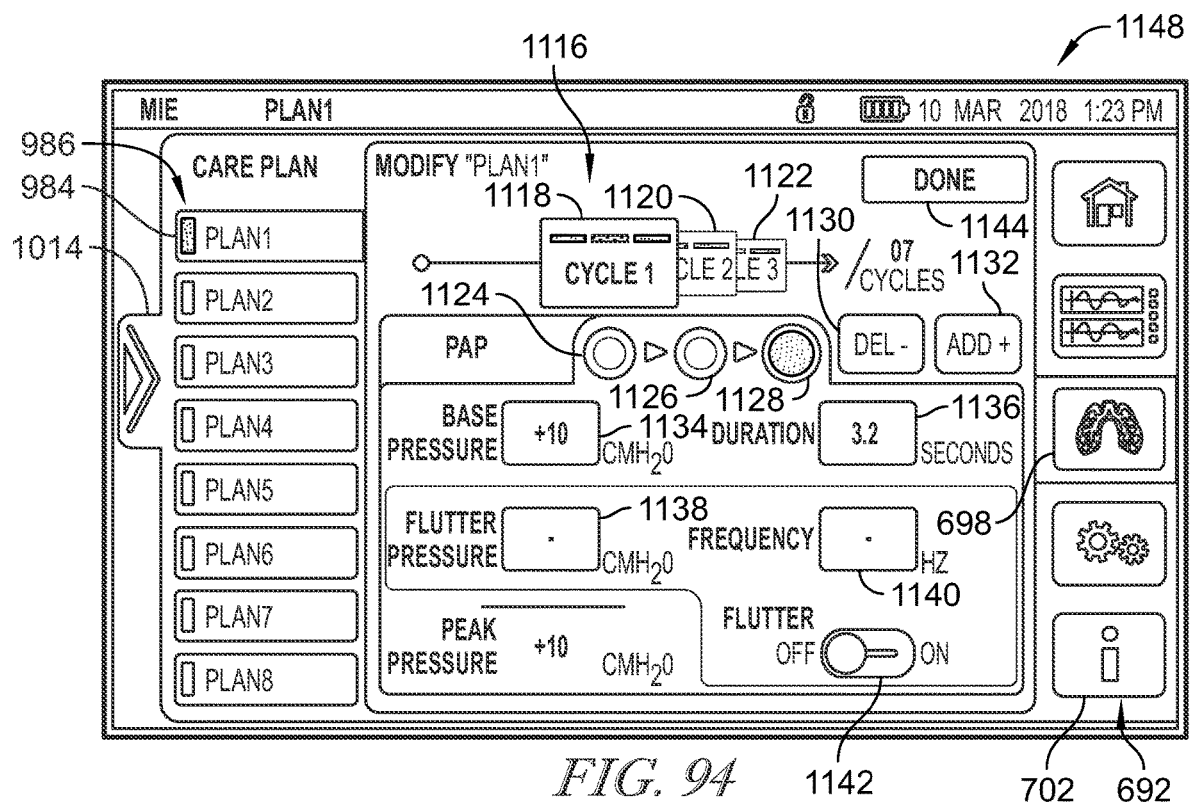
FIG. 94 is a screen shot of a third modify therapy screen that appears on the GUI in response to selection of the third radio button from among the first, second, and third radio buttons, the third radio button corresponding to the PAP portion of the selected cycle and plan number of the automatic MIE therapy.

Referring now to FIG. 94, a third modify therapy screen 1148 appears on GUI 16 in response to selection of third radio button 1128 from among the first, second, and third radio buttons 1124, 1126, 1128. Third radio button 1128 corresponds to the PAP portion of the selected cycle and plan number of the automatic MIE therapy as indicated by the text "PAP" appearing to the left of button 1124. Portions of screen 1148 of FIG. 94 that are substantially the same as like portions of screen 1114 of FIG. 92 are denoted with like reference numbers and the descriptions are not repeated. However, fields 1134, 1136, 1138, 1140 and flutter slider input 1142 pertain to the PAP portion of the automatic MIE therapy and not the inhale portion.

Slider input 1142 of screen 1146 is in the off position in the illustrative example, such that dashes "-" appear in the flutter pressure in box 1138 and in the frequency box 1140. Field 1134 of screen 1148 shows that the baseline pressure for the PAP phase of cycle 1 of plan 1 is +10 cmH$_2$O and field 1136 of screen 1136 shows that the PAP phase duration of cycle 1 of plan 1 is 3.2 seconds. Accordingly, the peak pressure shown beneath flutter pressure field 1138 in FIG. 94 is +10 cmH$_2$O.

Figure 95:
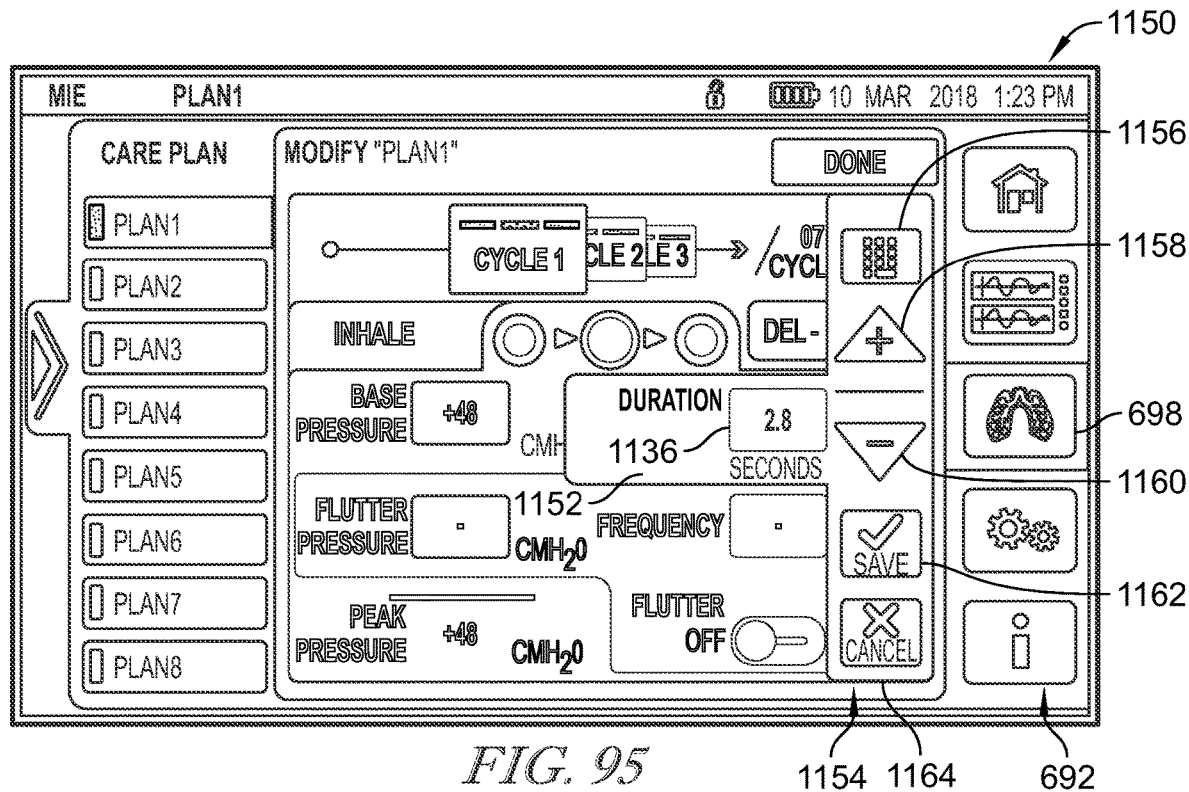
FIG. 95 is a screen shot of a fourth modify therapy screen that appears on the GUI in response to an inhale duration field of the first modify therapy screen of FIG. 92 having been selected for adjustment and showing keyboard, up arrow, down arrow, save, and cancel icons being illuminated for use in adjusting the inhale duration.

Referring now to FIG. 95, a fourth modify therapy screen 1150 appears on GUI 16 in response to inhale duration field 1136 of the first modify therapy screen 1114 of FIG. 92 having been selected for adjustment such that field 1136 is highlighted and appears in a tab 1152 that connects to a menu of icons 1154. On screen 1150, most everything else from screen 1114 is grayed out and inactive except that icon 698 of menu 692 remains highlighted and active. Menu 1154 of screen 1150 of FIG. 95 includes a keyboard icon 1156, an up arrow icon 1158, a down arrow icon 1160, a save icon 1162, and a cancel icon 1164 are activated for use in connection with inhale duration adjustment for the selected plan and cycle. The up arrow icon 1158 and down arrow icon 1160 then can be touched successively to increment or decrement, respectively, the corresponding inhale duration by 0.1 seconds. Alternatively, each of arrow icons 1158, 1160 can be selected and held continuously and the respective inhale duration will be incremented or decremented, respectively, by 0.1 seconds for every second held, up to five seconds, after which the inhale duration will be incremented or decremented, respectively, by 0.1 seconds for every ½ second held.

Figure 96:
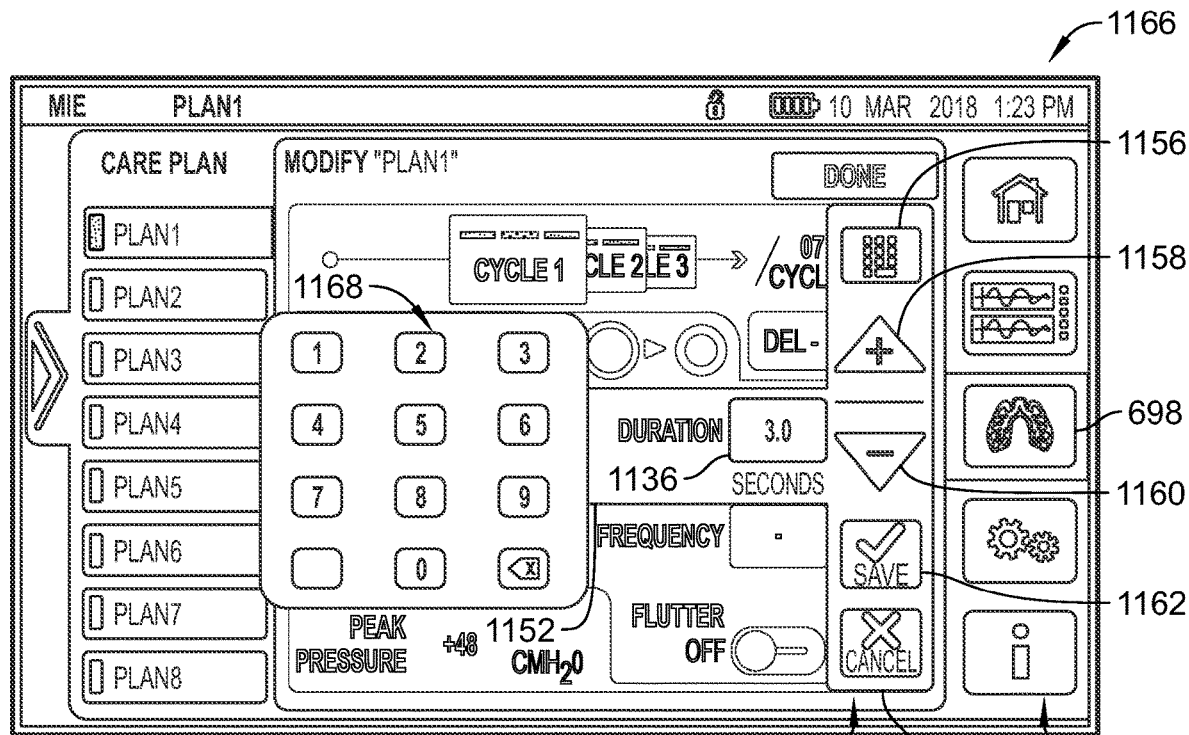
FIG. 96 is a screen shot of a fifth modify therapy screen that appears on the GUI after the keyboard icon of FIG. 95 is selected, the graphical keyboard being used to change the inhale duration from 2.8 seconds, shown in FIG. 95, to 3.0 seconds.

As shown in FIG. 96, a fifth modify therapy screen 1166 appears on GUI 16 in response to keyboard icon 1156 of FIG. 95 being selected. Screen 1166 includes a graphical keyboard 1168 that is located just to the left of tab 1152 and that is usable to directly type the new inhale duration value into field 1136. In the illustrative example, keyboard 1168 has been used to change the inhale duration from 2.8 seconds, shown in FIG. 95, to 3.0 seconds. After the user has incremented or decremented to the desired inhale duration value in field 1136 using arrow buttons 1158, 1160 or after the user has typed the desired inhale duration value in field 1136 using graphical keyboard 1168, save button 1162 of menu 1154 is selected to save the new inhale duration value for subsequent use during future automatic MIE therapy sessions in connection with the selected plan and selected cycle. If the user decides not to enter a new inhale duration value, then cancel button 1164 of menu 1154 is selected and the previous inhale duration value is used for future automatic MIE therapy sessions for the corresponding plan and cycle.

Figure 97:
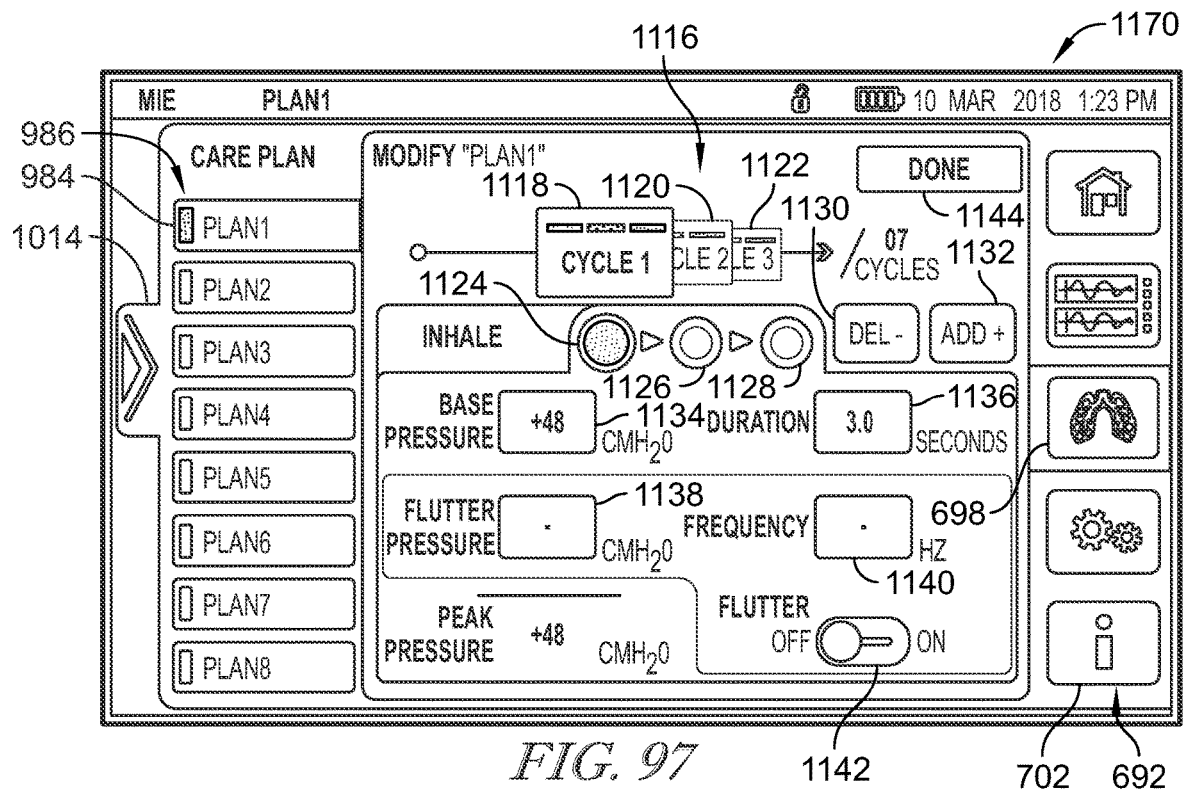
FIG. 97 is a screen shot of a sixth modify therapy screen showing the new inhale duration in the respective field after the save icon of the fifth modify therapy screen of FIG. 96 has been selected.

Referring now to FIG. 97, a sixth modify therapy screen 1170 appears on GUI 16 in response to selection of the save icon 1162 on screen 1166 of FIG. 96. Screen 1170 shows the new inhale duration of 3.0 seconds in the respective field 1136. Otherwise, screen 1170 of FIG. 97 is substantially the same as screen 1114 of FIG. 92 and so like reference numbers are used to denote like portions without repeating the descriptions.

Figure 98:
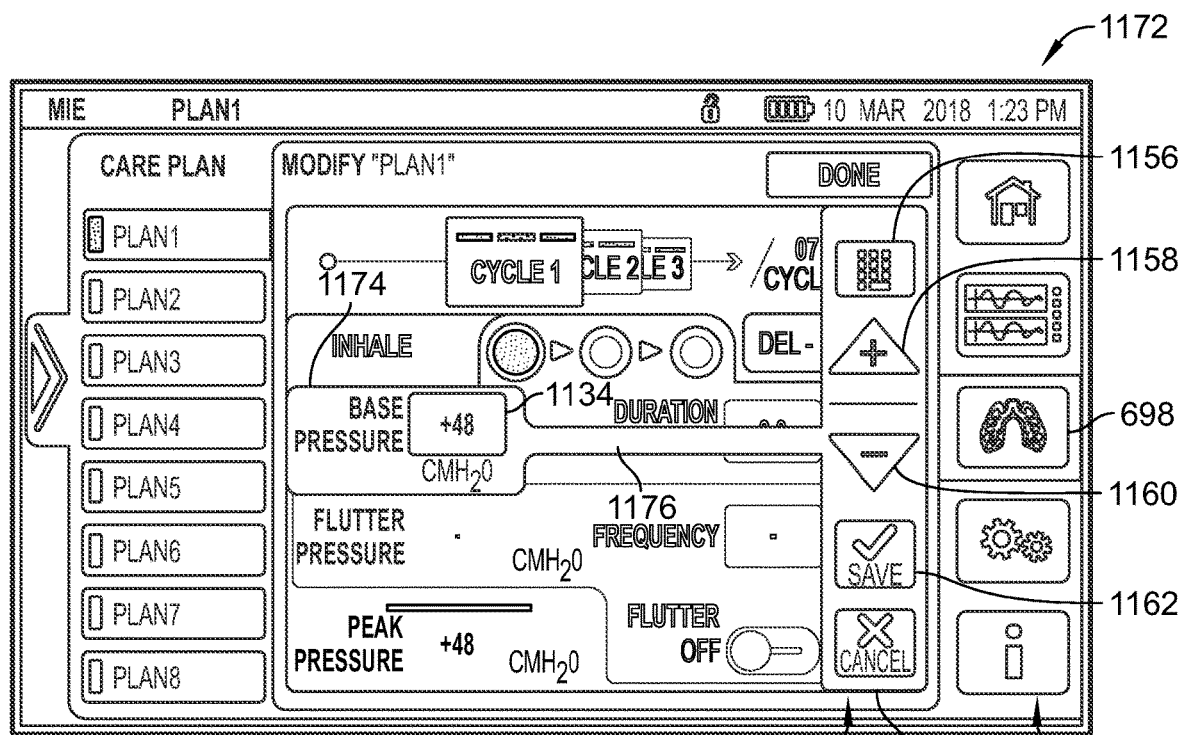
FIG. 98 is a screen shot of a seventh modify therapy screen that appears on the GUI in response to an inhale base pressure field of the first modify therapy screen of FIG. 92 or the inhale base pressure field of the sixth modify pressure screen of FIG. 97 having been selected for adjustment and showing the keyboard, up arrow, down arrow, save, and cancel icons being illuminated for use in adjusting the inhale base pressure.

Referring now to FIG. 98, a seventh modify therapy screen 1172 appears on GUI 16 response to inhale base pressure field 1134 of the first modify therapy screen 1114 of FIG. 92 or the sixth modify pressure screen 1170 of FIG. 97 having been selected for adjustment such that field 1134 is highlighted and appears in a bubble 1174. A connector segment 1176 extends from bubble 1176 to menu 1154 to indicate that keyboard icon 1156, up arrow icon 1158, down arrow icon 1160, save icon 1162, and cancel icon 1164 are activated for use in connection with inhale baseline pressure adjustment. Up arrow icon 1158 and down arrow icon 1160 are touched successively to increment or decrement, respectively, the corresponding inhale base pressure value by 1 cmH$_2$O. Alternatively, each of arrow icons 1158, 1160 can be selected and held continuously and the respective inhale base pressure value will be incremented or decremented, respectively, by 1 cmH$_2$O for every second held, up to five seconds, after which the inhale base pressure value will be incremented or decremented, respectively, by 1 cmH$_2$O for every ½ second held. If an upper pressure limit or lower pressure limit is reached for the inhale base pressure value in field 1134, then the up arrow button 1158 or down arrow button 1160, as the case may be, becomes inactive and continued selection of the particular arrow button 1158, 1160 has no effect. With regard to screen 1172 of FIG. 98, most everything else other than field 1134, bubble 1174, connector segment 1176, and icons 1156, 1158, 1160, 1162, 1164 of menu 1154 is grayed out and inactive except that icon 698 of menu 692 remains highlighted and active.

Figure 99:
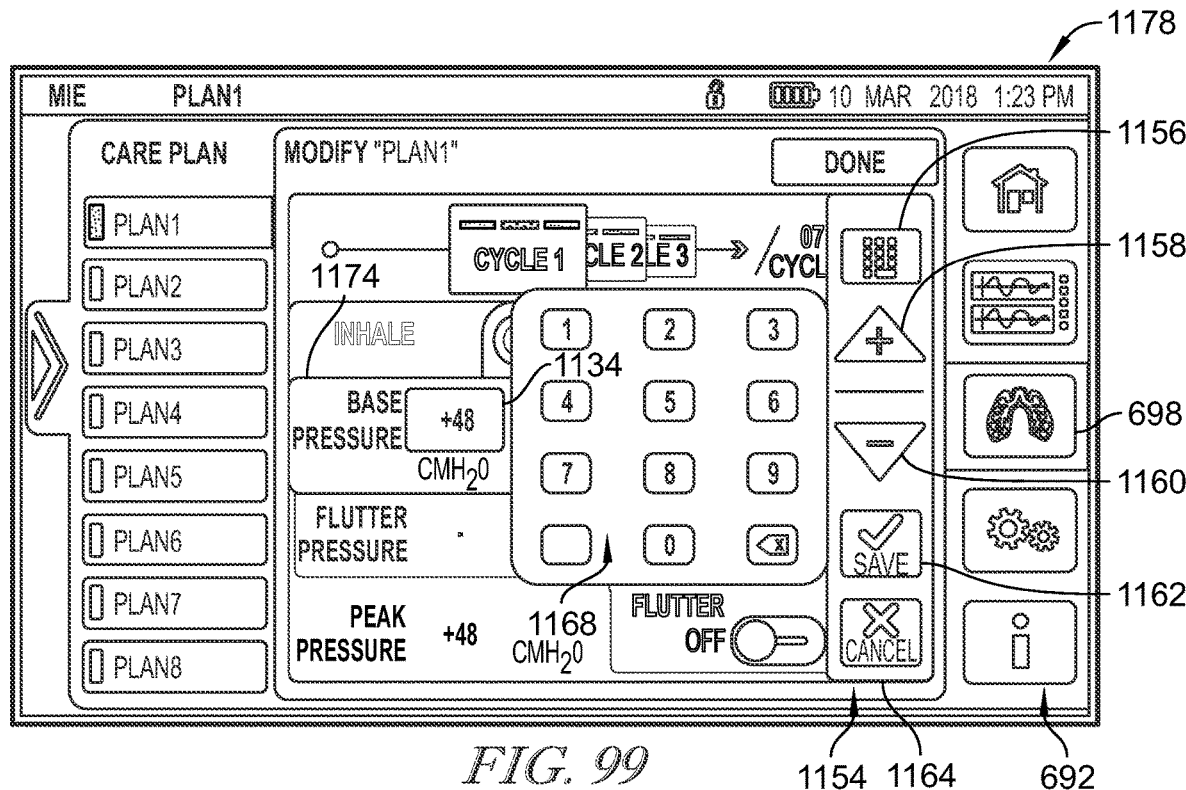
FIG. 99 is a screen shot of a eighth modify therapy screen that appears on the GUI after the keyboard icon of FIG. 98 is selected, showing the current inhale base pressure value and the graphical keyboard.
Figure 100:
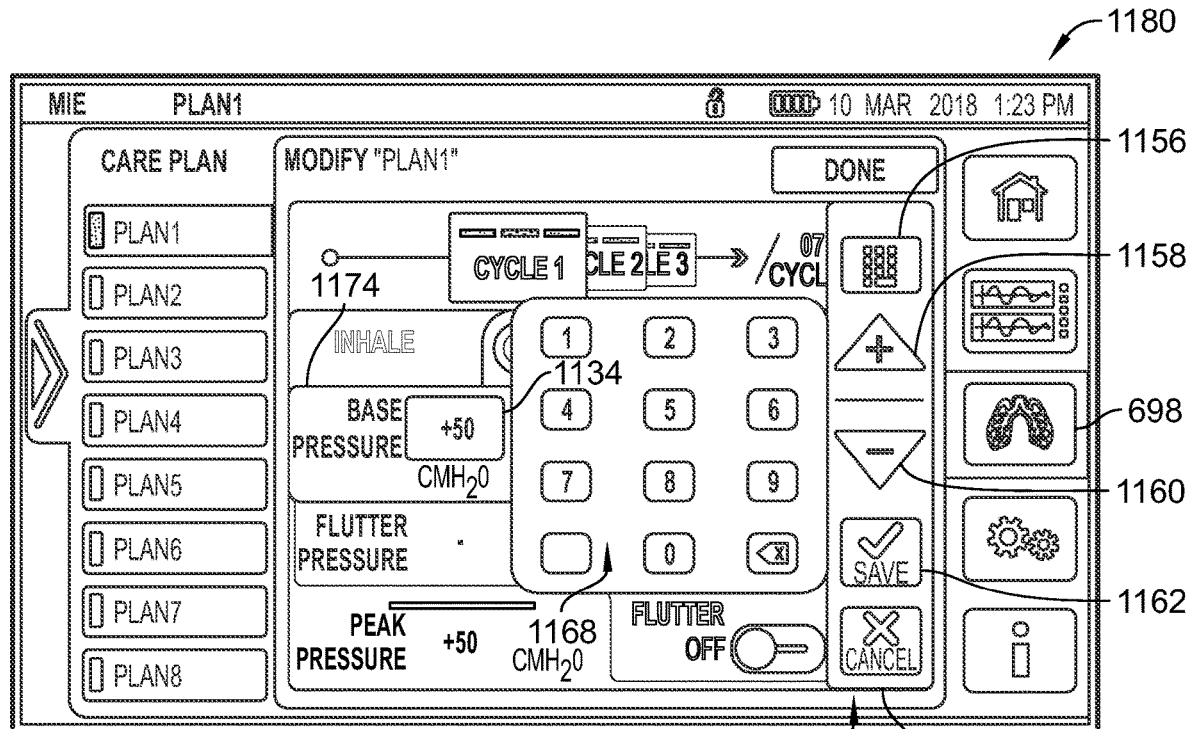
FIG. 100 is a screen shot of a ninth modify therapy screen that appears on the GUI after the graphical keyboard of FIG. 99 is used to change the inhale base pressure from 48 cmH$_2$O, shown in FIGS. 97-99, to 50 cmH$_2$O.

As shown in FIG. 99, an eighth modify therapy screen 1178 appears on GUI 16 in response to keyboard icon 1156 of FIG. 98 being selected so that graphical keyboard 1168 appears on screen 1178 between bubble 1174 and menu 1154. In some embodiments, arrow icons 1158, 1160 become grayed out and inactive when keyboard 1168 appears on GUI 16. In FIG. 99, the current inhale base pressure value of +48 cmH$_2$O is shown in field 1134. As shown in FIG. 100, a ninth modify therapy screen 1180 appears on GUI 16 after graphical keyboard 1168 of screen 1178 of FIG. 99 is used to change the inhale base pressure value from +48 cmH$_2$O to +50 cmH$_2$O. Otherwise, screen 1180 of FIG. 100 is substantially the same as screen 1178 of FIG. 99 and so like reference numbers are used to denote like portions without repeating the descriptions.

After the user has incremented or decremented to the desired inhale base pressure value in field 1134 using arrow buttons 1158, 1160 or after the user has typed the desired inhale base pressure value in field 1134 using graphical keyboard 1168, save button 1162 of menu 1154 is selected to save the new inhale base pressure value for subsequent use during future automatic MIE therapy sessions in connection with the selected plan and selected cycle. If the user decides not to enter a new inhale base pressure value, then cancel button 1164 of menu 1154 is selected and the previous inhale base pressure value is used for future automatic MIE therapy sessions for the corresponding plan and cycle.

Referring now to FIG. 101, a tenth modify therapy screen 1182 appears on GUI 16 in response to selection of the save icon 1162 on screen 1180 of FIG. 100. Screen 1182 shows the new inhale base pressure of +50 cmH$_2$O in the respective field 1134. Screen 1182 also shows that the peak pressure is +50 cmH$_2$O as compared to the peak pressure of +48 cmH$_2$O of screen 1170 of FIG. 97. Otherwise, screen 1182 of FIG. 101 is substantially the same as screen 1170 of FIG. 97 and so like reference numbers are used to denote like portions without repeating the descriptions.

Figure 102:
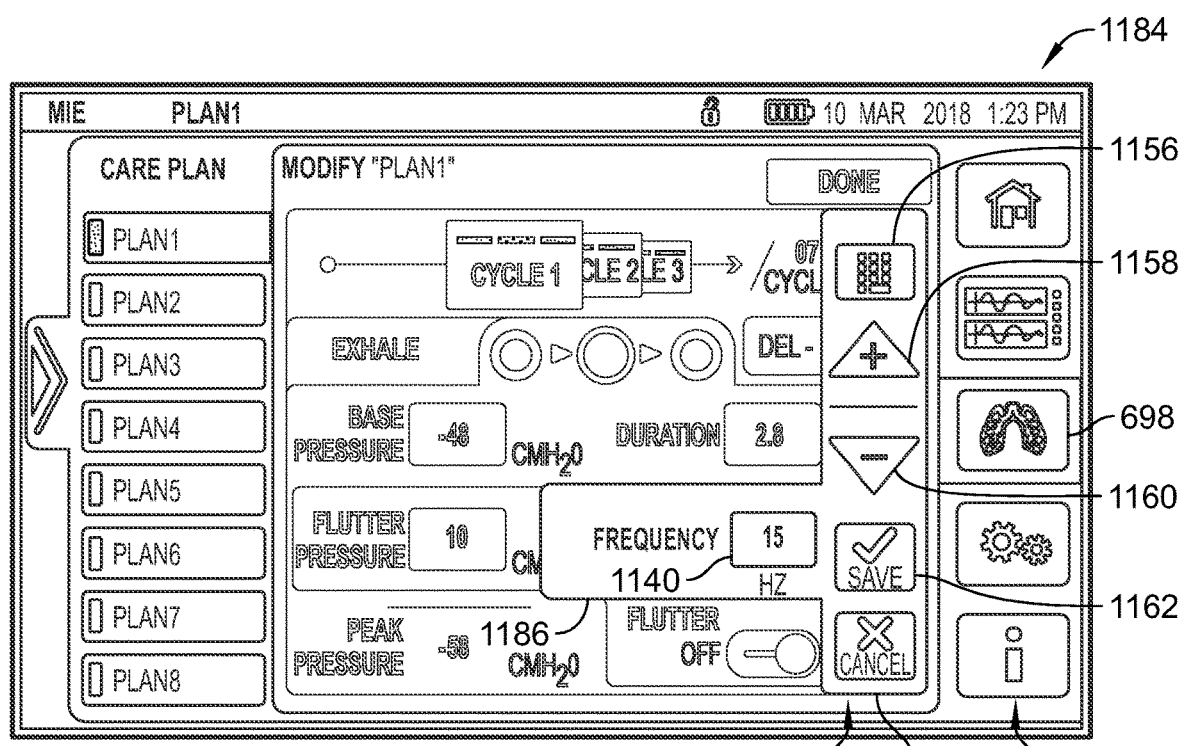
FIG. 102 is a screen shot of an eleventh modify therapy screen that appears on the GUI in response to an exhale flutter frequency field of the second modify therapy screen of FIG. 93 having been selected for adjustment and showing keyboard, up arrow, down arrow, save, and cancel icons being illuminated for use in adjusting the flutter frequency.

Referring now to FIG. 102, an eleventh modify therapy screen 1184 appears on GUI 16 in response to exhale flutter frequency field 1140 of second modify therapy screen 1146 of FIG. 93 having been selected for adjustment such that field 1140 is highlighted and appears in a tab 1186 that connects to menu of icons 1154. On screen 1184, most everything else from screen 1146 is grayed out and inactive except that icon 698 of menu 692 remains highlighted and active. Menu 1154 of screen 1184 of FIG. 102 has the same icons or buttons 1156, 1158, 160, 1162, 1164 as menu 1154 of screen 1150 of FIG. 95 and these are used in the same manner as described above. However, with regard to the exhale flutter frequency in field 1140, the up arrow icon 1158 and down arrow icon 1160 then can be touched successively to increment or decrement, respectively, the corresponding frequency by 1 Hz. Alternatively, each of arrow icons 1158, 1160 can be selected and held continuously and the respective exhale flutter frequency value will be incremented or decremented, respectively, by 1 Hz for every second held, up to five seconds, after which the flutter frequency will be incremented or decremented, respectively, by 1 Hz for every ½ second held.

Figure 103:
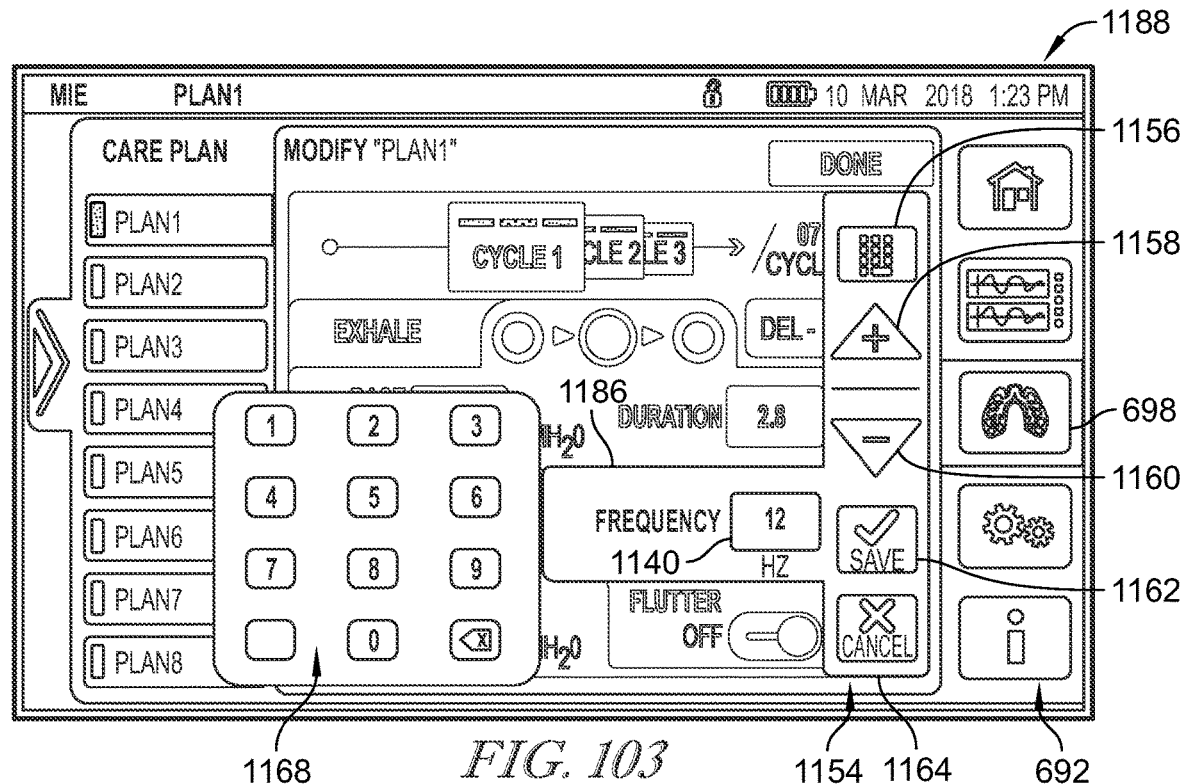
FIG. 103 is a screen shot of a twelfth modify therapy screen that appears on the GUI after the keyboard icon of FIG. 102 is selected, the graphical keyboard being used to change the exhale flutter frequency from 15 Hz, shown in FIGS. 93 and 102, to 12 Hz.

As shown in FIG. 103, a twelfth modify therapy screen 1188 appears on GUI 16 in response to keyboard icon 1156 of FIG. 102 being selected. Screen 1188 includes graphical keyboard 1168 just to the left of tab 1152. Keyboard 1168 is usable to directly type the new exhale flutter frequency value into field 1140. In the illustrative example, keyboard 1168 has been used to change the exhale flutter frequency from 15 Hz, shown in FIGS. 93 and 102, to 12 Hz as shown on screen 1188 of FIG. 103. After the user has incremented or decremented to the desired exhale flutter frequency value in field 1140 using arrow buttons 1158, 1160 or after the user has typed the desired exhale flutter frequency value in field 1140 using graphical keyboard 1168, save button 1162 of menu 1154 is selected to save the new exhale flutter frequency value for subsequent use during future automatic MIE therapy sessions in connection with the selected plan and selected cycle. If the user decides not to enter a new exhale flutter frequency value, then cancel button 1164 of menu 1154 is selected and the previous exhale flutter frequency value is used for future automatic MIE therapy sessions for the corresponding plan and cycle.

Figure 104:
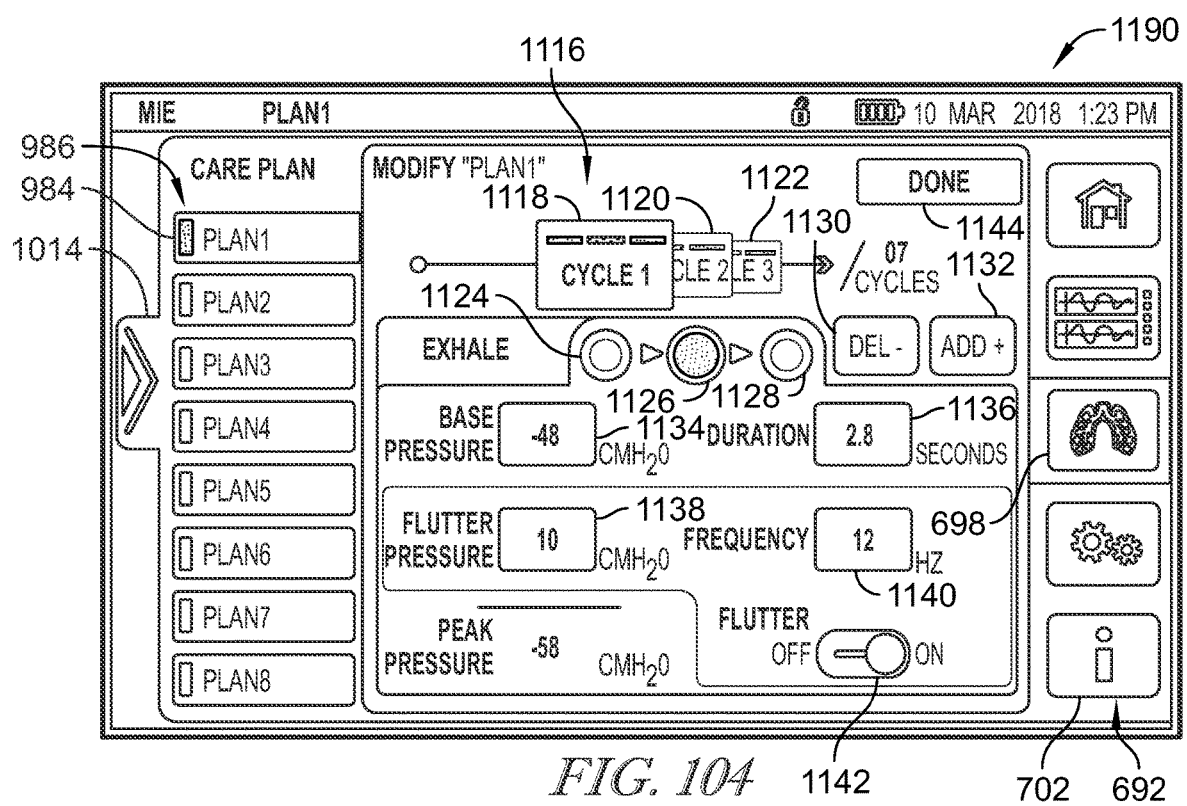
FIG. 104 is a screen shot of a thirteenth modify therapy screen showing the new exhale flutter frequency in the respective field after the save icon of the twelfth modify therapy screen of FIG. 103 has been selected.

Referring now to FIG. 104, a thirteenth modify therapy screen 1190 appears on GUI 16 in response to selection of the save icon 1162 on screen 1188 of FIG. 103. Screen 1190 shows the new exhale flutter frequency value of 12 Hz in the respective field 1140. Otherwise, screen 1190 of FIG. 104 is substantially the same as screen 1146 of FIG. 93 and so like reference numbers are used to denote like portions without repeating the descriptions.

Figure 105:
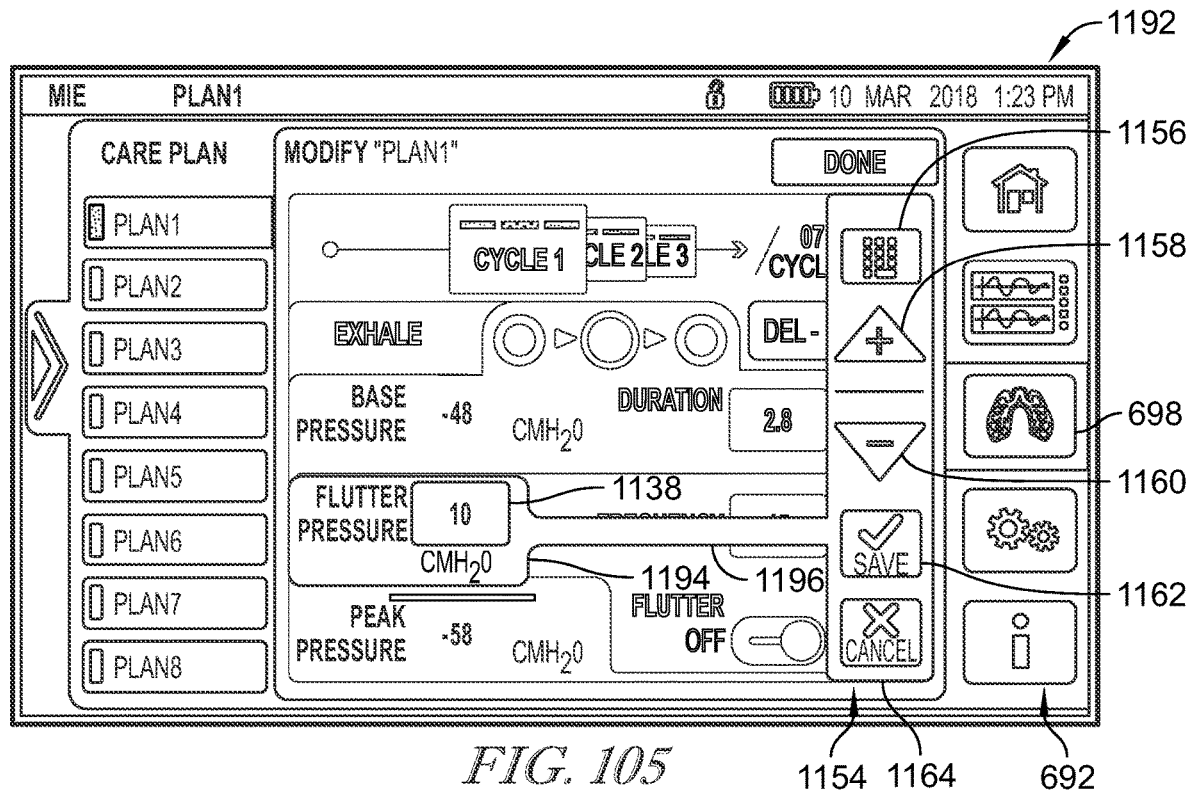
FIG. 105 is a screen shot of a fourteenth modify therapy screen that appears on the GUI in response to an exhale flutter pressure field of the second modify therapy screen of FIG. 93 or the exhale flutter pressure field of the thirteenth modify pressure screen of FIG. 104 having been selected for adjustment and showing the keyboard, up arrow, down arrow, save, and cancel icons being illuminated for use in adjusting the exhale flutter pressure.

Referring now to FIG. 105, a fourteenth modify therapy screen 1192 appears on GUI 16 in response to exhale flutter pressure field 1138 of the second modify therapy screen 1146 of FIG. 93 or the thirteenth modify pressure screen 1190 of FIG. 104 having been selected for adjustment such that field 1138 is highlighted and appears in a bubble 1194. A connector segment 1196 extends from bubble 1196 to menu 1154 to indicate that keyboard icon 1156, up arrow icon 1158, down arrow icon 1160, save icon 1162, and cancel icon 1164 are activated for use in connection with exhale flutter pressure adjustment. Up arrow icon 1158 and down arrow icon 1160 are touched successively to increment or decrement, respectively, the corresponding exhale flutter pressure value by 1 cmH$_2$O. Alternatively, each of arrow icons 1158, 1160 can be selected and held continuously and the respective exhale flutter pressure value will be incremented or decremented, respectively, by 1 cmH$_2$O for every second held, up to five seconds, after which the inhale base pressure value will be incremented or decremented, respectively, by 1 cmH$_2$O for every ½ second held. If an upper pressure limit or lower pressure limit is reached for the exhale flutter pressure value in field 1138, then the up arrow button 1158 or down arrow button 1160, as the case may be, becomes inactive and continued selection of the particular arrow button 1158, 1160 has no effect. With regard to screen 1192 of FIG. 105, most everything else other than field 1138, bubble 1194, connector segment 1196, and icons 1156, 1158, 1160, 1162, 1164 of menu 1154 is grayed out and inactive except that icon 698 of menu 692 remains highlighted and active.

Figure 106:
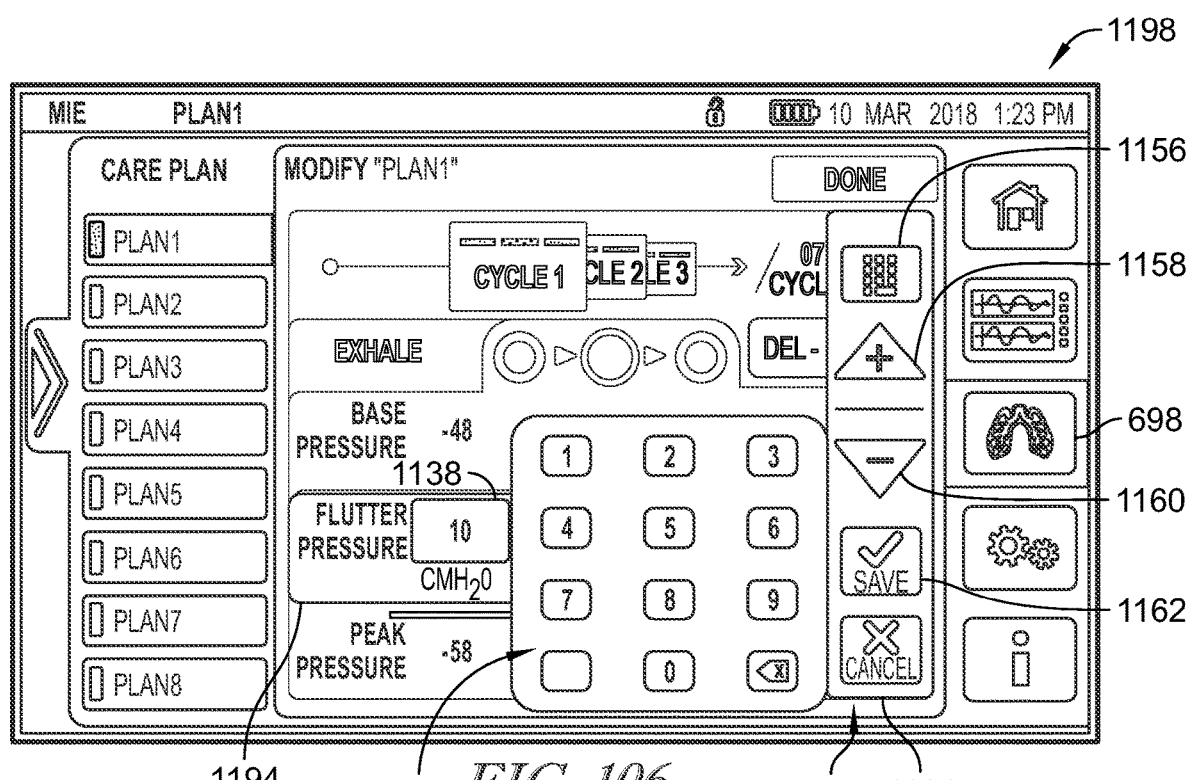
FIG. 106 is a screen shot of a fifteenth modify therapy screen that appears on the GUI after the keyboard icon of FIG. 105 is selected, showing the current exhale flutter pressure value and the graphical keyboard.
Figure 107:
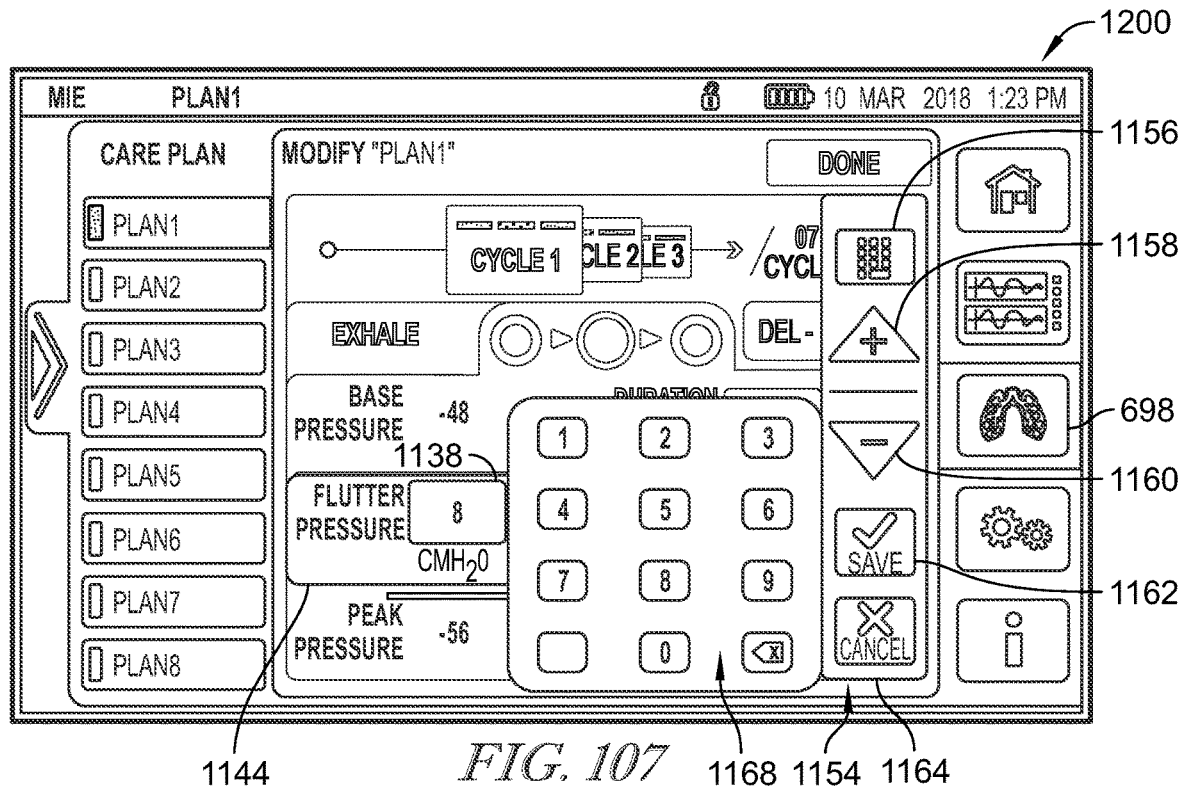
FIG. 107 is a screen shot of a sixteenth modify therapy screen that appears on the GUI after the graphical keyboard of FIG. 106 is used to change the exhale flutter pressure from 10 cmH$_2$O, shown in FIGS. 93 and 104-106, to 8 cmH$_2$O.

As shown in FIG. 106, an fifteenth modify therapy screen 1198 appears on GUI 16 in response to keyboard icon 1156 of FIG. 105 being selected so that graphical keyboard 1168 appears on screen 1198 between bubble 1194 and menu 1154. As noted above, arrow icons 1158, 1160 become grayed out and inactive when keyboard 1168 appears on GUI 16 in some embodiments. In FIG. 106, the current exhale flutter pressure value of 10 cmH$_2$O is shown in field 1138. As shown in FIG. 107, a sixteenth modify therapy screen 1200 appears on GUI 16 after graphical keyboard 1168 of screen 1198 of FIG. 106 is used to change the exhale flutter pressure value from 10 cmH$_2$O to 8 cmH$_2$O. Otherwise, screen 1200 of FIG. 107 is substantially the same as screen 1198 of FIG. 106 and so like reference numbers are used to denote like portions without repeating the descriptions.

After the user has incremented or decremented to the desired exhale flutter pressure value in field 1138 using arrow buttons 1158, 1160 or after the user has typed the desired exhale flutter pressure value in field 1138 using graphical keyboard 1168, save button 1162 of menu 1154 is selected to save the new exhale flutter pressure value for subsequent use during future automatic MIE therapy sessions in connection with the selected plan and selected cycle. If the user decides not to enter a new exhale flutter pressure value, then cancel button 1164 of menu 1154 is selected and the previous exhale flutter pressure value is used for future automatic MIE therapy sessions for the corresponding plan and cycle.

Figure 108:
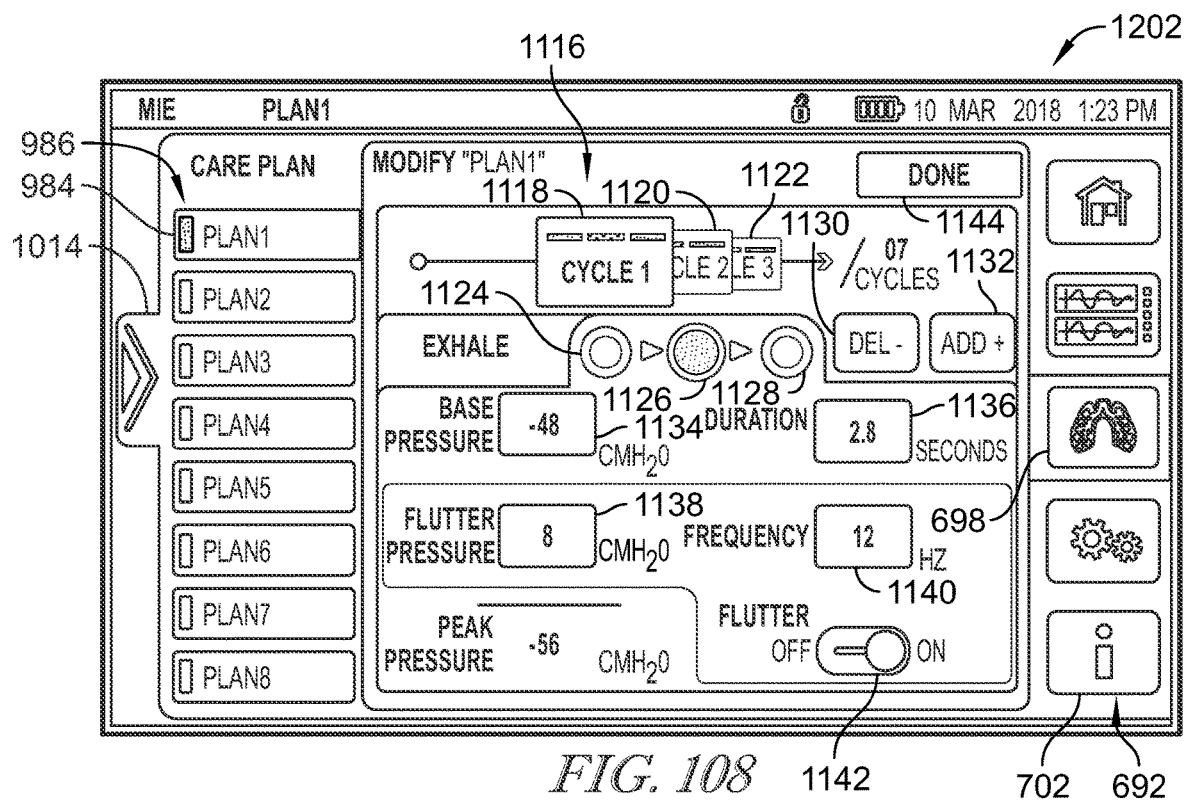
FIG. 108 is a screen shot of a seventeenth modify therapy screen showing the new exhale flutter pressure in the respective field after the save icon of the sixteenth modify therapy screen of FIG. 107 has been selected.

Referring now to FIG. 108, a seventeenth modify therapy screen 1202 appears on GUI 16 in response to selection of the save icon 1162 on screen 1200 of FIG. 107. Screen 1202 shows the new exhale flutter pressure of 8 cmH$_2$O in the respective field 1138. Screen 1202 also shows that the peak pressure is −56 cmH$_2$O as compared to the peak pressure of −58 cmH$_2$O of screen 1190 of FIG. 104. Otherwise, screen 1202 of FIG. 108 is substantially the same as screen 1190 of FIG. 104 and so like reference numbers are used to denote like portions without repeating the descriptions.

Figure 109:
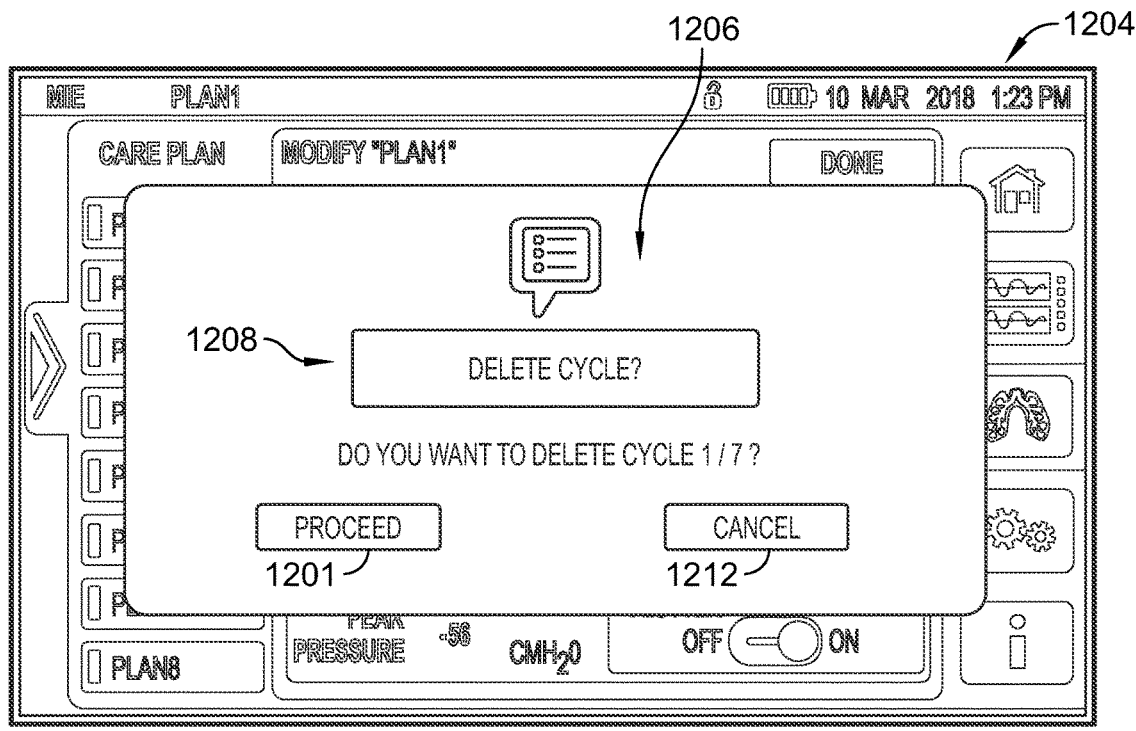
FIG. 109 is a screen shot of a delete cycle screen that appears on the GUI in response to selection of a delete button on the first, second or third modify therapy screens of FIGS. 92-94, respectively, the delete cycle screen having a proceed button that is selectable to delete the selected cycle and a cancel button that is selectable to abort the deletion and return to the previous screen.

Referring now to FIG. 109, a delete cycle screen 1204 appears on GUI 16 in response to selection of delete button 1130 on any of the above described screens on which button 1130 is active such as, for example, the first, second or third modify therapy screens 1114, 1146, 1148 of FIGS. 92-94, respectively. Delete cycle screen 1204 includes a window 1206 having a text box 1208 with the text "DELETE CYCLE?" therein. Beneath box 1208 is the explanatory text "DO YOU WANT TO DELETE CYCLE 1/7?" to indicate that user has selected delete button 1130 while viewing a phase of cycle 1. If the user was viewing, say cycle 3 of 12 cycles, then the explanatory text beneath box 1208 would be, "DO YOU WANT TO DELETE CYCLE 3/12?" just to give another arbitrary example.

Window 1206 of screen 1204 of FIG. 109 further includes a proceed button 1210 that is selectable to delete the selected cycle and a cancel button 1212 that is selectable to abort the deletion process and return to the previous screen (i.e., the screen on which the delete button 1130 was selected originally). In response to selection of proceed button 1210, the cycle that was being viewed when the delete button 1130 was pressed originally is deleted and each of the subsequent cycles has its cycle number decremented by one. In other words, if cycle 1 is deleted, then previous cycle 2 becomes the new cycle 1, previous cycle 3 becomes the new cycle 2, the previous cycle 4 becomes the new cycle 3, and so forth. To give another example, if cycle 3 is deleted, then previous cycles 1 and 2 remain as they were, previous cycle 4 becomes the new cycle 3, previous cycle 5 becomes the new cycle 4, and so forth.

Figure 110:
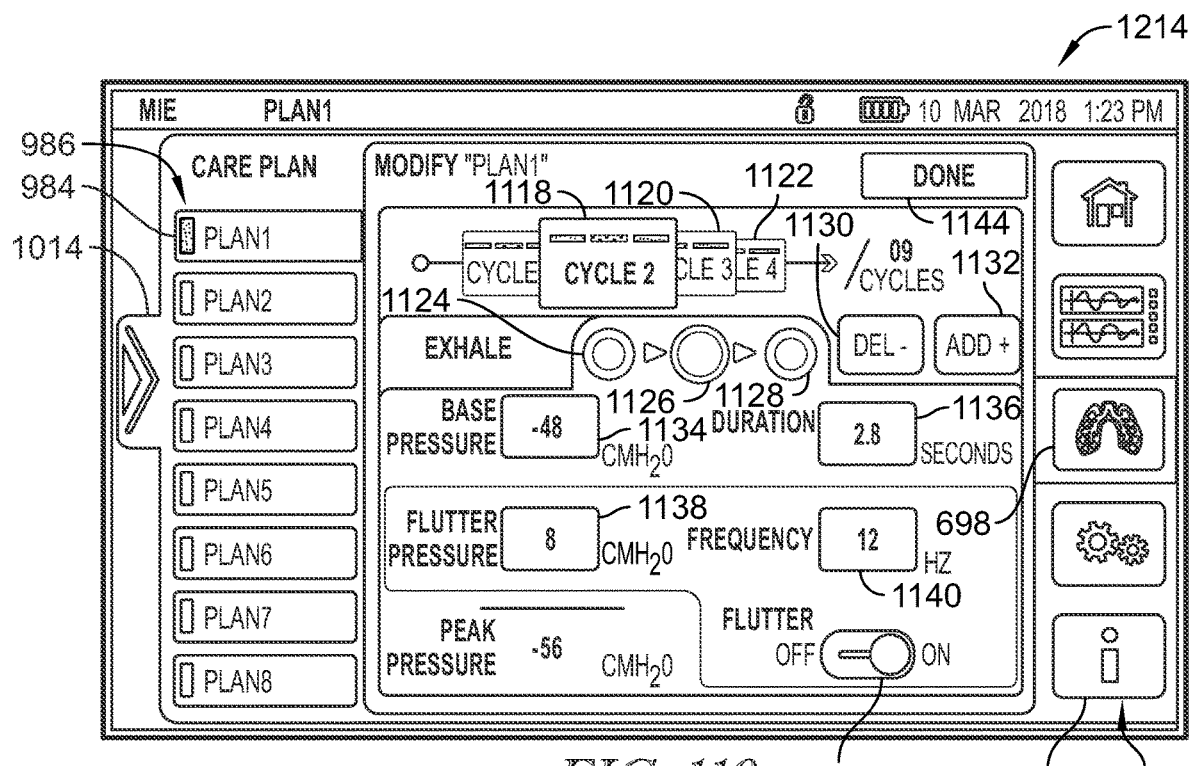
FIG. 110 is a screen shot of an add cycle screen that appears on the GUI in response to selection of an add cycle button on the seventeenth modify therapy screen of FIG. 108.

Referring now to FIG. 110, an add cycle screen 1214 appears on GUI 16 in response to selection of add cycle button 1132 on screen 1202 of FIG. 108. As shown in FIG. 110, the cycle being added is cycle 2 as indicated by the enlargement of the cycle 2 tile 1120 of the set of overlapped tiles. Cycle 2 is being added because cycle 1 was being displayed on screen 1202 of FIG. 108 when button 1132 was selected. Thus, if cycle 3 were being displayed on GUI 16 when add cycle button 1132 was selected, the addition of cycle 4 would result, just to give another arbitrary example. If there were previous cycles programmed in plan 1 to occur after cycle 1, then those previous cycles have the respective cycle numbers incremented by one after the addition of the new cycle. In other words, if cycle 2 is the new cycle being added, then previous cycle 2 becomes the new cycle 3, previous cycle 3 becomes the new cycle 4, the previous cycle 4 becomes the new cycle 5, and so forth. To give another example, if cycle 3 is the new cycle being added, then previous cycles 1 and 2 remain as they were, previous cycle 4 becomes the new cycle 5, previous cycle 5 becomes the new cycle 6, and so forth.

Still referring to FIG. 110, screen 1214 is substantially the same as screen 1202 of FIG. 108 and so like reference numbers are used to denote like portions without repeating the descriptions. Furthermore, in the illustrative example, the values populated in fields 1134, 1136, 1138, 1140 and the position of slider input 1142 on screen 1214 of FIG. 110 are carried over (e.g., copied) from these same respective fields 1134, 1138, 1140 and from the slider input position of exhale portion of screen 1202 of FIG. 108 because that is the screen being viewed on GUI 16 when add cycle button 1132 was selected in the illustrative example. Radio button 1126 is shown as the selected one of buttons 1124, 1126, 1128 on screen 1214 as well. The values from cycle 1 for the inhale phase and the PAP phase of cycle 1 are also carried over to the new cycle 2 but, initially, the exhale phase parameters are those that are shown on screen 1214 because the exhale portion of cycle 1 was being viewed on screen 1208 of FIG. 108 when button 1132 was selected in the given example.

As shown on screen 1214 of FIG. 110, a cycle 4 tile 1216 is added to the set of overlapping tiles in response to the cycle 2 tile becoming the enlarged tile. If the user is viewing a particular cycle on GUI 16 and wishes to edit some other previously programmed cycle, the user is able to swipe left or right, as the case may be, on the set of overlapping cycle tiles to view the previously programmed cycles. The parameters shown in fields 1134, 1136, 1138, 1140 and the position of slider input 1142 are in accordance with the previous programming in connection with whichever of the overlapping tiles is the enlarged tile.

Figure 111:
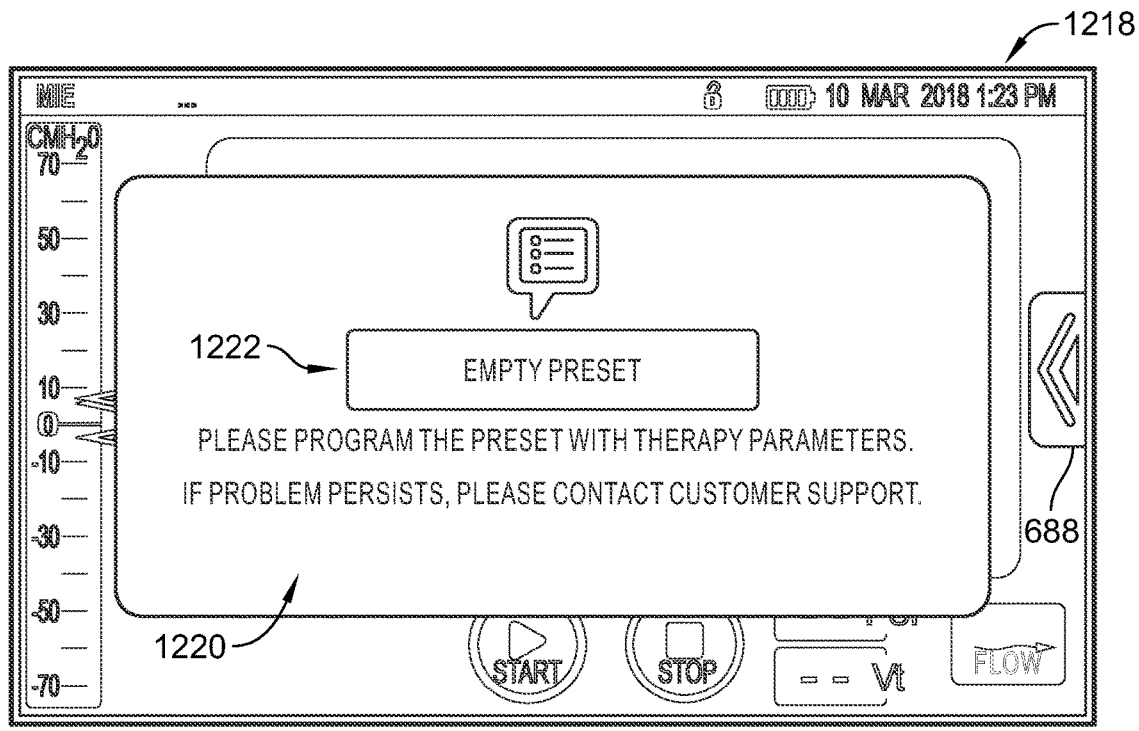
FIG. 111 is a screen shot of an empty preset screen that appears on the GUI if the automatic button of the main MIE therapy selection screen of FIG. 19 is selected and there are no care plans with any parameters entered for operation of the automatic MIE therapy.

Regardless of which portion (e.g., inhale, exhale, or PAP) of which cycle of which plan of the automatic MIE therapy is being viewed on GUI 16, the parameters are able to be adjusted (e.g., reprogrammed) in the manner described above in connection with FIGS. 63-110. In the discussion above of FIGS. 63-110, it was assumed that the various parameters and features of the automatic MIE therapy were programmed previously into control circuitry 500 of device 10. However, if automatic button 678 for MIE therapy is selected on screen 676 of FIG. 19 and there are no care plans with any parameters preprogrammed for operation of automatic MIE therapy in control circuitry 500 of device 10, then an empty preset screen 1218 appears on the GUI 16 as shown in FIG. 111. Screen 1218 includes a window 1220 with a text box 1222 having the text "EMPTY PRESET" therein. Beneath box 1222 is explanatory text which states, "PLEASE PROGRAM THE PRESET WITH THERAPY PARAMETERS. IF PROBLEM PERSISTS, PLEASE CONTACT CUSTOMER SUPPORT."

Figure 112:
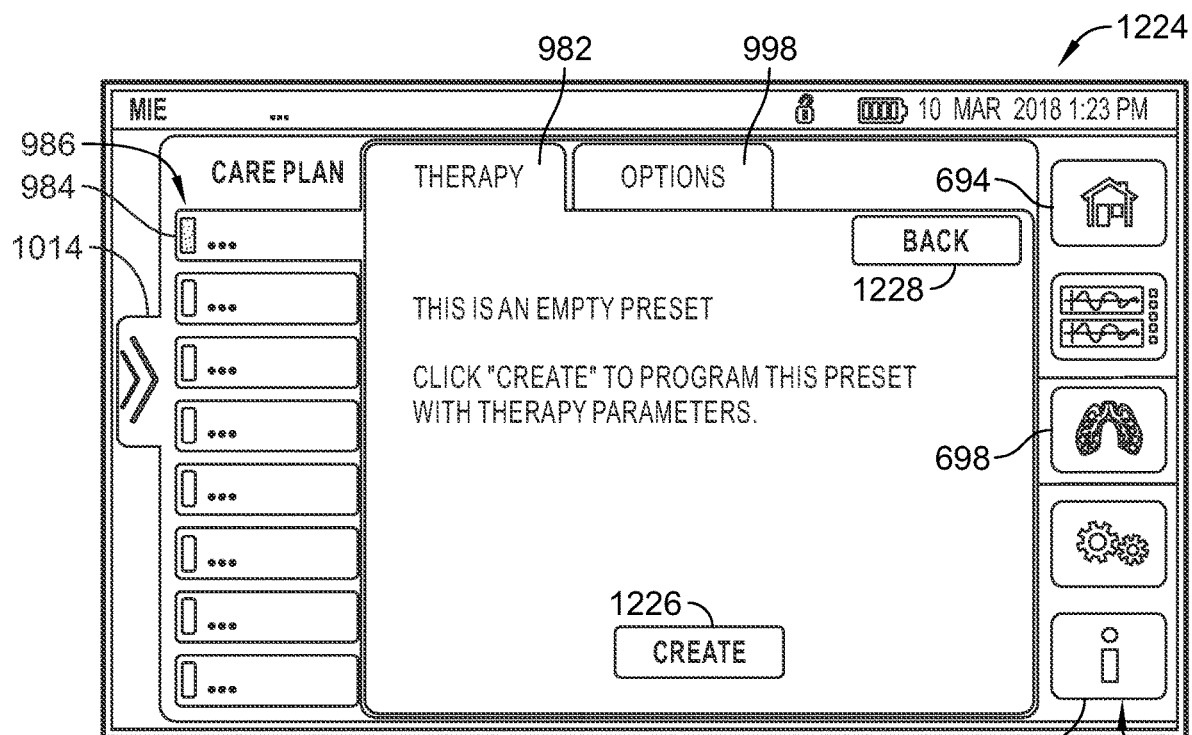
FIG. 112 is a screen shot of a create care plan screen that appears on the GUI after an arrow icon at the right hand side of the empty preset screen is selected to display the vertical menu of icons that are substantially the same as the vertical menu of icons shown in FIG. 39, and after the lung icon from the vertical menu of icons is selected, the create care plan screen having a create button that is selectable to create a new care plan.

To navigate to screens for creating a new care plan for automatic MIE therapy, the user first selects menu open icon 688 on screen 1218 of FIG. 111 to cause menu 692, shown on screen 846 of FIG. 39 for example, to appear on GUI 16 and then the user selects lung icon 698 from menu 692 which results in a create care plan screen 1224 appearing on GUI 16 as shown in FIG. 112. Screen 1224 initially opens with therapy tab 982 selected but with no table 988 of the type shown, for example, on screen 980 of FIG. 66. Instead, screen 1224 has the following explanatory text beneath tab 982: "THIS IS AN EMPTY PRESET. CLICK 'CREATE' TO PROGRAM THIS PRESET WITH THERAPY PARAMETERS." A create icon or button 1226 appears on screen 1224 beneath the explanatory text and is selectable to create a new care plan. Screen 1224 also has a back icon or button 1228 which is selectable to return the user back to screen 1218 of FIG. 111. Screen 1224 also includes the menu 986 of care plan buttons, with the first button 984 of menu being selected, but there are ellipses " . . . " that appear in each care plan button of menu 986 because no care plan has yet been programmed and named. Menu 692 of screen 1224 has buttons 694, 698, 702 highlighted and active with each of the other buttons of menu 692 being grayed out and inactive.

Figure 113:
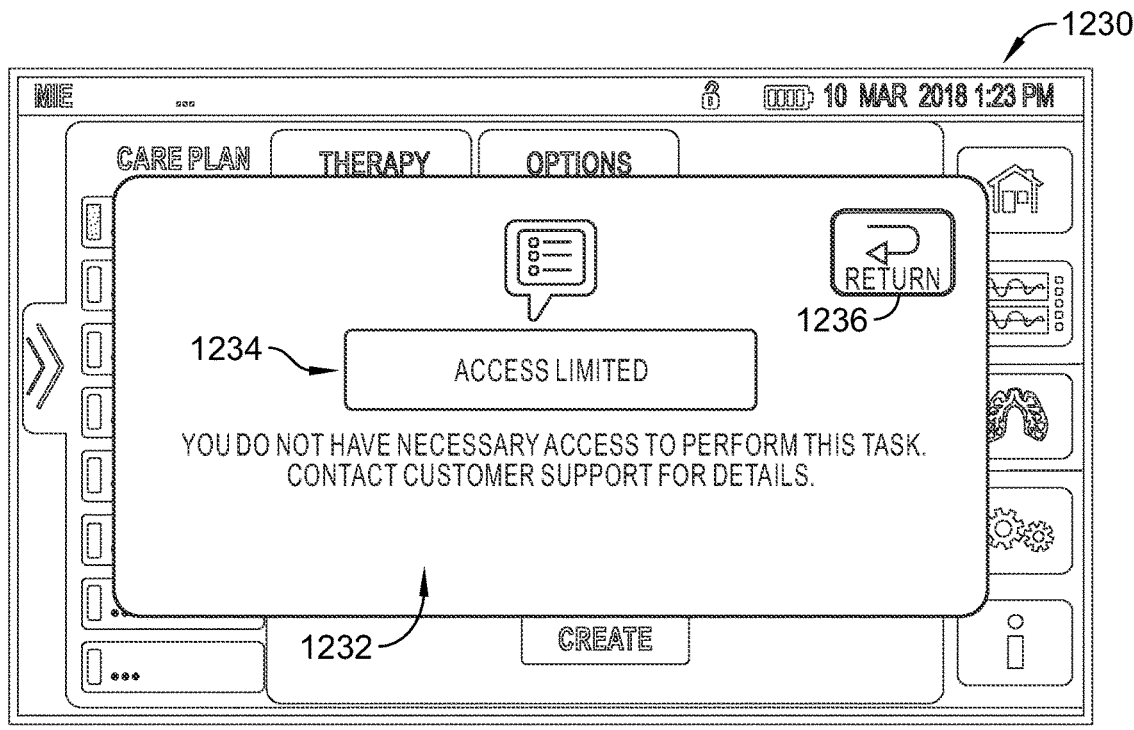
FIG. 113 is a screen shot of an access limited screen that appears on the GUI in response to selection of the create button of the create care plan screen of FIG. 112 if the clinical access feature of the respiratory therapy apparatus is turned off or disabled.

Referring now to FIG. 113, an access limited screen 1230 appears on GUI 16 in response to selection of the create button 1226 of the create care plan screen 1224 of FIG. 112 if the clinical access feature of the respiratory therapy apparatus 10 is turned off or disabled. Screen 1230 includes a window 1232 having a text box 1234 with the text "ACCESS LIMITED" therein. Beneath box 1234 is the explanatory text, "YOU DO NOT HAVE NECESSARY ACCESS TO PERFORM THIS TASK. CONTACT CUSTOMER SUPPORT FOR DETAILS." A return button 1236 is also provided in window 1232 of screen 1230 of FIG. 113. Selection of button 1232 returns the user back to screen 1224 of FIG. 112.

Figure 114:
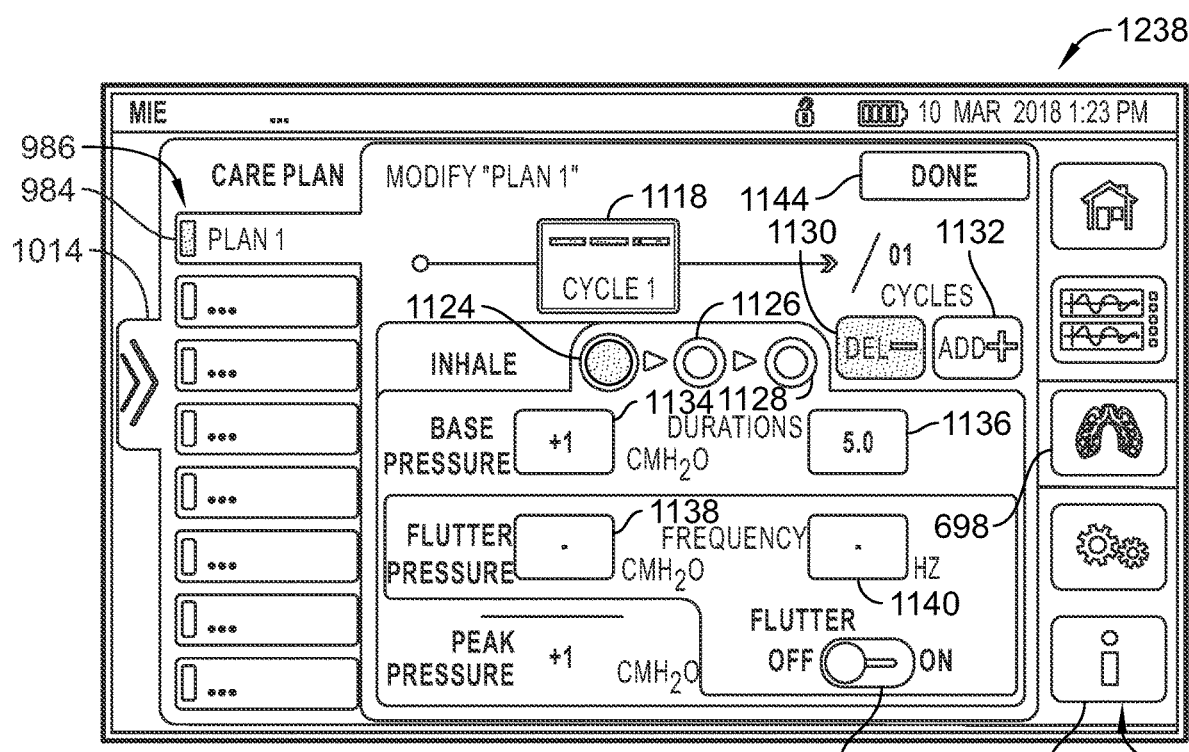
FIG. 114 is a screen shot of a first create new therapy screen that appears on the GUI in response to selection of the create button of the create care plan screen of FIG. 112 if the clinical access feature of the respiratory therapy apparatus is turned on or enabled, the first create new therapy screen showing that the inhale portion of cycle 1 of plan 1 of a new care plan for the automatic MIE therapy is selected for parameter adjustment and having the parameter fields populated with default parameter settings.

Referring now to FIG. 114, a first create new therapy screen 1238 appears on GUI 16 in response to selection of the create button 1226 of the create care plan screen 1224 of FIG. 112 if the clinical access feature of the respiratory therapy apparatus 10 is turned on or enabled. The first create new therapy screen 1238 of FIG. 114 is similar to screen 1114 of FIG. 92 and so like reference numbers are used to denote like portions without repeating the description. However, screen 1238 shows default values in fields 1134, 1136 for the inhale portion of cycle 1 of plan 1 of the automatic MIE therapy. In particular, field 1134 shows a default baseline pressure value of +1 cmH$_2$O and field 1136 shows a default inhale phase duration of 5.0 seconds. Also, screen 128 of FIG. 114 shows that the slider input 1142 defaults to the off position such that dashes "-" appear in fields 1138, 1140. Based on the default conditions, screen 1238 indicates a peak pressure of +1 cmH$_2$O for the inhale phase of cycle 1 of care plan 1.

Above radio button 1124 of screen 1238 of FIG. 114, only cycle 1 tile 1118 appears because no other cycles exist when cycle 1 is being created for the first time. Also, delete button 1130 is inactive on screen 1238 because deletion of cycle 1 results in empty preset condition once again. Care plan tab 984 of screen 1238 includes the generic name "PLAN 1" rather than the ellipses " . . . " that appeared in tab 984 previously on screen 1224 of FIG. 112. While not shown herein, the default conditions for the PAP phase of cycle 1 of the newly created care plan are the same as those of the inhale phase of FIG. 114. Furthermore, the default conditions for the exhale phase are the same as for the inhale phase except that the default exhale baseline pressure of field 1134 is −1 cmH$_2$O.

If desired, the user is able to select any of fields 1134, 1136, 1138, 1140 to adjust the respective parameters for any of the inhale, exhale, and PAP phases associated with the respective radio button 1124, 1126, 1128 and to move slider input 1142 to the on position for the newly created care plan in the same manner as described above in connection with FIGS. 92-108 for example. After one or more new care plans have been programmed as desired by the user, done button 1144 is selected to navigate to a screen similar to screen 980 of FIG. 66 but with the newly programmed parameter values appearing in table 988. In the illustrative example, if done button 1144 is selected on screen 1238 of FIG. 114 without the user having modified any of the operational parameters of fields 1134, 1136, 1138, 1140 from their default values or moving slider input 1142 to the on position, then a second create new therapy screen 1240 appears on GUI 16 as shown in FIG. 115. Screen 1240 of FIG. 115 is similar to screen 980 of FIG. 66 92 and so like reference numbers are used to denote like portions without repeating the description. However, screen 1238 shows the default values in table 988 for the inhale, exhale, and PAP stages of cycle of plan 1.

Referring now to FIG. 116, a first new automatic MIE therapy start screen 1242, similar to screens 798, 1020 of FIGS. 31 and 69, respectively, appears on GUI 16 if start button 992 of the second create new therapy screen 1240 of FIG. 115 is selected assuming the usage count of filter unit 390 is below the threshold and, if respiratory therapy apparatus 10 is operating under battery power, assuming the battery charge is greater than 20% of a full battery charge. Screen 1242 of FIG. 116 shows graph 770 with the default parameters indicated (e.g., inhale +1, exhale −1, and PAP +1). However, on graph 770 of screen 1242, the upper arrow 778 corresponding to inhale pressure, and the middle arrow 780 corresponding to the PAP pressure of the depicted cycle overlap or merge because both pressures are +1 cmH$_2$O under the default condition. Otherwise, portions of screen 1242 of FIG. 116 that are the same as like portions screens 798, 1020 of FIGS. 31 and 69, respectively, are denoted by the same reference numbers and the descriptions are not repeated.

Referring now to FIG. 117, a second new automatic MIE therapy start screen 1244, similar to screen 1242 of FIG. 116, appears on GUI 16 if back button 990 of the second create new therapy screen 1240 of FIG. 115 is selected. Screen 1244 shows graph 770 with the default parameters indicated and having start button 766 that can be selected by the user to start the depicted automatic MIE therapy. In other words, after back button 990 of screen 1240 is selected to navigate to screen 1244 of FIG. 117, the automatic MIE therapy does not start but rather, the user must select start button 766 on screen 1244 to start the automatic MIE therapy, if desired.

Referring now to FIG. 118, if the user selects edit button 994 of screen 1240 of FIG. 115, the user navigates to the edit therapy settings screen 1104 shown in FIG. 118. FIG. 118 is basically a duplicate of FIG. 91 and so the same reference numbers are used in FIGS. 91 and 118 to denote like portions. To navigate to screen 1104 of FIGS. 91 and 118 from the respective predecessor screens 980 of FIG. 66 and screen 1240 of FIG. 115, the clinical access feature of the respiratory therapy apparatus 10 must be turned on or enabled when edit button 994 is selected. In the illustrative examples of FIGS. 66 and 115, the clinical access feature is, in fact, enabled as indicated by the presence of unlock icon 733 in the header of screens 980, 1240.

As discussed above, screen 1104 includes window 1106 having text box 1108 with the text "EDIT THERAPY SETTINGS" therein. Beneath box 1108 is the explanatory text, "CHOOSE THE PRESET FUNCTION YOU INTEND TO PERFORM:." Beneath the explanatory text in window 1106 is delete button 1110 and modify button 1112. Selection of button 1110 begins the process of deleting the selected care plan (e.g., plan 1 of screen 980 of FIG. 66 or screen 1240 of FIG. 115 in the illustrative examples). Selection of button 1112 starts the process for editing the selected care plan as discussed above in connection with FIGS. 92-108. Window 1106 of screen 1104 of FIGS. 91 and 118 also includes return button 1102 the selection of which returns the user back to screen 980 of FIG. 66 or screen 1240 of FIG. 115 depending upon which of screens 980, 1240 was the predecessor screen when button 994 was selected.

Referring now to FIG. 119, a delete preset screen 1246 appears on GUI 16 in response to selection of delete button 1110 on the edit therapy settings screen 1104 of FIG. 91 or FIG. 118. Screen 1246 includes a window 1248 having a text box 1250 with the text "DELETE PRESET?" therein. Beneath box 1250 is the explanatory text, "DO YOU WANT TO DELETE 'PLAN 1'?" It should be noted that if a different plan was selected on menu 986 of FIGS. 66, 115 when button 994 was initially selected, then the explanatory text of screen 1246 would make reference to the selected plan (e.g., plan 2, plan 3, plan 4, and so forth).

Still referring to FIG. 119, beneath the explanatory text in window 1248 is a proceed button 1252 and a cancel button 1254. Selection of button 1252 results in the selected preset or care plan being deleted from control circuitry 500 of apparatus 10. Also, in response to selection of button 1252 on screen 1246 of FIG. 119, the user is returned to screen 1224 of FIG. 112 and the user is then able to navigate, as desired, from screen 1224. If the user decides not to cancel the selected preset, then cancel button 1254 is selected and the user is returned to screen 980 of FIG. 66 or screen 1240 of FIG. 115, as the case may be, depending upon which of screens 980, 1240 was the screen on which button 994 was previously selected.

As discussed above, apparatus 10 includes foot switch 294 having foot pedal 296 that rocks relative to base 298 to send signals to the control circuitry of device 10 to start and stop (or pause) the delivery of respiratory therapy to the patient. It should be appreciated that foot switch 294 is an optional accessory of apparatus 10. Thus, when foot switch 294 is coupled to control circuitry 500 of device 10, various ones of the screens of FIGS. 18-274 can receive inputs from foot switch 294 to control corresponding features of the respiratory therapy apparatus 10. To give one example, an alternative main automatic MIE therapy screen 764', similar to screen 764 of FIG. 29, appears on GUI 16 in response to the automatic button 678 of the main MIE therapy selection screen 676 of FIG. 19 being selected. Due to the similarities between screens 764 of FIG. 29 and screen 764' of FIG. 120, like reference numbers are used to denote like portions without repeating the description. However, unlike screen 764 of FIG. 29, screen 764' of FIG. 120 includes a foot switch control field 1256 having a plus indicator 1258 and a minus indicator 1260.

Still referring to FIG. 120, indicators 1258, 1260 of field 1256 are highlighted to indicate a status of an input from foot switch 294 of the respiratory therapy apparatus 10. For example, if the respiratory therapy has been started or resumed by moving foot pedal 296 of foot switch 294 to a first position (e.g., rocked forwardly), then plus indicator 1258 is colored green and minus indicator 1260 is colored a neutral color, such as gray. If the respiratory therapy has been stopped or paused by moving foot pedal 296 of foot switch 294 to a second position (e.g., rocked rearwardly), then minus indicator 1260 is colored green and plus indicator 1258 is colored the neutral color, such as gray. If foot pedal 296 of foot switch 294 is in the home position between the first and second positions, then both indicators 1258, 1260 have the neutral color.

In some instances, control circuitry 500 will ignore an input from foot switch 294 that is generated in response to foot switch 296 being moved to the first position or second position. In such instances, the respective indicator 1258, 1260 has an "X" superimposed thereon to indicate to the user that the corresponding input from the foot switch 294 will be ignored by the control circuitry 500. In some embodiments, the "X" appearing over the respective indicator 1258, 1260 is color coded red. When foot switch 294 is coupled to circuitry 500, user inputs can be provided by interacting with the various graphical icons, buttons, fields, etc. on GUI 16 or by use of foot switch 294. Priority is given to the first input (e.g., from GUI 16 or foot switch 294) and any later, conflicting input, will be ignored by the control circuitry 500.

With regard to the manual MIE therapy of apparatus 10, as described above in connection with FIGS. 41-48 for example, foot switch 294 is used in the following manner once the therapy starts. Movement of foot pedal 296 of foot switch 294 to the first position, corresponding to the plus indicator 1258 being highlighted, causes the inhale phase of the manual MIE therapy to be applied to the patient's airway. Movement of foot pedal 296 of foot switch 294 to the second position, corresponding to the minus indicator 1260 being highlighted, causes the exhale phase of the manual MIE therapy to be applied to the patient's airway. Movement of foot pedal 296 of foot switch 294 to the home position, corresponding to neither of indicators 1258, 1260 being highlighted, causes the PAP phase of the manual MIE therapy to be applied to the patient's airway. To stop the manual MIE therapy when foot switch 294 is coupled to control circuitry, stop button 892 of GUI 16 is selected by the user.

Referring now to FIG. 121, a main automatic OLE therapy screen 1262 appears on GUI 16 in response to selection of the automatic button 684 of main OLE therapy selection screen 682 of FIG. 20 assuming that the bar code scanning process discussed above in connection with FIGS. 23-28 has already occurred previously or is disabled from occurring such as if the clinical access function of device 10 is turned off. Main automatic OLE therapy screen 1262 includes a therapy duration clock 1264 that indicates a length of time that the selected automatic OLE therapy is programmed to occur. Clock 1264 is in minutes:seconds format and in the illustrative example of FIG. 121, clock 1264 indicates that the OLE therapy has a duration of 21 minutes (i.e. 21:00). During the automatic OLE therapy, clock 1264 counts down and then the therapy ends when the clock reaches 00:00 unless the therapy is terminated earlier by the user.

In the illustrative example of screen 1262, it is assumed that operational parameters for OLE therapy have been stored previously in control circuitry 500. Thus, in the illustrative example, screen 1262 defaults to showing details of plan 1 settings for the automatic mode of OLE therapy. As shown in FIG. 121, screen 1262 includes a start button 1266 which is selected to start the associated automatic OLE therapy and a stop button 1268 which is selected to stop the associated OLE therapy. Button 1268 is grayed out on screen 1262 because the therapy is not currently being delivered. Screen 1262 also has an information graph 1270 and an information bar 1272 in the form of a digital manometer.

Still referring to FIG. 121, graph 1270 displays numerical parameters for the associated portions of the automatic OLE therapy including the following: CPEP pressure for a first stage of the OLE therapy (25 cmH2O in the illustrative example), CHFO pressure for a second stage of the OLE therapy (25 cmH2O in the illustrative example), CPEP pressure for a third stage of the OLE therapy (25 cmH2O in the illustrative example), CHFO pressure for a fourth stage of the OLE therapy (25 cmH2O in the illustrative example), first stage duration (2 minutes in the illustrative example), second stage duration (1 minute 30 seconds in the illustrative example), third stage duration (1 minute 30 seconds in the illustrative example), and a fourth stage duration (2 minutes in the illustrative example). Graph 1270 also includes a therapy progress indicator 1274 which moves along the curve shown in graph 1270 during the associated therapy. Above graph 1270 on screen 1262 is text indicating the current stage of OLE therapy out of the total number of stages ("STAGE 01 of 10" in the illustrative example) and that state of nebulizer 66 ("OFF" in the illustrative example).

Digital manometer 1272 of screen 1262 of FIG. 121 includes a peak arrow box 1276 serving as a peak pressure marker to indicate the peak pressure that has occurred during the OLE therapy. In the illustrative example of screen 1262, the box portion of arrow box 1276 indicates a peak pressure of 0 $cmH_2O$ since the OLE therapy has not yet started. In some embodiments, the CPEP portions and CHFO portions of OLE therapy are color coded. For example, the CPEP portions of graph 1270 of OLE therapy are color coded orange and the CHFO portions of graph 1270 of OLE therapy are color coded blue. Thus, with reference to the screen 1262 example of FIG. 121, the text "CPEP 25" is orange in two places and the text "CHFO 25" is blue in two places. Other portions of screen 1262 of FIG. 121 are substantially the same as other screens discussed above. For example, illustrative screen 1262 includes Bluetooth icon 731, unlock icon 733, and battery charge icon 735 which have been described above. Screen 1262 also includes heart rate field 884 and pulse oximetry field 886. Screen 1262 further includes menu open tab 688 that, when selected results in menu 692 with icons 694, 696, 698, 700, 702 and close tab 708 appearing on GUI 16 in a similar as shown in FIG. 39, for example. Icons 694, 696, 698, 700, 702 and close tab 708 operate the same for OLE therapy as described above in connection with MIE therapy except that the resulting screens relate to feature and functions of the OLE therapy as appropriate.

In response to selection of start button 71266 on screen 1262 of FIG. 121, the control circuitry 500 of device 10 performs the RFID count check to confirm that filter unit 390 is equal to or below its usage count limit. As discussed above, reader 434 reads the usage count stored in transponder chip 422 of filter unit 390 to confirm that the usage count is equal to or below the threshold number of uses, such as 70 or 90 uses. If the usage count is greater than the usage count limit, then an error message is displayed on GUI 16 instructing the user to replace the old filter unit 390 with a new one. Until the filter unit 390 meets the usage count requirement (i.e., is equal to or below the threshold limit), device 10 is prevented from delivering any respiratory therapy to any patients in some embodiments.

In response to selection of start button 1266 on screen 1262 of FIG. 121, the control circuitry 500 of device 10 also checks for the amount of battery charge of battery 224 if device 10 is operating under battery power. If the battery charge amount is less than or equal to 20% of a full battery charge, then the low battery screen 790 appears on GUI 16 as shown in FIG. 30 and as discussed above. If filter unit 390 passes the RFID count check and if the battery charge check is passed (or device 10 is being operated under AC power) after start button 1266 is pressed on screen 1262, then an automatic OLE therapy start screen 1278 appears on GUI 16 as shown, for example, in FIG. 122. Screen 1278 of FIG. 122 is basically the same as screen 1262 of FIG. 121 except that start button 1266 of screen 1262 is converted graphically to a pause button 1280 on screen 1278. Also, stop button 1268 of screen 1278 is no longer grayed out and becomes active and menu tab 688, which is active on screen 1262 of FIG. 121, becomes grayed out and inactive on screen 1278 of FIG. 122.

Referring now to FIG. 123, a first automatic OLE therapy in process screen 1282 is shown on GUI 16 at a first arbitrary point in time during the delivery of automatic OLE therapy by device 10. As shown in FIG. 123, the graphical therapy progress indicator 1274 has moved along the graphical waveform of graph 1270 to indicate the therapy progress as of 19:16 on the therapy duration clock 1264. As shown in text at the top of graph 1270, the OLE therapy is still in stage 1 of 10 in FIG. 123 and nebulizer 66 is turned on during the stage 1 CPEP portion of the automatic OLE therapy. In FIG. 123, graph 1270 is filled in up to the progress indicator 1274 to indicate an amount of the current therapy cycle that has been completed. Thus, a CPEP region 1284 is filled in, in orange in some embodiments, up to the position of progress indicator 1274 on graph 1270.

As also shown in FIG. 123, peak arrow box 1276 has moved upwardly to reveal a mean arrow box 1288. Arrow box 1288 indicates the mean pressure that has been calculated thus far during the OLE therapy. In the illustrative example of screen 1282, the box portion of arrow box 1288 indicates a mean pressure of 12 $cmH_2O$ and the box portion of arrow box 1276 indicates a peak pressure of 20 $cmH_2O$. The arrow portions of arrow boxes 1276, 1288 point to their respective pressure values on digital manometer 1272. A peak pressure segment 1290 is superimposed on digital manometer 1272 from 0 $cmH_2O$ up to the arrow portion of arrow box 1276 to provide a graphical representation of the peak pressure during the automatic OLE therapy.

Referring now to FIG. 124, a second automatic OLE therapy in process screen 1292 is shown on GUI 16 at a second arbitrary point in time during the delivery of automatic OLE therapy by device 10. Screen 1292 of FIG. 124 is similar to screen 1282 of FIG. 123, except that the progress indicator 1274 has advanced into a CHFO portion of the therapy from the CPEP portion of the therapy. In particular, therapy duration clock 1264 has counted down further to a time of 18 minutes, 1 second. As shown in text at the top of graph 1270 of FIG. 124, the OLE therapy has advanced to stage 2 of 10 and nebulizer 66 is still turned on during the stage 2 CHFO portion of the automatic OLE therapy. In FIG. 124, graph 1270 is filled in up to the progress indicator 1274 to indicate an amount that the therapy cycles that have been completed. Thus, a CHFO region 1286 is filled in, in blue in some embodiments, up to the position of the progress indicator 1274 on graph 1270. Region 1284 of the stage 1 CPEP portion of the OLE therapy is completely filled in as well in FIG. 124. Progress indicator 1274 travels on graph 1270 from left to right until it reaches the right end of the graph 1270 (e.g., the end of stage 4 in the illustrative examples of FIGS. 123 and 124) and then starts over again at the left end of graph 1270 for the next stage (e.g., stage 5).

In response to pause button 1280 being pressed during automatic OLE therapy, an automatic OLE therapy paused screen 1294 appears on GUI 16 as shown in FIG. 125. Screen 1294 includes a window 1296 having a box 1298 with the text "THERAPY PAUSED" therein. Beneath box 1298 is explanatory text which, in the illustrative example, states "AUTOMATIC THERAPY STOP IN 3 MINUTES."

A timer 1300 is shown beneath the explanatory text in window 1296 to indicate, in some embodiments, how long the therapy has been paused or, in other embodiments, how much time is left until the therapy is automatically stopped. Thus, timer 1300 counts up in some embodiments and counts down in other embodiments.

After pause button 1280 is selected, it converts to a resume button 1302 as shown in FIG. 125. Thus, the user is able to select stop button 1278 on screen 1294 to stop the therapy altogether without having to wait for the three minute pause period to elapse, or the user can select the resume button 1302 to resume the automatic OLE therapy at the same place in the therapy cycle where pause button 1280 was originally selected.

According to the present disclosure, device 10 has a cough pause feature that can be turned on or enabled in connection with the automatic OLE therapy. As will be discussed in further detail below in connection with FIGS. 140-145, when the cough pause function is turned on, the automatic OLE therapy stops at programmed time intervals for a programmed amount of time and then the automatic OLE therapy resumes unless the user chooses to resume the automatically OLE therapy sooner. In this regard, a cough pause screen 1304 appears on GUI 16 if the cough pause function of the respiratory therapy apparatus 10 has been enabled and if the interval at which the cough pause is to occur has been reached as shown in FIG. 126.

Screen 1304 includes a window 1306 having a box 1308 with the text "COUGH PAUSE" therein. Beneath box 1308 is explanatory text which, in the illustrative example, states "THERAPY WILL AUTO-RESUME IN." A timer 1310 is shown beneath the explanatory text in window 1306 to indicate how much time is left until the therapy is automatically resumed. If desired, the user is able to select resume button 1302 on screen 1304 before the timer 1310 expires to resume the automatic OLE therapy sooner. The user is also able to select stop button 1278 on screen 1304 during the cough pause period if the user wishes to stop the automatic OLE therapy altogether.

Referring now to FIG. 127, a third automatic OLE therapy in process screen 1312 is shown on GUI 16 at a third arbitrary point in time during the delivery of automatic OLE therapy by device 10. Screen 1312 of FIG. 127 is similar to screens 1282, 1292 of FIGS. 123 and 124, respectively, except that the progress indicator 1274 has advanced into a CHFO portion of the last stage of the OLE therapy. In particular, therapy duration clock 1264 has counted down further to a time of 22 seconds and so the automatic OLE therapy is nearing completion. As shown in text at the top of graph 1270 of FIG. 127, the OLE therapy has advanced to stage 10 of 10 and nebulizer 66 is still turned on during the stage 10 CHFO portion of the automatic OLE therapy. In FIG. 127, graph 1270 is filled in up to the progress indicator 1274 to indicate an amount that the therapy cycles have been completed. Thus, CHFO region 1286 is filled in, in blue in some embodiments, up to the position of the progress indicator 1274 on graph 1270. Region 1284 of the stage 9 CPEP portion of the OLE therapy is completely filled in as well in FIG. 127.

After the automatic OLE therapy session is complete or in response to selection of stop button 1278 during delivery of the automatic OLE therapy, an automatic OLE therapy complete screen 1314 appears on GUI 16 as shown, for example, in FIG. 128. Automatic OLE therapy complete screen 1314 displays a variety of statistical data and other information pertaining to the automatic OLE therapy that has just been completed, or stopped. For example, screen 1314 includes a CHFO field 1316 and a CPEP field 1318. Each of fields 1316, 1318 includes text indicating the average peak pressure for the CHFO and CPEP portions of the OLE therapy and the duration of the CHFO and CPEP portions of the OLE therapy. Screen 1314 also includes a patient circuit count field 1320 which indicates the number of uses of the filter unit 390 that was attached to port 24 during the therapy session. As shown in the illustrative example, the usage count of the filter unit 390 has been incremented to 74 uses out of a maximum number of 90 uses. That is, the usage count number in field 1320 is the new usage count number for filter unit 390 after the completion of the therapy session resulting in display of screen 1314 on GUI 16.

Beneath field 1318 of FIG. 128, screen 1314 includes an indication regarding an amount of time that the nebulizer was turned on during the automatic OLE therapy session. In the illustrative example, the text "NEBULIZER DURATION: 16:00" appears beneath field 1318. Above field 1320 the following information is provided on screen 1314: date of the therapy, total time of the therapy, the start time of the therapy, the finish time of the therapy, the total number of stages completed during the therapy, the cough pause interval used during the therapy, and the cough duration used during the therapy. Screen 1314 also includes a back button 1322, the selection of which returns the user to screen 1262 of FIG. 121.

Referring now to FIG. 129, a first advanced view screen 1324 for automatic OLE therapy appears on GUI 16 in response to selection of the graph icon 696 of the vertical menu 692 of icons (see FIG. 39) if the menu open button 688 was selected on screen 1262 of FIG. 121 to view menu 692 during OLE therapy. The first advanced view screen 1324 of FIG. 121 has a first graph 1326 and a second graph 1328 for the automatic OLE therapy that are traced in substantially real time during the automatic OLE therapy. During the advanced view of the automatic OLE therapy, first graph 1326 shows a trace of pressure, in cmH$_2$O, over time, and second graph 1328 shows a trace of air flow, in liters per minute (LPM), over time.

In the upper right hand corner of screen 1324, informational text is shown and, in the illustrative example, states "01 OF 07 STAGES" and "14:30 TOTAL THERAPY TIME." Other portions of screen 1324 are the same as portions of other screens described above and so the same reference numbers are used for these without repeating the descriptions. After start button 1266 is selected on screen 1324, a second advanced view screen 1330 for automatic OLE therapy appears on GUI 16 as shown in FIG. 130, assuming the filter unit usage count is below the threshold number of uses and assuming the battery charge is greater than 20% of a full charge. Screen 1330 of FIG. 130 shows that the start button 1266 of screen 1324 of FIG. 129 is converted to pause button 1280. Furthermore, during the advanced view automatic OLE therapy, the pressure and flow values of graphs 1326, 1328, respectively, fill into graphs 1326, 1328 from left to right until the X-axis (e.g., time axis) of the graphs 1326, 1328 is fully covered and then graphs 1326, 1328 are cleared and continue to plot, once again, from left to right.

Referring now to FIG. 131, an advanced OLE therapy complete screen 1332 appears on GUI 16 in response to completion of the advanced OLE therapy or selection of stop button 1268 of screen 1330 of FIG. 130. Advanced OLE therapy complete screen 1332 is substantially the same as the OLE therapy complete screen 1314 of FIG. 128 and so similar references numbers are used to denote like portions without repeating the descriptions. Thus, similar to screen 1314 of FIG. 128, screen 1332 of FIG. 131 displays a variety of statistical data and other information pertaining to the automatic OLE therapy that was just completed. However, unlike screen 1314 of FIG. 128, screen 1332 of FIG. 131 also includes fields 884, 886, similar to fields 842, 844 of screen 840 of FIG. 38, showing vitals data relating to the patient's heart rate and blood oxygen saturation percentage. Furthermore, in response to selection of back button 1322 on screen 1332 of FIG. 131, the user is returned to screen 1324 of FIG. 129.

Referring now to FIG. 132, a cough pause screen 1334 appears on GUI 16 if the cough pause function of the respiratory therapy apparatus 10 has been enabled and if the interval at which the cough pause is to occur has been reached. Screen 1334 of FIG. 132 is substantially the same as screen 1304 of FIG. 126 and so the same reference numbers are used for like portions without repeating the descriptions. However, instead of resume button 1302 and stop button 1268 being located beneath window 1306 like screen 1304 of FIG. 126, resume button 1302 and stop button 1268 are to the right of window 1306 of screen 1334 of FIG. 132.

Referring now to FIG. 133, an alternative main automatic OLE therapy screen 1336 is shown as another example of a screen that appears on GUI 16 in response to selection of the automatic button 684 of the main OLE therapy selection screen 682 of FIG. 20. Screen 1336 of FIG. 133 is similar to screen 1262 of FIG. 121 and so like reference numbers are used to denote like portions without repeating the descriptions. As compared to screen 1262 of FIG. 121, however, screen 1336 of FIG. 133 does not include Bluetooth icon 731 and so fields 884, 886 do not appear on screen 1336 because there is no wireless communication with any patient physiological monitor in the illustrative example. Furthermore, graph 1270 of screen 1336 includes a nebulizer portion of the automatic OLE therapy that is programmed to occur between a first CHFO portion of the therapy and a second CPEP portion of the therapy. In other words, the nebulizer portion of the automatic OLE therapy shown in FIG. 133 is the third stage of the programmed therapy.

As indicated above the nebulizer portion of graph 1270 in FIG. 133, a positive pressure of 5 cmH$_2$O is provided by blower 260 of device 10 at outlet port 24 to ensure that a small amount of airflow through patient circuit 230 toward the patient exists during the operation of nebulizer 66. In some embodiments, the text "NEB" is color coded green on graph 1270 and the area under the nebulizer portion of graph 1270 is filled in with green as progress indicator 1274 moves along the nebulizer portion of graph 1270. Thus, OLE therapy according to the present disclosure includes various combinations of CPEP, CHFO, and nebulizer stages at the discretion of the user or programmer of device 10. The word nebulizer is sometimes shortened herein as NEB. If desired, the OLE therapy may omit one or more of the CPEP, CHFO, and/or NEB stages altogether, such that OLE therapy with only CPEP therapy, only CHFO therapy, or only NEB therapy are possibilities, as are OLE therapies including any two of CPEP, CHFO, and NEB stages but not the third.

Referring now to FIG. 134, a first care plan screen 1338 for automatic OLE therapy appears on GUI 16 after menu open tab 688 of screen 1336 is selected and then lung icon 698 of the resulting vertical menu 692 of icons is selected. See FIG. 39 for an example the menu 692 and lung icon 698. The first care plan screen 1338 for automatic OLE therapy defaults to having a therapy tab 1340 selected for a first care plan as indicated by highlighting in a first care plan button 1342 of a menu 1344 of care plan buttons. Screen 1338 of FIG. 66 also displays a table 1346 of the parameters for the CPEP, CHFO, and NEB stages of the automatic OLE therapy. From left to right in FIG. 134, table 1346 includes columns for stage number, therapy type (e.g., CPEP, CHFO, or NEB), baseline pressure for each stage, time duration for each stage, oscillation frequency level (low, medium, or high) for each of the CHFO stages, and whether the nebulizer is on or off for each stage. Text above table 1346 indicates that plan 1 of the automatic OLE therapy has ten total stages and lasts a total time of 22 minutes, 20 seconds (22:20). A back button 1348 is also shown above table 1338 in FIG. 134 and is selectable to return the user to screen 1336 of FIG. 133.

Screen 1338 of FIG. 134 further includes a start button 1350 and an edit button 1352 located beneath table 1346. Start button 1350 is selectable to begin the automatic OLE therapy according to the parameters in table 1346 of selected plan 1. Edit button 1352 is selectable to edit the parameters of the selected plan 1 shown in table 1346 as will be discussed below in connection with FIGS. 135-158. If another button of the menu 1344 of care plan buttons (e.g., plan 2 button, plan 3 button, plan 4 button, etc.) is selected, then table 1346 shows the parameters for the selected care plan and the start and edit buttons 1350, 1352 pertain to the selected care plan. A scroll bar 1354 to the left of table 988 includes a scroll slider 1356 that is touched and dragged downwardly to reveal other stages of OLE therapy on table 1346. In the illustrative example of FIG. 134, stages 1-9 are shown on table 1346 and so scroll slider 1356 is used to reveal stage 10, if desired, on table 1346.

Referring now to FIG. 135, an access limited screen 1358 appears on GUI 16 in response to selection of edit button 1352 of the first care plan screen 1338 of FIG. 134 if the clinical access feature of the respiratory therapy apparatus 10 is turned off or disabled. Screen 1358 includes a window 1360 having a text box 1362 with the text "ACCESS LIMITED" therein. Beneath box 1362 is the explanatory text, "YOU DO NOT HAVE NECESSARY ACCESS TO PERFORM THIS TASK. CONTACT CUSTOMER SUPPORT FOR DETAILS." A return button 1364 is also provided in window 1360 of screen 1358 of FIG. 135. Selection of button 1364 returns the user back to screen 1338 of FIG. 134.

Referring now to FIG. 136, an edit therapy settings screen 1104 appears on GUI 16 in response to selection of edit button 1352 of the first care plan screen 1338 of FIG. 134 if the clinical access feature of the respiratory therapy apparatus 10 is turned on or enabled. Screen 1366 includes a window 1368 having a text box 1370 with the text "EDIT THERAPY SETTINGS" therein. Beneath box 1370 is the explanatory text, "CHOOSE THE PRESET FUNCTION YOU INTEND TO PERFORM:" Beneath the explanatory text in window 1368 is a delete button 1372 and a modify button 1374. Selection of button 1372 begins the process of deleting the selected care plan (e.g., plan 1 in the illustrative example) as was discussed in further detail above in connection with FIG. 119. Selection of button 1374 starts the process for editing the selected care plan. Window 1368 of screen 1366 of FIG. 136 also includes return button 1364 the selection of which returns the user back to screen 1338 of FIG. 134.

Referring now to FIG. 137, a first modify therapy screen 1376 appears on GUI 16 in response to selection of modify button 1374 on the edit therapy settings screen 1366 of FIG. 136. First modify screen 1376 shows that the CPEP portion of stage 1 of plan 1 of the automatic OLE therapy is selected for parameter adjustment. In particular, plan 1 button 1342 of menu 1344 is highlighted and the text "MODIFY 'PLAN 1'" appears in the upper left corner of a window 1378 of screen 1376. Furthermore, a stage 1 tile 1380 of a set of overlapped tiles including a cycle 2 tile 1382 and a cycle 3 tile 1384 is enlarged near the top of window 1378 to indicate that the parameters in window 1378 pertain to stage 1 of plan 1. In some embodiments, each care plan for OLE therapy can have up to 20 stages. As shown to the right of tile 1384, the illustrative example of care plan 1 has ten stages.

Still referring to FIG. 137, window 1378 includes a base pressure box or field 1386 in which the baseline CPEP pressure is shown, a duration field or box 1388 in which the duration of the CPEP stage is shown, and a nebulizer slider input 1390 that is used to turn the nebulizer of the CPEP stage on and off. In the illustrative example, the CPEP baseline pressure in field 1386 is 25 cmH$_2$O, the duration of the CPEP stage in field 1388 is 2 minutes, and the nebulizer slider input 1390 is in the off position. Screen 1376 of FIG. 137 further includes a done button 1392 in the upper right corner of window 1378. Selection of done button 1392 returns the user back to screen 1338 of FIG. 134 but with the various new parameters for plan 1 shown on table 1346. On screen 1376 in some embodiments, icons 698 and 702 of menu 692 are active and can be selected by the user, but the other icons of menu 692 are inactive and grayed out. Beneath done button 1392 and above nebulizer slider input 1390 is a delete button 1394 and an add button 1396. A down arrow icon 1398 appears in window 1378 of screen 1376 of FIG. 137 just to the right of the text "CPEP" and is selectable to change the stage type (e.g., CPEP, CHFO, or NEB) as will be discussed in further detail below in connection with FIG. 153.

Referring now to FIG. 138, a second modify therapy screen 1400 appears on GUI 16 in response to selection of the stage 2 tile 1382 of the horizontally arranged, overlapping tiles of the first modify therapy screen 1376 of FIG. 137. In the illustrative example, stage 2 corresponds to a CHFO portion of plan 1 of the automatic OLE therapy as indicated by the text "CHFO" appearing to the left of arrow icon 1398. Portions of screen 1400 of FIG. 138 that are substantially the same as like portions of screen 1376 of FIG. 137 are denoted with like reference numbers and the descriptions are not repeated. However, fields 1386, 1388 and nebulizer slider input 1390 pertain to the CHFO portion of the stage 2 of the automatic OLE therapy and not the CPEP portion of stage 1.

On screen 1400 of FIG. 138, a stage 4 tile 1402 is revealed after selection of stage 2 tile 1382. Furthermore, in the FIG. 138 example, slider input 1390 is in the on position such that the nebulizer 66 will be turned on during the stage 2 CHFO portion of the OLE therapy. Also, because CHFO is the stage type of screen 1400 of FIG. 138, a set of frequency buttons in including a low frequency button 1404, a medium frequency button 1406, and a high frequency button 1408 appear near the bottom of window 1378 of screen 1400. Buttons 1404, 1406, 1408 are selectable like radio buttons (e.g., only one of buttons 1404, 1406, 1408 can be selected for any given CHFO stage) to establish the oscillation frequency for the CHFO portion of the OLE therapy. In some embodiments, the low oscillation frequency associated with button 1404 is about 3 Hz, the medium oscillation frequency associated with button 1406 is about 4 Hz, and the high oscillation frequency associated with button 1408 is about 5 Hz. Device 10 may be configured to use other frequency values in other embodiments.

According to the present disclosure, the base pressure value shown in field 1386 of FIG. 138 is the upper pressure number of the oscillating CHFO therapy delivered to the patient. Thus, the base pressure for CHFO is different than the base pressure of MIE therapy about which the flutter oscillations occur. During CHFO therapy, the rotatable plate of the rotary valve assembly 330 is moved between opened and closed positions at the frequency corresponding to the selected one of buttons 1404, 1406, 1404. Also, during the illustrative CHFO therapy, blower 260 is operated to deliver the base pressure shown in field 1386 of screen 1400 of FIG. 138 to the outlet port 24 when the rotatable plate of the rotary valve assembly 330 is in the opened position. Movement of the rotatable plate to the closed position causes the pressure delivered to outlet port 24 by blower 260 to drop down to 0 cmH2O or almost down to 0 cmH$_2$O (e.g., 2 or 3 cmH2O) because, in some embodiments, the rotary valve assembly 330 is configured to always have an opening, albeit a small one, in the closed position to allow pneumatic communication between blower 260 and/or atmosphere with outlet port 24. See, for example, FIG. 16 of U.S. Patent Application Publication No. 2018/0085541 A1 and the related discussion in this regard. Thus, CHFO therapy has wide ranging high frequency pressure changes from the base pressure down to about 0 cmH2O.

Referring now to FIG. 139, a third modify therapy screen 1410 appears on GUI 16 in response to selection of the stage 3 tile 1384 of the horizontally arranged, overlapping tiles of the first modify therapy screen 1376 of FIG. 137 or the second modify therapy screen 1400 of FIG. 138. In the illustrative example, stage 3 corresponds to a nebulizer portion of plan 1 of the automatic OLE as indicated by the text "NEB" appearing to the left of arrow icon 1398 in FIG. 139. Portions of screen 1410 of FIG. 139 that are substantially the same as like portions of screens 1376, 1400 of FIGS. 137 and 138, respectively, are denoted with like reference numbers and the descriptions are not repeated. However, on screen 1410 of FIG. 139, a stage 5 tile 1411 revealed after selection of stage 2 tile 1382. Beneath buttons 1394, 1396 of screen 1410 a nebulizer state field 1412 appears and indicates that the nebulizer is to be in the on state during the NEB portion of stage 3. A duration field 1414 appears on screen 1410 beneath arrow icon 1398 and to the left of field 1412. In the illustrative example, a time of 1 minute, 30 seconds (01:30) is shown in field 1414 and is the time duration of stage 3. Field 1414 is selectable to adjust the duration in a manner similar to that discussed below in connection with FIG. 149.

Referring now to FIG. 140, a second care plan screen 1416 for automatic OLE therapy appears on GUI 16 in response to selection of an options tab 1418 on the first care plan screen 1338 of FIG. 134. Beneath options tab 1418 of second care plan screen 1416 are a cough pause slider input 1420 for turning on and off the cough pause feature of the respiratory therapy apparatus 10, a cough pause interval field 1422, and a cough pause duration field 1424. In the illustrative example of FIG. 140, slider input 1420 is in the off position and so each fields 1422, 1424 has a dash "-" therein because no cough pause interval or duration is needed. Other portions of screen 1416 of FIG. 140 that are substantially the same as like portions of screen 1338 of FIG. 134 are denoted with like reference numbers and the descriptions are not repeated.

Referring now to FIG. 141, a cough pause settings screen 1426 for automatic OLE therapy appears on GUI 16 in response to cough pause slider 1420 of screen 1416 of FIG. 140 being moved from the off position to the on position. In the illustrative example, default cough pause parameter values are shown in cough pause interval field 1422 and cough pause duration field 1424. In particular, the cough pause interval defaults to beginning every five minutes during the automatic OLE therapy and the cough pause duration for each occurrence of the cough pause function defaults to a duration of 40 seconds. Other default cough pause parameter values are used in other embodiments of device 10 at the discretion of the system designer.

Referring now to FIG. 142, a fourth modify therapy screen 1428 appears on GUI 16 in response to cough pause interval field 1422 of the cough pause settings screen 1426 of FIG. 141 having been selected for adjustment. A connector segment 1430 extends from a bubble 1432 around field 1422 to a menu of icons 1434 to indicate that a keyboard icon 1436, an up arrow icon 1438, a down arrow icon 1440, a save icon 1442, and a cancel icon 1444 are activated for use in connection with cough pause interval adjustment. Up arrow icon 1438 and down arrow icon 1440 are touched successively to increment or decrement, respectively, the corresponding cough pause interval value by 1 minute. Alternatively, each of arrow icons 1438, 1440 can be selected and held continuously and the cough pause interval value will be incremented or decremented, respectively, by 1 minute for every second held, up to five seconds, after which the cough pause interval value will be incremented or decremented, respectively, by 1 minute for every ½ second held. If an upper cough pause interval limit or lower cough pause interval limit is reached for the cough pause interval value in field 1422, then the up arrow button 1438 or down arrow button 1440, as the case may be, becomes inactive and continued selection of the particular arrow button 1438, 1440 has no effect.

As shown in FIG. 143, a fifth modify therapy screen 1446 appears on GUI 16 in response to keyboard icon 1436 of screen 1428 of FIG. 142 being selected. Screen 1446 includes a graphical keyboard 1448 that is located just to the left of bubble 1432 and that is usable to directly type the new cough pause interval value into field 1422. In the illustrative example of screen 1446 of FIG. 143, the cough pause interval value has not yet been changed from the default setting of 5 minutes. After the user has incremented or decremented to the desired cough pause interval value in field 1422 using arrow buttons 1438, 1440 or after the user has typed the desired cough pause interval value in field 1422 using graphical keyboard 1448, save button 1442 of menu 1434 is selected to save the cough pause interval value for subsequent use during future automatic OLE therapy sessions. If the user decides not to enter a new cough pause interval value, then cancel button 1444 of menu 1434 is selected and the previous cough pause interval value is used for future automatic OLE therapy sessions.

Referring now to FIG. 144, a sixth modify therapy screen 1450 appears on GUI 16 in response to cough pause duration field 1424 of the cough pause settings screen 1426 of FIG. 141 having been selected for adjustment. A connector segment 1452 extends from a bubble 1454 around field 1424 to menu of icons 1434 to indicate that icons 1436, 1438, 1440, 1442, 1444 are activated for use in connection with cough pause duration adjustment. Up arrow icon 1438 and down arrow icon 1440 are touched successively to increment or decrement, respectively, the corresponding cough pause duration value by 1 second. Alternatively, each of arrow icons 1438, 1440 can be selected and held continuously and the cough pause duration value will be incremented or decremented, respectively, by 1 second for every second held, up to five seconds, after which the cough pause duration value will be incremented or decremented, respectively, by 1 second for every ½ second held. If an upper cough pause duration limit or lower cough pause duration limit is reached for the cough pause duration value in field 1424, then the up arrow button 1438 or down arrow button 1440, as the case may be, becomes inactive and continued selection of the particular arrow button 1438, 1440 has no effect.

As shown in FIG. 145, a seventh modify therapy screen 1456 appears on GUI 16 in response to keyboard icon 1436 of screen 1450 of FIG. 144 being selected. Screen 1456 includes graphical keyboard 1448 that is located just to the left of bubble 1454 and that is usable to directly type the new cough pause duration value into field 1424. In the illustrative example of screen 1456 of FIG. 145, the cough pause duration value has not yet been changed from the default setting of 40 seconds. After the user has incremented or decremented to the desired cough pause duration value in field 1424 using arrow buttons 1438, 1440 or after the user has typed the desired cough pause duration value in field 1424 using graphical keyboard 1448, save button 1442 of menu 1434 is selected to save the cough pause duration value for subsequent use during future automatic OLE therapy sessions. If the user decides not to enter a new cough pause duration value, then cancel button 1444 of menu 1434 is selected and the previous cough pause duration value is used for future automatic OLE therapy sessions.

Referring now to FIG. 146, an eighth modify therapy screen 1458 appears on GUI 16 in response to base pressure field 1386 of the second modify therapy screen 1400 of FIG. 138 having been selected for adjustment such that field 1386 is highlighted and appears in a bubble 1460. A connector segment 1462 extends from bubble 1460 to menu 1434 to indicate that icons 1436, 1438, 1440, 1442, 1444 are activated for use in connection with CHFO baseline pressure adjustment. Up arrow icon 1438 and down arrow icon 1440 are touched successively to increment or decrement, respectively, the corresponding CHFO base pressure value by 1 cmH$_2$O. Alternatively, each of arrow icons 1438, 1440 can be selected and held continuously and the respective CHFO base pressure value will be incremented or decremented, respectively, by 1 cmH$_2$O for every second held, up to five seconds, after which the CHFO base pressure value will be incremented or decremented, respectively, by 1 cmH$_2$O for every ½ second held. If an upper pressure limit or lower pressure limit is reached for the CHFO base pressure value in field 1386, then the up arrow button 1438 or down arrow button 1440, as the case may be, becomes inactive and continued selection of the particular arrow button 1438, 1440 has no effect. With regard to screen 1458 of FIG. 146, most everything else other than field 1386, bubble 1460, connector segment 1462, and icons 1436, 1438, 1440, 1442, 1444 of menu 1434 is grayed out and inactive except that icon 698 of menu 692 remains highlighted and active.

As shown in FIG. 147, a ninth modify therapy screen 1464 appears on GUI 16 in response to keyboard icon 1436 of FIG. 146 being selected so that graphical keyboard 1448 appears on screen 1464 between bubble 1460 and menu 1434. In some embodiments, arrow icons 1438, 1440 become grayed out and inactive when keyboard 1448 appears on GUI 16. In FIG. 147, the current CHFO base pressure value of 30 cmH$_2$O is shown in field 1386. However, graphical keyboard 1448 of screen 1464 of FIG. 147 is used to change the CHFO base pressure to another pressure at the discretion of the user.

After the user has incremented or decremented to the desired CHFO base pressure value in field 1386 using arrow buttons 1438, 1440 or after the user has typed the desired CHFO base pressure value in field 1386 using graphical keyboard 1448, save button 1442 of menu 1434 is selected to save the new CHFO base pressure value for subsequent use during future automatic OLE therapy sessions in connection with the selected plan and selected cycle. If the user decides not to enter a new CHFO base pressure value, then cancel button 1444 of menu 1434 is selected and the previous CHFO base pressure value is used for future automatic OLE therapy sessions for the corresponding plan and cycle.

Referring now to FIG. 148, a tenth modify therapy screen 1466 appears on GUI 16 in response to duration field 1388 of second modify therapy screen 1400 of FIG. 138 having been selected for adjustment such that field 1388 is highlighted and appears in a bubble 1468. A connector segment 1470 extends from bubble 1468 to menu 1434 to indicate that icons 1436, 1438, 1440, 1442, 1444 are activated for use in connection with CHFO duration adjustment. Up arrow icon 1438 and down arrow icon 1440 are touched successively to increment or decrement, respectively, the corresponding CHFO duration value by 1 second. Alternatively, each of arrow icons 1438, 1440 can be selected and held continuously and the respective CHFO duration value will be incremented or decremented, respectively, by 1 second for every second held, up to five seconds, after which the CHFO duration value will be incremented or decremented, respectively, by 1 second for every ½ second held. If an upper duration limit or lower duration limit is reached for the CHFO duration value in field 1388, then the up arrow button 1438 or down arrow button 1440, as the case may be, becomes inactive and continued selection of the particular arrow button 1438, 1440 has no effect. With regard to screen 1466 of FIG. 148, most everything else other than field 1388, bubble 1468, connector segment 1470, and icons 1436, 1438, 1440, 1442, 1444 of menu 1434 is grayed out and inactive except that icon 698 of menu 692 remains highlighted and active.

As shown in FIG. 149, an eleventh modify therapy screen 1472 appears on GUI 16 in response to keyboard icon 1436 of FIG. 148 being selected so that graphical keyboard 1448 appears on screen 1472 between bubble 1468 and menu 1434. In some embodiments, arrow icons 1438, 1440 become grayed out and inactive when keyboard 1448 appears on GUI 16. In FIG. 149, the CHFO duration value in field 1388 has been adjusted using keyboard 1448 to 05:00 minutes from the duration value of 01:30 minute (i.e., 1 minute, 30 seconds) shown in field 1388 of FIG. 148. Of course, graphical keyboard 1448 of screen 1472 of FIG. 149 can be used to change the CHFO duration to another duration at the discretion of the user.

After the user has incremented or decremented to the desired CHFO duration value in field 1388 using arrow buttons 1438, 1440 or after the user has typed the desired CHFO duration value in field 1388 using graphical keyboard 1448, save button 1442 of menu 1434 is selected to save the new CHFO duration value for subsequent use during future automatic OLE therapy sessions in connection with the selected plan and selected cycle. If the user decides not to enter a new CHFO duration value, then cancel button 1444 of menu 1434 is selected and the previous CHFO duration value is used for future automatic OLE therapy sessions for the corresponding plan and cycle. Although, FIGS. 146-149 have been discussed herein in connection with adjustment of CHFO base pressure and duration, it should be understood that CPEP base pressure and duration are adjusted in the same manner and therefore, the CPEP adjustments do need not need to be described herein in order to understand them.

Referring now to FIG. 150, a delete stage screen 1474 appears on GUI 16 in response to selection of delete button 1394 on any of the above described screens on which button 1394 is active such as, for example, the first, second or third modify therapy screens 1376, 1400, 1410 of FIGS. 137-139, respectively. Delete stage screen 1474 includes a window 1476 having a text box 1478 with the text "DELETE STAGE?" therein. Beneath box 1478 is the explanatory text "DO YOU WANT TO DELETE STAGE 1/14?" to indicate that user has selected delete button 1394 while viewing stage 1. If the user was viewing, say stage 3 of 12 stages, then the explanatory text beneath box 1478 would be, "DO YOU WANT TO DELETE STAGE 3/12?" just to give another arbitrary example.

Window 1476 of screen 1474 of FIG. 150 further includes a proceed button 1480 that is selectable to delete the selected stage and a cancel button 1482 that is selectable to abort the deletion process and return to the previous screen (i.e., the screen on which the delete button 1394 was selected originally). In response to selection of proceed button 1480, the stage that was being viewed when the delete button 1394 was pressed originally is deleted and each of the subsequent stages has its cycle number decremented by one. In other words, if stage 1 is deleted, then previous stage 2 becomes the new stage 1, previous stage 3 becomes the new stage 2, the previous stage 4 becomes the new stage 3, and so forth. To give another example, if stage 3 is deleted, then previous stages 1 and 2 remain as they were, previous stage 4 becomes the new stage 3, previous stage 5 becomes the new stage 4, and so forth.

In light of the foregoing discussion, FIG. 151 shows a twelfth modify therapy screen 1484 that appears on GUI 16 in response to selection of proceed button 1480 of FIG. 150, assuming screen 1376 of FIG. 137 was the screen being viewed when delete button 1394 was selected originally. Twelfth modify therapy screen 1484 is the same as screen 1400 of FIG. 138 except that it is now stage 1 of plan 1 of the automatic OLE therapy rather than stage 2. That is the CPEP stage 1 of FIG. 137 has been deleted from plan 1 and the CHFO stage which used to be stage 2 of the automatic OLE therapy, as shown in FIG. 138, has now become the new stage 1 of the automatic OLE therapy as shown in FIG. 151.

Referring now to FIG. 152, an add stage screen 1486 appears on GUI 16 in response to selection of add stage button 1396 on any of the above described screens on which button 1396 is active such as, for example, the first, second or third modify therapy screens 1376, 1400, 1410 of FIGS. 137-139, respectively. As shown in FIG. 152, the stage being added is stage 2 as indicated by the enlargement of the stage 2 tile 1382 of the set of overlapped tiles. Stage 2 is being added because stage 1 of plan 1 was being displayed on GUI 16 when button 1396 was selected. Thus, if stage 3 were being displayed on GUI 16 when add stage button 1396 was selected, the addition of stage 4 would result, just to give another arbitrary example. If there were previous stages programmed in plan 1 to occur after stage 1, then those previous stages have the respective stage numbers incremented by one after the addition of the new cycle. In other words, if stage 2 is the new stage being added, then previous stage 2 becomes the new stage 3, previous stage 3 becomes the new stage 4, the previous stage 4 becomes the new stage 5, and so forth. To give another example, if stage 3 is the new stage being added, then previous stages 1 and 2 remain as they were, previous stage 4 becomes the new stage 5, previous stage 5 becomes the new stage 6, and so forth.

Still referring to FIG. 152, screen 1486 of stage 2 is substantially the same as the screen of stage 1 appearing on GUI 16 when add stage button 1396 was selected. Thus, the values populated in fields 1386, 1388 and the position of slider input 1390 on screen 1486 of FIG. 152 are carried over (e.g., copied) from these same respective fields 1386, 1388 and from the slider input position of the previous screen being viewed on GUI 16 when add cycle button 1396 was selected. Furthermore, the type of OLE stage shown to the left of arrow icon 1398 is also carried over. Thus, in the illustrative example of FIG. 152, new stage 2 is a CPEP stage because stage 1 is a CPEP stage.

If the user wishes to change the type of stage of the particular stage being viewed on GUI 16, then selection of arrow icon 1398 results in a stage menu screen 1488 appearing on the GUI 16 as shown in FIG. 153. Stage menu screen 1488 of FIG. 153 includes a menu 1490 having CPEP, CHFO and NEB options labeled in respective buttons 1492, 1494, 1496 of menu 1490. The user simply selects the button 1492, 1494, 1496 corresponding to the stage type desired. For example, if CHFO button 1494 is selected on screen 1488 of FIG. 153, a stage 2 change screen 1498 appears on GUI 16 as shown in FIG. 154. Thus, selection of CHFO button 1494 on the menu 1490 of FIG. 153 changes stage 2 of the automatic OLE therapy from being the CPEP stage of FIG. 152 to being a CHFO stage. By comparing screens 1486 and 1498 of FIGS. 152 and 154, respectively, it can be seen that the values in fields 1386, 1388 and the position of slider input 1390 remain the same when stage 2 is changed from CPEP to CHFO. However, frequency buttons 1404, 1406, 1408 are added to screen 1498 because stage 2 has now become a CHFO stage, with low frequency button 1404 being the selected one of buttons 1404, 1406, 1408 by default in some embodiments.

If the user is viewing a particular stage of automatic OLE therapy on GUI 16 and wishes to edit some other previously programmed stage, the user is able to swipe left or right, as the case may be, on the set of overlapping stage tiles to view the previously programmed cycles. The values shown in fields 1386, 1388, the position of slider input 1390, the particular frequency icon 1404, 1406, 1408 selected (for CHFO stages), and value shown in nebulizer duration field 1414 (for NEB stages) are in accordance with the previous programming in connection with whichever of the overlapping tiles is the enlarged tile. For example, FIG. 155 is a screen shot of a stage 3 screen 1500 that appears on GUI 16 in response to swiping to the left on the stage 2 tile 1382 on FIG. 154. Stage 3 screen 1500 of FIG. 155 shows the settings for the current stage 3 of the automatic OLE therapy in fields 1386, 1388, along with the position of slider input 1390 and selected frequency button 1406.

Referring now to FIG. 156, another stage menu screen 1488', substantially the same as the stage menu screen 1488 of FIG. 153, appears on GUI 16 in response to selection of arrow icon 1398 of screen 1500 of FIG. 155. Screen 1488' of FIG. 156 is substantially the same as screen 1488 of FIG. 153 and so like reference numbers are used to denote like portions without repeating the descriptions. However, in the grayed out portions of FIGS. 153 and 156, it can be seen that the stage 2 tile 1382 is enlarged on screen 1488 of FIG. 153 whereas the stage 3 tile 1384 is enlarged on screen 1488' of FIG. 156.

Referring now to FIG. 157, a stage 3 change screen 1502 appears on GUI 16 in response to selection of NEB button 1496 on the menu 1490 of screen 1488' of FIG. 156 to change stage 3 of the automatic OLE therapy from being a CHFO stage to being a NEB stage. As shown on screen 1502 of FIG. 157, field 1412 automatically defaults to the on state and field 1414 shows the default nebulizer duration of 05:00 minutes. Also, the nebulizer pressure provided by blower 260 of device 10 defaults to 5 $cmH_2O$ for nebulizer stages of automatic OLE therapy in some embodiments.

After the user has modified the stages of the selected plan of automatic OLE therapy in the desired manner such as described above in connection with FIGS. 136-157, then selection of done button 1392 such as on screen 1502 of FIG. 157 for example, results in another first care plan screen 1338' for automatic OLE therapy, similar to screen 1338 of FIG. 134, appearing on GUI 16 of apparatus 10. Screen 1338' for automatic OLE therapy of FIG. 158 is substantially the same as screen 1338 of FIG. 134 except that table 1346 reflects the new values and settings for plan 1 of the automatic OLE therapy. Plans 2, 3, 4, etc. of automatic OLE therapy are modified similarly as desired after the user selects the corresponding plan button on menu 1344. Above table 1346 of screen 1338' of FIG. 158, is a line of text indicating that plan 1, as modified, has 15 total stages and a total time of 38 minutes, 20 seconds (38:20), whereas this same line of text above table 1346 of screen 1338 of FIG. 134 indicates that plan 1, prior to modification, had 10 total stages and a total time of 22 minutes, 20 seconds (22:20).

In the discussion above of FIGS. 121-158, it was assumed that the various parameters and features of the automatic OLE therapy were programmed previously into control circuitry 500 of device 10. However, if automatic button 684 for OLE therapy is selected on screen 682 of FIG. 20 and there are no care plans with any parameters preprogrammed for operation of automatic OLE therapy in control circuitry 500 of device 10, then an empty preset screen just like screen 1218 of FIG. 111 appears on the GUI 16. As discussed above, screen 1218 includes a window 1220 with a text box 1222 having the text "EMPTY PRESET" therein. Beneath box 1222 is explanatory text which states, "PLEASE PROGRAM THE PRESET WITH THERAPY PARAMETERS. IF PROBLEM PERSISTS, PLEASE CONTACT CUSTOMER SUPPORT." In other words, empty preset screen 1218 appears on GUI 16 in similar situations for automatic MIE therapy and automatic OLE therapy.

To navigate to screens for creating a new care plan for automatic OLE therapy, the user first selects menu open icon 688 on screen 1218 of FIG. 111 (assuming automatic button 684 for OLE therapy was selected on screen 682 of FIG. 20 originally) to cause menu 692, shown on screen 846 of FIG. 39 for example, to appear on GUI 16 and then the user selects lung icon 698 from menu 692 which results in a create care plan screen 1504 appearing on GUI 16 as shown in FIG. 159. Screen 1504 initially opens with therapy tab 1340 selected but with no table 1346 of the type shown, for example, on screen 1338 of FIG. 134. Instead, screen 1504 has the following explanatory text beneath tab 1340: "THIS IS AN EMPTY PRESET. CLICK 'CREATE' TO PROGRAM THIS PRESET WITH THERAPY PARAMETERS." A create icon or button 1506 appears on screen 1504 beneath the explanatory text and is selectable to create a new care plan. Screen 1504 also has a back icon or button 1508 which is selectable to return the user back to screen 1218 of FIG. 111. Screen 1504 also includes the menu 1344 of care plan buttons, with the first button 1342 of menu 1344 being selected, but there are ellipses " . . . " that appear in each care plan button of menu 1344 because no care plan has yet been programmed and named. Menu 692 of screen 1504 has buttons 694, 698, 700, 702 highlighted and active with each of the other buttons of menu 692 being grayed out and inactive.

Referring now to FIG. 160, a first create new therapy screen 1510 appears on GUI 16 in response to selection of create button 1506 on empty preset screen 1504 of FIG. 159 assuming the clinical access feature of the respiratory therapy apparatus 10 is turned on (i.e., is enabled). If the clinical access feature is turned off (i.e., is disabled), then an access limited screen, similar to screens 1098, 1230, 1358 of FIGS. 90, 113, and 135, respectively, appears on GUI 16 in response to selection of button 1506 on screen 1504. First create new therapy screen 1510 of FIG. 160 shows that a CPEP stage is the default stage for stage 1 of plan 1 of a new care plan for the automatic OLE therapy. Screen 1510 also shows fields 1386, 1388 populated with the default values of 5 cmH$_2$O and 10 seconds (00:10), respectively. Slider input 1390 defaults to the on position as also shown in FIG. 160. Delete button 1394 is grayed out on screen 1510 because only one stage is included in the care plan initially. That is, delete button 1394 becomes grayed out and is unusable whenever only one stage remains in the selected care plan.

If the user selects the done button 1392 on screen 1510 of FIG. 160 without modifying the CPEP parameter values or states in window 1378 and without adding any additional stages, then yet another first care plan screen 1338" for automatic OLE therapy, similar to screens 1338 and 1338" of FIGS. 134 and 158, respectively, appears on GUI 16 of apparatus 10 as shown in FIG. 161. Table 1346 of screen 1338" of FIG. 161 is similar to table 1346 of screens 1338, 1338' of FIGS. 134 and 158, respectively, except that table 1346 of screen 1338" of FIG. 161 reflects only the default values and settings for plan 1 of the automatic OLE therapy. Above table 1346 of screen 1338" of FIG. 161, is a line of text indicating that newly created plan 1, has 1 total stage and a total time of 10 seconds (00:10).

Referring now to FIG. 162, a first new automatic OLE therapy start screen 1512 appears on GUI 16 if start button 1350 of screen 1338" of FIG. 161 is selected while the respiratory therapy apparatus is operating under battery power and the battery charge is less than 20% of a full battery charge as indicated by only a single rectangle being shown in battery icon 735, but assuming the RFID count check for filter unit 390 is passed. Prior to screen 1512 of FIG. 162 appearing on GUI 16, however, a low battery screen similar to screen 790 of FIG. 30 appears on GUI 16 and the user selects a return button, like button 796 of screen 790. Screen 1512 of FIG. 162 is similar to screen 1262 of FIG. 121 and so like reference numbers are used to denote like portions without repeating the descriptions. However, first new automatic OLE therapy start screen 1512 of FIG. 162 shows graph 1270 with the default parameters indicated and start button 1266 can still be selected to start the therapy despite the battery power being less than 20%.

Referring now to FIG. 163, a second new automatic OLE therapy start screen 1514 appears on GUI 16 if start button 1350 of screen 1338" of FIG. 161 is selected while the respiratory therapy apparatus is operating under battery power and the battery charge is greater than 20% of a full battery charge and the filter unit 390 passes the RFID count check. Like graph 1270 of screen 1512 of FIG. 162, graph 1270 of screen 1514 of FIG. 163 has the default parameters indicated and, because the therapy has started automatically due to the battery charge check and RFID check having been passed, pause button 1280 appears on screen 1514 and can be selected to pause the therapy which has already started.

Referring now to FIG. 164, if the user selects edit button 1352 of screen 1338" of FIG. 161, the user navigates to an edit therapy settings screen 1366' which is basically a duplicate of screen 1366 of FIG. 136 and so the same reference numbers are used in FIGS. 136 and 164 to denote like portions. To navigate to screen 1366' of FIG. 164 from screen 1338" of FIG. 161, the clinical access feature of the respiratory therapy apparatus 10 must be turned on or enabled when edit button 1352 is selected. In the illustrative examples of FIG. 161, the clinical access feature is, in fact, enabled as indicated by the presence of unlock icon 733 in the header of screen 1338".

Referring now to FIG. 165, a delete preset screen 1516 appears on GUI 16 in response to selection of delete button 1372 on the edit therapy settings screen 1366' of FIG. 164. Screen 1516 includes a window 1518 having a text box 1520 with the text "DELETE PRESET?" therein. Beneath box 1520 is the explanatory text, "DO YOU WANT TO DELETE 'PLAN 1'?" It should be noted that if a different plan was selected on menu 1344 when edit button 1352 was initially selected, then the explanatory text of screen 1516 would make reference to the selected plan (e.g., plan 2, plan 3, plan 4, and so forth).

Still referring to FIG. 165, beneath the explanatory text in window 1518 is a proceed button 1522 and a cancel button 1524. Selection of button 1522 results in the selected preset or care plan being deleted from control circuitry 500 of apparatus 10. Also, in response to selection of button 1522 on screen 1516 of FIG. 165, the user is returned to screen 1504 of FIG. 159 and the user is then able to navigate, as desired, from screen 1504. If the user decides not to cancel the selected preset, then cancel button 1524 is selected and the user is returned to screen 1510 of FIG. 160, assuming screen 1338" was the screen on which button 1352 was previously selected.

Referring now to FIG. 166, a main manual OLE therapy screen 1526 appears on GUI 16 in response to manual button 686 of main OLE therapy selection screen 682 of FIG. 20 being selected. However, the bar code scanning process shown on screens 722, 726, 732, 738, 750, 756 of FIGS. 23-28 also occurs, as appropriate, prior to display of screen 1526 if the bar code scanning function of device 10 is turned on. The discussion above of screens 722, 726, 732, 750, 756 of FIGS. 23-28 after selection of button 678 of screen 676 is equally applicable with regard to selection of button 686 of screen 682 and thus, does not need to be repeated.

Main manual OLE therapy screen 1526 of FIG. 166 includes a start button 1528, an CPEP button 1530, a CHFO button 1532, and a nebulizer button 1534 between buttons 1530, 1532. Each of buttons 1530, 1532, 1534 includes a respective circular indicia 1536a, 1536b, 1536c. When the corresponding CPEP, CHFO, and nebulizer functions of device 10 are turned on the respective indicia 1536a, 1536, 1536c become highlighted and the area within the respective circle is filled in with color coding. The generally square shaped borders around buttons 1530, 1532, 1534 also become highlighted in the appropriate color coding when the respective CPEP, CHFO and nebulizer functions are active. As noted above, the color coding for the CPEP function is orange, the color coding for the CHFO function is blue, and the color coding for the nebulizer function is green in some embodiments.

Within each of CPEP button 1530 and CHFO button 1532 is a stage number beneath the text "STAGE:" that indicates which stage of the manual OLE therapy is active. Each of CPEP button 1530 and CHFO button 1532 also has a timer beneath the text "TIME:" to indicate the amount of time the current or most recent CPEP stage or CHFO stage, as the case may be, has occurred during the manual OLE therapy session. Within nebulizer button 1534, the word OFF or ON appears to indicate the state of the nebulizer 66 of device 10. If nebulizer tray 50 is not attached to housing 14 and connected to control circuitry 500 via cable 148 and connector 150, then button 1534 is not usable and remains grayed out in some embodiments or is omitted from screen 1526 in some embodiments.

Still referring to screen 1526 of FIG. 166, a main timer 1538 is shown above button 1534 and between buttons 1530, 1532. Timer 1538 indicates the overall time of the manual OLE therapy session. Timer 1538 and the timers in buttons 1530, 1532 are each in a minutes:seconds format and are each shown to be 00:00 in FIG. 166 since the manual OLE therapy session has not yet started. Screen 1526 has a CPEP pressure information and adjustment field 1540 beneath button 1530 and a CHFO pressure information and adjustment field 1542 beneath button 1532. Each of fields 1540, 1542 indicates the baseline pressure that is programmed for the corresponding CPEP stage or CHFO stage of the manual OLE therapy. In the illustrative example, field 1540 indicates that the baseline CPEP pressure is programmed for 22 cmH$_2$O and field 1542 indicates that the baseline CHFO pressure is programmed for 43 cmH$_2$O. In FIG. 166, button 1534 indicates that the nebulizer is currently in the OFF state.

Each of fields 1540, 1542 includes an up arrow icon 1544 and a down arrow icon 1546 which are touched successively to increment or decrement, respectively, the corresponding pressure value by 1 cmH$_2$O. Alternatively, each of arrow icons 1544, 1546 can be selected and held continuously and the respective pressure value will be incremented or decremented, respectively, by 1 cmH$_2$O for every second held, up to five seconds, after which the pressure value will be incremented or decremented, respectively, by 1 cmH$_2$O for every ½ second held. If an upper pressure limit or lower pressure limit is reached for the pressure values in fields 1540, 1542, then the up arrow icon 1544 or down arrow icon 1546, as the case may be, becomes inactive and continued selection of the particular arrow icon 1544, 1546 has no effect.

Some portions of screen 1526 of FIG. 166 are similar to like portions of the screens of FIGS. 121-124 and so like reference numbers are used to denote these like portions and the descriptions of these like portions above is equally applicable to screen 1526 of FIG. 166 and to subsequent Figs. herein. As shown in the header area of screen 1526, Bluetooth icon 731 appears which indicates that control circuitry 500 of device 10 is in wireless communication with some other device. In the illustrative example, circuitry 500 of device 10 is in communication with a pulse oximeter and so heart rate field 884 and blood oxygen saturation field 886 (aka saturation field 886 or SPO$_2$ field 886) appear on screen 1526 between bar 1272 and start button 1528. Also in the illustrative example, field 884 indicates that the patient's heart rate (HR) is 74 beats per minute (BPM) and the patient's blood oxygenation is 94%. Thus, values from the pulse oximeter are received by circuitry 500 and displayed on GUI 16 prior to the manual OLE therapy session even beginning in the depicted example.

Screen 1526 of FIG. 166 also includes a CHFO frequency button 1548 which, in the illustrative example, indicates that a medium level of frequency for the CHFO portion of manual OLE therapy is selected. CHFO frequency button 1548 is pressed to control the CHFO frequency of device 10 as will be discussed below in connection with FIG. 175.

Screen 1526 further includes an informational field 1549 located beneath nebulizer button 1534 and above start button 1528. In FIG. 166, field 1549 includes the text "PRESS START" to indicate to the user that start button 1528 needs to be pressed to start the manual OLE therapy session.

Referring now to FIG. 167, a manual OLE therapy preparation screen 1550 appears on GUI 16 in response to start button 1528 being selected on main manual OLE therapy screen 1526 of FIG. 166, and assuming that filter unit 390 attached to port 24 passes the RFID count check and that battery power is greater than 20% of a full battery charge in the event that device 10 is operating under battery power rather than being plugged in to an AC power outlet. If the RFID count check of filter unit 390 fails or if battery power is less than 20% of a full battery charge, again assuming device 10 is not plugged into an AC power outlet, then an appropriate alert message (e.g., screen 790 of FIG. 30) is shown on GUI 16 in this regard. Screen 1550 of FIG. 167 is very similar to screen 1526 of FIG. 166 expect that the start button 1528 of screen 1526 is converted to a stop button 1552 on screen 1550. Furthermore, the buttons 1530, 1532, 1534 remain grayed out on screen 1550 during a preparation operation of the manual OLE therapy in which the pneumatic system 320 is turned on. During the preparation stage, informational field 1549 is blank without any text in the illustrative example of screen 1550 of FIG. 167.

Referring now to FIG. 168, a manual OLE therapy ready screen 1554 appears on GUI 16 after the preparation operation. During the preparation operation, fields 1540, 1542 are grayed out on screen 1550 of FIG. 167. After the preparation operation is completed, screen 1554 of FIG. 168 has fields 1540, 1542 become illuminated to indicate that buttons 1530, 1532, 1534 are ready for use. As also shown on screen 1554 of FIG. 168, after the preparation stage is completed, the text "SELECT THERAPY" appears in informational field 1549 to indicate to the user that buttons 1530, 1532, 1534 are ready for use.

Referring now to FIG. 169, a manual OLE therapy CPEP on screen 1556 appears on GUI 16 in response to CPEP button 1530 being selected on screen 1554 of FIG. 168. Screen 1556 of FIG. 169 shows that CPEP icon 1536a is illuminated and filled in along with the surrounding border of button 1530 being highlighted after the user presses the CPEP button 1530 for delivery of CPEP therapy to the user's lungs by the respiratory therapy apparatus 10. In the illustrative example of screen 1556 of FIG. 169, nebulizer button 1534 continues to indicate that nebulizer 66 is in the off state, but the user has the option of selecting button 1534 at any time during the CPEP portion of manual OLE therapy to turn nebulizer 66 on, in which case button 1534 will indicate that nebulizer 66 is in the on state.

As also shown on screen 1556, the main timer 1538 indicates that the manual OLE therapy has been occurring for two minutes, three seconds (02:03) which matches the time shown by the timer within button 1530 since the first stage of manual OLE therapy is the stage of therapy currently being delivered. In this regard, button 1530 indicates that stage 1 is the current stage. Bar 1272 of screen 1556 of FIG. 169 also shows segment 1290 thereon and a portion of mean arrow box 1288 is revealed beneath arrow box 1276. During the delivery of the CPEP portion of the manual OLE therapy to the patient, informational field 1549 is blank as shown in FIG. 169.

Referring now to FIG. 170, a manual OLE therapy CPEP off screen 1558 appears on GUI 16 in response to the user selecting or pressing the CPEP button 1530 on screen 1556 of FIG. 169 to turn off the delivery of CPEP therapy. Thus, button 1530 is tapped once to turn on the CPEP portion of the manual OLE therapy and is tapped a second time to turn off the CPEP portion of the manual OLE therapy. Screen 1558 shows the CPEP and CHFO buttons both grayed out to indicate an off state. Thus, informational field 1549 once again includes the text "SELECT THERAPY" to inform the user that buttons 1530, 1532 are ready for use as desired to turn on the delivery of the respective CPEP or CHFO portion of the manual OLE therapy.

In the illustrative example of screen 1558 of FIG. 170, the user has decided to turn on nebulizer 66 by touching button 1534 and so the nebulizer icon 1536c in the nebulizer button 1534 is illuminated and filled in. The border around nebulizer button 1534 is also highlighted after the user presses nebulizer button 1534 for delivery of nebulized medication to the user's lungs by the respiratory therapy apparatus 10. Main timer 1538 indicates a time of 02:06 which is three seconds more than the time shown in button 1530. Thus, in the illustrative example, the user turned off the CPEP portion of the manual OLE therapy at a time of 02:03 and, at some point in the subsequent three seconds, turned on the nebulizer 66 using button 1534.

Referring now to FIG. 171, a manual OLE therapy CHFO on screen 1560 appears on GUI 16 in response to CHFO button 1532 being selected on screen 1558 of FIG. 170. Screen 1560 of FIG. 171 shows that CHFO icon 1536b is illuminated and filled in along with the surrounding border of button 1532 being highlighted after the user presses the CHFO button 1532 for delivery of CHFO therapy to the user's lungs by the respiratory therapy apparatus 10. In the illustrative example of screen 1560 of FIG. 171, nebulizer button 1534 continues to indicate that nebulizer 66 is in the on state, but the user has the option of selecting button 1534 at any time during the CHFO portion of manual OLE therapy to turn nebulizer 66 off, in which case button 1534 will no longer be highlighted and will indicate that nebulizer 66 is in the off state.

As also shown on screen 1560, the main timer 1538 indicates that the manual OLE therapy has been occurring for four minutes, nineteen seconds (04:19) with the timer within button 1530 indicating occurrence of CPEP for 02:03 and the timer within button 1532 indicating occurrence of CHFO for 02:13. Thus, the nebulizer 66 was turned on by itself without either of CPEP or CHFO portions of manual OLE therapy being turned on for three seconds. That is, the total time of 04:19 equals 02:03 of CPEP+02:13 of CHFO+3 seconds of nebulizer only. Furthermore, button 1532 of screen 1560 indicates that stage 1 is the current stage of CHFO. Thus, the stage numbers shown in buttons 1530, 1532 correspond to the number of stages that CPEP and CHFO portions of manual OLE therapy have each occurred which is not the same as the stage number in an overall series of stages like discussed above in connection with automatic OLE therapy. Also on screen 1560 of FIG. 171, bar 1272 once again shows segment 1290 thereon mean arrow box 1288 is viewable beneath arrow box 1276. Moreover, during the delivery of the CHFO portion of the manual OLE therapy to the patient, informational field 1549 is blank, once again, as shown in FIG. 171.

Referring now to FIG. 172, a manual OLE therapy CHFO off screen 1562 appears on GUI 16 in response to the user selecting or pressing the CHFO button 1532 on screen 1560 of FIG. 171 to turn off the delivery of CHFO therapy. FIG. 172 is substantially the same as FIG. 170 except that the main timer has advanced to 04:23 and the timer in button 1532 reads 02:13. Thus, similar to button 1530, button 1532 is tapped once to turn on the CHFO portion of the manual OLE therapy and is tapped a second time to turn off the CHFO portion of the manual OLE therapy. Screen 1562 of FIG. 172 shows the CPEP and CHFO buttons both grayed out to indicate an off state but the border of button 1534 and nebulizer icon 1536c continue to be highlighted because nebulizer 66 remains in the on state after button 1532 is tapped to turn off the CHFO therapy. As also shown on screen 1562, informational field 1549 once again includes the text "SELECT THERAPY" to inform the user that buttons 1530, 1532 are ready for use as desired to turn on the delivery of the respective CPEP or CHFO portion of the manual OLE therapy.

Based on the foregoing description of FIGS. 168-172, it should be appreciated that buttons 1530, 1532, 1534 are selected at the discretion of the user to turn on and off each of the CPEP therapy, the CHFO therapy, and the nebulizer 66 of apparatus 10 during the delivery of manual OLE therapy. If the user desires to change the baseline pressure of the CPEP portion of CHFO portion of the manual OLE therapy, up arrow buttons 1544 and down arrow buttons 1546, respectively, of fields 1540, 1542 are selected as described above. The present disclosure also contemplates an alternative manner of adjusting the CPEP and CHFO baseline pressures as shown in FIGS. 173 and 174. In particular, instead of selecting arrow icons 1544, 1546 in fields 1540, 1542, the user touches or presses the numerical pressure values appearing in fields 1540, 1542. In the illustrative example, arrow icons 1544, 1546 appear in the right half of respective fields 1540, 1542 and the numerical pressure values appear in the left half of respective fields 1540, 1542. Selection of the numerical pressure value in one of fields 1540, 1542 results in a graphical numerical keyboard 1564 appearing on GUI 16 for direct entry of a new pressure value.

As shown in FIG. 173, a manual OLE CPEP pressure adjustment screen 1566 appears on GUI 16 in response to the user selecting the CPEP numerical value in field 1540. The graphical numeric keypad 1564 of screen 1566 is then used to type in a new numerical value for the CPEP pressure. A typed value window 1568 overlies the region wherein the CPEP pressure value of field 1540 was shown previously. After the user types in the new CPEP pressure value, an enter button 1570 of graphical numeric keyboard 1564 is selected to save the new CPEP pressure value for subsequent use during future manual OLE therapy sessions. If the user decides not to enter a new inhale pressure value, then a cancel button 1572 of keyboard 1564 is selected and the previous CPEP pressure value is used for future manual OLE therapy sessions.

In a similar manner, a manual OLE CHFO pressure adjustment screen 1574, shown in FIG. 174, appears on the GUI 16 in response to the user selecting the CHFO numerical value in field 1542. The graphical numeric keypad 1564 of screen 1574 is then used to type in a new numerical value for the CHFO baseline pressure. In screen 1574, the typed value window 1568 overlies the region wherein the CHFO baseline pressure value of field 1542 was shown previously. After the user types in the new CHFO baseline pressure value, enter button 1570 of graphical numeric keyboard 1564 is selected to save the new CHFO baseline pressure value for subsequent use during future manual OLE therapy sessions. If the user decides not to enter a new CHFO baseline pressure value, then cancel button 1572 of keyboard 1564 is selected and the previous CHFO baseline pressure value is used for future manual OLE therapy sessions.

As mentioned above, CHFO frequency button 1548 is selectable to navigate to other screens to control the CHFO frequency of device 10 during the manual OLE therapy session. As shown in FIG. 175, a select CHFO frequency selection screen 1576 appears on GUI 16 in response to the user selecting the frequency button 1548 that appears beneath field 1542 in FIGS. 166-172. CHFO frequency selection screen has a menu 1578 of low, medium, and high frequency buttons 1547, 1548, 1551, respectively, that are selectable to establish the CHFO frequency at corresponding low, medium, and high frequency values. As noted above, the low CHFO frequency value is about 3 Hz, the medium CHFO frequency value is about 4 Hz, and the high CHFO frequency value is about 5 Hz. After selection of one of buttons 1547, 1548, 1551 on menu 1578, the previous screen is shown on GUI 16 once again, but with the selected one of buttons 1547, 1548, 1551 appearing beneath field 1542.

During manual OLE therapy, the user selects buttons 1530, 1532, 1534 as desired to command device 10 to deliver the CPEP, CHFO, and nebulizer portions of the manual OLE therapy. When the user decides to end the delivery of manual OLE therapy from device 10, stop button 1552 is selected on GUI 16. In response to selection of stop button 1552, a manual OLE therapy complete screen (not shown) appears on GUI 16. The manual OLE therapy complete screen is substantially the same as OLE therapy complete screen 1314 of FIG. 128 or advanced OLE therapy complete screen 1332 of FIG. 131, depending upon whether a patient monitor was wirelessly communicating with the circuitry 500 of device 10 for population of data in fields 884, 886 during the manual OLE therapy.

Referring now to FIG. 176, a settings screen 704', substantially the same as settings screen 704 of FIG. 22, appears on GUI 16 in response to selection of settings icon 700 of menu 692 on various OLE screens such as those of FIGS. 134, 140, 141, 158, 159, and 161. Portions of screen 704' of FIG. 176 that are the same as like portions of screen 704 of FIG. 22 are denoted with like reference numbers. Thus, for example, settings screen 704' includes window 706 that lists a variety of device information pertaining to the respiratory therapy apparatus 10. The information in window 706 is shown when about tab 710 is the selected one of tabs 710, 714, 716, 718.

Referring now FIG. 177, a data screen 1580 appears on GUI 16 in response to data button 716 of the settings screen 704 of FIG. 22 or setting screen 704' of FIG. 176 being selected. Data screen 1580 includes the following buttons: a therapy log review button 1582, a therapy log export button 1584, a device settings import button 1586, a device settings export button 1588, an error log review button 1590, an error log export button 1592, a firmware upgrade button 1594, and a health level seven (HL7) import button 1596. The functions of buttons 1582, 1584, 1586, 1588, 1590, 1592, 1594, 1596 are discussed below. In the illustrative example of screen 1580 of FIG. 177, all buttons except for the therapy log review button 1582 and the error log review button 1590 are grayed out because device 10, in its current state, is not communicating with any external device for purposes of importing or exporting data. Above buttons 1582, 1584 is a line of text stating "INSERT USB FOR DATA TRANSFER." Thus, to activate buttons 1584, 1586, 1588, 1592, 1596 for data transfer, or for firmware upgrade in the case of button 1594, a USB drive or USB cable, for example, are coupled to connector 306 of device 10.

Referring now to FIG. 178, a connect screen 1598 appears on GUI 16 in response to connect button 718 of settings screen 704 of FIG. 22 or setting screen 704' of FIG. 176 being selected. Illustrative screen 1598 of FIG. 178 has a Bluetooth tab 1600 and a WiFi tab 1602 with the Bluetooth tab 1600 being selected. A Bluetooth slider input 1604 appears on screen 1598 under Bluetooth tab 1600 and is used for turning Bluetooth functionality of the respiratory therapy apparatus 10 on and off. In the illustrative example of FIG. 178, slider input 1604 is in the off position.

Referring now to FIG. 179, a device screen 1606 appears on GUI 16 in response to device button 714 of settings screen 704 of FIG. 22 or setting screen 704' of FIG. 176 being selected. Device screen 1606 has a date-time tab 1608, a language tab 1610, and a controls tab 1612. When device tab 714 is selected, the date-time tab 1608 is the resulting default tab that appears on GUI 16 as being selected as shown. Screen 1606 includes a window 1614 including a list of selectable days and times with the currently selected line item on the list being highlighted as indicated by box 1616 in FIG. 179. The user is able to swipe up and down on the list in window 1614 to scroll to other days and times for viewing and selecting. In this regard, the line of text, "SCROLL TO SELECT DAY/TIME" is shown on screen 1606 above window 1614.

Still referring to FIG. 179, beneath window 1614 of screen 1606 is a time format slider input 1618, a date format slider input 1620, and a daylight savings time slider input 1622. Slider input 1618 is movable between a first position in which the time format is a 24 hours format and a second position in which the time format is a 12 hours format. In the illustrative example, slider input 1618 is in the second position. Slider input 1620 is movable between a first position in which the date format is DD/MM/YYYY (e.g., day/month/year) and a second position in which the date format is MM/DD/YYYY (e.g., month/day/year). In the illustrative example, slider input 1620 is in the first position. Slider input 1622 is movable between an off position and an on position in connection with daylight savings time. In the illustrative example, slider input 1622 is in the off position. A modify button 1624 is provided in the bottom right corner of screen 1606 and is selectable to modify time zone information for device 10. In the illustrative example, the text "TIME ZONE: UTC+8:00" appears on screen 1606 to the left of modify button 1624.

Referring now to FIG. 180, a language screen 1626 appears on GUI 16 in response to language tab 1610 of device screen 1606 of FIG. 179 being selected. Language screen 1626 has one or more language buttons 1628 for languages that are available for use in connection with the textual information displayed on the screens of FIGS. 18-274 of the respiratory therapy apparatus 10. In the illustrative example, only an English button 1628 appears on screen 1626. In other embodiments, additional buttons like button 1628 are provided on screen 1626 under tab 1610 for other languages such as French, German, Japanese, Chinese, Korean, Russian, and Spanish just to name a few. In embodiments having multiple language buttons 1628, the currently selected button 1628 is highlighted and the user has the option of selecting a different one of buttons 1628 to change the language of the textual information displayed on GUI 16 of device 10.

Referring now to FIG. 181, a controls screen 1630 appears on GUI 16 in response to selection of controls tab 1612 of screen 1606 of FIG. 179 or screen 1626 of FIG. 180. Controls screen 1630 includes a slider bar 1632 with a movable slider 1634 for adjusting screen brightness, a barcode detection slider input 1636 for turning barcode reading functionality of the respiratory therapy apparatus 10 on and off, and a clinical access slider input 1638 for turning clinical access functionality of the respiratory therapy apparatus 10 on and off. In the illustrative example, slider input 1636 is in the on position and slider input 1638 is in the off position. Thus, the bar code scanning functionality of apparatus 10 discussed above in connection with FIGS. 23-28 is enabled or activated (e.g., turned on) and the clinical access functionality of apparatus 10 is not activated. Because clinical access functionality is off in the FIG. 181 example, clinical access button 721 and lock icon 733 show the lock image in a locked state.

Still referring to screen 1630 of FIG. 181, a brightness indicia 1633 appears above slider bar 1632 and has an elongated, generally horizontal triangle to indicate a relative level of brightness between a low brightness level, indicated by a low brightness icon, shown to the left of the elongated triangle and a high brightness level, indicated by high brightness icon, shown to the right of the elongated triangle. In the illustrative example of FIG. 181, slider 1634 is closer to the low brightness icon than to the high brightness icon.

Screen 1630 of FIG. 181 also includes a pressure management window 1640 including an up arrow icon 1642 and a down arrow icon 1644 for setting a pressure ceiling (PC) value for the respiratory therapy apparatus 10. In the illustrative example, the pressure ceiling is set at 50 cmH$_2$O as shown to the left of arrow icons 1642, 1644. To the right of arrow icons 1642, 1644 is the text "*PC MUST BED≥HPP HIGHEST PROGRAMMED PRESSURE (HPP) 43 cmH$_2$O." That is, the highest programmed pressure that is set to occur during either the MIE therapy or the OLE therapy cannot exceed the pressure ceiling value. In some embodiments, selection of arrow icons 1642, 1644 of screen 1630 results in a 5 cmH$_2$O pressure increase or 5 cm H2O pressure decrease, respectively, of the pressure ceiling value. Thus, arrow icons 1642, 1644 are tapped multiple times to change the ceiling pressure by more than 5 cmH$_2$O. In other embodiments, arrow icons 1642, 1644 of screen 1630 operate as described above in connection with other similar up and down arrow icons for pressure adjustment. In some embodiments, 70 cmH$_2$O is the maximum pressure ceiling value that can be programmed for apparatus 10. Thus, when 70 cmH$_2$O is reached for the pressure ceiling value, the up arrow icon 1642 becomes grayed out and inactive while the down arrow icon 1644 remains active for decreasing the pressure ceiling value, if desired.

Referring now to FIG. 182, a modify date-time screen 1646 appears on GUI 16 in response to modify button 1624 of the device screen 1606 of FIG. 179 being selected. Modify date-time screen 1646 includes a window 1648 having a table or list of selectable times zones with the currently selected line item on the list being highlighted as indicated by box 1650 in FIG. 182. The user is able to swipe up and down on the list in window 1648 to scroll to other time zones for viewing and selecting. In this regard, the line of text, "SCROLL TO CHANGE TIME ZONE" is shown on screen 1646 above window 1648. Screen 1646 of FIG. 182 further includes a save button 1652 that is selected to save the time zone highlighted in table 1648 for use by device 10 in displaying date and time information on GUI 16 such as shown to the right of battery icon 735 in the header of the screens shown in FIGS. 18-274. A cancel button 1654 appears on screen 1646 to the right of the save button 1652 and is selected if the user decides not to change zone information such that the previous time zone information is used by apparatus 10 in displaying date and time information on GUI 16.

Referring now to FIG. 183, a confirm language screen 1656 appears on GUI 16 in response to selection of one of the language buttons 1628 of language screen 1626 of FIG. 180. Screen 1656 includes a window 1658 having a text box 1660 with the language selected on screen 1626 shown therein. Above text box 1660 in the illustrative example is the text "YOU HAVE SELECTED:" and beneath text box 1660 in the illustrative example is the text "AS THE LANGUAGE DEFAULT" on a first line followed by the text "PRESS 'SAVE' TO CONTINUE" on a second line. The word "ENGLISH" appears in box 1660 in the given example but if some other language (e.g., Spanish, German, French, Korean, etc.) had been selected on screen 1626, then box 1660 would reflect that alternative language selection. Screen 1656 of FIG. 183 further includes a save button 1662 that is selected to save the selected language shown in box 1660 for use by device 10 in displaying text information on GUI 16. A cancel button 1664 also appears on screen 1656 beneath the save button 1662 and is selected if the user decides not to change the language such that the previous language is used by apparatus 10 in displaying text information on GUI 16.

Referring now to FIG. 184, a first access advanced features screen 1666 appears on GUI 16 in response to an attempt to move the clinical access slider input 1638 of screen 1630 of FIG. 181 from the off position to the on position. First access advanced features screen 1666 includes a graphical numeric keypad 1668 for entering a key code to unlock access to the advanced features of device 10. A number entry box or field 1670 is provided at the top of keypad 1668 and the text "KEYCODE: TO UNLOCK SETTINGS" appears to the left of box 1670. To the left of keypad 1668 on screen 1666 is the text "ENTER CODE TO ACCESS ADVANCED FEATURES." Keypad 1668 also includes an enter button 1672 and a cancel button 1674 beneath the numeric keys of keypad 1668. As the user enters the keycode using keypad 1668, asterisks appear in field 1670 for each number entered. For example, as shown in FIG. 185, a second access advanced features screen 1676, substantially the same as FIG. 184, appears on GUI 16 after the user had entered a 4-digit keycode into field 1670 using keypad 1668. Thus, four asterisks appear in field 1670.

Still referring to screen 1676 of FIG. 185, if the user believes a mistake was made in entering the keycode, cancel button 1674 is selected on keypad 1668 to return the user back to screen 1666 of FIG. 184 so that another attempt can be made to enter the proper keycode into field 1670 using keypad 1668. If the user selects cancel button on screen 166 of FIG. 184, the user is returned back to screen 1630 of FIG. 181. If the user believes a valid keycode has been entered into field 1670 using keypad 1668, the user selects enter 1672 and, if the keycode entered into field 1670 is a valid keycode, then GUI 16 displays a clinical access on screen 1678 as shown, for example, in FIG. 186. Screen 1678 of FIG. 186 is substantially the same as screen 1630 of FIG. 181, except that the clinical access slider input is shown in the on position and the lock image of button 721 and icon 733 is shown in the unlocked position to indicate that the clinical access functionality of device 10 is unlocked.

Referring now to FIG. 187, an import/export/upgrade enabled screen 1680 appears on GUI 16 in response to an external device, such a memory stick, thumb drive, USB cable, and the like, being successfully connected to data port 306 of device 10. Screen 1680 of FIG. 187 is substantially similar to screen 1580 of FIG. 177 except that import buttons 1586, 1596, export buttons 1584, 1588, 1592, and upgrade button 1594 are active and no longer grayed out, thereby indicating that the respiratory therapy apparatus 10 is successfully communicating with the external device connected to port 306. As a result of the successful communication with the external device coupled to port 306, a memory stick icon 1681 is displayed in the header area of screen 1680 of FIG. 187 to the left of clinical access icon 733.

Referring now to FIG. 188, a loading screen 1682 appears on GUI 16 in response to selection of any of the export buttons 1584, 1588, 1592 on screen 1680 of FIG. 187. Loading screen 1682 includes a window 1684 having a text box 1686 with the text "LOADING" therein. Beneath box 1686 is the explanatory text, "MEMORY CHECKING. PLEASE WAIT . . . " During the appearance of screen 1682 on GUI 16, control circuitry 500 is checking to may sure that the external device connected to port 306 has sufficient space in memory to receive the data to be exported. The data to be exported corresponds to the particular one of buttons 1584, 1588, 1592 that was selected to begin the memory checking process (e.g., therapy log, device settings, or error log).

If the external device does not have sufficient space in memory to receive the therapy log, device settings, or error log data to be exported from device 10, then an insufficient memory screen 1688 appears on GUI 16 as shown in FIG. 189. Insufficient memory screen 1688 includes a window 1690 having a text box 1692 with the text "INSUFFICIENT MEMORY" therein. Beneath box 1686 is the explanatory text, "ACTION CANNOT BE PERFORMED DUE TO INADEQUATE FREE SPACE IN USB DRIVE. CHECK AVAILABLE SPACE AND TRY AGAIN. IF PROBLEM PERSISTS, CONTACT CUSTOMER SUPPORT." Window 1690 of screen 1688 of FIG. 189 also includes a return button 1694. Selection of button 1694 on screen 1688 returns the user back to screen 1680 of FIG. 187. If the external device connected to port 306 does have sufficient memory, then the respective therapy log, device settings, or error log data to be exported from device 10, as the case may be, is transmitted or exported to the external device as will be discussed in further detail below in connection with FIGS. 196-204.

Referring now to FIG. 190, a pressure ceiling confirm screen 1696 appears on GUI 16 in response to selection of the device settings import button 1586 on screen 1680 of FIG. 187 if the clinical access function of the respiratory therapy apparatus 10 is turned on or enabled and if the device settings data being imported includes a pressure ceiling value different than the one, if any, currently stored in control circuitry 500. Pressure ceiling confirm screen 1696 includes a window 1698 having a text box 1700 with the text "PRESSURE CEILING CHANGE" therein. Beneath box 1700 is the explanatory text, "PRESSURE CEILING WILL ALSO BE CHANGED TO THE IMPORTED VALUE. DO YOU WANT TO PROCEED WITH THE IMPORT?."

Window 1698 of screen 1696 of FIG. 190 further includes a proceed button 1702 and a cancel button 1704. Button 1702 is selected if the user wishes to proceed with import of device setting data from the external device coupled to port 306. Button 1704 is selected if the user decides not to import any device settings data from the external device. If cancel button 1704 is selected, the user is returned to screen 1680 of FIG. 187. If proceed button 1702 is selected, then the device settings data is imported from the external device to control circuitry 500 of device 10 via port 306 as will be discussed in further detail below in connection with FIGS. 206-208. If the clinical access function of apparatus 10 is turned off (i.e., disabled) when button 1586 is selected, then an access limited screen, similar to screens 1098, 1230, 1358 of FIGS. 90, 113, and 135, respectively, appears on GUI 16. Selection of the return button on the access limited screen appearing on GUI in response to selection of button 1586 results in the user being returned back to screen 1680 of FIG. 187.

Referring now to FIG. 191, a first error log review screen 1706 appears on GUI 16 in response to selection of error log review button 1590 of screen 1580 of FIG. 177 or screen 1680 of FIG. 187. First error log review screen 1706 has a list 1708 showing dates and times at which recent errors have occurred in the respiratory therapy apparatus 10. A scroll bar 1710 with a scroll slider 1712 is provided to the right of list 1708 on screen 1706 for use in scrolling to additional dates and times of logged errors, as desired. A back button 1714 is provided in the upper right corner of screen 1706. Selection of back button 1714 on screen 1706 returns the user back to screen 1580 of FIG. 177 or screen 1680 of FIG. 187 depending upon which screen the user was viewing originally when button 1590 was selected.

Referring now to FIG. 192, a second error log review screen 1716 appears on GUI 16 in response to selection of one of the error log dates and times from list 1708 of first error log review screen 1706 of FIG. 191. In the illustrative example, the third date and time of list 1708 ("FEB 10-2018 11:24") is selected on screen 1706 and so appears in bold on screen 1716. To the right of scroll bar 1710, an error code corresponding to the selected error log date and time appears on screen 1716. In the illustrative example, the text "ERROR CODE:" appears on screen 1716 with a series of "X's" provided to generically represent the text corresponding to the error that occurred at the selected date and time. Similar to screen 1706, selection of back button 1714 on screen 1716 returns the user back to screen 1580 of FIG. 177 or screen 1680 of FIG. 187 depending upon which screen the user was viewing originally when button 1590 was selected.

The following Table 1 lists examples of error message text that appears on GUI 16 in response to the indicated error conditions being detected. In other words, the message text is what appears on GUI 16 at the time the error occurs. Some or all of the message text shown in Table 1 also appears on screen 1716 when the corresponding date and time is selected on list 1708. Each set of message text is given a message ID in some embodiments and so Table 1 below also provides examples of message ID's. The message ID also appears on screen 1716 in some embodiments.

TABLE 1

| Message ID | Message Text |
| --- | --- |
| MSG_CAUTION_1 | Ventilation Fan failure detected |
| | Make sure the Ventilation Fan is not blocked. |
| | If problem persists, contact Customer Support. |
| | Refer Error Code 007: Ventilation Fan Failure in User Manual. |
| MSG_CAUTION_2 | Battery below 10% |
| | Device may turn off during use. Charge Battery immediately. |
| | If problem persists, contact Customer Support. |
| | Refer Error Code 011: Low Battery in User Manual. |

TABLE 1-continued

| Message ID | Message Text |
|---|---|
| MSG_CAUTION_3 | Foot Switch Malfunction detected<br>Ensure Foot Switch is connected properly before restarting the Therapy.<br>If problem persists, contact Customer Support.<br>Refer Error Code 012: Foot Switch failure in User Manual. |
| MSG_CAUTION_4 | Hardware Malfunction detected<br>Some features may be restricted due to the Malfunction.<br>If problem persists, contact Customer Support.<br>Refer Error Code 013: Manifold Malfunction in User Manual. |
| MSG_CAUTION_5 | Excessive Therapy Pressure detected.<br>Ensure correct Patient Circuit setup before restarting the Therapy.<br>If problem persists, contact Customer Support.<br>Refer Error Code 014: Excessive Therapy Pressure in User Manual. |
| MSG_CAUTION_6 | System Over-heating Detected<br>Let the device cool down for 5 minutes before restarting the Therapy.<br>If problem persists, contact Customer Support.<br>Refer Error Code 015: System Overheat in User Manual. |
| MSG_CAUTION_7 | System Over-heating Detected<br>Let the device cool down for 5 minutes before restarting the Therapy.<br>If problem persists, contact Customer Support.<br>Refer Error Code 016: System Overheat in User Manual. |
| MSG_CAUTION_8 | System Over-heating Detected<br>Let the device cool down for 5 minutes before restarting the Therapy.<br>If problem persists, contact Customer Support.<br>Refer Error Code 017: System Overheat in User Manual. |
| MSG_CAUTION_9 | System Over-heating Detected<br>Let the device cool down for 5 minutes before restarting the Therapy.<br>If problem persist, contact Customer Support.<br>Refer Error Code 018: System Overheat in User Manual. |
| MSG_CAUTION_10 | Battery Charging Failure detected<br>Remove and reinstall Battery before charging again.<br>If problem persists, contact Customer Support.<br>Refer Error Code 019: Battery Charging Failure in User Manual. |
| MSG_CAUTION_11 | Communication Module Failure detected<br>Some features may be restricted due to the Failure.<br>If problem persists, contact Customer Support.<br>Refer Error Code 020: Communication Module Failure in User Manual. |
| MSG_CAUTION_12 | Extended Inhale/Exhale beyond 10 seconds<br>Extended Inhale/Exhale durations could cause patient discomfort.<br>Exercise Caution during Manual Therapy.<br>Refer Error Code 021: Extended Inhale/Exhale in User Manual. |
| MSG_CAUTION_13 | Inadequate Therapy Pressure<br>Ensure correct Patient Circuit setup before restarting the Therapy.<br>If problem persists, contact Customer Support.<br>Refer Error Code 022: Inadequate Therapy Pressure in User Manual. |
| MSG_CAUTION_14 | Bio-Filter not detected<br>Ensure a valid Bio-Filter is connected before restarting the Therapy.<br>If problem persists, contact Customer Support.<br>Refer Error Code 023: Bio-Filter Check in User Manual. |
| MSG_CAUTION_15 | Excessive air leakage detected<br>Check for leakage in patient circuit before restarting the Therapy.<br>If problem persists, contact Customer Service.<br>Refer Error Code 024: Excessive Air Leak in User Manual. |
| MSG_CAUTION_16 | Multiple Bio-Filters detected<br>Remove any unused Bio-Filters present near the controller and try again.<br>If problem persists, contact Customer Support.<br>Refer Error Code 025: Bio-Filter Check in User Manual. |
| MSG_CAUTION_17 | Bio-Filter Over-Use detected<br>Install a new Bio-Filter before restarting the Therapy.<br>If problem persists, contact Customer Support.<br>Refer Error Code 026: Bio-Filter Check in User Manual. |

TABLE 1-continued

| Message ID | Message Text |
| --- | --- |
| MSG_CAUTION_18 | Device below Operational Temperature<br>Leave the device in a warmer surrounding for 5 minutes and retry.<br>If problem persists, contact Customer Support.<br>Refer Error Code 029: Low Temperature Warning in User Manual. |
| MSG_CAUTION_19 | RTC battery depleted<br>Timestamps on Therapy and Error Logs could be impacted.<br>Contact Customer Support for Battery Replacement.<br>Refer Error Code 030: Depleted RTC Battery in User Manual. |
| MSG_WARN_2 | Communication Failure detected<br>Please switch off the device and restart.<br>If problem persists, contact Customer Support.<br>Refer Error Code 002: Internal Communication Failure in User Manual. |
| MSG_WARN_3 | Communication Failure detected<br>Please switch off the device and restart.<br>If problem persists, contact Customer Support.<br>Refer Error Code 003: Internal Communication Failure in User Manual. |
| MSG_WARN_4 | Communication Failure detected<br>Please switch off the device and restart.<br>If problem persists, contact Customer Support.<br>Refer Error Code 004: Internal Communication Failure in User Manual. |
| MSG_WARN_5 | Sensor failure detected<br>Please switch off the device and restart.<br>If problem persists, contact Customer Support.<br>Refer Error Code 005: Sensor Failure in User Manual. |
| MSG_WARN_6 | Sensor failure detected<br>Please switch off the device and restart.<br>If problem persists, contact Customer Support.<br>Refer Error Code 006: Sensor Failure in User Manual. |
| MSG_WARN_7 | Error in Data Storage<br>Please switch off the device and restart.<br>If problem persists, contact Customer Support.<br>Refer Error Code 008: Internal Storage Failure in User Manual. |
| MSG_WARN_8 | Communication Failure detected<br>Please switch off the device and restart.<br>If problem persists, contact Customer Support.<br>Refer Error Code 009: Internal Communication Failure in User Manual. |
| MSG_WARN_9 | Nebulizer not functioning<br>Please Reboot device once before starting a new Therapy.<br>If problem persists, contact Customer Support.<br>Refer Error Code 010: Nebulizer Malfunction in User Manual. |
| MSG_WARN_10 | Calibration Incomplete<br>Calibration is not completely performed on this device.<br>If problem persists, contact Customer Support.<br>Refer Error Code 032: Incomplete Calibration in User Manual. |

Referring now to FIG. 193, a first therapy log review screen 1718 appears on GUI 16 in response to selection of therapy log review button 1582 of screen 1580 of FIG. 177 or screen 1680 of FIG. 187. First therapy log review screen 1718 has a list 1720 showing dates and times at which recent therapy sessions have occurred using the respiratory therapy apparatus 10. Scroll bar 1710 and scroll slider 1712 are provided to the right of list 1720 on screen 1706 for use in scrolling to additional dates and times of logged therapy sessions, as desired. Back button 1714 is also provided in the upper right corner of screen 1718. Selection of back button 1714 on screen 1718 returns the user back to screen 1580 of FIG. 177 or screen 1680 of FIG. 187 depending upon which screen the user was viewing originally when button 1582 was selected.

Referring now to FIG. 194, a second therapy log review screen 1722 appears on GUI 16 in response to selection of one of the therapy log dates and times from list 1720 of first therapy log review screen 1718 of FIG. 193. In the illustrative example, the third date and time of list 1720 ("JAN-10 2018 11:24") is selected on screen 1718 and so appears in bold on screen 1722. To the right of scroll bar 1710, data pertaining to the therapy session that occurred at the selected therapy log date and time appears on screen 1722. In the illustrative example, the following information is provided on screen 1722: therapy type (e.g., MIE or OLE), the date of the therapy (should match the date selected on list 1720), start time, finish time, and total stages (since OLE is the therapy type, otherwise, total cycles is provided for MIE therapy). Also in the illustrative example of FIG. 194, because OLE is the therapy type, the following information is also shown for CHFO: total duration, peak pressure, and mean pressure. Similar information is provided for CPEP and MIE.

Still referring to screen 1722 of FIG. 194, a second scroll bar 1724 having a second scroll slider 1726 is provided to the right of the therapy information shown on screen 1722 for use in scrolling to additional therapy information, as desired. For example, any of the therapy information and data shown on screens 828, 840, 1066, 1314, 1332 of FIGS. 37, 38, 79, 128, 131, respectively, is viewable on screen 1722 in some embodiments. Similar to screens 1706, 1716, 1718 of FIGS. 191-193, respectively, screen 1722 includes back button 1714 which is selectable to return the user back to screen 1580 of FIG. 177 or screen 1680 of FIG. 187 depending upon which screen the user was viewing originally when button 1582 was selected. An alternative second therapy log review screen 1722', similar to screen 1722 of FIG. 194, is shown in FIG. 195. Screen 1722' is basically the same as screen 1722 except that scroll slider 1712 is omitted on screen 1722' due to less than seven recent therapies being listed on the list 1720 of recent therapies.

Referring now to FIG. 196, a therapy log export in process screen 1728 appears on GUI 16 in response to selection of therapy log export button 1584 of screen 1680 of FIG. 187, but only after the respiratory therapy apparatus confirms that the external device connected to port 306 of apparatus 10 has sufficient memory to receive the therapy log data. Screen 1728 includes a window 1730 having a dynamic progress icon 1732 to indicate progress toward exporting the therapy log to the recipient device connected to port 306. In the illustrative example of FIG. 196, progress icon 1732 comprises a numerical percentage representing an amount toward export completion and a circle around the percentage having a portion of its periphery filled in by an amount that matches the numerical percentage. The text "THERAPY LOG:" appears on screen 1738 above icon 1732 to indicate to the user that it is the therapy log data that is in the process of being exported. A cancel button 1734 appears on screen 1728 beneath icon 1732 and is selectable by the user to stop the therapy log export process.

Referring now to FIG. 197, a therapy log export complete screen 1736 appears on GUI 16 after the therapy log data has been exported to the external device via port 306. Screen 1736 includes a window 1738 having the text "THERAPY LOG: EXPORT COMPLETE" therein. A return button 1740 appears in the upper right corner of window 1730 and is selectable to return the user back to screen 1680 of FIG. 187. If the user selects the cancel button 1734 on screen 1728 of FIG. 196 during the therapy log export process, or if some other event occurs that interrupts the therapy log export process, then a therapy log export interrupted screen 1742 appears on GUI 16 as shown in FIG. 198. Screen 1742 includes a window 1744 having the text "THERAPY LOG: EXPORT INTERRUPTED" therein and having return button 1740 in its upper right corner. Selection of button 1740 on screen 1742 of FIG. 198 returns the user back to screen 1680 of FIG. 187.

Referring now to FIG. 199, a device settings export in process screen 1746 appears on GUI 16 in response to selection of device settings export button 1588 of screen 1680 of FIG. 187, but only after the respiratory therapy apparatus confirms that the external device connected to port 306 of apparatus 10 has sufficient memory to receive the device settings data. Similar to screen 1728 of FIG. 196, screen 1746 of FIG. 199 includes a window 1748 having dynamic progress icon 1732 and having cancel button 1734. The description above of icon 1732 and button 1734 in connection with screen 1728 of FIG. 196 is equally applicable to screen 1746 of FIG. 199 and so does not need to be repeated. However, icon 1732 of screen 1746 relates to the progress toward exporting the device settings to the recipient device connected to port 306 rather than the therapy log. Also, the text "DEVICE SETTINGS:" appears on screen 1746 above icon 1732 to indicate to the user that it is the device settings data that is in the process of being exported.

Referring now to FIG. 200, a device settings export complete screen 1750 appears on GUI 16 after the device settings data has been exported to the external device via port 306. Screen 1750 includes a window 1752 having the text "DEVICE SETTINGS: EXPORT COMPLETE" therein. Screen 1750 also has return button 1740 in the upper right corner of window 1752 which is selectable to return the user back to screen 1680 of FIG. 187. If the user selects the cancel button 1734 on screen 1746 of FIG. 199 during the device settings export process, or if some other event occurs that interrupts the device settings export process, then a device settings export interrupted screen 1754 appears on GUI 16 as shown in FIG. 201. Screen 1754 includes a window 1756 having the text "DEVICE SETTINGS: EXPORT INTERRUPTED" therein and having return button 1740 which is selectable to return the user back to screen 1680 of FIG. 187.

Referring now to FIG. 202, an error log export in process screen 1758 appears on GUI 16 in response to selection of error log button 1592 of screen 1680 of FIG. 187, but only after the respiratory therapy apparatus confirms that the external device connected to port 306 of apparatus 10 has sufficient memory to receive the error log data. Similar to screen 1728 of FIG. 196 and screen 1746 of FIG. 199, screen 1758 of FIG. 202 includes a window 1760 having dynamic progress icon 1732 and having cancel button 1734. The description above of icon 1732 and button 1734 in connection with screen 1728 of FIG. 196 is equally applicable to screen 1758 of FIG. 202 and so does not need to be repeated. However, icon 1732 of screen 1758 relates to the progress toward exporting the error log to the recipient device connected to port 306 rather than the therapy log. Also, the text "ERROR LOG:" appears on screen 1758 above icon 1732 to indicate to the user that it is the error log data that is in the process of being exported.

Referring now to FIG. 203, an error log export complete screen 1762 appears on GUI 16 after the error log data has been exported to the external device via port 306. Screen 1762 includes a window 1764 having the text "ERROR LOG: EXPORT COMPLETE" therein. Screen 1762 also has return button 1740 in the upper right corner of window 1764 which is selectable to return the user back to screen 1680 of FIG. 187. If the user selects the cancel button 1734 on screen 1758 of FIG. 202 during the error log export process, or if some other event occurs that interrupts the error log export process, then an error log export interrupted screen 1766 appears on GUI 16 as shown in FIG. 204. Screen 1766 includes a window 1768 having the text "ERROR LOG: EXPORT INTERRUPTED" therein and having return button 1740 which is selectable to return the user back to screen 1680 of FIG. 187.

FIG. 205 is the same as FIG. 190 which was discussed above in connection with selection of device settings import button 1586 of FIG. 187. Thus, the same reference numbers are used in FIG. 205 as were used in FIG. 190 and the description is not repeated. If cancel button 1704 of screen 1696 of FIG. 205 is selected, the user is returned back to screen 1680 of FIG. 187. If proceed button 1702 of screen 1696 of FIG. 205 is selected, then loading screen 1682 of FIG. 188 appears on GUI 16 while circuitry 500 is accessing the device settings data file to be imported.

Referring now to FIG. 206, a device settings import in process screen 1770 appears on GUI 16 in response to selection of device settings import button 1586 of screen 1680 of FIG. 187, but only after the respiratory therapy apparatus 10 confirms that the circuitry 500 of apparatus 10 has sufficient memory to receive the device settings data. Screen 1770 includes a window 1772 having a dynamic progress icon 1774 to indicate progress toward importing the device settings to circuitry 500 from the device connected to port 306. In the illustrative example of FIG. 206, progress icon 1774 comprises a numerical percentage representing an amount toward import completion and a circle around the percentage having a portion of its periphery filled in by an amount that matches the numerical percentage. Thus, icon 1774 relating to import of data to apparatus 10 looks the same as icon 1732 relating to export of data from apparatus 10. The text "DEVICE SETTINGS:" appears on screen 1770 above icon 1774 to indicate to the user that it is the device settings data that is in the process of being imported. A cancel button 1776 appears on screen 1770 beneath icon 1774 and is selectable by the user to stop the device settings import process.

Referring now to FIG. 207, a device settings import complete screen 1778 appears on GUI 16 after the device settings data has been imported to the control circuitry 500 of apparatus 10 via port 306. Screen 1778 includes a window 1780 having the text "DEVICE SETTINGS: IMPORT COMPLETE" and "DEVICE RESTART IN 5 SECONDS" therein. Thus, after new device settings data is successfully imported, apparatus 10 automatically restarts and operates according to the new device settings. If the user selects the cancel button 1776 on screen 1770 of FIG. 206 during the device settings import process, or if some other event occurs that interrupts the device settings import process, then a device settings import interrupted screen 1782 appears on GUI 16 as shown in FIG. 208. Screen 1782 includes a window 1784 having the text "DEVICE SETTINGS: IMPORT INTERRUPTED" therein and having return button 1740 in its upper right corner. Selection of button 1740 on screen 1782 of FIG. 208 returns the user back to screen 1680 of FIG. 187.

Referring now to FIG. 209, a connect AC power screen 1786 appears on GUI 16 in response to selection of the upgrade button 1594 of screen 1680 of FIG. 187 if AC power is not already connected to the respiratory therapy apparatus 10. Thus, in the illustrative embodiment, apparatus 10 is required to be plugged into AC power before new firmware can be downloaded to control circuitry 500 of device 10 from an external device coupled to port 218 as described above. Screen 1786 includes a window 1788 having a text box 1790 that includes the text "CONNECT AC POWER." Beneath box 1790, window 1788 of screen 1786 includes the text "CONNECT AC POWER: CONSISTENT POWER IS REQUIRED TO ENSURE PROPER SOFTWARE INSTALLATION. THIS MESSAGE WILL APPEAR WHEN AC POWER IS NOT CONNECTED." Window 1788 of screen 1786 also has button 1740 which is selectable to return the user back to screen 1680 of FIG. 187.

Referring now to FIG. 210, a firmware download in process screen 1792 that appears on the GUI after the upgrade button 1594 of FIG. 187 has been selected and the circuitry 500 of respiratory therapy apparatus 10 confirms that it has been connected to AC power. Similar to screen 1770 of FIG. 206, screen 1792 of FIG. 210 includes a window 1794 having dynamic progress icon 1774 and having cancel button 1776. The description above of icon 1774 and button 1776 in connection with screen 1770 of FIG. 206 is equally applicable to screen 1792 of FIG. 210 and so does not need to be repeated. However, icon 1774 of screen 1792 relates to the progress toward downloading the new firmware to circuitry 500 of apparatus 10 from the external device connected to port 218 rather than importing device settings to circuitry 500 of apparatus 10 from the external device connected to port 306. Also, the text "FIRMWARE:" and "DOWNLOADING" appears on screen 1792 above icon 1774 to indicate to the user that it is the new firmware that is in the process of being downloaded or imported into apparatus 10.

Referring now to FIG. 211, a firmware download complete screen 1796 appears on GUI 16 after the new firmware has been downloaded to the control circuitry 500 of apparatus 10 via port 218. Screen 1796 includes a window 1798 having the text "FIRMWARE: DOWNLOAD COMPLETE" and "DEVICE RESTART IN 5 SECONDS" therein. Thus, after the new firmware is successfully downloaded, apparatus 10 automatically restarts and operates according to the new firmware. If the user selects the cancel button 1776 on screen 1792 of FIG. 210 during the firmware download process, or if some other event occurs that interrupts the firmware download process, then a firmware download interrupted screen 1800 appears on GUI 16 as shown in FIG. 212. Screen 1800 includes a window 1802 having the text "FIRMWARE: DOWNLOAD INTERRUPTED" therein and having return button 1740 in its upper right corner. Selection of button 1740 on screen 1800 of FIG. 212 returns the user back to screen 1680 of FIG. 187.

Referring now to FIG. 213, a firmware upgrade file present screen 1804 appears on GUI 16 in response to a thumb drive or other external device with a valid firmware upgrade file stored in memory being connected to USB port 218 of the display control board (DCB) 350 of circuitry 500 of the respiratory therapy apparatus 10. Screen 1804 is similar to screen 1580 of FIG. 177 and so like reference numbers are used to denote like portions. However, on screen 1804 of FIG. 213, buttons 1584, 1588, 1592, 1594 are no longer grayed out but are shown as active. The memory stick icon 1681 also appears in the header of screen 1804. Thus, not only can button 1594 be used to initiate the firmware download process on screen 1804, but buttons 1584, 1588, 1592 on screen 1804 can be selected to initiate the export process for the therapy log, device settings, and error log, respectively. The exported therapy log or error log or device settings under this scenario is transmitted from circuitry 500 to the external device via port 218.

Referring now to FIG. 214, an HL7 file present screen 1806 appears on the GUI 16 in response to a thumb drive or similar external device with a valid HL7 file stored in memory being connected to main control board (MCB) USB 306 port of the respiratory therapy apparatus 10. Screen 1806 is similar to screen 1580 of FIG. 177 and so like reference numbers are used to denote like portions. However, on screen 1806 of FIG. 214, buttons 1584, 1588, 1592, 1596 are no longer grayed out but are shown as active. The memory stick icon 1681 also appears in the header of screen 1806. Thus, button 1596 is selectable on screen 1806 to initiate an HL7 file import process and buttons 1584, 1588, 1592 are selectable on screen 1806 to initiate the export process for the therapy log, device settings, and error log, respectively. The exported therapy log or error log or device settings under this scenario is transmitted from circuitry 500 to the external device via port 306.

Referring now to FIG. 215, a device settings file present screen 1808 appears on the GUI 16 in response to a thumb drive or other external device with a valid device settings file stored in memory being connected to the MCB USB port 306 of the respiratory therapy apparatus 10. Screen 1808 is similar to screen 1580 of FIG. 177 and so like reference numbers are used to denote like portions. However, on screen 1808 of FIG. 215, buttons 1584, 1586, 1588, 1592 are no longer grayed out but are shown as active. The memory stick icon 1681 also appears in the header of screen 1808. Thus, button 1586 is selectable on screen 1808 to initiate the device settings import process and buttons 1584, 1588, 1592 are selectable on screen 1808 to initiate the export process for the therapy log, device settings, and error log, respectively. The exported therapy log or error log or device settings under this scenario is transmitted from circuitry 500 to the external device via port 306.

Referring now to FIG. 216, a firmware upgrade status screen 1810 appears on GUI 16 in response to the conclusion of the restart operation of the respiratory therapy apparatus 10 that automatically occurs after the firmware upgrade operation. Firmware upgrade status screen 1810 includes a window 1812 having a text box 1814 with the text "FIRMWARE UPGRADE" therein. Beneath text box 1814 on screen 1810 is a list of successful and failed upgrades for Bluetooth, near field communication (NFC), MCB, and DCB circuitry of the respiratory therapy apparatus. In the illustrative example of FIG. 216, the firmware upgrades for Bluetooth, NFC, and MCB circuitry are indicated as successful and the firmware upgrade for the DCB circuitry is indicated as failed. Screen 1810 further includes a return button 1816 the selection of which returns the user to screen 670 of FIG. 18.

Referring now to FIG. 217, an HL7 import in process screen 1818 appears on GUI 16 after HL7 import button 1596 of HL7 file present screen 1806 of FIG. 214 is selected to begin the HL7 import process, but only after the respiratory therapy apparatus 10 confirms that the circuitry 500 of apparatus 10 has sufficient memory to receive the HL7 data. Similar to screen 1770 of FIG. 206, screen 1818 of FIG. 217 includes a window 1820 having dynamic progress icon 1774 and having cancel button 1776. The description above of icon 1774 and button 1776 in connection with screen 1770 of FIG. 206 is equally applicable to screen 1818 of FIG. 217 and so does not need to be repeated. However, icon 1774 of screen 1818 relates to the progress toward importing HL7 data to circuitry 500 of apparatus 10 from the external device connected to port 306 rather than importing device settings. Also, the text "HL7:" and "IMPORTING" appears on screen 1818 above icon 1774 to indicate to the user that it is HL7 data that is in the process of being downloaded or imported into apparatus 10.

Referring now to FIG. 218, an HL7 import complete screen 1822 appears on GUI 16 after the HL7 data has been imported to the control circuitry 500 of apparatus 10 via port 306. Screen 1822 includes a window 1824 having the text "HL7: IMPORT COMPLETE" therein. Window 1824 also includes a return button 1826 which is selectable to return the user to screen 1806 of FIG. 214. If the user selects the cancel button 1776 on screen 1818 of FIG. 217 during the HL7 data import process, or if some other event occurs that interrupts the HL7 data import process, then an HL7 import interrupted screen 1828 appears on GUI 16 as shown in FIG. 219. Screen 1828 includes a window 1830 having the text "HL7: IMPORT INTERRUPTED" therein and having return button 1826 in its upper right corner. Selection of button 1826 on screen 1828 of FIG. 219 returns the user back to screen 1806 of FIG. 214.

FIG. 220 is the same as FIG. 178 which was discussed above in connection with selection of connect button 718 of settings screen 704 of FIG. 22 or settings screen 704' of FIG. 176 being selected. Thus, the same reference numbers are used in FIG. 220 as were used in FIG. 178 and the description is not repeated. If slider input 1604 of Bluetooth tab 1600 is moved from the off position shown in FIG. 220 to the on position when the clinical access functionality of device 10 is turned off, then a first Bluetooth on screen 1832 appears on GUI 16 as shown in FIG. 221, but only if the Bluetooth functionality of the respiratory therapy apparatus 10 is turned on. First Bluetooth on screen 1832 shows a list of devices that are paired in Bluetooth communication with the respiratory therapy apparatus 10. In the illustrative example of screen 1832 of FIG. 221, the text "SPO$_2$ PAIRED DEVICE: UNKNOWN. MAC ID: - -" and "BARCODE PAIRED DEVICE: DATALOGIC SCANNER. MAC ID: 007BE1EED99." Thus, in the depicted example of FIG. 221, there is no external patient monitor communicating wirelessly via Bluetooth with device 10 but there is a bar code scanner communicating wirelessly via Bluetooth with device 10.

If slider input 1604 of Bluetooth tab 1600 is moved from the off position shown in FIG. 220 to the on position when the clinical access functionality of device 10 is turned on, then a second Bluetooth on screen 1834 appears on GUI 16 as shown in FIG. 222, but only if the Bluetooth functionality of the respiratory therapy apparatus 10 is also turned on. Second Bluetooth on screen 1834 includes an SPO$_2$ tab 1836 and a barcode tab 1838 with the SPO$_2$ tab 1836 being the default selected tab. A table 1840 appears on screen 1834 of FIG. 222 under tab 1836 with a table heading of "AVAILABLE DEVICES" and column headings of "DEVICE NAME," "MAC ID," and "PAIRED." In FIG. 222, table 1840 is blank because no patient monitor devices for measuring SPO$_2$ are paired yet with circuitry 500 of apparatus 10. A scan button 1842 appears on screen 1834 to the right of slider input 1604 and a manual setup button 1844 appears beneath table 1840. The text "PAIRED DEVICE: UNKNOWN" and MAC ID: - -" appears to the left of manual setup button 1844.

Referring now to FIG. 223, a Bluetooth scan screen 1846 appears on GUI 16 in response to scan button 1842 of the second Bluetooth on screen 1834 of FIG. 222 being selected. Bluetooth scan screen 1846 of FIG. 223 is substantially similar to screen 1834 of FIG. 222 and so like reference numbers are used in FIG. 223 to denote like portions without repeating the descriptions. However, screen 1846 of FIG. 223 includes a progress icon 1848 that shows the progress of the Bluetooth scanning process. In the illustrative example of FIG. 223, progress icon 1848 is a circular icon that has its circumference filled in as the scanning process progresses. While the scanning process takes place, buttons 1842, 1844 on screen 1846 become grayed out to indicate that buttons 1842, 1844 are disabled.

Referring now to FIG. 224, a scan results screen 1850 appears on GUI 16 after the Bluetooth scanning process is complete. In table 1840, scan results screen 1850 shows a list of available SpO2 devices that are in Bluetooth communication range of the respiratory therapy apparatus 10 and that were discovered for possible Bluetooth pairing during the scanning process. Table 1840 has device names and MAC ID's for five external devices as shown by the text in the corresponding DEVICE NAME and MAC ID columns of table 1840. However, the PAIRED column of table 1840 is still blank because none of the five discovered external devices have yet been paired with apparatus 10.

Referring now to FIG. 225, a device selected screen 1852 appears on GUI 16 after one of the devices on the list of table 1840 has been selected by the user. In the illustrative example of FIG. 225, the fourth listed device on table 1840 has been selected and becomes highlighted as indicated by box 1854. In response to selection of one of the patient monitor devices on table 1840 as shown on screen 1852 of FIG. 225, a pair new device screen 1856 appears on GUI 16 as shown in FIG. 226. Screen 1856 includes a window 1858 having a text box 1860 with the text "PAIR NEW DEVICE" therein. Beneath box 1860 is the question, "DO YOU WANT TO PAIR CONTROLLER WITH THE SELECTED SPO$_2$ SENSOR?" The CONTROLLER referenced in the question of window 1858 refers to the control circuitry 500 of device 10. Window 1858 of screen 1856 of FIG. 226 further includes a proceed button 1862 and a cancel button 1864. Button 1862 is selected if the user wishes to proceed with Bluetooth pairing between the selected external device and circuitry 500 of device 10. Button 1864 is selected if the user decides not to pair the selected external device with circuitry 500. If cancel button 1864 is selected, the user is returned to screen 1850 of FIG. 224.

Referring now to FIG. 227, a device paired screen 1866 appears on the GUI 16 in response to proceed button 1862 of the pair new device screen 1856 of FIG. 226 being selected. Device paired screen 1866 is substantially the same as screens 1850, 1852 of FIGS. 224 and 225, respectively, but with a couple differences. One difference is that a check mark appears in the PAIRED column of table 1840 in the row corresponding to the device that was selected for Bluetooth pairing and the row of table 1840 with the check mark is no longer highlighted. Also, the Bluetooth icon 731 appears in the header of screen 1866 to indicate that Bluetooth communication has been established between circuitry 500 of apparatus 10 and the selected external device. Beneath table 1840 and to the left of manual setup button 1844, the selected device name appears next to the text "PAIRED DEVICE:" and the MAC ID of the selected device appears next to the text "MAC ID." As is apparent in FIG. 227, the device name and MAC ID for the selected device shown under table 1840 matches the selected device information in the row of table 1840 having the check mark in the PAIRED column. In some embodiments, the check mark in table 1840 of screen 1866 is color coded green.

If Bluetooth communication with the selected device becomes lost such as if the selected device is moved out of communication range with apparatus 10 or if the battery power of the selected device becomes too low, then the user is able to select scan button 1842 on screen 1866 of FIG. 227 to initiate a new scan for devices that are available for Bluetooth pairing with apparatus 10. After scan button 1842 is selected on screen 1866 to initiate a rescanning process, then screen 1846 of FIG. 223 once again appears on GUI 16 with table 1840 being blanked out. After the Bluetooth rescanning process is completed, a Bluetooth rescanning complete screen 1868 appears on GUI 16 as shown, for example, in FIG. 228. Screen 1868 of FIG. 228 is substantially the same as screen 1850 of FIG. 224 and so like reference numbers are used to denote like portions without repeating the descriptions. However, table 1840 of screen 1868 of FIG. 228 only lists three available external devices for possible Bluetooth pairing with apparatus 10.

Referring now to FIG. 229, a manual setup screen 1870 appears on GUI 16 in response to manual setup button of any of the screens 1850, 1852, 1866, 1868 of FIG. 224, 225, 227 or 228, respectively, being selected. Manual set up screen 1870 includes a graphical keyboard 1872 that is used to enter a media access control (MAC) address into a MAC address field 1874. The entered MAC address should correspond to an external device that is desired for Bluetooth pairing with the respiratory therapy apparatus 10 and that is in communication range with the respiratory therapy apparatus 10. After the user types the MAC address into field 1874, an enter button 1876 of graphical keyboard 1872 is selected to pair the associated external device with apparatus 10. If the entered MAC address corresponds to one of the devices listed in table 1840, then a check mark is added to the PAIRED column for the particular external device. If the user decides not to enter a MAC address in field 1874 for Bluetooth pairing, then cancel button 1878 of keyboard 1872 is selected and the user is returned to the screen on which the manual setup button 1844 was originally selected.

Referring now to FIG. 230, a MAC address entered screen 1880 appears on GUI 16 if the enter button 1876 of screen 1870 of FIG. 229 is selected and the MAC address entered in field 1874 does not match any of the devices listed in table 1840 or if no devices are listed table 1840 to begin with. Under this scenario, the MAC ID that was entered in the MAC address field 1874 of FIG. 229 is shown beneath table 1840 of FIG. 230 next to the text "MAC ID:" and the word "UNKNOWN" is shown next to the text "PAIRED DEVICE:." The paired device name is updated on screen 1880 when the external device corresponding to the MAC ID is discovered by circuitry 500 of apparatus 10 during a future Bluetooth scanning process. The discovered device name, MAC ID, and check mark is also added to table 1840 in the corresponding columns after the designated external device is discovered.

Referring now to FIG. 231, a third Bluetooth on screen 1882 appears on GUI 16 in response to barcode tab 1838 of the second Bluetooth on screen 1834 of FIG. 222 being selected. Thus, the illustrative third Bluetooth on screen 1882 has progress icon 1848 shown to indicate the progress of an automatic scan for barcode scanners that occurs in response to selection of the barcode tab 1838. Bluetooth scan screen 1882 of FIG. 231 is substantially similar to screen 1846 of FIG. 223 and so like reference numbers are used in FIG. 231 to denote like portions without repeating the descriptions. However, the prime character "'" is used for table 1840', scan button 1842', and manual setup button 1844' since these relate to Bluetooth pairing with barcode scanners and not patient monitors. While the scanning process takes place, buttons 1842', 1844' on screen 1882 become grayed out to indicate that buttons 1842', 1844' are disabled.

Referring now to FIG. 232, a barcode scan results screen 1884 appears on GUI 16 after the Bluetooth scanning process is complete. In table 1840', scan results screen 1884 shows a list of available barcode scanners that are in Bluetooth communication range of the respiratory therapy apparatus 10 and that were discovered for possible Bluetooth pairing during the scanning process. Table 1840' has device names and MAC ID's for three barcode scanners as shown by the text in the corresponding DEVICE NAME and MAC ID columns of table 1840'. However, the PAIRED column of table 1840' is still blank because none of the three discovered barcode scanners have yet been paired with apparatus 10.

Referring now to FIG. 233, a device selected screen 1886 appears on GUI 16 after one of the barcode scanner devices on the list of table 1840' has been selected by the user. In the illustrative example of FIG. 233, the second listed device on table 1840' has been selected and becomes highlighted as indicated by box 1854'. In response to selection of one of the patient monitor devices on table 1840' as shown on screen 1886 of FIG. 233, a pair new device screen, substantially the same as screen 1856 of FIG. 226, appears on GUI 16. The pair new device screen for barcode scanner pairing includes a window having a text box with the text "PAIR NEW DEVICE" therein just like window 1858 and text box 1860 of FIG. 226. Beneath the text box, however, is the question, "DO YOU WANT TO PAIR CONTROLLER WITH THE SELECTED BARCODE SCANNER?" Proceed and cancel buttons just like buttons 1862, 1864, respectively, of FIG. 226 are provided on the pair new device screen for barcode scanners. However, if the cancel button is selected on the pair new device screen for barcode scanners, the user is returned to screen 1884 of FIG. 232.

Referring now to FIG. 234, a device paired screen 1888 appears on the GUI 16 in response to the proceed button of the pair new device screen for barcode scanners being selected. Device paired screen 1888 is substantially the same as screens 1884, 1886 of FIGS. 232 and 234, respectively, but with a couple differences. One difference is that a check mark appears in the PAIRED column of table 1840' in the row corresponding to the barcode scanner device that was selected for Bluetooth pairing and the row of table 1840' with the check mark is no longer highlighted. Also, the Bluetooth icon 731 appears in the header of screen 1888 to indicate that Bluetooth communication has been established between circuitry 500 of apparatus 10 and the selected barcode scanner. Beneath table 1840' and to the left of manual setup button 1844', the selected device name appears next to the text "PAIRED DEVICE:" and the MAC ID of the selected device appears next to the text "MAC ID." As is apparent in FIG. 234, the device name and MAC ID for the selected device shown under table 1840' matches the selected device information in the row of table 1840' having the check mark in the PAIRED column. In some embodiments, the check mark in table 1840' of screen 1866 is color coded green.

If Bluetooth communication with the selected barcode scanner becomes lost such as if the selected barcode scanner is moved out of communication range with apparatus 10 or if the battery power of the selected barcode scanner becomes too low, then the user is able to select scan button 1842' on screen 1888 of FIG. 234 to initiate a new scan for barcode scanner devices that are available for Bluetooth pairing with apparatus 10. After scan button 1842' is selected on screen 1888 to initiate a rescanning process, then screen 1882 of FIG. 231 once again appears on GUI 16 with table 1840' being blanked out. After the Bluetooth rescanning process is completed, a Bluetooth rescanning complete screen 1890 appears on GUI 16 as shown, for example, in FIG. 235.

Screen 1890 of FIG. 235 is substantially the same as screen 1882 of FIG. 231 and so like reference numbers are used to denote like portions without repeating the descriptions. If manual setup button 1844' is selected on any of screens 1884, 1886, 1888, 1890 of FIGS. 232, 233, 234 and 235, respectively, then screen 1870 of FIG. 229 appears on GUI 16 and is used in the same way as described above to manually enter a MAC ID (aka a MAC address) for the barcode scanner to be paired with apparatus 10. After enter button 1876 of screen 1870 is selected a screen substantially the same as screen 1880 appears on GUI 16 but with the information beneath table 1840' corresponding to the manually entered barcode scanner MAC ID.

Referring now to FIG. 236, a first WiFi on screen 1892 appears on GUI 16 in response to the selection of WiFi tab 1602 on screen 1598 of FIG. 220, for example, and in response to a WiFi slider 1894 of screen 1892 being moved from an off position to an on position. First WiFi on screen 1892 has a scan button 1896 that becomes active in response to movement of WiFi slider 1894 to the on position. A WiFi icon 1898 also appears in the header area of screen 1892 to the left of unlock icon 733 in response to slider 1894 being moved to the on position. Screen 1892 includes an available tab 1900 and a settings tab 1902 with the available tab 1900 being the default selected tab. A table 1904 appears on screen 1892 of FIG. 236 under tab 1900 with column headings of "ACCESS POINTS," "SECURITY," and "SIGNAL." In FIG. 236, table 1904 is blank because no WiFi access points have been discovered yet by circuitry 500 of apparatus 10. Scan button 1896 is located on screen 1892 beneath table 1904 in the illustrative example.

Referring now to FIG. 237, a WiFi scan screen 1906 appears on GUI 16 in response to scan button 1896 of the screen 1892 of FIG. 236 being selected. WiFi scan screen 1906 of FIG. 237 is substantially similar to screen 1892 of FIG. 236 and so like reference numbers are used in FIG. 237 to denote like portions without repeating the descriptions. However, screen 1906 of FIG. 237 includes a progress icon 1908 that shows the progress of the scanning process to discover WiFi access points. In the illustrative example of FIG. 237, progress icon 1908 is a circular icon that has its circumference filled in as the scanning process progresses. While the scanning process takes place, button 1896 on screen 1906 become grayed out to indicate that button 1896 is disabled.

Referring now to FIG. 238, a scan results screen 1910 appears on GUI 16 after the WiFi scanning process is complete. In table 1904, scan results screen 1904 shows a list of available wireless access points (WAP's) that are in WiFi communication range of the respiratory therapy apparatus 10. Table 1840 has WAP names for five different WAP's in the ACCESS POINTS column and security information pertaining to each WAP in the SECURITY column. Table 1904 also has WiFi signal strength icons for each of the WAP's in the SIGNAL column.

Referring now to FIG. 239, a WAP selected screen 1912 appears on GUI 16 after one of the WAP's on the list of table 1904 has been selected by the user. In the illustrative example of FIG. 239, the third listed WAP on table 1904 has been selected and becomes highlighted as indicated by box 1914. The selected WAP indicated by box 1914 is the WAP with the highest signal strength in the illustrative example. In response to selection of one of the WAP's on table 1904 as shown on screen 1912 of FIG. 239, an enterprise setup screen 1916 appears on GUI 16 as shown in FIG. 240. Screen 1916 includes a window 1918 including the following fields for entry of enterprise setup information regarding the selected WAP: a user ID field 1920, a password field 1922, an extensible authentication protocol (EAP) configuration field 1924, an inner method field 1926, and an opportunistic key caching (OKC) field 1928. Each of fields 1924, 1926, 1928 includes a menu arrow 1930 to indicate that selection of the respective field results in a corresponding menu being displayed with menu items that are selectable by the user.

Still referring to FIG. 240, the menu items of the menu that appears on GUI 16 in response to selection of menu arrow 1930 of field 1924 include the following four items: EAP-transport layer security (EAP-TLS), EAP-tunneled transport layer security (EAP-TTLS), EAP-protected extensible authentication protocol (EAP-PEAP), and EAP-flexible authentication via secure tunneling (EAP-FAST). In the illustrative example of screen 1916 of FIG. 240, EAP-PEAP is shown in field 1924. Depending upon the selection made in field 1924, the menu items of the menu that appears on GUI 16 in response to selection of menu arrow 1930 of field 1926 include, at maximum, the following two items: Microsoft Challenge-Handshake Authentication Protocol (MSCHAP) and MSCHAP version 2 (MSCHAP V2). If EAP-TLS is selected for field 1924, then field 1926 becomes disabled and neither of MSCHAP and MSCHAP V2 is available for selection in connection with field 1926. If EAP-TTLS or EAP-PEAP is selected for field 1924, then both MSCHAP and MSCHAP V2 are available for selection in connection with field 1926. If EAP-FAST is selected for field 1924, then only MSCHAP V2 is available for selection in connection with field 1926.

In response to selection of user ID field 1920 on screen 1916 of FIG. 240, an enter user ID screen 1932 appears on GUI 16 as shown in FIG. 241. Screen 1932 of FIG. 241 includes a graphical keyboard 1934 that is usable to enter a user ID for connection to a WiFi network associated with the WAP selected on the WAP selected screen 1912 of FIG. 239. In the illustrative example, the text "STANLEY74" has been entered into a text box 1936 that is provided beneath the heading "ENTER USER ID:" of graphical keyboard 1934. After the user ID has been typed into box 1936, an enter button 1938 of keyboard 1934 is selected by the user to return the user back to screen 1916 of FIG. 240 but with the user ID entered on screen 1932 appearing in field 1920. If the user does not wish to enter a user ID, then a cancel button 1940 is selected by the user which results in the user being returned back to screen 1916 of FIG. 240 with the user ID field 1920 remaining blank.

In response to selection of password field 1922 on screen 1916 of FIG. 240, an enter password screen 1942 appears on GUI 16 as shown in FIG. 242. Screen 1942 has a graphical keyboard 1934' that is usable to enter a password for connection to the WiFi network associated with the WAP selected on the WAP selected screen of FIG. 239. Keyboard 1934' of FIG. 242 is substantially similar to keyboard 1934 of FIG. 241 except that the text "ENTER PASSWORD:" appears above box 1936 and that during entry of the password using the keys of keyboard 1934', asterisks "*" appear within box 1936 rather than the characters that are typed. In some embodiments, the most recently typed character appears in box 1936 for a threshold period of time, such as 1 to 10 seconds, for example, before converting to an asterisk so that the user has time to verify that the desired character was, in fact, typed by the user.

After the password has been typed into box 1936 of FIG. 242, enter button 1938 of keyboard 1934' is selected by the user to return the user back to screen 1916 of FIG. 240 but with asterisks generated while typing the password entered on screen 1942 appearing in field 1922. If the user does not wish to enter a password, then cancel button 1940 is selected by the user which results in the user being returned back to screen 1916 of FIG. 240 with the user password field 1922 remaining blank. Window 1918 of screen 1916 of FIG. 240 further includes a proceed button 1944 and a cancel button 1946. Button 1944 is selected if the user wishes to proceed with connecting circuitry 500 of device 10 with the selected WAP for WiFi communication with the network associated with the selected WAP. Button 1946 is selected if the user decides not to establish a WiFi communication connection between the selected WAP and circuitry 500. If cancel button 1946 is selected, the user is returned to screen 1910 of FIG. 238.

Referring now to FIG. 243, an authentication in progress screen 1948 appears on GUI 16 in response to selection of proceed button 1944 on the enterprise setup screen 1916 of FIG. 240 after the user has entered valid user ID and password information in the user ID and password fields 1920, 1922 and made the desired selections in fields 1924, 1926, 1928. Authentication in progress screen 1948 of FIG. 243 is substantially similar to screen 1910 of FIG. 238 and so like reference numbers are used in FIG. 243 to denote like portions without repeating the descriptions. However, screen 1948 of FIG. 243 includes a progress icon 1950 that shows the progress of the WiFi authentication process. In the illustrative example of FIG. 243, progress icon 1950 is a circular icon that has its circumference filled in as the authentication process progresses. While the authentication process takes place, button 1896 on screen 1948 become grayed out to indicate that button 1896 are disabled.

Referring now to FIG. 244, a successful authentication screen 1952 appears on GUI 16 in response to a successful authentication between device 10 and the WiFi network associated with the selected WAP. Screen 1952 is substantially the same as screens 1910, 1948 of FIGS. 238 and 243, respectively, but with a couple differences. One difference is that a check mark appears in the ACCESS POINTS column of table 1904 in the row corresponding to the WAP that was selected on screen 1912 of FIG. 239 for WiFi communication and the row of table 1904 with the check mark is no longer highlighted. Also, a status tab 1954 appears on screen 1952 to the right of settings tab 1902.

Referring now to FIG. 245, an unable to connect screen 1956 appears on GUI 16 in response to the circuitry of 500 of respiratory therapy apparatus 10 being unable to connect to the WiFi network associated with the WAP selected on screen 1912 of FIG. 239. Screen 1956 includes a window 1958 having a box 1960 with the text "UNABLE TO CONNECT" therein. Beneath box 1960 is the explanatory text "DEVICE CANNOT CONNECT TO SELECTED WIFI NETWORK. IF THIS PROBLEM PERSISTS, PLEASE CONTACT CUSTOMER SUPPORT." Window 1958 of screen 1956 also includes a return button 1962, the selection of which returns the user to screen 1910 of FIG. 238.

Referring now to FIG. 246, a WiFi status screen 1964 appears on GUI 16 after selection of status tab 1954 of screen 1952 of FIG. 244. WiFi status screen 1964 includes a table 1966 having information regarding the WiFi network to which the respiratory therapy apparatus 10 is connected. In the illustrative example of FIG. 246, table 1966 includes the following information for the WAP and associated WiFi network: service set identifier (SSID) name, security type, MAC address, Internet protocol (IP) address, subnet mask, and gateway.

Referring now to FIG. 247, a first WiFi settings screen 1968 appears on GUI 16 in response to selection of settings tab 1902 on the WiFi status screen 1964 of FIG. 246, for example. WiFi settings screen 1968 includes a network window 1970 and a server window 1972 beneath the setting tab 1902. Window 1970 includes a first slider input 1974 to select between a static position in which a static IP address is assigned to the respiratory therapy apparatus 10 and a DHCP position in which an IP address is assigned to the respiratory therapy apparatus 10 based on a Dynamic Host Configuration Protocol (DHCP). In the illustrative example of FIG. 1968, first slider 1974 of screen 1968 is in the static position.

Window 1972 includes a second slider input 1976 to select between communication with first or second servers of the WiFi network. In the illustrative example, the first server is an electronic medical records (EMR) server and the second server is a VisiView server. The VisiView server is a server included as part of the VISIVIEW® Health Portal marketed by Hill-Rom Company, Inc. of Batesville, Indiana. The VISIVIEW® Health Portal is a system that receives the therapy session data from apparatus 10 and makes it accessible to the patient's respiratory care team. In other embodiments, the second server is some other designated server. In the illustrative example of FIG. 247, the second slider 1976 of screen 1968 is in a first position (aka the EMR position) but, if desired is movable to a second position (aka the VisiView position).

Still referring to FIG. 247, network window 1970 includes an IP address field 1978, a gateway field 1980, a subnet field 1982, and a domain name system (DNS) field 1984. Server window 1972 includes a server IP field 1986, a port field 1988, and a network time protocol (NTP) IP field 1990. Beneath field 1990, window 1972 further includes a test connection button 1992. As will be discussed below, each of fields 1978, 1980, 1982, 1984, 1986, 1988, 1990 is selectable by the user to type in the desired information. Fields 1978, 1980, 1982, 1984, 1986, 1990 are each formatted according to the dotted quad convention for network addresses of computer devices. In the illustrative example of screen 1968 of FIG. 247, fields 1978, 1980, 1982, 1984, 1986, 1990 each default to the network address of 0.0.0.0. Also in the illustrative example of FIG. 247, the port number in field 1988 defaults to zero. Portions of screen 1968 of FIG. 247 that are the same as other screens discussed above are denoted with like reference numbers and the descriptions are not repeated.

Referring now to FIG. 248, a second WiFi settings screen 1994 appears on GUI 16 in response to first slider input 1974 of window 1970 being moved from the static position to the DHCP position. As shown in FIG. 248, when slider input 1974 is in the DHCP position, fields 1978, 1980, 1982, 1984 are omitted from window 1970. This is because the DHCP of the network to which apparatus 10 is connected assigns the IP address, gateway address, etc. to apparatus 10 each time apparatus 10 is powered up and sends a broadcast query for receipt by the DHCP server to request the assigned address information. Otherwise, screen 1994 of FIG. 248 is substantially the same as screen 1968 of FIG. 247 and so like reference numbers are used for like portions without repeating the descriptions. Screen 1994 of FIG. 248 includes button 721 whereas screen 1968 of FIG. 247 does not.

Referring now to FIG. 249, a third WiFi settings screen 1996 appears on GUI 16 in response to second slider input 1976 of window 1972 of screen 1994 of FIG. 248 being moved from the first position to the second position. As shown in FIG. 249, when slider input 1976 is in the second position, fields 1986, 1988, 1990 are omitted from window 1972. This is because the IP address for the second server (e.g., the VisiView server in the illustrative example) and/or other network address information regarding the second server is programmed into apparatus 10 by the manufacturer such that users of apparatus 10 are not permitted to change such address information for the second server. Otherwise, screen 1996 of FIG. 249 is substantially the same as screen 1994 of FIG. 248 and so like reference numbers are used for like portions without repeating the descriptions. In FIG. 250, a fourth WiFi settings screen 1998 is shown, similar to FIG. 247, but having the second slider input 1976 moved to the second position with the first slider input 1974 remaining in the static position. Thus, FIGS. 247-250 show the four possible combinations of the positions of slider inputs 1974, 1976 and examples of the resulting screens 1968, 1994, 1996, 1998, respectively.

Referring now to FIG. 251, a first settings adjustment screen 2000 appears on GUI 16 in response to selection of subnet field 1982 in window 1970. In response to the selection by the user, the subnet field 1982 becomes highlighted such as being colored yellow in some embodiments. The unselected fields 1978, 1980, 1984 of window 1970 remain unhighlighted, such as being colored white. However, selection of any of the other fields 1978, 1980, 1984 beneath first slider input 1974 of window 1970 results in a screen similar to FIG. 251 but with the selected one of fields 1978, 1980, 1984 being highlighted rather than field 1982 being highlighted as shown in the illustrative example of FIG. 251. Screen 2000 has a graphical numeric keyboard 2002 for editing the IP address shown in subnet field 1982 (or whichever of fields 1978, 1980, 1984 was selected in other scenarios). Because one of the fields 1978, 1980, 1982, 1984 of window 1970 was selected, keyboard 2002 of screen 2000 is superimposed on window 1972 so that the fields 1978, 1980, 1982, 1984 are still able to be seen for editing.

Because screen 2000 resulted due to one of the fields 1978, 1980, 1982, 1984 of window 1970 being selected, keyboard 2002 of screen 2000 is superimposed on window 1972 so that the fields 1978, 1980, 1982, 1984 of window 1970 are still able to be seen for editing. After the user types in the desired IP address in the selected field, which is field 1982 in the illustrative example of FIG. 251, the user is able to select another one of fields 1978, 1980, 1984 of window 1970 to edit using keyboard 2002, if desired. Alternatively, if the user is finished editing fields 1978, 1980, 1982, 1984, the user can tap or select the currently highlighted field, or on a dead space region of screen 2000, to close keyboard 2002 from being displayed on GUI 16.

Referring now to FIG. 252, a second settings adjustment screen 2004 appears on GUI 16 in response to selection of port field 1988 in window 1972. In response to the selection by the user, the port field 1988 becomes highlighted such as being colored yellow in some embodiments. The unselected fields 1986, 1990 of window 1972 remain unhighlighted, such as being colored white. However, selection of any of the other fields 1986, 1990 beneath second slider input 1976 of window 1972 results in a screen similar to FIG. 252 but with the selected one of fields 1986, 1990 highlighted rather than field 1988 being highlighted as shown in the illustrative example of FIG. 252. Like screen 2000, screen 2004 also has graphical numeric keyboard 2002 for editing the IP address shown in port field 1988 (or whichever of fields 1986, 1990 was selected in other scenarios).

Because screen 2004 resulted due to one of the fields 1986, 1988, 1990 of window 1972 being selected, keyboard 2002 of screen 2004 is superimposed on window 1970 so that the fields 1986, 1988, 1990 of window 1972 are still able to be seen for editing. After the user types in the desired port number or IP address in the selected field, which is port field 1988 in the illustrative example of FIG. 252, the user is able to select another one of fields 1986, 1990 to edit using keyboard 2002, if desired. Alternatively, if the user is finished editing fields 1986, 1988, 1990, the user can tap or select the currently highlighted field, or on a dead space region of screen 2004, to close keyboard 2002 from being displayed on GUI 16.

Referring now to FIG. 253, a fifth WiFi settings screen 2006, similar to FIG. 247, appears on GUI 16 in response to settings tab 1902 being selected but in the situation when no WAP has been selected and/or set up for communication with the respiratory therapy apparatus 10. In the illustrative example of FIG. 253, zeroes in dotted quad format are populated for the IP addresses in all of fields 1978, 1980, 1982, 1984, 1986, 1990 beneath the respective slider inputs 1974, 1976 of corresponding windows 1970, 1972. Also, test connection button 1992 of screen 1968 shown in FIG. 247 is omitted from screen 2006 of FIG. 253 as a result of apparatus 10 not being set up for communication with any WAP of a corresponding network. Status tab 1954 of screen 1968 of FIG. 247 is also omitted from screen 2006 of FIG. 253 for this same reason.

Referring now to FIG. 254, a sixth WiFi settings screen 2008, similar to FIG. 247, appears on GUI 16 after all of fields 1978, 1980, 1982, 1984, 1986, 1988, 1990 beneath respective slider inputs 1974, 1976 of corresponding windows 1970, 1972 have been populated with relevant IP address and port address information. Screen 2008 shows test connection button 1992 available for use which means that apparatus 10 has been set up for communication with a selected WAP of a corresponding network. While illustrative screen 2008 of FIG. 254 is similar to screen 1968 of FIG. 247 due to slider inputs 1974, 1976 each being in their first positions (e.g., static position and EMR position, respectively), it should be noted that test connection button 1992 is available for use for all four position combinations of slider inputs 1974, 1976, shown in FIGS. 247-250, for example, assuming a WAP has been selected for communication with apparatus 10 as shown, for example, on screen 1952 of FIG. 244.

Referring now to FIG. 255, a connection test in progress screen 2010 appears on GUI 16 in response to selection of test connection button 1992 on any of screens 1968, 1994, 1996, 1998, 2008 of FIGS. 247-250 and 254, respectively. Connection test in progress screen 2010 includes a window 2012 having a text box 2014 with the text "CONNECTION TEXT" therein. Beneath box 2014 the explanatory "TESTING IN PROGRESS, PLEASE WAIT . . . " appears. A progress icon 2016 appears beneath the explanatory text on screen 2010 and shows the progress of the WiFi network connection testing process. In the illustrative example of FIG. 255, progress icon 2016 is a circular icon that has its circumference filled in as the connection testing process progresses.

If the WiFi network connection testing process of apparatus 10 fails due apparatus 10 being unable to connect to the network under test, an unable to connect screen 2018, similar to screen 1956 of FIG. 245, appears on GUI 16. Screen 2018 includes a window 2020 having a text box 2022 with the text "UNABLE TO CONNECT" therein. Beneath box 2022 is the explanatory text "UNABLE TO CONNECT WITH SELECTED NETWORK. IF THIS PROBLEM PERSISTS, PLEASE CONTACT CUSTOMER SUPPORT." Window 2020 of screen 2018 of FIG. 256 also includes a return button 2024, the selection of which returns the user to the screen on which test connection button 1992 was selected initially to start the WiFi network connection testing process.

Referring now to FIG. 257, a first connection results screen 2026 appears on GUI 16 after the connection test is completed according to a first scenario. In particular, the first scenario corresponds to a network connection test portion of the WiFi network connection test being successful and a server connection test portion of the WiFi network connection test being unsuccessful. The network connection test relates to testing the information provided in network window 1970 and the server connection test relates to testing the information provided in server window 1972 of the screen on which test connection button 1992 was selected initially to start the WiFi network connection testing process.

Still referring to FIG. 257, screen 2026 includes a window 2028 having a text box 2030 with the text "CONNECTION RESULTS" therein. Beneath box 2030 is the explanatory text "NETWORK CONNECTION SUCCESSFUL. SERVER CONNECTION UNSUCCESSFUL. CHECK CONFIGURATION AND TRY AGAIN." Thus, the explanatory text of screen 2026 is instructing the user to double check the accuracy of the information provided in the server window 1972 that was subject to the testing and to make appropriate edits as needed. Window 2028 of screen 2026 of FIG. 257 also includes return button 2024 which is used to return the user back to the screen on which test connection button 1992 was selected initially to start the WiFi network connection testing process.

Referring now to FIG. 258, a second connection results screen 2032 appears on GUI 16 after the connection test is completed according to a second scenario. In particular, the second scenario corresponds to the network connection test portion of the WiFi network connection test being successful and the server connection test portion of the WiFi network connection test also being successful. Screen 2032 includes a window 2034 having text box 2030 with the text "CONNECTION RESULTS" therein, but the explanatory text beneath box 2030 of screen 2032 is slightly different than that of screen 2026. In particular, the explanatory text of window 2034 of FIG. 258 is as follows: "NETWORK CONNECTION SUCCESSFUL. SERVER CONNECTION SUCCESSFUL." Window 2034 of screen 2032 of FIG. 258 also includes return button 2024 which is used to return the user back to the screen on which test connection button 1992 was selected initially to start the WiFi network connection testing process.

Referring now to FIG. 259, a first long term evolution (LTE) on screen 2036 appears on GUI 16 in response to selection of an LTE tab 1602' that is provided in lieu of the WiFi tab 1602 of FIGS. 220 and 236, for example, if the respiratory therapy apparatus 10 is configured for connection to an LTE network rather than a WiFi network. In this regard, as discussed above with regard to FIG. 16A, the type of module 540 connected to port 218 of apparatus 10 determines whether apparatus 10 is configured for WiFi communication or LTE communication or both. Thus, if module 540 has WiFi communication circuitry, then apparatus 10 includes WiFi tab 1602 on the appropriate screens as shown, for example, in FIGS. 220-258. Similarly, if module 540 has LTE communication circuitry, then apparatus 10 includes LTE tab 1602' on the appropriate screens as shown, for example, in FIGS. 259-262. In contemplated embodiments in which module 540 has both WiFi and LTE communication circuitry, then WiFi tab 1602 and LTE tab 1602' both appear on the appropriate screens of apparatus 10 when connect button 718 is selected. First LTE on screen 2036 has a 4G slider input 1894' which in FIG. 259 is in an off position.

Referring now to FIG. 260, a second LTE on screen 2038, similar to screen 2036 of FIG. 259, appears on GUI 16 in response to 4G slider input 1894' being moved from the off position of FIG. 259 to the on position of FIG. 260. Second LTE on screen 2038 includes an LTE progress icon 1950' to indicate the progress of a search for an LTE carrier with which to communicate. In the illustrative example of FIG. 260, progress icon 1950' is a circular icon that has its circumference filled in as the LTE carrier search process progresses. As also shown on screen 2038 of FIG. 260, LTE informational headings of "CARRIER NAME:," "INTERNATIONAL MOBILE EQUIPMENT IDENTITY (IMEI):," and "SIM CARD ID:" appear beneath slider input 1894' and LTE tab 1602'.

Referring now to FIG. 261, a no carrier found screen 2040 appears on GUI 16 if no LTE carrier is found after 4G slider input 1894' is moved to the on position. The information next to each of the CARRIER NAME:, INTERNATIONAL MOBILE EQUIPMENT IDENTITY (IMEI):, and SIM CARD ID: headings includes a series of ten "X's" in the illustrative example to indicate to the user that no LTE carrier network was found during the LTE carrier search conducted in connection with screen 2038 of FIG. 260. With reference to FIG. 262, a carrier found screen 2042 appears on GUI 16 if an LTE carrier is found after 4G slider input 1894' is moved to the on position.

Carrier found screen 2042 of FIG. 262 has information about the LTE carrier automatically populated in the carrier name field to the right of the CARRIER NAME: heading. In the illustrative example of FIG. 262, an international mobile equipment identity (IMEI) field and a subscriber identity module (SIM) card ID field to the right of the corresponding headings still have the series of ten "X's" shown, but these fields are also automatically populated with the relevant information if discovered during the LTE carrier search. Screen 2042 further includes a test connection button 1992' which is selectable to test the connection between apparatus 10 and the LTE network that was found during the LTE carrier search. Screens 2010, 2018, 2026, 2032 of FIGS. 255-258, respectively, appear on GUI 16 under the same circumstances as discussed above in response to selection of test connection button 1992' but the information on the resulting screens relate to connection with the LTE network under test rather than the WiFi network being tested as described above.

Referring now to FIG. 263, a help category screen 2044 appears on GUI 16 in response to selection of the information or help icon 702 after tab 688 has been selected on one of screens 676, 682 resulting in display of menu 692 of icons such as is shown on menu screen 690 of FIG. 21, for example. Help category screen 2044 includes a table 2046 having a set of buttons corresponding to a list of categories for which help is available. In the illustrative example, the set of buttons include an automatic therapy button 2048, a manual therapy button 2050, a therapy overview button 2052, a therapy options button 2054, and a modify therapy button 2056. A return button 2058 is provided in the lower right corner of window of window 2046 and is selectable to return the user back to the previous screen on which help icon 702 was originally selected, such as screen 690 of FIG. 21.

Still referring to FIG. 263, a header 2060 of window 2046 includes the text "SELECT CATEGORY FOR HELP" situated above button 2048 and also has the text "OLE" at its far right. Thus, selection of any of buttons 2048, 2050, 2052, 2054, 2056 on table 2046 of screen 2044 results in a respective help screen being shown on GUI 16 that relates to the OLE therapy of apparatus 10 as will be discussed below in connection with FIGS. 264-266, 268 and 269. This is because, the menu 692 having icon 702 was originally displayed as a result of selecting tab 688 when viewing OLE therapy selection screen 682 of FIG. 20. If the user was viewing MIE therapy selection screen 676 of FIG. 19 when tab 688 was selected and then icon 702 was selected from the resulting menu 692, then a help category screen relating to MIE therapy is shown on GUI 16. The help category screen relating to MIE therapy is the same as screen 2044 of FIG. 263 except that "MIE" appears at the right of header 2060 instead of "OLE" and selection of buttons 2048, 2050, 2052, 2054, 2056 results in a respective help screen being shown on GUI 16 that relates to the MIE therapy of apparatus 10 as will be discussed below in connection with FIGS. 270-274.

Referring now to FIG. 264, an automatic OLE therapy help screen 2062 appears on GUI 16 in response to selection of automatic therapy button 2048 on the help category screen 2044 of FIG. 263, if navigated to from the main OLE therapy selection screen 682 of FIG. 20, for example. Screen 2062 includes an image 1262i that is substantially similar to main automatic OLE therapy screen 1262 of FIG. 121. Thus, the same reference numbers are used in image 1262i of screen 2062 of FIG. 264 that were used in connection with screen 1262 of FIG. 121 and the descriptions are not repeated. Screen 2062 includes textual annotations regarding features and functions of screen 1262 as depicted in image 1262i.

The textual annotations on screen 2062 of FIG. 264 are self-explanatory and so do not need to be discussed further herein. However, with regard to graph 1270 of screen 2062, it is worth noting that the graphical trace itself is annotated as "THERAPY PROGRESS INDICATOR" and so therapy progress indicator 1274 discussed above may just as well be considered as a therapy progress icon 1274 that moves along the therapy progress indicator graph 1270. Screen 2062 of FIG. 264 also includes a return button 2064 that is selectable to return the user back to screen 2044 of FIG. 263. It should be noted that screen 2062 can also be navigated to via screen 2044, as desired, starting from any OLE screen having menu button 688 active for bringing up menu 692 on GUI 16 with help icon 702 active. Thus, screen 2044 results from the selection of help icon 702 and then screen 2062 results from selection of button 2048 on screen 2044 regardless of how the user navigated to screen 2044. It is also worth noting that screen 2062 reflects the various parameter values such as pressure settings, clock times, number of stages, nebulizer status, etc. as programmed in apparatus 10 at the time that button 702 was selected to start the process of navigating to screen 2062.

Referring now to FIG. 265, a manual OLE therapy help screen 2066 appears on GUI 16 in response to selection of manual therapy button 2050 on help category screen 2044 of FIG. 263, if screen 2044 was navigated to from a prior screen relating to OLE therapy as discussed above. Screen 2066 includes an image 1526i that is substantially similar to main manual OLE therapy screen 1526 of FIG. 166. Thus, the same reference numbers are used in image 1526i of screen 2066 of FIG. 265 that were used in connection with screen 1526 of FIG. 166 and the descriptions are not repeated. Screen 2066 includes textual annotations regarding features and functions of screen 1526 as depicted in image 1526i. The textual annotations on screen 2066 of FIG. 265 are self-explanatory and so do not need to be discussed further herein. Screen 2066 of FIG. 265 also includes return button 2064 that is selectable to return the user back to screen 2044 of FIG. 263. It is also worth noting that screen 2066 reflects the various parameter values such as pressure settings, clock times, number of stages, nebulizer status, etc. as programmed in apparatus 10 at the time that button 702 was selected to start the process of navigating to screen 2066.

Referring now to FIG. 266, an OLE therapy overview help screen 2068 appears on GUI 16 in response to selection of therapy overview button 2052 on help category screen 2044 of FIG. 263, if screen 2044 was navigated to from a prior screen relating to OLE therapy as discussed above. Screen 2066 includes an image 1338i that is substantially similar to first care plan screen 1338 of FIG. 134. Thus, the same reference numbers are used in image 1338i of screen 2068 of FIG. 266 that were used in connection with screen 1338 of FIG. 134 and the descriptions are not repeated. Screen 2068 includes textual annotations regarding features and functions of screen 1338 as depicted in image 1338i. The textual annotations on screen 2068 of FIG. 266 are self-explanatory and so do not need to be discussed further herein. However, it is worth noting the care plan names of the tabs or buttons of menu 1344 of image 1338*i* of FIG. 266 are different than those shown on screen 1338 of FIG. 134. Thus, screen 2068 reflects the currently programmed care plan names, number of stages, pressure values, duration times, etc. of apparatus 10 for the OLE therapy at the time that button 702 was selected to start the process of navigating to screen 2068. Screen 2068 of FIG. 266 also includes return button 2064 that is selectable to return the user back to screen 2044 of FIG. 263.

Referring now to FIG. 267, an example is given of a return from help screen 2070 showing a predecessor screen that is returned to if return button 2058 of help category screen 2044 of FIG. 263 is selected, assuming the help category screen 2044 was originally navigated to in response to selection of help icon 702 from the options tab 1418 of the screen 1426 for automatic OLE therapy of FIG. 141. This example is given as a possible return scenario from cough pause settings screen 2044 of FIG. 263 using button 2058. As alluded to above, selection of button 2058 on screen 2044 of FIG. 263 returns the user back to whatever screen the user was viewing when the active help icon 702 was selected. Screen 2070 of FIG. 267 is basically a duplicate of screen 1426 of FIG. 141 and so the same reference numbers are used in FIG. 267 for like portions without repeating the descriptions. However, it is worth noting the care plan names of the tabs or buttons of menu 1344 of image screen 2070 of FIG. 267 are different than those shown on screen 1426 of FIG. 141.

Referring now to FIG. 268, an OLE therapy options help screen 2072 appears on GUI 16 in response to selection of therapy options button 2054 on the help category screen of FIG. 263, if screen 2044 was navigated to from a screen similar to screen 2070 of FIG. 267. Screen 2072 includes an image 2070*i* that is substantially similar to cough pause settings screen 2070 of FIG. 267. However, the button names in menu 1344 are different on screen 2072 than on screen 2070. However, the same reference numbers are used in image 2070*i* of screen 2072 of FIG. 268 that were used in connection with screen 2070 of FIG. 267 and the descriptions are not repeated. Screen 2072 includes textual annotations regarding features and functions of screen 2070 as depicted in image 2070*i*. The textual annotations on screen 2072 of FIG. 268 are self-explanatory and so do not need to be discussed further herein. Screen 2072 of FIG. 268 also includes return button 2064 that is selectable to return the user back to screen 2044 of FIG. 263.

Referring now to FIG. 269, an OLE modify therapy help screen 2074 appears on GUI 16 in response to selection of modify therapy overview button 2056 on help category screen 2044 of FIG. 263, if screen 2044 was navigated to from a prior screen relating to OLE therapy as discussed above. Screen 2074 includes an image 1400*i* that is substantially similar to second modify therapy screen 1400 of FIG. 138. Thus, the same reference numbers are used in image 1400*i* of screen 2074 of FIG. 268 that were used in connection with screen 1400 of FIG. 138 and the descriptions are not repeated. Screen 2074 includes textual annotations regarding features and functions of screen 1400 as depicted in image 1400*i*. The textual annotations on screen 2074 of FIG. 268 are self-explanatory and so do not need to be discussed further herein. However, it is worth noting the care plan names of the tabs or buttons of menu 1344 of image 1400*i* of FIG. 268 are different than those shown on screen 1400 of FIG. 138. Thus, screen 2074 reflects the currently programmed care plan names, number of stages, pressure values, duration times, etc. of apparatus 10 for the OLE therapy at the time that button 702 was selected to start the process of navigating to screen 2074. Screen 2074 of FIG. 268 also includes return button 2064 that is selectable to return the user back to screen 2044 of FIG. 263.

Referring now to FIG. 270, an automatic MIE therapy help screen 2076 appears on GUI 16 in response to selection of automatic therapy button 2048 on the help category screen 2044 of FIG. 263, if screen 2044 was navigated to from a prior screen relating to MIE therapy such as main MIE therapy selection screen 676 of FIG. 19, for example. Screen 2076 includes an image 764*i* that is substantially similar to main automatic MIE therapy screen 764 of FIG. 29. Thus, the same reference numbers are used in image 764*i* of screen 2076 of FIG. 270 that were used in connection with screen 764 of FIG. 29 and the descriptions are not repeated. Screen 2076 includes textual annotations regarding features and functions of screen 764 as depicted in image 764*i*. The textual annotations on screen 2076 of FIG. 270 are self-explanatory and so do not need to be discussed further herein. Screen 2076 of FIG. 270 also includes return button 2064 that is selectable to return the user back to screen 2044 of FIG. 263. It is also worth noting that screen 2076 reflects the various parameter values such as pressure settings, clock times, number of cycles or steps, flow setting, etc. as programmed in apparatus 10 at the time that button 702 was selected to start the process of navigating to screen 2076.

Referring now to FIG. 271, a manual MIE therapy help screen 2078 appears on GUI 16 in response to selection of manual therapy button 2050 on the help category screen 2044 of FIG. 263, if screen 2044 was navigated to from a prior screen relating to MIE therapy. Screen 2078 includes an image 862*i* that is substantially similar to main manual MIE therapy screen 862 of FIG. 41. Thus, the same reference numbers are used in image 862*i* of screen 2078 of FIG. 271 that were used in connection with screen 862 of FIG. 41 and the descriptions are not repeated. Screen 2078 includes textual annotations regarding features and functions of screen 862 as depicted in image 862*i*. The textual annotations on screen 2078 of FIG. 271 are self-explanatory and so do not need to be discussed further herein. Screen 2078 of FIG. 271 also includes return button 2064 that is selectable to return the user back to screen 2044 of FIG. 263. It is also worth noting that screen 2078 reflects the various parameter values such as pressure settings, clock times, flow setting, etc. as programmed in apparatus 10 at the time that button 702 was selected to start the process of navigating to screen 2078.

Referring now to FIG. 272, an MIE therapy overview help screen 2080 appears on GUI 16 in response to selection of therapy overview button 2052 on the help category screen 2044 of FIG. 263, if screen 2044 was navigated to from a prior screen relating to MIE therapy as discussed above. Screen 2080 includes an image 980*i* that is substantially similar to first care plan screen 980 for automatic MIE therapy of FIG. 66. Thus, the same reference numbers are used in image 980*i* of screen 2080 of FIG. 272 that were used in connection with screen 980 of FIG. 66 and the descriptions are not repeated. Screen 2080 includes textual annotations regarding features and functions of screen 980 as depicted in image 980*i*. The textual annotations on screen 2080 of FIG. 272 are self-explanatory and so do not need to be discussed further herein. However, it is worth noting the care plan names of the tabs or buttons of menu 986 of image 980*i* of FIG. 272 are different than those shown on screen 980 of FIG. 66. Thus, screen 2080 reflects the currently programmed care plan names, number of cycles, pressure values, duration times, etc. of apparatus 10 for the MIE therapy at the time that button 702 was selected to start the process of navigating to screen 2080. Screen 2080 of FIG. 272 also includes return button 2064 that is selectable to return the user back to screen 2044 of FIG. 263.

Referring now to FIG. 273, an MIE therapy options help screen 2082 appears on GUI 16 in response to selection of the therapy options button 2054 on help category screen 2044 of FIG. 263, if screen 2044 was navigated to from a prior screen relating to MIE therapy as discussed above. Screen 2082 includes an image 996i that is substantially similar to second care plan screen 996 of FIG. 67. Thus, the same reference numbers are used in image 996i of screen 2082 of FIG. 273 that were used in connection with screen 996 of FIG. 67 and the descriptions are not repeated. Screen 2082 includes textual annotations regarding features and functions of screen 996 as depicted in image 996i. The textual annotations on screen 2082 of FIG. 273 are self-explanatory and so do not need to be discussed further herein. However, it is worth noting the care plan names of the tabs or buttons of menu 986 of image 996i of FIG. 273 are different than those shown on screen 996 of FIG. 67. Thus, screen 2082 reflects the currently programmed care plan names, pressure values, duration times, etc. of apparatus 10 for the MIE therapy at the time that button 702 was selected to start the process of navigating to screen 2082. Screen 2082 of FIG. 273 also includes return button 2064 that is selectable to return the user back to screen 2044 of FIG. 263.

Referring now to FIG. 274, an MIE modify therapy help screen 2084 appears on GUI 16 in response to selection of modify therapy button 2056 on help category screen 2044 of FIG. 263, if screen 2044 was navigated to from a prior screen relating to MIE therapy as discussed above. Screen 2084 includes an image 1182i that is substantially similar to add cycle screen 1182 of FIG. 101. Thus, the same reference numbers are used in image 1182i of screen 2084 of FIG. 274 that were used in connection with screen 1182 of FIG. 101 and the descriptions are not repeated. Screen 2084 includes textual annotations regarding features and functions of screen 1182 as depicted in image 1182i. The textual annotations on screen 2084 of FIG. 274 are self-explanatory and so do not need to be discussed further herein. However, it is worth noting the care plan names of the tabs or buttons of menu 986 of image 1182i of FIG. 274 are different than those shown on screen 1182 of FIG. 101. Thus, screen 2084 reflects the currently programmed care plan names, number of cycles, pressure values, duration times, etc. of apparatus 10 for the MIE therapy at the time that button 702 was selected to start the process of navigating to screen 2084. Screen 2084 of FIG. 274 also includes return button 2064 that is selectable to return the user back to screen 2044 of FIG. 263.

Although certain illustrative embodiments have been described in detail above, variations and modifications exist within the scope and spirit of this disclosure as described and as defined in the following claims.

The invention claimed is:

1. A respiratory therapy apparatus comprising
a housing having a hose port extending from a front wall of the housing and defining a pneumatic passage through the front wall,
a tag reader located in the housing and having a first antenna situated adjacent an inner surface of the front wall and surrounding the hose port,
a filter housing sized to couple to the hose port, the filter housing having a filter receiving space positioned between a filter inlet and a filter outlet, a filter passage extending though the filter housing between the filter inlet and the filter outlet,
a filter located in the filter receiving space,
a second antenna coupled to the filter housing and surrounding the filter passage, and
an identification (ID) chip carried by the filter housing and coupled to the second antenna, wherein the tag reader is configured to read the ID chip via wireless signals between the first antenna and the second antenna to confirm the filter housing is an authorized filter housing for use with the respiratory therapy apparatus, wherein the first antenna comprises a substantially flat annular ring that is substantially parallel with the filter and a set of mounting ears extending radially outwardly from the substantially flat annular ring.

2. The respiratory therapy apparatus of claim 1, wherein the ID chip is a radio frequency (RF) ID chip and the wireless signals comprise RF signals communicated between the first antenna and the second antenna.

3. The respiratory therapy apparatus of claim 2, further comprising control circuitry located in the housing and electronically coupled to the tag reader, the control circuitry being configured to command operation of a pressure source located in the housing, the RF signals include data regarding a prior number of uses of the filter, and the control circuitry disabling operation of the pressure source if the prior number of uses of the filter exceeds a threshold number of uses.

4. The respiratory therapy apparatus of claim 3, wherein the control circuitry is configured to command the tag reader to write new data to the RF ID chip, the new data being transmitted from the first antenna to the second antenna, and the new data including a new total number of uses of the filter which comprises incrementing by one the number of prior uses of the filter.

5. The respiratory therapy apparatus of claim 3, further comprising a display, wherein the prior number of uses of the filter is shown on the display in response to the filter housing being coupled to the hose port.

6. The respiratory therapy apparatus of claim 5, wherein, if the prior number of uses of the filter exceeds the threshold number of uses a notification is provided on the display.

7. The respiratory therapy apparatus of claim 6, wherein the notification indicates that the filter needs to be replaced.

8. The respiratory therapy apparatus of claim 6, wherein the notification comprises an icon shown on the display.

9. The respiratory therapy apparatus of claim 3, further comprising an alarm and wherein the alarm is triggered if the prior number of uses of the filter exceeds the threshold number of uses.

10. The respiratory therapy apparatus of claim 1, wherein the tag reader is configured to use the first antenna to emit energy to the second antenna to power the ID chip.

11. The respiratory therapy apparatus of claim 1, wherein the filter has a first substantially circular outer periphery of a first diameter, the second antenna has a second substantially circular periphery of a second diameter, and the first diameter is larger than the second diameter.

12. The respiratory therapy apparatus of claim 11, wherein the second antenna is also configured as a substantially flat annular ring and is substantially parallel with the filter.

13. The respiratory therapy apparatus of claim 1, wherein the second antenna also is configured as a substantially flat annular ring.

14. The respiratory therapy apparatus of claim 13, wherein the second antenna is sandwiched between a face material and a substrate.

15. The respiratory therapy apparatus of claim 14, wherein either or both of the face material and the substrate comprises a polyethylene terephthalate (PET) material.

16. The respiratory therapy apparatus of claim 14, wherein the face material and the substrate are both configured as substantially flat annular rings.

17. The respiratory therapy apparatus of claim 14, further comprising an adhesive layer on the substrate and backing paper attached to the adhesive layer such that the adhesive layer is situated between the backing paper and the substrate.

18. The respiratory therapy apparatus of claim 17, wherein the backing paper comprises a silicon liner or a siliconized paper.

19. The respiratory therapy apparatus of any of claim 1, wherein the second antenna is made of copper.

20. The respiratory therapy apparatus of claim 1, wherein the filter housing includes a substantially cylindrical first tubular portion that includes the filter inlet, a substantially cylindrical second tubular portion that includes the filter outlet, a first substantially frustoconical portion extending from the first tubular portion, and a second substantially frustoconical portion extending from the second tubular portion, the first and second substantially frustoconical portions meeting at a joint defining an annular apex of the filter housing, wherein a shoulder wall portion is formed on the second substantially frustoconical portion and the second antenna is mounted to the shoulder wall portion.

21. The respiratory therapy apparatus of claim 20, wherein the first and second tubular portions are aligned along an axis of the filter passage, the shoulder wall portion includes a shoulder surface that surrounds the axis and that is substantially perpendicular to the axis of the filter passage, and the second antenna is mounted to the shoulder surface.

22. The respiratory therapy apparatus of claim 21, wherein the second antenna is formed as a substantially flat annular ring that mounts to the shoulder surface.

23. The respiratory therapy apparatus of claim 21, wherein the filter comprises a substantially circular disk that is substantially parallel with the second antenna and the shoulder surface.

24. The respiratory therapy apparatus of claim 20, wherein the filter comprises a substantially circular disk having an outer periphery adjacent the annular apex of the joint.

25. The respiratory therapy apparatus of claim 1, wherein the ID chip and the second antenna cooperate to send and receive wireless communications within a frequency range between about 12 Mega Hertz (MHz) and about 14 MHz.

26. The respiratory therapy apparatus of claim 1, further comprising control circuitry coupled to the reader and including a graphical user interface (GUI) and a controller, the controller being configured to command the GUI to display a plurality of navigable screens that are usable to control features and functions of the respiratory therapy apparatus, a first group of screens of the plurality of navigable screens being usable to establish wireless communication between the control circuitry and a bar code scanner, which is operable to scan identification (ID) bar codes of a patient and a respiratory therapist for storage in a memory of the control circuitry, a second group of screens of the plurality of navigable screens being usable to select a first set of operating parameters for a first respiratory therapy, a third group of screens of the plurality of navigable screens being usable to select a second set of operating parameters for a second respiratory therapy, and a fourth group of screens of the plurality of navigable screens being usable to establish wireless communication between the control circuitry and a patient monitor that is operable to sense a physiological parameter of the patient.

* * * * *

UNITED STATES PATENT AND TRADEMARK OFFICE
CERTIFICATE OF CORRECTION

| | |
|---|---|
| PATENT NO. | : 12,280,207 B2 |
| APPLICATION NO. | : 18/183329 |
| DATED | : April 22, 2025 |
| INVENTOR(S) | : Jack Barney Sing et al. |

Page 1 of 1

It is certified that error appears in the above-identified patent and that said Letters Patent is hereby corrected as shown below:

In the Claims

Column 159, Line 17, Claim 19, delete the words "of any".

Signed and Sealed this
Seventeenth Day of June, 2025

Coke Morgan Stewart
*Acting Director of the United States Patent and Trademark Office*